US012630604B2

(12) United States Patent
Treanor et al.

(10) Patent No.: US 12,630,604 B2
(45) Date of Patent: May 19, 2026

(54) METHODS OF MAKING CHIMERIC ANTIGEN RECEPTOR-EXPRESSING CELLS

(71) Applicant: Novartis AG, Basel (CH)

(72) Inventors: Louise Mary Treanor, Cambridge, MA (US); Michael R. Greene, Groton, MA (US); Jennifer Brogdon, Sudbury, MA (US); Boris Engels, Arlington, MA (US); Glenn Dranoff, Sudbury, MA (US); Olja Kodrasi, Quincy, MA (US); Hyungwook Lim, Cambridge, MA (US); Akash Sohoni, Cambridge, MA (US); Elizabeth Dorothy Pratico, East Boston, MA (US); Anniesha Hack, East Hanover, NJ (US); Aida Abujoub, Winchester, MA (US); Tony Fleming, Stow, MA (US); Lu Huang, West Roxbury, MA (US); Connie Hong, Somerville, MA (US); John Blankenship, Acton, MA (US); Brian Holmberg, Somerville, MA (US); Chonghui Zhang, Cambridge, MA (US); Dexiu Bu, Melrose, MA (US); Andrew Patrick Price, Cambridge, MA (US); Xu Zhu, Cambridge, MA (US); Andrew Marc Stein, Cambridge, MA (US); Attilio Bondanza, Basel (CH)

(73) Assignee: Novartis AG, Basel (CH)

( * ) Notice: Subject to any disclaimer, the term of this patent is extended or adjusted under 35 U.S.C. 154(b) by 1423 days.

(21) Appl. No.: 17/271,430

(22) PCT Filed: Aug. 30, 2019

(86) PCT No.: PCT/US2019/049127
§ 371 (c)(1),
(2) Date: Feb. 25, 2021

(87) PCT Pub. No.: WO2020/047452
PCT Pub. Date: Mar. 5, 2020

(65) Prior Publication Data

US 2022/0364055 A1 Nov. 17, 2022

Related U.S. Application Data

(60) Provisional application No. 62/858,482, filed on Jun. 7, 2019, provisional application No. 62/773,679, filed
(Continued)

(51) Int. Cl.
*C12N 5/0783* (2010.01)
*A61K 31/519* (2006.01)
(Continued)

(52) U.S. Cl.
CPC ...... *C07K 14/70517* (2013.01); *A61K 31/519* (2013.01); *A61K 38/2093* (2013.01); *A61K 40/11* (2025.01); *A61K 40/31* (2025.01); *A61K 40/4211* (2025.01); *A61K 40/4215* (2025.01); *C07K 14/70578* (2013.01); *C07K 16/2809* (2013.01); *C07K 16/2878* (2013.01); *C07K 16/2887* (2013.01); *C12N 5/0636* (2013.01); *C12N 5/0638* (2013.01); *A61K 2239/31* (2023.05); *A61K 2239/38* (2023.05); *C07K 2317/53* (2013.01); *C07K 2319/02* (2013.01); *C07K 2319/03* (2013.01); *C12N 2501/2315* (2013.01)

(58) Field of Classification Search
CPC ............ A61K 38/2093; A61K 39/4611; A61K 39/4631; C07K 16/2809; C07K 2317/53; C07K 2317/622; C07K 14/7051; C12N 5/0636; C12N 2501/2315; C12N 2501/2302; C12N 2501/505; C12N 2501/515; C12N 2501/2306; C12N 2501/2307; C12N 2501/2321; G01N 33/56972
See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |

(Continued)

FOREIGN PATENT DOCUMENTS

| | | | |
|---|---|---|---|
| CN | 107384963 | A | 11/2017 |
| EP | 0574512 | A1 | 12/1993 |

(Continued)

OTHER PUBLICATIONS

Redmond, P., Grimes, T.C., McDonnell, R., Boland, F., Hughes, C. and Fahey, T., 2018. Impact of medication reconciliation for improving transitions of care. Cochrane Database of Systematic Reviews, (8). (Year: 2018).*

(Continued)

*Primary Examiner* — Jeremy C Flinders
*Assistant Examiner* — Masudur Rahman
(74) *Attorney, Agent, or Firm* — K&L Gates LLP

(57) ABSTRACT

The present disclosure pertains to methods of making immune effector cells (for example, T cells or NK cells) that express a chimeric antigen receptor (CAR), and compositions generated by such methods. Also disclosed herein are methods of using such compositions for treating a disease, for example, cancer, in a subject.

38 Claims, 118 Drawing Sheets

Specification includes a Sequence Listing.

Related U.S. Application Data on Nov. 30, 2018, provisional application No. 62/726,155, filed on Aug. 31, 2018.

(51) Int. Cl.

| | |
|---|---|
| ***A61K 35/17*** | (2025.01) |
| ***A61K 38/20*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 16/28*** | (2006.01) |

(56) References Cited

U.S. PATENT DOCUMENTS 5,712,149 A 1/1998 Roberts
5,858,358 A 1/1999 June et al.
5,874,240 A 2/1999 Ni et al.
5,883,223 A 3/1999 Gray
5,906,936 A 5/1999 Eshhar et al.
6,103,521 A 8/2000 Capon et al.
6,319,494 B1 11/2001 Capon et al.
6,352,694 B1 3/2002 June et al.
6,355,779 B1 3/2002 Goodwin et al.
6,410,319 B1 6/2002 Raubitschek et al.
6,534,055 B1 3/2003 June et al.
6,569,997 B1 5/2003 Kwon
6,692,964 B1 2/2004 June et al.
6,797,514 B2 9/2004 Berenson et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
7,049,136 B2 5/2006 Seed et al.
7,052,906 B1 5/2006 Lawson et al.
7,067,318 B2 6/2006 June et al.
7,070,995 B2 7/2006 Jensen
7,144,575 B2 12/2006 June et al.
7,172,869 B2 2/2007 June et al.
7,175,843 B2 2/2007 June et al.
7,232,566 B2 6/2007 June et al.
7,265,209 B2 9/2007 Jensen
7,319,143 B2 1/2008 Gross et al.
7,320,787 B2 1/2008 Seed et al.
7,446,190 B2 11/2008 Sadelain et al.
7,446,191 B2 11/2008 Jensen
7,514,537 B2 4/2009 Jensen
7,638,326 B2 12/2009 June et al.
7,741,465 B1 6/2010 Eshhar et al.
7,745,140 B2 6/2010 June et al.
7,754,482 B2 7/2010 Riley et al.
7,994,298 B2 8/2011 Zhang et al.
8,211,422 B2 7/2012 Eshhar et al.
8,252,914 B2 8/2012 Zhang et al.
8,389,282 B2 3/2013 Sadelain et al.
8,399,645 B2 3/2013 Campana et al.
8,465,743 B2 6/2013 Rosenberg et al.
8,637,307 B2 1/2014 June et al.
8,679,492 B2 * 3/2014 Blein ...................... A61P 43/00
435/328
8,722,400 B2 5/2014 Riley et al.
8,906,682 B2 12/2014 June et al.
8,911,993 B2 12/2014 June et al.
8,916,381 B1 12/2014 June et al.
8,975,071 B1 3/2015 June et al.
9,101,584 B2 8/2015 June et al.
9,102,760 B2 8/2015 June et al.
9,102,761 B2 8/2015 June et al.
9,394,368 B2 7/2016 Brogdon et al.
9,499,629 B2 * 11/2016 June ................. C07K 14/70521
9,573,988 B2 2/2017 Brogdon et al.
9,745,368 B2 8/2017 Milone et al.
9,777,061 B2 10/2017 Ebersbach et al.
9,815,901 B2 11/2017 Brogdon et al.
10,287,354 B2 5/2019 Brogdon et al.
2003/0060444 A1 3/2003 Finney et al.
2003/0077249 A1 4/2003 Bebbington et al.
2003/0147869 A1 8/2003 Riley et al.
2003/0148982 A1 8/2003 Brenner et al.
2003/0224520 A1 12/2003 June et al.
2004/0038886 A1 2/2004 Finney et al.
2004/0043401 A1 3/2004 Sadelain et al.
2004/0101519 A1 5/2004 June et al.
2004/0110290 A1 6/2004 June et al.
2005/0113564 A1 5/2005 Campana et al.
2005/0129671 A1 6/2005 Cooper et al.
2006/0034810 A1 2/2006 Riley et al.
2006/0121005 A1 6/2006 Berenson et al.
2007/0036773 A1 2/2007 Cooper et al.
2008/0131415 A1 6/2008 Riddell et al.
2009/0257994 A1 10/2009 Jensen
2010/0261269 A1 10/2010 June et al.
2011/0052554 A1 3/2011 Zakrzewski et al.
2011/0262467 A1 10/2011 Riley et al.
2012/0148552 A1 6/2012 Jensen
2012/0321667 A1 12/2012 Sentman
2013/0071409 A1 3/2013 Riley et al.
2013/0071414 A1 3/2013 Dotti et al.
2013/0149337 A1 6/2013 Cooper et al.
2013/0155909 A1 6/2013 Jackson et al.
2013/0266551 A1 * 10/2013 Campana ....... A61K 39/464412
435/328
2013/0287748 A1 10/2013 June et al.
2013/0288368 A1 10/2013 June et al.
2013/0309258 A1 11/2013 June et al.
2014/0050708 A1 2/2014 Powell et al.
2014/0099309 A1 4/2014 Powell, Jr. et al.
2014/0099340 A1 4/2014 June et al.
2014/0106449 A1 4/2014 June et al.
2014/0186947 A1 7/2014 June et al.
2014/0212446 A1 7/2014 Riley et al.
2014/0219975 A1 8/2014 June et al.
2014/0227237 A1 8/2014 June et al.
2014/0271635 A1 9/2014 Brogdon et al.
2014/0322169 A1 10/2014 Harper et al.
2014/0322183 A1 10/2014 Milone et al.
2014/0322212 A1 10/2014 Brogdon et al.
2014/0322275 A1 10/2014 Brogdon et al.
2014/0370017 A1 12/2014 June et al.
2014/0370045 A1 12/2014 June et al.
2015/0017141 A1 1/2015 June et al.
2015/0024482 A1 1/2015 Frigault et al.
2015/0050729 A1 2/2015 June et al.
2015/0093822 A1 4/2015 June et al.
2015/0099299 A1 4/2015 June et al.
2015/0118202 A1 4/2015 June et al.
2015/0140019 A1 5/2015 June et al.
2015/0190428 A1 7/2015 June et al.
2015/0202286 A1 7/2015 June et al.
2015/0283178 A1 10/2015 June et al.
2015/0290244 A1 10/2015 June et al.
2015/0342994 A1 12/2015 Riley et al.
2016/0046724 A1 2/2016 Brogdon et al.
2016/0051651 A1 2/2016 Brogdon et al.
2016/0068601 A1 3/2016 Brogdon et al.
2016/0096892 A1 4/2016 Brogdon et al.
2016/0185861 A1 6/2016 Bedoya et al.
2016/0311907 A1 10/2016 Brogdon et al.
2016/0311917 A1 10/2016 Beatty et al.
2016/0340406 A1 11/2016 Zhao et al.
2016/0362472 A1 12/2016 Bitter et al.
2017/0008963 A1 1/2017 Brogdon et al.
2017/0081411 A1 3/2017 Engels et al.
2017/0137783 A1 5/2017 Bedoya et al.
2017/0183415 A1 6/2017 Brogdon et al.
2017/0209492 A1 7/2017 June et al.
2017/0211055 A1 7/2017 Brogdon et al.
2017/0226495 A1 8/2017 Guimaraes
2017/0239294 A1 8/2017 Thomas-Tikhonenko et al.
2017/0260268 A1 9/2017 Beatty et al.
2017/0274014 A1 9/2017 Brogdon et al.
2017/0306416 A1 10/2017 Bedoya et al.

(56) References Cited

U.S. PATENT DOCUMENTS

2017/0335281 A1 11/2017 Loew et al.
2018/0022795 A1 1/2018 Milone et al.
2018/0044423 A1 2/2018 Ebersbach et al.
2018/0044424 A1 2/2018 June et al.
2018/0118834 A1 5/2018 Brogdon et al.
2018/0125892 A1 5/2018 Brannetti et al.
2018/0133296 A1 5/2018 Barrett et al.
2018/0140602 A1 5/2018 Angst et al.
2018/0230193 A1 8/2018 Loew et al.
2018/0252727 A1 9/2018 Garfall et al.
2018/0258149 A1 9/2018 Motz et al.
2018/0298068 A1 10/2018 Albelda
2018/0312595 A1 11/2018 Brogdon et al.
2019/0000880 A1 1/2019 Motz et al.
2019/0000944 A1 1/2019 Brogdon et al.
2019/0135894 A1 5/2019 Ma et al.
2019/0135940 A1 5/2019 Brogdon et al.
2019/0151365 A1 5/2019 Anak et al.
2019/0153061 A1 5/2019 Brogdon et al.
2019/0161542 A1 5/2019 Gill et al.
2019/0263914 A1 8/2019 Brogdon et al.
2019/0269727 A1 9/2019 Fachin et al.
2019/0292238 A1 9/2019 Bitter et al.
2019/0292257 A1 9/2019 Bedoya et al.
2019/0298715 A1 10/2019 Motz et al.
2019/0330356 A1 10/2019 Brogdon et al.
2019/0336504 A1 11/2019 Gill et al.
2019/0375815 A1 12/2019 Engels et al.
2019/0382500 A1 12/2019 Abujoub et al.
2019/0388471 A1 12/2019 June et al.
2019/0389928 A1 12/2019 Posey et al.
2020/0048359 A1 2/2020 Albelda et al.
2020/0055948 A1 2/2020 Daley et al.
2020/0061113 A1 2/2020 Kassim et al.
2020/0085869 A1 3/2020 Schuster et al.
2020/0087376 A1 3/2020 Fraietta et al.
2020/0113941 A1 4/2020 Brannetti et al.
2020/0179511 A1 6/2020 Daley et al.
2020/0215171 A1 7/2020 Brogdon et al.
2020/0281973 A1 9/2020 Dranoff
2020/0283729 A1 9/2020 Loew et al.
2020/0291354 A1 9/2020 Johnson et al.
2020/0339704 A1 10/2020 Bradner et al.
2020/0360431 A1 11/2020 Garfall et al.
2020/0370012 A1 11/2020 Fraietta et al.
2020/0371091 A1 11/2020 Pruteanu-Malinici et al.
2020/0399383 A1 12/2020 Scholler et al.
2021/0002377 A1 1/2021 Brogdon et al.
2021/0047405 A1 2/2021 Nobles et al.
2021/0079073 A1 3/2021 Milone et al.
2021/0087279 A1 3/2021 Engels et al.
2021/0139595 A1 5/2021 Ebersbach et al.
2021/0171909 A1 6/2021 Golovina
2021/0172020 A1 6/2021 Bedoya et al.
2021/0177896 A1 6/2021 Porter et al.
2021/0177900 A1 6/2021 Engels et al.
2021/0213063 A1 7/2021 Isaacs et al.
2021/0220404 A1 7/2021 Abujoub et al.
2021/0246423 A1 8/2021 Bedoya et al.
2021/0284752 A1 9/2021 Brogdon et al.
2021/0317183 A1 10/2021 Zhao et al.
2021/0347851 A1 11/2021 Isaacs et al.
2021/0396739 A1 12/2021 Pruteanu-Malinici et al.
2022/0047633 A1 2/2022 Grupp
2022/0064316 A1 3/2022 Brogdon et al.
2022/0089750 A1 3/2022 June et al.
2022/0152150 A1 5/2022 Koshy et al.
2022/0168389 A1 6/2022 Ghassemi et al.
2022/0195010 A1 6/2022 Bitter et al.
2022/0251152 A1 8/2022 Carbonneau et al.
2022/0364055 A1 11/2022 Treanor et al.
2022/0387486 A1 12/2022 Brannetti et al.
2023/0026049 A1 1/2023 Brogdon et al.
2023/0071283 A1 3/2023 Golosov et al.
2023/0074800 A1 3/2023 Berger et al.
2023/0111593 A1 4/2023 Schuster et al.
2023/0139800 A1 5/2023 Motz et al.
2023/0174933 A1 6/2023 Brogdon et al.
2023/0183368 A1 6/2023 Abujoub et al.
2023/0220090 A1 7/2023 Brogdon et al.
2023/0250179 A1 8/2023 Abujoub et al.
2023/0256017 A1 8/2023 Brogdon et al.
2023/0295296 A1 9/2023 Bedoya et al.
2023/0302155 A1 9/2023 Koshy et al.
2023/0312677 A1 10/2023 Posey et al.
2023/0332104 A1 10/2023 Estevez Silva et al.
2023/0357717 A1 11/2023 Johnson et al.
2023/0374105 A1 11/2023 Bitter et al.
2023/0416390 A1 12/2023 Abujoub et al.
2024/0024360 A1 1/2024 Fachin et al.
2024/0033358 A1 2/2024 Chadbourne et al.
2024/0083968 A1 3/2024 Loew et al.
2024/0139244 A1 5/2024 Dranoff
2024/0238396 A1 7/2024 Brogdon et al.
2024/0252538 A1 8/2024 Brannetti et al.
2024/0288444 A1 8/2024 Garfall et al.
2024/0343783 A1 10/2024 Milone et al.
2024/0384007 A1 11/2024 Bradner et al.
2024/0390492 A1 11/2024 Engels et al.
2024/0398913 A1 12/2024 Barrett et al.

FOREIGN PATENT DOCUMENTS

EP 0871495 A1 10/1998
EP 1226244 A2 7/2002
EP 2711418 B1 8/2017
WO 1992015322 A1 9/1992
WO 199530014 A1 11/1995
WO 9623814 A1 8/1996
WO 9624671 A1 8/1996
WO 1997015669 A1 5/1997
WO 9723613 A2 7/1997
WO 9818809 A1 5/1998
WO 9900494 A2 1/1999
WO 9957268 A1 11/1999
WO 0014257 A1 3/2000
WO 0132709 A2 5/2001
WO 2002033101 A1 4/2002
WO 02077029 A2 10/2002
WO 02088334 A1 11/2002
WO 2003057171 A2 7/2003
WO 2005019429 A2 3/2005
WO 2005044996 A2 5/2005
WO 2005/118788 A2 12/2005
WO 2006060878 A1 6/2006
WO 2008045437 A2 4/2008
WO 2010085660 A2 7/2010
WO 2011059836 A2 5/2011
WO 2011097477 A1 8/2011
WO 2012058460 A2 5/2012
WO 2012079000 A1 6/2012
WO 2012082841 A2 6/2012
WO 2012/099973 A2 7/2012
WO 2012127464 A2 9/2012
WO 2012129514 A1 9/2012
WO 2012135854 A2 10/2012
WO 2012138858 A1 10/2012
WO 2013019615 A2 2/2013
WO 2013033626 A2 3/2013
WO 2013040371 A2 3/2013
WO 2013040557 A2 3/2013
WO 2013059593 A1 4/2013
WO 2013/126712 A1 8/2013
WO 2013126729 A1 8/2013
WO 2013126733 A1 8/2013
WO 2014/011984 A1 1/2014
WO 2014/011987 A1 1/2014
WO 2014/011993 A2 1/2014
WO 2014/012001 A2 1/2014
WO 2014011988 A2 1/2014
WO 2014011996 A1 1/2014
WO 2014031687 A1 2/2014
WO 2014039513 A2 3/2014
WO 2014/055442 A2 4/2014

(56) References Cited

FOREIGN PATENT DOCUMENTS

| | | | |
|---|---|---|---|
| WO | 2014048920 | A1 | 4/2014 |
| WO | 2014055657 | A1 | 4/2014 |
| WO | 2014/066527 | A2 | 5/2014 |
| WO | 2014130635 | A1 | 8/2014 |
| WO | 2014/145252 | A2 | 9/2014 |
| WO | 2014186469 | A2 | 11/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |
| WO | 2015162211 | A1 | 10/2015 |
| WO | 2015164745 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |
| WO | 2016100236 | A2 | 6/2016 |
| WO | 2016109410 | A2 | 7/2016 |
| WO | 2017068421 | A1 | 4/2017 |
| WO | 2017/117112 | A1 | 7/2017 |
| WO | 2017165245 | A2 | 9/2017 |
| WO | 2018067992 | A1 | 4/2018 |
| WO | 2018106732 | A1 | 6/2018 |
| WO | 2019074973 | A2 | 4/2019 |
| WO | 2019079569 | A1 | 4/2019 |
| WO | 2019089592 | A1 | 5/2019 |
| WO | 2020033927 | A2 | 2/2020 |
| WO | 2020047452 | A2 | 3/2020 |
| WO | 2020114491 | A1 | 8/2020 |
| WO | 2021108661 | A2 | 6/2021 |
| WO | 2021173985 | A2 | 9/2021 |
| WO | 2021173995 | A2 | 9/2021 |
| WO | 2021260064 | A1 | 12/2021 |
| WO | 2022040586 | A2 | 2/2022 |

OTHER PUBLICATIONS

Shirasu et al., "Functional Design of Chimeric T-Cell Antigen Receptors for Adoptive Immunotherapy of Cancer: Architecture and Outcomes," AntiCancer Res. 32: 2377-2384 (2012).
Smith et al., "Ex vivo expansion of human T cells for adoptive immunotherapy using the novel Xeno-free CTSTM Immune Cell Serum Replacement" Clinical & Translational Immunology (2015) vol. 4, No. 1, e31, pp. 1-10.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Wang et al. "Clinical manufacturing of CAR T cells: foundation of a promising therapy" Molecular Therapy—Oncolytics (2016) vol. 3, No. 16015, pp. 1-7.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zhu et al. "Closed-system manufacturing of CD19 and dual-targeted CD20/19 chimeric antigen receptor T cells using the CliniMACS Prodigy device at an academic medical center" Cytotherapy (2018) vol. 20, pp. 394-406.
Zufferey et al., "Multiply attenuated lentiviral vector achieves efficient gene delivery in vivo" Nature Biotechnology (1997) vol. 15 pp. 871-876.
Baeksgaard & Sorensen, "Acute tumor lysis syndrome in solid tumors—a case report and review of the literature" Cancer Chemotherapy Pharmacology (2003) vol. 51 pp. 187-192.
Berg et al. "Selective Expansion of a Peripheral Blood CD81 Memory T Cell Subset Expressing Both Granzyme B and L-Selectin During Primary Viral Infection in Renal Allograft Recipients" Transplant Proc. (1998) vol. 30, No. 8, pp. 3975-3977.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Cohen et al., "B cell maturation antigen-specific CAR T cells are clinically active in multiple myeloma" J Clin Invest (2019) vol. 129, No. 6, pp. 2210-2221.
Davila et al. "B Cell Aplasia In a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

(56) References Cited

OTHER PUBLICATIONS

Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Fraietta et al., "Determinants of response and resistance to CD19 chimeric antigen receptor (CAR) T cell therapy of chronic lymphocytic leukemia" Nat Med (2018) vol. 24, No. 5, pp. 563-571.
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Galla et al., "Retroviral Pseudotransduction for Targeted Cell Manipulation" Mol Cell (2004) vol. 16, No. 2, pp. 309-315.
Garland et al. "The use of Teflon cell culture bags to expand functionally active CD8q cytotoxic T lymphocytes" Journal of Immunological Methods (1999) vol. 227, pp. 53-56.
Gattinoni et al. "Acquisition of full effector function in vitro paradoxically impairs the in vivo antitumor efficacy of adoptively transferred CD8+ T cells" The Journal of Clinical Investigation (2005) vol. 115, No. 6, pp. 1616-1626.
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Giavridis et al."CAR T cell-induced cytokine release syndrome is mediated by macrophages and abated by IL-1 blockade" Nat Med (2018) vol. 24, No. 6, pp. 731-738.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Haanen et al., "Selective Expansion of Cross-reactive CD81 Memory T Cells by Viral Variants" J. Exp. Med. (1999) vol. 190, No. 9, pp. 1319-1328.
Haas et al., "Critical factors influencing stable transduction of human CD34(+) cells with HIV-1-derived lentiviral vectors" Mol Ther (2000) vol. 2, No. 1, pp. 71-80.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:zeta-CHIMERA" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Preliminary Report on Patentability for International Application No. PCT/US2019/049127 dated Mar. 2, 2021.
International Search Report and Written Opinion for International Application No. PCT/US2019/049127 dated March 9. 2020.
International Search Report from PCT/US2011/064191 dated Jan. 5, 2012.
Invitation to Pay Additional Fees and Partial Search Report for International Application No. PCT/US2019/049127 dated Jan. 14, 2020.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-Of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously

(56) References Cited

OTHER PUBLICATIONS

Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Lu et al. "A Rapid Cell Expansion Process for Production of Engineered Autologous CART-T Cell Therapies" Human Gene Therapy Methods (2016) vol. 27, No. 6, pp. 209-218.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Mueller et al: "Cellular kinetics of CTL019 in relapsed/refractory B-cell acute lymphoblastic leukemia and chronic lymphocytic leukemia" Blood (2017) vol. 130, No. 21, pp. 2317-2325.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Neurauter et al. "Cell Isolation and Expansion Using Dynabeads" Adv Biochem Engin/Biotechnol (2007) vol. 106, pp. 41-73.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Norelli et al."Monocyte-derived IL-1 and IL-6 are differentially required for cytokine-release syndrome and neurotoxicity due to CAR T cells" Nat Med. (2018) vol. 24, No. 6, pp. 739-748.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Brunner et al., "Cytotoxic T cells: Double-barreled shot guns," Nature Medicine (1999) vol. 5, No. 1, p. 20.
Dondelinger et al., "Understanding the Significance and Implications of Antibody Numbering and Antigen-Binding Surface/Residue Definition," Frontiers in Immunology (2018) vol. 9, Article 2278, 15 pages.
Drechsel et al.: "Towards Automated Manufacturing of Clinical Scale Gene-Modified T Cells", Molecular Therapy 22, Supplement 1, May 1, 2014 (May 10, 2014), p. S286, XP055681179, Retrieved from cell.com/molecular-therapy-family/molecular-therapy/fulltext/S1525-0016(16)35752-5 [retrieved on Mar. 31, 2020].
Ghassemi et al., "Reducing Ex Vivo Culture Improves the Antileukemic Activity of Chimeric Antigen Receptor (CAR) T Cells," Cancer Immunology Research (2018) vol. 6, No. 9, pp. 1100-1109.
Husain et al: "Expanding the Boundaries of Biotherapeutics with Bispecific Antibodies", Biodrugs, vol. 32, No. 5, Aug. 21, 2018 (Aug. 21, 2018), pp. 441-464.
International Search Report and Written Opinion issued in International Application No. PCT/IB2022/057799, mailed Jan. 31, 2023, 15 pages.
International Search Report and Written Opinion issued in PCT/US2021/019889 mailed Sep. 16, 2021, 19 pages.
Roitt et al., "Immunology," Moscow, "Mir" (2000) pp. 4-6. Russian.
Sela-Culang et al., "The structural basis of antibody-antigen recognition," Frontiers in Immunology (2013) vol. 4, Article 302, 13 pages.
Ghassemi et al., "Simple, 1-Day Manufacturing of Quiescent Chimeric Antigen Receptor T Cells for Adoptive Immunotherapy," Blood (2019) vol. 134, p. 4436, Abstract 703.

(56) References Cited

OTHER PUBLICATIONS

Golubovskaya et al., "Different Subsets of T Cells, Memory, Effector Functions, and CAR-T Immunotherapy," Cancerts (2016) vol. 8, No. 3, Article 8030036, 12 pages.
International Search Report and Written Opinion issued in International Application No. PCT/US2021/019904, mailed Nov. 2, 2021, 33 pages.
Stock et al., "Optimizing Manufacturing Protocols of Chimeric Antigen Receptor T Cells for Improved Anticancer Immunotherapy," International Journal of Molecular Sciences (2019) vol. 20, No. 24, p. 6223.
Vormittag et al., "A guide to manufacturing CAR T cell therapies," Current Opinion in Biotechnology (2018) vol. 53, pp. 164-181.

* cited by examiner

No changes in Naive phenotype.
Less Central memory observed after 24hrs

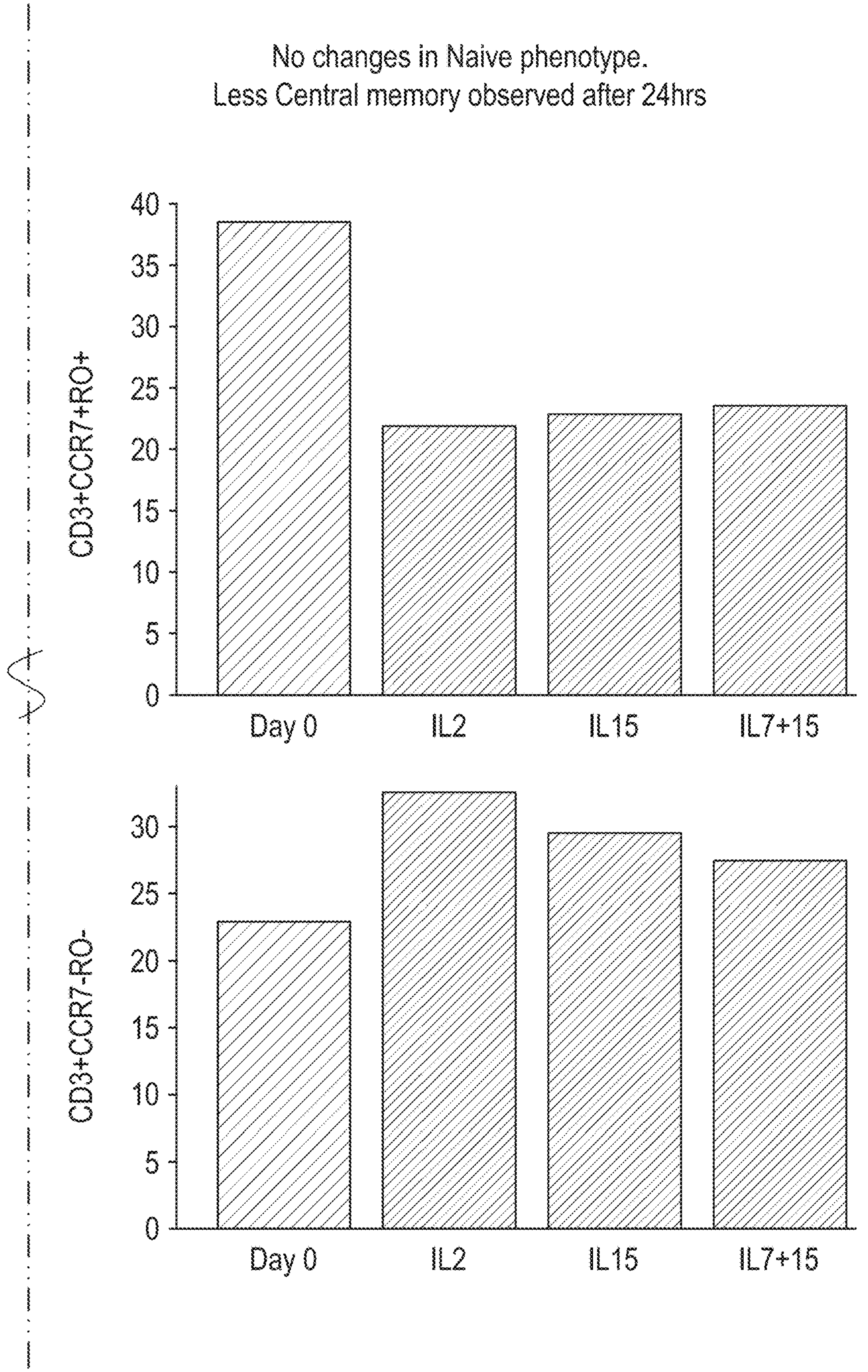
FIG. 1H Cont.

CD3+ Naive phenotype maintained after 24hrs in culture in all conditions
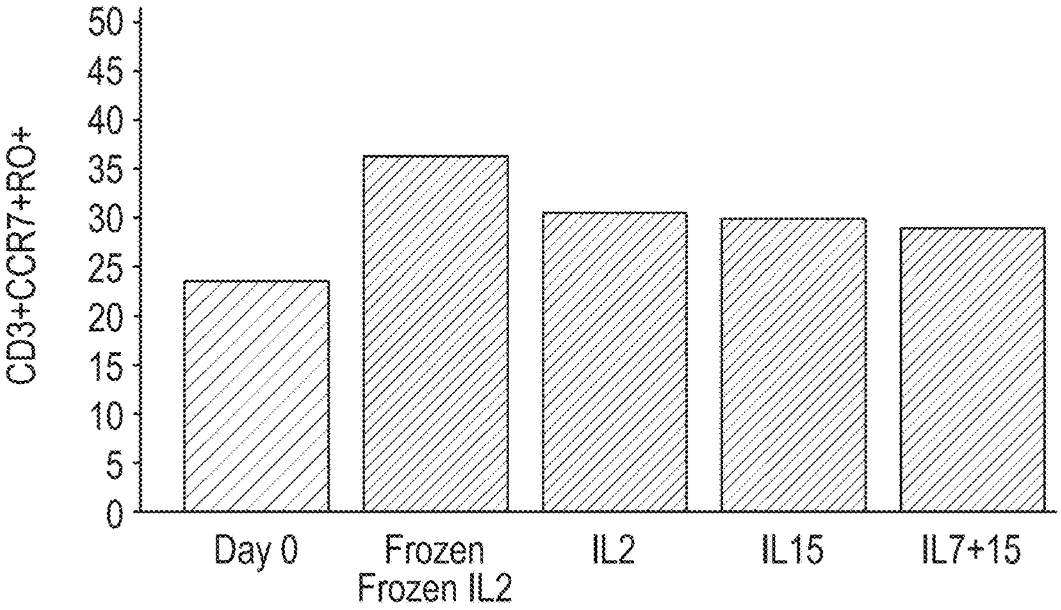
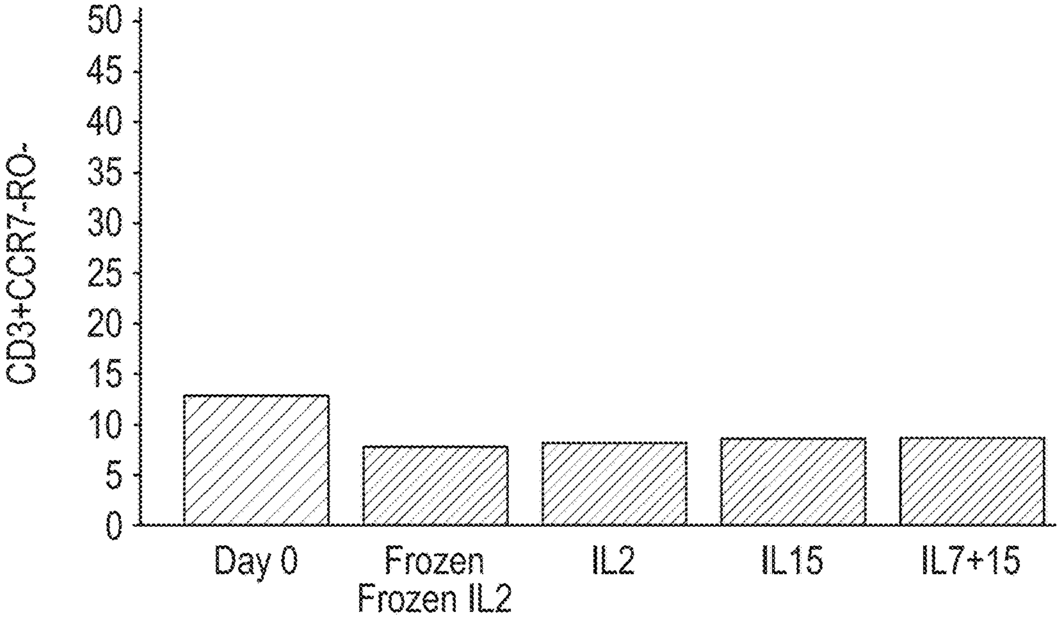
Fig. 1I Cont.

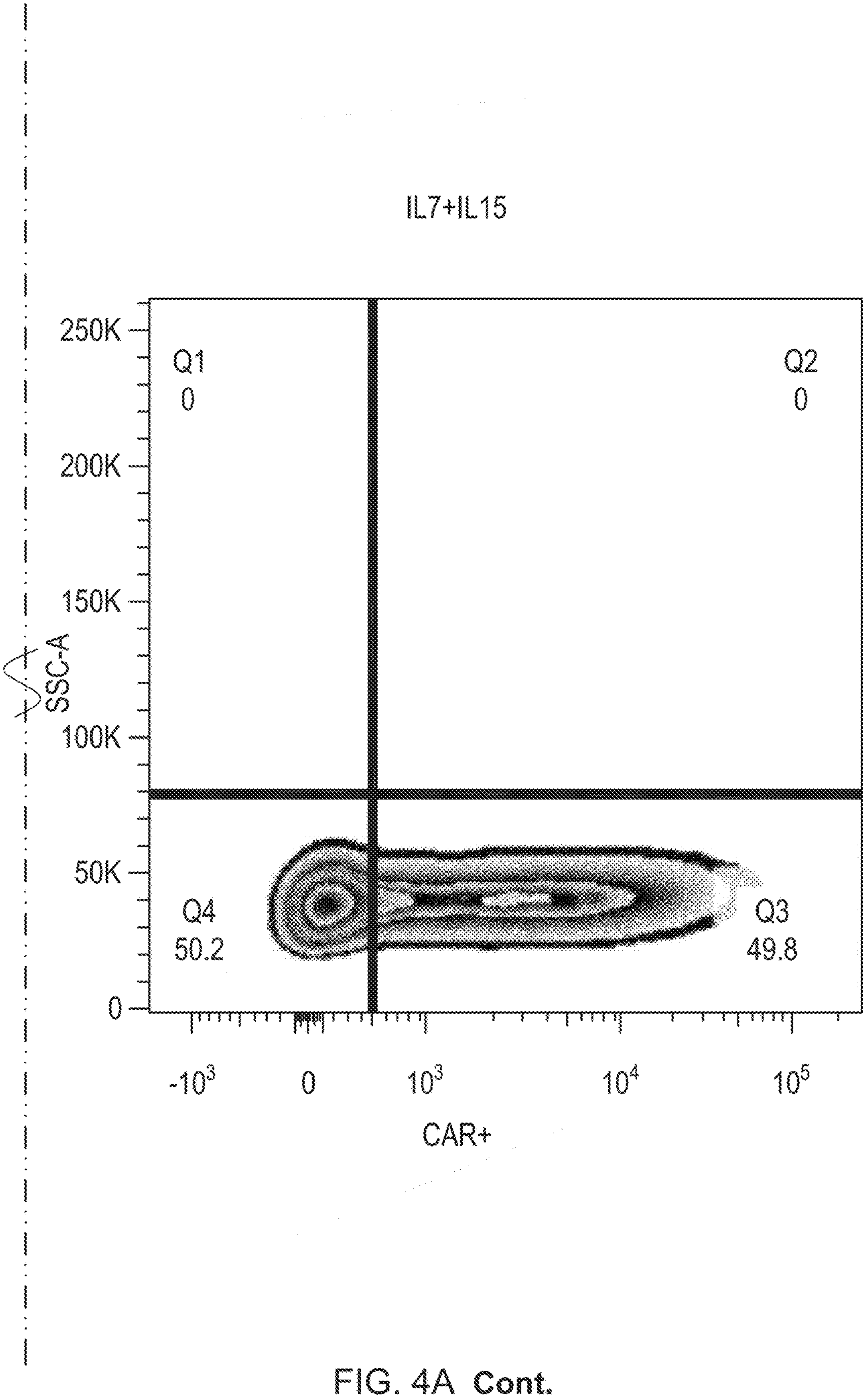
FIG. 4A Cont.

FACS Panel

| Stain | Dilution | Voltage |
|---|---|---|
| FSC | | 430 |
| SSC | | 255 |
| CD3 BUV395 | 1/200 | 330 |
| CD4 PerCP Cy5.5 | 1/100 | 430 |
| rBCMA Alexa 647 | 1/380 (3ug/ml) | 440 |
| CD8 APC H7 | 1/200 | 490 |
| Live/Dead Aqua | 1/500 | 400 |

FIG. 28D

| | LKPK | Input | TM-UTD | TM-CD19 CAR | | ARM-UTD | ARM-CD19 CAR | |
|---|---|---|---|---|---|---|---|---|
| | | | | bulk | $CAR^+$ | | bulk | $CAR^+$ |
| Teff | 0.8 | 1.4 | 0.8 | 0.9 | 0.2 | 3.8 | 3.2 | 0.8 |
| Tem | 8.7 | 10.7 | 17.3 | 13.7 | 18.0 | 11.1 | 8.1 | 6.2 |
| Tcm | 59.5 | 59.4 | 67.4 | 68.6 | 77.3 | 37.2 | 43.6 | 55.5 |
| Tn | 30.9 | 28.6 | 14.6 | 16.9 | 4.5 | 48.0 | 45.1 | 37.5 |

The TM process mainly resulted in central-memory T cells (TCM) (CD45RO+/CCR7+), while the naive-like T cell population is almost gone in the CAR+T cells with TM process

TM product

ARM processed BCMA CAR-T cells demonstrates BCMA-specific activation and secretes higher levels of IL2 and IFNg ARM products TM products Medians:
D1: -0.084
D9: 0.035
Input: -0.1

Medians:
D1: -0.082
D9: 0.087
Input: -0.071

Medians:
D1: -0.062
D9: 0.14
Input: -0.081

Medians:
D1: 0.019
D9: 0.11
Input: -0.096

Medians:
D1: 0.066
D9: 0.11
Input: -0.09

1 Historical apheresis collection may be used
2 Lymphodepletion (LD) of Fludarabine/Cyclophosphamide, delivered over 3 continuous days within the Day -8 to Day -2 period prior to anti-BCMA CAR-T cell administration
3 Long term follow-up protocol conducted under a separate protocol per Health Authority guidance.

| Post viral addition Samples | 24h | 48h | 72h | 96h | 168h |
|---|---|---|---|---|---|
| UTD | 0.45% | 0.29% | 0.49% | 0.32% | 0.6% |
| ARM-BCMA CAR | 1.84% | 5.06% | 11.4% | 15% | 16.5% |
| ARM-BCMA CAR+ 30μM AZT | 1.97% | 0.43% | 0.3% | 0.36% | 1.12% |
| ARM-BCMA CAR+ 100μM AZT | 1.61% | 0.44% | 0.33% | 0.5% | 1.3% |

BCMA-Fc-Alexa647

Outline of xenograft efficacy study to test ARM-BCMA CAR

Day 0
Tumor inoculation
(1×10⁶ KMS11 i.v.)

Day 7
Monitor BLI for
tumor burden;
Randomize
(1-2×10⁶ p/s)

Day 8
CAR-T
infusion (i.v.)

Day 31 + 32
Takedown:
Bone marrow +
Spleen for
flow cytometry 2x week BLI+BW
Days 2, 7, 14, 21 post CAR-T plasma for cytokine assay
1x week whole blood for flow cytometry

SEQUENCE LISTING

<160> NUMBER OF SEQ ID NOS: 309

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 2
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 3
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140
```

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys Met
225 230

<210> SEQ ID NO 4
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Arg Trp Pro Glu Ser Pro Lys Ala Gln Ala Ser Ser Val Pro Thr Ala
1 5 10 15

Gln Pro Gln Ala Glu Gly Ser Leu Ala Lys Ala Thr Thr Ala Pro Ala
20 25 30

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys
165 170 175

Leu Ser Leu Asn Leu Leu Ala Ser Ser Asp Pro Pro Glu Ala Ala Ser
180 185 190

Trp Leu Leu Cys Glu Val Ser Gly Phe Ser Pro Pro Asn Ile Leu Leu
195 200 205

Met Trp Leu Glu Asp Gln Arg Glu Val Asn Thr Ser Gly Phe Ala Pro
210 215 220

Ala Arg Pro Pro Pro Gln Pro Gly Ser Thr Thr Phe Trp Ala Trp Ser
225 230 235 240

Val Leu Arg Val Pro Ala Pro Pro Ser Pro Gln Pro Ala Thr Tyr Thr
245 250 255

-continued

```
Cys Val Val Ser His Glu Asp Ser Arg Thr Leu Leu Asn Ala Ser Arg
            260                 265                 270

Ser Leu Glu Val Ser Tyr Val Thr Asp His
        275                 280
```

<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

```
Gly Gly Gly Gly Ser Gly Gly Gly Gly Ser
1               5                   10
```

<210> SEQ ID NO 6
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 7
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 8
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
```

35 40 45

<210> SEQ ID NO 9
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 10
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 11
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
cgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184
```

<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12

```
atggccctgc ctgtgacagc cctgctgctg cctctggctc tgctgctgca tgccgctaga     60

ccc                                                                   63
```

<210> SEQ ID NO 13
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135
```

<210> SEQ ID NO 14
<211> LENGTH: 690
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 14
gagagcaagt acggccctcc ctgccccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 15
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 15
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgcccccca 480 cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 19
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 20
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180

```
gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 21
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 22
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
```

-continued

```
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370


<210> SEQ ID NO 23
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360

acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960
```

-continued

```
cgcggccggg accccgaaat gggcgggaag cctagaagaa agaaccctca ggaaggcctg     1020

tataacgagc tgcagaagga caagatggcc gaggcctact ccgaaattgg gatgaaggga     1080

gagcggcgga ggggaaaggg gcacgacggc ctgtaccaag gactgtccac cgccaccaag     1140

gacacatacg atgccctgca catgcaggcc cttccccctc gc                        1182
```

```
<210> SEQ ID NO 24
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
        130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
            195                 200                 205

Arg Gly Leu Asp Phe Ala Cys Asp Ile Tyr Ile Trp Ala Pro Leu Ala
        210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
                260                 265                 270

Pro Glu Glu Glu Glu Gly Gly Cys Glu Leu Arg Val Lys Phe Ser Arg
            275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320
```

```
Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Gly Gly Ser
1               5


<210> SEQ ID NO 26
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 1-6 'Gly Gly
      Gly Gly Ser' repeating units"

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Gly Gly Gly Ser Gly Gly Gly Gly Ser Gly Gly Gly Gly Ser Gly
1               5                   10                  15

Gly Gly Gly Ser
            20


<210> SEQ ID NO 28
<211> LENGTH: 15
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic peptide"

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 29

Gly Gly Gly Ser
1

<210> SEQ ID NO 30
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: misc_feature
<222> LOCATION: (1)..(5000)
<223> OTHER INFORMATION: /note="This sequence may encompass 50-5000
nucleotides"

<400> SEQUENCE: 30
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200

-continued aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 31
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 31
tttttttttt tttttttttt tttttttttt tttttttttt tttttttttt tttttttttt 60
tttttttttt tttttttttt tttttttttt tttttttttt 100

<210> SEQ ID NO 32
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: misc_feature
<222> LOCATION: (1)..(5000)
<223> OTHER INFORMATION: /note="This sequence may encompass 50-5000

-continued nucleotides"

<400> SEQUENCE: 32

```
tttttttttt tttttttttt tttttttttt tttttttttt tttttttttt tttttttttt     60
tttttttttt tttttttttt tttttttttt tttttttttt tttttttttt tttttttttt    120
tttttttttt tttttttttt tttttttttt tttttttttt tttttttttt tttttttttt    180
tttttttttt tttttttttt tttttttttt tttttttttt tttttttttt tttttttttt    240
tttttttttt tttttttttt tttttttttt tttttttttt tttttttttt tttttttttt    300
tttttttttt tttttttttt tttttttttt tttttttttt tttttttttt tttttttttt    360
tttttttttt tttttttttt tttttttttt tttttttttt tttttttttt tttttttttt    420
tttttttttt tttttttttt tttttttttt tttttttttt tttttttttt tttttttttt    480
tttttttttt tttttttttt tttttttttt tttttttttt tttttttttt tttttttttt    540
tttttttttt tttttttttt tttttttttt tttttttttt tttttttttt tttttttttt    600
tttttttttt tttttttttt tttttttttt tttttttttt tttttttttt tttttttttt    660
tttttttttt tttttttttt tttttttttt tttttttttt tttttttttt tttttttttt    720
tttttttttt tttttttttt tttttttttt tttttttttt tttttttttt tttttttttt    780
tttttttttt tttttttttt tttttttttt tttttttttt tttttttttt tttttttttt    840
tttttttttt tttttttttt tttttttttt tttttttttt tttttttttt tttttttttt    900
tttttttttt tttttttttt tttttttttt tttttttttt tttttttttt tttttttttt    960
tttttttttt tttttttttt tttttttttt tttttttttt tttttttttt tttttttttt   1020
tttttttttt tttttttttt tttttttttt tttttttttt tttttttttt tttttttttt   1080
tttttttttt tttttttttt tttttttttt tttttttttt tttttttttt tttttttttt   1140
tttttttttt tttttttttt tttttttttt tttttttttt tttttttttt tttttttttt   1200
tttttttttt tttttttttt tttttttttt tttttttttt tttttttttt tttttttttt   1260
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
```

-continued tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 33
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 100-5000 nucleotides"

<400> SEQUENCE: 33
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440

-continued aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840

-continued

```
aaaaaaaaaa aaaaaaaaaa aaaaaaaaaa aaaaaaaaaa aaaaaaaaaa aaaaaaaaaa   3900

aaaaaaaaaa aaaaaaaaaa aaaaaaaaaa aaaaaaaaaa aaaaaaaaaa aaaaaaaaaa   3960

aaaaaaaaaa aaaaaaaaaa aaaaaaaaaa aaaaaaaaaa aaaaaaaaaa aaaaaaaaaa   4020

aaaaaaaaaa aaaaaaaaaa aaaaaaaaaa aaaaaaaaaa aaaaaaaaaa aaaaaaaaaa   4080

aaaaaaaaaa aaaaaaaaaa aaaaaaaaaa aaaaaaaaaa aaaaaaaaaa aaaaaaaaaa   4140

aaaaaaaaaa aaaaaaaaaa aaaaaaaaaa aaaaaaaaaa aaaaaaaaaa aaaaaaaaaa   4200

aaaaaaaaaa aaaaaaaaaa aaaaaaaaaa aaaaaaaaaa aaaaaaaaaa aaaaaaaaaa   4260

aaaaaaaaaa aaaaaaaaaa aaaaaaaaaa aaaaaaaaaa aaaaaaaaaa aaaaaaaaaa   4320

aaaaaaaaaa aaaaaaaaaa aaaaaaaaaa aaaaaaaaaa aaaaaaaaaa aaaaaaaaaa   4380

aaaaaaaaaa aaaaaaaaaa aaaaaaaaaa aaaaaaaaaa aaaaaaaaaa aaaaaaaaaa   4440

aaaaaaaaaa aaaaaaaaaa aaaaaaaaaa aaaaaaaaaa aaaaaaaaaa aaaaaaaaaa   4500

aaaaaaaaaa aaaaaaaaaa aaaaaaaaaa aaaaaaaaaa aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa aaaaaaaaaa   4680

aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000
```

<210> SEQ ID NO 34
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(400)
<223> OTHER INFORMATION: /note="This sequence may encompass 100-400 nucleotides"

<400> SEQUENCE: 34

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

<210> SEQ ID NO 35
<211> LENGTH: 2000
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 35

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000
```

-continued

<210> SEQ ID NO 36
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 37
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 38
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Thr Lys Lys Lys Tyr Ser Ser Ser Val His Asp Pro Asn Gly Glu Tyr
1 5 10 15

Met Phe Met Arg Ala Val Asn Thr Ala Lys Lys Ser Arg Leu Thr Asp
20 25 30

Val Thr Leu
35

<210> SEQ ID NO 39
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39
acaaaaaaga agtattcatc cagtgtgcac gaccctaacg gtgaatacat gttcatgaga 60
gcagtgaaca cagccaaaaa atccagactc acagatgtga cccta 105

<210> SEQ ID NO 40
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40

ggtggcggag gttctggagg tgggggttcc                                        30


<210> SEQ ID NO 41
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 41

Gly Gly Gly Ser
1


<210> SEQ ID NO 42
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-10 'Gly
      Gly Gly Ser' repeating units"

<400> SEQUENCE: 42

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 43
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Ser Thr Ser Gly Ser Gly Lys Pro Gly Ser Gly Glu Gly Ser Thr
1               5                   10                  15

Lys Gly


<210> SEQ ID NO 44
<211> LENGTH: 5
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic peptide"

<400> SEQUENCE: 44

Ser Tyr Ala Met Ser
1 5

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 45

Ala Ile Ser Gly Ser Gly Gly Ser Thr Tyr Tyr Ala Asp Ser Val Lys
1 5 10 15

Gly

<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 46

Arg Glu Trp Val Pro Tyr Asp Val Ser Trp Tyr Phe Asp Tyr
1 5 10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 47

Gly Phe Thr Phe Ser Ser Tyr
1 5

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 48

Ser Gly Ser Gly Gly Ser
1 5

<210> SEQ ID NO 49
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 49

Gly Phe Thr Phe Ser Ser Tyr Ala
1 5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Ile Ser Gly Ser Gly Gly Ser Thr
1 5

<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

Ala Arg Arg Glu Trp Val Pro Tyr Asp Val Ser Trp Tyr Phe Asp Tyr
1 5 10 15

<210> SEQ ID NO 52
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Glu Trp Val Pro Tyr Asp Val Ser Trp Tyr Phe Asp Tyr
100 105 110

Trp Gly Gln Gly Thr Leu Val Thr Val Ser Ser
115 120

<210> SEQ ID NO 53
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 53
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tgggtgccct acgatgtcag ctggtacttc gactactggg gacagggcac tctcgtgact 360
gtgtcctcc 369

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 54

Arg Ala Ser Gln Ser Ile Ser Ser Tyr Leu Asn
1 5 10

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 55

Ala Ala Ser Ser Leu Gln Ser
1 5

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 56

Gln Gln Ser Tyr Ser Thr Pro Leu Thr
1 5

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 57

Ser Gln Ser Ile Ser Ser Tyr
1 5

<210> SEQ ID NO 58
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

```
Ala Ala Ser
1
```

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

```
Ser Tyr Ser Thr Pro Leu
1               5
```

<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

```
Gln Ser Ile Ser Ser Tyr
1               5
```

<210> SEQ ID NO 61
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 62
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gacattcaaa tgactcagtc cccgtcctcc ctctccgcct ccgtgggaga tcgcgtcacg 60
atcacgtgca gggccagcca gagcatctcc agctacctga actggtacca gcagaagcca 120
gggaaggcac cgaagctcct gatctacgcc gctagctcgc tgcagtccgg cgtcccttca 180
cggttctcgg gatcgggctc aggcaccgac ttcaccctga ccattagcag cctgcagccg 240
gaggacttcg cgacatacta ctgtcagcag tcatactcca cccctctgac cttcggccaa 300
gggaccaaag tggagatcaa g 321

<210> SEQ ID NO 63
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 64
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140
```

```
Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gln Gly Thr Lys Val Glu Ile Lys
                245                 250
```

<210> SEQ ID NO 65
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

```
gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300

tgggtgccct acgatgtcag ctggtacttc gactactggg gacagggcac tctcgtgact    360

gtgtcctccg gtggtggtgg atcggggggt ggtggttcgg gcggaggagg atctggagga    420

ggagggtcgg acattcaaat gactcagtcc ccgtcctccc tctccgcctc cgtgggagat    480

cgcgtcacga tcacgtgcag ggccagccag agcatctcca gctacctgaa ctggtaccag    540

cagaagccag ggaaggcacc gaagctcctg atctacgccg ctagctcgct gcagtccggc    600

gtcccttcac ggttctcggg atcgggctca ggcaccgact tcaccctgac cattagcagc    660

ctgcagccgg aggacttcgc gacatactac tgtcagcagt catactccac ccctctgacc    720

ttcggccaag ggaccaaagt ggagatcaag                                     750
```

<210> SEQ ID NO 66
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gln Gly Thr Lys Val Glu Ile Lys Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460
```

Leu His Met Gln Ala Leu Pro Pro Arg
465 470

<210> SEQ ID NO 67
<211> LENGTH: 1419
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tgggtgccct acgatgtcag ctggtacttc gactactggg gacagggcac tctcgtgact 360
gtgtcctccg gtggtggtgg atcggggggt ggtggttcgg gcggaggagg atctggagga 420
ggagggtcgg acattcaaat gactcagtcc ccgtcctccc tctccgcctc cgtgggagat 480
cgcgtcacga tcacgtgcag ggccagccag agcatctcca gctacctgaa ctggtaccag 540
cagaagccag ggaaggcacc gaagctcctg atctacgccg ctagctcgct gcagtccggc 600
gtcccttcac ggttctcggg atcgggctca ggcaccgact tcaccctgac cattagcagc 660
ctgcagccgg aggacttcgc gacatactac tgtcagcagt catactccac ccctctgacc 720
ttcggccaag ggaccaaagt ggagatcaag accactaccc cagcaccgag gccacccacc 780
ccggctccta ccatcgcctc ccagcctctg tccctgcgtc cggaggcatg tagacccgca 840
gctggtgggg ccgtgcatac ccggggtctt gacttcgcct gcgatatcta catttgggcc 900
cctctggctg gtacttgcgg ggtcctgctg ctttcactcg tgatcactct ttactgtaag 960
cgcggtcgga agaagctgct gtacatcttt aagcaaccct tcatgaggcc tgtgcagact 1020
actcaagagg aggacggctg ttcatgccgg ttcccagagg aggaggaagg cggctgcgaa 1080
ctgcgcgtga aattcagccg cagcgcagat gctccagcct accagcaggg gcagaaccag 1140
ctctacaacg aactcaatct tggtcggaga gaggagtacg acgtgctgga caagcggaga 1200
ggacgggacc cagaaatggg cgggaagccg cgcagaaaga atccccaaga gggcctgtac 1260
aacgagctcc aaaaggataa gatggcagaa gcctatagcg agattggtat gaaaggggaa 1320
cgcagaagag gcaaaggcca cgacggactg taccagggac tcagcaccgc caccaaggac 1380
acctatgacg ctcttcacat gcaggccctg ccgcctcgg 1419

<210> SEQ ID NO 68
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 68

Arg Glu Trp Trp Tyr Asp Asp Trp Tyr Leu Asp Tyr
1 5 10

<210> SEQ ID NO 69
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 69

```
Ala Arg Arg Glu Trp Trp Tyr Asp Asp Trp Tyr Leu Asp Tyr
1               5                   10
```

<210> SEQ ID NO 70
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Tyr Asp Asp Trp Tyr Leu Asp Tyr Trp Gly
            100                 105                 110

Gln Gly Thr Leu Val Thr Val Ser Ser
        115                 120
```

<210> SEQ ID NO 71
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 71

```
gaagtgcagt tgctggagtc aggcggagga ctggtgcagc ccggaggatc gcttcgcttg      60

agctgcgcag cctcaggctt taccttctcc tcctacgcca tgtcctgggt cagacaggct     120

cccgggaagg gactggaatg ggtgtccgcc attagcggtt ccggcggaag cacttactat     180

gccgactctg tgaagggccg cttcactatc tcccgggaca actccaagaa caccctgtat     240

ctccaaatga attccctgag ggccgaagat accgcggtgt actactgcgc tagacgggag     300

tggtggtacg acgattggta cctggactac tggggacagg gcactctcgt gactgtgtcc     360

tcc                                                                   363
```

<210> SEQ ID NO 72

<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Tyr Asp Asp Trp Tyr Leu Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys
                245
```

<210> SEQ ID NO 73
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 73

```
gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300
```

```
tggtggtacg acgattggta cctggactac tggggacagg gcactctcgt gactgtgtcc    360

tccggtggtg gtggatcggg gggtggtggt tcgggcggag gaggatctgg aggaggaggg    420

tcggacattc aaatgactca gtccccgtcc tccctctccg cctccgtggg agatcgcgtc    480

acgatcacgt gcagggccag ccagagcatc tccagctacc tgaactggta ccagcagaag    540

ccagggaagg caccgaagct cctgatctac gccgctagct cgctgcagtc cggcgtccct    600

tcacggttct cgggatcggg ctcaggcacc gacttcaccc tgaccattag cagcctgcag    660

ccggaggact tcgcgacata ctactgtcag cagtcatact ccacccctct gaccttcggc    720

caagggacca aagtggagat caag                                           744
```

```
<210> SEQ ID NO 74
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Tyr Asp Asp Trp Tyr Leu Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270
```

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 75
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tggtggtacg acgattggta cctggactac tggggacagg gcactctcgt gactgtgtcc 360
tccggtggtg gtggatcggg gggtggtggt tcgggcggag gaggatctgg aggaggaggg 420
tcggacattc aaatgactca gtccccgtcc tccctctccg cctccgtggg agatcgcgtc 480
acgatcacgt gcagggccag ccagagcatc tccagctacc tgaactggta ccagcagaag 540
ccagggaagg caccgaagct cctgatctac gccgctagct cgctgcagtc cggcgtccct 600
tcacggttct cgggatcggg ctcaggcacc gacttcaccc tgaccattag cagcctgcag 660
ccggaggact tcgcgacata ctactgtcag cagtcatact ccacccctct gaccttcggc 720
caagggacca aagtggagat caagaccact accccagcac cgaggccacc caccccggct 780
cctaccatcg cctcccagcc tctgtccctg cgtccggagg catgtagacc cgcagctggt 840

```
ggggccgtgc atacccgggg tcttgacttc gcctgcgata tctacatttg ggcccctctg    900

gctggtactt gcggggtcct gctgctttca ctcgtgatca ctctttactg taagcgcggt    960

cggaagaagc tgctgtacat ctttaagcaa cccttcatga ggcctgtgca gactactcaa   1020

gaggaggacg gctgttcatg ccggttccca gaggaggagg aaggcggctg cgaactgcgc   1080

gtgaaattca gccgcagcgc agatgctcca gcctaccagc aggggcagaa ccagctctac   1140

aacgaactca atcttggtcg gagagaggag tacgacgtgc tggacaagcg gagaggacgg   1200

gacccagaaa tgggcgggaa gccgcgcaga aagaatcccc aagagggcct gtacaacgag   1260

ctccaaaagg ataagatggc agaagcctat agcgagattg gtatgaaagg ggaacgcaga   1320

agaggcaaag gccacgacgg actgtaccag ggactcagca ccgccaccaa ggacacctat   1380

gacgctcttc acatgcaggc cctgccgcct cgg                                1413


<210> SEQ ID NO 76
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Arg Glu Trp Trp Gly Glu Ser Trp Leu Phe Asp Tyr
1               5                   10


<210> SEQ ID NO 77
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ala Arg Arg Glu Trp Trp Gly Glu Ser Trp Leu Phe Asp Tyr
1               5                   10


<210> SEQ ID NO 78
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser
        115                 120
```

<210> SEQ ID NO 79
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300

tggtggggag aaagctggct gttcgactac tggggacagg gcactctcgt gactgtgtcc    360

tcc                                                                  363
```

<210> SEQ ID NO 80
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175
```

```
Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys
                245
```

<210> SEQ ID NO 81
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gaagtgcagt tgctggagtc aggcggagga ctggtgcagc ccggaggatc gcttcgcttg      60

agctgcgcag cctcaggctt taccttctcc tcctacgcca tgtcctgggt cagacaggct     120

cccgggaagg gactggaatg ggtgtccgcc attagcggtt ccggcggaag cacttactat     180

gccgactctg tgaagggccg cttcactatc tcccgggaca actccaagaa caccctgtat     240

ctccaaatga attccctgag ggccgaagat accgcggtgt actactgcgc tagacgggag     300

tggtggggag aaagctggct gttcgactac tggggacagg gcactctcgt gactgtgtcc     360

tccggtggtg gtggatcggg gggtggtggt tcgggcggag gaggatctgg aggaggaggg     420

tcggacattc aaatgactca gtccccgtcc tccctctccg cctccgtggg agatcgcgtc     480

acgatcacgt gcagggccag ccagagcatc tccagctacc tgaactggta ccagcagaag     540

ccagggaagg caccgaagct cctgatctac gccgctagct cgctgcagtc cggcgtccct     600

tcacggttct cgggatcggg ctcaggcacc gacttcaccc tgaccattag cagcctgcag     660

ccggaggact tcgcgacata ctactgtcag cagtcatact ccacccctct gaccttcggc     720

caagggacca aagtggagat caag                                            744
```

<210> SEQ ID NO 82
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 83
<211> LENGTH: 1413

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83

gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300

tggtggggag aaagctggct gttcgactac tggggacagg gcactctcgt gactgtgtcc    360

tccggtggtg gtggatcggg gggtggtggt tcgggcggag gaggatctgg aggaggaggg    420

tcggacattc aaatgactca gtccccgtcc tccctctccg cctccgtggg agatcgcgtc    480

acgatcacgt gcagggccag ccagagcatc tccagctacc tgaactggta ccagcagaag    540

ccagggaagg caccgaagct cctgatctac gccgctagct cgctgcagtc cggcgtccct    600

tcacggttct cgggatcggg ctcaggcacc gacttcaccc tgaccattag cagcctgcag    660

ccggaggact tcgcgacata ctactgtcag cagtcatact ccacccctct gaccttcggc    720

caagggacca aagtggagat caagaccact accccagcac cgaggccacc cacccccggct    780

cctaccatcg cctcccagcc tctgtccctg cgtccggagg catgtagacc cgcagctggt    840

ggggccgtgc atacccgggg tcttgacttc gcctgcgata tctacatttg ggcccctctg    900

gctggtactt gcggggtcct gctgctttca ctcgtgatca ctctttactg taagcgcggt    960

cggaagaagc tgctgtacat ctttaagcaa cccttcatga ggcctgtgca gactactcaa   1020

gaggaggacg gctgttcatg ccggttccca gaggaggagg aaggcggctg cgaactgcgc   1080

gtgaaattca gccgcagcgc agatgctcca gcctaccagc aggggcagaa ccagctctac   1140

aacgaactca atcttggtcg gagagaggag tacgacgtgc tggacaagcg gagaggacgg   1200

gacccagaaa tgggcgggaa gccgcgcaga aagaatcccc aagagggcct gtacaacgag   1260

ctccaaaagg ataagatggc agaagcctat agcgagattg gtatgaaagg ggaacgcaga   1320

agaggcaaag gccacgacgg actgtaccag ggactcagca ccgccaccaa ggacacctat   1380

gacgctcttc acatgcaggc cctgccgcct cgg                                 1413


<210> SEQ ID NO 84
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace=" "
<220> FEATURE:
<221> NAME/KEY: VARIANT
<222> LOCATION: (5)..(5)
<223> OTHER INFORMATION: /replace=" "
<220> FEATURE:
<221> NAME/KEY: VARIANT
<222> LOCATION: (6)..(6)
<223> OTHER INFORMATION: /replace="Tyr"
<220> FEATURE:
```

<221> NAME/KEY: VARIANT
<222> LOCATION: (7)..(7)
<223> OTHER INFORMATION: /replace="Tyr" or "Asp"
<220> FEATURE:
<221> NAME/KEY: VARIANT
<222> LOCATION: (8)..(8)
<223> OTHER INFORMATION: /replace="Asp" or "Val"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (11)..(11)
<223> OTHER INFORMATION: /replace="Tyr"
<220> FEATURE:
<221> NAME/KEY: VARIANT
<222> LOCATION: (12)..(12)
<223> OTHER INFORMATION: /replace="Leu"
<220> FEATURE:
<221> NAME/KEY: SITE
<222> LOCATION: (1)..(14)
<223> OTHER INFORMATION: /note="Variant residues given in the sequence have no preference with respect to those in the annotations for variant positions"

<400> SEQUENCE: 84

Arg Glu Trp Val Pro Trp Gly Glu Ser Trp Leu Phe Asp Tyr
1 5 10

<210> SEQ ID NO 85
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (6)..(6)
<223> OTHER INFORMATION: /replace=" "
<220> FEATURE:
<221> NAME/KEY: VARIANT
<222> LOCATION: (7)..(7)
<223> OTHER INFORMATION: /replace=" "
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: VARIANT
<222> LOCATION: (9)..(9)
<223> OTHER INFORMATION: /replace="Tyr" or "Asp"
<220> FEATURE:
<221> NAME/KEY: VARIANT
<222> LOCATION: (10)..(10)
<223> OTHER INFORMATION: /replace="Asp" or "Val"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: VARIANT
<222> LOCATION: (13)..(13)
<223> OTHER INFORMATION: /replace="Tyr"
<220> FEATURE:
<221> NAME/KEY: VARIANT
<222> LOCATION: (14)..(14)
<223> OTHER INFORMATION: /replace="Leu"
<220> FEATURE:
<221> NAME/KEY: SITE
<222> LOCATION: (1)..(16)
<223> OTHER INFORMATION: /note="Variant residues given in the sequence have no preference with respect to those in the annotations for variant positions"

<400> SEQUENCE: 85

Ala Arg Arg Glu Trp Val Pro Trp Gly Glu Ser Trp Leu Phe Asp Tyr
1 5 10 15

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

Ser Tyr Gly Met His
1 5

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 87

Val Ile Ser Tyr Asp Gly Ser Asn Lys Tyr Tyr Ala Asp Ser Val Lys
1 5 10 15

Gly

<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 88

Ser Gly Tyr Ala Leu His Asp Asp Tyr Tyr Gly Leu Asp Val
1 5 10

<210> SEQ ID NO 89
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 89

Ser Tyr Asp Gly Ser Asn
1 5

<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 90

Gly Phe Thr Phe Ser Ser Tyr Gly
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 91

Ile Ser Tyr Asp Gly Ser Asn Lys
1               5

<210> SEQ ID NO 92
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 92

Gly Gly Ser Gly Tyr Ala Leu His Asp Asp Tyr Tyr Gly Leu Asp Val
1               5                   10                  15

<210> SEQ ID NO 93
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 93

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser
        115                 120

<210> SEQ ID NO 94
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94
caagtgcagc tgcaggaatc cggtggcgga gtcgtgcagc ctggaaggag cctgagactc 60
tcatgcgccg cgtcagggtt cacctttttcc tcctacggga tgcattgggt cagacaggcc 120
cccggaaagg gactcgaatg ggtggctgtg atcagctacg acggctccaa caagtactac 180
gccgactccg tgaaaggccg gttcactatc tcccgggaca actccaagaa cacgctgtat 240
ctgcaaatga attcactgcg cgcggaggat accgctgtgt actactgcgg tggctccggt 300
tacgccctgc acgatgacta ttacggcctt gacgtctggg gccagggaac cctcgtgact 360
gtgtccagc 369

<210> SEQ ID NO 95
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 95

Thr Gly Thr Ser Ser Asp Val Gly Gly Tyr Asn Tyr Val Ser
1 5 10

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 96

Asp Val Ser Asn Arg Pro Ser
1 5

<210> SEQ ID NO 97
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 97

Ser Ser Tyr Thr Ser Ser Ser Thr Leu Tyr Val
1 5 10

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 98

Thr Ser Ser Asp Val Gly Gly Tyr Asn Tyr
1 5 10

<210> SEQ ID NO 99
<211> LENGTH: 3

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Asp Val Ser
1

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 100

Tyr Thr Ser Ser Ser Thr Leu Tyr
1 5

<210> SEQ ID NO 101
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 101

Ser Ser Asp Val Gly Gly Tyr Asn Tyr
1 5

<210> SEQ ID NO 102
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu Tyr Val Phe Gly Ser Gly Thr Lys Val Thr Val Leu
100 105 110

<210> SEQ ID NO 103
<211> LENGTH: 333
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103

```
cagagcgcac tgactcagcc ggcatccgtg tccggtagcc ccggacagtc gattaccatc      60

tcctgtaccg gcacctcctc cgacgtggga gggtacaact acgtgtcgtg gtaccagcag     120

cacccaggaa aggcccctaa gttgatgatc tacgatgtgt caaaccgccc gtctggagtc     180

tccaaccggt tctccggctc caagtccggc aacaccgcca gcctgaccat tagcgggctg     240

caagccgagg atgaggccga ctactactgc tcgagctaca catcctcgag caccctctac     300

gtgttcggct cggggactaa ggtcaccgtg ctg                                  333
```

<210> SEQ ID NO 104
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

```
Gly Gly Gly Gly Ser Gly Gly Gly Gly Ser Gly Gly Gly Gly Ser
1               5                   10                  15
```

<210> SEQ ID NO 105
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gln Ser Ala Leu Thr Gln
    130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175
```

-continued

```
Gln Gln His Pro Gly Lys Ala Pro Lys Leu Met Ile Tyr Asp Val Ser
            180                 185                 190

Asn Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Ser Ser Ser Thr Leu Tyr Val Phe
225                 230                 235                 240

Gly Ser Gly Thr Lys Val Thr Val Leu
                245


<210> SEQ ID NO 106
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106

caagtgcagc tgcaggaatc cggtggcgga gtcgtgcagc ctggaaggag cctgagactc      60

tcatgcgccg cgtcagggtt caccttttcc tcctacggga tgcattgggt cagacaggcc     120

cccggaaagg gactcgaatg ggtggctgtg atcagctacg acggctccaa caagtactac     180

gccgactccg tgaaaggccg gttcactatc tcccgggaca actccaagaa cacgctgtat     240

ctgcaaatga attcactgcg cgcggaggat accgctgtgt actactgcgg tggctccggt     300

tacgccctgc acgatgacta ttacggcctt gacgtctggg gccagggaac cctcgtgact     360

gtgtccagcg gtggaggagg ttcgggcgga ggaggatcag gagggggtgg atcgcagagc     420

gcactgactc agccggcatc cgtgtccggt agccccggac agtcgattac catctcctgt     480

accggcacct cctccgacgt gggagggtac aactacgtgt cgtggtacca gcagcaccca     540

ggaaaggccc ctaagttgat gatctacgat gtgtcaaacc gcccgtctgg agtctccaac     600

cggttctccg gctccaagtc cggcaacacc gccagcctga ccattagcgg gctgcaagcc     660

gaggatgagg ccgactacta ctgctcgagc tacacatcct cgagcaccct ctacgtgttc     720

ggctcgggga ctaaggtcac cgtgctg                                         747


<210> SEQ ID NO 107
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

-continued 65 70 75 80

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val
100 105 110

Trp Gly Gln Gly Thr Leu Val Thr Val Ser Ser Gly Gly Gly Gly Ser
115 120 125

Gly Gly Gly Gly Ser Gly Gly Gly Gly Ser Gln Ser Ala Leu Thr Gln
130 135 140

Pro Ala Ser Val Ser Gly Ser Pro Gly Gln Ser Ile Thr Ile Ser Cys
145 150 155 160

Thr Gly Thr Ser Ser Asp Val Gly Gly Tyr Asn Tyr Val Ser Trp Tyr
165 170 175

Gln Gln His Pro Gly Lys Ala Pro Lys Leu Met Ile Tyr Asp Val Ser
180 185 190

Asn Arg Pro Ser Gly Val Ser Asn Arg Phe Ser Gly Ser Lys Ser Gly
195 200 205

Asn Thr Ala Ser Leu Thr Ile Ser Gly Leu Gln Ala Glu Asp Glu Ala
210 215 220

Asp Tyr Tyr Cys Ser Ser Tyr Thr Ser Ser Ser Thr Leu Tyr Val Phe
225 230 235 240

Gly Ser Gly Thr Lys Val Thr Val Leu Thr Thr Thr Pro Ala Pro Arg
245 250 255

Pro Pro Thr Pro Ala Pro Thr Ile Ala Ser Gln Pro Leu Ser Leu Arg
260 265 270

Pro Glu Ala Cys Arg Pro Ala Ala Gly Gly Ala Val His Thr Arg Gly
275 280 285

Leu Asp Phe Ala Cys Asp Ile Tyr Ile Trp Ala Pro Leu Ala Gly Thr
290 295 300

Cys Gly Val Leu Leu Leu Ser Leu Val Ile Thr Leu Tyr Cys Lys Arg
305 310 315 320

Gly Arg Lys Lys Leu Leu Tyr Ile Phe Lys Gln Pro Phe Met Arg Pro
325 330 335

Val Gln Thr Thr Gln Glu Glu Asp Gly Cys Ser Cys Arg Phe Pro Glu
340 345 350

Glu Glu Glu Gly Gly Cys Glu Leu Arg Val Lys Phe Ser Arg Ser Ala
355 360 365

Asp Ala Pro Ala Tyr Gln Gln Gly Gln Asn Gln Leu Tyr Asn Glu Leu
370 375 380

Asn Leu Gly Arg Arg Glu Glu Tyr Asp Val Leu Asp Lys Arg Arg Gly
385 390 395 400

Arg Asp Pro Glu Met Gly Gly Lys Pro Arg Arg Lys Asn Pro Gln Glu
405 410 415

Gly Leu Tyr Asn Glu Leu Gln Lys Asp Lys Met Ala Glu Ala Tyr Ser
420 425 430

Glu Ile Gly Met Lys Gly Glu Arg Arg Arg Gly Lys Gly His Asp Gly
435 440 445

Leu Tyr Gln Gly Leu Ser Thr Ala Thr Lys Asp Thr Tyr Asp Ala Leu
450 455 460

His Met Gln Ala Leu Pro Pro Arg
465 470

<210> SEQ ID NO 108

-continued

<211> LENGTH: 1416
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 108
caagtgcagc tgcaggaatc cggtggcgga gtcgtgcagc ctggaaggag cctgagactc 60
tcatgcgccg cgtcagggtt caccttttcc tcctacggga tgcattgggt cagacaggcc 120
cccggaaagg gactcgaatg ggtggctgtg atcagctacg acggctccaa caagtactac 180
gccgactccg tgaaaggccg gttcactatc tcccgggaca actccaagaa cacgctgtat 240
ctgcaaatga attcactgcg cgcggaggat accgctgtgt actactgcgg tggctccggt 300
tacgccctgc acgatgacta ttacggcctt gacgtctggg gccagggaac cctcgtgact 360
gtgtccagcg gtggaggagg ttcgggcgga ggaggatcag gagggggtgg atcgcagagc 420
gcactgactc agccggcatc cgtgtccggt agccccggac agtcgattac catctcctgt 480
accggcacct cctccgacgt gggagggtac aactacgtgt cgtggtacca gcagcaccca 540
ggaaaggccc ctaagttgat gatctacgat gtgtcaaacc gcccgtctgg agtctccaac 600
cggttctccg gctccaagtc cggcaacacc gccagcctga ccattagcgg gctgcaagcc 660
gaggatgagg ccgactacta ctgctcgagc tacacatcct cgagcaccct ctacgtgttc 720
ggctcgggga ctaaggtcac cgtgctgacc actaccccag caccgaggcc acccaccccg 780
gctcctacca tcgcctccca gcctctgtcc ctgcgtccgg aggcatgtag acccgcagct 840
ggtggggccg tgcatacccg gggtcttgac ttcgcctgcg atatctacat ttgggcccct 900
ctggctggta cttgcggggt cctgctgctt tcactcgtga tcactcttta ctgtaagcgc 960
ggtcggaaga agctgctgta catctttaag caacccttca tgaggcctgt gcagactact 1020
caagaggagg acggctgttc atgccggttc ccagaggagg aggaaggcgg ctgcgaactg 1080
cgcgtgaaat tcagccgcag cgcagatgct ccagcctacc agcaggggca gaaccagctc 1140
tacaacgaac tcaatcttgg tcggagagag gagtacgacg tgctggacaa gcggagagga 1200
cgggacccag aaatgggcgg gaagccgcgc agaaagaatc cccaagaggg cctgtacaac 1260
gagctccaaa aggataagat ggcagaagcc tatagcgaga ttggtatgaa aggggaacgc 1320
agaagaggca aaggccacga cggactgtac cagggactca gcaccgccac caaggacacc 1380
tatgacgctc ttcacatgca ggccctgccg cctcgg 1416

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 109

Val Ile Ser Tyr Lys Gly Ser Asn Lys Tyr Tyr Ala Asp Ser Val Lys
1 5 10 15

Gly

<210> SEQ ID NO 110
<211> LENGTH: 6
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 110

Ser Tyr Lys Gly Ser Asn
1 5

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 111

Ile Ser Tyr Lys Gly Ser Asn Lys
1 5

<210> SEQ ID NO 112
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 112

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Lys Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val
100 105 110

Trp Gly Gln Gly Thr Leu Val Thr Val Ser Ser
115 120

<210> SEQ ID NO 113
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 113
caagtgcagc ttgtcgaatc gggaggcgga gtggtgcagc ctggacgatc gctccggctc 60
tcatgtgccg cgagcggatt caccttctcg agctacggca tgcactgggt cagacaagcc 120
ccaggaaagg gcctggaatg ggtggctgtc atctcgtaca agggctcaaa caagtactac 180
gccgactccg tgaagggccg gttcaccatc tcccgcgata actccaagaa taccctctat 240
ctgcaaatga acagcctgag ggccgaggat actgcagtgt actactgcgg gggttcaggc 300
tacgcgctgc acgacgacta ctacggattg gacgtctggg gccaaggaac tcttgtgacc 360
gtgtcctct 369

<210> SEQ ID NO 114
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 114

Glu Val Ser Asn Arg Leu Arg
1 5

<210> SEQ ID NO 115
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 115

Ser Ser Tyr Thr Ser Ser Ser Ala Leu Tyr Val
1 5 10

<210> SEQ ID NO 116
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 116

Glu Val Ser
1

<210> SEQ ID NO 117
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 117

Tyr Thr Ser Ser Ser Ala Leu Tyr
1 5

<210> SEQ ID NO 118
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 118

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Leu Arg Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ala Leu Tyr Val Phe Gly Ser Gly Thr Lys Val Thr Val Leu
            100                 105                 110
```

<210> SEQ ID NO 119
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 119

```
cagagcgcgc tgactcagcc tgcctccgtg agcggttcgc cgggacagtc cattaccatt     60

tcgtgcaccg ggacctcctc cgacgtggga ggctacaact acgtgtcctg gtaccagcag    120

catcccggaa aggccccgaa gctgatgatc tacgaagtgt cgaacagact gcggggagtc    180

tccaaccgct tttccgggtc caagtccggc aacaccgcca gcctgaccat cagcgggctc    240

caggcagaag atgaggctga ctattactgc tcctcctaca cgtcaagctc cgccctctac    300

gtgttcgggt ccgggaccaa agtcactgtg ctg                                 333
```

<210> SEQ ID NO 120
<211> LENGTH: 254
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 120

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110
```

```
Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Ala Leu Tyr Val Phe Gly Ser Gly Thr Lys Val Thr Val Leu
                245                 250
```

```
<210> SEQ ID NO 121
<211> LENGTH: 762
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121

caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcaggggggt ggcggatctg gggtggtgg ttccgggga    420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

gccctctacg tgttcgggtc cgggaccaaa gtcactgtgc tg                        762
```

```
<210> SEQ ID NO 122
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Gln Leu Val Glu Ser Gly Gly Gly Val Val Gln Pro Gly Arg
```

-continued

```
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Ala Leu Tyr Val Phe Gly Ser Gly Thr Lys Val Thr Val Leu Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430
```

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475

<210> SEQ ID NO 123
<211> LENGTH: 1431
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 123
caagtgcagc ttgtcgaatc gggaggcgga gtggtgcagc ctggacgatc gctccggctc 60
tcatgtgccg cgagcggatt caccttctcg agctacggca tgcactgggt cagacaagcc 120
ccaggaaagg gcctggaatg ggtggctgtc atctcgtaca agggctcaaa caagtactac 180
gccgactccg tgaagggccg gttcaccatc tcccgcgata actccaagaa taccctctat 240
ctgcaaatga acagcctgag ggccgaggat actgcagtgt actactgcgg gggttcaggc 300
tacgcgctgc acgacgacta ctacggattg gacgtctggg gccaaggaac tcttgtgacc 360
gtgtcctctg gtggaggcgg atcagggggt ggcggatctg gggtggtgg ttccggggga 420 ggaggatcgc agagcgcgct gactcagcct gcctccgtga gcggttcgcc gggacagtcc 480
attaccattt cgtgcaccgg gacctcctcc gacgtgggag gctacaacta cgtgtcctgg 540
taccagcagc atcccggaaa ggccccgaag ctgatgatct acgaagtgtc gaacagactg 600
cggggagtct ccaaccgctt ttccgggtcc aagtccggca acaccgccag cctgaccatc 660
agcgggctcc aggcagaaga tgaggctgac tattactgct cctcctacac gtcaagctcc 720
gccctctacg tgttcgggtc cgggaccaaa gtcactgtgc tgaccactac cccagcaccg 780
aggccaccca ccccggctcc taccatcgcc tcccagcctc tgtccctgcg tccggaggca 840
tgtagacccg cagctggtgg ggccgtgcat acccggggtc ttgacttcgc ctgcgatatc 900
tacatttggg cccctctggc tggtacttgc ggggtcctgc tgctttcact cgtgatcact 960
ctttactgta agcgcggtcg gaagaagctg ctgtacatct ttaagcaacc cttcatgagg 1020
cctgtgcaga ctactcaaga ggaggacggc tgttcatgcc ggttcccaga ggaggaggaa 1080
ggcggctgcg aactgcgcgt gaaattcagc cgcagcgcag atgctccagc ctaccagcag 1140
gggcagaacc agctctacaa cgaactcaat cttggtcgga gagaggagta cgacgtgctg 1200
gacaagcgga gaggacggga cccagaaatg ggcgggaagc cgcgcagaaa gaatccccaa 1260
gagggcctgt acaacgagct ccaaaaggat aagatggcag aagcctatag cgagattggt 1320
atgaaagggg aacgcagaag aggcaaaggc cacgacggac tgtaccaggg actcagcacc 1380
gccaccaagg acacctatga cgctcttcac atgcaggccc tgccgcctcg g 1431

<210> SEQ ID NO 124
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Leu Arg Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Ser Gly Thr Lys Val Thr Val Leu
            100                 105                 110
```

<210> SEQ ID NO 125
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
cagagcgcgc tgactcagcc tgcctccgtg agcggttcgc cgggacagtc cattaccatt     60

tcgtgcaccg ggacctcctc cgacgtggga ggctacaact acgtgtcctg gtaccagcag    120

catcccggaa aggccccgaa gctgatgatc tacgaagtgt cgaacagact gcggggagtc    180

tccaaccgct tttccgggtc caagtccggc aacaccgcca gcctgaccat cagcgggctc    240

caggcagaag atgaggctga ctattactgc tcctcctaca cgtcaagctc caccctctac    300

gtgttcgggt ccgggaccaa agtcactgtg ctg                                 333
```

<210> SEQ ID NO 126
<211> LENGTH: 254
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
```

```
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Thr Leu Tyr Val Phe Gly Ser Gly Thr Lys Val Thr Val Leu
                245                 250
```

<210> SEQ ID NO 127
<211> LENGTH: 762
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127

```
caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcagggggt ggcggatctg gggtggtgg ttccgggga    420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

accctctacg tgttcgggtc cgggaccaaa gtcactgtgc tg                       762
```

<210> SEQ ID NO 128
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 128

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Thr Leu Tyr Val Phe Gly Ser Gly Thr Lys Val Thr Val Leu Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
```

```
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475


<210> SEQ ID NO 129
<211> LENGTH: 1431
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcagggggt ggcggatctg gggtggtgg ttccgggggga    420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

accctctacg tgttcgggtc cgggaccaaa gtcactgtgc tgaccactac cccagcaccg    780

aggccaccca ccccggctcc taccatcgcc tcccagcctc tgtccctgcg tccggaggca    840

tgtagacccg cagctggtgg ggccgtgcat acccggggtc ttgacttcgc ctgcgatatc    900

tacatttggg cccctctggc tggtacttgc ggggtcctgc tgctttcact cgtgatcact    960

ctttactgta agcgcggtcg gaagaagctg ctgtacatct ttaagcaacc cttcatgagg   1020

cctgtgcaga ctactcaaga ggaggacggc tgttcatgcc ggttcccaga ggaggaggaa   1080

ggcggctgcg aactgcgcgt gaaattcagc cgcagcgcag atgctccagc ctaccagcag   1140

gggcagaacc agctctacaa cgaactcaat cttggtcgga gagaggagta cgacgtgctg   1200

gacaagcgga gaggacggga cccagaaatg ggcgggaagc cgcgcagaaa gaatccccaa   1260

gagggcctgt acaacgagct ccaaaaggat aagatggcag aagcctatag cgagattggt   1320

atgaaagggg aacgcagaag aggcaaaggc cacgacggac tgtaccaggg actcagcacc   1380

gccaccaagg acacctatga cgctcttcac atgcaggccc tgccgcctcg g             1431


<210> SEQ ID NO 130
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"
<220> FEATURE:
<221> NAME/KEY: VARIANT
<222> LOCATION: (5)..(5)
<223> OTHER INFORMATION: /replace="Lys"
<220> FEATURE:
<221> NAME/KEY: SITE
<222> LOCATION: (1)..(17)
<223> OTHER INFORMATION: /note="Variant residues given in the sequence have no preference with respect to those in the annotations for variant positions"

<400> SEQUENCE: 130

Val Ile Ser Tyr Asp Gly Ser Asn Lys Tyr Tyr Ala Asp Ser Val Lys
1 5 10 15

Gly

<210> SEQ ID NO 131
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 131

Asp Val Ser Asn Arg Pro Ser
1 5

<210> SEQ ID NO 132
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (8)..(8)
<223> OTHER INFORMATION: /replace="Ala"
<220> FEATURE:
<221> NAME/KEY: SITE
<222> LOCATION: (1)..(11)
<223> OTHER INFORMATION: /note="Variant residues given in the sequence have no preference with respect to those in the annotations for variant positions"

<400> SEQUENCE: 132

Ser Ser Tyr Thr Ser Ser Ser Thr Leu Tyr Val
1 5 10

<210> SEQ ID NO 133

<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 133

Ser Tyr Asp Gly Ser Asn
1               5

<210> SEQ ID NO 134
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: SITE
<222> LOCATION: (1)..(3)
<223> OTHER INFORMATION: /note="Variant residues given in the sequence
      have no preference with respect to those in the annotations
      for variant positions"

<400> SEQUENCE: 134

Asp Val Ser
1

<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Ala"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 135

Tyr Thr Ser Ser Ser Thr Leu Tyr
1               5

<210> SEQ ID NO 136
<211> LENGTH: 8
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Lys"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 136

Ile Ser Tyr Asp Gly Ser Asn Lys
1               5


<210> SEQ ID NO 137
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Gly Phe Trp Met Ser
1               5


<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Asn Ile Lys Gln Asp Gly Ser Glu Lys Tyr Tyr Val Asp Ser Val Arg
1               5                   10                  15

Gly


<210> SEQ ID NO 139
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Ala Leu Asp Tyr Tyr Gly Met Asp Val
1               5


<210> SEQ ID NO 140
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Phe Thr Phe Ser Gly Phe
```

1 5

<210> SEQ ID NO 141
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Lys Gln Asp Gly Ser Glu
1 5

<210> SEQ ID NO 142
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Gly Phe Thr Phe Ser Gly Phe Trp
1 5

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 143

Ile Lys Gln Asp Gly Ser Glu Lys
1 5

<210> SEQ ID NO 144
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Ala Arg Ala Leu Asp Tyr Tyr Gly Met Asp Val
1 5 10

<210> SEQ ID NO 145
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Gly Phe
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Arg Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ala Leu Asp Tyr Tyr Gly Met Asp Val Trp Gly Gln Gly Thr
100 105 110

Thr Val Thr Val Ser Ser
115

<210> SEQ ID NO 146
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 146
gaagtgcaac tggtggagag cggtggaggg cttgtccagc ccggaggatc gctgcggctg 60
tcctgtgctg cgtccgggtt caccttctcc ggcttctgga tgtcctgggt cagacaggca 120
ccgggaaagg gcctcgaatg ggtggccaac atcaagcagg atggctccga gaagtactac 180
gtcgactccg tgagaggccg cttcaccatc tcccgggaca acgccaagaa ctcgctgtac 240
ctccaaatga atagcctcag ggcggaagat actgctgtgt attactgcgc acgcgccctt 300
gactactacg gcatggacgt ctggggccaa gggaccactg tgaccgtgtc tagc 354

<210> SEQ ID NO 147
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Arg Ser Ser Gln Ser Leu Leu Asp Ser Asp Asp Gly Asn Thr Tyr Leu
1 5 10 15

Asp

<210> SEQ ID NO 148
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Thr Leu Ser Tyr Arg Ala Ser
1 5

<210> SEQ ID NO 149
<211> LENGTH: 10
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 149

Thr Gln Arg Leu Glu Phe Pro Ser Ile Thr
1 5 10

<210> SEQ ID NO 150
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 150

Ser Gln Ser Leu Leu Asp Ser Asp Asp Gly Asn Thr Tyr
1 5 10

<210> SEQ ID NO 151
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 151

Thr Leu Ser
1

<210> SEQ ID NO 152
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 152

Arg Leu Glu Phe Pro Ser Ile
1 5

<210> SEQ ID NO 153
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 153

Gln Ser Leu Leu Asp Ser Asp Asp Gly Asn Thr Tyr
1 5 10

<210> SEQ ID NO 154
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 154

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Tyr Leu Gln Lys Pro Gly Gln
35 40 45

Ser Pro Arg Leu Leu Ile Tyr Thr Leu Ser Tyr Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Leu Tyr Tyr Cys Thr Gln
85 90 95

Arg Leu Glu Phe Pro Ser Ile Thr Phe Gly Gln Gly Thr Arg Leu Glu
100 105 110

Ile Lys

<210> SEQ ID NO 155
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 155
gatatcgtga tgacccagac tcccctgtcc ctgcctgtga ctcccggaga accagcctcc 60
atttcctgcc ggtcctccca gtccctgctg gacagcgacg acggcaacac ttacctggac 120
tggtacttgc agaagccggg ccaatcgcct cgcctgctga tctataccct gtcataccgg 180
gcctcaggag tgcctgaccg cttctcggga tcagggagcg ggaccgattt caccctgaaa 240
atttcccgag tggaagccga ggacgtcgga ctgtactact gcacccagcg cctcgaattc 300
ccgtcgatta cgtttggaca gggtacccgg cttgagatca ag 342

<210> SEQ ID NO 156
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 156

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Gly Phe
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Arg Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys

-continued

```
                85                  90                  95

Ala Arg Ala Leu Asp Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Arg Leu Leu Ile
            180                 185                 190

Tyr Thr Leu Ser Tyr Arg Ala Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Leu Tyr Tyr Cys Thr Gln Arg Leu Glu Phe Pro Ser
225                 230                 235                 240

Ile Thr Phe Gly Gln Gly Thr Arg Leu Glu Ile Lys
                245                 250


<210> SEQ ID NO 157
<211> LENGTH: 756
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157

gaagtgcaac tggtggagag cggtggaggg cttgtccagc ccggaggatc gctgcggctg      60

tcctgtgctg cgtccgggtt caccttctcc ggcttctgga tgtcctgggt cagacaggca     120

ccgggaaagg gcctcgaatg ggtggccaac atcaagcagg atggctccga gaagtactac     180

gtcgactccg tgagaggccg cttcaccatc tcccgggaca acgccaagaa ctcgctgtac     240

ctccaaatga atagcctcag ggcggaagat actgctgtgt attactgcgc acgcgccctt     300

gactactacg gcatggacgt ctggggccaa gggaccactg tgaccgtgtc tagcggaggc     360

ggaggttcag gggcggtgg atcaggcgga ggaggatcgg ggggtggtgg atcggatatc     420

gtgatgaccc agactcccct gtccctgcct gtgactcccg gagaaccagc ctccatttcc     480

tgccggtcct cccagtccct gctggacagc gacgacggca acacttacct ggactggtac     540

ttgcagaagc cgggccaatc gcctcgcctg ctgatctata ccctgtcata ccgggcctca     600

ggagtgcctg accgcttctc gggatcaggg agcgggaccg atttcaccct gaaaatttcc     660

cgagtggaag ccgaggacgt cggactgtac tactgcaccc agcgcctcga attcccgtcg     720

attacgtttg gacagggtac ccggcttgag atcaag                               756


<210> SEQ ID NO 158
<211> LENGTH: 475
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Arg Leu Leu Ile
            180                 185                 190

Tyr Thr Leu Ser Tyr Arg Ala Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Leu Tyr Tyr Cys Thr Gln Arg Leu Glu Phe Pro Ser
225                 230                 235                 240

Ile Thr Phe Gly Gln Gly Thr Arg Leu Glu Ile Lys Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn

```
            405                 410                 415

Pro Gln Glu Gly Leu Tyr Asn Glu Leu Gln Lys Asp Lys Met Ala Glu
        420                 425                 430

Ala Tyr Ser Glu Ile Gly Met Lys Gly Glu Arg Arg Arg Gly Lys Gly
    435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 159
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159

gaagtgcaac tggtggagag cggtggaggg cttgtccagc ccggaggatc gctgcggctg     60

tcctgtgctg cgtccgggtt caccttctcc ggcttctgga tgtcctgggt cagacaggca    120

ccgggaaagg gcctcgaatg ggtggccaac atcaagcagg atggctccga gaagtactac    180

gtcgactccg tgagaggccg cttcaccatc tcccgggaca acgccaagaa ctcgctgtac    240

ctccaaatga atagcctcag ggcggaagat actgctgtgt attactgcgc acgcgccctt    300

gactactacg gcatggacgt ctggggccaa gggaccactg tgaccgtgtc tagcggaggc    360

ggaggttcag gggcggtgg atcaggcgga ggaggatcgg ggggtggtgg atcggatatc    420

gtgatgaccc agactcccct gtccctgcct gtgactcccg gagaaccagc ctccatttcc    480

tgccggtcct cccagtccct gctggacagc gacgacggca acacttacct ggactggtac    540

ttgcagaagc cgggccaatc gcctcgcctg ctgatctata ccctgtcata ccgggcctca    600

ggagtgcctg accgcttctc gggatcaggg agcgggaccg atttcaccct gaaaatttcc    660

cgagtggaag ccgaggacgt cggactgtac tactgcaccc agcgcctcga attcccgtcg    720

attacgtttg gacagggtac ccggcttgag atcaagacca ctaccccagc accgaggcca    780

cccaccccgg ctcctaccat cgcctcccag cctctgtccc tgcgtccgga ggcatgtaga    840

cccgcagctg gtggggccgt gcatacccgg ggtcttgact tcgcctgcga tatctacatt    900

tgggcccctc tggctggtac ttgcggggtc ctgctgcttt cactcgtgat cactctttac    960

tgtaagcgcg gtcggaagaa gctgctgtac atctttaagc aacccttcat gaggcctgtg   1020

cagactactc aagaggagga cggctgttca tgccggttcc cagaggagga ggaaggcggc   1080

tgcgaactgc gcgtgaaatt cagccgcagc gcagatgctc cagcctacca gcaggggcag   1140

aaccagctct acaacgaact caatcttggt cggagagagg agtacgacgt gctggacaag   1200

cggagaggac gggacccaga aatgggcggg aagccgcgca gaaagaatcc ccaagagggc   1260

ctgtacaacg agctccaaaa ggataagatg gcagaagcct atagcgagat tggtatgaaa   1320

ggggaacgca gaagaggcaa aggccacgac ggactgtacc agggactcag caccgccacc   1380

aaggacacct atgacgctct tcacatgcag gccctgccgc ctcgg                  1425


<210> SEQ ID NO 160
<211> LENGTH: 5
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic peptide"

<400> SEQUENCE: 160

Ser Phe Arg Met Asn
1 5

<210> SEQ ID NO 161
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Ser Ile Ser Ser Ser Ser Ser Tyr Ile Tyr Tyr Ala Asp Ser Val Lys
1 5 10 15

Gly

<210> SEQ ID NO 162
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 162

Trp Leu Ser Tyr Tyr Gly Met Asp Val
1 5

<210> SEQ ID NO 163
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 163

Gly Phe Thr Phe Ser Ser Phe
1 5

<210> SEQ ID NO 164
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 164

Ser Ser Ser Ser Ser Tyr
1 5

<210> SEQ ID NO 165
<211> LENGTH: 8
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 165

Gly Phe Thr Phe Ser Ser Phe Arg
1               5


<210> SEQ ID NO 166
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ile Ser Ser Ser Ser Ser Tyr Ile
1               5


<210> SEQ ID NO 167
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Ala Arg Trp Leu Ser Tyr Tyr Gly Met Asp Val
1               5                   10


<210> SEQ ID NO 168
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Leu Ser Tyr Tyr Gly Met Asp Val Trp Gly Gln Gly Thr
            100                 105                 110

Thr Val Thr Val Ser Ser
        115


<210> SEQ ID NO 169
<211> LENGTH: 354
<212> TYPE: DNA
<213> ORGANISM: Artificial Sequence
```

<220> FEATURE:
<221> NAME/KEY: source
<223> OTHER INFORMATION: /note="Description of Artificial Sequence:
Synthetic polynucleotide"

<400> SEQUENCE: 169
gaagtgcaac tggtggagag cggtggaggg cttgtcaagc ccggaggatc gctgcggctg 60
tcctgtgctg cgtccgggtt caccttctcc tcgttccgca tgaactgggt cagacaggca 120
ccgggaaagg gcctcgaatg ggtgtcctca atctcatcgt cctcgtccta catctactac 180
gccgactccg tgaaaggccg cttcaccatc tcccgggaca acgccaagaa ctcgctgtac 240
ctccaaatga atagcctcag ggcggaagat actgctgtgt attactgcgc acgctggctt 300
tcctactacg gcatggacgt ctggggccaa gggaccactg tgaccgtgtc tagc 354

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 170

Thr Leu Ser Phe Arg Ala Ser
1 5

<210> SEQ ID NO 171
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 171

Met Gln Arg Ile Gly Phe Pro Ile Thr
1 5

<210> SEQ ID NO 172
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 172

Arg Ile Gly Phe Pro Ile
1 5

<210> SEQ ID NO 173
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 173

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
            20                      25                  30

Asp Asp Gly Asn Thr Tyr Leu Asp Trp Tyr Leu Gln Lys Pro Gly Gln
        35                      40              45

Ser Pro Gln Leu Leu Ile Tyr Thr Leu Ser Phe Arg Ala Ser Gly Val
    50                      55                  60

Pro Asp Arg Phe Ser Gly Ser Gly Ser Gly Thr Asp Phe Thr Leu Lys
65                      70                  75                  80

Ile Arg Arg Val Glu Ala Glu Asp Val Gly Val Tyr Tyr Cys Met Gln
                    85                  90                  95

Arg Ile Gly Phe Pro Ile Thr Phe Gly Gln Gly Thr Arg Leu Glu Ile
                100                     105                 110

Lys

<210> SEQ ID NO 174
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
gatatcgtga tgacccagac tcccctgtcc ctgcctgtga ctcccggaga accagcctcc      60
atttcctgcc ggtcctccca gtccctgctg gacagcgacg acggcaacac ttacctggac     120
tggtacttgc agaagccggg ccaatcgcct cagctgctga tctataccct gtcattccgg     180
gcctcaggag tgcctgaccg cttctcggga tcagggagcg ggaccgattt caccctgaaa     240
attaggcgag tggaagccga ggacgtcgga gtgtactact gcatgcagcg catcggcttc     300
ccgattacgt ttggacaggg tacccggctt gagatcaag                            339

<210> SEQ ID NO 175
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                      25                  30

Arg Met Asn Trp Val Arg Gln Ala Pro Gly Lys Gly Leu Glu Trp Val
        35                      40              45

Ser Ser Ile Ser Ser Ser Ser Ser Tyr Ile Tyr Tyr Ala Asp Ser Val
    50                      55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                    85                  90                  95

Ala Arg Trp Leu Ser Tyr Tyr Gly Met Asp Val Trp Gly Gln Gly Thr
                100                     105                 110

Thr Val Thr Val Ser Ser Gly Gly Gly Gly Ser Gly Gly Gly Gly Ser
            115                     120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Gln Leu Leu Ile
            180                 185                 190

Tyr Thr Leu Ser Phe Arg Ala Ser Gly Val Pro Asp Arg Phe Ser Gly
        195                 200                 205

Ser Gly Ser Gly Thr Asp Phe Thr Leu Lys Ile Arg Arg Val Glu Ala
    210                 215                 220

Glu Asp Val Gly Val Tyr Tyr Cys Met Gln Arg Ile Gly Phe Pro Ile
225                 230                 235                 240

Thr Phe Gly Gln Gly Thr Arg Leu Glu Ile Lys
                245                 250

<210> SEQ ID NO 176
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176
gaagtgcaac tggtggagag cggtggaggg cttgtcaagc ccggaggatc gctgcggctg     60
tcctgtgctg cgtccgggtt caccttctcc tcgttccgca tgaactgggt cagacaggca    120
ccgggaaagg gcctcgaatg ggtgtcctca atctcatcgt cctcgtccta catctactac    180
gccgactccg tgaaaggccg cttcaccatc tcccgggaca acgccaagaa ctcgctgtac    240
ctccaaatga atagcctcag ggcggaagat actgctgtgt attactgcgc acgctggctt    300
tcctactacg gcatggacgt ctggggccaa gggaccactg tgaccgtgtc tagcggaggc    360
ggaggttcag gggcggtgg atcaggcgga ggaggatcgg ggggtggtgg atcggatatc    420
gtgatgaccc agactcccct gtccctgcct gtgactcccg gagaaccagc ctccatttcc    480
tgccggtcct cccagtccct gctggacagc gacgacggca acacttacct ggactggtac    540
ttgcagaagc cgggccaatc gcctcagctg ctgatctata ccctgtcatt ccgggcctca    600
ggagtgcctg accgcttctc gggatcaggg agcgggaccg atttcaccct gaaaattagg    660
cgagtggaag ccgaggacgt cggagtgtac tactgcatgc agcgcatcgg cttcccgatt    720
acgtttggac agggtacccg gcttgagatc aag                                 753

<210> SEQ ID NO 177
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe

-continued

```
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Leu Ser Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Gln Leu Leu Ile
            180                 185                 190

Tyr Thr Leu Ser Phe Arg Ala Ser Gly Val Pro Asp Arg Phe Ser Gly
        195                 200                 205

Ser Gly Ser Gly Thr Asp Phe Thr Leu Lys Ile Arg Arg Val Glu Ala
    210                 215                 220

Glu Asp Val Gly Val Tyr Tyr Cys Met Gln Arg Ile Gly Phe Pro Ile
225                 230                 235                 240

Thr Phe Gly Gln Gly Thr Arg Leu Glu Ile Lys Thr Thr Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
        275                 280                 285

Arg Gly Leu Asp Phe Ala Cys Asp Ile Tyr Ile Trp Ala Pro Leu Ala
    290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445
```

```
Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470


<210> SEQ ID NO 178
<211> LENGTH: 1422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 178

gaagtgcaac tggtggagag cggtggaggg cttgtcaagc ccggaggatc gctgcggctg     60

tcctgtgctg cgtccgggtt caccttctcc tcgttccgca tgaactgggt cagacaggca    120

ccgggaaagg gcctcgaatg ggtgtcctca atctcatcgt cctcgtccta catctactac    180

gccgactccg tgaaaggccg cttcaccatc tcccgggaca acgccaagaa ctcgctgtac    240

ctccaaatga atagcctcag ggcggaagat actgctgtgt attactgcgc acgctggctt    300

tcctactacg gcatggacgt ctggggccaa gggaccactg tgaccgtgtc tagcggaggc    360

ggaggttcag gggcggtgg atcaggcgga ggaggatcgg ggggtggtgg atcggatatc    420

gtgatgaccc agactcccct gtccctgcct gtgactcccg gagaaccagc ctccatttcc    480

tgccggtcct cccagtccct gctggacagc gacgacggca acacttacct ggactggtac    540

ttgcagaagc cgggccaatc gcctcagctg ctgatctata ccctgtcatt ccgggcctca    600

ggagtgcctg accgcttctc gggatcaggg agcgggaccg atttcaccct gaaaattagg    660

cgagtggaag ccgaggacgt cggagtgtac tactgcatgc agcgcatcgg cttcccgatt    720

acgtttggac agggtacccg gcttgagatc aagaccacta ccccagcacc gaggccaccc    780

accccggctc ctaccatcgc ctcccagcct ctgtccctgc gtccggaggc atgtagaccc    840

gcagctggtg gggccgtgca tacccggggt cttgacttcg cctgcgatat ctacatttgg    900

gcccctctgg ctggtacttg cggggtcctg ctgctttcac tcgtgatcac tctttactgt    960

aagcgcggtc ggaagaagct gctgtacatc tttaagcaac ccttcatgag gcctgtgcag   1020

actactcaag aggaggacgg ctgttcatgc cggttcccag aggaggagga aggcggctgc   1080

gaactgcgcg tgaaattcag ccgcagcgca gatgctccag cctaccagca ggggcagaac   1140

cagctctaca acgaactcaa tcttggtcgg agagaggagt acgacgtgct ggacaagcgg   1200

agaggacggg acccagaaat gggcgggaag ccgcgcagaa agaatcccca agagggcctg   1260

tacaacgagc tccaaaagga taagatggca gaagcctata gcgagattgg tatgaaaggg   1320

gaacgcagaa gaggcaaagg ccacgacgga ctgtaccagg gactcagcac cgccaccaag   1380

gacacctatg acgctcttca catgcaggcc ctgccgcctc gg                       1422


<210> SEQ ID NO 179
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
```

<223> OTHER INFORMATION: /replace="Ser"
<220> FEATURE:
<221> NAME/KEY: VARIANT
<222> LOCATION: (3)..(3)
<223> OTHER INFORMATION: /replace="Arg"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: SITE
<222> LOCATION: (1)..(5)
<223> OTHER INFORMATION: /note="Variant residues given in the sequence have no preference with respect to those in the annotations for variant positions"

<400> SEQUENCE: 179

Gly Phe Trp Met Ser
1 5

<210> SEQ ID NO 180
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (12)..(12)
<223> OTHER INFORMATION: /replace="Ala"
<220> FEATURE:
<221> NAME/KEY: VARIANT
<222> LOCATION: (16)..(16)
<223> OTHER INFORMATION: /replace="Lys"
<220> FEATURE:
<221> NAME/KEY: SITE
<222> LOCATION: (1)..(17)
<223> OTHER INFORMATION: /note="Variant residues given in the sequence have no preference with respect to those in the annotations for variant positions"

<400> SEQUENCE: 180

Asn Ile Lys Gln Asp Gly Ser Glu Lys Tyr Tyr Val Asp Ser Val Arg
1 5 10 15

Gly

<210> SEQ ID NO 181
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Trp"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: SITE
<222> LOCATION: (1)..(9)
<223> OTHER INFORMATION: /note="Variant residues given in the sequence have no preference with respect to those in the annotations for variant positions"

<400> SEQUENCE: 181

Ala Leu Asp Tyr Tyr Gly Met Asp Val
1               5

<210> SEQ ID NO 182
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Phe"
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 182

Thr Leu Ser Tyr Arg Ala Ser
1               5

<210> SEQ ID NO 183
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Met"
<220> FEATURE:
<221> NAME/KEY: VARIANT
<222> LOCATION: (4)..(4)
<223> OTHER INFORMATION: /replace="Ile"
<220> FEATURE:
<221> NAME/KEY: VARIANT
<222> LOCATION: (5)..(5)
<223> OTHER INFORMATION: /replace="Gly"
<220> FEATURE:
<221> NAME/KEY: VARIANT
<222> LOCATION: (8)..(8)

<223> OTHER INFORMATION: /replace=" "
<220> FEATURE:
<221> NAME/KEY: SITE
<222> LOCATION: (1)..(10)
<223> OTHER INFORMATION: /note="Variant residues given in the sequence have no preference with respect to those in the annotations for variant positions"

<400> SEQUENCE: 183

Thr Gln Arg Leu Glu Phe Pro Ser Ile Thr
1 5 10

<210> SEQ ID NO 184
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 184

Gly Phe Thr Phe Ser Gly Phe
1 5

<210> SEQ ID NO 185
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (6)..(6)
<223> OTHER INFORMATION: /replace="Tyr"
<220> FEATURE:
<221> NAME/KEY: SITE
<222> LOCATION: (1)..(6)
<223> OTHER INFORMATION: /note="Variant residues given in the sequence have no preference with respect to those in the annotations for variant positions"

<400> SEQUENCE: 185

Lys Gln Asp Gly Ser Glu
1 5

<210> SEQ ID NO 186
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (6)..(6)
<223> OTHER INFORMATION: /replace=" "
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 186

Arg Leu Glu Phe Pro Ser Ile
1 5

<210> SEQ ID NO 187
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (8)..(8)
<223> OTHER INFORMATION: /replace="Arg"
<220> FEATURE:
<221> NAME/KEY: SITE
<222> LOCATION: (1)..(8)
<223> OTHER INFORMATION: /note="Variant residues given in the sequence have no preference with respect to those in the annotations for variant positions"

<400> SEQUENCE: 187

Gly Phe Thr Phe Ser Gly Phe Trp
1 5

<210> SEQ ID NO 188
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (3)..(3)
<223> OTHER INFORMATION: /replace="Ser"

<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (7)..(7)
<223> OTHER INFORMATION: /replace="Tyr"
<220> FEATURE:
<221> NAME/KEY: VARIANT
<222> LOCATION: (8)..(8)
<223> OTHER INFORMATION: /replace="Ile"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 188

```
Ile Lys Gln Asp Gly Ser Glu Lys
1               5
```

<210> SEQ ID NO 189
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Trp"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 189

```
Ala Arg Ala Leu Asp Tyr Tyr Gly Met Asp Val
1               5                   10
```

<210> SEQ ID NO 190
<211> LENGTH: 521
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190

```
acccctctct ccagccacta agccagttgc tccctcggct gacggctgca cgcgaggcct      60

ccgaacgtct tacgccttgt ggcgcgcccg tccttgtccc gggtgtgatg gcggggtgtg     120

gggcggaggg cgtggcgggg aagggccggc gacgagagcc gcgcgggacg actcgtcggc     180

gataaccggt gtcgggtagc gccagccgcg cgacggtaac gagggaccgc gacaggcaga     240

cgctcccatg atcactctgc acgccgaagg caaatagtgc aggccgtgcg gcgcttggcg     300
```

ttccttggaa gggctgaatc cccgcctcgt ccttcgcagc ggcccccgg gtgttcccat 360 cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 191
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 191
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac g 221

<210> SEQ ID NO 192
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 192
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccg 324

<210> SEQ ID NO 193
<211> LENGTH: 422
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 193
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggcccccgg gtgttcccat 360 cgccgcttct aggcccactg cgacgcttgc ctgcacttct tacacgctct gggtcccagc 420
cg 422

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 198
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 199
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 199
atggccctcc ctgtcaccgc cctgctgctt ccgctggctc ttctgctcca cgccgctcgg 60
ccc 63

<210> SEQ ID NO 200

<400> SEQUENCE: 200

000

<210> SEQ ID NO 201

<400> SEQUENCE: 201

000

<210> SEQ ID NO 202
<211> LENGTH: 69
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 202

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Ile Tyr Ile
35 40 45

Trp Ala Pro Leu Ala Gly Thr Cys Gly Val Leu Leu Leu Ser Leu Val
50 55 60

Ile Thr Leu Tyr Cys
65

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234
<400> SEQUENCE: 234
000

<210> SEQ ID NO 235
<400> SEQUENCE: 235
000

<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 252
atggccctcc ctgtcaccgc tctgttgctg ccgcttgctc tgctgctcca cgcagcgcga 60
ccg 63

<210> SEQ ID NO 253
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 253
caggtacaat tgcaggagtc tggaggcggt gtggtgcaac ccggtcgcag cttgcgcctg 60
agttgtgctg cgtctggatt tacattttca tcttacggaa tgcattgggt acgccaggca 120
ccggggaaag gccttgaatg ggtggctgta atttcatacg atggttccaa caaatactat 180
gctgactcag tcaagggtcg atttacaatt agtcgggaca actccaagaa caccctttat 240
cttcaaatga attcccttag agcagaggat acggcggtct attactgtgg tggcagtggt 300
tatgcacttc atgatgatta ctatggcttg gatgtctggg ggcaagggac gcttgtaact 360
gtatcctctg gtggtggtgg tagtggtggg ggaggctccg gcggtggcgg ctctcaatct 420
gctctgactc aaccagcaag cgtatcaggg tcaccgggac agagtattac cataagttgc 480
acggggacct ctagcgatgt agggggggtat aattatgtat cttggtatca acaacacccc 540
gggaaagccc ctaaattgat gatctacgac gtgagcaatc gacctagtgg cgtatcaaat 600
cgcttctctg gtagcaagag tgggaatacg gcgtccctta ctattagcgg attgcaagca 660
gaagatgagg ccgattacta ctgcagctcc tatactagct cttctacatt gtacgtcttt 720
gggagcggaa caaaagtaac agtactc 747

<210> SEQ ID NO 254
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 254
acaacaacac ctgccccgag accgcctaca ccagccccga ctattgccag ccagcctctg 60
agcctcaggc ctgaggcctg taggcccgca gcgggcggcg cagttcatac acggggcttg 120
gatttcgctt gtgatattta tatttgggct cctttggcgg ggacatgtgg cgtgctgctt 180
ctgtcacttg ttattacact gtactgt 207

<210> SEQ ID NO 255
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 255
aaacgcgggc gaaaaaaatt gctgtatatt tttaagcagc catttatgag gcccgttcag 60
acgacgcagg aggaggacgg ttgctcttgc aggttcccag aagaggaaga agggggctgt 120
gaattg 126

<210> SEQ ID NO 256
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 256
cgggttaaat tttcaagatc cgcagacgct ccagcatacc aacagggaca aaaccaactc 60
tataacgagc tgaatcttgg aagaagggag gaatatgatg tgctggataa acggcgcggt 120
agagatccgg agatgggcgg aaaaccaagg cgaaaaaacc ctcaggaggg actctacaac 180
gaactgcaga aagacaaaat ggcggaggct tattccgaaa taggcatgaa gggcgagcgg 240
aggcgaggga aagggcacga cggactgtat caaggcctct caaccgcgac taaggatacg 300
tacgacgccc tgcacatgca ggccctgcct ccgaga 336

<210> SEQ ID NO 257
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 257

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Gly Gly Val
20 25 30

Val Gln Pro Gly Arg Ser Leu Arg Leu Ser Cys Ala Ala Ser Gly Phe
35 40 45

Thr Phe Ser Ser Tyr Gly Met His Trp Val Arg Gln Ala Pro Gly Lys
50 55 60

Gly Leu Glu Trp Val Ala Val Ile Ser Tyr Asp Gly Ser Asn Lys Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Gly Gly Ser Gly Tyr Ala Leu His Asp Asp Tyr
115 120 125

Tyr Gly Leu Asp Val Trp Gly Gln Gly Thr Leu Val Thr Val Ser Ser
130 135 140

Gly Gly Gly Gly Ser Gly Gly Gly Gly Ser Gly Gly Gly Gly Ser Gln
145 150 155 160

Ser Ala Leu Thr Gln Pro Ala Ser Val Ser Gly Ser Pro Gly Gln Ser
165 170 175

Ile Thr Ile Ser Cys Thr Gly Thr Ser Ser Asp Val Gly Gly Tyr Asn
180 185 190

Tyr Val Ser Trp Tyr Gln Gln His Pro Gly Lys Ala Pro Lys Leu Met
195 200 205

Ile Tyr Asp Val Ser Asn Arg Pro Ser Gly Val Ser Asn Arg Phe Ser
210 215 220

Gly Ser Lys Ser Gly Asn Thr Ala Ser Leu Thr Ile Ser Gly Leu Gln
225 230 235 240

Ala Glu Asp Glu Ala Asp Tyr Tyr Cys Ser Ser Tyr Thr Ser Ser Ser
245 250 255

Thr Leu Tyr Val Phe Gly Ser Gly Thr Lys Val Thr Val Leu Thr Thr
260 265 270

Thr Pro Ala Pro Arg Pro Pro Thr Pro Ala Pro Thr Ile Ala Ser Gln
275 280 285

Pro Leu Ser Leu Arg Pro Glu Ala Cys Arg Pro Ala Ala Gly Gly Ala
290 295 300

Val His Thr Arg Gly Leu Asp Phe Ala Cys Asp Ile Tyr Ile Trp Ala
305 310 315 320

```
Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

```
<210> SEQ ID NO 258
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258

atggccctcc ctgtcaccgc tctgttgctg ccgcttgctc tgctgctcca cgcagcgcga     60

ccgcaggtac aattgcagga gtctggaggc ggtgtggtgc aacccggtcg cagcttgcgc    120

ctgagttgtg ctgcgtctgg atttacattt tcatcttacg gaatgcattg ggtacgccag    180

gcaccgggga aaggccttga atgggtggct gtaatttcat acgatggttc caacaaatac    240

tatgctgact cagtcaaggg tcgatttaca attagtcggg acaactccaa gaacaccctt    300

tatcttcaaa tgaattccct tagagcagag gatacggcgg tctattactg tggtggcagt    360

ggttatgcac ttcatgatga ttactatggc ttggatgtct gggggcaagg gacgcttgta    420

actgtatcct ctggtggtgg tggtagtggt gggggaggct ccggcggtgg cggctctcaa    480

tctgctctga ctcaaccagc aagcgtatca gggtcaccgg gacagagtat taccataagt    540

tgcacgggga cctctagcga tgtagggggg tataattatg tatcttggta tcaacaacac    600

cccgggaaag cccctaaatt gatgatctac gacgtgagca atcgacctag tggcgtatca    660

aatcgcttct ctggtagcaa gagtgggaat acggcgtccc ttactattag cggattgcaa    720

gcagaagatg aggccgatta ctactgcagc tcctatacta gctcttctac attgtacgtc    780

tttgggagcg gaacaaaagt aacagtactc acaacaacac ctgccccgag accgcctaca    840

ccagccccga ctattgccag ccagcctctg agcctcaggc ctgaggcctg taggcccgca    900

gcgggcggcg cagttcatac acggggcttg gatttcgctt gtgatattta tatttgggct    960

cctttggcgg ggacatgtgg cgtgctgctt ctgtcacttg ttattacact gtactgtaaa   1020
```

-continued

```
cgcgggcgaa aaaaattgct gtatattttt aagcagccat ttatgaggcc cgttcagacg   1080

acgcaggagg aggacggttg ctcttgcagg ttcccagaag aggaagaagg gggctgtgaa   1140

ttgcgggtta aattttcaag atccgcagac gctccagcat accaacaggg acaaaaccaa   1200

ctctataacg agctgaatct tggaagaagg gaggaatatg atgtgctgga taaacggcgc   1260

ggtagagatc cggagatggg cggaaaacca aggcgaaaaa accctcagga gggactctac   1320

aacgaactgc agaaagacaa aatggcggag gcttattccg aaataggcat gaagggcgag   1380

cggaggcgag ggaaagggca cgacggactg tatcaaggcc tctcaaccgc gactaaggat   1440

acgtacgacg ccctgcacat gcaggccctg cctccgaga                          1479
```

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 275

```
Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95
```

```
Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130


<210> SEQ ID NO 276
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105


<210> SEQ ID NO 277
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90


<210> SEQ ID NO 278
<211> LENGTH: 95
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 278

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 279
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 279

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 280
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 280

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala

```
65                  70                  75                  80

Trp Asp Leu Tyr Tyr His Val Phe Arg Arg Ile Ser Lys Thr Ser
                85                  90                  95


<210> SEQ ID NO 281
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 281

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95


<210> SEQ ID NO 282
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 283
<211> LENGTH: 95
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 283

```
Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```

<210> SEQ ID NO 284
<211> LENGTH: 1132
<212> TYPE: PRT
<213> ORGANISM: Homo sapiens

<400> SEQUENCE: 284

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255
```

```
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

```
Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                 1005

Ala Tyr  Arg Phe His Ala Cys  Val Leu Gln Leu Pro  Phe His Gln
    1010                 1015                 1020

Gln Val  Trp Lys Asn Pro Thr  Phe Phe Leu Arg Val  Ile Ser Asp
    1025                 1030                 1035

Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Val  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
```

```
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130


<210> SEQ ID NO 285
<211> LENGTH: 253
<212> TYPE: PRT
<213> ORGANISM: Homo sapiens

<400> SEQUENCE: 285

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Met Leu Ser Asn
            20                  25                  30

Ser Asp Thr Trp Asn Trp Ile Arg Gln Ser Pro Ser Arg Gly Leu Glu
        35                  40                  45

Trp Leu Gly Arg Thr Tyr His Arg Ser Thr Trp Tyr Asp Asp Tyr Ala
    50                  55                  60

Ser Ser Val Arg Gly Arg Val Ser Ile Asn Val Asp Thr Ser Lys Asn
65                  70                  75                  80

Gln Tyr Ser Leu Gln Leu Asn Ala Val Thr Pro Glu Asp Thr Gly Val
                85                  90                  95

Tyr Tyr Cys Ala Arg Val Arg Leu Gln Asp Gly Asn Ser Trp Ser Asp
            100                 105                 110

Ala Phe Asp Val Trp Gly Gln Gly Thr Met Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Ala Ser Ala Ser Gly Ser Pro Gly Gln Ser Val
145                 150                 155                 160

Thr Ile Ser Cys Thr Gly Thr Ser Ser Asp Val Gly Gly Tyr Asn Tyr
                165                 170                 175

Val Ser Trp Tyr Gln Gln His Pro Gly Lys Ala Pro Lys Leu Met Ile
            180                 185                 190

Tyr Asp Val Ser Asn Arg Pro Ser Gly Val Ser Asn Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Ser Ser Tyr Thr Ser Ser Ser Thr
225                 230                 235                 240

Leu Tyr Val Phe Gly Thr Gly Thr Gln Leu Thr Val Leu
                245                 250


<210> SEQ ID NO 286
<211> LENGTH: 127
<212> TYPE: PRT
<213> ORGANISM: Homo sapiens

<400> SEQUENCE: 286

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Met Leu Ser Asn
```

```
            20                  25                  30

Ser Asp Thr Trp Asn Trp Ile Arg Gln Ser Pro Ser Arg Gly Leu Glu
        35                  40                  45

Trp Leu Gly Arg Thr Tyr His Arg Ser Thr Trp Tyr Asp Asp Tyr Ala
    50                  55                  60

Ser Ser Val Arg Gly Arg Val Ser Ile Asn Val Asp Thr Ser Lys Asn
65                  70                  75                  80

Gln Tyr Ser Leu Gln Leu Asn Ala Val Thr Pro Glu Asp Thr Gly Val
                85                  90                  95

Tyr Tyr Cys Ala Arg Val Arg Leu Gln Asp Gly Asn Ser Trp Ser Asp
            100                 105                 110

Ala Phe Asp Val Trp Gly Gln Gly Thr Met Val Thr Val Ser Ser
        115                 120                 125


<210> SEQ ID NO 287
<211> LENGTH: 111
<212> TYPE: PRT
<213> ORGANISM: Homo sapiens

<400> SEQUENCE: 287

Gln Ser Ala Leu Thr Gln Pro Ala Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Gln Leu Thr Val Leu
            100                 105                 110


<210> SEQ ID NO 288
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gly Asp Ser Met Leu Ser Asn Ser Asp Thr Trp Asn
1               5                   10


<210> SEQ ID NO 289
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Ser Asn Ser Asp Thr Trp Asn
1               5
```

<210> SEQ ID NO 290
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 290

```
Arg Thr Tyr His Arg Ser Thr Trp Tyr Asp Asp Tyr Ala Ser Ser Val
1               5                   10                  15

Arg Gly
```

<210> SEQ ID NO 291
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 291

```
Val Arg Leu Gln Asp Gly Asn Ser Trp Ser Asp Ala Phe Asp Val
1               5                   10                  15
```

<210> SEQ ID NO 292
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 292

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190
```

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser Thr Thr Thr Pro Ala Pro Arg Pro Pro Thr Pro Ala Pro Thr
245 250 255

Ile Ala Ser Gln Pro Leu Ser Leu Arg Pro Glu Ala Cys Arg Pro Ala
260 265 270

Ala Gly Gly Ala Val His Thr Arg Gly Leu Asp Phe Ala Cys Asp Ile
275 280 285

Tyr Ile Trp Ala Pro Leu Ala Gly Thr Cys Gly Val Leu Leu Leu Ser
290 295 300

Leu Val Ile Thr Leu Tyr Cys Lys Arg Gly Arg Lys Lys Leu Leu Tyr
305 310 315 320

Ile Phe Lys Gln Pro Phe Met Arg Pro Val Gln Thr Thr Gln Glu Glu
325 330 335

Asp Gly Cys Ser Cys Arg Phe Pro Glu Glu Glu Glu Gly Gly Cys Glu
340 345 350

Leu Arg Val Lys Phe Ser Arg Ser Ala Asp Ala Pro Ala Tyr Lys Gln
355 360 365

Gly Gln Asn Gln Leu Tyr Asn Glu Leu Asn Leu Gly Arg Arg Glu Glu
370 375 380

Tyr Asp Val Leu Asp Lys Arg Arg Gly Arg Asp Pro Glu Met Gly Gly
385 390 395 400

Lys Pro Arg Arg Lys Asn Pro Gln Glu Gly Leu Tyr Asn Glu Leu Gln
405 410 415

Lys Asp Lys Met Ala Glu Ala Tyr Ser Glu Ile Gly Met Lys Gly Glu
420 425 430

Arg Arg Arg Gly Lys Gly His Asp Gly Leu Tyr Gln Gly Leu Ser Thr
435 440 445

Ala Thr Lys Asp Thr Tyr Asp Ala Leu His Met Gln Ala Leu Pro Pro
450 455 460

Arg
465

<210> SEQ ID NO 293
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 293

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
130 135 140

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

Glu Thr Thr Tyr Tyr Gln Ser Ser Leu Lys Ser Arg Val Thr Ile Ser
180 185 190

Lys Asp Asn Ser Lys Asn Gln Val Ser Leu Lys Leu Ser Ser Val Thr
195 200 205

Ala Ala Asp Thr Ala Val Tyr Tyr Cys Ala Lys His Tyr Tyr Tyr Gly
210 215 220

Gly Ser Tyr Ala Met Asp Tyr Trp Gly Gln Gly Thr Leu Val Thr Val
225 230 235 240

Ser Ser

<210> SEQ ID NO 294
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 294

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
130 135 140

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

```
Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465


<210> SEQ ID NO 295
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Asp Tyr Gly Val Ser
1               5


<210> SEQ ID NO 296
<211> LENGTH: 16
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic peptide"

<400> SEQUENCE: 296

Val Ile Trp Gly Ser Glu Thr Thr Tyr Tyr Asn Ser Ala Leu Lys Ser
1 5 10 15

<210> SEQ ID NO 297
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 297

His Tyr Tyr Tyr Gly Gly Ser Tyr Ala Met Asp Tyr
1 5 10

<210> SEQ ID NO 298
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 298

Arg Ala Ser Gln Asp Ile Ser Lys Tyr Leu Asn
1 5 10

<210> SEQ ID NO 299
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 299

His Thr Ser Arg Leu His Ser
1 5

<210> SEQ ID NO 300
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 300

Gln Gln Gly Asn Thr Leu Pro Tyr Thr
1 5

<210> SEQ ID NO 301
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 301

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ile Lys Asp Asn Ser Lys Ser Gln Val Phe Leu Lys
210 215 220

Met Asn Ser Leu Gln Thr Asp Asp Thr Ala Ile Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Lys Arg Gly Arg
325 330 335

Lys Lys Leu Leu Tyr Ile Phe Lys Gln Pro Phe Met Arg Pro Val Gln
340 345 350

Thr Thr Gln Glu Glu Asp Gly Cys Ser Cys Arg Phe Pro Glu Glu Glu
355 360 365

Glu Gly Gly Cys Glu Leu Arg Val Lys Phe Ser Arg Ser Ala Asp Ala
370 375 380

Pro Ala Tyr Lys Gln Gly Gln Asn Gln Leu Tyr Asn Glu Leu Asn Leu
385 390 395 400

Gly Arg Arg Glu Glu Tyr Asp Val Leu Asp Lys Arg Arg Gly Arg Asp
405 410 415

```
Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 302
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 302

```
atggccttac cagtgaccgc cttgctcctg ccgctggcct tgctgctcca cgccgccagg     60

ccggacatcc agatgacaca gactacatcc tccctgtctg cctctctggg agacagagtc    120

accatcagtt gcagggcaag tcaggacatt agtaaatatt taaattggta tcagcagaaa    180

ccagatggaa ctgttaaact cctgatctac catacatcaa gattacactc aggagtccca    240

tcaaggttca gtggcagtgg gtctggaaca gattattctc tcaccattag caacctggag    300

caagaagata ttgccactta cttttgccaa cagggtaata cgcttccgta cacgttcgga    360

ggggggacca agctggagat cacaggtggc ggtggctcgg gcggtggtgg gtcgggtggc    420

ggcggatctg aggtgaaact gcaggagtca ggacctggcc tggtggcgcc ctcacagagc    480

ctgtccgtca catgcactgt ctcaggggtc tcattacccg actatggtgt aagctggatt    540

cgccagcctc cacgaaaggg tctggagtgg ctgggagtaa tatggggtag tgaaaccaca    600

tactataatt cagctctcaa atccagactg accatcatca aggacaactc caagagccaa    660

gttttcttaa aaatgaacag tctgcaaact gatgacacag ccatttacta ctgtgccaaa    720

cattattact acggtggtag ctatgctatg gactactggg gccaaggaac ctcagtcacc    780

gtctcctcaa ccacgacgcc agcgccgcga ccaccaacac cggcgcccac catcgcgtcg    840

cagcccctgt ccctgcgccc agaggcgtgc cggccagcgg cggggggcgc agtgcacacg    900

agggggctgg acttcgcctg tgatatctac atctgggcgc ccttggccgg gacttgtggg    960

gtccttctcc tgtcactggt tatcaccctt tactgcaaac ggggcagaaa gaaactcctg   1020

tatatattca aacaaccatt tatgagacca gtacaaacta ctcaagagga agatggctgt   1080

agctgccgat ttccagaaga agaagaagga ggatgtgaac tgagagtgaa gttcagcagg   1140

agcgcagacg cccccgcgta caagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgc                                                 1458
```

<210> SEQ ID NO 303
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 303

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 304
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 304

```
Val Ile Trp Gly Ser Glu Thr Thr Tyr Tyr Gln Ser Ser Leu Lys Ser
1               5                   10                  15
```

<210> SEQ ID NO 305
<211> LENGTH: 813
<212> TYPE: DNA
<213> ORGANISM: Artificial Sequence
<220> FEATURE:

-continued

<221> NAME/KEY: source
<223> OTHER INFORMATION: /note="Description of Artificial Sequence: Synthetic polynucleotide"

<400> SEQUENCE: 305

```
atggccctcc ctgtcaccgc cctgctgctt ccgctggctc ttctgctcca cgccgctcgg     60

cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcc aggtccaact ccaagaaagc ggaccgggtc ttgtgaagcc atcagaaact    480

ctttcactga cttgtactgt gagcggagtg tctctccccg attacggggt gtcttggatc    540

agacagccac cggggaaggg tctggaatgg attggagtga tttggggctc tgagactact    600

tactaccaat catccctcaa gtcacgcgtc accatctcaa aggacaactc taagaatcag    660

gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagcc accaccatca tcaccatcac cat                                 813
```

<210> SEQ ID NO 306
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175
```

```
Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 307
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 307

```
atggccctcc ctgtcaccgc cctgctgctt ccgctggctc ttctgctcca cgccgctcgg      60

cccgaaattg tgatgaccca gtcacccgcc actcttagcc tttcacccgg tgagcgcgca     120

accctgtctt gcagagcctc ccaagacatc tcaaaatacc ttaattggta tcaacagaag     180

cccggacagg ctcctcgcct tctgatctac cacaccagcc ggctccattc tggaatccct     240
```

gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactaccaat catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagca ccactacccc agcaccgagg ccacccaccc cggctcctac catcgcctcc 840
cagcctctgt ccctgcgtcc ggaggcatgt agacccgcag ctggtggggc cgtgcatacc 900
cggggtcttg acttcgcctg cgatatctac atttgggccc ctctggctgg tacttgcggg 960
gtcctgctgc tttcactcgt gatcactctt tactgtaagc gcggtcggaa gaagctgctg 1020
tacatcttta agcaaccctt catgaggcct gtgcagacta ctcaagagga ggacggctgt 1080
tcatgccggt tcccagagga ggaggaaggc ggctgcgaac tgcgcgtgaa attcagccgc 1140
agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 308
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 308

Leu Ala Glu Ala Ala Ala Lys
1 5

<210> SEQ ID NO 309
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 309

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu

-continued

```
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ile Thr Cys Pro Pro Pro Met Ser Val Glu His Ala Asp Ile
        115                 120                 125

Trp Val Lys Ser Tyr Ser Leu Tyr Ser Arg Glu Arg Tyr Ile Cys Asn
    130                 135                 140

Ser Gly Phe Lys Arg Lys Ala Gly Thr Ser Ser Leu Thr Glu Cys Val
145                 150                 155                 160

Leu Asn Lys Ala Thr Asn Val Ala His Trp Thr Thr Pro Ser Leu Lys
                165                 170                 175

Cys Ile Arg Asp Pro Ala Leu Val His Gln Arg Pro Ala Pro Pro Ser
            180                 185                 190

Thr Val Thr Thr Ala Gly Val Thr Pro Gln Pro Glu Ser Leu Ser Pro
        195                 200                 205

Ser Gly Lys Glu Pro Ala Ala Ser Ser Pro Ser Ser Asn Asn Thr Ala
    210                 215                 220

Ala Thr Thr Ala Ala Ile Val Pro Gly Ser Gln Leu Met Pro Ser Lys
225                 230                 235                 240

Ser Pro Ser Thr Gly Thr Thr Glu Ile Ser Ser His Glu Ser Ser His
                245                 250                 255

Gly Thr Pro Ser Gln Thr Thr Ala Lys Asn Trp Glu Leu Thr Ala Ser
            260                 265                 270

Ala Ser His Gln Pro Pro Gly Val Tyr Pro Gln Gly
        275                 280
```

METHODS OF MAKING CHIMERIC ANTIGEN RECEPTOR-EXPRESSING CELLS

RELATED APPLICATIONS

This application is a U.S. National Stage Application under 35 U.S.C. § 371 of International Application No. PCT/US2019/049127, filed Aug. 30, 2019, which claims priority to U.S. Provisional Application 62/726,155 filed on Aug. 31, 2018, U.S. Provisional Application 62/773,679 filed on Nov. 30, 2018, and U.S. Provisional Application 62/858,482 filed on Jun. 7, 2019, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Aug. 16, 2019, is named N2067-7153WO-_SL.txt and is 260,532 bytes in size.

FIELD OF THE INVENTION

The present invention relates generally to methods of making immune effector cells (for example, T cells or NK cells) engineered to express a Chimeric Antigen Receptor (CAR), and compositions comprising the same.

BACKGROUND OF THE INVENTION

Adoptive cell transfer (ACT) therapy with T cells, especially with T cells transduced with Chimeric Antigen Receptors (CARs), has shown promise in several hematologic cancer trials. The manufacture of gene-modified T cells is currently a complex process. There exists a need for methods and processes to improve production of the CAR-expressing cell therapy product, enhance product quality, and maximize the therapeutic efficacy of the product.

SUMMARY OF THE INVENTION

The present disclosure pertains to methods of making immune effector cells (for example, T cells or NK cells) engineered to express a CAR, and compositions generated using such methods. Also disclosed are methods of using such compositions for treating a disease, for example, cancer, in a subject.

In some embodiments, this invention features a method of making a population of cells (for example, T cells) that express a chimeric antigen receptor (CAR), the method comprising: (i) contacting (for example, binding) a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule (for example, a DNA or RNA molecule) encoding the CAR, thereby providing a population of cells (for example, T cells) comprising the nucleic acid molecule, and (iii) harvesting the population of cells (for example, T cells) for storage (for example, reformulating the population of cells in cryopreservation media) or administration, wherein: (a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 26 hours after the beginning of step (i), for example, no later than 22, 23, 24, or 25 hours after the beginning of step (i), for example, no later than 24 hours after the beginning of step (i); (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii); or (c) the population of cells from step (iii) are not expanded, or expanded by no more than 5, 6, 7, 8, 9, 10, 11, 12, 13, 14, 15, 16, 17, 18, 19, 20, 25, 30, 35, or 40%, for example, no more than 10%, for example, as assessed by the number of living cells, compared to the population of cells at the beginning of step (i). In some embodiments, the nucleic acid molecule in step (ii) is a DNA molecule. In some embodiments, the nucleic acid molecule in step (ii) is an RNA molecule. In some embodiments, the nucleic acid molecule in step (ii) is on a viral vector, for example, a viral vector chosen from a lentivirus vector, an adenoviral vector, or a retrovirus vector. In some embodiments, the nucleic acid molecule in step (ii) is on a non-viral vector. In some embodiments, the nucleic acid molecule in step (ii) is on a plasmid. In some embodiments, the nucleic acid molecule in step (ii) is not on any vector. In some embodiments, step (ii) comprises transducing the population of cells (for example, T cells) with a viral vector comprising a nucleic acid molecule encoding the CAR. In some embodiments, step (ii) is performed together with step (i). In some embodiments, step (ii) is performed no later than 20 hours after the beginning of step (i). In some embodiments, step (ii) is performed no later than 12, 13, 14, 15, 16, 17, or 18 hours after the beginning of step (i). In some embodiments, step (ii) is performed no later than 18 hours after the beginning of step (i). In some embodiments, step (iii) is performed no later than 26 hours after the beginning of step (i). In some embodiments, step (iii) is performed no later than 22, 23, 24, or 25 hours after the beginning of step (i). In some embodiments, step (iii) is performed no later than 24 hours after the beginning of step (i). In some embodiments, step (iii) is performed no later than 30 hours after the beginning of step (ii). In some embodiments, step (iii) is performed no later than 22, 23, 24, 25, 26, 27, 28, 29, or 30 hours after the beginning of step (ii).

In some embodiments, the population of cells from step (iii) are not expanded. In some embodiments, the population of cells from step (iii) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (i). In some embodiments, the population of cells from step (iii) are expanded by no more than 10%, for example, as assessed by the number of living cells, compared to the population of cells at the beginning of step (i).

In some embodiments, the agent that stimulates a CD3/TCR complex is an agent that stimulates CD3. In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a CD3/TCR complex does not comprise a bead. In some embodiments, the agent that stimulates a costimulatory molecule does not comprise a bead. In some embodiments, the agent that stimulates a CD3/TCR complex comprises an anti-CD3 antibody. In some embodiments, the agent that stimulates a costimulatory molecule comprises an anti-CD28 antibody. In some embodiments, the agent that stimulates a CD3/TCR complex comprises an anti-CD3 antibody covalently attached to a colloidal polymeric nanomatrix. In some embodiments, the agent that stimulates a costimulatory molecule comprises an anti-CD28 antibody covalently attached to a colloidal polymeric nanomatrix. In some embodiments, the agent that stimulates a CD3/TCR complex and the agent that stimulates a costimulatory molecule comprise T Cell TransAct™.

In some embodiments, the agent that stimulates a CD3/TCR complex does not comprise hydrogel. In some embodiments, the agent that stimulates a costimulatory molecule does not comprise hydrogel. In some embodiments, the agent that stimulates a CD3/TCR complex does not comprise alginate. In some embodiments, the agent that stimulates a costimulatory molecule does not comprise alginate.

In some embodiments, the agent that stimulates a CD3/TCR complex comprises hydrogel. In some embodiments, the agent that stimulates a costimulatory molecule comprises hydrogel. In some embodiments, the agent that stimulates a CD3/TCR complex comprises alginate. In some embodiments, the agent that stimulates a costimulatory molecule comprises alginate. In some embodiments, the agent that stimulates a CD3/TCR complex or the agent that stimulates a costimulatory molecule comprises MagCloudz™ from Quad Technologies.

In some embodiments, step (i) increases the percentage of CAR-expressing cells in the population of cells from step (iii), for example, the population of cells from step (iii) shows a higher percentage of CAR-expressing cells (for example, at least 10, 20, 30, 40, 50, or 60% higher), compared with cells made by an otherwise similar method without step (i).

In some embodiments, the percentage of naïve cells, for example, naïve T cells, for example, CD45RA+ CD45RO− CCR7+ T cells, in the population of cells from step (iii) is the same as the percentage of naïve cells, for example, naïve T cells, for example, CD45RA+ CD45RO− CCR7+ cells, in the population of cells at the beginning of step (i). In some embodiments, the percentage of naïve cells, for example, naïve T cells, for example, CD45RA+ CD45RO− CCR7+ T cells, in the population of cells from step (iii) differs by no more than 3, 4, 5, 6, 7, 8, 9, 10, 11, or 12% from the percentage of naïve cells, for example, naïve T cells, for example, CD45RA+ CD45RO− CCR7+ cells, in the population of cells at the beginning of step (i). In some embodiments, the percentage of naïve cells, for example, naïve T cells, for example, CD45RA+ CD45RO− CCR7+ T cells, in the population of cells from step (iii) differs by no more than 5 or 10% from the percentage of naïve cells, for example, naïve T cells, for example, CD45RA+ CD45RO− CCR7+ cells, in the population of cells at the beginning of step (i).

In some embodiments, the population of cells from step (iii) shows a higher percentage of naïve cells, for example, naïve T cells, for example, CD45RA+ CD45RO− CCR7+ T cells (for example, at least 10, 11, 12, 13, 14, 15, 16, 17, 18, 19, 20, 25, 30, 35, or 40% higher), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii) shows a higher percentage of naïve cells, for example, naïve T cells, for example, CD45RA+ CD45RO− CCR7+ T cells (for example, at least 10, 11, 12, 13, 14, 15, 16, 17, 18, 19, 20, 25, 30, 35, or 40% higher), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the percentage of central memory cells, for example, central memory T cells, for example, CD95+ central memory T cells, in the population of cells from step (iii) is the same as the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (iii) differs by no more than 3, 4, 5, 6, 7, 8, 9, 10, 11, or 12% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (iii) differs by no more than 5 or 10% from the percentage of central memory cells, for example, central memory T cells, for example, CD95+ central memory T cells, in the population of cells at the beginning of step (i).

In some embodiments, the population of cells from step (iii) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the percentage of stem memory T cells, for example, CD45RA+CD95+IL-2 receptor β+CCR7+CD62L+ T cells, in the population of cells from step (iii) is increased, as compared to the percentage of stem memory T cells, for example, CD45RA+CD95+IL-2 receptor β+CCR7+CD62L+ T cells, in the population of cells at the beginning of step (i). In some embodiments, the percentage of CAR-expressing stem memory T cells, for example, CAR-expressing CD45RA+CD95+IL-2 receptor β+CCR7+CD62L+ T cells, in the population of cells from step (iii) is increased, as compared to the percentage of CAR-expressing stem memory T cells, for example, CAR-expressing CD45RA+CD95+IL-2 receptor β+CCR7+ CD62L+ T cells, in the population of cells at the beginning of step (i). In some embodiments, the percentage of stem memory T cells, for example, CD45RA+CD95+IL-2 receptor β+CCR7+CD62L+ T cells, in the population of cells from step (iii) is higher than the percentage of stem memory T cells, for example, CD45RA+CD95+IL-2 receptor β+CCR7+CD62L+ T cells, in cells made by an otherwise similar method in which step (iii) is performed more than 26 hours after the beginning of step (i), for example, more than 5, 6, 7, 8, 9, 10, 11, or 12 days after the beginning of step (i). In some embodiments, the percentage of CAR-expressing stem memory T cells, for example, CAR-expressing CD45RA+CD95+IL-2 receptor β+CCR7+CD62L+ T cells, in the population of cells from step (iii) is higher than the percentage of CAR-expressing stem memory T cells, for example, CAR-expressing CD45RA+CD95+IL-2 receptor β+CCR7+CD62L+ T cells, in cells made by an otherwise similar method in which step (iii) is performed more than 26 hours after the beginning of step (i), for example, more than 5, 6, 7, 8, 9, 10, 11, or 12 days after the beginning of step (i). In some embodiments, the percentage of stem memory T cells, for example, CD45RA+CD95+IL-2 receptor β+CCR7+CD62L+ T cells, in the population of cells from step (iii) is higher than the percentage of stem memory T cells, for example, CD45RA+CD95+IL-2 receptor β+CCR7+CD62L+ T cells, in cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the percentage of CAR-expressing stem memory T cells, for example, CAR-expressing CD45RA+CD95+IL-2 receptor β+CCR7+ CD62L+ T cells, in the population of cells from step (iii) is higher than the percentage of CAR-expressing stem memory T cells, for example, CAR-expressing CD45RA+CD95+ IL-2 receptor β+CCR7+CD62L+ T cells, in cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the median GeneSetScore (Up TEM vs. Down TSCM) of the population of cells from step (iii) is about the same as or differs by no more than (for example, increased by no more than) about 25, 50, 75, 100, or 125% from the median GeneSetScore (Up TEM vs. Down TSCM) of the population of cells at the beginning of step (i). In some embodiments, the median GeneSetScore (Up TEM vs. Down TSCM) of the population of cells from step (iii) is lower (for example, at least about 100, 150, 200, 250, or 300% lower) than the median GeneSetScore (Up TEM vs. Down TSCM) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up TEM vs. Down TSCM) of the population of cells from step (iii) is lower (for example, at least about 100, 150, 200, 250, or 300% lower) than the median GeneSetScore (Up TEM vs. Down TSCM) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up Treg vs. Down Teff) of the population of cells from step (iii) is about the same as or differs by no more than (for example, increased by no more than) about 25, 50, 100, 150, or 200% from the median GeneSetScore (Up Treg vs. Down Teff) of the population of cells at the beginning of step (i). In some embodiments, the median GeneSetScore (Up Treg vs. Down Teff) of the population of cells from step (iii) is lower (for example, at least about 50, 100, 125, 150, or 175% lower) than the median GeneSetScore (Up Treg vs. Down Teff) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up Treg vs. Down Teff) of the population of cells from step (iii) is lower (for example, at least about 50, 100, 125, 150, or 175% lower) than the median GeneSetScore (Up Treg vs. Down Teff) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Down stemness) of the population of cells from step (iii) is about the same as or differs by no more than (for example, increased by no more than) about 25, 50, 100, 150, 200, or 250% from the median GeneSetScore (Down stemness) of the population of cells at the beginning of step (i). In some embodiments, the median GeneSetScore (Down stemness) of the population of cells from step (iii) is lower (for example, at least about 50, 100, or 125% lower) than the median GeneSetScore (Down stemness) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Down stemness) of the population of cells from step (iii) is lower (for example, at least about 50, 100, or 125% lower) than the median GeneSetScore (Down stemness) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up hypoxia) of the population of cells from step (iii) is about the same as or differs by no more than (for example, increased by no more than) about 125, 150, 175, or 200% from the median GeneSetScore (Up hypoxia) of the population of cells at the beginning of step (i). In some embodiments, the median GeneSetScore (Up hypoxia) of the population of cells from step (iii) is lower (for example, at least about 40, 50, 60, 70, or 80% lower) than the median GeneSetScore (Up hypoxia) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up hypoxia) of the population of cells from step (iii) is lower (for example, at least about 40, 50, 60, 70, or 80% lower) than the median GeneSetScore (Up hypoxia) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up autophagy) of the population of cells from step (iii) is about the same as or differs by no more than (for example, increased by no more than) about 180, 190, 200, or 210% from the median GeneSetScore (Up autophagy) of the population of cells at the beginning of step (i). In some embodiments, the median GeneSetScore (Up autophagy) of the population of cells from step (iii) is lower (for example, at least 20, 30, or 40% lower) than the median GeneSetScore (Up autophagy) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up autophagy) of the population of cells from step (iii) is lower (for example, at least 20, 30, or 40% lower) than the median GeneSetScore (Up autophagy) of cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii), after being incubated with a cell expressing an antigen recognized by the CAR, secretes IL-2 at a higher level (for example, at least 2, 4, 6, 8, 10, 12, or 14-fold higher) than cells made by an otherwise similar method in which step (iii) is performed more than 26 hours after the beginning of step (i), for example, more than 5, 6, 7, 8, 9, 10, 11, or 12 days after the beginning of step (i), or cells made by an otherwise similar method which further comprises, after step (ii) and prior to step (iii), expanding the population of cells (for example, T cells) in vitro for more than 3 days, for example, for 5, 6, 7, 8 or 9 days, for example, as assessed using methods described in Example 8 with respect to FIGS. 29C-29D.

In some embodiments, the population of cells from step (iii), after being administered in vivo, persists longer or expands at a higher level (for example, at least 20, 25, 30, 35, 40, 45, 50, 55, 60, 65, 70, 75, 80, 85, or 90% higher) (for example, as assessed using methods described in Example 1 with respect to FIG. 4C), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii), after being administered in vivo, persists longer or expands at a higher level (for example, at least 20, 25, 30, 35, 40, 45, 50, 55, 60, 65, 70, 75, 80, 85, or 90% higher) (for example, as assessed using methods described in Example 1 with respect to FIG. 4C), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii), after being administered in vivo, shows a stronger anti-tumor activity (for example, a stronger anti-tumor activity at a low dose, for example, a dose no more than $0.15\times10^6$, $0.2\times10^6$, $0.25\times10^6$, or $0.3\times10^6$ viable CAR-expressing cells) than cells made by an otherwise similar method in which step (iii) is performed more than 26 hours after the beginning of step (i), for example, more than 5, 6, 7, 8, 9, 10, 11, or 12 days after the beginning of step (i), or cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii) are not expanded, for example, as assessed by the number of living cells, compared to the population of cells at the beginning of step (i). In some embodiments, the population of cells from step (iii) decreases from the number of living cells in the population of cells at the beginning of step (i), for example, as assessed by the number of living cells. In some embodiments, the population of cells from step (iii) are expanded by no more than 5, 6, 7, 8, 9, 10, 11, 12, 13, 14, 15, 16, 17, 18, 19, 20, 25, 30, 35, or 40%, for example, no more than 10%, for example, as assessed by the number of living cells, compared to the population of cells at the beginning of step (i). In some embodiments, the population of cells from step (iii) are not expanded, or expanded by less than 0.5, 1, 1.5, or 2 hours, for example, less than 1 or 1.5 hours, compared to the population of cells at the beginning of step (i).

In some embodiments, steps (i) and (ii) are performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, steps (i) and (ii) are performed in cell media (for example, serum-free media) comprising IL-7, IL-21, or a combination thereof. In some embodiments, steps (i) and (ii) are performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, step (i) is performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, step (ii) is performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, step (i) is performed in cell media (for example, serum-free media) comprising IL-7, IL-21, or a combination thereof. In some embodiments, step (ii) is performed in cell media (for example, serum-free media) comprising IL-7, IL-21, or a combination thereof. In some embodiments, step (i) is performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, step (ii) is performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, the cell media is a serum-free media comprising a serum replacement. In some embodiments, the serum replacement is CTS™ Immune Cell Serum Replacement (ICSR).

In some embodiments, the aforementioned methods further comprise prior to step (i): (iv) receiving a fresh leukapheresis product (or an alternative source of hematopoietic tissue such as a fresh whole blood product, a fresh bone marrow product, or a fresh tumor or organ biopsy or removal (for example, a fresh product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a fresh leukapheresis product (or an alternative source of hematopoietic tissue such as a fresh whole blood product, a fresh bone marrow product, or a fresh tumor or organ biopsy or removal (for example, a fresh product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the aforementioned methods further comprise prior to step (i): receiving cryopreserved T cells isolated from a leukapheresis product (or an alternative source of hematopoietic tissue such as cryopreserved T cells isolated from whole blood, bone marrow, or tumor or organ biopsy or removal (for example, thymectomy)) from an entity, for example, a laboratory, hospital, or healthcare provider.

In some embodiments, the aforementioned methods further comprise prior to step (i): (iv) receiving a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, this invention features a method of making a population of cells (for example, T cells) that express a chimeric antigen receptor (CAR), the method comprising: (1) contacting a population of cells (for example, T cells, for example, T cells isolated from a frozen leukapheresis product) with a cytokine chosen from IL-2, IL-7, IL-15, IL-21, IL-6, or a combination thereof, (2) contacting the population of cells (for example, T cells) with a nucleic acid molecule (for example, a DNA or RNA molecule) encoding the CAR, thereby providing a population of cells (for example, T cells) comprising the nucleic acid molecule, and (3) harvesting the population of cells (for example, T cells) for storage (for example, reformulating the population of cells in cryopreservation media) or administration, wherein: (a) step (2) is performed together with step (1) or no later than 5 hours after the beginning of step (1), for example, no later than 1, 2, 3, 4, or 5 hours after the beginning of step (1), and step (3) is performed no later than 26 hours after the beginning of step (1), for example, no later than 22, 23, 24, or 25 hours after the beginning of step (1), for example, no later than 24 hours after the beginning of step (1), or (b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1). In some embodiments, the nucleic acid molecule in step (2) is a DNA molecule. In some embodiments, the nucleic acid molecule in step (2) is an RNA molecule. In some embodiments, the nucleic acid molecule in step (2) is on a viral vector, for example, a viral vector chosen from a lentivirus vector, an adenoviral vector, or a retrovirus vector. In some embodiments, the nucleic acid molecule in step (2) is on a non-viral vector. In some embodiments, the nucleic acid molecule in step (2) is on a plasmid. In some embodiments, the nucleic acid molecule in step (2) is not on any vector. In some embodiments, step (2) comprises transducing the population of cells (for example, T cells) with a viral vector comprising a nucleic acid molecule encoding the CAR.

In some embodiments, step (2) is performed together with step (1). In some embodiments, step (2) is performed no later than 5 hours after the beginning of step (1). In some embodiments, step (2) is performed no later than 1, 2, 3, 4, or 5 hours after the beginning of step (1). In some embodiments, step (3) is performed no later than 26 hours after the beginning of step (1). In some embodiments, step (3) is performed no later than 22, 23, 24, or 25 hours after the beginning of step (1). In some embodiments, step (3) is performed no later than 24 hours after the beginning of step (1).

In some embodiments, the population of cells from step (3) are not expanded, for example, as assessed by the number of living cells, compared to the population of cells at the beginning of step (1). In some embodiments, the population of cells from step (3) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (1). In some embodiments, the population of cells from step (3) are expanded by no more than 10%, for example, as assessed by the number of living cells, compared to the population of cells at the beginning of step (1).

In some embodiments, step (1) comprises contacting the population of cells (for example, T cells) with IL-2. In some embodiments, step (1) comprises contacting the population of cells (for example, T cells) with IL-7. In some embodiments, step (1) comprises contacting the population of cells (for example, T cells) with IL-15 (for example, hetIL-15 (IL15/sIL-15Ra)). In some embodiments, step (1) comprises contacting the population of cells (for example, T cells) with IL-21. In some embodiments, step (1) comprises contacting the population of cells (for example, T cells) with IL-6 (for example, IL-6/sIL-6Ra). In some embodiments, step (1) comprises contacting the population of cells (for example, T cells) with IL-2 and IL-7. In some embodiments, step (1) comprises contacting the population of cells (for example, T cells) with IL-2 and IL-15 (for example, hetIL-15 (IL15/sIL-15Ra)). In some embodiments, step (1) comprises contacting the population of cells (for example, T cells) with IL-2 and IL-21. In some embodiments, step (1) comprises contacting the population of cells (for example, T cells) with IL-2 and IL-6 (for example, IL-6/sIL-6Ra). In some embodiments, step (1) comprises contacting the population of cells (for example, T cells) with IL-7 and IL-15 (for example, hetIL-15 (IL15/sIL-15Ra)). In some embodiments, step (1) comprises contacting the population of cells (for example, T cells) with IL-7 and IL-21. In some embodiments, step (1) comprises contacting the population of cells (for example, T cells) with IL-7 and IL-6 (for example, IL-6/sIL-6Ra). In some embodiments, step (1) comprises contacting the population of cells (for example, T cells) with IL-15 (for example, hetIL-15 (IL15/sIL-15Ra)) and IL-21. In some embodiments, step (1) comprises contacting the population of cells (for example, T cells) with IL-15 (for example, hetIL-15 (IL15/sIL-15Ra)) and IL-6 (for example, IL-6/sIL-6Ra). In some embodiments, step (1) comprises contacting the population of cells (for example, T cells) with IL-21 and IL-6 (for example, IL-6/sIL-6Ra). In some embodiments, step (1) comprises contacting the population of cells (for example, T cells) with IL-7, IL-15 (for example, hetIL-15 (IL15/sIL-15Ra)), and IL-21.

In some embodiments, the population of cells from step (3) shows a higher percentage of naïve cells among CAR-expressing cells (for example, at least 10, 11, 12, 13, 14, 15, 16, 17, 18, 19, 20, 25, 30, 35, or 40% higher), compared with cells made by an otherwise similar method which further comprises contacting the population of cells with, for example, an anti-CD3 antibody.

In some embodiments, the percentage of naïve cells, for example, naïve T cells, for example, CD45RA+ CD45RO− CCR7+ T cells, in the population of cells from step (3) is the same as the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) differs by no more than 3, 4, 5, 6, 7, 8, 9, 10, 11, or 12% from the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) differs by no more than 5 or 10% from the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) is increased as compared to the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) is increased by at least 10, 11, 12, 13, 14, 15, 16, 17, 18, 19, or 20%, as compared to the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) is increased by at least 10 or 20%, as compared to the percentage of naïve cells, for example, naïve T cells, for example, CD45RA+ CD45RO− CCR7+ cells, in the population of cells at the beginning of step (1).

In some embodiments, the population of cells from step (3) shows a higher percentage of naïve cells, for example, naïve T cells, for example, CD45RA+ CD45RO− CCR7+ T cells (for example, at least 10, 11, 12, 13, 14, 15, 16, 17, 18, 19, 20, 25, 30, 35, or 40% higher), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3) shows a higher percentage of naïve cells, for example, naïve T cells, for example, CD45RA+ CD45RO− CCR7+ T cells (for example, at least 10, 11, 12, 13, 14, 15, 16, 17, 18, 19, 20, 25, 30, 35, or 40% higher), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the percentage of central memory cells, for example, central memory T cells, for example, CD95+ central memory T cells, in the population of cells from step (3) is the same as the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) differs by no more than 3, 4, 5, 6, 7, 8, 9, 10, 11, or 12% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) differs by no more than 5 or 10% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) is decreased as compared to the percentage of central memory cells, for example, central memory T cells, for example, CD95+ central memory T cells, in the population of cells at the beginning of step (1). In some embodiments, the percentage of central memory cells, for example, central memory T cells, for example, CD95+ central memory T cells, in the population of cells from step (3) is decreased by at least 10 or 20%, as compared to the percentage of central memory cells, for example, central memory T cells, for example, CD95+ central memory T cells, in the population of cells at the beginning of step (1). In some embodiments, the percentage of central memory cells, for example, central memory T cells, for example, CD95+ central memory T cells, in the population of cells from step (3) is decreased by at least 10, 11, 12, 13, 14, 15, 16, 17, 18, 19, or 20%, as compared to the percentage of central memory cells, for example, central memory T cells, for example, CD95+ central memory T cells, in the population of cells at the beginning of step (1).

In some embodiments, the population of cells from step (3) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the population of cells from step (3), after being administered in vivo, persists longer or expands at a higher level (for example, at least 20, 25, 30, 35, 40, 45, 50, 55, 60, 65, 70, 75, 80, 85, or 90% higher) (for example, as assessed using methods described in Example 1 with respect to FIG. 4C), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3), after being administered in vivo, persists longer or expands at a higher level (for example, at least 20, 25, 30, 35, 40, 45, 50, 55, 60, 65, 70, 75, 80, 85, or 90% higher) (for example, as assessed using methods described in Example 1 with respect to FIG. 4C), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the population of cells from step (3) are not expanded, for example, as assessed by the number of living cells, compared to the population of cells at the beginning of step (1). In some embodiments, the population of cells from step (3) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (1). In some embodiments, the population of cells from step (3) are expanded by no more than 10%, for example, as assessed by the number of living cells, compared to the population of cells at the beginning of step (1). In some embodiments, the number of living cells in the population of cells from step (3) decreases from the number of living cells in the population of cells at the beginning of step (1), for example, as assessed by the number of living cells.

In some embodiments, the population of cells from step (3) are not expanded compared to the population of cells at the beginning of step (1), for example, as assessed by the number of living cells. In some embodiments, the population of cells from step (3) are expanded by less than 0.5, 1, 1.5, or 2 hours, for example, less than 1 or 1.5 hours, compared to the population of cells at the beginning of step (1).

In some embodiments, the population of cells is not contacted in vitro with an agent that stimulates a CD3/TCR complex and/or an agent that stimulates a costimulatory molecule on the surface of the cells, or if contacted, the contacting step is less than 2 hours, for example, no more than 1 or 1.5 hours. In some embodiments, the agent that stimulates a CD3/TCR complex is an agent that stimulates CD3 (for example, an anti-CD3 antibody). In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex or the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand).

In some embodiments, steps (1) and/or (2) are performed in cell media comprising no more than 5, 4, 3, 2, 1, or 0% serum. In some embodiments, steps (1) and/or (2) are performed in cell media comprising no more than 2% serum. In some embodiments, steps (1) and/or (2) are performed in cell media comprising about 2% serum. In some embodiments, steps (1) and/or (2) are performed in cell media comprising a LSD1 inhibitor or a MALT1 inhibitor. In some embodiments, step (1) is performed in cell media comprising no more than 5, 4, 3, 2, 1, or 0% serum. In some embodiments, step (1) is performed in cell media comprising no more than 2% serum. In some embodiments, step (1) is performed in cell media comprising about 2% serum. In some embodiments, step (2) is performed in cell media comprising no more than 5, 4, 3, 2, 1, or 0% serum. In some embodiments, step (2) is performed in cell media comprising no more than 2% serum. In some embodiments, step (2) is performed in cell media comprising about 2% serum. In some embodiments, step (1) is performed in cell media comprising a LSD1 inhibitor or a MALT1 inhibitor. In some embodiments, step (2) is performed in cell media comprising a LSD1 inhibitor or a MALT1 inhibitor.

In some embodiments, the aforementioned methods further comprise prior to step (i): (iv) receiving a fresh leukapheresis product (or an alternative source of hematopoietic tissue such as a fresh whole blood product, a fresh bone marrow product, or a fresh tumor or organ biopsy or removal (for example, a fresh product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a fresh leukapheresis product (or an alternative source of hematopoietic tissue such as a fresh whole blood product, a fresh bone marrow product, or a fresh tumor or organ biopsy or removal (for example, a fresh product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the aforementioned methods further comprise prior to step (i): receiving cryopreserved T cells isolated from a leukapheresis product (or an alternative source of hematopoietic tissue such as cryopreserved T cells isolated from whole blood, bone marrow, or tumor or organ biopsy or removal (for example, thymectomy)) from an entity, for example, a laboratory, hospital, or healthcare provider.

In some embodiments, the aforementioned methods further comprise prior to step (i): (iv) receiving a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+

T cells) contacted in step (i) from a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the population of cells at the beginning of step (i) or step (1) has been enriched for IL6R-expressing cells (for example, cells that are positive for IL6Rα and/or IL6Rβ). In some embodiments, the population of cells at the beginning of step (i) or step (1) comprises no less than 40, 45, 50, 55, 60, 65, or 70% of IL6R-expressing cells (for example, cells that are positive for IL6Rα and/or IL6Rβ).

In some embodiments, steps (i) and (ii) or steps (1) and (2) are performed in cell media comprising IL-15 (for example, hetIL-15 (IL15/sIL-15Ra)). In some embodiments, IL-15 increases the ability of the population of cells to expand, for example, 10, 15, 20, or 25 days later. In some embodiments, IL-15 increases the percentage of IL6Rβ-expressing cells in the population of cells.

In some embodiments of the aforementioned methods, the methods are performed in a closed system. In some embodiments, T cell separation, activation, transduction, incubation, and washing are all performed in a closed system. In some embodiments of the aforementioned methods, the methods are performed in separate devices. In some embodiments, T cell separation, activation and transduction, incubation, and washing are performed in separate devices.

In some embodiments of the aforementioned methods, the methods further comprise adding an adjuvant or a transduction enhancement reagent in the cell culture medium to enhance transduction efficiency. In some embodiments, the adjuvant or transduction enhancement reagent comprises a cationic polymer. In some embodiments, the adjuvant or transduction enhancement reagent is chosen from: LentiBOOST™ (Sirion Biotech), vectofusin-1, F108, hexadimethrine bromide (Polybrene), PEA, Pluronic F68, Pluronic F127, Synperonic or LentiTrans™. In some embodiments, the adjuvant is LentiBOOST™ (Sirion Biotech).

In some embodiments of the aforementioned methods, the transducing the population of cells (for example, T cells) with a viral vector comprises subjecting the population of cells and viral vector to a centrifugal force under conditions such that transduction efficiency is enhanced. In an embodiment, the cells are transduced by spinoculation.

In some embodiments of the aforementioned methods, cells (e.g., T cells) are activated and transduced in a cell culture flask comprising a gas-permeable membrane at the base that supports large media volumes without substantially compromising gas exchange. In some embodiments, cell growth is achieved by providing access, e.g., substantially uninterrupted access, to nutrients through convection.

In some embodiments of the aforementioned methods, the CAR comprises an antigen binding domain, a transmembrane domain, and an intracellular signaling domain.

In some embodiments, the antigen binding domain binds to an antigen chosen from: CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (for example, ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In some embodiments, the antigen binding domain comprises a CDR, VH, VL, scFv or a CAR sequence disclosed herein. In some embodiments, the antigen binding domain comprises a VH and a VL, wherein the VH and VL are connected by a linker, optionally wherein the linker comprises the amino acid sequence of SEQ ID NO: 63 or 104.

In some embodiments, the transmembrane domain comprises a transmembrane domain of a protein chosen from the alpha, beta or zeta chain of T-cell receptor, CD28, CD3 epsilon, CD45, CD4, CD5, CD8, CD9, CD16, CD22, CD33, CD37, CD64, CD80, CD86, CD134, CD137 and CD154. In some embodiments, the transmembrane domain comprises a transmembrane domain of CD8. In some embodiments, the transmembrane domain comprises the amino acid sequence of SEQ ID NO: 6, or an amino acid sequence having at least about 85%, 90%, 95%, or 99% sequence identity thereof. In some embodiments, the nucleic acid molecule comprises a nucleic acid sequence encoding the transmembrane domain, wherein the nucleic acid sequence comprises the nucleic acid sequence of SEQ ID NO: 17, or a nucleic acid sequence having at least about 85%, 90%, 95%, or 99% sequence identity thereof.

In some embodiments, the antigen binding domain is connected to the transmembrane domain by a hinge region. In some embodiments, the hinge region comprises the amino acid sequence of SEQ ID NO: 2, 3, or 4, or an amino acid sequence having at least about 85%, 90%, 95%, or 99% sequence identity thereof. In some embodiments, the nucleic acid molecule comprises a nucleic acid sequence encoding the hinge region, wherein the nucleic acid sequence comprises the nucleic acid sequence of SEQ ID NO: 13, 14, or 15, or a nucleic acid sequence having at least about 85%, 90%, 95%, or 99% sequence identity thereof.

In some embodiments, the intracellular signaling domain comprises a primary signaling domain. In some embodiments, the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d.

In some embodiments, the primary signaling domain comprises a functional signaling domain derived from CD3 zeta. In some embodiments, the primary signaling domain comprises the amino acid sequence of SEQ ID NO: 9 or 10, or an amino acid sequence having at least about 85%, 90%, 95%, or 99% sequence identity thereof. In some embodiments, the nucleic acid molecule comprises a nucleic acid sequence encoding the primary signaling domain, wherein the nucleic acid sequence comprises the nucleic acid sequence of SEQ ID NO: 20 or 21, or a nucleic acid sequence having at least about 85%, 90%, 95%, or 99% sequence identity thereof.

In some embodiments, the intracellular signaling domain comprises a costimulatory signaling domain. In some embodiments, the costimulatory signaling domain comprises a functional signaling domain derived from a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83. In some embodiments, the costimulatory signaling domain comprises a functional signaling domain derived from 4-1BB. In some embodiments, the costimulatory signaling domain comprises the amino acid sequence of SEQ ID NO: 7, or an amino acid sequence having at least about 85%, 90%, 95%, or 99% sequence identity thereof. In some embodiments, the nucleic acid molecule comprises a nucleic acid sequence encoding the costimulatory signaling domain, wherein the nucleic acid sequence comprises the nucleic acid sequence of SEQ ID NO: 18, or a nucleic acid sequence having at least about 85%, 90%, 95%, or 99% sequence identity thereof.

In some embodiments, the intracellular signaling domain comprises a functional signaling domain derived from 4-1BB and a functional signaling domain derived from CD3 zeta. In some embodiments, the intracellular signaling domain comprises the amino acid sequence of SEQ ID NO: 7 (or an amino acid sequence having at least about 85%, 90%, 95%, or 99% sequence identity thereof) and the amino acid sequence of SEQ ID NO: 9 or 10 (or an amino acid sequence having at least about 85%, 90%, 95%, or 99% sequence identity thereof). In some embodiments, the intracellular signaling domain comprises the amino acid sequence of SEQ ID NO: 7 and the amino acid sequence of SEQ ID NO: 9 or 10.

In some embodiments, the CAR further comprises a leader sequence comprising the amino acid sequence of SEQ ID NO: 1.

In some embodiments, this invention features a population of CAR-expressing cells (for example, autologous or allogeneic CAR-expressing T cells or NK cells) made by any of the aforementioned methods or any other method disclosed herein. In some embodiments, disclosed herein is a pharmaceutical composition comprising a population of CAR-expressing cells disclosed herein and a pharmaceutically acceptable carrier.

In some embodiments, in the final CAR cell product manufactured using the methods described herein, the total amount of beads (e.g., CD4 beads, CD8 beads, and/or TransACT beads) is no more than 0.04, 0.05, 0.06, 0.07, 0.08, 0.09, 0.1, 0.2, 0.3, 0.4, or 0.5% of the total amount of beads added during the manufacturing process.

In some embodiments, this invention features a population of CAR-expressing cells (for example, autologous or allogeneic CAR-expressing T cells or NK cells) comprising one or more of the following characteristics: (a) about the same percentage of naïve cells, for example, naïve T cells, for example, CD45RO− CCR7+ T cells, as compared to the percentage of naïve cells, for example, naïve T cells, for example, CD45RO− CCR7+ cells, in the same population of cells prior to being engineered to express the CAR; (b) a change within about 5% to about 10% of naïve cells, for example, naïve T cells, for example, CD45RO− CCR7+ T cells, for example, as compared to the percentage of naïve cells, for example, naïve T cells, for example, CD45RO− CCR7+ cells, in the same population of cells prior to being engineered to express the CAR; (c) an increased percentage of naïve cells, for example, naïve T cells, for example, CD45RO− CCR7+ T cells, for example, increased by at least 1.2, 1.4, 1.6, 1.8, 2.0, 2.2, 2.4, 2.6, 2.8, or 3-fold, as compared to the percentage of naïve cells, for example, naïve T cells, for example, CD45RO− CCR7+ cells, in the same population of cells prior to being engineered to express the CAR; (d) about the same percentage of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR; (e) a change within about 5% to about 10% of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR; (f) a decreased percentage of central memory cells, for example, central memory T cells, for example, CCR7+CD45RO+ T cells, for example, decreased by at least 20, 25, 30, 35, 40, 45, or 50%, as compared to the percentage of central memory cells, for example, central memory T cells, for example, CCR7+CD45RO+ T cells, in the same population of cells prior to being engineered to express the CAR; (g) about the same percentage of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR; (h) a change within about 5% to about 10% of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR; or (i) an increased percentage of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR.

In some embodiments, this invention features a population of CAR-expressing cells (for example, autologous or allogeneic CAR-expressing T cells or NK cells), wherein: (a) the median GeneSetScore (Up TEM vs. Down TSCM) of the population of cells is about the same as or differs by no more than (for example, increased by no more than) about 25, 50, 75, 100, or 125% from the median GeneSetScore (Up TEM vs. Down TSCM) of the same population of cells prior to being engineered to express the CAR; (b) the median GeneSetScore (Up Treg vs. Down Teff) of the population of cells is about the same as or differs by no more than (for example, increased by no more than) about 25, 50, 100, 150, or 200% from the median GeneSetScore (Up Treg vs. Down Teff) of the population of cells prior to being engineered to express the CAR; (c) the median GeneSetScore (Down stemness) of the population of cells is about the same as or differs by no more than (for example, increased by no more than) about 25, 50, 100, 150, 200, or 250% from the median GeneSetScore (Down stemness) of the population of cells prior to being engineered to express the CAR; (d) the median GeneSetScore (Up hypoxia) of the population of cells is about the same as or differs by no more than (for example, increased by no more than) about 125, 150, 175, or 200% from the median GeneSetScore (Up hypoxia) of the population of cells prior to being engineered to express the CAR; or (e) the median GeneSetScore (Up autophagy) of the population of cells is about the same as or differs by no more than (for example, increased by no more than) about 180, 190, 200, or 210% from the median GeneSetScore (Up autophagy) of the population of cells prior to being engineered to express the CAR.

In some embodiments, this invention features a method of increasing an immune response in a subject, comprising administering a population of CAR-expressing cells disclosed herein or a pharmaceutical composition disclosed herein to the subject, thereby increasing an immune response in the subject.

In some embodiments, disclosed herein is a method of treating a cancer in a subject, comprising administering a population of CAR-expressing cells disclosed herein or a pharmaceutical composition disclosed herein to the subject, thereby treating the cancer in the subject. In some embodiments, the cancer is a solid cancer, for example, chosen from: one or more of mesothelioma, malignant pleural mesothelioma, non-small cell lung cancer, small cell lung cancer, squamous cell lung cancer, large cell lung cancer, pancreatic cancer, pancreatic ductal adenocarcinoma, esophageal adenocarcinoma, breast cancer, glioblastoma, ovarian cancer, colorectal cancer, prostate cancer, cervical cancer, skin cancer, melanoma, renal cancer, liver cancer, brain cancer, thymoma, sarcoma, carcinoma, uterine cancer, kidney cancer, gastrointestinal cancer, urothelial cancer, pharynx cancer, head and neck cancer, rectal cancer, esophagus cancer, or bladder cancer, or a metastasis thereof. In some embodiments, the cancer is a liquid cancer, for example, chosen from: chronic lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, chronic myeloid leukemia, myeloproliferative neoplasms, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia, myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, acute myeloid leukemia (AML), or unclassifiable lymphoma.

In some embodiments, the method further comprises administering a second therapeutic agent to the subject. In some embodiments, the second therapeutic agent is an anti-cancer therapeutic agent, for example, a chemotherapy, a radiation therapy, or an immune-regulatory therapy. In some embodiments, the second therapeutic agent is IL-15 (for example, hetIL-15 (IL15/sIL-15Ra)).

Although methods and materials similar or equivalent to those described herein can be used in the practice or testing of the present invention, suitable methods and materials are described below. All publications, patent applications, patents, and other references (for example, sequence database reference numbers) mentioned herein are incorporated by reference in their entirety. For example, all GenBank, Unigene, and Entrez sequences referred to herein, for example, in any Table herein, are incorporated by reference. When one gene or protein references a plurality of sequence accession numbers, all of the sequence variants are encompassed.

In addition, the materials, methods, and examples are illustrative only and not intended to be limiting. Headings, sub-headings or numbered or lettered elements, for example, (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE FIGURES

FIG. 1A is a graph showing exemplary cytokine process. FIG. 1B is a pair of graphs showing the percentages of CD3+CAR+ cells at each indicated time point after transduction. FIG. 1C is a set of graphs showing the transduction within the CD3+CCR7+CD45RO− population in a CD3/CD28 bead stimulated populations (left) compared to cytokines only populations (right) in two independent donors. For the sample referred to as "Short stim IL7+IL15" in FIG. 1C, the cells were stimulated with beads for 2 days and then they were removed in the presence of IL7 and IL15. FIGS. 1D, 1E, and 1F are a set of flow cytometry graphs showing the transduction of T-cell subsets cultured with IL2 (FIG. 1D), IL15 (FIG. 1E), and IL7+IL15 (FIG. 1F) daily over a three-day period. FIG. 1G is a set of flow cytometry graphs showing the T cell differentiation on day 0 (left) and on day 1 (right) for CCR7 and CD45RO after stimulation with IL2 (upper right panel) or IL-15 (lower right panel). FIGS. 1H and 1I are a set of graphs showing the percentages of CD3+CCR7+RO−, CD3+CCR7+RO+, CD3+CCR7-RO+, and CD3+CCR7-RO− cells at day 0 or after 24-hour incubation with the indicated cytokines.

FIG. 2A: Purified T cells were transduced with a MOI of 1 and in all the cytokine conditions tested, the percentages of CAR-expressing cells observed at day 1 and day 10 were similar. The CARTs were generated within one day and expanded via CD3/CD28 beads after harvest for 9 days to mimic the in vivo setting. FIG. 2A is a pair of graphs showing the average percentages of CD3+CAR+ cells under each condition for day 1 CARTs (left) and day 10 CARTs (right). FIG. 2B: The cytotoxicity capacity of the day 1 CARTs post expansion was measured using Nalm6 as the target cells. FIG. 2B is a graph showing % killing of CD19 positive Nalm6 cells by CARTs from each condition. Day 10 CARTs expanded using CD3/CD28 beads are marked as "Day 10." All the other samples were day 1 CARTs. FIG. 2C: The secretion of IFNg of the expanded day 1 CARTs in response to Nalm6 target cells was tested. FIG. 2C is a graph showing the amount of IFN-gamma secretion by CARTs from each condition in the presence of CD19 positive or CD19 negative target cells. FIG. 2D: The proliferative capacity of the day 1 CARTs was tested by measurement of the incorporation of EDU. FIG. 2D is a graph showing the average percentages of EDU-positive cells for each condition. Similar to FIG. 2B, day 10 CARTs are marked as "Day 10" and all the other samples were day 1 CARTs.

FIG. 3A: Purified T cells were transduced with a range of MOIs from 1 to 10 in the presence of IL15, IL2+IL15, IL2+IL7, or IL7+IL15. Regardless of cytokine used, a linear increase in transduction was observed. FIG. 3A is a set of graphs where the percentages of CD3+CAR+ cells are plotted against MOIs for each condition tested. FIG. 3B: The composition of the media impacted the transduction in the cytokine process. FIG. 3B is a pair of graphs showing the percentages of CD3+CAR+ cells on day 1 (left) or day 8 (right) for each condition tested. "2.50" indicates a MOI of 2.50. "5.00" indicates a MOI of 5.00.

FIG. 4A: Purified T cells were transduced with CAR19 and 24 hours later were harvested. FIG. 4A is a set of flow cytometry plots showing the transduction of T cells with CAR19 that were cultured with IL2, IL15 and IL7+IL15, illustrating the transduction with each cytokine condition. FIG. 4B: A graph showing average viability which was above 80% in all the conditions tested. FIG. 4C: The expansion of the day 1 CARTs in the peripheral blood is increased in vivo as compared to their day 10 counterparts. The percentage of live CD45+CD11b-CD3+CAR+ cells at indicated time points after infusion for each condition tested. The day 10 CARTs are marked as "D10 1e6" or "D10 5e6" and all the other samples were day 1 CARTs. FIG. 4D: The day 1 CARTs could eliminate tumor in vivo although with a delayed kinetics as compared to the day 10 CARTs. FIG. 4D is a graph showing total flux at indicated time points after tumor inoculation for each condition tested. CARTs were administered 4 days after tumor inoculation. The day 10 CARTs are marked as "5e6 d. 10" and all the other samples were day 1 CARTs.

FIG. 5A: The T cells were enriched on a CliniMACS® Prodigy® and the B cell compartment was reduced to less than 1%. FIG. 5A is a set of flow cytometry plots showing the staining of cells with an anti-CD3 antibody (left) or an anti-CD19 antibody and an anti-CD14 antibody (right) for leukopak cells (upper) or cells post CD4+CD8+ enrichment (lower). FIG. 5B: Purified T cells from a frozen apheresis were transduced with CAR19 in either a 24 well plate or a PL30 bag post enrichment. The CARTs were harvested 24 hours later. FIG. 5B is a set of flow cytometry plots showing staining for CD3 and CAR of cells manufactured in the presence of either IL2 or hetIL-15 (IL15/sIL-15Ra).

FIGS. 6A and 6B are graphs where tumor burden is plotted against the indicated time point after tumor implantation. "d. 1" indicates CARTs manufactured using the activation process. "d. 9" indicates CARTs manufactured with a traditional 9-day expansion protocol, serving as a positive control in this study. FIG. 6C is a set of representative images showing bioluminescence from mice.

FIG. 19A is a panel of histograms showing BCMA CAR expression as measured by flow cytometry. FIG. 19B is a table listing reagents/conditions used in the flow cytometry analysis.

FIG. 20A is a panel of histograms showing CAR expression at the indicated time points measured by flow cytometry. FIGS. 20B and 20C are graphs showing CAR+% and MFI values over time, respectively.

FIG. 21A is a panel of histograms showing the day 1 and day 7 CAR expression in the CART cells. FIG. 21B is a graph showing the tumor kinetics (BLI level) after CART treatment.

FIG. 22A is a panel of histograms showing the CAR expression at day 1 and day 3. FIG. 22B is a graph showing tumor intake kinetics after CART treatment using two different doses: a dose of 1.5e5 CAR+ T cells and a dose of 5e4 CAR+ T cells. The doses of CAR+ cells were normalized based on the day 3 CAR expression. FIG. 22C is a graph showing body weight kinetics over the course of this study.

FIGS. 23A and 23B are graphs showing percentage of T cell expressing the CAR on their cell surface (FIG. 23A) and mean fluorescence intensity (MFI) of CD3+CAR+ cells (FIG. 23B) observed over time (replicate efficiencies are averaged from the two flow panels shown in FIG. 23C). FIG. 23C is a panel of flow cytometry plots showing gating strategy for surface CAR expression on viable CD3+ cells, as based on UTD samples. Numbers in the plots indicate percent CAR positive.

FIG. 24A is a graph showing end-to-end composition of the starting material (Prodigy® product) and at harvest at various time points after culture initiation. Naive (n), central memory (cm), effector memory (em), and effector (eff) subsets were defined by CD4, CD8, CCR7, and CD45RO surface expression or lack thereof. CD4 composition is indicated. For each time point, the left bar shows cell composition of the overall CD3+ population (bulk) and the right bar shows cell composition of the CAR+ fraction. FIG. 24B is a panel of flow cytometry plots showing gating strategy applied on live CD3+ events to determine overall transduction efficiency (top row), CD4/CD8 composition (middle row), and memory subsets (bottom row) within the overall CD3+ population (bulk) and the CAR+ fraction.

FIGS. 28A, 28B, 28C, and 28D. FIG. 28A is a graph showing composition of the starting material (healthy donor leukopak; LKPK) and the T cell-enriched product as analyzed by flow cytometry. Numbers indicate % of parent (live, single cells). T: T cells; mono: monocytes; B: B cells; CD56 (NK): NK cells. FIG. 28B is a panel of flow cytometry plots showing gating strategy on live CD3+ events used to determine transduction rate (forward scatter FSC vs. CAR) and T cell subsets (CD4 vs. CD8 and CCR7 vs. CD45RO). For ARM-CD19 CAR (CD19 CART cells manufactured using the Activated Rapid Manufacturing (ARM) process) and TM-CD19 CAR (CD19 CART cells manufactured using the traditional manufacturing (TM) process), the left lower panels represent bulk cultures, while the right panels represent CAR+ T cells. "ARM-UTD" and "TM-UTD" refer to untransduced T cells (UTD) manufactured according to the ARM and the TM processes, respectively. Numbers in quadrants indicate % of parental population. Boxes in the TM-UTD and TM-CD19 CAR plots indicate skewing toward a $T_{CM}$ phenotype for the TM process. Boxes in the ARM-UTD and ARM-CD19 CAR plots indicate the maintenance of naïve-like cells by the ARM process. NA: not applicable. FIG. 28C is a graph showing end-to-end T cell composition of ARM-CD19 CAR and TM-CD19 CAR. Composition is shown for "bulk" and "CAR+" populations where applicable. The percentage of the respective populations refers to % of parental, either CD3+ or CAR+CD3+ as applicable. The % of CD4 cells of the respective bulk or CAR+ population is indicated. LKPK: Leukopak starting material; 4 and 8: CD4+ and CD8+, respectively; eff: effector; em: effector memory; cm: central memory; n: naïve-like. Data is representative of 3 full-scale runs with 3 different healthy donors (n=3) and several small-scale runs used to optimize the process. FIG. 28D is a table showing the percentages shown in FIG. 28C.

FIGS. 29A and 29C: TM-CD19 CAR, ARM-CD19 CAR, and respective UTD were co-cultured with NALM6-WT (ALL), TMD-8 (DLBCL), or without cancer cells (T cells alone). Supernatant was collected 48 h later. FIGS. 29B and 29D: ARM-CD19 CAR was cocultured with NALM6-WT, NALM6-19K0 (CD19-negative) or alone. Supernatant was collected after 24 h or 48 h. To further assess antigen-specific cytokine secretion, ARM-CD19 CAR was cultured alone for 24 h, washed and then co-cultured with target cells for 24 h. Data shown is derived from 2 healthy donor T cells and is representative of 2 experiments with three donors total.

FIG. 30A is a graph outlining the xenograft mouse model to study the anti-tumor activity of ARM-CD19 CAR. FIG. 30B is a panel of flow cytometry plots showing determination of CAR expression on ARM-CD19 CAR cells from a sentinel vial. ARM-CD19 CAR cells were cultured for the time period described in the figure, prior to flow-cytometry analysis. Gating for CAR expression was based on an isotype control (Iso) staining. FIG. 30C is a graph showing in vivo efficacy of ARM-CD19 CAR in the xenograft mouse model. NSG mice were injected with the pre-B ALL line NALM6, expressing the luciferase reporter gene; the tumor burden is expressed as total body luminescence (p/s), depicted as mean tumor burden with 95% confidence interval. On day 7 post tumor inoculation, mice were treated with ARM-CD19 CAR or TM-CD19 CAR at the respective doses (number of viable CAR+ T cells). High dose ARM-CD19 CAR group was terminated on day 33 due to onset of X-GVHD. Vehicle (PBS) and non-transduced T cells (UTD) served as negative controls. n=5 mice for all groups, except n=4 for ARM-UTD $1\times10^6$ dose and all TM-CD19 CAR dose groups. Five xenograft studies were run with CAR-T cells generated from 5 different healthy donors, three of which included a comparison to TM-CD19 CAR.

FIG. 38D is a violin plot showing the distribution of gene set scores for a gene set comprised of genes that characterize a resting vs. activated T cell state for Day 1 cells, Day 9 cells, and input cells. In FIG. 38D, a higher gene set score (Up resting vs. Down activated) indicates an increasing resting T cell phenotype, whereas a lower gene set score (Up resting vs. Down activated) indicates an increasing activated T cell phenotype. Input cells were overall in more of a resting state compared to Day 9 and Day 1 cells. Day 1 cells show the greatest activation gene set score.

In FIG. 39A, a higher gene set score for the gene set "Up TEM vs. Down TSCM" indicates an increasing effector memory T cell (TEM) phenotype of the cells in that sample, whereas a lower gene set score indicates an increasing stem cell memory T cell (TSCM) phenotype. In FIG. 39B, a higher gene set score for the gene set "Up Treg vs. Down Teff" indicates an increasing regulatory T cell (Treg) phenotype, whereas a lower gene set score indicates an increasing effector T cell (Teff) phenotype. In FIG. 39C, a lower gene set score for the gene set "Down stemness" indicates an increasing stemness phenotype. In FIG. 39D, a higher gene set score for the gene set "Up hypoxia" indicates an increasing hypoxia phenotype. In FIG. 39E, a higher gene set score for the gene set "Up autophagy" indicates an increasing autophagy phenotype. Day 1 cells looked similar to the input cells in terms of memory, stem-like and differentiation signature. Day 9 cells, on the other hand, show a higher enrichment for metabolic stress.

FIGS. 40A-40C are violin plots showing the gene set scores from gene set analysis of the four clusters of the input cells. Each dot overlaying the violin plots in FIGS. 40A-40C represents a cell's gene set score. In FIG. 40A, a higher gene set score of the gene set "Up Treg vs. Down Teff" indicates an increasing Treg cell phenotype, whereas a lower gene set score of the gene set "Up Treg vs. Down Teff" indicates an increasing Teff cell phenotype. In FIG. 40B, a higher gene set score of the gene set "Progressively up in memory differentiation" indicates an increasing late memory T cell phenotype, whereas a lower gene set score of the gene set "Progressively up in memory differentiation" indicates an increasing early memory T cell phenotype. In FIG. 40C, a higher gene set score of the gene set "Up TEM vs. Down TN" indicates an increasing effector memory T cell phenotype, whereas a lower gene set score of the gene set "Up TEM vs. Down TN" indicates an increasing naïve T cell phenotype. The cells in Cluster 3 are shown to be in a later memory, further differentiated T cell state compared to the cells in Cluster 1 and Cluster 2 which are in an early memory, less differentiated T cell state. Cluster 0 appears to be in an intermediate T cell state. Taken together, this data shows that there is a considerable level of heterogeneity within input cells.

DETAILED DESCRIPTION

Definitions

Figure 1A:
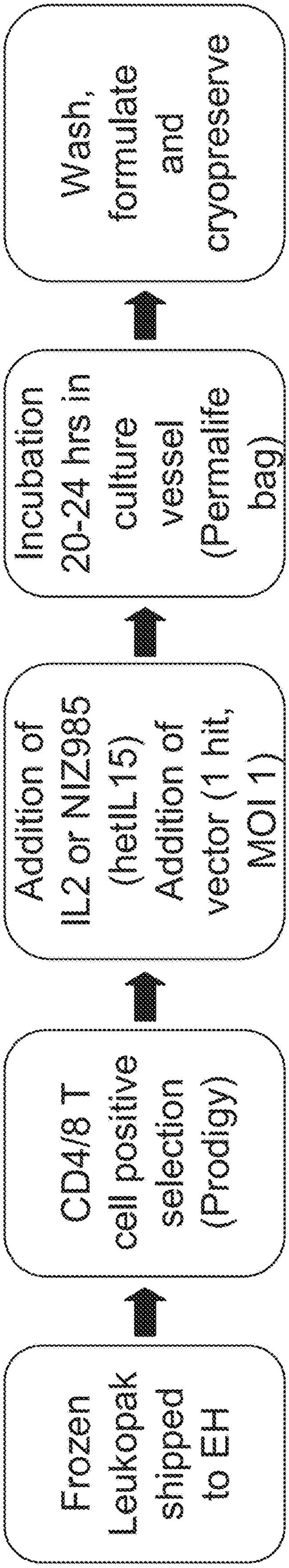
FIGS. 1A-1I: When purified T cells were incubated with cytokines, the naïve cells were the predominant population transduced.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The compositions and methods of the present invention encompass polypeptides and nucleic acids having the sequences specified, or sequences substantially identical or similar thereto, for example, sequences at least 85%, 90%, or 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity, for example, amino acid sequences that contain a common structural domain having at least about 85%, 90%. 91%, 92%, 93%, 94%, 95%, 96%, 97%, 98% or 99% identity to a reference sequence, for example, a sequence provided herein.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 75%, 80%, 85%, 90%, 91%, 92%, 93%, 94%, 95%, 96%, 97%, 98% or 99% identity to a reference sequence, for example, a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

The term cytokine (for example, IL-2, IL-7, IL-15, IL-21, or IL-6) includes full length, a fragment or a variant, for example, a functional variant, of a naturally-occurring cytokine (including fragments and functional variants thereof having at least 10%, 30%, 50%, or 80% of the activity, e.g., the immunomodulatory activity, of the naturally-occurring cytokine). In some embodiments, the cytokine has an amino acid sequence that is substantially identical (e.g., at least about 85%, 90%, 91%, 92%, 93%, 94%, 95%, 96%, 97%, 98% or 99% identity) to a naturally-occurring cytokine, or is encoded by a nucleotide sequence that is substantially identical (e.g., at least about 75%, 80%, 85%, 90%, 91%, 92%, 93%, 94%, 95%, 96%, 97%, 98% or 99% identity) to a naturally-occurring nucleotide sequence encoding a cytokine. In some embodiments, as understood in context, the cytokine further comprises a receptor domain, e.g., a cytokine receptor domain (e.g., an IL-15/IL-15R).

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, for example, comprise a chimeric fusion protein. In some embodiments, the domains in the CAR polypeptide construct are not contiguous with each other, for example, are in different polypeptide chains, for example, as provided in an RCAR as described herein.

In some embodiments, the cytoplasmic signaling domain comprises a primary signaling domain (for example, a primary signaling domain of CD3-zeta). In some embodiments, the cytoplasmic signaling domain further comprises one or more functional signaling domains derived from at least one costimulatory molecule as defined below. In some embodiments, the costimulatory molecule is chosen from 41BB (i.e., CD137), CD27, ICOS, and/or CD28. In some embodiments, the CAR comprises a chimeric fusion protein comprising an extracellular antigen recognition domain, a transmembrane domain and an intracellular signaling domain comprising a functional signaling domain derived from a stimulatory molecule. In some embodiments, the CAR comprises a chimeric fusion protein comprising an extracellular antigen recognition domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen recognition domain, a transmembrane domain and an intracellular signaling domain comprising two functional signaling domains derived from one or more costimulatory molecule(s) and a functional signaling domain derived from a stimulatory molecule. In some embodiments, the CAR comprises a chimeric fusion protein comprising an extracellular antigen recognition domain, a transmembrane domain and an intracellular signaling domain comprising at least two functional signaling domains derived from one or more costimulatory molecule(s) and a functional signaling domain derived from a stimulatory molecule. In some embodiments the CAR comprises an optional leader sequence at the amino-terminus (N-terminus) of the CAR fusion protein. In some embodiments, the CAR further comprises a leader sequence at the N-terminus of the extracellular antigen recognition domain, wherein the leader sequence is optionally cleaved from the antigen recognition domain (for example, an scFv) during cellular processing and localization of the CAR to the cellular membrane.

A CAR that comprises an antigen binding domain (for example, an scFv, a single domain antibody, or TCR (for example, a TCR alpha binding domain or TCR beta binding domain)) that targets a specific tumor marker X, wherein X can be a tumor marker as described herein, is also referred to as XCAR. For example, a CAR that comprises an antigen binding domain that targets BCMA is referred to as BCMA CAR. The CAR can be expressed in any cell, for example, an immune effector cell as described herein (for example, a T cell or an NK cell).

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule, which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, for example, an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, for example, two, Fab fragments linked by a disulfide bridge at the hinge region, or two or more, for example, two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, for example, with respect to the N-terminal and C-terminal ends of the polypeptide, the scFv may comprise VL-linker-VH or may comprise VH-linker-VL. In some embodiments, the scFv may comprise the structure of $NH_2$-$V_L$-linker-$V_H$-COOH or $NH_2$-$V_H$-linker-$V_L$-COOH.

The terms "complementarity determining region" or "CDR," as used herein, refer to the sequences of amino acids within antibody variable regions which confer antigen specificity and binding affinity. For example, in general, there are three CDRs in each heavy chain variable region (for example, HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof. In a combined Kabat and Chothia numbering scheme, in some embodiments, the CDRs correspond to the amino acid residues that are part of a Kabat CDR, a Chothia CDR, or both.

The portion of the CAR composition of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), or for example, a human or humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In some embodiments, the antigen binding domain of a CAR composition of the invention comprises an antibody fragment. In some embodiments, the CAR comprises an antibody fragment that comprises an scFv.

As used herein, the term "binding domain" or "antibody molecule" (also referred to herein as "anti-target binding domain") refers to a protein, for example, an immunoglobulin chain or fragment thereof, comprising at least one immunoglobulin variable domain sequence. The term "binding domain" or "antibody molecule" encompasses antibodies and antibody fragments. In some embodiments, an antibody molecule is a multispecific antibody molecule, for example, it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In some embodiments, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The terms "bispecific antibody" and "bispecific antibodies" refer to molecules that combine the antigen binding sites of two antibodies within a single molecule. Thus, a bispecific antibody is able to bind two different antigens simultaneously or sequentially. Methods for making bispecific antibodies are well known in the art. Various formats for combining two antibodies are also known in the art. Forms of bispecific antibodies of the invention include, but are not limited to, a diabody, a single-chain diabody, Fab dimerization (Fab-Fab), Fab-scFv, and a tandem antibody, as known to those of skill in the art.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The terms "anti-tumor effect" and "anti-cancer effect" are used interchangeably and refer to a biological effect which can be manifested by various means, including but not limited to, for example, a decrease in tumor volume or cancer volume, a decrease in the number of tumor cells or cancer cells, a decrease in the number of metastases, an increase in life expectancy, a decrease in tumor cell proliferation or cancer cell proliferation, a decrease in tumor cell survival or cancer cell survival, or amelioration of various physiological symptoms associated with the cancerous condition. An "anti-tumor effect" or "anti-cancer effect" can also be manifested by the ability of the peptides, polynucleotides, cells and antibodies of the invention in prevention of the occurrence of tumor or cancer in the first place.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some embodiments, allogeneic material from individuals of the same species may be sufficiently unlike genetically to interact antigenically.

The term "xenogeneic" refers to a graft derived from an animal of a different species.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, for example, by retransfusion. Thus, in the context of "an apheresis sample" refers to a sample obtained using apheresis.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments cancers treated by the methods described herein include multiple myeloma, Hodgkin's lymphoma or non-Hodgkin's lymphoma.

The terms "tumor" and "cancer" are used interchangeably herein, for example, both terms encompass solid and liquid, for example, diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, for example, it does not mean that, to provide the intracellular signaling domain, one must start with a CD3zeta sequence and delete unwanted sequence, or impose mutations, to arrive at the intracellular signaling domain.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative substitutions are ones in which the amino acid residue is replaced with an amino acid residue having a similar side chain. Families of amino acid residues having similar side chains have been defined in the art. These families include amino acids with basic side chains (for example, lysine, arginine, histidine), acidic side chains (for example, aspartic acid, glutamic acid), uncharged polar side chains (for example, glycine, asparagine, glutamine, serine, threonine, tyrosine, cysteine, tryptophan), nonpolar side chains (for example, alanine, valine, leucine, isoleucine, proline, phenylalanine, methionine), beta-branched side chains (for example, threonine, valine, isoleucine) and aromatic side chains (for example, tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation" in the context of stimulation by a stimulatory and/or costimulatory molecule refers to a response, for example, a primary or secondary response, induced by binding of a stimulatory molecule (for example, a TCR/CD3 complex) and/or a costimulatory molecule (for example, CD28 or 4-1BB) with its cognate ligand thereby mediating a signal transduction event, such as, but not limited to, signal transduction via the TCR/CD3 complex. Stimulation can mediate altered expression of certain molecules and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In some embodiments, the ITAM-containing domain within the CAR recapitulates the signaling of the primary TCR independently of endogenous TCR complexes. In some embodiments, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI and CD66d, DAP10 and DAP12. In a specific CAR of the invention, the intracellular signaling domain in any one or more CAR5 of the invention comprises an intracellular signaling sequence, for example, a primary signaling sequence of CD3-zeta. The term "antigen presenting cell" or "APC" refers to an immune system cell such as an accessory cell (for example, a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain generates a signal that promotes an immune effector function of the CAR containing cell, for example, a CART cell. Examples of immune effector function, for example, in a CART cell, include cytolytic activity and helper activity, including the secretion of cytokines.

In some embodiments, the intracellular signaling domain can comprise a primary intracellular signaling domain. Exemplary primary intracellular signaling domains include those derived from the molecules responsible for primary stimulation, or antigen dependent simulation. In some embodiments, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as "ICOS"), FcεRI, CD66d, DAP10 and DAP12.

The term "zeta" or alternatively "zeta chain", "CD3-zeta" or "TCR-zeta" refers to CD247. Swiss-Prot accession number P20963 provides exemplary human CD3 zeta amino acid sequences. A "zeta stimulatory domain" or alternatively a "CD3-zeta stimulatory domain" or a "TCR-zeta stimulatory domain" refers to a stimulatory domain of CD3-zeta or a variant thereof (for example, a molecule having mutations, for example, point mutations, fragments, insertions, or deletions). In some embodiments, the cytoplasmic domain of zeta comprises residues 52 through 164 of GenBank Acc. No. BAG36664.1 or a variant thereof (for example, a molecule having mutations, for example, point mutations, fragments, insertions, or deletions). In some embodiments, the "zeta stimulatory domain" or a "CD3-zeta stimulatory domain" is the sequence provided as SEQ ID NO: 9 or 10, or a variant thereof (for example, a molecule having mutations, for example, point mutations, fragments, insertions, or deletions).

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, TNF receptor proteins, Immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term "4-1BB" refers to CD137 or Tumor necrosis factor receptor superfamily member 9. Swiss-Prot accession number P20963 provides exemplary human 4-1BB amino acid sequences. A "4-1BB costimulatory domain" refers to a costimulatory domain of 4-1BB, or a variant thereof (for example, a molecule having mutations, for example, point mutations, fragments, insertions, or deletions). In some embodiments, the "4-1BB costimulatory domain" is the sequence provided as SEQ ID NO: 7 or a variant thereof (for example, a molecule having mutations, for example, point mutations, fragments, insertions, or deletions).

"Immune effector cell," as that term is used herein, refers to a cell that is involved in an immune response, for example, in the promotion of an immune effector response. Examples of immune effector cells include T cells, for example, alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, for example, of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and costimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence. In some embodiments, expression comprises translation of an mRNA introduced into a cell.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (for example, naked or contained in liposomes) and viruses (for example, lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, for example, the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, for example, between two nucleic acid molecules, such as, two DNA molecules or two RNA molecules, or between two polypeptide molecules. When a subunit position in both of the two molecules is occupied by the same monomeric subunit; for example, if a position in each of two DNA molecules is occupied by adenine, then they are homologous or identical at that position. The homology between two sequences is a direct function of the number of matching or homologous positions; for example, if half (for example, five positions in a polymer ten subunits in length) of the positions in two sequences are homologous, the two sequences are 50% homologous; if 90% of the positions (for example, 9 of 10), are matched or homologous, the two sequences are 90% homologous.

"Humanized" forms of non-human (for example, murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Operably linked DNA sequences can be contiguous with each other and, for example, where necessary to join two protein coding regions, are in the same reading frame.

The term "parenteral" administration of an immunogenic composition includes, for example, subcutaneous (s.c.), intravenous (i.v.), intramuscular (i.m.), or intrasternal injection, intratumoral, or infusion techniques.

The term "nucleic acid," "nucleic acid molecule," "polynucleotide," or "polynucleotide molecule" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. In some embodiments, a "nucleic acid," "nucleic acid molecule," "polynucleotide," or "polynucleotide molecule" comprise a nucleotide/nucleoside derivative or analog. Unless otherwise indicated, a particular nucleic acid sequence also implicitly encompasses conservatively modified variants thereof (for example, degenerate codon substitutions, for example, conservative substitutions), alleles, orthologs, SNPs, and complementary sequences as well as the sequence explicitly indicated. Specifically, degenerate codon substitutions, for example, conservative substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen," "tumor antigen," "hyperproliferative disorder antigen," and "antigen associated with a hyperproliferative disorder" interchangeably refer to antigens that are common to specific hyperproliferative disorders. In some embodiments, these terms refer to a molecule (typically a protein, carbohydrate or lipid) that is expressed on the surface of a cancer cell, either entirely or as a fragment (for example, MHC/peptide), and which is useful for the preferential targeting of a pharmacological agent to the cancer cell. In some embodiments, a tumor antigen is a marker expressed by both normal cells and cancer cells, for example, a lineage marker, for example, CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (for example, MHC/peptide), and not synthesized or expressed on the surface of a normal cell. In some embodiments, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer (for example, castrate-resistant or therapy-resistant prostate cancer, or metastatic prostate cancer), ovarian cancer, pancreatic cancer, and the like, or a plasma cell proliferative disorder, for example, asymptomatic myeloma (smoldering multiple myeloma or indolent myeloma), monoclonal gammopathy of undetermined significance (MGUS), Waldenstrom's macroglobulinemia, plasmacytomas (for example, plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome). In some embodiments, the CARs of the present invention include CARs comprising an antigen binding domain (for example, antibody or antibody fragment) that binds to a MHC presented peptide. Normally, peptides derived from endogenous proteins fill the pockets of Major histocompatibility complex (MHC) class I molecules and are recognized by T cell receptors (TCRs) on CD8+ T lymphocytes. The MHC class I complexes are constitutively expressed by all nucleated cells. In cancer, virus-specific and/or tumor-specific peptide/

MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, for example, Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, for example, by promoting their growth or survival for example, resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of an scFv refers to a peptide linker that consists of amino acids such as glycine and/or serine residues used alone or in combination, to link variable heavy and variable light chain regions together. In some embodiments, the flexible polypeptide linker is a Gly/Ser linker and comprises the amino acid sequence (Gly-Gly-Gly-Ser)n, where n is a positive integer equal to or greater than 1 (SEQ ID NO: 41). For example, n=1, n=2, n=3. n=4, n=5 and n=6, n=7, n=8, n=9 and n=10 In some embodiments, the flexible polypeptide linkers include, but are not limited to, (Gly4 Ser)4 (SEQ ID NO: 27) or (Gly4 Ser)3 (SEQ ID NO: 28). In some embodiments, the linkers include multiple repeats of (Gly2Ser), (GlySer) or (Gly3Ser) (SEQ ID NO: 25). Also included within the scope of the invention are linkers described in WO2012/138475, incorporated herein by reference.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA that has been synthesized in vitro. In some embodiments the RNA is mRNA. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In some embodiments of a construct for transient expression, the poly(A) is between 50 and 5000. In some embodiments the poly(A) is greater than 64. In some embodiments the poly(A) is greater than 100. In some embodiments the poly(A) is greater than 300. In some embodiments the poly(A) is greater than 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (for example, one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, for example, stabilization of a discernible symptom, physiologically by, for example, stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (for example, mammals, for example, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In some embodiments, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (for example, a stimulatory and/or costimulatory molecule present on a T cell) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with intracellular signal generation. In some embodiments, an RCAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, for example, are in different polypeptide chains. In some embodiments, the RCAR includes a dimerization switch that, upon the presence of a dimerization molecule, can couple the polypeptides to one another, for example, can couple an antigen binding domain to an intracellular signaling domain. In some embodiments, the RCAR is expressed in a cell (for example, an immune effector cell) as described herein, for example, an RCAR-expressing cell (also referred to herein as "RCARX cell"). In some embodiments the RCARX cell is a T cell and is referred to as a RCART cell. In some embodiments the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, for example, a myristoyl group, sufficient to anchor an extracellular or intracellular domain to the plasma membrane.

"Switch domain," as that term is used herein, for example, when referring to an RCAR, refers to an entity, typically a polypeptide-based entity, that, in the presence of a dimerization molecule, associates with another switch domain. The association results in a functional coupling of a first entity linked to, for example, fused to, a first switch domain, and a second entity linked to, for example, fused to, a second switch domain. A first and second switch domain are collectively referred to as a dimerization switch. In embodiments, the first and second switch domains are the same as one another, for example, they are polypeptides having the same primary amino acid sequence and are referred to collectively as a homodimerization switch. In embodiments, the first and second switch domains are different from one another, for example, they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, for example, FKBP or FRB-based, and the dimerization molecule is small molecule, for example, a rapalogue. In embodiments, the switch domain is a polypeptide-based entity, for example, an scFv that binds a myc peptide, and the dimerization molecule is a polypeptide, a fragment thereof, or a multimer of a polypeptide, for example, a myc ligand or multimers of a myc ligand that bind to one or more myc scFvs. In embodiments, the switch domain is a polypeptide-based entity, for example, myc receptor, and the dimerization molecule is an antibody or fragments thereof, for example, myc antibody.

"Dimerization molecule," as that term is used herein, for example, when referring to an RCAR, refers to a molecule that promotes the association of a first switch domain with a second switch domain. In embodiments, the dimerization molecule does not naturally occur in the subject or does not occur in concentrations that would result in significant dimerization. In embodiments, the dimerization molecule is a small molecule, for example, rapamycin or a rapalogue, for example, RAD001.

The term "low, immune enhancing, dose" when used in conjunction with an mTOR inhibitor, for example, an allosteric mTOR inhibitor, for example, RAD001 or rapamycin, or a catalytic mTOR inhibitor, refers to a dose of mTOR inhibitor that partially, but not fully, inhibits mTOR activity, for example, as measured by the inhibition of P70 S6 kinase activity. Methods for evaluating mTOR activity, for example, by inhibition of P70 S6 kinase, are discussed herein. The dose is insufficient to result in complete immune suppression but is sufficient to enhance the immune response. In some embodiments, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In some embodiments, the low, immune enhancing, dose of mTOR inhibitor results in an increase in the number of naive T cells. In some embodiments, the low, immune enhancing, dose of mTOR inhibitor results in one or more of the following:

an increase in the expression of one or more of the following markers: $CD62L^{high}$, $CD127^{high}$, $CD27^{+}$, and BCL2, for example, on memory T cells, for example, memory T cell precursors;

a decrease in the expression of KLRG1, for example, on memory T cells, for example, memory T cell precursors; and an increase in the number of memory T cell precursors, for example, cells with any one or combination of the following characteristics: increased $CD62L^{high}$, increased $CD127^{high}$, increased $CD27^{+}$, decreased KLRG1, and increased BCL2;

wherein any of the changes described above occurs, for example, at least transiently, for example, as compared to a non-treated subject.

"Refractory" as used herein refers to a disease, for example, cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (for example, cancer) or the signs and symptoms of a disease such as cancer after a period of improvement or responsiveness, for example, after prior treatment of a therapy, for example, cancer therapy. The initial period of responsiveness may involve the level of cancer cells falling below a certain threshold, for example, below 20%, 1%, 10%, 5%, 4%, 3%, 2%, or 1%. The reappearance may involve the level of cancer cells rising above a certain threshold, for example, above 20%, 1%, 10%, 5%, 4%, 3%, 2%, or 1%. For example, for example, in the context of B-ALL, the reappearance may involve, for example, a reappearance of blasts in the blood, bone marrow (>5%), or any extramedullary site, after a complete response. A complete response, in this context, may involve <5% BM blast. More generally, in some embodiments, a response (for example, complete response or partial response) can involve the absence of detectable MRD (minimal residual disease). In some embodiments, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various embodiments of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

A "gene editing system" as the term is used herein, refers to a system, for example, one or more molecules, that direct and effect an alteration, for example, a deletion, of one or more nucleic acids at or near a site of genomic DNA targeted by said system. Gene editing systems are known in the art and are described more fully below.

Administered "in combination", as used herein, means that two (or more) different treatments are delivered to the subject during the course of the subject's affliction with the disorder, for example, the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, for example, an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The term "depletion" or "depleting", as used interchangeably herein, refers to the decrease or reduction of the level or amount of a cell, a protein, or macromolecule in a sample after a process, for example, a selection step, for example, a negative selection, is performed. The depletion can be a complete or partial depletion of the cell, protein, or macromolecule. In some embodiments, the depletion is at least a 1%, 2%, 5%, 10%, 15%, 20%, 25%, 30%, 35%, 40%, 45%, 50%, 55%, 60%, 65%, 70%, 75%, 80%, 85%, 90%, 95%, or 99% decrease or reduction of the level or amount of a cell, a protein, or macromolecule, as compared to the level or amount of the cell, protein or macromolecule in the sample before the process was performed.

As used herein, a "naïve T cell" refers to a T cell that is antigen-inexperienced. In some embodiments, an antigen-inexperienced T cell has encountered its cognate antigen in the thymus but not in the periphery. In some embodiments, naïve T cells are precursors of memory cells. In some embodiments, naïve T cells express both CD45RA and CCR7, but do not express CD45RO. In some embodiments, naïve T cells may be characterized by expression of CD62L, CD27, CCR7, CD45RA, CD28, and CD127, and the absence of CD95 or CD45RO isoform. In some embodiments, naïve T cells express CD62L, IL-7 receptor-α, IL-6 receptor, and CD132, but do not express CD25, CD44, CD69, or CD45RO. In some embodiments, naïve T cells express CD45RA, CCR7, and CD62L and do not express CD95 or IL-2 receptor β. In some embodiments, surface expression levels of markers are assessed using flow cytometry.

The term "central memory T cells" refers to a subset of T cells that in humans are CD45RO positive and express CCR7. In some embodiments, central memory T cells express CD95. In some embodiments, central memory T cells express IL-2R, IL-7R and/or IL-15R. In some embodiments, central memory T cells express CD45RO, CD95, IL-2 receptor β, CCR7, and CD62L. In some embodiments, surface expression levels of markers are assessed using flow cytometry.

The term "stem memory T cells," "stem cell memory T cells," "stem cell-like memory T cells," "memory stem T cells," "T memory stem cells," "T stem cell memory cells" or "TSCM cells" refers to a subset of memory T cells with stem cell-like ability, for example, the ability to self-renew and/or the multipotent capacity to reconstitute memory and/or effector T cell subsets. In some embodiments, stem memory T cells express CD45RA, CD95, IL-2 receptor β, CCR7, and CD62L. In some embodiments, surface expression levels of markers are assessed using flow cytometry. In some embodiments, exemplary stem memory T cells are disclosed in Gattinoni et al., Nat Med. 2017 Jan. 6; 23(1): 18-27, herein incorporated by reference in its entirety.

For clarity purposes, unless otherwise noted, classifying a cell or a population of cells as "not expressing," or having an "absence of" or being "negative for" a particular marker may not necessarily mean an absolute absence of the marker. The skilled artisan can readily compare the cell against a positive and/or a negative control, and/or set a predetermined threshold, and classify the cell or population of cells as not expressing or being negative for the marker when the cell has an expression level below the predetermined threshold or a population of cells has an overall expression level below the predetermined threshold using conventional detection methods, e.g., using flow cytometry, for example, as described in the Examples herein. For example, representative gating strategies are shown in FIG. 1G. For example, CCR7 positive, CD45RO negative cells are shown in the top left quadrant in FIG. 1G.

As used herein, the term "GeneSetScore (Up TEM vs. Down TSCM)" of a cell refers to a score that reflects the degree at which the cell shows an effector memory T cell (TEM) phenotype vs. a stem cell memory T cell (TSCM) phenotype. A higher GeneSetScore (Up TEM vs. Down TSCM) indicates an increasing TEM phenotype, whereas a lower GeneSetScore (Up TEM vs. Down TSCM) indicates an increasing TSCM phenotype. In some embodiments, the GeneSetScore (Up TEM vs. Down TSCM) is determined by measuring the expression of one or more genes that are up-regulated in TEM cells and/or down-regulated in TSCM cells, for example, one or more genes selected from the group consisting of MXRA7, CLIC1, NAT13, TBC1D2B, GLCCI1, DUSP10, APOBEC3D, CACNB3, ANXA2P2, TPRG1, EOMES, MATK, ARHGAP10, ADAM8, MAN1A1, SLFN12L, SH2D2A, EIF2C4, CD58, MYO1F, RAB27B, ERN1, NPC1, NBEAL2, APOBEC3G, SYTL2, SLC4A4, PIK3AP1, PTGDR, MAF, PLEKHA5, ADRB2, PLXND1, GNAO1, THBS1, PPP2R2B, CYTH3, KLRF1, FLJ16686, AUTS2, PTPRM, GNLY, and GFPT2. In some embodiments, the GeneSetScore (Up TEM vs. Down TSCM) is determined for each cell using RNA-seq, for example, single-cell RNA-seq (scRNA-seq), for example, as exemplified in Example 10 with respect to FIG. 39A. In some embodiments, the GeneSetScore (Up TEM vs. Down TSCM) is calculated by taking the mean log normalized gene expression value of all of the genes in the gene set.

As used herein, the term "GeneSetScore (Up Treg vs. Down Teff)" of a cell refers to a score that reflects the degree at which the cell shows a regulatory T cell (Treg) phenotype vs. an effector T cell (Teff) phenotype. A higher GeneSetScore (Up Treg vs. Down Teff) indicates an increasing Treg phenotype, whereas a lower GeneSetScore (Up Treg vs. Down Teff) indicates an increasing Teff phenotype. In some embodiments, the GeneSetScore (Up Treg vs. Down Teff) is determined by measuring the expression of one or more genes that are up-regulated in Treg cells and/or down-regulated in Teff cells, for example, one or more genes selected from the group consisting of C12orf75, SELPLG, SWAP70, RGS1, PRR11, SPATS2L, SPATS2L, TSHR, C14orf145, CASP8, SYT11, ACTN4, ANXA5, GLRX, HLA-DMB, PMCH, RAB11FIP1, IL32, FAM160B1, SHMT2, FRMD4B, CCR3, TNFRSF13B, NTNG2, CLDND1, BARD1, FCER1G, TYMS, ATP1B1, GJB6, FGL2, TK1, SLC2A8, CDKN2A, SKAP2, GPR55, CDCA7, S100A4, GDPD5, PMAIP1, ACOT9, CEP55, SGMS1, ADPRH, AKAP2, HDAC9, IKZF4, CARD17, VAV3, OBFC2A, ITGB1, CIITA, SETD7, HLA-DMA, CCR10, KIAA0101, SLC14A1, PTTG3P, DUSP10, FAM164A, PYHIN1, MYO1F, SLC1A4, MYBL2, PTTG1, RRM2, TP53INP1, CCR5, ST8SIA6, TOX, BFSP2, ITPRIPL1, NCAPH, HLA-DPB2, SYT4, NINJ2, FAM46C, CCR4, GBP5, C15orf53, LMCD1, MKI67, NUSAP1, PDE4A, E2F2, CD58, ARHGEF12, LOC100188949, FAS, HLA-DPB1, SELP, WEE1, HLA-DPA1, FCRL1, ICA1, CNTNAP1, OAS1, METTL7A, CCR6, HLA-DRB4, ANXA2P3, STAM, HLA-DQB2, LGALS1, ANXA2, PI16, DUSP4, LAYN, ANXA2P2, PTPLA, ANXA2P1, ZNF365, LAIR2, LOC541471, RASGRP4, BCAS1, UTS2, MIAT, PRDM1, SEMA3G, FAM129A, HPGD, NCF4, LGALS3, CEACAM4, JAKMIP1, TIGIT, HLA-DRA, IKZF2, HLA-DRB1, FANK1, RTKN2, TRIB1, FCRL3, and FOXP3. In some embodiments, the GeneSetScore (Up Treg vs. Down Teff) is determined using RNA-seq, for example, single-cell RNA-seq (scRNA-seq), for example, as exemplified in Example 10 with respect to FIG. 39B. In some embodiments, the GeneSetScore (Up Treg vs. Down Teff) is calculated by taking the mean log normalized gene expression value of all of the genes in the gene set.

As used herein, the term "GeneSetScore (Down stemness)" of a cell refers to a score that reflects the degree at which the cell shows a stemness phenotype. A lower GeneSetScore (Down stemness) indicates an increasing stemness phenotype. In some embodiments, the GeneSetScore (Down stemness) is determined by measuring the expression of one or more genes that are upregulated in a differentiating stem cell vs downregulated in a hematopoietic stem cell, for example, one or more genes selected from the group consisting of ACE, BATF, CDK6, CHD2, ERCC2, HOXB4, MEOX1, SFRP1, SP7, SRF, TAL1, and XRCC5. In some embodiments, the GeneSetScore (Down stemness) is determined using RNA-seq, for example, single-cell RNA-seq (scRNA-seq), for example, as exemplified in Example 10 with respect to FIG. 39C. In some embodiments, the GeneSetScore (Down stemness) is calculated by taking the mean log normalized gene expression value of all of the genes in the gene set.

As used herein, the term "GeneSetScore (Up hypoxia)" of a cell refers to a score that reflects the degree at which the cell shows a hypoxia phenotype. A higher GeneSetScore (Up hypoxia) indicates an increasing hypoxia phenotype. In some embodiments, the GeneSetScore (Up hypoxia) is determined by measuring the expression of one or more genes that are up-regulated in cells undergoing hypoxia, for example, one or more genes selected from the group consisting of ABCB1, ACAT1, ADM, ADORA2B, AK2, AK3, ALDH1A1, ALDH1A3, ALDOA, ALDOC, ANGPT2, ANGPTL4, ANXA1, ANXA2, ANXA5, ARHGAP5, ARSE, ART1, BACE2, BATF3, BCL2L1, BCL2L2, BHLHE40, BHLHE41, BIK, BIRC2, BNIP3, BNIP3L, BPI, BTG1, C11orf2, C7orf68, CA12, CA9, CALD1, CCNG2, CCT6A, CD99, CDK1, CDKN1A, CDKN1B, CITED2, CLK1, CNOT7, COL4A5, COL5A1, COL5A2, COL5A3, CP, CTSD, CXCR4, D4S234E, DDIT3, DDIT4, 1-Dec, DKC1, DR1, EDN1, EDN2, EFNA1, EGF, EGR1, EIF4A3, ELF3, ELL2, ENG, ENO1, ENO3, ENPEP, EPO, ERRFI1, ETS1, F3, FABP5, FGF3, FKBP4, FLT1, FN1, FOS, FTL, GAPDH, GBE1, GLRX, GPI, GPRC5A, HAP1, HBP1, HDAC1, HDAC9, HERC3, HERPUD1, HGF, HIF1A, HK1, HK2, HLA-DQB1, HMOX1, HMOX2, HSPA5, HSPD1, HSPH1, HYOU1, ICAM1, ID2, IFI27, IGF2, IGFBP1, IGFBP2, IGFBP3, IGFBP5, IL6, IL8, INSIG1, IRF6, ITGA5, JUN, KDR, KRT14, KRT18, KRT19, LDHA, LDHB, LEP, LGALS1, LONP1, LOX, LRP1, MAP4, MET, MIF, MMP13, MMP2, MMP7, MPI, MT1L, MTL3P, MUC1, MXI1, NDRG1, NFIL3, NFKB1, NFKB2, NOS1, NOS2, NOS2P1, NOS2P2, NOS3, NR3C1, NR4A1, NT5E, ODC1, P4HA1, P4HA2, PAICS, PDGFB, PDK3, PFKFB1, PFKFB3, PFKFB4, PFKL, PGAM1, PGF, PGK1, PGK2, PGM1, PIM1, PIM2, PKM2, PLAU, PLAUR, PLIN2, PLOD2, PNN, PNP, POLM, PPARA, PPAT, PROK1, PSMA3, PSMD9, PTGS1, PTGS2, QSOX1, RBPJ, RELA, RIOK3, RNASEL, RPL36A, RRP9, SAT1, SERPINB2, SERPINE1, SGSM2, SIAH2, SIN3A, SIRPA, SLC16A1, SLC16A2, SLC20A1, SLC2A1, SLC2A3, SLC3A2, SLC6A10P, SLC6A16, SLC6A6, SLC6A8, SORL1, SPP1, SRSF6, SSSCA1, STC2, STRA13, SYT7, TBPL1, TCEAL1, TEK, TF, TFF3, TFRC, TGFA, TGFB1, TGFB3, TGFBI, TGM2, TH, THBS1, THBS2, TIMM17A, TNFAIP3, TP53, TPBG, TPD52, TPI1, TXN, TXNIP, UMPS, VEGFA, VEGFB, VEGFC, VIM, VPS11, and XRCC6. In some embodiments, the GeneSetScore (Up hypoxia) is determined using RNA-seq, for example, single-cell RNA-seq (scRNA-seq), for example, as exemplified in Example 10 with respect to FIG. 39D. In some embodiments, the GeneSetScore (Up hypoxia) is calculated by taking the mean log normalized gene expression value of all of the genes in the gene set.

As used herein, the term "GeneSetScore (Up autophagy)" of a cell refers to a score that reflects the degree at which the cell shows an autophagy phenotype. A higher GeneSetScore (Up autophagy) indicates an increasing autophagy phenotype. In some embodiments, the GeneSetScore (Up autophagy) is determined by measuring the expression of one or more genes that are up-regulated in cells undergoing autophagy, for example, one or more genes selected from the group consisting of ABL1, ACBD5, ACIN1, ACTRT1, ADAMTS7, AKR1E2, ALKBH5, ALPK1, AMBRA1, ANXA5, ANXA7, ARSB, ASB2, ATG10, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATP13A2, ATP1B1, ATPAF1-AS1, ATPIF1, BECN1, BECN1P1, BLOC1S1, BMP2KL, BNIP1, BNIP3, BOC, C11orf2, C11orf41, C12orf44, C12orf5, C14orf133, C1orf210, C5, C6orf106, C7orf59, C7orf68, C8orf59, C9orf72, CA7, CALCB, CALCOCO2, CAPS, CCDC136, CD163L1, CD93, CDC137, CDKN2A, CHAF1B, CHMP2A, CHMP2B, CHMP3, CHMP4A, CHMP4B, CHMP4C, CHMP6, CHST3, CISD2, CLDN7, CLEC16A, CLN3, CLVS1, COX8A, CPA3, CRNKL1, CSPG5, CTSA, CTSB, CTSD, CXCR7, DAP, DKKL1, DNAAF2, DPF3, DRAM1, DRAM2, DYNLL1, DYNLL2, DZANK1, EI24, EIF2S1, EPG5, EPM2A, FABP1, FAM125A, FAM131B, FAM134B, FAM13B, FAM176A, FAM176B, FAM48A, FANCC, FANCF, FANCL, FBXO7, FCGR3B, FGF14, FGF7, FGFBP1, FIS1, FNBP1L, FOXO1, FUNDC1, FUNDC2, FXR2, GABARAP, GABARAPL1, GABARAPL2, GABARAPL3, GABRA5, GDF5, GMIP, HAP1, HAPLN1, HBXIP, HCAR1, HDAC6, HGS, HIST1H3A, HIST1H3B, HIST1H3C, HIST1H3D, HIST1H3E, HIST1H3F, HIST1H3G, HIST1H3H, HIST1H3I, HIST1H3J, HK2, HMGB1, HPR, HSF2BP, HSP90AA1, HSPA8, IFI16, IPPK, IRGM, IST1, ITGB4, ITPKC, KCNK3, KCNQ1, KIAA0226, KIAA1324, KRCC1, KRT15, KRT73, LAMP1, LAMP2, LAMTOR1, LAMTOR2, LAMTOR3, LARP1B, LENG9, LGALS8, LIX1, LIX1L, LMCD1, LRRK2, LRSAM1, LSM4, MAP1A, MAP1LC3A, MAP1LC3B, MAP1LC3B2, MAP1LC3C, MAP1S, MAP2K1, MAP3K12, MARK2, MBD5, MDH1, MEX3C, MFN1, MFN2, MLST8, MRPS10, MRPS2, MSTN, MTERFD1, MTMR14, MTMR3, MTOR, MTSS1, MYH11, MYLK, MYOM1, NBR1, NDUFB9, NEFM, NHLRC1, NME2, NPC1, NR2C2, NRBF2, NTHL1, NUP93, OBSCN, OPTN, P2RX5, PACS2, PARK2, PARK7, PDK1, PDK4, PEX13, PEX3, PFKP, PGK2, PHF23, PHYHIP, PI4K2A, PIK3C3, PIK3CA, PIK3CB, PIK3R4, PINK1, PLEKHM1, PLOD2, PNPO, PPARGC1A, PPY, PRKAA1, PRKAA2, PRKAB1, PRKAB2, PRKAG1, PRKAG2, PRKAG3, PRKD2, PRKG1, PSEN1, PTPN22, RAB12, RAB1A, RAB1B, RAB23, RAB24, RAB33B, RAB39, RAB7A, RB1CC1, RBM18, REEP2, REP15, RFWD3, RGS19, RHEB, RIMS3, RNF185, RNF41, RPS27A, RPTOR, RRAGA, RRAGB, RRAGC, RRAGD, S100A8, S100A9, SCN1A, SERPINB10, SESN2, SFRP4, SH3GLB1, SIRT2, SLC1A3, SLC1A4, SLC22A3, SLC25A19, SLC35B3, SLC35C1, SLC37A4, SLC6A1, SLCO1A2, SMURF1, SNAP29, SNAPIN, SNF8, SNRPB, SNRPB2, SNRPD1, SNRPF, SNTG1, SNX14, SPATA18, SQSTM1, SRPX, STAM, STAM2, STAT2, STBD1, STK11, STK32A, STOM, STX12, STX17, SUPT3H, TBC1D17, TBC1D25, TBC1D5, TCIRG1, TEAD4, TECPR1, TECPR2, TFEB, TM9SF1, TMBIM6, TMEM203, TMEM208, TMEM39A, TMEM39B, TMEM59, TMEM74, TMEM93, TNIK, TOLLIP, TOMM20, TOMM22, TOMM40, TOMM5, TOMM6, TOMM7, TOMM70A, TP53INP1, TP53INP2, TRAPPC8, TREM1, TRIM17, TRIMS, TSG101, TXLNA, UBA52, UBB, UBC, UBQLN1, UBQLN2, UBQLN4, ULK1, ULK2, ULK3, USP10, USP13, USP30, UVRAG, VAMP7, VAMP8, VDAC1, VMP1, VPS11, VPS16, VPS18, VPS25, VPS28, VPS33A, VPS33B, VPS36, VPS37A, VPS37B, VPS37C, VPS37D, VPS39, VPS41, VPS4A, VPS4B, VTA1, VTI1A, VTI1B, WDFY3, WDR45, WDR45L, WIPI1, WIPI2, XBP1, YIPF1, ZCCHC17, ZFYVE1, ZKSCAN3, ZNF189, ZNF593, and ZNF681. In some embodiments, the GeneSetScore (Up autophagy) is determined using RNA-seq, for example, single-cell RNA-seq (scRNA-seq), for example, as exemplified in Example 10 with respect to FIG. 39E. In some embodiments, the GeneSetScore (Up autophagy) is calculated by taking the mean log normalized gene expression value of all of the genes in the gene set.

As used herein, the term "GeneSetScore (Up resting vs. Down activated)" of a cell refers to a score that reflects the degree at which the cell shows a resting T cell phenotype vs. an activated T cell phenotype. A higher GeneSetScore (Up resting vs. Down activated) indicates an increasing resting T cell phenotype, whereas a lower GeneSetScore (Up resting vs. Down activated) indicates an increasing activated T cell phenotype. In some embodiments, the GeneSetScore (Up resting vs. Down activated) is determined by measuring the expression of one or more genes that are up-regulated in resting T cells and/or down-regulated in activated T cells, for example, one or more genes selected from the group consisting of ABCA7, ABCF3, ACAP2, AMT, ANKH, ATF7IP2, ATG14, ATP1A1, ATXN7, ATXN7L3B, BCL7A, BEX4, BSDC1, BTG1, BTG2, BTN3A1, C11orf21, C19orf22, C21orf2, CAMK2G, CARS2, CCNL2, CD248, CD5, CD55, CEP164, CHKB, CLK1, CLK4, CTSL1, DBP, DCUN1D2, DENND1C, DGKD, DLG1, DUSP1, EAPP, ECE1, ECHDC2, ERBB2IP, FAM117A, FAM134B, FAM134C, FAM169A, FAM190B, FAU, FJL10038, FOXJ2, FOXJ3, FOXL1, FOXO1, FXYD5, FYB, HLA-E, HSPA1L, HYAL2, ICAM2, IFIT5, IFITM1, IKBKB, IQSEC1, IRS4, KIAA0664L3, KIAA0748, KLF3, KLF9, KRT18, LEF1, LINC00342, LIPA, LIPT1, LLGL2, LMBR1L, LPAR2, LTBP3, LYPD3, LZTFL1, MANBA, MAP2K6, MAP3K1, MARCH8, MAU2, MGEA5, MMP8, MPO, MSL1, MSL3, MYH3, MYLIP, NAGPA, NDST2, NISCH, NKTR, NLRP1, NOSIP, NPIP, NUMA1, PAIP2B, PAPD7, PBXIP1, PCIF1, PI4KA, PLCL2, PLEKHA1, PLEKHF2, PNISR, PPFIBP2, PRKCA, PRKCZ, PRKD3, PRMT2, PTP4A3, PXN, RASA2, RASA3, RASGRP2, RBM38, REPIN1, RNF38, RNF44, ROR1, RPL30, RPL32, RPLP1, RPS20, RPS24, RPS27, RPS6, RPS9, RXRA, RYK, SCAND2, SEMA4C, SETD1B, SETD6, SETX, SF3B1, SH2B1, SLC2A4RG, SLC35E2B, SLC46A3, SMAGP, SMARCE1, SMPD1, SNPH, SP140L, SPATA6, SPG7, SREK1IP1, SRSF5, STAT5B, SVIL, SYF2, SYNJ2BP, TAF1C, TBC1D4, TCF20, TECTA, TES, TMEM127, TMEM159, TMEM30B, TMEM66, TMEM8B, TP53TG1, TPCN1, TRIM22, TRIM44, TSC1, TSC22D1, TSC22D3, TSPYL2, TTC9, TTN, UBE2G2, USP33, USP34, VAMP1, VILL, VIPR1, VPS13C, ZBED5, ZBTB25, ZBTB40, ZC3H3, ZFP161, ZFP36L1, ZFP36L2, ZHX2, ZMYM5, ZNF136, ZNF148, ZNF318, ZNF350, ZNF512B, ZNF609, ZNF652, ZNF83, ZNF862, and ZNF91. In some embodiments, the GeneSetScore (Up resting vs. Down activated) is determined using RNA-seq, for example, single-cell RNA-seq (scRNA-seq), for example, as exemplified in Example 10 with respect to FIG. 38D. In some embodiments, the GeneSetScore (Up resting vs. Down activated) is calculated by taking the mean log normalized gene expression value of all of the genes in the gene set.

As used herein, the term "GeneSetScore (Progressively up in memory differentiation)" of a cell refers to a score that reflects the stage of the cell in memory differentiation. A higher GeneSetScore (Progressively up in memory differentiation) indicates an increasing late memory T cell phenotype, whereas a lower GeneSetScore (Progressively up in memory differentiation) indicates an increasing early memory T cell phenotype. In some embodiments, the GeneSetScore (Up autophagy) is determined by measuring the expression of one or more genes that are up-regulated during memory differentiation, for example, one or more genes selected from the group consisting of MTCH2, RAB6C, KIAA0195, SETD2, C2orf24, NRD1, GNA13, COPA, SELT, TNIP1, CBFA2T2, LRP10, PRKCI, BRE, ANKS1A, PNPLA6, ARL6IP1, WDFY1, MAPK1, GPR153, SHKBP1, MAP1LC3B2, PIP4K2A, HCN3, GTPBP1, TLN1, C4orf34, KIF3B, TCIRG1, PPP3CA, ATG4D, TYMP, TRAF6, C17orf76, WIPF1, FAM108A1, MYL6, NRM, SPCS2, GGT3P, GALK1, CLIP4, ARL4C, YWHAQ, LPCAT4, ATG2A, IDS, TBC1D5, DMPK, ST6GALNAC6, REEP5, ABHD6, KIAA0247, EMB, TSEN54, SPIRE2, PIWIL4, ZSCAN22, ICAM1, CHD9, LPIN2, SETD8, ZC3H12A, ULBP3, IL15RA, HLA-DQB2, LCP1, CHP, RUNX3, TMEM43, REEP4, MEF2D, ABL1, TMEM39A, PCBP4, PLCD1, CHST12, RASGRP1, C1orf58, C11orf63, C6orf129, FHOD1, DKFZp434F142, PIK3CG, ITPR3, BTG3, C4orf50, CNNM3, IFI16, AK1, CDK2AP1, REL, BCL2L1, MVD, TTC39C, PLEKHA2, FKBP11, EML4, FANCA, CDCA4, FUCA2, MFSD10, TBCD, CAPN2, IQGAP1, CHST11, PIK3R1, MYO5A, KIR2DL3, DLG3, MXD4, RALGDS, S1PR5, WSB2, CCR3, TIPARP, SP140, CD151, SOX13, KRTAP5-2, NF1, PEA15, PARP8, RNF166, UEVLD, LIMK1, CACNB1, TMX4, SLC6A6, LBA1, SV2A, LLGL2, IRF1, PPP2R5C, CD99, RAPGEF1, PPP4R1, OSBPL7, FOXP4, SLA2, TBC1D2B, ST7, JAZF1, GGA2, PI4K2A, CD68, LPGAT1, STX11, ZAK, FAM160B1, RORA, C8orf80, APOBEC3F, TGFBI, DNAJC1, GPR114, LRP8, CD69, CMIP, NAT13, TGFB1, FLJ00049, ANTXR2, NR4A3, IL12RB1, NTNG2, RDX, MLLT4, GPRIN3, ADCY9, CD300A, SCD5, ABI3, PTPN22, LGALS1, SYTL3, BMPR1A, TBK1, PMAIP1, RASGEF1A, GCNT1, GABARAPL1, STOM, CALHM2, ABCA2, PPP1R16B, SYNE2, PAM, C12orf75, CLCF1, MXRA7, APOBEC3C, CLSTN3, ACOT9, HIP1, LAG3, TNFAIP3, DCBLD1, KLF6, CACNB3, RNF19A, RAB27A, FADS3, DLG5, APOBEC3D, TNFRSF1B, ACTN4, TBKBP1, ATXN1, ARAP2, ARHGEF12, FAM53B, MAN1A1, FAM38A, PLXNC1, GRLF1, SRGN, HLA-DRB5, B4GALT5, WIPI1, PTPRJ, SLFN11, DUSP2, ANXA5, AHNAK, NEO1, CLIC1, EIF2C4, MAP3K5, IL2RB, PLEKHG1, MYO6, GTDC1, EDARADD, GALM, TARP, ADAM8, MSC, HNRPLL, SYT11, ATP2B4, NHSL2, MATK, ARHGAP18, SLFN12L, SPATS2L, RAB27B, PIK3R3, TP53INP1, MBOAT1, GYG1, KATNAL1, FAM46C, ZC3HAV1L, ANXA2P2, CTNNA1, NPC1, C3AR1, CRIM1, SH2D2A, ERN1, YPEL1, TBX21, SLC1A4, FASLG, PHACTR2, GALNT3, ADRB2, PIK3AP1, TLR3, PLEKHA5, DUSP10, GNAO1, PTGDR, FRMD4B, ANXA2, EOMES, CADM1, MAF, TPRG1, NBEAL2, PPP2R2B, PELO, SLC4A4, KLRF1, FOSL2, RGS2, TGFBR3, PRF1, MYO1F, GAB3, C17orf66, MICAL2, CYTH3, TOX, HLA-DRA, SYNE1, WEE1, PYHIN1, F2R, PLD1, THBS1, CD58, FAS, NETO2, CXCR6, ST6GALNAC2, DUSP4, AUTS2, C1orf21, KLRG1, TNIP3, GZMA, PRR5L, PRDM1, ST8SIA6, PLXND1, PTPRM, GFPT2, MYBL1, SLAMF7, FLJ16686, GNLY, ZEB2, CST7, IL18RAP, CCL5, KLRD1, and KLRB1. In some embodiments, the GeneSetScore (Progressively up in memory differentiation) is determined using RNA-seq, for example, single-cell RNA-seq (scRNA-seq), for example, as exemplified in Example 10 with respect to FIG. 40B. In some embodiments, the GeneSetScore (Progressively up in memory differentiation) is calculated by taking the mean log normalized gene expression value of all of the genes in the gene set.

As used herein, the term "GeneSetScore (Up TEM vs. Down TN)" of a cell refers to a score that reflects the degree at which the cell shows an effector memory T cell (TEM) phenotype vs. a naïve T cell (TN) phenotype. A higher GeneSetScore (Up TEM vs. Down TN) indicates an increasing TEM phenotype, whereas a lower GeneSetScore (Up TEM vs. Down TN) indicates an increasing TN phenotype. In some embodiments, the GeneSetScore (Up TEM vs. Down TN) is determined by measuring the expression of one or more genes that are up-regulated in TEM cells and/or down-regulated in TN cells, for example, one or more genes selected from the group consisting of MYO5A, MXD4, STK3, S1PR5, GLCCI1, CCR3, SOX13, KRTAP5-2, PEA15, PARP8, RNF166, UEVLD, LIMK1, SLC6A6, SV2A, KPNA2, OSBPL7, ST7, GGA2, PI4K2A, CD68, ZAK, RORA, TGFBI, DNAJC1, JOSD1, ZFYVE28, LRP8, OSBPL3, CMIP, NAT13, TGFB1, ANTXR2, NR4A3, RDX, ADCY9, CHN1, CD300A, SCD5, PTPN22, LGALS1, RASGEF1A, GCNT1, GLUL, ABCA2, CLDND1, PAM, CLCF1, MXRA7, CLSTN3, ACOT9, METRNL, BMPR1A, LRIG1, APOBEC3G, CACNB3, RNF19A, RAB27A, FADS3, ACTN4, TBKBP1, FAM53B, MAN1A1, FAM38A, GRLF1, B4GALT5, WIPI1, DUSP2, ANXA5, AHNAK, CLIC1, MAP3K5, ST8SIA1, TARP, ADAM8, MATK, SLFN12L, PIK3R3, FAM46C, ANXA2P2, CTNNA1, NPC1, SH2D2A, ERN1, YPEL1, TBX21, STOM, PHACTR2, GBP5, ADRB2, PIK3AP1, DUSP10, PTGDR, EOMES, MAF, TPRG1, NBEAL2, NCAPH, SLC4A4, FOSL2, RGS2, TGFBR3, MYO1F, C17orf66, CYTH3, WEE1, PYHIN1, F2R, THBS1, CD58, AUTS2, FAM129A, TNIP3, GZMA, PRR5L, PRDM1, PLXND1, PTPRM, GFPT2, MYBL1, SLAMF7, ZEB2, CST7, CCL5, GZMK, and KLRB1. In some embodiments, the GeneSetScore (Up TEM vs. Down TN) is determined using RNA-seq, for example, single-cell RNA-seq (scRNA-seq), for example, as exemplified in Example 10 with respect to FIG. 40C. In some embodiments, the GeneSetScore (Up TEM vs. Down TN) is calculated by taking the mean log normalized gene expression value of all of the genes in the gene set.

Figure 39A:
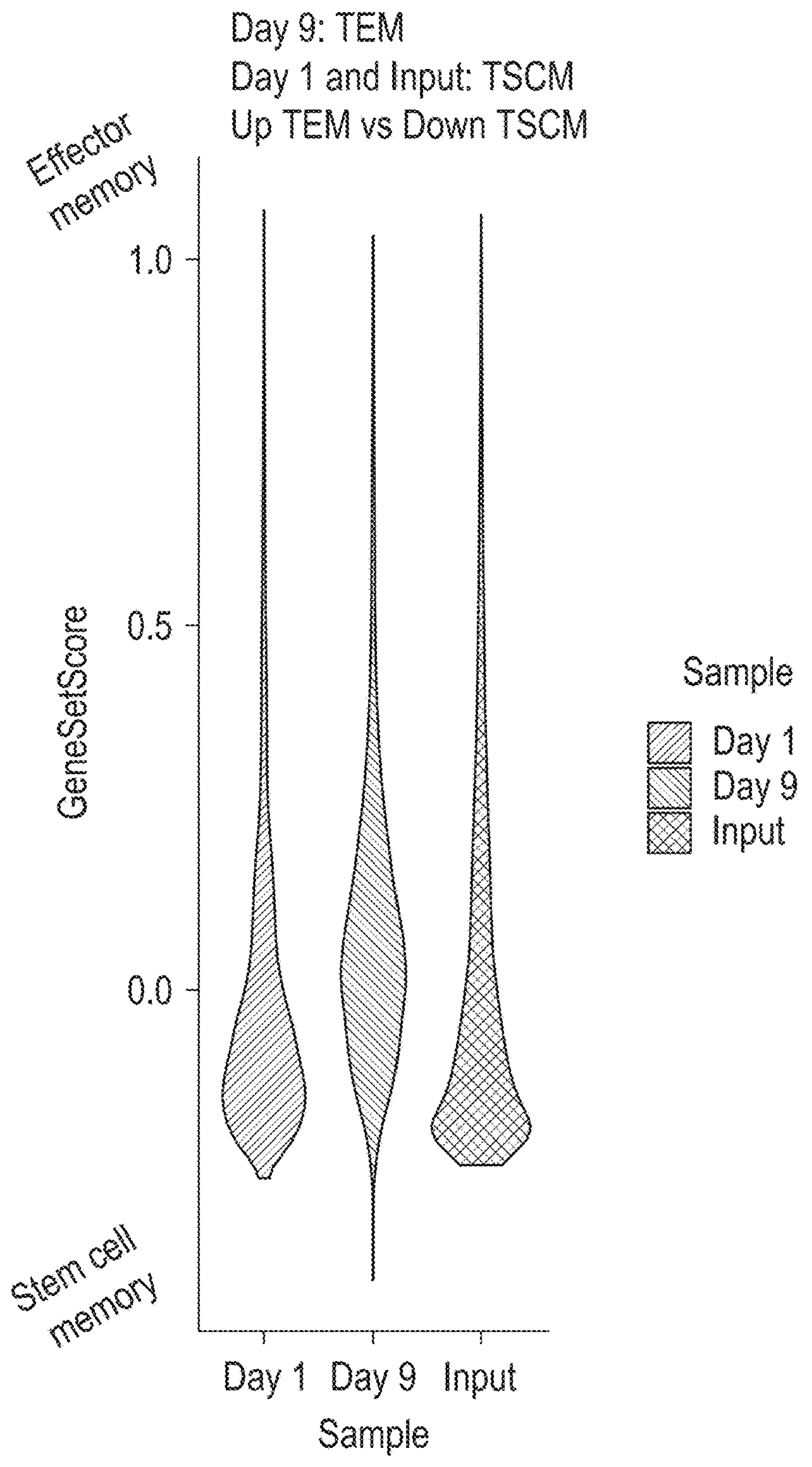
FIGS. 39A, 39B, 39C, 39D and 39E. Gene set analysis for input cells, Day 1 cells, and Day 9 cells.

In the context of GeneSetScore values (e.g., median GeneSetScore values), when a positive GeneSetScore is reduced by 100%, the value becomes 0. When a negative GeneSetScore is increased by 100%, the value becomes 0. For example, in FIG. 39A, the median GeneSetScore of the Day1 sample is −0.084; the median GeneSetScore of the Day9 sample is 0.035; and the median GeneSetScore of the input sample is −0.1. In FIG. 39A, increasing the median GeneSetScore of the input sample by 100% leads to a GeneSetScore value of 0; and increasing the median GeneSetScore of the input sample by 200% leads to a GeneSetScore value of 0.1. In FIG. 39A, decreasing the median GeneSetScore of the Day9 sample by 100% leads to a GeneSetScore value of 0; and decreasing the median GeneSetScore of the Day9 sample by 200% leads to a GeneSetScore value of −0.035.

As used herein, the term "bead" refers to a discrete particle with a solid surface, ranging in size from approximately 0.1 μm to several millimeters in diameter. Beads may be spherical (for example, microspheres) or have an irregular shape. Beads may comprise a variety of materials including, but not limited to, paramagnetic materials, ceramic, plastic, glass, polystyrene, methylstyrene, acrylic polymers, titanium, latex, Sepharose™, cellulose, nylon and the like. In some embodiments, the beads are relatively uniform, about 4.5 μm in diameter, spherical, superparamagnetic polystyrene beads, for example, coated, for example, covalently coupled, with a mixture of antibodies against CD3 (for example, CD3 epsilon) and CD28. In some embodiments, the beads are Dynabeads®. In some embodiments, both anti-CD3 and anti-CD28 antibodies are coupled to the same bead, mimicking stimulation of T cells by antigen presenting cells. The property of Dynabeads® and the use of Dynabeads® for cell isolation and expansion are well known in the art, for example, see, Neurauter et al., *Cell isolation and expansion using Dynabeads*, Adv Biochem Eng Biotechnol. 2007; 106:41-73, herein incorporated by reference in its entirety.

As used herein, the term "nanomatrix" refers to a nanostructure comprising a matrix of mobile polymer chains. The nanomatrix is 1 to 500 nm, for example, 10 to 200 nm, in size. In some embodiments, the matrix of mobile polymer chains is attached to one or more agonists which provide activation signals to T cells, for example, agonist anti-CD3 and/or anti-CD28 antibodies. In some embodiments, the nanomatrix comprises a colloidal polymeric nanomatrix attached, for example, covalently attached, to an agonist of one or more stimulatory molecules and/or an agonist of one or more costimulatory molecules. In some embodiments, the agonist of one or more stimulatory molecules is a CD3 agonist (for example, an anti-CD3 agonistic antibody). In some embodiments, the agonist of one or more costimulatory molecules is a CD28 agonist (for example, an anti-CD28 agonistic antibody). In some embodiments, the nanomatrix is characterized by the absence of a solid surface, for example, as the attachment point for the agonists, such as anti-CD3 and/or anti-CD28 antibodies. In some embodiments, the nanomatrix is the nanomatrix disclosed in WO2014/048920A1 or as given in the MACS® GMP T Cell TransAct™ kit from Miltenyi Biotcc GmbH, herein incorporated by reference in their entirety. MACS® GMP T Cell TransAct™ consists of a colloidal polymeric nanomatrix covalently attached to humanized recombinant agonist antibodies against human CD3 and CD28.

Various embodiments of the compositions and methods herein are described in further detail below. Additional definitions are set out throughout the specification.

DESCRIPTION

Provided herein are methods of manufacturing immune effector cells (for example, T cells or NK cells) engineered to express a CAR, for example, a CAR described herein, compositions comprising such cells, and methods of using such cells for treating a disease, such as cancer, in a subject. In some embodiments, the methods disclosed herein may manufacture immune effector cells engineered to express a CAR in less than 24 hours. Without wishing to be bound by theory, the methods provided herein preserve the undifferentiated phenotype of T cells, such as naïve T cells, during the manufacturing process. These CAR-expressing cells with an undifferentiated phenotype may persist longer and/or expand better in vivo after infusion. In some embodiments, CART cells produced by the manufacturing methods provided herein comprise a higher percentage of stem cell memory T cells, compared to CART cells produced by the traditional manufacturing process, e.g., as measured using scRNA-seq (e.g., as measured using methods described in Example 10 with respect to FIG. 39A). In some embodiments, CART cells produced by the manufacturing methods provided herein comprise a higher percentage of effector T cells, compared to CART cells produced by the traditional manufacturing process, e.g., as measured using scRNA-seq (e.g., as measured using methods described in Example 10 with respect to FIG. 39B). In some embodiments, CART cells produced by the manufacturing methods provided herein better preserve the stemness of T cells, compared to CART cells produced by the traditional manufacturing process, e.g., as measured using scRNA-seq (e.g., as measured using methods described in Example 10 with respect to FIG. 39C). In some embodiments, CART cells produced by the manufacturing methods provided herein show a lower level of hypoxia, compared to CART cells produced by the traditional manufacturing process, e.g., as measured using scRNA-seq (e.g., as measured using methods described in Example 10 with respect to FIG. 39D). In some embodiments, CART cells produced by the manufacturing methods provided herein show a lower level of autophagy, compared to CART cells produced by the traditional manufacturing process, e.g., as measured using scRNA-seq (e.g., as measured using methods described in Example 10 with respect to FIG. 39E).

In some embodiments, the methods disclosed herein do not involve using a bead, such as Dynabeads® (for example, CD3/CD28 Dynabeads®), and do not involve a de-beading step. In some embodiments, the CART cells manufactured by the methods disclosed herein may be administered to a subject with minimal ex vivo expansion, for example, less than 1 day, less than 12 hours, less than 8 hours, less than 6 hours, less than 4 hours, less than 3 hours, less than 2 hours, less than 1 hour, or no ex vivo expansion. Accordingly, the methods described herein provide a fast manufacturing process of making improved CAR-expressing cell products for use in treating a disease in a subject.

Cytokine Process

In some embodiments, the present disclosure provides methods of making a population of cells (for example, T cells) that express a chimeric antigen receptor (CAR) comprising: (1) contacting a population of cells with a cytokine chosen from IL-2, IL-7, IL-15, IL-21, IL-6, or a combination thereof, (2) contacting the population of cells (for example, T cells) with a nucleic acid molecule (for example, a DNA or RNA molecule) encoding the CAR, thereby providing a population of cells (for example, T cells) comprising the nucleic acid molecule, and (3) harvesting the population of cells (for example, T cells) for storage (for example, reformulating the population of cells in cryopreservation media) or administration, wherein: (a) step (2) is performed together with step (1) or no later than 5 hours after the beginning of step (1), for example, no later than 1, 2, 3, 4, or 5 hours after the beginning of step (1), and step (3) is performed no later than 26 hours after the beginning of step (1), for example, no later than 22, 23, or 24 hours after the beginning of step (1), for example, no later than 24 hours after the beginning of step (1), or (b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1). In some embodiments, the nucleic acid molecule in step (2) is a DNA molecule. In some embodiments, the nucleic acid molecule in step (2) is an RNA molecule. In some embodiments, the nucleic acid molecule in step (2) is on a viral vector, for example, a viral vector chosen from a lentivirus vector, an adenoviral vector, or a retrovirus vector. In some embodiments, the nucleic acid molecule in step (2) is on a non-viral vector. In some embodiments, the nucleic acid molecule in step (2) is on a plasmid. In some embodiments, the nucleic acid molecule in step (2) is not on any vector. In some embodiments, step (2) comprises transducing the population of cells (for example, T cells) with a viral vector comprising a nucleic acid molecule encoding the CAR.

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. The frozen apheresis sample is then thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, at the end of the cytokine process, the CAR T cells are cryopreserved and later thawed and administered to the subject. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the cytokine process described herein.

In some embodiments, after cells (for example, T cells) are seeded, one or more cytokines (for example, one or more cytokines chosen from IL-2, IL-7, IL-15 (for example, hetIL-15 (IL15/sIL-15Ra)), IL-21, or IL-6 (for example, IL-6/sIL-6R)) as well as vectors (for example, lentiviral vectors) encoding a CAR are added to the cells. After incubation for 20-24 hours, the cells are washed and formulated for storage or administration.

Different from traditional CART manufacturing approaches, the cytokine process provided herein does not involve CD3 and/or CD28 stimulation, or ex vivo T cell expansion. T cells that are contacted with anti-CD3 and anti-CD28 antibodies and expanded extensively ex vivo tend to show differentiation towards a central memory phenotype. Without wishing to be bound by theory, the cytokine process provided herein preserves or increases the undifferentiated phenotype of T cells during CART manufacturing, generating a CART product that may persist longer after being infused into a subject.

In some embodiments, the population of cells is contacted with one or more cytokines (for example, one or more cytokines chosen from IL-2, IL-7, IL-15 (for example, hetIL-15 (IL15/sIL-15Ra)), IL-21, or IL-6 (for example, IL-6/sIL-6Ra).

In some embodiments, the population of cells is contacted with IL-2. In some embodiments, the population of cells is contacted with IL-7. In some embodiments, the population of cells is contacted with IL-15 (for example, hetIL-15 (IL15/sIL-15Ra)). In some embodiments, the population of cells is contacted with IL-21. In some embodiments, the population of cells is contacted with IL-6 (for example, IL-6/sIL-6Ra). In some embodiments, the population of cells is contacted with IL-2 and IL-7. In some embodiments, the population of cells is contacted with IL-2 and IL-15 (for example, hetIL-15 (IL15/sIL-15Ra)). In some embodiments, the population of cells is contacted with IL-2 and IL-21. In some embodiments, the population of cells is contacted with IL-2 and IL-6 (for example, IL-6/sIL-6Ra). In some embodiments, the population of cells is contacted with IL-7 and IL-15 (for example, hetIL-15 (IL15/sIL-15Ra)). In some embodiments, the population of cells is contacted with IL-7 and IL-21. In some embodiments, the population of cells is contacted with IL-7 and IL-6 (for example, IL-6/sIL-6Ra). In some embodiments, the population of cells is contacted with IL-15 (for example, hetIL-15 (IL15/sIL-15Ra)) and IL-21. In some embodiments, the population of cells is contacted with IL-15 (for example, hetIL-15 (IL15/sIL-15Ra)) and IL-6 (for example, IL-6/sIL-6Ra). In some embodiments, the population of cells is contacted with IL-21 and IL-6 (for example, IL-6/sIL-6Ra). In some embodiments, the population of cells is contacted with IL-7, IL-15 (for example, hetIL-15 (IL15/sIL-15Ra)), and IL-21. In some embodiments, the population of cells is further contacted with a LSD1 inhibitor. In some embodiments, the population of cells is further contacted with a MALT1 inhibitor.

In some embodiments, the population of cells is contacted with 20, 30, 40, 50, 60, 70, 80, 90, 100, 110, 120, 130, 140, 150, 160, 170, 180, 190, 200, 210, 220, 230, 240, 250, 260, 270, 280, 290, or 300 U/ml of IL-2. In some embodiments, the population of cells is contacted with 1, 2, 3, 4, 5, 6, 7, 8, 9, 10, 11, 12, 13, 14, 15, 16, 17, 18, 19, or 20 ng/ml of IL-7. In some embodiments, the population of cells is contacted with 1, 2, 3, 4, 5, 6, 7, 8, 9, 10, 11, 12, 13, 14, 15, 16, 17, 18, 19, or 20 ng/ml of IL-15.

In some embodiments, the population of cells is contacted with a nucleic acid molecule encoding a CAR. In some embodiments, the population of cells is transduced with a DNA molecule encoding a CAR.

In some embodiments, contacting the population of cells with the nucleic acid molecule encoding the CAR occurs simultaneously with contacting the population of cells with the one or more cytokines described above. In some embodiments, contacting the population of cells with the nucleic acid molecule encoding the CAR occurs no later than 1, 1.5, 2, 2.5, 3, 3.5, 4, 4.5, 5, 5.5, 6, 6.5, 7, 7.5, 8, 8.5, 9, 9.5 or 10 hours after the beginning of contacting the population of cells with the one or more cytokines described above. In some embodiments, contacting the population of cells with the nucleic acid molecule encoding the CAR occurs no later than 5 hours after the beginning of contacting the population of cells with the one or more cytokines described above. In some embodiments, contacting the population of cells with the nucleic acid molecule encoding the CAR occurs no later than 4 hours after the beginning of contacting the population of cells with the one or more cytokines described above. In some embodiments, contacting the population of cells with the nucleic acid molecule encoding the CAR occurs no later than 3 hours after the beginning of contacting the population of cells with the one or more cytokines described above. In some embodiments, contacting the population of cells with the nucleic acid molecule encoding the CAR occurs no later than 2 hours after the beginning of contacting the population of cells with the one or more cytokines described above. In some embodiments, contacting the population of cells with the nucleic acid molecule encoding the CAR occurs no later than 1 hour after the beginning of contacting the population of cells with the one or more cytokines described above.

In some embodiments, the population of cells is harvested for storage or administration.

In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the one or more cytokines described above. In some embodiments, the population of cells is harvested for storage or administration no later than 26 hours after the beginning of contacting the population of cells with the one or more cytokines described above. In some embodiments, the population of cells is harvested for storage or administration no later than 25 hours after the beginning of contacting the population of cells with the one or more cytokines described above. In some embodiments, the population of cells is harvested for storage or administration no later than 24 hours after the beginning of contacting the population of cells with the one or more cytokines described above. In some embodiments, the population of cells is harvested for storage or administration no later than 23 hours after the beginning of contacting the population of cells with the one or more cytokines described above. In some embodiments, the population of cells is harvested for storage or administration no later than 22 hours after the beginning of contacting the population of cells with the one or more cytokines described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the one or more cytokines described above. In some embodiments, the population of cells is expanded by no more than 5%, for example, as assessed by the number of living cells, compared to the population of cells before it is contacted with the one or more cytokines described above. In some embodiments, the population of cells is expanded by no more than 10%, for example, as assessed by the number of living cells, compared to the population of cells before it is contacted with the one or more cytokines described above. In some embodiments, the population of cells is expanded by no more than 15%, for example, as assessed by the number of living cells, compared to the population of cells before it is contacted with the one or more cytokines described above. In some embodiments, the population of cells is expanded by no more than 20%, for example, as assessed by the number of living cells, compared to the population of cells before it is contacted with the one or more cytokines described above. In some embodiments, the population of cells is expanded by no more than 25%, for example, as assessed by the number of living cells, compared to the population of cells before it is contacted with the one or more cytokines described above. In some embodiments, the population of cells is expanded by no more than 30%, for example, as assessed by the number of living cells, compared to the population of cells before it is contacted with the one or more cytokines described above. In some embodiments, the population of cells is expanded by no more than 35%, for example, as assessed by the number of living cells, compared to the population of cells before it is contacted with the one or more cytokines described above. In some embodiments, the population of cells is expanded by no more than 40%, for example, as assessed by the number of living cells, compared to the population of cells before it is contacted with the one or more cytokines described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the population of cells is not contacted in vitro with an agent that stimulates a CD3/TCR complex (for example, an anti-CD3 antibody) and/or an agent that stimulates a costimulatory molecule on the surface of the cells (for example, an anti-CD28 antibody), or if contacted, the contacting step is less than 1, 1.5, 2, 2.5, 3, 3.5, 4, 4.5, or 5 hours.

In some embodiments, the population of cells is contacted in vitro with an agent that stimulates a CD3/TCR complex (for example, an anti-CD3 antibody) and/or an agent that stimulates a costimulatory molecule on the surface of the cells (for example, an anti-CD28 antibody) for 20, 21, 22, 23, 24, 25, 26, 27, or 28 hours.

In some embodiments, the population of cells manufactured using the cytokine process provided herein shows a higher percentage of naïve cells among CAR-expressing cells (for example, at least 5, 6, 7, 8, 9, 10, 11, 12, 13, 14, 15, 16, 17, 18, 19, 20, 25, 30, 35, 40, 45, 50, 55, or 60% higher), compared with cells made by an otherwise similar method which further comprises contacting the population of cells with, for example, an agent that binds a CD3/TCR complex (for example, an anti-CD3 antibody) and/or an agent that binds a costimulatory molecule on the surface of the cells (for example, an anti-CD28 antibody).

In some embodiments, the cytokine process provided herein is conducted in cell media comprising no more than 0, 0.5, 1, 1.5, 2, 2.5, 3, 3.5, 4, 4.5, 5, 5.5, 6, 6.5, 7, 7.5, or 8% serum. In some embodiments, the cytokine process provided herein is conducted in cell media comprising a LSD1 inhibitor, a MALT1 inhibitor, or a combination thereof.

Activation Process

In some embodiments, the present disclosure provides methods of making a population of cells (for example, T cells) that express a chimeric antigen receptor (CAR) comprising: (i) contacting a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule (for example, a DNA or RNA molecule) encoding the CAR, thereby providing a population of cells (for example, T cells) comprising the nucleic acid molecule, and (iii) harvesting the population of cells (for example, T cells) for storage (for example, reformulating the population of cells in cryopreservation media) or administration, wherein: (a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 26 hours after the beginning of step (i), for example, no later than 22, 23, or 24 hours after the beginning of step (i), for example, no later than 24 hours after the beginning of step (i); (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii); or (c) the population of cells from step (iii) are not expanded, or expanded by no more than 5, 10, 15, 20, 25, 30, 35, or 40%, for example, no more than 10%, for example, as assessed by the number of living cells, compared to the population of cells at the beginning of step (i). In some embodiments, the nucleic acid molecule in step (ii) is a DNA molecule. In some embodiments, the nucleic acid molecule in step (ii) is an RNA molecule. In some embodiments, the nucleic acid molecule in step (ii) is on a viral vector, for example, a viral vector chosen from a lentivirus vector, an adenoviral vector, or a retrovirus vector. In some embodiments, the nucleic acid molecule in step (ii) is on a non-viral vector. In some embodiments, the nucleic acid molecule in step (ii) is on a plasmid. In some embodiments, the nucleic acid molecule in step (ii) is not on any vector. In some embodiments, step (ii) comprises transducing the population of cells (for example, T cells) a viral vector comprising a nucleic acid molecule encoding the CAR.

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. Then the frozen apheresis sample is thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the activation process described herein.

In some embodiments, cells (for example, T cells) are contacted with anti-CD3 and anti-CD28 antibodies for, for example, 12 hours, followed by transduction with a vector (for example, a lentiviral vector) encoding a CAR. 24 hours after culture initiation, the cells are washed and formulated for storage or administration.

Without wishing to be bound by theory, brief CD3 and CD28 stimulation may promote efficient transduction of self-renewing T cells. Compared to traditional CART manufacturing approaches, the activation process provided herein does not involve prolonged ex vivo expansion. Similar to the cytokine process, the activation process provided herein also preserves undifferentiated T cells during CART manufacturing.

In some embodiments, the population of cells is contacted with an agent that stimulates a CD3/TCR complex and/or an agent that stimulates a costimulatory molecule on the surface of the cells.

In some embodiments, the agent that stimulates a CD3/TCR complex is an agent that stimulates CD3. In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a CD3/TCR complex is an antibody. In some embodiments, the agent that stimulates a CD3/TCR complex is an anti-CD3 antibody. In some embodiments, the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a costimulatory molecule is an antibody. In some embodiments, the agent that stimulates a costimulatory molecule is an anti-CD28 antibody. In some embodiments, the agent that stimulates a CD3/TCR complex or the agent that stimulates a costimulatory molecule does not comprise a bead. In some embodiments, the agent that stimulates a CD3/TCR complex comprises an anti-CD3 antibody covalently attached to a colloidal polymeric nanomatrix. In some embodiments, the agent that stimulates a costimulatory molecule comprises an anti-CD28 antibody covalently attached to a colloidal polymeric nanomatrix. In some embodiments, the agent that stimulates a CD3/TCR complex and the agent that stimulates a costimulatory molecule comprise T Cell TransAct™.

In some embodiments, the matrix comprises or consists of a polymeric, for example, biodegradable or biocompatible inert material, for example, which is non-toxic to cells. In some embodiments, the matrix is composed of hydrophilic polymer chains, which obtain maximal mobility in aqueous solution due to hydration of the chains. In some embodiments, the mobile matrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate. Other polymers may include polyesters, polyethers, polyacrylates, polyacrylamides, polyamines, polyethylene imines, polyquaternium polymers, polyphosphazenes, polyvinylalcohols, polyvinylacetates, polyvinylpyrrolidones, block copolymers, or polyurethanes. In some embodiments, the mobile matrix is a polymer of dextran.

In some embodiments, the population of cells is contacted with a nucleic acid molecule encoding a CAR. In some embodiments, the population of cells is transduced with a DNA molecule encoding a CAR.

In some embodiments, contacting the population of cells with the nucleic acid molecule encoding the CAR occurs simultaneously with contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 20 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 19 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 18 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 17 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 16 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 15 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 13 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 12 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 11 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 10 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 9 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 8 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 7 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 6 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 4 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 3 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 2 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 1 hour after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR occurs no later than 30 minutes after the beginning of contacting the population of cells with the agent that stimulates a CD3/TCR complex and/or the agent that stimulates a costimulatory molecule on the surface of the cells described above.

In some embodiments, the population of cells is harvested for storage or administration.

In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 26 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 25 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 24 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 23 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 22 hours after the beginning of contacting the population of cells with the agent that stimulates a CD3/TCR complex and/or the agent that stimulates a costimulatory molecule on the surface of the cells described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 5%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 10%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 15%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 20%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 25%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 30%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 35%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 40%, for example, as assessed by the number of living cells, compared to the population of cells before it is contacted with the agent that stimulates a CD3/TCR complex and/or the agent that stimulates a costimulatory molecule on the surface of the cells described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the activation process is conducted in serum free cell media. In some embodiments, the activation process is conducted in cell media comprising one or more cytokines chosen from: IL-2, IL-15 (for example, hetIL-15 (IL15/sIL-15Ra)), or IL-6 (for example, IL-6/sIL-6Ra). In some embodiments, hetIL-15 comprises the amino acid sequence of NWVNVISDLKKIEDLIQSMHIDATLYTESDVHPSCKVTAMKCFLLELQVISLESGDASIH DTVENLIILANNSLSSNGNVTESGCKECEELEEKNIKEFLQSFVHIVQMFINTSITCPPPM SVEHADIWVKSYSLYSRERYICNSGFKRKAGTSSLTECVLNKATNVAHWTTPSLKCIR DPALVHQRPAPPSTVTTAGVTPQPESLSPSGKEPAASSPSSNNTAATTAAIVPGSQLMPS KSPSTGTTEISSHESSHGTPSQTTAKNWELTASASHQPPGVYPQG (SEQ ID NO: 309). In some embodiments, hetIL-15 comprises an amino acid sequence having at least about 70, 75, 80, 85, 90, 95, or 99% identity to SEQ ID NO: 309. In some embodiments, the activation process is conducted in cell media comprising a LSD1 inhibitor. In some embodiments, the activation process is conducted in cell media comprising a MALT1 inhibitor. In some embodiments, the serum free cell media comprises a serum replacement. In some embodiments, the serum replacement is CTS™ Immune Cell Serum Replacement (ICSR). In some embodiments, the level of ICSR can be, for example, up to 5%, for example, about 1%, 2%, 3%, 4%, or 5%. Without wishing to be bound by theory, using cell media, for example, Rapid Media shown in Table 21 or Table 25, comprising ICSR, for example, 2% ICSR, may improve cell viability during a manufacture process described herein.

In some embodiments, the present disclosure provides methods of making a population of cells (for example, T cells) that express a chimeric antigen receptor (CAR) comprising: (a) providing an apheresis sample (for example, a fresh or cryopreserved leukapheresis sample) collected from a subject; (b) selecting T cells from the apheresis sample (for example, using negative selection, positive selection, or selection without beads); (c) seeding isolated T cells at, for example, $1\times10^6$ to $1\times10^7$ cells/mL; (d) contacting T cells with an agent that stimulates T cells, for example, an agent that stimulates a CD3/TCR complex and/or an agent that stimulates a costimulatory molecule on the surface of the cells (for example, contacting T cells with anti-CD3 and/or anti-CD28 antibody, for example, contacting T cells with TransAct); (e) contacting T cells with a nucleic acid molecule (for example, a DNA or RNA molecule) encoding the CAR (for example, contacting T cells with a virus comprising a nucleic acid molecule encoding the CAR) for, for example, 6-48 hours, for example, 20-28 hours; and (f) washing and harvesting T cells for storage (for example, reformulating T cells in cryopreservation media) or administration. In some embodiments, step (f) is performed no later than 30 hours after the beginning of step (d) or (e), for example, no later than 22, 23, 24, 25, 26, 27, 28, 29, or 30 hours after the beginning of step (d) or (e).

Population of CAR-Expressing Cells Manufactured by the Processes Disclosed Herein In some embodiments, the disclosure features an immune effector cell (for example, T cell or NK cell), for example, made by any of the manufacturing methods described herein, engineered to express a CAR, wherein the engineered immune effector cell exhibits an antitumor property. In some embodiments, the CAR comprises an antigen binding domain, a transmembrane domain, and an intracellular signaling domain. An exemplary antigen is a cancer associated antigen described herein. In some embodiments, the cell (for example, T cell or NK cell) is transformed with the CAR and the CAR is expressed on the cell surface. In some embodiments, the cell (for example, T cell or NK cell) is transduced with a viral vector encoding the CAR. In some embodiments, the viral vector is a retroviral vector. In some embodiments, the viral vector is a lentiviral vector. In some such embodiments, the cell may stably express the CAR. In some embodiments, the cell (for example, T cell or NK cell) is transfected with a nucleic acid, for example, mRNA, cDNA, or DNA, encoding a CAR. In some such embodiments, the cell may transiently express the CAR.

In some embodiments, provided herein is a population of cells (for example, immune effector cells, for example, T cells or NK cells) made by any of the manufacturing processes described herein (for example, the cytokine process, or the activation process described herein), engineered to express a CAR.

In some embodiments, the percentage of naïve cells, for example, naïve T cells, for example, CD45RA+ CD45RO− CCR7+ T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15%, from, or (3) is increased, for example, by at least 5, 6, 7, 8, 9, 10, 11, 12, 13, 14, 15, 16, 17, 18, 19, 20, 21, 22, 23, 24, or 25%, as compared to, the percentage of naïve cells, for example, naïve T cells, for example, CD45RA+ CD45RO− CCR7+ cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a higher percentage of naïve cells, for example, naïve T cells, for example, CD45RA+ CD45RO− CCR7+ T cells (for example, at least 5, 6, 7, 8, 9, 10, 11, 12, 13, 14, 15, 16, 17, 18, 19, 20, 25, 30, 35, 40, 45, or 50% higher), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of naïve cells, for example, naïve T cells, for example, CD45RA+ CD45RO− CCR7+ T cells, in the population of cells at the end of the manufacturing process (for example, at the end of the cytokine process or the activation process described herein) is not less than 20, 25, 30, 35, 40, 45, 50, 55, or 60%.

In some embodiments, the percentage of central memory cells, for example, central memory T cells, for example, CD95+ central memory T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15% from, or (3) is decreased, for example, by at least 5, 6, 7, 8, 9, 10, 11, 12, 13, 14, 15, 16, 17, 18, 19, 20, 21, 22, 23, 24, or 25%, as compared to, the percentage of central memory cells, for example, central memory T cells, for example, CD95+ central memory T cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a lower percentage of central memory cells, for example, central memory T cells, for example, CD95+ central memory T cells (for example, at least 5, 6, 7, 8, 9, 10, 11, 12, 13, 14, 15, 16, 17, 18, 19, 20, 25, 30, 35, 40, 45, or 50% lower), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of central memory cells, for example, central memory T cells, for example, CD95+ central memory T cells, in the population of cells at the end of the manufacturing process (for example, at the end of the cytokine process or the activation process described herein) is no more than 40, 45, 50, 55, 60, 65, 70, 75, or 80%.

Figure 4A:
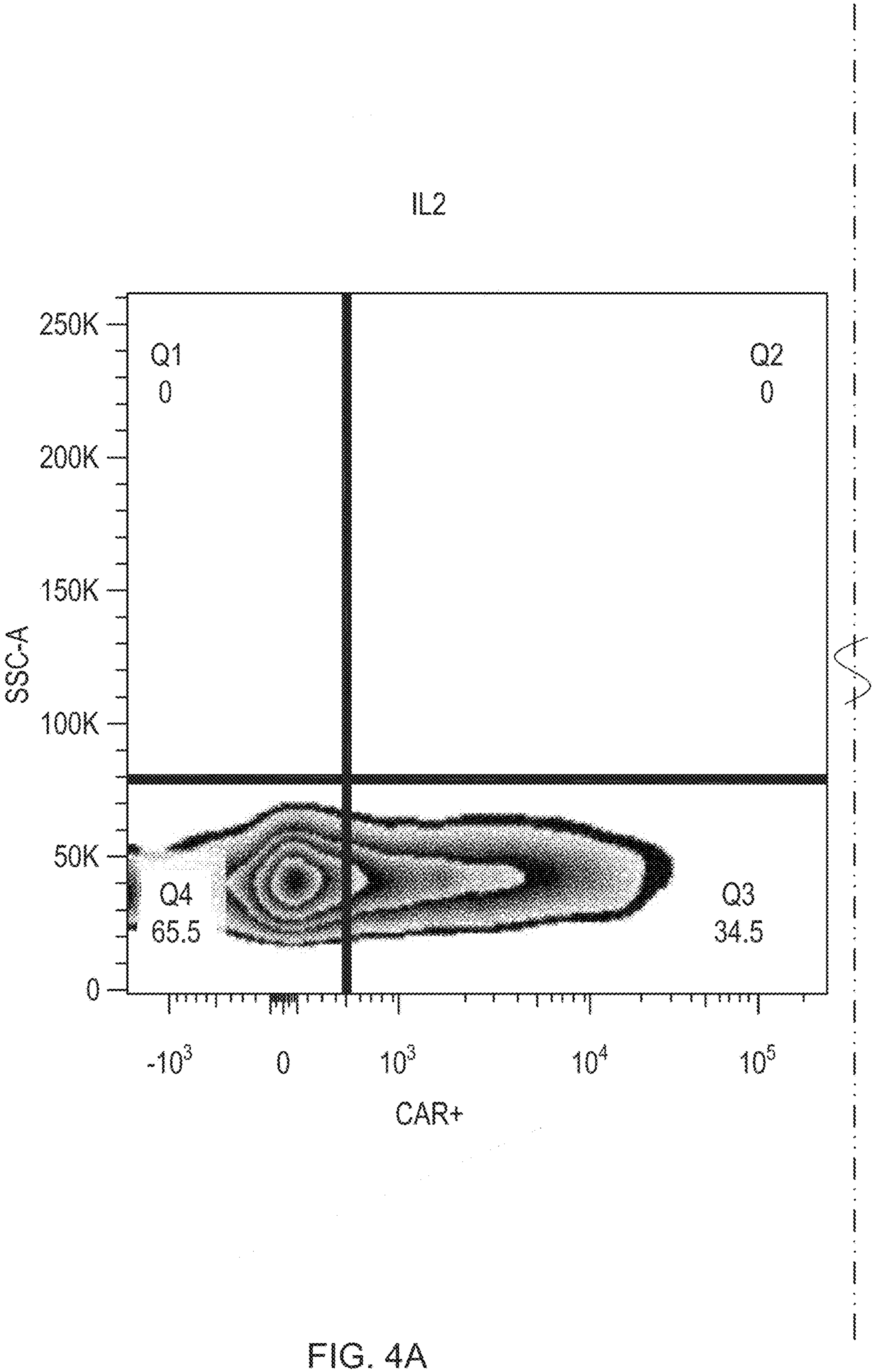
FIGS. 4A-4D: CAR T cells generated within 24 hours can eliminate tumor.
Figure 4A:
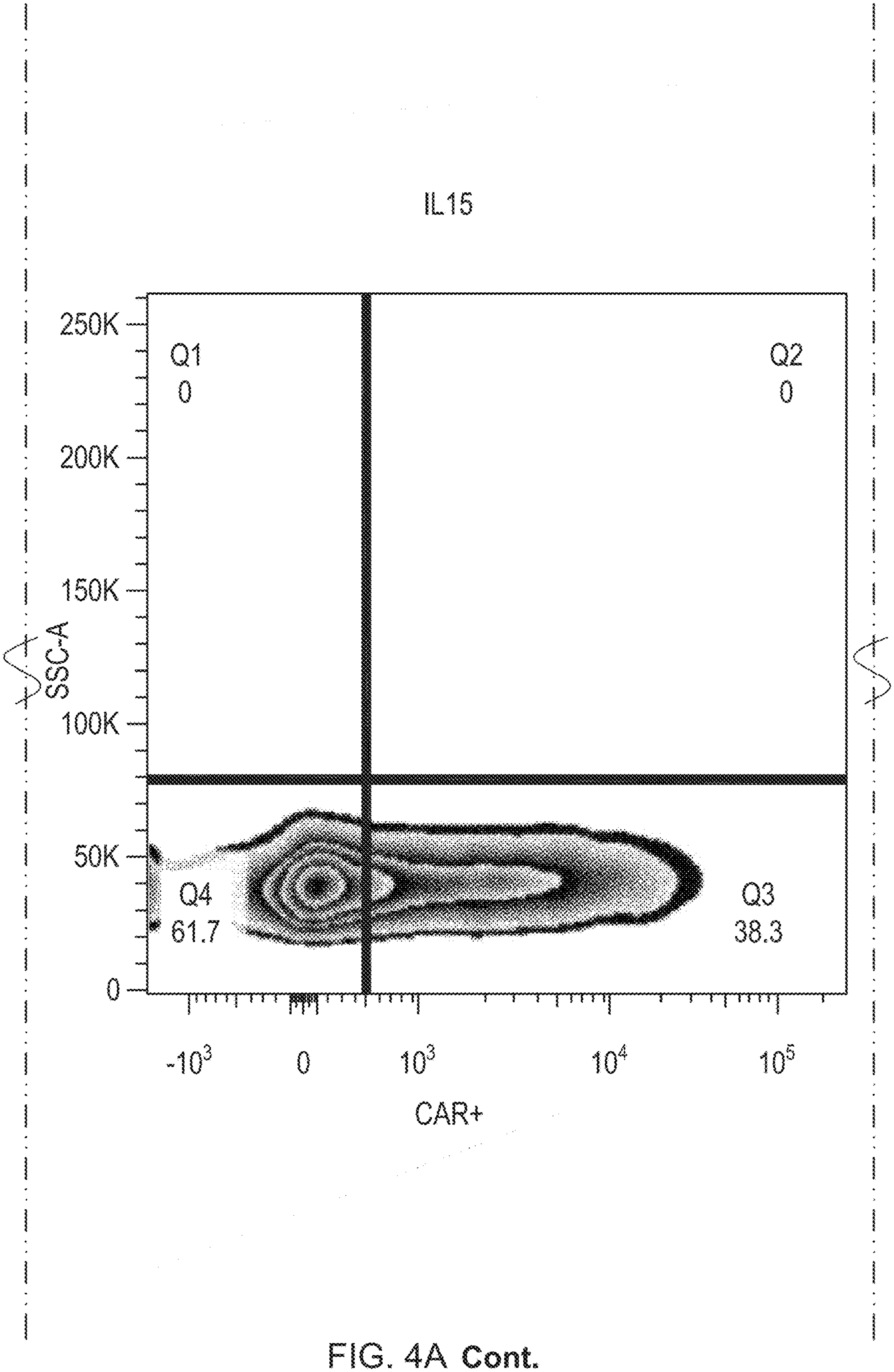
Figure 4B:
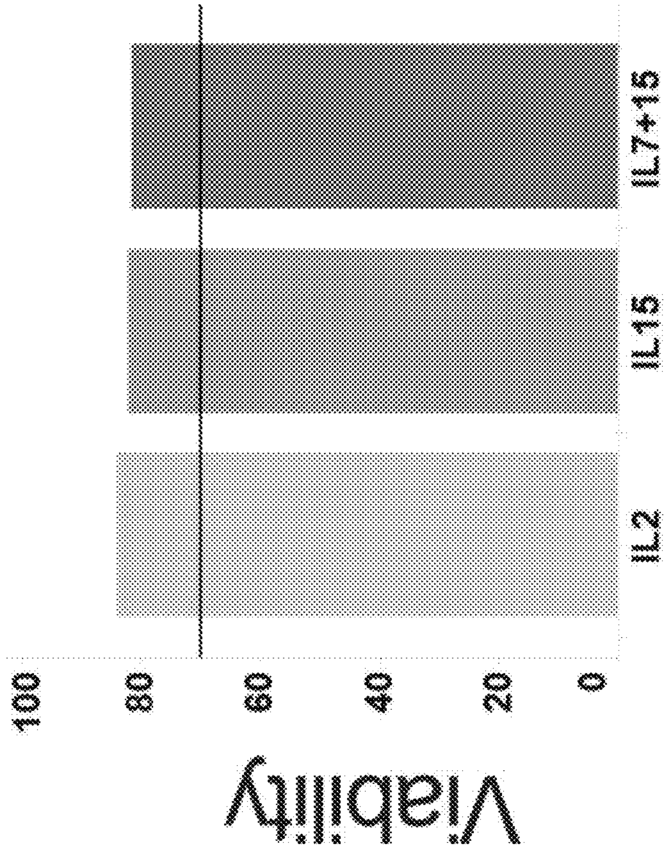
Figure 4C:
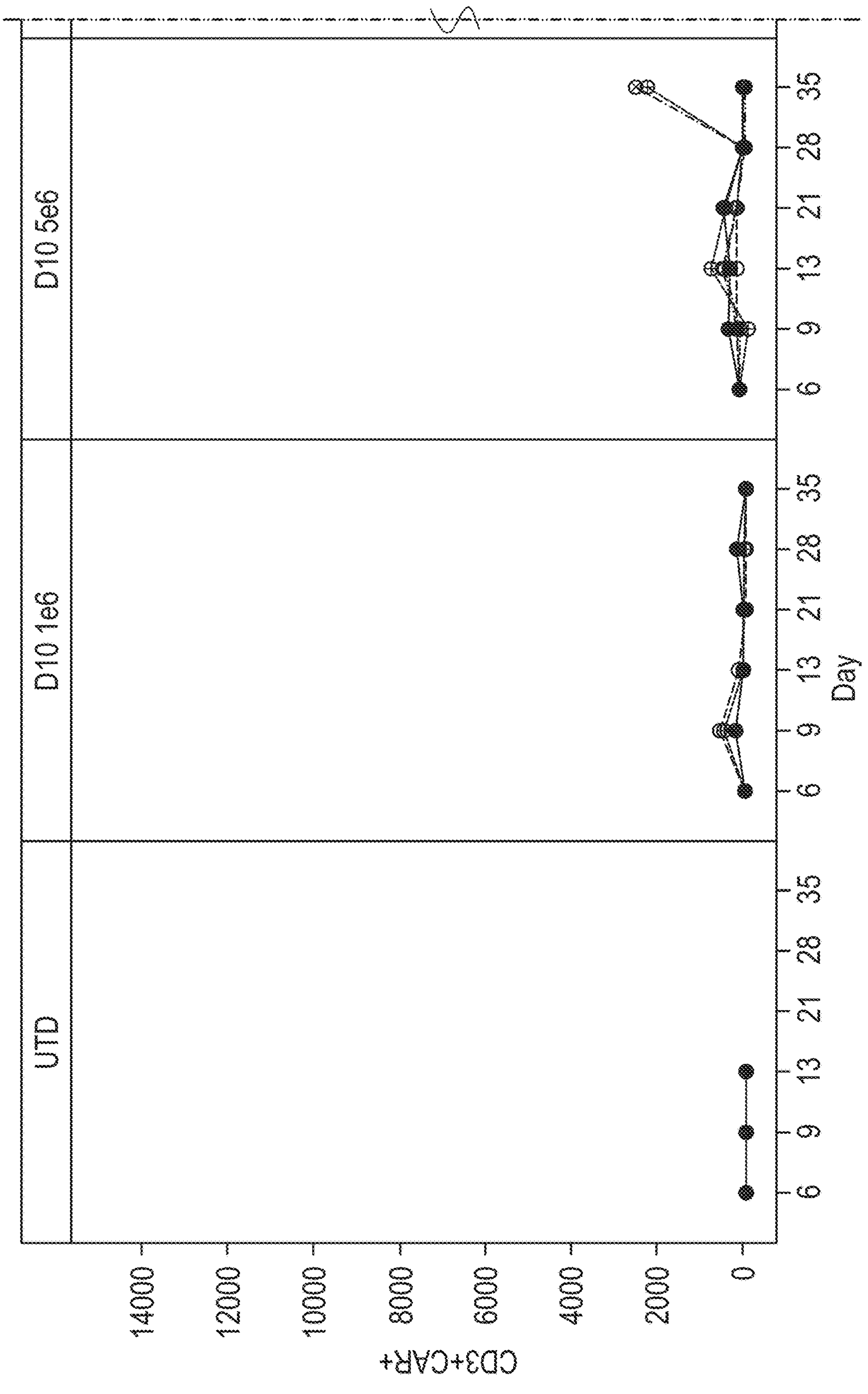
Figure 4C:
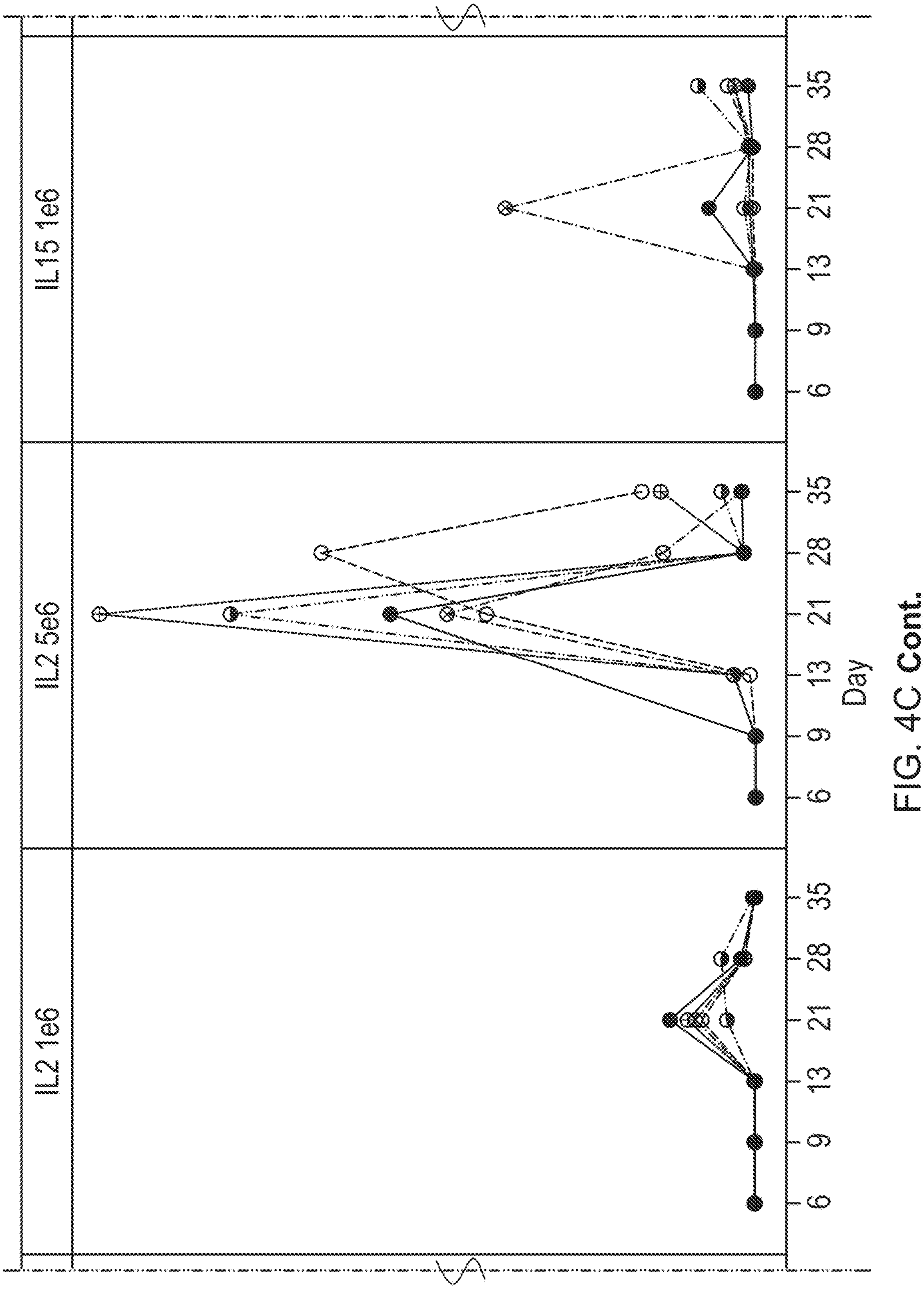
Figure 4C:
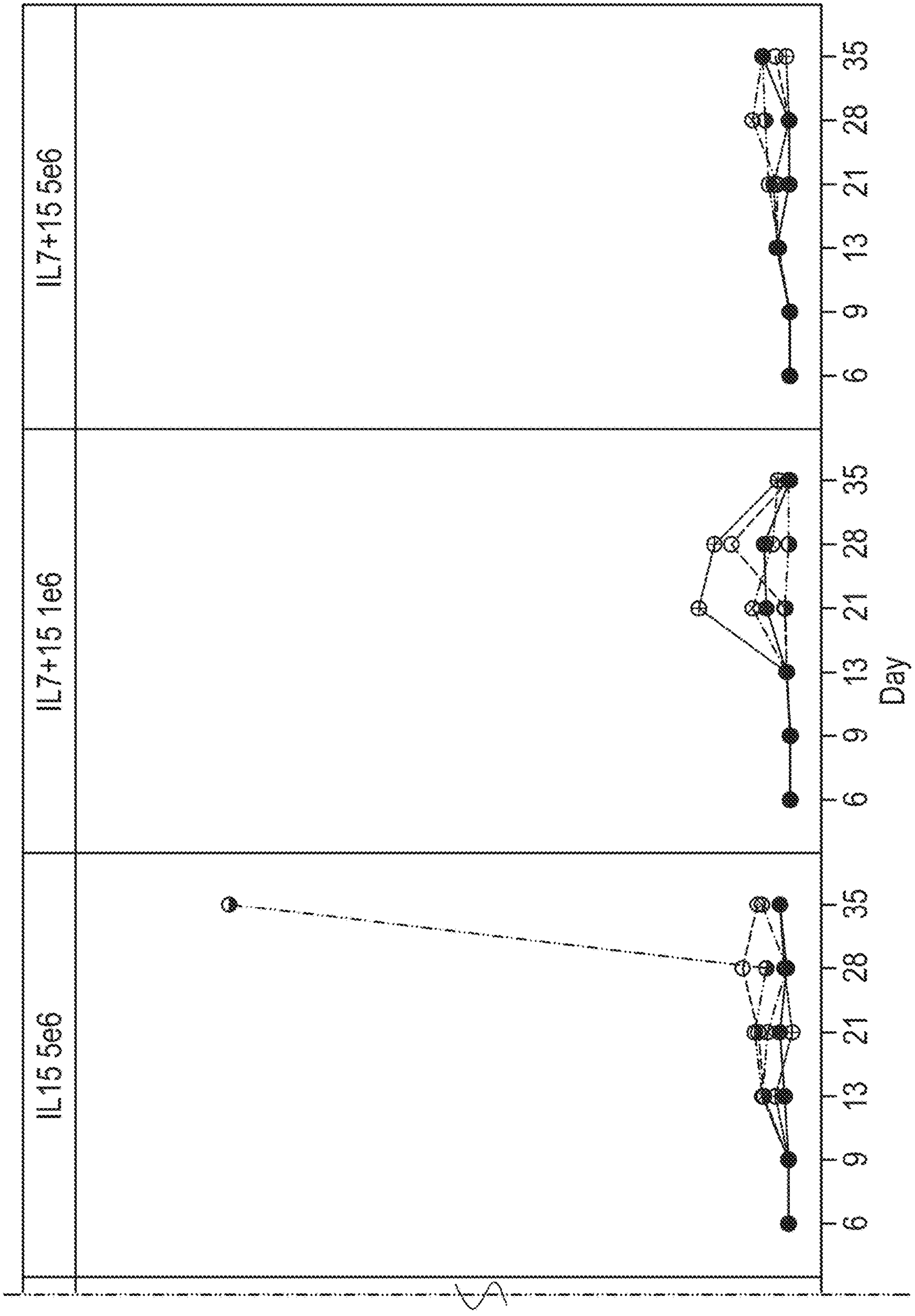

In some embodiments, the population of cells at the end of the manufacturing process (for example, at the end of the cytokine process or the activation process described herein) after being administered in vivo, persists longer or expands at a higher level (for example, at least 20, 25, 30, 35, 40, 45, 50, 55, 60, 65, 70, 75, 80, 85, or 90% higher) (for example, as assessed using methods described in Example 1 with respect to FIG. 4C), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the population of cells has been enriched for IL6R-expressing cells (for example, cells that are positive for IL6Rα and/or IL6Rβ) prior to the beginning of the manufacturing process (for example, prior to the beginning of the cytokine process or the activation process described herein). In some embodiments, the population of cells comprises, for example, no less than 30, 35, 40, 45, 50, 55, 60, 65, 70, 75, or 80% of IL6R-expressing cells (for example, cells that are positive for IL6Rα and/or IL6Rβ) at the beginning of the manufacturing process (for example, at the beginning of the cytokine process or the activation process described herein).

Pharmaceutical Composition

Furthermore, the present disclosure provides CAR-expressing cell compositions and their use in medicaments or methods for treating, among other diseases, cancer or any malignancy or autoimmune diseases involving cells or tissues which express a tumor antigen as described herein. In some embodiments, provided herein are pharmaceutical compositions comprising a CAR-expressing cell, for example, a plurality of CAR-expressing cells, made by a manufacturing process described herein (for example, the cytokine process, or the activation process described herein), in combination with one or more pharmaceutically or physiologically acceptable carriers, diluents or excipients.

Chimeric Antigen Receptor (CAR)

The present invention provides immune effector cells (for example, T cells or NK cells) that are engineered to contain one or more CARs that direct the immune effector cells to cancer. This is achieved through an antigen binding domain on the CAR that is specific for a cancer associated antigen. There are two classes of cancer associated antigens (tumor antigens) that can be targeted by the CARs described herein: (1) cancer associated antigens that are expressed on the surface of cancer cells; and (2) cancer associated antigens that themselves are intracellular, however, fragments (peptides) of such antigens are presented on the surface of the cancer cells by MHC (major histocompatibility complex).

Accordingly, an immune effector cell, for example, obtained by a method described herein, can be engineered to contain a CAR that targets one of the following cancer associated antigens (tumor antigens): CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6,E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, and mut hsp70-2.

Sequences of non-limiting examples of various components that can be part of a CAR molecule described herein are listed in Table 1, where "aa" stands for amino acids, and "na" stands for nucleic acids that encode the corresponding peptide.

TABLE 1

| Sequences of various components of CAR | | |
|---|---|---|
| SEQ ID NO | Description | Sequence |
| SEQ ID NO: 11 | EF-1α promoter (na) | CGTGAGGCTCCGGTGCCCGTCAGTGGGCAGAGCGCACAT CGCCCACAGTCCCCGAGAAGTTGGGGGGAGGGGTCGGC AATTGAACCGGTGCCTAGAGAAGGTGGCGCGGGGTAAA CTGGGAAAGTGATGTCGTGTACTGGCTCCGCCTTTTTCCC GAGGGTGGGGGAGAACCGTATATAAGTGCAGTAGTCGC CGTGAACGTTCTTTTTCGCAACGGGTTTGCCGCCAGAAC ACAGGTAAGTGCCGTGTGTGGTTCCCGCGGGCCTGGCCT CTTTACGGGTTATGGCCCTTGCGTGCCTTGAATTACTTCC ACCTGGCTGCAGTACGTGATTCTTGATCCCGAGCTTCGG GTTGGAAGTGGGTGGGAGAGTTCGAGGCCTTGCGCTTAA GGAGCCCCTTCGCCTCGTGCTTGAGTTGAGGCCTGGCCT GGGCGCTGGGGCCGCCGCGTGCGAATCTGGTGGCACCTT CGCGCCTGTCTCGCTGCTTTCGATAAGTCTCTAGCCATTT AAAATTTTTGATGACCTGCTGCGACGCTTTTTTTCTGGCA AGATAGTCTTGTAAATGCGGGCCAAGATCTGCACACTGG TATTTCGGTTTTTGGGGCCGCGGGCGGCGACGGGGCCCG TGCGTCCCAGCGCACATGTTCGGCGAGGCGGGGCCTGCG AGCGCGGCCACCGAGAATCGGACGGGGGTAGTCTCAAG CTGGCCGGCCTGCTCTGGTGCCTGGCCTCGCGCCGCCGT GTATCGCCCCGCCCTGGGCGGCAAGGCTGGCCCGGTCGG CACCAGTTGCGTGAGCGGAAAGATGGCCGCTTCCCGGCC CTGCTGCAGGGAGCTCAAAATGGAGGACGCGGCGCTCG GGAGAGCGGGCGGGTGAGTCACCCACACAAAGGAAAAG GGCCTTTCCGTCCTCAGCCGTCGCTTCATGTGACTCCACG GAGTACCGGGCGCCGTCCAGGCACCTCGATTAGTTCTCG AGCTTTTGGAGTACGTCGTCTTTAGGTTGGGGGGAGGGG TTTTATGCGATGGAGTTTCCCCACACTGAGTGGGTGGAG ACTGAAGTTAGGCCAGCTTGGCACTTGATGTAATTCTCC TTGGAATTTGCCCTTTTTGAGTTTGGATCTTGGTTCATTC TCAAGCCTCAGACAGTGGTTCAAAGTTTTTTTCTTCCATT TCAGGTGTCGTGA |
| SEQ ID NO: 1 | Leader (aa) | MALPVTALLLPLALLLHAARP |
| SEQ ID NO: 12 | Leader (na) | ATGGCCCTGCCTGTGACAGCCCTGCTGCTGCCTCTGGCTC TGCTGCTGCATGCCGCTAGACCC |
| SEQ ID NO: 199 | Leader (na) | ATGGCCCTCCCTGTCACCGCCCTGCTGCTTCCGCTGGCTC TTCTGCTCCACGCCGCTCGGCCC |
| SEQ ID NO: 2 | CD8 hinge (aa) | TTTPAPRPPTPAPTIASQPLSLRPEACRPAAGGAVHTRGLDF ACD |
| SEQ ID NO: 13 | CD8 hinge (na) | ACCACGACGCCAGCGCCGCGACCACCAACACCGGCGCC CACCATCGCGTCGCAGCCCCTGTCCCTGCGCCCAGAGGC GTGCCGGCCAGCGGCGGGGGGCGCAGTGCACACGAGGG GGCTGGACTTCGCCTGTGAT |
| SEQ ID NO: 3 | Ig4 hinge (aa) | ESKYGPPCPPCPAPEFLGGPSVFLFPPKPKDTLMISRTPEVTC VVVDVSQEDPEVQFNWYVDGVEVHNAKTKPREEQFNSTY RVVSVLTVLHQDWLNGKEYKCKVSNKGLPSSIEKTISKAK GQPREPQVYTLPPSQEEMTKNQVSLTCLVKGFYPSDIAVEW ESNGQPENNYKTTPPVLDSDGSFFLYSRLTVDKSRWQEGN VFSCSVMHEALHNHYTQKSLSLSLGKM |
| SEQ ID NO: 14 | Ig4 hinge (na) | GAGAGCAAGTACGGCCCTCCCTGCCCCCCTTGCCCTGCC CCCGAGTTCCTGGGCGGACCCAGCGTGTTCCTGTTCCCC CCCAAGCCCAAGGACACCCTGATGATCAGCCGGACCCCC GAGGTGACCTGTGTGGTGGTGGACGTGTCCCAGGAGGAC CCCGAGGTCCAGTTCAACTGGTACGTGGACGGCGTGGAG GTGCACAACGCCAAGACCAAGCCCCGGGAGGAGCAGTT CAATAGCACCTACCGGGTGGTGTCCGTGCTGACCGTGCT GCACCAGGACTGGCTGAACGGCAAGGAATACAAGTGTA AGGTGTCCAACAAGGGCCTGCCCAGCAGCATCGAGAAA ACCATCAGCAAGGCCAAGGGCCAGCCTCGGGAGCCCCA GGTGTACACCCTGCCCCCTAGCCAAGAGGAGATGACCAA GAACCAGGTGTCCCTGACCTGCCTGGTGAAGGGCTTCTA CCCCAGCGACATCGCCGTGGAGTGGGAGAGCAACGGCC AGCCCGAGAACAACTACAAGACCACCCCCCCTGTGCTGG ACAGCGACGGCAGCTTCTTCCTGTACAGCCGGCTGACCG TGGACAAGAGCCGGTGGCAGGAGGGCAACGTCTTTAGC TGCTCCGTGATGCACGAGGCCCTGCACAACCACTACACC CAGAAGAGCCTGAGCCTGTCCCTGGGCAAGATG |

TABLE 1-continued

| Sequences of various components of CAR | | |
|---|---|---|
| SEQ ID NO | Description | Sequence |
| SEQ ID NO: 4 | IgD hinge (aa) | RWPESPKAQASSVPTAQPQAEGSLAKATTAPATTRNTGRG GEEKKKEKEKEEQEERETKTPECPSHTQPLGVYLLTPAVQD LWLRDKATFTCFVVGSDLKDAHLTWEVAGKVPTGGVEEG LLERHSNGSQSQHSRLTLPRSLWNAGTSVTCTLNHPSLPPQ RLMALREPAAQAPVKLSLNLLASSDPPEAASWLLCEVSGFS PPNILLMWLEDQREVNTSGFAPARPPPQPGSTTFWAWSVLR VPAPPSPQPATYTCVVSHEDSRTLLNASRSLEVSYVTDH |
| SEQ ID NO: 15 | IgD hinge (na) | AGGTGGCCCGAAAGTCCCAAGGCCCAGGCATCTAGTGTT CCTACTGCACAGCCCCAGGCAGAAGGCAGCCTAGCCAA AGCTACTACTGCACCTGCCACTACGCGCAATACTGGCCG TGGCGGGGAGGAGAAGAAAAAGGAGAAAGAGAAAGAA GAACAGGAAGAGAGGGAGACCAAGACCCCTGAATGTCC ATCCCATACCCAGCCGCTGGGCGTCTATCTCTTGACTCCC GCAGTACAGGACTTGTGGCTTAGAGATAAGGCCACCTTT ACATGTTTCGTCGTGGGCTCTGACCTGAAGGATGCCCAT TTGACTTGGGAGGTTGCCGGAAAGGTACCCACAGGGGG GGTTGAGGAAGGGTTGCTGGAGCGCCATTCCAATGGCTC TCAGAGCCAGCACTCAAGACTCACCCTTCCGAGATCCCT GTGGAACGCCGGGACCTCTGTCACATGTACTCTAAATCA TCCTAGCCTGCCCCCACAGCGTCTGATGGCCCTTAGAGA GCCAGCCGCCCAGGCACCAGTTAAGCTTAGCCTGAATCT GCTCGCCAGTAGTGATCCCCCAGAGGCCGCCAGCTGGCT CTTATGCGAAGTGTCCGGCTTTAGCCCGCCCAACATCTT GCTCATGTGGCTGGAGGACCAGCGAGAAGTGAACACCA GCGGCTTCGCTCCAGCCCGGCCCCCACCCCAGCCGGGTT CTACCACATTCTGGGCCTGGAGTGTCTTAAGGGTCCCAG CACCACCTAGCCCCCAGCCAGCCACATACACCTGTGTTG TGTCCCATGAAGATAGCAGGACCCTGCTAAATGCTTCTA GGAGTCTGGAGGTTTCCTACGTGACTGACCATT |
| SEQ ID NO: 6 | CD8 Transmembrane (aa) | IYIWAPLAGTCGVLLLSLVITLYC |
| SEQ ID NO: 17 | CD8 Transmembrane (na) | ATCTACATCTGGGCGCCCTTGGCCGGGACTTGTGGGGTC CTTCTCCTGTCACTGGTTATCACCCTTTACTGC |
| SEQ ID NO: 7 | 4-1BB intracellular domain (aa) | KRGRKKLLYIFKQPFMRPVQTTQEEDGCSCRFPEEEEGGCE L |
| SEQ ID NO: 18 | 4-1BB intracellular domain (na) | AAACGGGGCAGAAAGAAACTCCTGTATATATTCAAACA ACCATTTATGAGACCAGTACAAACTACTCAAGAGGAAG ATGGCTGTAGCTGCCGATTTCCAGAAGAAGAAGAAGGA GGATGTGAACTG |
| SEQ ID NO: 8 | CD27 (aa) | QRRKYRSNKGESPVEPAEPCRYSCPREEEGSTIPIQEDYRKP EPACSP |
| SEQ ID NO: 19 | CD27 (na) | AGGAGTAAGAGGAGCAGGCTCCTGCACAGTGACTACAT GAACATGACTCCCCGCCGCCCCGGGCCCACCCGCAAGCA TTACCAGCCCTATGCCCCACCACGCGACTTCGCAGCCTA TCGCTCC |
| SEQ ID NO: 9 | CD3-zeta (aa) (Q/K mutant) | RVKFSRSADAPAYKQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR |
| SEQ ID NO: 20 | CD3-zeta (na) (Q/K mutant) | AGAGTGAAGTTCAGCAGGAGCGCAGACGCCCCCGCGTA CAAGCAGGGCCAGAACCAGCTCTATAACGAGCTCAATCT AGGACGAAGAGAGGAGTACGATGTTTTGGACAAGAGAC GTGGCCGGGACCCTGAGATGGGGGGAAAGCCGAGAAGG AAGAACCCTCAGGAAGGCCTGTACAATGAACTGCAGAA AGATAAGATGGCGGAGGCCTACAGTGAGATTGGGATGA AAGGCGAGCGCCGGAGGGGCAAGGGGCACGATGGCCTT TACCAGGGTCTCAGTACAGCCACCAAGGACACCTACGAC GCCCTTCACATGCAGGCCCTGCCCCCTCGC |
| SEQ ID NO: 10 | CD3-zeta (aa) (NCBI Reference Sequence NM_000734.3) | RVKFSRSADAPAYQQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR |

TABLE 1-continued

Sequences of various components of CAR

| SEQ ID NO | Description | Sequence |
|---|---|---|
| SEQ ID NO: 21 | CD3-zeta (na) (NCBI Reference Sequence NM_000734.3) | AGAGTGAAGTTCAGCAGGAGCGCAGACGCCCCCGCGTA CCAGCAGGGCCAGAACCAGCTCTATAACGAGCTCAATCT AGGACGAAGAGAGGAGTACGATGTTTTGGACAAGAGAC GTGGCCGGGACCCTGAGATGGGGGGAAAGCCGAGAAGG AAGAACCCTCAGGAAGGCCTGTACAATGAACTGCAGAA AGATAAGATGGCGGAGGCCTACAGTGAGATTGGGATGA AAGGCGAGCGCCGGAGGGGCAAGGGGCACGATGGCCTT TACCAGGGTCTCAGTACAGCCACCAAGGACACCTACGAC GCCCTTCACATGCAGGCCCTGCCCCCTCGC |
| SEQ ID NO: 36 | CD28 Intracellular domain (amino acid sequence) | RSKRSRLLHSDYMNMTPRRPGPTRKHYQPYAPPRDFAAYR S |
| SEQ ID NO: 37 | CD28 Intracellular domain (nucleotide sequence) | AGGAGTAAGAGGAGCAGGCTCCTGCACAGTGACTACAT GAACATGACTCCCCGCCGCCCCGGGCCCACCCGCAAGCA TTACCAGCCCTATGCCCCACCACGCGACTTCGCAGCCTA TCGCTCC |
| SEQ ID NO: 38 | ICOS Intracellular domain (amino acid sequence) | T K K K Y S S S V H D P N G E Y M F M R A V N T A K K S R L T D V T L |
| SEQ ID NO: 39 | ICOS Intracellular domain (nucleotide sequence) | ACAAAAAAGAAGTATTCATCCAGTGTGCACGACCCTAAC GGTGAATACATGTTCATGAGAGCAGTGAACACAGCCAA AAAATCCAGACTCACAGATGTGACCCTA |
| SEQ ID NO: 5 | GS hinge/linker (aa) | GGGGSGGGGS |
| SEQ ID NO: 16 | GS hinge/linker (na) | GGTGGCGGAGGTTCTGGAGGTGGAGGTTCC |
| SEQ ID NO: 40 | GS hinge/linker (na) | GGTGGCGGAGGTTCTGGAGGTGGGGGTTCC |
| SEQ ID NO: 25 | linker | GGGGS |
| SEQ ID NO: 26 | linker | (Gly-Gly-Gly-Gly-Ser)n, where n = 1-6, for example, GGGGSGGGGS GGGGSGGGGS GGGGSGGGGS |
| SEQ ID NO: 27 | linker | GGGGSGGGGSGGGGSGGGGS |
| SEQ ID NO: 28 | linker | GGGGSGGGGSGGGGS |
| SEQ ID NO: 29 | linker | GGGS |
| SEQ ID NO: 41 | linker | (Gly-Gly-Gly-Ser)n where n is a positive integer equal to or greater than 1 |
| SEQ ID NO: 42 | linker | (Gly-Gly-Gly-Ser)n, where n = 1-10, for example, GGGSGGGSGG GSGGGSGGGS GGGSGGGSGG GSGGGSGGGS |
| SEQ ID NO: 43 | linker | GSTSGSGKPGSGEGSTKG |
| SEQ ID NO: 30 | poly(A) | $(A)_{5000}$ This sequence may encompass 50-5000 adenines. |
| SEQ ID NO: 31 | polyT | $(T)_{100}$ |
| SEQ ID NO: 32 | polyT | $(T)_{5000}$ This sequence may encompass 50-5000 thymines. |
| SEQ ID NO: 33 | poly(A) | $(A)_{5000}$ This sequence may encompass 100-5000 adenines. |
| SEQ ID NO: 34 | poly(A) | $(A)_{400}$ This sequence may encompass 100-400 adenines. |

TABLE 1-continued

Sequences of various components of CAR

| SEQ ID NO | Description | Sequence |
|---|---|---|
| SEQ ID NO: 35 | poly(A) | $(A)_{2000}$<br>This sequence may encompass 50-2000 adenines. |
| SEQ ID NO: 22 | PD1 CAR (aa) | pgwfldspdrpwnpptfspallvvtegdnatftcsfsntsesfylnwyrmspsnqtdklaaf<br>pedrsqpgqdcrfrvtqlpngrdfhmsvvrarrndsgtylcgaislapkaqikeslraelrvt<br>erraevptahpspsprpagqfqtlvtttapaprpptpaptiasqplslrpeacrpaaggavhtrg<br>ldfacdiyiwaplagtcgvlllslvitlyckrgrkkllyifkqpfmrpvqttqeedgcscrfpe<br>eeeggcelrvkfsrsadapaykqgqnqlynelnlgrreeydvldlargrdpemggkprrk<br>npqeglynelqkdkmaeayseigmkgerrrgkghdglyqglstatkdtydalhmqalpp<br>r |
| SEQ ID NO: 23 | PD-1 CAR (na) (PD1 ECD underlined) | atggccctccctgtcactgccctgcttctccccctcgcactcctgctccacgccgctagaccac<br>ccggatggtttctggactctccggatcgcccgtggaatcccccaaccttctcaccggcactctt<br>ggttgtgactgagggcgataatgcgaccttcacgtgctcgttctccaacacctccgaatcattc<br>gtgctgaactggtaccgcatgagcccgtcaaaccagaccgacaagctcgccgcgtttccgga<br>agatcggtcgcaaccgggacaggattgtcggaccgcgtgactcaactgccgaatggcagag<br>acttccacatgagcgtggtccgcgctaggcgaaacgactccgggacctacctgtgcggagc<br>catctcgctggcgcctaaggcccaaatcaaagagagcttgagggccgaactgagagtgacc<br>gagcgcagagctgaggtgccaactgcacatccatccccatcgcctcggcctgcggggcagt<br>ttcagaccctggtcacgaccactccggcgccgcgcccaccgactccggccccaactatcgc<br>gagccagcccctgtcgctgaggccggaagcatgccgccctgccgccggaggtgctgtgcat<br>acccggggattggacttcgcatgcgacatctacatttgggctcctctcgccggaacttgtggcg<br>tgctccttctgtccctggtcatcaccctgtactgcaagcggggtcggaaaaagcttctgtacattt<br>tcaagcagcccttcatgaggcccgtgcaaaccacccaggaggaggacggttgctcctgccg<br>gttccccgaagaggaagaaggaggttgcgagctgcgcgtgaagttctcccggagcgccgac<br>gcccccgcctataagcagggccagaaccagctgtacaacgaactgaacctgggacggcgg<br>gaagagtacgatgtgctggacaagcggcgcggccgggaccccgaaatgggcgggaagcc<br>tagaagaaagaaccctcaggaaggcctgtataacgagctgcagaaggacaagatggccga<br>ggcctactccgaaattgggatgaagggagagcggcggaggggaaaggggcacgacggcc<br>tgtaccaaggactgtccaccgccaccaaggacacatacgatgccctgcacatgcaggccctt<br>ccccctcgc |
| SEQ ID NO: 24 | PD-1 CAR (aa) with signal (PD1 ECD underlined) | Malpvtalllplalllhaarppgwfldspdrpwnpptfspallvvtegdnatftcsfsntsesf<br>vlnwyrmspsnqtdklaafpedrsqpgqdcrfrvtqlpngrdfhmsvvrarrndsgtylc<br>gaislapkaqikeslraelryterraevptahpspsprpagqfqtlvtttpaprpptpaptiasq<br>plslrpeacrpaaggavhtrgldfacdiyiwaplagtcgvlllslvitlyckrgrkkllyifkqp<br>fmrpvqttqeedgcscrfpeeeeggcelrvkfsrsadapaykqgqnqlynelnlgrreeyd<br>vldkagrdpemggkprrknpqeglynelqkdkmaeayseigmkgeragkghdglyq<br>glstatkdtydalhmqalppr |

Bispecific CARs

In some embodiments a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In some embodiments the first and second epitopes are on the same antigen, for example, the same protein (or subunit of a multimeric protein). In some embodiments the first and second epitopes overlap. In some embodiments the first and second epitopes do not overlap. In some embodiments the first and second epitopes are on different antigens, for example, different proteins (or different subunits of a multimeric protein). In some embodiments a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In some embodiments a bispecific antibody molecule comprises a half antibody having binding specificity for a first epitope and a half antibody having binding specificity for a second epitope. In some embodiments a bispecific antibody molecule comprises a half antibody, or fragment thereof, having binding specificity for a first epitope and a half antibody, or fragment thereof, having binding specificity for a second epitope. In some embodiments a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (for example, a bispecific or a trispecific) antibody molecule. Protocols for generating bispecific or heterodimeric antibody molecules, and various configurations for bispecific antibody molecules, are described in, for example, paragraphs 455-458 of WO2015/142675, filed Mar. 13, 2015, which is incorporated by reference in its entirety.

In some embodiments, the bispecific antibody molecule is characterized by a first immunoglobulin variable domain sequence, for example, a scFv, which has binding specificity for CD19, for example, comprises a scFv as described herein, or comprises the light chain CDRs and/or heavy chain CDRs from a scFv described herein, and a second immunoglobulin variable domain sequence that has binding specificity for a second epitope on a different antigen.

Chimeric TCR

In some embodiments, the antibodies and antibody fragments of the present invention (for example, CD19 antibodies and fragments) can be grafted to one or more constant domain of a T cell receptor ("TCR") chain, for example, a TCR alpha or TCR beta chain, to create a chimeric TCR.

Without being bound by theory, it is believed that chimeric TCRs will signal through the TCR complex upon antigen binding. For example, an scFv as disclosed herein, can be grafted to the constant domain, for example, at least a portion of the extracellular constant domain, the transmembrane domain and the cytoplasmic domain, of a TCR chain, for example, the TCR alpha chain and/or the TCR beta chain. As another example, an antibody fragment, for example a VL domain as described herein, can be grafted to the constant domain of a TCR alpha chain, and an antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an antibody or antibody fragment may be grafted into a TCR alpha and/or beta chain to create a chimeric TCR. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced, for example, by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4): 365-74).

Non-Antibody Scaffolds

In embodiments, the antigen binding domain comprises a non-antibody scaffold, for example, a fibronectin, ankyrin, domain antibody, lipocalin, small modular immuno-pharmaceutical, maxybody, Protein A, or affilin. The non-antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, MA), ankyrin (Molecular Partners AG, Zurich, Switzerland), domain antibodies (Domantis, Ltd., Cambridge, MA, and Ablynx nv, Zwijnaarde, Belgium), lipocalin (Pieris Proteolab AG, Freising, Germany), small modular immunopharmaceuticals (Trubion Pharmaceuticals Inc., Seattle, WA), maxybodies (Avidia, Inc., Mountain View, CA), Protein A (Affibody AG, Sweden), and affilin (gamma-crystallin or ubiquitin) (Scil Proteins GmbH, Halle, Germany).

In some embodiments the antigen binding domain comprises the extracellular domain, or a counter-ligand binding fragment thereof, of molecule that binds a counterligand on the surface of a target cell.

The immune effector cells can comprise a recombinant DNA construct comprising sequences encoding a CAR, wherein the CAR comprises an antigen binding domain (for example, antibody or antibody fragment, TCR or TCR fragment) that binds specifically to a tumor antigen, for example, a tumor antigen described herein, and an intracellular signaling domain. The intracellular signaling domain can comprise a costimulatory signaling domain and/or a primary signaling domain, for example, a zeta chain. As described elsewhere, the methods described herein can include transducing a cell, for example, from the population of T regulatory-depleted cells, with a nucleic acid encoding a CAR, for example, a CAR described herein.

In some embodiments, a CAR comprises a scFv domain, wherein the scFv may be preceded by an optional leader sequence such as provided in SEQ ID NO: 1, and followed by an optional hinge sequence such as provided in SEQ ID NO:2 or SEQ ID NO:36 or SEQ ID NO:38, a transmembrane region such as provided in SEQ ID NO:6, an intracellular signaling domain that includes SEQ ID NO:7 or SEQ ID NO:16 and a CD3 zeta sequence that includes SEQ ID NO:9 or SEQ ID NO:10, for example, wherein the domains are contiguous with and in the same reading frame to form a single fusion protein.

In some embodiments, an exemplary CAR constructs comprise an optional leader sequence (for example, a leader sequence described herein), an extracellular antigen binding domain (for example, an antigen binding domain described herein), a hinge (for example, a hinge region described herein), a transmembrane domain (for example, a transmembrane domain described herein), and an intracellular stimulatory domain (for example, an intracellular stimulatory domain described herein). In some embodiments, an exemplary CAR construct comprises an optional leader sequence (for example, a leader sequence described herein), an extracellular antigen binding domain (for example, an antigen binding domain described herein), a hinge (for example, a hinge region described herein), a transmembrane domain (for example, a transmembrane domain described herein), an intracellular costimulatory signaling domain (for example, a costimulatory signaling domain described herein) and/or an intracellular primary signaling domain (for example, a primary signaling domain described herein).

An exemplary leader sequence is provided as SEQ ID NO: 1. An exemplary hinge/spacer sequence is provided as SEQ ID NO: 2 or SEQ ID NO:36 or SEQ ID NO:38. An exemplary transmembrane domain sequence is provided as SEQ ID NO:6. An exemplary sequence of the intracellular signaling domain of the 4-1BB protein is provided as SEQ ID NO: 7. An exemplary sequence of the intracellular signaling domain of CD27 is provided as SEQ ID NO:16. An exemplary CD3zeta domain sequence is provided as SEQ ID NO: 9 or SEQ ID NO:10.

In some embodiments, the immune effector cell comprises a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, for example, CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

Nucleic acids encoding a CAR can be introduced into the immune effector cells using, for example, a retroviral or lentiviral vector construct.

Nucleic acids encoding a CAR can also be introduced into the immune effector cell using, for example, an RNA construct that can be directly transfected into a cell. A method for generating mRNA for use in transfection involves in vitro transcription (IVT) of a template with specially designed primers, followed by poly(A) addition, to produce a construct containing 3' and 5' untranslated sequence ("UTR") (for example, a 3' and/or 5' UTR described herein), a 5' cap (for example, a 5' cap described herein) and/or Internal Ribosome Entry Site (IRES) (for example, an IRES described herein), the nucleic acid to be expressed, and a poly(A) tail, typically 50-2000 bases in length (for example, described in the Examples, for example, SEQ ID NO:35). RNA so produced can efficiently transfect different kinds of cells. In some embodiments, the template includes sequences for the CAR. In some embodiments, an RNA CAR vector is transduced into a cell, for example, a T cell by electroporation.

Antigen Binding Domain

In some embodiments, a plurality of the immune effector cells, for example, the population of T regulatory-depleted cells, include a nucleic acid encoding a CAR that comprises a target-specific binding element otherwise referred to as an antigen binding domain. The choice of binding element depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR described herein include those associated with viral, bacterial and parasitic infections, autoimmune disease and cancer cells.

In some embodiments, the portion of the CAR comprising the antigen binding domain comprises an antigen binding domain that targets a tumor antigen, for example, a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, for example, single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

CD19 CAR

In some embodiments, the CAR-expressing cell described herein is a CD19 CAR-expressing cell (for example, a cell expressing a CAR that binds to human CD19).

In some embodiments, the antigen binding domain of the CD19 CAR has the same or a similar binding specificity as the FMC63 scFv fragment described in Nicholson et al. Mol. Immun. 34 (16-17): 1157-1165 (1997). In some embodiments, the antigen binding domain of the CD19 CAR includes the scFv fragment described in Nicholson et al. *Mol. Immun.* 34 (16-17): 1157-1165 (1997).

In some embodiments, the CD19 CAR includes an antigen binding domain (for example, a humanized antigen binding domain) according to Table 3 of WO2014/153270, incorporated herein by reference. WO2014/153270 also describes methods of assaying the binding and efficacy of various CAR constructs.

In some embodiments, the parental murine scFv sequence is the CAR19 construct provided in PCT publication WO2012/079000 (incorporated herein by reference). In some embodiments, the anti-CD19 binding domain is a scFv described in WO2012/079000.

In some embodiments, the CAR molecule comprises the fusion polypeptide sequence provided as SEQ ID NO: 12 in PCT publication WO2012/079000, which provides an scFv fragment of murine origin that specifically binds to human CD19.

In some embodiments, the CD19 CAR comprises an amino acid sequence provided as SEQ ID NO: 12 in PCT publication WO2012/079000.

In some embodiments, the amino acid sequence is:

```
                                          (SEQ ID NO: 292)
Diqmtqttsslsaslgdrvtiscrasqdiskylnwyqqkpdgtvklliyh

tsrlhsgvpsrfsgsgsgtdysltisnleqediatyfcqqgntlpytfgg

gtkleitggggsggggsggggsevklqesgpglvapsqslsvtctvsgvs

lpdygvswirqpprkglewlgviwgsettyynsalksrltiikdnsksqv

flkmnslqtddtaiyycakhyyyggsyamdywgqgtsvtvssttpaprp

ptpaptiasqplslrpeacrpaaggavhtrgldfacdiyiwaplagtcgv

lllslvitlyckrgrkkllyifkqpfmrpvqttqeedgcscrfpeeeegg

celrvkfsrsadapaykqgqnqlynelnlgrreeydvldkrrgrdpemgg

kprrknpqeglynelqkdkmaeayseigmkgerrrgkghdglyqglstat

kdtydalhmqalppr,
```

or a sequence substantially homologous thereto.

In some embodiments, the CD19 CAR has the USAN designation TISAGENLECLEUCEL-T. In embodiments, CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CD19 CAR comprises an antigen binding domain (for example, a humanized antigen binding domain) according to Table 3 of WO2014/153270, incorporated herein by reference.

Humanization of murine CD19 antibody is desired for the clinical setting, where the mouse-specific residues may induce a human-anti-mouse antigen (HAMA) response in patients who receive CART19 treatment, i.e., treatment with T cells transduced with the CAR19 construct. The production, characterization, and efficacy of humanized CD19 CAR sequences is described in International Application WO2014/153270 which is herein incorporated by reference in its entirety, including Examples 1-5 (p. 115-159).

In some embodiments, the CAR molecule is a humanized CD19 CAR comprising the amino acid sequence of:

```
                                          (SEQ ID NO: 293)
EIVMTQSPATLSLSPGERATLSCRASQDISKYLNWYQQKPGQAPRLLIYH

TSRLHSGIPARFSGSGSGTDYTLTISSLQPEDFAVYFCQQGNTLPYTFGQ
```

-continued

GTKLEIKGGGGSGGGGSGGGGSQVQLQESGPGLVKPSETLSLTCTVSGVS

LPDYGVSWIRQPPGKGLEWIGVIWGSETTYYQSSLKSRVTISKDNSKNQV

SLKLSSVTAADTAVYYCAKHYYYGGSYAMDYWGQGTLVTVSS

In some embodiments, the CAR molecule is a humanized CD19 CAR comprising the amino acid sequence of:

(SEQ ID NO: 294)

EIVMTQSPATLSLSPGERATLSCRASQDISKYLNWYQQKPGQAPRLLIYH

TSRLHSGIPARFSGSGSGTDYTLTISSLQPEDFAVYFCQQGNTLPYTFGQ

GTKLEIKGGGGSGGGGSGGGGSQVQLQESGPGLVKPSETLSLTCTVSGVS

LPDYGVSWIRQPPGKGLEWIGVIWGSETTYYQSSLKSRVTISKDNSKNQV

SLKLSSVTAADTAVYYCAKHYYYGGSYAMDYWGQGTLVTVSSTTTPAPRP

PTPAPTIASQPLSLRPEACRPAAGGAVHTRGLDFACDIYIWAPLAGTCGV

LLLSLVITLYCKRGRKKLLYIFKQPFMRPVQTTQEEDGCSCRFPEEEEGG

CELRVKFSRSADAPAYKQGQNQLYNELNLGRREEYDVLDKRRGRDPEMGG

KPRRKNPQEGLYNELQKDKMAEAYSEIGMKGERRRGKGHDGLYQGLSTAT

KDTYDALHMQALPPR

Any known CD19 CAR, for example, the CD19 antigen binding domain of any known CD19 CAR, in the art can be used in accordance with the present disclosure. For example, LG-740; CD19 CAR described in the U.S. Pat. Nos. 8,399,645; 7,446,190; Xu et al., Leuk Lymphoma. 2013 54(2): 255-260(2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

Exemplary CD19 CARs include CD19 CARs described herein or an anti-CD19 CAR described in Xu et al. Blood 123.24(2014):3750-9; Kochenderfer et al. Blood 122.25 (2013):4129-39, Cruz et al. Blood 122.17(2013):2965-73, NCT00586391, NCT01087294, NCT02456350, NCT00840853, NCT02659943, NCT02650999, NCT02640209, NCT01747486, NCT02546739, NCT02656147, NCT02772198, NCT00709033, NCT02081937, NCT00924326, NCT02735083, NCT02794246, NCT02746952, NCT01593696, NCT02134262, NCT01853631, NCT02443831, NCT02277522, NCT02348216, NCT02614066, NCT02030834, NCT02624258, NCT02625480, NCT02030847, NCT02644655, NCT02349698, NCT02813837, NCT02050347, NCT01683279, NCT02529813, NCT02537977, NCT02799550, NCT02672501, NCT02819583, NCT02028455, NCT01840566, NCT01318317, NCT01864889, NCT02706405, NCT01475058, NCT01430390, NCT02146924, NCT02051257, NCT02431988, NCT01815749, NCT02153580, NCT01865617, NCT02208362, NCT02685670, NCT02535364, NCT02631044, NCT02728882, NCT02735291, NCT01860937, NCT02822326, NCT02737085, NCT02465983, NCT02132624, NCT02782351, NCT01493453, NCT02652910, NCT02247609, NCT01029366, NCT01626495, NCT02721407, NCT01044069, NCT00422383, NCT01680991, NCT02794961, or NCT02456207, each of which is incorporated herein by reference in its entirety.

In some embodiments, CD19 CARs comprise a sequence, for example, a CDR, VH, VL, scFv, or full-CAR sequence, disclosed in Table 2, or a sequence having at least 80%, 85%, 90%, 95%, or 99% identity thereto.

TABLE 2

Amino acid sequences of exemplary anti-CD19 molecules

| SEQ ID NO | Region | Sequence |
|---|---|---|
| CTL019 | | |
| 295 | HCDR1 (Kabat) | DYGVS |
| 296 | HCDR2 (Kabat) | VIWGSETTYYNSALKS |
| 297 | HCDR3 (Kabat) | HYYYGGSYAMDY |
| 298 | LCDR1 (Kabat) | RASQDISKYLN |
| 299 | LCDR2 (Kabat) | HTSRLHS |
| 300 | LCDR3 (Kabat) | QQGNTLPYT |
| 301 | CTL019 Full amino acid sequence | MALPVTALLLPLALLLHAARPDIQMTQTTSSLSASLGDRVTISCRA SQDISKYLNWYQQKPDGTVKLLIYHTSRLHSGVPSRFSGSGSGTD YSLTISNLEQEDIATYFCQQGNTLPYTFGGGTKLEITGGGGSGGGG SGGGGSEVKLQESGPGLVAPSQSLSVTCTVSGVSLPDYGVSWIRQ PPRKGLEWLGVIWGSETTYYNSALKSRLTIIKDNSKSQVFLKMNS LQTDDTAIYYCAKHYYYGGSYAMDYWGQGTSVTVSSTTTPAPR PPTPAPTIASQPLSLRPEACRPAAGGAVHTRGLDFACDIYIWAPLA GTCGVLLLSLVITLYCKRGRKKLLYIFKQPFMRPVQTTQEEDGCS CRFPEEEEGGCELRVKFSRSADAPAYKQGQNQLYNELNLGRREE |

TABLE 2-continued

Amino acid sequences of exemplary anti-CD19 molecules

| SEQ ID NO | Region | Sequence |
|---|---|---|
| | | YDVLDKRRGRDPEMGGKPRRKNPQEGLYNELQKDKMAEAYSEI GMKGERRRGKGHDGLYQGLSTATKDTYDALHMQALPPR |
| 302 | CTL019 Full nucleotide sequence | ATGGCCTTACCAGTGACCGCCTTGCTCCTGCCGCTGGCCTTGCT GCTCCACGCCGCCAGGCCGGACATCCAGATGACACAGACTAC ATCCTCCCTGTCTGCCTCTCTGGGAGACAGAGTCACCATCAGT TGCAGGGCAAGTCAGGACATTAGTAAATATTTAAATTGGTATC AGCAGAAACCAGATGGAACTGTTAAACTCCTGATCTACCATAC ATCAAGATTACACTCAGGAGTCCCATCAAGGTTCAGTGGCAGT GGGTCTGGAACAGATTATTCTCTCACCATTAGCAACCTGGAGC AAGAAGATATTGCCACTTACTTTTGCCAACAGGGTAATACGCT TCCGTACACGTTCGGAGGGGGGACCAAGCTGGAGATCACAGG TGGCGGTGGCTCGGGCGGTGGTGGGTCGGGTGGCGGCGGATC TGAGGTGAAACTGCAGGAGTCAGGACCTGGCCTGGTGGCGCC CTCACAGAGCCTGTCCGTCACATGCACTGTCTCAGGGGTCTCA TTACCCGACTATGGTGTAAGCTGGATTCGCCAGCCTCCACGAA AGGGTCTGGAGTGGCTGGGAGTAATATGGGGTAGTGAAACCA CATACTATAATTCAGCTCTCAAATCCAGACTGACCATCATCAA GGACAACTCCAAGAGCCAAGTTTTCTTAAAAATGAACAGTCTG CAAACTGATGACACAGCCATTTACTACTGTGCCAAACATTATT ACTACGGTGGTAGCTATGCTATGGACTACTGGGGCCAAGGAAC CTCAGTCACCGTCTCCTCAACCACGACGCCAGCGCCGCGACCA CCAACACCGGCGCCCACCATCGCGTCGCAGCCCCTGTCCCTGC GCCCAGAGGCGTGCCGGCCAGCGGCGGGGGGCGCAGTGCACA CGAGGGGGCTGGACTTCGCCTGTGATATCTACATCTGGGCGCC CTTGGCCGGGACTTGTGGGGTCCTTCTCCTGTCACTGGTTATCA CCCTTTACTGCAAACGGGGCAGAAAGAAACTCCTGTATATATT CAAACAACCATTTATGAGACCAGTACAAACTACTCAAGAGGA AGATGGCTGTAGCTGCCGATTTCCAGAAGAAGAAGAAGGAGG ATGTGAACTGAGAGTGAAGTTCAGCAGGAGCGCAGACGCCCC CGCGTACAAGCAGGGCCAGAACCAGCTCTATAACGAGCTCAA TCTAGGACGAAGAGAGGAGTACGATGTTTTGGACAAGAGACG TGGCCGGGACCCTGAGATGGGGGGAAAGCCGAGAAGGAAGA ACCCTCAGGAAGGCCTGTACAATGAACTGCAGAAAGATAAGA TGGCGGAGGCCTACAGTGAGATTGGGATGAAAGGCGAGCGCC GGAGGGGCAAGGGGCACGATGGCCTTTACCAGGGTCTCAGTA CAGCCACCAAGGACACCTACGACGCCCTTCACATGCAGGCCCT GCCCCCTCGC |
| 303 | CTL019 scFv domain | DIQMTQTTSSLSASLGDRVTISCRASQDISKYLNWYQQKPDGTVK LLIYHTSRLHSGVPSRFSGSGSGTDYSLTISNLEQEDIATYFCQQGN TLPYTFGGGTKLEITGGGGSGGGGSGGGGSEVKLQESGPGLVAPS QSLSVTCTVSGVSLPDYGVSWIRQPPRKGLEWLGVIWGSETTYY NSALKSRLTIIKDNSKSQVFLKMNSLQTDDTAIYYCAKHYYYGGS YAMDYWGQGTSVTVSS |
| Humanized CAR2 | | |
| 295 | HCDR1 (Kabat) | DYGVS |
| 304 | HCDR2 (Kabat) | VIWGSETTYYQSSLKS |
| 297 | HCDR3 (Kabat) | HYYYGGSYAMDY |
| 298 | LCDR1 (Kabat) | RASQDISKYLN |
| 299 | LCDR2 (Kabat) | HTSRLHS |
| 300 | LCDR3 (Kabat) | QQGNTLPYT |
| 293 | CAR2 scFv domain - aa (Linker is underlined) | EIVMTQSPATLSLSPGERATLSCRASQDISKYLNWYQQKPGQAPR LLIYHTSRLHSGIPARFSGSGSGTDYTLTISSLQPEDFAVYFCQQGN TLPYTFGQGTKLEIKGGGGSGGGGSGGGGSQVQLQESGPGLVKP SETLSLTCTVSGVSLPDYGVSWIRQPPGKGLEWIGVIWGSETTYY QSSLKSRVTISKDNSKNQVSLKLSSVTAADTAVYYCAKHYYYGG SYAMDYWGQGTLVTVSS |
| 305 | CAR2 scFv domain - nt | atggccctccctgtcaccgccctgctgcttccgctggctcttctgctccacgccgctcggcccgaaattgt gatgacccagtcacccgccactcttagcctttcacccggtgagcgcgcaaccctgtcttgcagagcctcc |

TABLE 2-continued

Amino acid sequences of exemplary anti-CD19 molecules

| SEQ ID NO | Region | Sequence |
|---|---|---|
| | | caagacatctcaaaataccttaattggtatcaacagaagcccggacaggctcctcgccttctgatctacca<br>caccagccggctccattctggaatccctgccaggttcagcggtagcggatctgggaccgactacaccct<br>cactatcagctcactgcagccagaggacttcgctgtctatttctgtcagcaagggaacaccctgccctac<br>acctttggacagggcaccaagctcgagattaaaggtggaggtggcagcggaggaggtgggtccggc<br>ggtggaggaagccaggtccaactccaagaaagcggaccgggtcttgtgaagccatcagaaactctttc<br>actgacttgtactgtgagcggagtgtctctccccgattacggggtgtcttggatcagacagccaccgggg<br>aagggtctggaatggattggagtgatttggggctctgagactacttactaccaatcatccctcaagtcacg<br>cgtcaccatctcaaaggacaactctaagaatcaggtgtcactgaaactgtcatctgtgaccgcagccgac<br>accgccgtgtactattgcgctaagcattactattatggcgggagctacgcaatggattactggggacagg<br>gtactctggtcaccgtgtccagccaccaccatcatcaccatcaccat |
| 306 | CAR 2 - Full - aa | MALPVTALLLPLALLLHAARPEIVMTQSPATLSLSPGERATLSCRA<br>SQDISKYLNWYQQKPGQAPRLLIYHTSRLHSGIPARFSGSGSGTD<br>YTLTISSLQPEDFAVYFCQQGNTLPYTFGQGTKLEIKGGGGSGGG<br>GSGGGGSQVQLQESGPGLVKPSETLSLTCTVSGVSLPDYGVSWIR<br>QPPGKGLEWIGVIWGSETTYYQSSLKSRVTISKDNSKNQVSLKLS<br>SVTAADTAVYYCAKHYYYGGSYAMDYWGQGTLVTVSSTTTPAP<br>RPPTPAPTIASQPLSLRPEACRPAAGGAVHTRGLDFACDIYIWAPL<br>AGTCGVLLLSLVITLYCKRGRKKLLYIFKQPFMRPVQTTQEEDGC<br>SCRFPEEEEGGCELRVKFSRSADAPAYKQGQNQLYNELNLGRRE<br>EYDVLDKRRGRDPEMGGKPRRKNPQEGLYNELQKDKMAEAYSE<br>IGMKGERRRGKGHDGLYQGLSTATKDTYDALHMQALPPR |
| 307 | CAR 2 - Full - nt | atggccctccctgtcaccgccctgctgcttccgctggctcttctgctccacgccgctcggcccgaaattgt<br>gatgacccagtcacccgccactcttagcctttcacccggtgagcgcgcaaccctgtcttgcagagcctcc<br>caagacatctcaaaataccttaattggtatcaacagaagcccggacaggctcctcgccttctgatctacca<br>caccagccggctccattctggaatccctgccaggttcagcggtagcggatctgggaccgactacaccct<br>cactatcagctcactgcagccagaggacttcgctgtctatttctgtcagcaagggaacaccctgccctac<br>acctttggacagggcaccaagctcgagattaaaggtggaggtggcagcggaggaggtgggtccggc<br>ggtggaggaagccaggtccaactccaagaaagcggaccgggtcttgtgaagccatcagaaactctttc<br>actgacttgtactgtgagcggagtgtctctccccgattacggggtgtcttggatcagacagccaccgggg<br>aagggtctggaatggattggagtgatttggggctctgagactacttactaccaatcatccctcaagtcacg<br>cgtcaccatctcaaaggacaactctaagaatcaggtgtcactgaaactgtcatctgtgaccgcagccgac<br>accgccgtgtactattgcgctaagcattactattatggcgggagctacgcaatggattactggggacagg<br>gtactctggtcaccgtgtccagcaccactaccccagcaccgaggccacccaccccggctcctaccatc<br>gcctcccagcctctgtccctgcgtccggaggcatgtagacccgcagctggtggggccgtgcatacccg<br>ggtcttgacttcgcctgcgatatctacatttgggcccctctggctggtacttgcggggtcctgctgctttc<br>actcgtgatcactctttactgtaagcgcggtcggaagaagctgctgtacatctttaagcaacccttcatgag<br>gcctgtgcagactactcaagaggaggacggctgttcatgccggttcccagaggaggaggaaggcggc<br>tgcgaactgcgcgtgaaattcagccgcagcgcagatgctccagcctacaagcaggggcagaaccagc<br>tctacaacgaactcaatcttggtcggagagaggagtacgacgtgctggacaagcggagaggacggga<br>cccagaaatgggcgggaagccgcgcagaaagaatccccaagagggcctgtacaacgagctccaaaa<br>ggataagatggcagaagcctatagcgagattggtatgaaaggggaacgcagaagaggcaaaggcca<br>cgacggactgtaccagggactcagcaccgccaccaaggacacctatgacgctcttcacatgcaggccc<br>tgccgcctcgg |

BCMA CAR

In some embodiments, the CAR-expressing cell described herein is a BCMA CAR-expressing cell (for example, a cell expressing a CAR that binds to human BCMA). Exemplary BCMA CARs can include sequences disclosed in Table 1 or 16 of WO2016/014565, incorporated herein by reference. The BCMA CAR construct can include an optional leader sequence; an optional hinge domain, for example, a CD8 hinge domain; a transmembrane domain, for example, a CD8 transmembrane domain; an intracellular domain, for example, a 4-1BB intracellular domain; and a functional signaling domain, for example, a CD3 zeta domain. In certain embodiments, the domains are contiguous and in the same reading frame to form a single fusion protein. In other embodiments, the domains are in separate polypeptides, for example, as in an RCAR molecule as described herein.

In some embodiments, the BCMA CAR molecule includes one or more CDRs, VH, VL, scFv, or full-length sequences of BCMA-1, BCMA-2, BCMA-3, BCMA-4, BCMA-5, BCMA-6, BCMA-7, BCMA-8, BCMA-9, BCMA-10, BCMA-11, BCMA-12, BCMA-13, BCMA-14, BCMA-15, 149362, 149363, 149364, 149365, 149366, 149367, 149368, 149369, BCMA_EBB-C1978-A4, BCMA_EBB-C1978-G1, BCMA_EBB-C1979-C1, BCMA_EBB-C1978-C7, BCMA_EBB-C1978-D10, BCMA_EBB-C1979-C12, BCMA_EBB-C1980-G4, BCMA_EBB-C1980-D2, BCMA_EBB-C1978-A10, BCMA_EBB-C1978-D4, BCMA_EBB-C1980-A2, BCMA_EBB-C1981-C3, BCMA_EBB-C1978-G4, A7D12.2, C11D5.3, C12A3.2, or C13F12.1 disclosed in WO2016/014565, or a sequence substantially (for example, 95-99%) identical thereto.

Additional exemplary BCMA-targeting sequences that can be used in the anti-BCMA CAR constructs are disclosed in WO 2017/021450, WO 2017/011804, WO 2017/025038, WO 2016/090327, WO 2016/130598, WO 2016/210293, WO 2016/090320, WO 2016/014789, WO 2016/094304, WO 2016/154055, WO 2015/166073, WO 2015/188119, WO 2015/158671, U.S. Pat. Nos. 9,243,058, 8,920,776, 9,273,141, 7,083,785, 9,034,324, US 2007/0049735, US 2015/0284467, US 2015/0051266, US 2015/0344844, US 2016/0131655, US 2016/0297884, US 2016/0297885, US 2017/0051308, US 2017/0051252, US 2017/0051252, WO 2016/020332, WO 2016/087531, WO 2016/079177, WO 2015/172800, WO 2017/008169, U.S. Pat. No. 9,340,621, US 2013/0273055, US 2016/0176973, US 2015/0368351, US 2017/0051068, US 2016/0368988, and US 2015/0232557, herein incorporated by reference in their entirety. In some embodiments, additional exemplary BCMA CAR constructs are generated using the VH and VL sequences from PCT Publication WO2012/0163805 (the contents of which are hereby incorporated by reference in its entirety).

In some embodiments, BCMA CARs comprise a sequence, for example, a CDR, VH, VL, scFv, or full-CAR sequence, disclosed in Tables 3-15, or a sequence having at least 80%, 85%, 90%, 95%, or 99% identity thereto. In some embodiments, the antigen binding domain comprises a human antibody or a human antibody fragment. In some embodiments, the human anti-BCMA binding domain comprises one or more (for example, all three) LC CDR1, LC CDR2, and LC CDR3 of a human anti-BCMA binding domain described herein (for example, in Tables 3-10 and 12-15), and/or one or more (for example, all three) HC CDR1, HC CDR2, and HC CDR3 of a human anti-BCMA binding domain described herein (for example, in Tables 3-10 and 12-15). In some embodiments, the human anti-BCMA binding domain comprises a human VL described herein (for example, in Tables 3, 7, and 12) and/or a human VH described herein (for example, in Tables 3, 7, and 12). In some embodiments, the anti-BCMA binding domain is a scFv comprising a VL and a VH of an amino acid sequence of Tables 3, 7, and 12. In some embodiments, the anti-BCMA binding domain (for example, an scFv) comprises: a VL comprising an amino acid sequence having at least one, two or three modifications (for example, substitutions, for example, conservative substitutions) but not more than 30, 20 or 10 modifications (for example, substitutions, for example, conservative substitutions) of an amino acid sequence provided in Tables 3, 7, and 12, or a sequence with 95-99% identity with an amino acid sequence of Tables 3, 7, and 12, and/or a VH comprising an amino acid sequence having at least one, two or three modifications (for example, substitutions, for example, conservative substitutions) but not more than 30, 20 or 10 modifications (for example, substitutions, for example, conservative substitutions) of an amino acid sequence provided in Tables 3, 7, and 12, or a sequence with 95-99% identity to an amino acid sequence of Tables 3, 7, and 12.

TABLE 3

Amino acid and nucleic acid sequences of exemplary PALLAS-derived anti-BCMA molecules

| SEQ ID NO | Name/ Description | Sequence |
|---|---|---|
| R1B6 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 46 | HCDR3 (Kabat) | REWVPYDVSWYFDY |
| SEQ ID NO: 47 | HCDR1 (Chothia) | GFTFSSY |
| SEQ ID NO: 48 | HCDR2 (Chothia) | SGSGGS |
| SEQ ID NO: 46 | HCDR3 (Chothia) | REWVPYDVSWYFDY |
| SEQ ID NO: 49 | HCDR1 (IMGT) | GFTFSSYA |
| SEQ ID NO: 50 | HCDR2 (IMGT) | ISGSGGST |
| SEQ ID NO: 51 | HCDR3 (IMGT) | ARREWVPYDVSWYFDY |
| SEQ ID NO: 52 | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWVPYDVSWYFDYWGQGTLVTVSS |
| SEQ ID NO: 53 | DNA VH | GAAGTGCAGTTGCTGGAGTCAGGCGGAGGACTGGTGCAGCCCGGAGGATCGCTTCGCTTGAGCTGCGCAGCCTCAGGCTTTACCTTCTCCTCCTACGCCATGTCCTGGGTCAGACAGGCTCCCGGGAAGGGACTGGAATGGGTGTCCGCCATTAGCGGTTCCGGCGGAAGCACTTACTATGCCGACTCTGTGAAGGGCCGCTTCACTATCTCCCGGGACAACTCCAAGAACACCCTGTATCTCCAAATGAATTCCCTGAGGGCCGAAGATACCGCGGTGTACTACTGCGCTAGACGGGAGTGGGTGCCCTACGATGTCAGCTGGTACTTCGACTACTGGGGACAGGGCACTCTCGTGACTGTGTCCTCC |
| SEQ ID NO: 54 | LCDR1 (Kabat) | RASQSISSYLN |

TABLE 3-continued

Amino acid and nucleic acid sequences of exemplary PALLAS-derived anti-BCMA molecules

| SEQ ID NO | Name/ Description | Sequence |
|---|---|---|
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK |
| SEQ ID NO: 62 | DNA VL | GACATTCAAATGACTCAGTCCCCGTCCTCCCTCTCCGCCTCCGTGGGAGATCGCGTCACGATCACGTGCAGGGCCAGCCAGAGCATCTCCAGCTACCTGAACTGGTACCAGCAGAAGCCAGGGAAGGCACCGAAGCTCCTGATCTACGCCGCTAGCTCGCTGCAGTCCGGCGTCCCTTCACGGTTCTCGGGATCGGGCTCAGGCACCGACTTCACCCTGACCATTAGCAGCCTGCAGCCGGAGGACTTCGCGACATACTACTGTCAGCAGTCATACTCCACCCCTCTGACCTTCGGCCAAGGGACCAAAGTGGAGATCAAG |
| SEQ ID NO: 63 | Linker | GGGGSGGGGSGGGGSGGGGS |
| SEQ ID NO: 64 | scFv (VH-linker-VL) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWVPYDVSWYFDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK |
| SEQ ID NO: 65 | DNA scFv | GAAGTGCAGTTGCTGGAGTCAGGCGGAGGACTGGTGCAGCCCGGAGGATCGCTTCGCTTGAGCTGCGCAGCCTCAGGCTTTACCTTCTCCTCCTACGCCATGTCCTGGGTCAGACAGGCTCCCGGGAAGGGACTGGAATGGGTGTCCGCCATTAGCGGTTCCGGCGGAAGCACTTACTATGCCGACTCTGTGAAGGGCCGCTTCACTATCTCCCGGGACAACTCCAAGAACACCCTGTATCTCCAAATGAATTCCCTGAGGGCCGAAGATACCGCGGTGTACTACTGCGCTAGACGGGAGTGGGTGCCCTACGATGTCAGCTGGTACTTCGACTACTGGGGACAGGGCACTCTCGTGACTGTGTCCTCCGGTGGTGGTGGATCGGGGGGTGGTGGTTCGGGCGGAGGAGGATCTGGAGGAGGAGGGTCGGACATTCAAATGACTCAGTCCCCGTCCTCCCTCTCCGCCTCCGTGGGAGATCGCGTCACGATCACGTGCAGGGCCAGCCAGAGCATCTCCAGCTACCTGAACTGGTACCAGCAGAAGCCAGGGAAGGCACCGAAGCTCCTGATCTACGCCGCTAGCTCGCTGCAGTCCGGCGTCCCTTCACGGTTCTCGGGATCGGGCTCAGGCACCGACTTCACCCTGACCATTAGCAGCCTGCAGCCGGAGGACTTCGCGACATACTACTGTCAGCAGTCATACTCCACCCCTCTGACCTTCGGCCAAGGGACCAAAGTGGAGATCAAG |
| SEQ ID NO: 66 | Full CAR amino acid sequence | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWVPYDVSWYFDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEE |

TABLE 3-continued

Amino acid and nucleic acid sequences of exemplary PALLAS-derived anti-BCMA molecules

| SEQ ID NO | Name/ Description | Sequence |
|---|---|---|
| | | DGCSCRFPEEEEGGCELRVKFSRSADAPAYQQGQNQLYNELNL GRREEYDVLDKRRGRDPEMGGKPRRKNPQEGLYNELQKDKMAE AYSEIGMKGERRRGKGHDGLYQGLSTATKDTYDALHMQALPPR |
| SEQ ID NO: 67 | Full CAR DNA sequence | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGGTGCCCTACGATGTCAGCTGGTACTTCGACTACTGGGGACA GGGCACTCTCGTGACTGTGTCCTCCGGTGGTGGTGGATCGGGG GGTGGTGGTTCGGGCGGAGGAGGATCTGGAGGAGGAGGGTCGG ACATTCAAATGACTCAGTCCCCGTCCTCCCTCTCCGCCTCCGT GGGAGATCGCGTCACGATCACGTGCAGGGCCAGCCAGAGCATC TCCAGCTACCTGAACTGGTACCAGCAGAAGCCAGGGAAGGCAC CGAAGCTCCTGATCTACGCCGCTAGCTCGCTGCAGTCCGGCGT CCCTTCACGGTTCTCGGGATCGGGCTCAGGCACCGACTTCACC CTGACCATTAGCAGCCTGCAGCCGGAGGACTTCGCGACATACT ACTGTCAGCAGTCATACTCCACCCCTCTGACCTTCGGCCAAGG GACCAAAGTGGAGATCAAGACCACTACCCCAGCACCGAGGCCA CCCACCCCGGCTCCTACCATCGCCTCCCAGCCTCTGTCCCTGC GTCCGGAGGCATGTAGACCCGCAGCTGGTGGGGCCGTGCATAC CCGGGGTCTTGACTTCGCCTGCGATATCTACATTTGGGCCCCT CTGGCTGGTACTTGCGGGGTCCTGCTGCTTTCACTCGTGATCA CTCTTTACTGTAAGCGCGGTCGGAAGAAGCTGCTGTACATCTT TAAGCAACCCTTCATGAGGCCTGTGCAGACTACTCAAGAGGAG GACGGCTGTTCATGCCGGTTCCCAGAGGAGGAGGAAGGCGGCT GCGAACTGCGCGTGAAATTCAGCCGCAGCGCAGATGCTCCAGC CTACCAGCAGGGGCAGAACCAGCTCTACAACGAACTCAATCTT GGTCGGAGAGAGGAGTACGACGTGCTGGACAAGCGGAGAGGAC GGGACCCAGAAATGGGCGGGAAGCCGCGCAGAAAGAATCCCCA AGAGGGCCTGTACAACGAGCTCCAAAAGGATAAGATGGCAGAA GCCTATAGCGAGATTGGTATGAAAGGGGAACGCAGAAGAGGCA AAGGCCACGACGGACTGTACCAGGGACTCAGCACCGCCACCAA GGACACCTATGACGCTCTTCACATGCAGGCCCTGCCGCCTCGG |
| R1F2 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 68 | HCDR3 (Kabat) | REWWYDDWYLDY |
| SEQ ID NO: 47 | HCDR1 (Chothia) | GFTFSSY |
| SEQ ID NO: 48 | HCDR2 (Chothia) | SGSGGS |
| SEQ ID NO: 68 | HCDR3 (Chothia) | REWWYDDWYLDY |
| SEQ ID NO: 49 | HCDR1 (IMGT) | GFTFSSYA |
| SEQ ID NO: 50 | HCDR2 (IMGT) | ISGSGGST |
| SEQ ID NO: 69 | HCDR3 (IMGT) | ARREWWYDDWYLDY |
| SEQ ID NO: 70 | VH | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWYDDWYLDYWGQGTLVTVSS |
| SEQ ID NO: 71 | DNA VH | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG |

TABLE 3-continued

| Amino acid and nucleic acid sequences of exemplary PALLAS-derived anti-BCMA molecules | | |
|---|---|---|
| SEQ ID NO | Name/ Description | Sequence |
| | | GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGTACGACGATTGGTACCTGGACTACTGGGGACAGGGCAC TCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKA PKLLIYAASSLQSGVPSRFSGSGSGTDFTLTISSLQPEDFATY YCQQSYSTPLTFGQGTKVEIK |
| SEQ ID NO: 62 | DNA VL | GACATTCAAATGACTCAGTCCCCGTCCTCCCTCTCCGCCTCCG TGGGAGATCGCGTCACGATCACGTGCAGGGCCAGCCAGAGCAT CTCCAGCTACCTGAACTGGTACCAGCAGAAGCCAGGGAAGGCA CCGAAGCTCCTGATCTACGCCGCTAGCTCGCTGCAGTCCGGCG TCCCTTCACGGTTCTCGGGATCGGGCTCAGGCACCGACTTCAC CCTGACCATTAGCAGCCTGCAGCCGGAGGACTTCGCGACATAC TACTGTCAGCAGTCATACTCCACCCCTCTGACCTTCGGCCAAG GGACCAAAGTGGAGATCAAG |
| SEQ ID NO: 63 | Linker | GGGGSGGGGSGGGGSGGGGS |
| SEQ ID NO: 72 | scFv (VH-linker-VL) | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWYDDWYLDYWGQGTLVTVSSGGGGSGGG GSGGGGSGGGGSDIQMTQSPSSLSASVGDRVTITCRASQSISS YLNWYQQKPGKAPKLLIYAASSLQSGVPSRFSGSGSGTDFTLT ISSLQPEDFATYYCQQSYSTPLTFGQGTKVEIK |
| SEQ ID NO: 73 | DNA scFv | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGTACGACGATTGGTACCTGGACTACTGGGGACAGGGCAC TCTCGTGACTGTGTCCTCCGGTGGTGGTGGATCGGGGGGTGGT GGTTCGGGCGGAGGAGGATCTGGAGGAGGAGGGTCGGACATTC AAATGACTCAGTCCCCGTCCTCCCTCTCCGCCTCCGTGGGAGA TCGCGTCACGATCACGTGCAGGGCCAGCCAGAGCATCTCCAGC TACCTGAACTGGTACCAGCAGAAGCCAGGGAAGGCACCGAAGC TCCTGATCTACGCCGCTAGCTCGCTGCAGTCCGGCGTCCCTTC ACGGTTCTCGGGATCGGGCTCAGGCACCGACTTCACCCTGACC |

TABLE 3-continued

Amino acid and nucleic acid sequences of exemplary PALLAS-derived anti-BCMA molecules

| SEQ ID NO | Name/ Description | Sequence |
|---|---|---|
| | | ATTAGCAGCCTGCAGCCGGAGGACTTCGCGACATACTACTGTC AGCAGTCATACTCCACCCCTCTGACCTTCGGCCAAGGGACCAA AGTGGAGATCAAG |
| SEQ ID NO: 74 | Full CAR amino acid sequence | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWYDDWYLDYWGQGTLVTVSSGGGGSGGG GSGGGGSGGGGSDIQMTQSPSSLSASVGDRVTITCRASQSISS YLNWYQQKPGKAPKLLIYAASSLQSGVPSRFSGSGSGTDFTLT ISSLQPEDFATYYCQQSYSTPLTFGQGTKVEIKTTTPAPRPPT PAPTIASQPLSLRPEACRPAAGGAVHTRGLDFACDIYIWAPLA GTCGVLLLSLVITLYCKRGRKKLLYIFKQPFMRPVQTTQEEDG CSCRFPEEEEGGCELRVKFSRSADAPAYQQGQNQLYNELNLGR REEYDVLDKRRGRDPEMGGKPRRKNPQEGLYNELQKDKMAEAY SEIGMKGERRRGKGHDGLYQGLSTATKDTYDALHMQALPPR |
| SEQ ID NO: 75 | Full CAR DNA sequence | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGTACGACGATTGGTACCTGGACTACTGGGGACAGGGCAC TCTCGTGACTGTGTCCTCCGGTGGTGGTGGATCGGGGGGTGGT GGTTCGGGCGGAGGAGGATCTGGAGGAGGAGGGTCGGACATTC AAATGACTCAGTCCCCGTCCTCCCTCTCCGCCTCCGTGGGAGA TCGCGTCACGATCACGTGCAGGGCCAGCCAGAGCATCTCCAGC TACCTGAACTGGTACCAGCAGAAGCCAGGGAAGGCACCGAAGC TCCTGATCTACGCCGCTAGCTCGCTGCAGTCCGGCGTCCCTTC ACGGTTCTCGGGATCGGGCTCAGGCACCGACTTCACCCTGACC ATTAGCAGCCTGCAGCCGGAGGACTTCGCGACATACTACTGTC AGCAGTCATACTCCACCCCTCTGACCTTCGGCCAAGGGACCAA AGTGGAGATCAAGACCACTACCCCAGCACCGAGGCCACCCACC CCGGCTCCTACCATCGCCTCCCAGCCTCTGTCCCTGCGTCCGG AGGCATGTAGACCCGCAGCTGGTGGGGCCGTGCATACCCGGGG TCTTGACTTCGCCTGCGATATCTACATTTGGGCCCCTCTGGCT GGTACTTGCGGGGTCCTGCTGCTTTCACTCGTGATCACTCTTT ACTGTAAGCGCGGTCGGAAGAAGCTGCTGTACATCTTTAAGCA ACCCTTCATGAGGCCTGTGCAGACTACTCAAGAGGAGGACGGC TGTTCATGCCGGTTCCCAGAGGAGGAGGAAGGCGGCTGCGAAC TGCGCGTGAAATTCAGCCGCAGCGCAGATGCTCCAGCCTACCA GCAGGGGCAGAACCAGCTCTACAACGAACTCAATCTTGGTCGG AGAGAGGAGTACGACGTGCTGGACAAGCGGAGAGGACGGGACC CAGAAATGGGCGGGAAGCCGCGCAGAAAGAATCCCCAAGAGGG CCTGTACAACGAGCTCCAAAAGGATAAGATGGCAGAAGCCTAT AGCGAGATTGGTATGAAAGGGGAACGCAGAAGAGGCAAAGGCC ACGACGGACTGTACCAGGGACTCAGCACCGCCACCAAGGACAC CTATGACGCTCTTCACATGCAGGCCCTGCCGCCTCGG |
| R1G5 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 76 | HCDR3 (Kabat) | REWWGESWLFDY |
| SEQ ID NO: 47 | HCDR1 (Chothia) | GFTFSSY |
| SEQ ID NO: 48 | HCDR2 (Chothia) | SGSGGS |
| SEQ ID NO: 76 | HCDR3 (Chothia) | REWWGESWLFDY |
| SEQ ID NO: 49 | HCDR1 (IMGT) | GFTFSSYA |

TABLE 3-continued

Amino acid and nucleic acid sequences of exemplary PALLAS-derived anti-BCMA molecules

| SEQ ID NO | Name/ Description | Sequence |
|---|---|---|
| SEQ ID NO: 50 | HCDR2 (IMGT) | ISGSGGST |
| SEQ ID NO: 77 | HCDR3 (IMGT) | ARREWWGESWLFDY |
| SEQ ID NO: 78 | VH | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWGESWLFDYWGQGTLVTVSS |
| SEQ ID NO: 79 | DNA VH | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGGGAGAAAGCTGGCTGTTCGACTACTGGGGACAGGGCAC TCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKA PKLLIYAASSLQSGVPSRFSGSGSGTDFTLTISSLQPEDFATY YCQQSYSTPLTFGQGTKVEIK |
| SEQ ID NO: 62 | DNA VL | GACATTCAAATGACTCAGTCCCCGTCCTCCCTCTCCGCCTCCG TGGGAGATCGCGTCACGATCACGTGCAGGGCCAGCCAGAGCAT CTCCAGCTACCTGAACTGGTACCAGCAGAAGCCAGGGAAGGCA CCGAAGCTCCTGATCTACGCCGCTAGCTCGCTGCAGTCCGGCG TCCCTTCACGGTTCTCGGGATCGGGCTCAGGCACCGACTTCAC CCTGACCATTAGCAGCCTGCAGCCGGAGGACTTCGCGACATAC TACTGTCAGCAGTCATACTCCACCCCTCTGACCTTCGGCCAAG GGACCAAAGTGGAGATCAAG |
| SEQ ID NO: 63 | Linker | GGGGSGGGGSGGGGSGGGGS |
| SEQ ID NO: 80 | scFv (VH-linker-VL) | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWGESWLFDYWGQGTLVTVSSGGGGSGGG GSGGGGSGGGGSDIQMTQSPSSLSASVGDRVTITCRASQSISS YLNWYQQKPGKAPKLLIYAASSLQSGVPSRFSGSGSGTDFTLT ISSLQPEDFATYYCQQSYSTPLTFGQGTKVEIK |
| SEQ ID NO: 81 | DNA scFv | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG |

TABLE 3-continued

| Amino acid and nucleic acid sequences of exemplary PALLAS-derived anti-BCMA molecules | | |
|---|---|---|
| SEQ ID NO | Name/ Description | Sequence |
| | | GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGGGAGAAAGCTGGCTGTTCGACTACTGGGGACAGGGCAC TCTCGTGACTGTGTCCTCCGGTGGTGGTGGATCGGGGGGTGGT GGTTCGGGCGGAGGAGGATCTGGAGGAGGAGGGTCGGACATTC AAATGACTCAGTCCCCGTCCTCCCTCTCCGCCTCCGTGGGAGA TCGCGTCACGATCACGTGCAGGGCCAGCCAGAGCATCTCCAGC TACCTGAACTGGTACCAGCAGAAGCCAGGGAAGGCACCGAAGC TCCTGATCTACGCCGCTAGCTCGCTGCAGTCCGGCGTCCCTTC ACGGTTCTCGGGATCGGGCTCAGGCACCGACTTCACCCTGACC ATTAGCAGCCTGCAGCCGGAGGACTTCGCGACATACTACTGTC AGCAGTCATACTCCACCCCTCTGACCTTCGGCCAAGGGACCAA AGTGGAGATCAAG |
| SEQ ID NO: 82 | Full CAR amino acid sequence | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARREWWGESWLFDYWGQGTLVTVSSGGGGSGGG GSGGGGSGGGGSDIQMTQSPSSLSASVGDRVTITCRASQSISS YLNWYQQKPGKAPKLLIYAASSLQSGVPSRFSGSGSGTDFTLT ISSLQPEDFATYYCQQSYSTPLTFGQGTKVEIKTTTPAPRPPT PAPTIASQPLSLRPEACRPAAGGAVHTRGLDFACDIYIWAPLA GTCGVLLLSLVITLYCKRGRKKLLYIFKQPFMRPVQTTQEEDG CSCRFPEEEEGGCELRVKFSRSADAPAYQQGQNQLYNELNLGR REEYDVLDKRRGRDPEMGGKPRRKNPQEGLYNELQKDKMAEAY SEIGMKGERRRGKGHDGLYQGLSTATKDTYDALHMQALPPR |
| SEQ ID NO: 83 | Full CAR DNA sequence | GAAGTGCAGTTGCTGGAGTCAGGCGGAGGACTGGTGCAGCCCG GAGGATCGCTTCGCTTGAGCTGCGCAGCCTCAGGCTTTACCTT CTCCTCCTACGCCATGTCCTGGGTCAGACAGGCTCCCGGGAAG GGACTGGAATGGGTGTCCGCCATTAGCGGTTCCGGCGGAAGCA CTTACTATGCCGACTCTGTGAAGGGCCGCTTCACTATCTCCCG GGACAACTCCAAGAACACCCTGTATCTCCAAATGAATTCCCTG AGGGCCGAAGATACCGCGGTGTACTACTGCGCTAGACGGGAGT GGTGGGGAGAAAGCTGGCTGTTCGACTACTGGGGACAGGGCAC TCTCGTGACTGTGTCCTCCGGTGGTGGTGGATCGGGGGGTGGT GGTTCGGGCGGAGGAGGATCTGGAGGAGGAGGGTCGGACATTC AAATGACTCAGTCCCCGTCCTCCCTCTCCGCCTCCGTGGGAGA TCGCGTCACGATCACGTGCAGGGCCAGCCAGAGCATCTCCAGC TACCTGAACTGGTACCAGCAGAAGCCAGGGAAGGCACCGAAGC TCCTGATCTACGCCGCTAGCTCGCTGCAGTCCGGCGTCCCTTC ACGGTTCTCGGGATCGGGCTCAGGCACCGACTTCACCCTGACC ATTAGCAGCCTGCAGCCGGAGGACTTCGCGACATACTACTGTC AGCAGTCATACTCCACCCCTCTGACCTTCGGCCAAGGGACCAA AGTGGAGATCAAGACCACTACCCCAGCACCGAGGCCACCCACC CCGGCTCCTACCATCGCCTCCCAGCCTCTGTCCCTGCGTCCGG AGGCATGTAGACCCGCAGCTGGTGGGGCCGTGCATACCCGGGG TCTTGACTTCGCCTGCGATATCTACATTTGGGCCCCTCTGGCT GGTACTTGCGGGGTCCTGCTGCTTTCACTCGTGATCACTCTTT ACTGTAAGCGCGGTCGGAAGAAGCTGCTGTACATCTTTAAGCA ACCCTTCATGAGGCCTGTGCAGACTACTCAAGAGGAGGACGGC TGTTCATGCCGGTTCCCAGAGGAGGAGGAAGGCGGCTGCGAAC TGCGCGTGAAATTCAGCCGCAGCGCAGATGCTCCAGCCTACCA GCAGGGGCAGAACCAGCTCTACAACGAACTCAATCTTGGTCGG AGAGAGGAGTACGACGTGCTGGACAAGCGGAGAGGACGGGACC CAGAAATGGGCGGGAAGCCGCGCAGAAAGAATCCCCAAGAGGG CCTGTACAACGAGCTCCAAAAGGATAAGATGGCAGAAGCCTAT AGCGAGATTGGTATGAAAGGGGAACGCAGAAGAGGCAAAGGCC ACGACGGACTGTACCAGGGACTCAGCACCGCCACCAAGGACAC CTATGACGCTCTTCACATGCAGGCCCTGCCGCCTCGG |

TABLE 4

| Kabat CDRs of exemplary PALLAS-derived anti-BCMA molecules | | | | | | |
|---|---|---|---|---|---|---|
| Kubat | HCDR1 | HCDR2 | HCDR3 | LCDR1 | LCDR2 | LCDR3 |
| R1B6 | SYAMS (SEQ ID NO: 44) | AISGSGGST YYADSVKG (SEQ ID NO: 45) | REWVPYD VSWYFDY (SEQ ID NO: 46) | RASQSISS YLN (SEQ ID NO: 54) | AASSLQS (SEQ ID NO: 55) | QQSYSTP LT (SEQ ID NO: 56) |
| R1F2 | SYAMS (SEQ ID NO: 44) | AISGSGGST YYADSVKG (SEQ ID NO: 45) | REWWYDD WYLDY (SEQ ID NO: 68) | RASQSISS YLN (SEQ ID NO: 54) | AASSLQS (SEQ ID NO: 55) | QQSYSTP LT (SEQ ID NO: 56) |
| R1G5 | SYAMS (SEQ ID NO: 44) | AISGSGGST YYADSVKG (SEQ ID NO: 45) | REWWGES WLFDY (SEQ ID NO: 76) | RASQSISS YLN (SEQ ID NO: 54) | AASSLQS (SEQ ID NO: 55) | QQSYSTP LT (SEQ ID NO: 56) |
| Consensus | SYAMS (SEQ ID NO: 44) | AISGSGGST YYADSVKG (SEQ ID NO: 45) | REW$X_1X_2$ $X_3X_4X_5$ $X_6$W$X_7X_8$ DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 84) | RASQSISS YLN (SEQ ID NO: 54) | AASSLQS (SEQ ID NO: 55) | QQSYSTP LT (SEQ ID NO: 56) |

TABLE 5

| Chothia CDRs of exemplary PALLAS-derived anti-BCMA molecules | | | | | | |
|---|---|---|---|---|---|---|
| Chothia | HCDR1 | HCDR2 | HCDR3 | LCDR1 | LCDR2 | LCDR3 |
| R1B6 | GFTFSSY (SEQ ID NO: 47) | SGSGGS (SEQ ID NO: 48) | REWVPYDVS WYFDY (SEQ ID NO: 46) | SQSISSY (SEQ ID NO: 57) | AAS (SEQ ID NO: 58) | SYSTPL (SEQ ID NO: 59) |
| R1F2 | GFTFSSY (SEQ ID NO: 47) | SGSGGS (SEQ ID NO: 48) | REWWYDD WYLDY (SEQ ID NO: 68) | SQSISSY (SEQ ID NO: 57) | AAS (SEQ ID NO: 58) | SYSTPL (SEQ ID NO: 59) |
| RIG5 | GFTFSSY (SEQ ID NO: 47) | SGSGGS (SEQ ID NO: 48) | REWWGESW LFDY (SEQ ID NO: 76) | SQSISSY (SEQ ID NO: 57) | AAS (SEQ ID NO: 58) | SYSTPL (SEQ ID NO: 59) |
| Consensus | GFTFSSY (SEQ ID NO: 47) | SGSGGS (SEQ ID NO: 48) | REW$X_1X_2X_3$ $X_4X_5X_6$W$X_7$ $X_8$DY, wherein $X_1$ is absent or V; $X_2$ | SQSISSY (SEQ ID NO: 57) | AAS (SEQ ID NO: 58) | SYSTPL (SEQ ID NO: 59) |

TABLE 5-continued

Chothia CDRs of exemplary PALLAS-derived anti-BCMA molecules

| Chothia | HCDR1 | HCDR2 | HCDR3 | LCDR1 | LCDR2 | LCDR3 |
|---|---|---|---|---|---|---|
| | | | is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 84) | | | |

TABLE 6

IMGT CDRs of exemplary PALLAS-derived anti-BCMA molecules

| IMGT | HCDR1 | HCDR2 | HCDR3 | LCDR1 | LCDR2 | LCDR3 |
|---|---|---|---|---|---|---|
| R1B6 | GFTFSSYA (SEQ ID NO: 49) | ISGSGGST (SEQ ID NO: 50) | ARREWVPYDVSWYFDY (SEQ ID NO: 51) | QSISSY (SEQ ID NO: 60) | AAS (SEQ ID NO: 58) | QQSYSTPLT (SEQ ID NO: 56) |
| R1F2 | GFTFSSYA (SEQ ID NO: 49) | ISGSGGST (SEQ ID NO: 50) | ARREWWYDDWYLDY (SEQ ID NO: 69) | QSISSY (SEQ ID NO: 60) | AAS (SEQ ID NO: 58) | QQSYSTPLT (SEQ ID NO: 56) |
| RIGS | GFTFSSYA (SEQ ID NO: 49) | ISGSGGST (SEQ ID NO: 50) | ARREWWGESWLFDY (SEQ ID NO: 77) | QSISSY (SEQ ID NO: 60) | AAS (SEQ ID NO: 58) | QQSYSTPLT (SEQ ID NO: 56) |
| Consensus | GFTFSSYA (SEQ ID NO: 49) | ISGSGGST (SEQ ID NO: 50) | ARREW$X_1X_2X_3X_4X_5X_6$W$X_7X_8$DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 85) | QSISSY (SEQ ID NO: 60) | AAS (SEQ ID NO: 58) | QQSYSTPLT (SEQ ID NO: 56) |

TABLE 7

Amino acid and nucleic acid sequences of exemplary B cell-derived anti-BCMA molecules

| SEQ ID NO | Name/ Description | Sequence |
|---|---|---|
| PI61 | | |
| SEQ ID NO: 86 | HCDR1 (Kabat) | SYGMH |
| SEQ ID NO: 87 | HCDR2 (Kabat) | VISYDGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 89 | HCDR2 (Chothia) | SYDGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 91 | HCDR2 (IMGT) | ISYDGSNK |
| SEQ ID NO: 92 | HCDR3 (IMGT) | GGSGYALHDDYYGLDV |
| SEQ ID NO: 93 | VH | QVQLQESGGGVVQPGRSLRLSCAASGFTFSSYGMHWVRQAPGKG LEWVAVISYDGSNKYYADSVKGRFTISRDNSKNTLYLQMNSLRA EDTAVYYCGGSGYALHDDYYGLDVWGQGTLVTVSS |
| SEQ ID NO: 94 | DNA VH | CAAGTGCAGCTGCAGGAATCCGGTGGCGGAGTCGTGCAGCCTGG AAGGAGCCTGAGACTCTCATGCGCCGCGTCAGGGTTCACCTTTT CCTCCTACGGGATGCATTGGGTCAGACAGGCCCCCGGAAAGGGA CTCGAATGGGTGGCTGTGATCAGCTACGACGGCTCCAACAAGTA CTACGCCGACTCCGTGAAAGGCCGGTTCACTATCTCCCGGGACA ACTCCAAGAACACGCTGTATCTGCAAATGAATTCACTGCGCGCG GAGGATACCGCTGTGTACTACTGCGGTGGCTCCGGTTACGCCCT GCACGATGACTATTACGGCCTTGACGTCTGGGGCCAGGGAACCC TCGTGACTGTGTCCAGC |
| SEQ ID NO: 95 | LCDR1 (Kabat) | TGTSSDVGGYNYVS |
| SEQ ID NO: 96 | LCDR2 (Kabat) | DVSNRPS |
| SEQ ID NO: 97 | LCDR3 (Kabat) | SSYTSSSTLYV |
| SEQ ID NO: 98 | LCDR1 (Chothia) | TSSDVGGYNY |
| SEQ ID NO: 99 | LCDR2 (Chothia) | DVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 99 | LCDR2 (IMGT) | DVS |
| SEQ ID NO: 97 | LCDR3 (IMGT) | SSYTSSSTLYV |
| SEQ ID NO: 102 | VL | QSALTQPASVSGSPGQSITISCTGTSSDVGGYNYVSWYQQHPGK APKLMIYDVSNRPSGVSNRFSGSKSGNTASLTISGLQAEDEADY YCSSYTSSSTLYVFGSGTKVTVL |

TABLE 7-continued

Amino acid and nucleic acid sequences of exemplary B cell-derived anti-BCMA molecules

| SEQ ID NO | Name/ Description | Sequence |
|---|---|---|
| SEQ ID NO: 103 | DNA VL | CAGAGCGCACTGACTCAGCCGGCATCCGTGTCCGGTAGCCCCGG<br>ACAGTCGATTACCATCTCCTGTACCGGCACCTCCTCCGACGTGG<br>GAGGGTACAACTACGTGTCGTGGTACCAGCAGCACCCAGGAAAG<br>GCCCCTAAGTTGATGATCTACGATGTGTCAAACCGCCCGTCTGG<br>AGTCTCCAACCGGTTCTCCGGCTCCAAGTCCGGCAACACCGCCA<br>GCCTGACCATTAGCGGGCTGCAAGCCGAGGATGAGGCCGACTAC<br>TACTGCTCGAGCTACACATCCTCGAGCACCCTCTACGTGTTCGG<br>CTCGGGGACTAAGGTCACCGTGCTG |
| SEQ ID NO: 104 | Linker | GGGGSGGGGSGGGGS |
| SEQ ID NO: 105 | scFv (VH-linker-VL) | QVQLQESGGGVVQPGRSLRLSCAASGFTFSSYGMHWVRQAPGKG<br>LEWVAVISYDGSNKYYADSVKGRFTISRDNSKNTLYLQMNSLRA<br>EDTAVYYCGGSGYALHDDYYGLDVWGQGTLVTVSSGGGGSGGGG<br>SGGGGSQSALTQPASVSGSPGQSITISCTGTSSDVGGYNYVSWY<br>QQHPGKAPKLMIYDVSNRPSGVSNRFSGSKSGNTASLTISGLQA<br>EDEADYYCSSYTSSSTLYVFGSGTKVTVL |
| SEQ ID NO: 106 | DNA scFv | CAAGTGCAGCTGCAGGAATCCGGTGGCGGAGTCGTGCAGCCTGG<br>AAGGAGCCTGAGACTCTCATGCGCCGCGTCAGGGTTCACCTTTT<br>CCTCCTACGGGATGCATTGGGTCAGACAGGCCCCCGGAAAGGGA<br>CTCGAATGGGTGGCTGTGATCAGCTACGACGGCTCCAACAAGTA<br>CTACGCCGACTCCGTGAAAGGCCGGTTCACTATCTCCCGGGACA<br>ACTCCAAGAACACGCTGTATCTGCAAATGAATTCACTGCGCGCG<br>GAGGATACCGCTGTGTACTACTGCGGTGGCTCCGGTTACGCCCT<br>GCACGATGACTATTACGGCCTTGACGTCTGGGGCCAGGGAACCC<br>TCGTGACTGTGTCCAGCGGTGGAGGAGGTTCGGGCGGAGGAGGA<br>TCAGGAGGGGGTGGATCGCAGAGCGCACTGACTCAGCCGGCATC<br>CGTGTCCGGTAGCCCCGGACAGTCGATTACCATCTCCTGTACCG<br>GCACCTCCTCCGACGTGGGAGGGTACAACTACGTGTCGTGGTAC<br>CAGCAGCACCCAGGAAAGGCCCCTAAGTTGATGATCTACGATGT<br>GTCAAACCGCCCGTCTGGAGTCTCCAACCGGTTCTCCGGCTCCA<br>AGTCCGGCAACACCGCCAGCCTGACCATTAGCGGGCTGCAAGCC<br>GAGGATGAGGCCGACTACTACTGCTCGAGCTACACATCCTCGAG<br>CACCCTCTACGTGTTCGGCTCGGGGACTAAGGTCACCGTGCTG |
| SEQ ID NO: 107 | Full CAR amino acid sequence | QVQLQESGGGVVQPGRSLRLSCAASGFTFSSYGMHWVRQAPGKG<br>LEWVAVISYDGSNKYYADSVKGRFTISRDNSKNTLYLQMNSLRA<br>EDTAVYYCGGSGYALHDDYYGLDVWGQGTLVTVSSGGGGSGGGG<br>SGGGGSQSALTQPASVSGSPGQSITISCTGTSSDVGGYNYVSWY<br>QQHPGKAPKLMIYDVSNRPSGVSNRFSGSKSGNTASLTISGLQA<br>EDEADYYCSSYTSSSTLYVFGSGTKVTVLTTTPAPRPPTPAPTI<br>ASQPLSLRPEACRPAAGGAVHTRGLDFACDIYIWAPLAGTCGVL<br>LLSLVITLYCKRGRKKLLYIFKQPFMRPVQTTQEEDGCSCRFPE<br>EEEGGCELRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 108 | Full CAR DNA sequence | CAAGTGCAGCTGCAGGAATCCGGTGGCGGAGTCGTGCAGCCTGG<br>AAGGAGCCTGAGACTCTCATGCGCCGCGTCAGGGTTCACCTTTT<br>CCTCCTACGGGATGCATTGGGTCAGACAGGCCCCCGGAAAGGGA<br>CTCGAATGGGTGGCTGTGATCAGCTACGACGGCTCCAACAAGTA<br>CTACGCCGACTCCGTGAAAGGCCGGTTCACTATCTCCCGGGACA<br>ACTCCAAGAACACGCTGTATCTGCAAATGAATTCACTGCGCGCG<br>GAGGATACCGCTGTGTACTACTGCGGTGGCTCCGGTTACGCCCT<br>GCACGATGACTATTACGGCCTTGACGTCTGGGGCCAGGGAACCC<br>TCGTGACTGTGTCCAGCGGTGGAGGAGGTTCGGGCGGAGGAGGA<br>TCAGGAGGGGGTGGATCGCAGAGCGCACTGACTCAGCCGGCATC<br>CGTGTCCGGTAGCCCCGGACAGTCGATTACCATCTCCTGTACCG<br>GCACCTCCTCCGACGTGGGAGGGTACAACTACGTGTCGTGGTAC<br>CAGCAGCACCCAGGAAAGGCCCCTAAGTTGATGATCTACGATGT<br>GTCAAACCGCCCGTCTGGAGTCTCCAACCGGTTCTCCGGCTCCA<br>AGTCCGGCAACACCGCCAGCCTGACCATTAGCGGGCTGCAAGCC<br>GAGGATGAGGCCGACTACTACTGCTCGAGCTACACATCCTCGAG<br>CACCCTCTACGTGTTCGGCTCGGGGACTAAGGTCACCGTGCTGA<br>CCACTACCCCAGCACCGAGGCCACCCACCCCGGCTCCTACCATC<br>GCCTCCCAGCCTCTGTCCCTGCGTCCGGAGGCATGTAGACCCGC<br>AGCTGGTGGGGCCGTGCATACCCGGGGTCTTGACTTCGCCTGCG<br>ATATCTACATTTGGGCCCCTCTGGCTGGTACTTGCGGGGTCCTG<br>CTGCTTTCACTCGTGATCACTCTTTACTGTAAGCGCGGTCGGAA<br>GAAGCTGCTGTACATCTTTAAGCAACCCTTCATGAGGCCTGTGC<br>AGACTACTCAAGAGGAGGACGGCTGTTCATGCCGGTTCCCAGAG<br>GAGGAGGAAGGCGGCTGCGAACTGCGCGTGAAATTCAGCCGCAG |

TABLE 7-continued

Amino acid and nucleic acid sequences of exemplary B cell-derived anti-BCMA molecules

| SEQ ID NO | Name/ Description | Sequence |
|---|---|---|
| | | CGCAGATGCTCCAGCCTACCAGCAGGGGCAGAACCAGCTCTACAACGAACTCAATCTTGGTCGGAGAGAGGAGTACGACGTGCTGGACAAGCGGAGAGGACGGGACCCAGAAATGGGCGGGAAGCCGCGCAGAAAGAATCCCCAAGAGGGCCTGTACAACGAGCTCCAAAAGGATAAGATGGCAGAAGCCTATAGCGAGATTGGTATGAAAGGGGAACGCAGAAGAGGCAAAGGCCACGACGGACTGTACCAGGGACTCAGCACCGCCACCAAGGACACCTATGACGCTCTTCACATGCAGGCCCTGCCGCCTCGG |
| B61-02 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKGLEWVAVISYKGSNKYYADSVKGRFTISRDNSKNTLYLQMNSLRAEDTAVYYCGGSGYALHDDYYGLDVWGQGTLVTVSS |
| SEQ ID NO: 113 | DNA VH | CAAGTGCAGCTTGTCGAATCGGGAGGCGGAGTGGTGCAGCCTGGACGATCGCTCCGGCTCTCATGTGCCGCGAGCGGATTCACCTTCTCGAGCTACGGCATGCACTGGGTCAGACAAGCCCCAGGAAAGGGCCTGGAATGGGTGGCTGTCATCTCGTACAAGGGCTCAAACAAGTACTACGCCGACTCCGTGAAGGGCCGGTTCACCATCTCCCGCGATAACTCCAAGAATACCCTCTATCTGCAAATGAACAGCCTGAGGGCCGAGGATACTGCAGTGTACTACTGCGGGGGTTCAGGCTACGCGCTGCACGACGACTACTACGGATTGGACGTCTGGGGCCAAGGAACTCTTGTGACCGTGTCCTCT |
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 115 | LCDR3 (Kabat) | SSYTSSSALYV |
| SEQ ID NO: 98 | LCDR1 (Chothia) | TSSDVGGYNY |
| SEQ ID NO: 116 | LCDR2 (Chothia) | EVS |
| SEQ ID NO: 117 | LCDR3 (Chothia) | YTSSSALY |
| SEQ ID NO: 101 | LCDR1 (IMGT) | SSDVGGYNY |

TABLE 7-continued

Amino acid and nucleic acid sequences of exemplary B cell-derived anti-BCMA molecules

| SEQ ID NO | Name/ Description | Sequence |
|---|---|---|
| SEQ ID NO: 116 | LCDR2 (IMGT) | EVS |
| SEQ ID NO: 115 | LCDR3 (IMGT) | SSYTSSSALYV |
| SEQ ID NO: 118 | VL | QSALTQPASVSGSPGQSITISCTGTSSDVGGYNYVSWYQQHPGK APKLMIYEVSNRLRGVSNRFSGSKSGNTASLTISGLQAEDEADY YCSSYTSSSALYVFGSGTKVTVL |
| SEQ ID NO: 119 | DNA VL | CAGAGCGCGCTGACTCAGCCTGCCTCCGTGAGCGGTTCGCCGGG ACAGTCCATTACCATTTCGTGCACCGGGACCTCCTCCGACGTGG GAGGCTACAACTACGTGTCCTGGTACCAGCAGCATCCCGGAAAG GCCCCGAAGCTGATGATCTACGAAGTGTCGAACAGACTGCGGGG AGTCTCCAACCGCTTTTCCGGGTCCAAGTCCGGCAACACCGCCA GCCTGACCATCAGCGGGCTCCAGGCAGAAGATGAGGCTGACTAT TACTGCTCCTCCTACACGTCAAGCTCCGCCCTCTACGTGTTCGG GTCCGGGACCAAAGTCACTGTGCTG |
| SEQ ID NO: 63 | Linker | GGGGSGGGGSGGGGSGGGGS |
| SEQ ID NO: 120 | scFv (VH-linker-VL) | QVQLVESGGGVVQPGRSLRLSCAASGFTFSSYGMHWVRQAPGKG LEWVAVISYKGSNKYYADSVKGRFTISRDNSKNTLYLQMNSLRA EDTAVYYCGGSGYALHDDYYGLDVWGQGTLVTVSSGGGGSGGGG SGGGGSGGGGSQSALTQPASVSGSPGQSITISCTGTSSDVGGYN YVSWYQQHPGKAPKLMIYEVSNRLRGVSNRFSGSKSGNTASLTI SGLQAEDEADYYCSSYTSSSALYVFGSGTKVTVL |
| SEQ ID NO: 121 | DNA scFv | CAAGTGCAGCTTGTCGAATCGGGAGGCGGAGTGGTGCAGCCTGG ACGATCGCTCCGGCTCTCATGTGCCGCGAGCGGATTCACCTTCT CGAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGCT GACTCAGCCTGCCTCCGTGAGCGGTTCGCCGGGACAGTCCATTA CCATTTCGTGCACCGGGACCTCCTCCGACGTGGGAGGCTACAAC TACGTGTCCTGGTACCAGCAGCATCCCGGAAAGGCCCCGAAGCT GATGATCTACGAAGTGTCGAACAGACTGCGGGGAGTCTCCAACC GCTTTTCCGGGTCCAAGTCCGGCAACACCGCCAGCCTGACCATC AGCGGGCTCCAGGCAGAAGATGAGGCTGACTATTACTGCTCCTC CTACACGTCAAGCTCCGCCCTCTACGTGTTCGGGTCCGGGACCA AAGTCACTGTGCTG |
| SEQ ID NO: 122 | Full CAR amino acid sequence | QVQLVESGGGVVQPGRSLRLSCAASGFTFSSYGMHWVRQAPGKG LEWVAVISYKGSNKYYADSVKGRFTISRDNSKNTLYLQMNSLRA EDTAVYYCGGSGYALHDDYYGLDVWGQGTLVTVSSGGGGSGGGG SGGGGSGGGGSQSALTQPASVSGSPGQSITISCTGTSSDVGGYN YVSWYQQHPGKAPKLMIYEVSNRLRGVSNRFSGSKSGNTASLTI SGLQAEDEADYYCSSYTSSSALYVFGSGTKVTVLTTTPAPRPPT PAPTIASQPLSLRPEACRPAAGGAVHTRGLDFACDIYIWAPLAG TCGVLLLSLVITLYCKRGRKKLLYIFKQPFMRPVQTTQEEDGCS CRFPEEEEGGCELRVKFSRSADAPAYQQGQNQLYNELNLGRREE YDVLDKRRGRDPEMGGKPRRKNPQEGLYNELQKDKMAEAYSEIG MKGERRRGKGHDGLYQGLSTATKDTYDALHMQALPPR |
| SEQ ID NO: 123 | Full CAR DNA sequence | CAAGTGCAGCTTGTCGAATCGGGAGGCGGAGTGGTGCAGCCTGG ACGATCGCTCCGGCTCTCATGTGCCGCGAGCGGATTCACCTTCT CGAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGCT GACTCAGCCTGCCTCCGTGAGCGGTTCGCCGGGACAGTCCATTA CCATTTCGTGCACCGGGACCTCCTCCGACGTGGGAGGCTACAAC TACGTGTCCTGGTACCAGCAGCATCCCGGAAAGGCCCCGAAGCT |

TABLE 7-continued

Amino acid and nucleic acid sequences of exemplary B cell-derived anti-BCMA molecules

| SEQ ID NO | Name/ Description | Sequence |
| --- | --- | --- |
| | | GATGATCTACGAAGTGTCGAACAGACTGCGGGGAGTCTCCAACC GCTTTTCCGGGTCCAAGTCCGGCAACACCGCCAGCCTGACCATC AGCGGGCTCCAGGCAGAAGATGAGGCTGACTATTACTGCTCCTC CTACACGTCAAGCTCCGCCCTCTACGTGTTCGGGTCCGGGACCA AAGTCACTGTGCTGACCACTACCCCAGCACCGAGGCCACCCACC CCGGCTCCTACCATCGCCTCCCAGCCTCTGTCCCTGCGTCCGGA GGCATGTAGACCCGCAGCTGGTGGGGCCGTGCATACCCGGGGTC TTGACTTCGCCTGCGATATCTACATTTGGGCCCCTCTGGCTGGT ACTTGCGGGGTCCTGCTGCTTTCACTCGTGATCACTCTTTACTG TAAGCGCGGTCGGAAGAAGCTGCTGTACATCTTTAAGCAACCCT TCATGAGGCCTGTGCAGACTACTCAAGAGGAGGACGGCTGTTCA TGCCGGTTCCCAGAGGAGGAGGAAGGCGGCTGCGAACTGCGCGT GAAATTCAGCCGCAGCGCAGATGCTCCAGCCTACCAGCAGGGGC AGAACCAGCTCTACAACGAACTCAATCTTGGTCGGAGAGAGGAG TACGACGTGCTGGACAAGCGGAGAGGACGGGACCCAGAAATGGG CGGGAAGCCGCGCAGAAAGAATCCCCAAGAGGGCCTGTACAACG AGCTCCAAAAGGATAAGATGGCAGAAGCCTATAGCGAGATTGGT ATGAAAGGGGAACGCAGAAGAGGCAAAGGCCACGACGGACTGTA CCAGGGACTCAGCACCGCCACCAAGGACACCTATGACGCTCTTC ACATGCAGGCCCTGCCGCCTCGG |
| B61-10 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKG LEWVAVISYKGSNKYYADSVKGRFTISRDNSKNTLYLQMNSLRA EDTAVYYCGGSGYALHDDYYGLDVWGQGTLVTVSS |
| SEQ ID NO: 113 | DNA VH | CAAGTGCAGCTTGTCGAATCGGGAGGCGGAGTGGTGCAGCCTGG ACGATCGCTCCGGCTCTCATGTGCCGCGAGCGGATTCACCTTCT CGAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCT |
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 97 | LCDR3 (Kabat) | SSYTSSSTLYV |

TABLE 7-continued

Amino acid and nucleic acid sequences of exemplary B cell-derived anti-BCMA molecules

| SEQ ID NO | Name/ Description | Sequence |
|---|---|---|
| SEQ ID NO: 98 | LCDR1 (Chothia) | TSSDVGGYNY |
| SEQ ID NO: 116 | LCDR2 (Chothia) | EVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 116 | LCDR2 (IMGT) | EVS |
| SEQ ID NO: 97 | LCDR3 (IMGT) | SSYTSSSTLYV |
| SEQ ID NO: 124 | VL | QSALTQPASVSGSPGQSITISCTGTSSDVGGYNYVSWYQQHPGK APKLMIYEVSNRLRGVSNRFSGSKSGNTASLTISGLQAEDEADY YCSSYTSSSTLYVFGSGTKVTVL |
| SEQ ID NO: 125 | DNA VL | CAGAGCGCGCTGACTCAGCCTGCCTCCGTGAGCGGTTCGCCGGG ACAGTCCATTACCATTTCGTGCACCGGGACCTCCTCCGACGTGG GAGGCTACAACTACGTGTCCTGGTACCAGCAGCATCCCGGAAAG GCCCCGAAGCTGATGATCTACGAAGTGTCGAACAGACTGCGGGG AGTCTCCAACCGCTTTTCCGGGTCCAAGTCCGGCAACACCGCCA GCCTGACCATCAGCGGGCTCCAGGCAGAAGATGAGGCTGACTAT TACTGCTCCTCCTACACGTCAAGCTCCACCCTCTACGTGTTCGG GTCCGGGACCAAAGTCACTGTGCTG |
| SEQ ID NO: 63 | Linker | GGGGSGGGGSGGGGSGGGGS |
| SEQ ID NO: 126 | scFv (VH-linker-VL) | QVQLVESGGGVVQPGRSLRLSCAASGFTFSSYGMHWVRQAPGKG LEWVAVISYKGSNKYYADSVKGRFTISRDNSKNTLYLQMNSLRA EDTAVYYCGGSGYALHDDYYGLDVWGQGTLVTVSSGGGGSGGGG SGGGGSGGGGSQSALTQPASVSGSPGQSITISCTGTSSDVGGYN YVSWYQQHPGKAPKLMIYEVSNRLRGVSNRFSGSKSGNTASLTI SGLQAEDEADYYCSSYTSSSTLYVFGSGTKVTVL |
| SEQ ID NO: 127 | DNA scFv | CAAGTGCAGCTTGTCGAATCGGGAGGCGGAGTGGTGCAGCCTGG ACGATCGCTCCGGCTCTCATGTGCCGCGAGCGGATTCACCTTCT CGAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGCT GACTCAGCCTGCCTCCGTGAGCGGTTCGCCGGGACAGTCCATTA CCATTTCGTGCACCGGGACCTCCTCCGACGTGGGAGGCTACAAC TACGTGTCCTGGTACCAGCAGCATCCCGGAAAGGCCCCGAAGCT GATGATCTACGAAGTGTCGAACAGACTGCGGGGAGTCTCCAACC GCTTTTCCGGGTCCAAGTCCGGCAACACCGCCAGCCTGACCATC AGCGGGCTCCAGGCAGAAGATGAGGCTGACTATTACTGCTCCTC CTACACGTCAAGCTCCACCCTCTACGTGTTCGGGTCCGGGACCA AAGTCACTGTGCTG |
| SEQ ID NO: 128 | Full CAR amino acid sequence | QVQLVESGGGVVQPGRSLRLSCAASGFTFSSYGMHWVRQAPGKG LEWVAVISYKGSNKYYADSVKGRFTISRDNSKNTLYLQMNSLRA EDTAVYYCGGSGYALHDDYYGLDVWGQGTLVTVSSGGGGSGGGG SGGGGSGGGGSQSALTQPASVSGSPGQSITISCTGTSSDVGGYN YVSWYQQHPGKAPKLMIYEVSNRLRGVSNRFSGSKSGNTASLTI SGLQAEDEADYYCSSYTSSSTLYVFGSGTKVTVLTTTPAPRPPT PAPTIASQPLSLRPEACRPAAGGAVHTRGLDFACDIYIWAPLAG TCGVLLLSLVITLYCKRGRKKLLYIFKQPFMRPVQTTQEEDGCS CRFPEEEEGGCELRVKFSRSADAPAYQQGQNQLYNELNLGRREE YDVLDKRRGRDPEMGGKPRRKNPQEGLYNELQKDKMAEAYSEIG MKGERRRGKGHDGLYQGLSTATKDTYDALHMQALPPR |

TABLE 7-continued

| Amino acid and nucleic acid sequences of exemplary B cell-derived anti-BCMA molecules | | |
|---|---|---|
| SEQ ID NO | Name/ Description | Sequence |
| SEQ ID NO: 129 | Full CAR DNA sequence | CAAGTGCAGCTTGTCGAATCGGGAGGCGGAGTGGTGCAGCCTGG ACGATCGCTCCGGCTCTCATGTGCCGCGAGCGGATTCACCTTCT CGAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGCT GACTCAGCCTGCCTCCGTGAGCGGTTCGCCGGGACAGTCCATTA CCATTTCGTGCACCGGGACCTCCTCCGACGTGGGAGGCTACAAC TACGTGTCCTGGTACCAGCAGCATCCCGGAAAGGCCCCGAAGCT GATGATCTACGAAGTGTCGAACAGACTGCGGGGAGTCTCCAACC GCTTTTCCGGGTCCAAGTCCGGCAACACCGCCAGCCTGACCATC AGCGGGCTCCAGGCAGAAGATGAGGCTGACTATTACTGCTCCTC CTACACGTCAAGCTCCACCCTCTACGTGTTCGGGTCCGGGACCA AAGTCACTGTGCTGACCACTACCCCAGCACCGAGGCCACCCACC CCGGCTCCTACCATCGCCTCCCAGCCTCTGTCCCTGCGTCCGGA GGCATGTAGACCCGCAGCTGGTGGGGCCGTGCATACCCGGGGTC TTGACTTCGCCTGCGATATCTACATTTGGGCCCCTCTGGCTGGT ACTTGCGGGGTCCTGCTGCTTTCACTCGTGATCACTCTTTACTG TAAGCGCGGTCGGAAGAAGCTGCTGTACATCTTTAAGCAACCCT TCATGAGGCCTGTGCAGACTACTCAAGAGGAGGACGGCTGTTCA TGCCGGTTCCCAGAGGAGGAGGAAGGCGGCTGCGAACTGCGCGT GAAATTCAGCCGCAGCGCAGATGCTCCAGCCTACCAGCAGGGGC AGAACCAGCTCTACAACGAACTCAATCTTGGTCGGAGAGAGGAG TACGACGTGCTGGACAAGCGGAGAGGACGGGACCCAGAAATGGG CGGGAAGCCGCGCAGAAAGAATCCCCAAGAGGGCCTGTACAACG AGCTCCAAAAGGATAAGATGGCAGAAGCCTATAGCGAGATTGGT ATGAAAGGGGAACGCAGAAGAGGCAAAGGCCACGACGGACTGTA CCAGGGACTCAGCACCGCCACCAAGGACACCTATGACGCTCTTC ACATGCAGGCCCTGCCGCCTCGG |

TABLE 8

| Kabat CDRs of exemplary B cell-derived anti-BCMA molecules | | | | | | |
|---|---|---|---|---|---|---|
| Kabat | HCDR1 | HCDR2 | HCDR3 | LCDR1 | LCDR2 | LCDR3 |
| PI61 | SYGMH (SEQ ID NO: 86) | VISYDGSNK YYADSVKG (SEQ ID NO: 87) | SGYALHDD YYGLDV (SEQ ID NO: 88) | TGTSSDV GGYNYVS (SEQ ID NO: 95) | DVSNRPS (SEQ ID NO: 96) | SSYTSSS TLYV (SEQ ID NO: 97) |
| B61-02 | SYGMH (SEQ ID NO: 86) | VISYKGSNK YYADSVKG (SEQ ID NO: 109) | SGYALHDD YYGLDV (SEQ ID NO: 88) | TGTSSDV GGYNYVS (SEQ ID NO: 95) | EVSNRLR (SEQ ID NO: 114) | SSYTSSS ALYV (SEQ ID NO: 115) |
| B61-10 | SYGMH (SEQ ID NO: 86) | VISYKGSNK YYADSVKG (SEQ ID NO: 109) | SGYALHDD YYGLDV (SEQ ID NO: 88) | TGTSSDV GGYNYVS (SEQ ID NO: 95) | EVSNRLR (SEQ ID NO: 114) | SSYTSSS TLYV (SEQ ID NO: 97) |
| Consensus | SYGMH (SEQ ID NO: 86) | VISYXGSNK YYADSVKG, wherein X is D or K (SEQ ID NO: 130) | SGYALHDD YYGLDV (SEQ ID NO: 88) | TGTSSDV GGYNYVS (SEQ ID NO: 95) | $X_1VSNRX_2X_3$, wherein $X_1$ is D or E; $X_2$ is P or L; and $X_3$ is S or R (SEQ ID NO: 131) | SSYTSSS XLYV, wherein X is T or A (SEQ ID NO: 132) |

TABLE 9

Chothia CDRs of exemplary B cell-derived anti-BCMA molecules

| Chothia | HCDR1 | HCDR2 | HCDR3 | LCDR1 | LCDR2 | LCDR3 |
|---|---|---|---|---|---|---|
| PI61 | GFTFSSY (SEQ ID NO: 47) | SYDGSN (SEQ ID NO: 89) | SGYALHDDY YGLDV (SEQ ID NO: 88) | TSSDVGG YNY (SEQ ID NO: 98) | DVS (SEQ ID NO: 99) | YTSSSTLY (SEQ ID NO: 100) |
| B61-02 | GFTFSSY (SEQ ID VNO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSAL Y (SEQ ID NO: 117) |
| B61-10 | GFTFSSY V(SEQ ID NO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSTLY (SEQ ID NO: 100) |
| Consensus | GFTFSSY (SEQ ID NO: 47) | SYXGSN, wherein X is D or K (SEQ ID NO: 133) | SGYALHDDY YGLDV (SEQ ID NO: 88) | TSSDVGG YNY (SEQ ID NO: 98) | XVS, wherein X is D or E (SEQ ID NO: 134) | YTSSSXL Y, wherein X is T or A (SEQ ID NO: 135) |

TABLE 10

IMGT CDRs of exemplary B cell-derived anti-BCMA molecules

| IMGT | HCDR1 | HCDR2 | HCDR3 | LCDR1 | LCDR2 | LCDR3 |
|---|---|---|---|---|---|---|
| PI61 | GFTFSSYG (SEQ ID NO: 90) | ISYDGSN K (SEQ ID NO: 91) | GGSGYALHDD YYGLDV (SEQ ID NO: 92) | SSDVGGY NY (SEQ ID NO: 101) | DVS (SEQ ID NO: 99) | SSYTSSSTL YV (SEQ ID NO: 97) |
| B61-02 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSA LYV (SEQ ID NO: 115) |
| B61-10 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSTL YV (SEQ ID NO: 97) |
| Consensus | GFTFSSYG (SEQ ID NO: 90) | ISYXGSN K, wherein X is D or K (SEQ ID NO: 136) | GGSGYALHDD YYGLDV (SEQ ID NO: 92) | SSDVGGY NY (SEQ ID NO: 101) | XVS, wherein X is D or E (SEQ ID NO: 134) | SSYTSSSX LYV, wherein X is T or A (SEQ ID NO: 132) |

TABLE 11

Amino acid and nucleic acid sequences of exemplary anti-BCMA molecules based on PI61

| Identification | Protein sequence | DNA sequence (5'-3') |
|---|---|---|
| Signal peptide | MALPVTALLLPLALLLHAA RP (SEQ ID NO: 1) | Atggccctccctgtcaccgctctgttgctgccgcttgctctgctg ctccacgcagcgcgaccg (SEQ ID NO: 252) |
| ScFv PI61 | QVQLQESGGGVVQPGRSLR LSCAASGFTFSSYGMHWVR QAPGKGLEWVAVISYDGSN KYYADSVKGRFTISRDNSK NTLYLQMNSLRAEDTAVYY CGGSGYALHDDYYGLDVW GQGTLVTVSSGGGGSGGGG SGGGGSQSALTQPASVSGSP GQSITISCTGTSSDVGGYNY VSWYQQHPGKAPKLMIYD VSNRPSGVSNRFSGSKSGNT ASLTISGLQAEDEADYYCSS YTSSSTLYVFGSGTKVTVL (SEQ ID NO: 105) | CaggtacaattgcaggagtctggaggcggtgtgGtgcaacc cggtcgcagcttgcgcctgagttgtGctgcgtctggatttacatt ttcatcttacggaAtgcattgggtacgccaggcaccggggaa aggcCttgaatgggtggctgtaatttcatacgatggtTccaac aaatactatgctgactcagtcaagggtCgatttacaattagtcg ggacaactccaagaacAccctttatcttcaaatgaattcccttag agcaGaggatacggcggtctattactgtggtggcagtGgttat gcacttcatgatgattactatggcttgGatgtctgggggcaagg gacgcttgtaactgtaTcctctggtggtggtggtagtggtggg ggaggcTccggcggtggcggctctcaatctgctctgactCaa ccagcaagcgtatcagggtcaccgggacagAgtattaccata agttgcacggggacctctagcGatgtagggggtataattatg tatcttggtatCaacaacaccccgggaaagcccctaaattgatg AtctacgacgtgagcaatcgacctagtggcgtaTcaaatcgc ttctctggtagcaagagtgggaatAcggcgtcccttactattag |

TABLE 11-continued

Amino acid and nucleic acid sequences of exemplary anti-BCMA molecules based on PI61

| Identification | Protein sequence | DNA sequence (5'-3') |
|---|---|---|
| | | cggattgcaagcaGaagatgaggccgattactactgcagctc<br>ctatActagctcttctacattgtacgtctttgggagcggaacaaa<br>agtaacagtactc (SEQ ID NO: 253) |
| Transmembrane domain and hinge | TTTPAPRPPTPAPTIASQPLS<br>LRPEACRPAAGGAVHTRGL<br>DFACDIYIWAPLAGTCGVLL<br>LSLVITLYC (SEQ ID NO: 202) | AcaacaacacctgccccgagaccgcctacaccaGccccga<br>ctattgccagccagcctctgagcctcAggcctgaggcctgtag<br>gcccgcagcgggcggcGcagttcatacacggggcttggattt<br>cgcttgtGatatttatatttgggctcctttggcggggacaTgtgg<br>cgtgctgcttctgtcacttgttattacactgtactgt (SEQ ID NO: 254) |
| 4-1BB | KRGRKKLLYIFKQPFMRPV<br>QTTQEEDGCSCRFPEEEEGG<br>CEL (SEQ ID NO: 7) | AaacgcgggcgaaaaaaattgctgtatatttttAagcagccat<br>ttatgaggcccgttcagacgacgCaggaggaggacggttgct<br>cttgcaggttcccagaagaggaagaagggggctgtgaattg<br>(SEQ ID NO: 255) |
| CD3zeta | RVKFSRSADAPAYQQGQNQ<br>LYNELNLGRREEYDVLDKR<br>RGRDPEMGGKPRRKNPQEG<br>LYNELQKDKMAEAYSEIGM<br>KGERRRGKGHDGLYQGLST<br>ATKDTYDALHMQALPPR<br>(SEQ ID NO: 10) | CgggttaaattttcaagatccgcagacgctccaGcataccaac<br>agggacaaaaccaactctataacGagctgaatcttggaagaa<br>gggaggaatatgatGtgctggataaacggcgcggtagagatc<br>cggagAtgggcggaaaaccaaggcgaaaaaccctcagG<br>agggactctacaacgaactgcagaaagacaaaAtggcggag<br>gcttattccgaaataggcatgaagGgcgagcggaggcgagg<br>gaaagggcacgacggaCtgtatcaaggcctctcaaccgcga<br>ctaaggatAcgtacgacgccctgcacatgcaggccctgcctc<br>cgaga (SEQ ID NO: 256) |
| PI61 full CAR construct | MALPVTALLLPLALLLHAA<br>RPQVQLQESGGGVVQPGRS<br>LRLSCAASGFTFSSYGMHW<br>VRQAPGKGLEWVAVISYDG<br>SNKYYADSVKGRFTISRDNS<br>KNTLYLQMNSLRAEDTAVY<br>YCGGSGYALHDDYYGLDV<br>WGQGTLVTVSSGGGGSGG<br>GGSGGGGSQSALTQPASVS<br>GSPGQSITISCTGTSSDVGGY<br>NYVSWYQQHPGKAPKLMI<br>YDVSNRPSGVSNRFSGSKSG<br>NTASLTISGLQAEDEADYYC<br>SSYTSSSTLYVFGSGTKVTV<br>LTTTPAPRPPTPAPTIASQPL<br>SLRPEACRPAAGGAVHTRG<br>LDFACDIYIWAPLAGTCGVL<br>LLSLVITLYCKRGRKKLLYI<br>FKQPFMRPVQTTQEEDGCS<br>CRFPEEEEGGCELRVKFSRS<br>ADAPAYQQGQNQLYNELN<br>LGRREEYDVLDKRRGRDPE<br>MGGKPRRKNPQEGLYNELQ<br>KDKMAEAYSEIGMKGERRR<br>GKGHDGLYQGLSTATKDTY<br>DALHMQALPPR (SEQ ID NO: 257) | ATGGCCCTCCCTGTCACCGCTCTGTTG<br>CTGCCGCTTGCTCTGCTGCTCCACGCA<br>GCGCGACCGCAGGTACAATTGCAGGA<br>GTCTGGAGGCGGTGTGGTGCAACCCG<br>GTCGCAGCTTGCGCCTGAGTTGTGCTG<br>CGTCTGGATTTACATTTTCATCTTACGG<br>AATGCATTGGGTACGCCAGGCACCGG<br>GGAAAGGCCTTGAATGGGTGGCTGTA<br>ATTTCATACGATGGTTCCAACAAATAC<br>TATGCTGACTCAGTCAAGGGTCGATTT<br>ACAATTAGTCGGGACAACTCCAAGAA<br>CACCCTTTATCTTCAAATGAATTCCCTT<br>AGAGCAGAGGATACGGCGGTCTATTA<br>CTGTGGTGGCAGTGGTTATGCACTTCA<br>TGATGATTACTATGGCTTGGATGTCTG<br>GGGGCAAGGGACGCTTGTAACTGTATC<br>CTCTGGTGGTGGTGGTAGTGGTGGGGG<br>AGGCTCCGGCGGTGGCGGCTCTCAATC<br>TGCTCTGACTCAACCAGCAAGCGTATC<br>AGGGTCACCGGGACAGAGTATTACCA<br>TAAGTTGCACGGGGACCTCTAGCGATG<br>TAGGGGGGTATAATTATGTATCTTGGT<br>ATCAACAACACCCCGGGAAAGCCCCT<br>AAATTGATGATCTACGACGTGAGCAAT<br>CGACCTAGTGGCGTATCAAATCGCTTC<br>TCTGGTAGCAAGAGTGGGAATACGGC<br>GTCCCTTACTATTAGCGGATTGCAAGC<br>AGAAGATGAGGCCGATTACTACTGCA<br>GCTCCTATACTAGCTCTTCTACATTGTA<br>CGTCTTTGGGAGCGGAACAAAAGTAA<br>CAGTACTCACAACAACACCTGCCCCGA<br>GACCGCCTACACCAGCCCCGACTATTG<br>CCAGCCAGCCTCTGAGCCTCAGGCCTG<br>AGGCCTGTAGGCCCGCAGCGGGCGGC<br>GCAGTTCATACACGGGGCTTGGATTTC<br>GCTTGTGATATTTATATTTGGGCTCCTT<br>TGGCGGGGACATGTGGCGTGCTGCTTC<br>TGTCACTTGTTATTACACTGTACTGTA<br>AACGCGGGCGAAAAAAATTGCTGTAT<br>ATTTTTAAGCAGCCATTTATGAGGCCC<br>GTTCAGACGACGCAGGAGGAGGACGG<br>TTGCTCTTGCAGGTTCCCAGAAGAGGA<br>AGAAGGGGGCTGTGAATTGCGGGTTA<br>AATTTTCAAGATCCGCAGACGCTCCAG<br>CATACCAACAGGGACAAAACCAACTC<br>TATAACGAGCTGAATCTTGGAAGAAG<br>GGAGGAATATGATGTGCTGGATAAAC<br>GGCGCGGTAGAGATCCGGAGATGGGC<br>GGAAAACCAAGGCGAAAAAACCCTCA<br>GGAGGGACTCTACAACGAACTGCAGA |

TABLE 11-continued

Amino acid and nucleic acid sequences of exemplary anti-BCMA molecules based on PI61

| Identification | Protein sequence | DNA sequence (5'-3') |
|---|---|---|
| | | AAGACAAAATGGCGGAGGCTTATTCC GAAATAGGCATGAAGGGCGAGCGGAG GCGAGGGAAAGGGCACGACGGACTGT ATCAAGGCCTCTCAACCGCGACTAAGG ATACGTACGACGCCCTGCACATGCAGG CCCTGCCTCCGAGA (SEQ ID NO: 258) |
| PI61 mature CAR protein | QVQLQESGGGVVQPGRSLR LSCAASGFTFSSYGMHWVR QAPGKGLEWVAVISYDGSN KYYADSVKGRFTISRDNSK NTLYLQMNSLRAEDTAVYY CGGSGYALHDDYYGLDVW GQGTLVTVSSGGGGSGGGG SGGGGSQSALTQPASVSGSP GQSITISCTGTSSDVGGYNY VSWYQQHPGKAPKLMIYD VSNRPSGVSNRFSGSKSGNT ASLTISGLQAEDEADYYCSS YTSSSTLYVFGSGTKVTVLT TTPAPRPPTPAPTIASQPLSL RPEACRPAAGGAVHTRGLD FACDIYIWAPLAGTCGVLLL SLVITLYCKRGRKKLLYIFK QPFMRPVQTTQEEDGCSCR FPEEEEGGCELRVKFSRSAD APAYQQGQNQLYNELNLG RREEYDVLDKRRGRDPEMG GKPRRKNPQEGLYNELQKD KMAEAYSEIGMKGERRRGK GHDGLYQGLSTATKDTYDA LHMQALPPR (SEQ ID NO: 107) | |

TABLE 12

Amino acid and nucleic acid sequences of exemplary hybridoma-derived anti-BCMA molecules

| SEQ ID NO | Name/ Description | Sequence |
|---|---|---|
| Hy03 | | |
| SEQ ID NO: 137 | HCDR1 (Kabat) | GFWMS |
| SEQ ID NO: 138 | HCDR2 (Kabat) | NIKQDGSEKYYVDSVRG |
| SEQ ID NO: 139 | HCDR3 (Kabat) | ALDYYGMDV |
| SEQ ID NO: 140 | HCDR1 (Chothia) | GFTFSGF |
| SEQ ID NO: 141 | HCDR2 (Chothia) | KQDGSE |
| SEQ ID NO: 139 | HCDR3 (Chothia) | ALDYYGMDV |
| SEQ ID NO: 142 | HCDR1 (IMGT) | GFTFSGFW |
| SEQ ID NO: 143 | HCDR2 (IMGT) | IKQDGSEK |
| SEQ ID NO: 144 | HCDR3 (IMGT) | ARALDYYGMDV |

TABLE 12-continued

Amino acid and nucleic acid sequences of
exemplary hybridoma-derived anti-BCMA molecules

| SEQ ID NO | Name/ Description | Sequence |
|---|---|---|
| SEQ ID NO: 145 | VH | EVQLVESGGGLVQPGGSLRLSCAASGFTFSGFWMSWVRQAPGKG LEWVANIKQDGSEKYYVDSVRGRFTISRDNAKNSLYLQMNSLRAE DTAVYYCARALDYYGMDVWGQGTTVTVSS |
| SEQ ID NO: 146 | DNA VH | GAAGTGCAACTGGTGGAGAGCGGTGGAGGGCTTGTCCAGCCCG GAGGATCGCTGCGGCTGTCCTGTGCTGCGTCCGGGTTCACCTTC TCCGGCTTCTGGATGTCCTGGGTCAGACAGGCACCGGGAAAGG GCCTCGAATGGGTGGCCAACATCAAGCAGGATGGCTCCGAGAA GTACTACGTCGACTCCGTGAGAGGCCGCTTCACCATCTCCCGGG ACAACGCCAAGAACTCGCTGTACCTCCAAATGAATAGCCTCAG GGCGGAAGATACTGCTGTGTATTACTGCGCACGCGCCCTTGACT ACTACGGCATGGACGTCTGGGGCCAAGGGACCACTGTGACCGT GTCTAGC |
| SEQ ID NO: 147 | LCDR1 (Kabat) | RSSQSLLDSDDGNTYLD |
| SEQ ID NO: 148 | LCDR2 (Kabat) | TLSYRAS |
| SEQ ID NO: 149 | LCDR3 (Kabat) | TQRLEFPSIT |
| SEQ ID NO: 150 | LCDR1 (Chothia) | SQSLLDSDDGNTY |
| SEQ ID NO: 151 | LCDR2 (Chothia) | TLS |
| SEQ ID NO: 152 | LCDR3 (Chothia) | RLEFPSI |
| SEQ ID NO: 153 | LCDR1 (IMGT) | QSLLDSDDGNTY |
| SEQ ID NO: 151 | LCDR2 (IMGT) | TLS |
| SEQ ID NO: 149 | LCDR3 (IMGT) | TQRLEFPSIT |
| SEQ ID NO: 154 | VL | DIVMTQTPLSLPVTPGEPASISCRSSQSLLDSDDGNTYLDWYLQKP GQSPRLLIYTLSYRASGVPDRFSGSGSGTDFTLKISRVEAEDVGLYY CTQRLEFPSITFGQGTRLEIK |
| SEQ ID NO: 155 | DNA VL | GATATCGTGATGACCCAGACTCCCCTGTCCCTGCCTGTGACTCC CGGAGAACCAGCCTCCATTTCCTGCCGGTCCTCCCAGTCCCTGC TGGACAGCGACGACGGCAACACTTACCTGGACTGGTACTTGCA GAAGCCGGGCCAATCGCCTCGCCTGCTGATCTATACCCTGTCAT ACCGGGCCTCAGGAGTGCCTGACCGCTTCTCGGGATCAGGGAG CGGGACCGATTTCACCCTGAAAATTTCCCGAGTGGAAGCCGAG GACGTCGGACTGTACTACTGCACCCAGCGCCTCGAATTCCCGTC GATTACGTTTGGACAGGGTACCCGGCTTGAGATCAAG |
| SEQ ID NO: 63 | Linker | GGGGSGGGGSGGGGSGGGGS |
| SEQ ID NO: 156 | scFv (VH- linker-VL) | EVQLVESGGGLVQPGGSLRLSCAASGFTFSGFWMSWVRQAPGKG LEWVANIKQDGSEKYYVDSVRGRFTISRDNAKNSLYLQMNSLRAE DTAVYYCARALDYYGMDVWGQGTTVTVSSGGGGSGGGGSGGG GSGGGGSDIVMTQTPLSLPVTPGEPASISCRSSQSLLDSDDGNTYLD WYLQKPGQSPRLLIYTLSYRASGVPDRFSGSGSGTDFTLKISRVEA EDVGLYYCTQRLEFPSITFGQGTRLEIK |
| SEQ ID NO: 157 | DNA scFv | GAAGTGCAACTGGTGGAGAGCGGTGGAGGGCTTGTCCAGCCCG GAGGATCGCTGCGGCTGTCCTGTGCTGCGTCCGGGTTCACCTTC TCCGGCTTCTGGATGTCCTGGGTCAGACAGGCACCGGGAAAGG GCCTCGAATGGGTGGCCAACATCAAGCAGGATGGCTCCGAGAA GTACTACGTCGACTCCGTGAGAGGCCGCTTCACCATCTCCCGGG ACAACGCCAAGAACTCGCTGTACCTCCAAATGAATAGCCTCAG GGCGGAAGATACTGCTGTGTATTACTGCGCACGCGCCCTTGACT ACTACGGCATGGACGTCTGGGGCCAAGGGACCACTGTGACCGT GTCTAGCGGAGGCGGAGGTTCAGGGGGCGGTGGATCAGGCGGA |

TABLE 12-continued

Amino acid and nucleic acid sequences of exemplary hybridoma-derived anti-BCMA molecules

| SEQ ID NO | Name/ Description | Sequence |
|---|---|---|
| | | GGAGGATCGGGGGGTGGTGGATCGGATATCGTGATGACCCAGA CTCCCCTGTCCCTGCCTGTGACTCCCGGAGAACCAGCCTCCATT TCCTGCCGGTCCTCCCAGTCCCTGCTGGACAGCGACGACGGCAA CACTTACCTGGACTGGTACTTGCAGAAGCCGGGCCAATCGCCTC GCCTGCTGATCTATACCCTGTCATACCGGGCCTCAGGAGTGCCT GACCGCTTCTCGGGATCAGGGAGCGGGACCGATTTCACCCTGA AAATTTCCCGAGTGGAAGCCGAGGACGTCGGACTGTACTACTG CACCCAGCGCCTCGAATTCCCGTCGATTACGTTTGGACAGGGTA CCCGGCTTGAGATCAAG |
| SEQ ID NO: 158 | Full CAR amino acid sequence | EVQLVESGGGLVQPGGSLRLSCAASGFTFSGFWMSWVRQAPGKG LEWVANIKQDGSEKYYVDSVRGRFTISRDNAKNSLYLQMNSLRAE DTAVYYCARALDYYGMDVWGQGTTVTVSSGGGGSGGGGSGGG GSGGGGSDIVMTQTPLSLPVTPGEPASISCRSSQSLLDSDDGNTYLD WYLQKPGQSPRLLIYTLSYRASGVPDRFSGSGSGTDFTLKISRVEA EDVGLYYCTQRLEFPSITFGQGTRLEIKTTTPAPRPPTPAPTIASQPL SLRPEACRPAAGGAVHTRGLDFACDIYIWAPLAGTCGVLLLSLVIT LYCKRGRKKLLYIFKQPFMRPVQTTQEEDGCSCRFPEEEEGGCELR VKFSRSADAPAYQQGQNQLYNELNLGRREEYDVLDKRRGRDPEM GGKPRRKNPQEGLYNELQKDKMAEAYSEIGMKGERRRGKGHDG LYQGLSTATKDTYDALHMQALPPR |
| SEQ ID NO: 159 | Full CAR DNA sequence | GAAGTGCAACTGGTGGAGAGCGGTGGAGGGCTTGTCCAGCCCG GAGGATCGCTGCGGCTGTCCTGTGCTGCGTCCGGGTTCACCTTC TCCGGCTTCTGGATGTCCTGGGTCAGACAGGCACCGGGAAAGG GCCTCGAATGGGTGGCCAACATCAAGCAGGATGGCTCCGAGAA GTACTACGTCGACTCCGTGAGAGGCCGCTTCACCATCTCCCGGG ACAACGCCAAGAACTCGCTGTACCTCCAAATGAATAGCCTCAG GGCGGAAGATACTGCTGTGTATTACTGCGCACGCGCCCTTGACT ACTACGGCATGGACGTCTGGGGCCAAGGGACCACTGTGACCGT GTCTAGCGGAGGCGGAGGTTCAGGGGGCGGTGGATCAGGCGGA GGAGGATCGGGGGGTGGTGGATCGGATATCGTGATGACCCAGA CTCCCCTGTCCCTGCCTGTGACTCCCGGAGAACCAGCCTCCATT TCCTGCCGGTCCTCCCAGTCCCTGCTGGACAGCGACGACGGCAA CACTTACCTGGACTGGTACTTGCAGAAGCCGGGCCAATCGCCTC GCCTGCTGATCTATACCCTGTCATACCGGGCCTCAGGAGTGCCT GACCGCTTCTCGGGATCAGGGAGCGGGACCGATTTCACCCTGA AAATTTCCCGAGTGGAAGCCGAGGACGTCGGACTGTACTACTG CACCCAGCGCCTCGAATTCCCGTCGATTACGTTTGGACAGGGTA CCCGGCTTGAGATCAAGACCACTACCCCAGCACCGAGGCCACC CACCCCGGCTCCTACCATCGCCTCCCAGCCTCTGTCCCTGCGTC CGGAGGCATGTAGACCCGCAGCTGGTGGGGCCGTGCATACCCG GGGTCTTGACTTCGCCTGCGATATCTACATTTGGGCCCCTCTGG CTGGTACTTGCGGGGTCCTGCTGCTTTCACTCGTGATCACTCTTT ACTGTAAGCGCGGTCGGAAGAAGCTGCTGTACATCTTTAAGCA ACCCTTCATGAGGCCTGTGCAGACTACTCAAGAGGAGGACGGC TGTTCATGCCGGTTCCCAGAGGAGGAGGAAGGCGGCTGCGAAC TGCGCGTGAAATTCAGCCGCAGCGCAGATGCTCCAGCCTACCA GCAGGGGCAGAACCAGCTCTACAACGAACTCAATCTTGGTCGG AGAGAGGAGTACGACGTGCTGGACAAGCGGAGAGGACGGGAC CCAGAAATGGGCGGGAAGCCGCGCAGAAAGAATCCCCAAGAG GGCCTGTACAACGAGCTCCAAAAGGATAAGATGGCAGAAGCCT ATAGCGAGATTGGTATGAAAGGGGAACGCAGAAGAGGCAAAG GCCACGACGGACTGTACCAGGGACTCAGCACCGCCACCAAGGA CACCTATGACGCTCTTCACATGCAGGCCCTGCCGCCTCGG |
| Hy52 | | |
| SEQ ID NO: 160 | HCDR1 (Kabat) | SFRMN |
| SEQ ID NO: 161 | HCDR2 (Kabat) | SISSSSSYIYYADSVKG |
| SEQ ID NO: 162 | HCDR3 (Kabat) | WLSYYGMDV |
| SEQ ID NO: 163 | HCDR1 (Chothia) | GFTFSSF |
| SEQ ID NO: 164 | HCDR2 (Chothia) | SSSSSY |

TABLE 12-continued

Amino acid and nucleic acid sequences of exemplary hybridoma-derived anti-BCMA molecules

| SEQ ID NO | Name/ Description | Sequence |
|---|---|---|
| SEQ ID NO: 162 | HCDR3 (Chothia) | WLSYYGMDV |
| SEQ ID NO: 165 | HCDR1 (IMGT) | GFTFSSFR |
| SEQ ID NO: 166 | HCDR2 (IMGT) | ISSSSSYI |
| SEQ ID NO: 167 | HCDR3 (IMGT) | ARWLSYYGMDV |
| SEQ ID NO: 168 | VH | EVQLVESGGGLVKPGGSLRLSCAASGFTFSSFRMNWVRQAPGKGL EWVSSISSSSSYIYYADSVKGRFTISRDNAKNSLYLQMNSLRAEDT AVYYCARWLSYYGMDVWGQGTTVTVSS |
| SEQ ID NO: 169 | DNA VH | GAAGTGCAACTGGTGGAGAGCGGTGGAGGGCTTGTCAAGCCCG GAGGATCGCTGCGGCTGTCCTGTGCTGCGTCCGGGTTCACCTTC TCCTCGTTCCGCATGAACTGGGTCAGACAGGCACCGGGAAAGG GCCTCGAATGGGTGTCCTCAATCTCATCGTCCTCGTCCTACATC TACTACGCCGACTCCGTGAAAGGCCGCTTCACCATCTCCCGGGA CAACGCCAAGAACTCGCTGTACCTCCAAATGAATAGCCTCAGG GCGGAAGATACTGCTGTGTATTACTGCGCACGCTGGCTTTCCTA CTACGGCATGGACGTCTGGGGCCAAGGGACCACTGTGACCGTG TCTAGC |
| SEQ ID NO: 147 | LCDR1 (Kabat) | RSSQSLLDSDDGNTYLD |
| SEQ ID NO: 170 | LCDR2 (Kabat) | TLSFRAS |
| SEQ ID NO: 171 | LCDR3 (Kabat) | MQRIGFPIT |
| SEQ ID NO: 150 | LCDR1 (Chothia) | SQSLLDSDDGNTY |
| SEQ ID NO: 151 | LCDR2 (Chothia) | TLS |
| SEQ ID NO: 172 | LCDR3 (Chothia) | RIGFPI |
| SEQ ID NO: 153 | LCDR1 (IMGT) | QSLLDSDDGNTY |
| SEQ ID NO: 151 | LCDR2 (IMGT) | TLS |
| SEQ ID NO: 171 | LCDR3 (IMGT) | MQRIGFPIT |
| SEQ ID NO: 173 | VL | DIVMTQTPLSLPVTPGEPASISCRSSQSLLDSDDGNTYLDWYLQKP GQSPQLLIYTLSFRASGVPDRFSGSGSGTDFTLKIRRVEAEDVGVY YCMQRIGFPITFGQGTRLEIK |
| SEQ ID NO: 174 | DNA VL | GATATCGTGATGACCCAGACTCCCCTGTCCCTGCCTGTGACTCC CGGAGAACCAGCCTCCATTTCCTGCCGGTCCTCCCAGTCCCTGC TGGACAGCGACGACGGCAACACTTACCTGGACTGGTACTTGCA GAAGCCGGGCCAATCGCCTCAGCTGCTGATCTATACCCTGTCAT TCCGGGCCTCAGGAGTGCCTGACCGCTTCTCGGGATCAGGGAG CGGGACCGATTTCACCCTGAAAATTAGGCGAGTGGAAGCCGAG GACGTCGGAGTGTACTACTGCATGCAGCGCATCGGCTTCCCGAT TACGTTTGGACAGGGTACCCGGCTTGAGATCAAG |
| SEQ ID NO: 63 | Linker | GGGGSGGGGSGGGGSGGGGS |
| SEQ ID NO: 175 | scFv (VH-linker-VL) | EVQLVESGGGLVKPGGSLRLSCAASGFTFSSFRMNWVRQAPGKGL EWVSSISSSSSYIYYADSVKGRFTISRDNAKNSLYLQMNSLRAEDT AVYYCARWLSYYGMDVWGQGTTVTVSSGGGGSGGGGSGGGGS GGGGSDIVMTQTPLSLPVTPGEPASISCRSSQSLLDSDDGNTYLDW |

TABLE 12-continued

Amino acid and nucleic acid sequences of exemplary hybridoma-derived anti-BCMA molecules

| SEQ ID NO | Name/ Description | Sequence |
|---|---|---|
| | | YLQKPGQSPQLLIYTLSFRASGVPDRFSGSGSGTDFTLKIRRVEAED VGVYYCMQRIGFPITFGQGTRLEIK |
| SEQ ID NO: 176 | DNA scFv | GAAGTGCAACTGGTGGAGAGCGGTGGAGGGCTTGTCAAGCCCG GAGGATCGCTGCGGCTGTCCTGTGCTGCGTCCGGGTTCACCTTC TCCTCGTTCCGCATGAACTGGGTCAGACAGGCACCGGGAAAGG GCCTCGAATGGGTGTCCTCAATCTCATCGTCCTCGTCCTACATC TACTACGCCGACTCCGTGAAAGGCCGCTTCACCATCTCCCGGGA CAACGCCAAGAACTCGCTGTACCTCCAAATGAATAGCCTCAGG GCGGAAGATACTGCTGTGTATTACTGCGCACGCTGGCTTTCCTA CTACGGCATGGACGTCTGGGGCCAAGGGACCACTGTGACCGTG TCTAGCGGAGGCGGAGGTTCAGGGGGCGGTGGATCAGGCGGAG GAGGATCGGGGGGTGGTGGATCGGATATCGTGATGACCCAGAC TCCCCTGTCCCTGCCTGTGACTCCCGGAGAACCAGCCTCCATTT CCTGCCGGTCCTCCCAGTCCCTGCTGGACAGCGACGACGGCAA CACTTACCTGGACTGGTACTTGCAGAAGCCGGGCCAATCGCCTC AGCTGCTGATCTATACCCTGTCATTCCGGGCCTCAGGAGTGCCT GACCGCTTCTCGGGATCAGGGAGCGGGACCGATTTCACCCTGA AAATTAGGCGAGTGGAAGCCGAGGACGTCGGAGTGTACTACTG CATGCAGCGCATCGGCTTCCCGATTACGTTTGGACAGGGTACCC GGCTTGAGATCAAG |
| SEQ ID NO: 177 | Full CAR amino acid sequence | EVQLVESGGGLVKPGGSLRLSCAASGFTFSSFRMNWVRQAPGKGL EWVSSISSSSSYIYYADSVKGRFTISRDNAKNSLYLQMNSLRAEDT AVYYCARWLSYYGMDVWGQGTTVTVSSGGGGSGGGGSGGGGS GGGGSDIVMTQTPLSLPVTPGEPASISCRSSQSLLDSDDGNTYLDW YLQKPGQSPQLLIYTLSFRASGVPDRFSGSGSGTDFTLKIRRVEAED VGVYYCMQRIGFPITFGQGTRLEIKTTTPAPRPPTPAPTIASQPLSLR PEACRPAAGGAVHTRGLDFACDIYIWAPLAGTCGVLLLSLVITLYC KRGRKKLLYIFKQPFMRPVQTTQEEDGCSCRFPEEEEGGCELRVKF SRSADAPAYQQGQNQLYNELNLGRREEYDVLDKRRGRDPEMGG KPRRKNPQEGLYNELQKDKMAEAYSEIGMKGERRRGKGHDGLY QGLSTATKDTYDALHMQALPPR |
| SEQ ID NO: 178 | Full CAR DNA sequence | GAAGTGCAACTGGTGGAGAGCGGTGGAGGGCTTGTCAAGCCCG GAGGATCGCTGCGGCTGTCCTGTGCTGCGTCCGGGTTCACCTTC TCCTCGTTCCGCATGAACTGGGTCAGACAGGCACCGGGAAAGG GCCTCGAATGGGTGTCCTCAATCTCATCGTCCTCGTCCTACATC TACTACGCCGACTCCGTGAAAGGCCGCTTCACCATCTCCCGGGA CAACGCCAAGAACTCGCTGTACCTCCAAATGAATAGCCTCAGG GCGGAAGATACTGCTGTGTATTACTGCGCACGCTGGCTTTCCTA CTACGGCATGGACGTCTGGGGCCAAGGGACCACTGTGACCGTG TCTAGCGGAGGCGGAGGTTCAGGGGGCGGTGGATCAGGCGGAG GAGGATCGGGGGGTGGTGGATCGGATATCGTGATGACCCAGAC TCCCCTGTCCCTGCCTGTGACTCCCGGAGAACCAGCCTCCATTT CCTGCCGGTCCTCCCAGTCCCTGCTGGACAGCGACGACGGCAA CACTTACCTGGACTGGTACTTGCAGAAGCCGGGCCAATCGCCTC AGCTGCTGATCTATACCCTGTCATTCCGGGCCTCAGGAGTGCCT GACCGCTTCTCGGGATCAGGGAGCGGGACCGATTTCACCCTGA AAATTAGGCGAGTGGAAGCCGAGGACGTCGGAGTGTACTACTG CATGCAGCGCATCGGCTTCCCGATTACGTTTGGACAGGGTACCC GGCTTGAGATCAAGACCACTACCCCAGCACCGAGGCCACCCAC CCCGGCTCCTACCATCGCCTCCCAGCCTCTGTCCCTGCGTCCGG AGGCATGTAGACCCGCAGCTGGTGGGGCCGTGCATACCCGGGG TCTTGACTTCGCCTGCGATATCTACATTTGGGCCCCTCTGGCTG GTACTTGCGGGGTCCTGCTGCTTTCACTCGTGATCACTCTTTACT GTAAGCGCGGTCGGAAGAAGCTGCTGTACATCTTTAAGCAACC CTTCATGAGGCCTGTGCAGACTACTCAAGAGGAGGACGGCTGT TCATGCCGGTTCCCAGAGGAGGAGGAAGGCGGCTGCGAACTGC GCGTGAAATTCAGCCGCAGCGCAGATGCTCCAGCCTACCAGCA GGGGCAGAACCAGCTCTACAACGAACTCAATCTTGGTCGGAGA GAGGAGTACGACGTGCTGGACAAGCGGAGAGGACGGGACCCA GAAATGGGCGGGAAGCCGCGCAGAAAGAATCCCCAAGAGGGC CTGTACAACGAGCTCCAAAAGGATAAGATGGCAGAAGCCTATA GCGAGATTGGTATGAAAGGGGAACGCAGAAGAGGCAAAGGCC ACGACGGACTGTACCAGGGACTCAGCACCGCCACCAAGGACAC CTATGACGCTCTTCACATGCAGGCCCTGCCGCCTCGG |

TABLE 13

Kabat CDRs of exemplary hybridoma-derived anti-BCMA molecules

| Kabat | HCDR1 | HCDR2 | HCDR3 | LCDR1 | LCDR2 | LCDR3 |
|---|---|---|---|---|---|---|
| Hy03 | GFWMS (SEQ ID NO: 137) | NIKQDGSEKYYVDSVRG (SEQ ID NO: 138) | ALDYYGMDV (SEQ ID NO: 139) | RSSQSLLDSDDGNTYLD (SEQ ID NO: 147) | TLSYRAS (SEQ ID NO: 148) | TQRLEFPSIT (SEQ ID NO: 149) |
| Hy52 | SFRMN (SEQ ID NO: 160) | SISSSSSYIYYADSVKG (SEQ ID NO: 161) | WLSYYGMDV (SEQ ID NO: 162) | RSSQSLLDSDDGNTYLD (SEQ ID NO: 147) | TLSFRAS (SEQ ID NO: 170) | MQRIGFPIT (SEQ ID NO: 171) |
| Consensus | $X_1FX_2MX_3$, wherein $X_1$ is G or S; $X_2$ iS W or R; and $X_3$ is S or N (SEQ ID NO: 179) | $X_1IX_2X_3X_4X_5SX_6X_7YYX_8DSVX_9G$, wherein $X_1$ is N or S; $X_2$ is K or S; $X_3$ is Q or S; $X_4$ is D or S; $X_5$ is G or S; $X_6$ is E or Y; $X_7$ is K or I; $X_8$ is V or A; and $X_9$ is R or K (SEQ ID NO: 180) | $X_1LX_2YYGMDV$, wherein $X_1$ is A or W; and $X_2$ is D or S (SEQ ID NO: 181) | RSSQSLLDSDDGNTYLD (SEQ ID NO: 147) | TLSXRAS, wherein X is Y or F (SEQ ID NO: 182) | $X_1QRX_2X_3FPX_4IT$, wherein $X_1$ is T or M; $X_2$ is L or I; $X_3$ is E or G; and $X_4$ iS S or absent (SEQ ID NO: 183) |

TABLE 14

Chothia CDRs of exemplary hybridoma-derived anti-BCMA molecules

| Chothia | HCDR1 | HCDR2 | HCDR3 | LCDR1 | LCDR2 | LCDR3 |
|---|---|---|---|---|---|---|
| Hy03 | GFTFSGF (SEQ ID NO: 140) | KQDGSE (SEQ ID NO: 141) | ALDYYGMDV (SEQ ID NO: 139) | SQSLLDSDDGNTY (SEQ ID NO: 150) | TLS (SEQ ID NO: 151) | RLEFPSI (SEQ ID NO: 152) |
| Hy52 | GFTFSSF (SEQ ID NO: 163) | SSSSSY (SEQ ID NO: 164) | WLSYYGMDV (SEQ ID NO: 162) | SQSLLDSDDGNTY (SEQ ID NO: 150) | TLS (SEQ ID NO: 151) | RIGFPI (SEQ ID NO: 172) |
| Consensus | GFTFSXF, wherein X is G or S (SEQ ID NO: 184) | $X_1X_2X_3X_4SX_5$, wherein $X_1$ is K or S; $X_2$ is Q or S; $X_3$ is D or S; $X_4$ is G or S; and $X_5$ is E or Y (SEQ ID NO: 185) | $X_1LX_2YYGMDV$, wherein $X_1$ is A or W; and $X_2$ is D or S (SEQ ID NO: 181) | SQSLLDSDDGNTY (SEQ ID NO: 150) | TLS (SEQ ID NO: 151) | $RX_1X_2FPX_3I$, wherein $X_1$ is L or I; $X_2$ is E or G; and $X_3$ is S or absent (SEQ ID NO: 186) |

TABLE 15

IMGT CDRs of exemplary hybridoma-derived anti-BCMA molecules

| IMGT | HCDR1 | HCDR2 | HCDR3 | LCDR1 | LCDR2 | LCDR3 |
|---|---|---|---|---|---|---|
| Hy03 | GFTFSGFW (SEQ ID NO: 142) | IKQDGSEK (SEQ ID NO: 143) | ARALDYYGMDV (SEQ ID NO: 144) | QSLLDSDDGNTY (SEQ ID NO: 153) | TLS (SEQ ID NO: 151) | TQRLEFPSIT (SEQ ID NO: 149) |
| Hy52 | GFTFSSFR (SEQ ID NO: 165) | ISSSSSYI (SEQ ID NO: 166) | ARWLSYYGMDV (SEQ ID NO: 167) | QSLLDSDDGNTY (SEQ ID NO: 153) | TLS (SEQ ID NO: 151) | MQRIGFPIT (SEQ ID NO: 171) |

TABLE 15-continued

| IMGT CDRs of exemplary hybridoma-derived anti-BCMA molecules | | | | | | |
|---|---|---|---|---|---|---|
| IMGT | HCDR1 | HCDR2 | HCDR3 | LCDR1 | LCDR2 | LCDR3 |
| Consensus | GFTFSX$_1$FX$_2$, wherein X$_1$ is G or S; and X$_2$ is W or R (SEQ ID NO: 187) | IX$_1$X$_2$X$_3$X$_4$SX$_5$X$_6$, wherein X$_1$ is K or S; X$_2$ is Q or S; X$_3$ is D or S; X$_4$ is G or S; X$_5$ is E or Y; and X$_6$ is K or I (SEQ ID NO: 188) | ARX$_1$LX$_2$YYGMDV, wherein X$_1$ is A or W; and X$_2$ is D or S (SEQ ID NO: 189) | QSLLDSDDGNTY (SEQ ID NO: 153) | TLS (SEQ ID NO: 151) | X$_1$QRX$_2$X$_3$FPX$_4$IT, wherein X$_1$ is T or M; X$_2$ is L or I; X$_3$ is E or G; and X$_4$ is S or absent (SEQ ID NO: 183) |

In some embodiments, the human anti-BCMA binding domain comprises a HC CDR1, HC CDR2, HC CDR3, LC CDR1, LC CDR2, and LC CDR3.

In certain embodiments, the CAR molecule described herein or the anti-BCMA binding domain described herein includes:

(1) one, two, or three light chain (LC) CDRs chosen from:

(i) a LC CDR1 of SEQ ID NO: 54, LC CDR2 of SEQ ID NO: 55 and LC CDR3 of SEQ ID NO: 56; and/or (2) one, two, or three heavy chain (HC) CDRs from one of the following:

(i) a HC CDR1 of SEQ ID NO: 44, HC CDR2 of SEQ ID NO: 45 and HC CDR3 of SEQ ID NO: 84; (ii) a HC CDR1 of SEQ ID NO: 44, HC CDR2 of SEQ ID NO: 45 and HC CDR3 of SEQ ID NO: 46; (iii) a HC CDR1 of SEQ ID NO: 44, HC CDR2 of SEQ ID NO: 45 and HC CDR3 of SEQ ID NO: 68; or (iv) a HC CDR1 of SEQ ID NO: 44, HC CDR2 of SEQ ID NO: 45 and HC CDR3 of SEQ ID NO: 76.

In certain embodiments, the CAR molecule described herein or the anti-BCMA binding domain described herein includes:

(1) one, two, or three light chain (LC) CDRs from one of the following:

(i) a LC CDR1 of SEQ ID NO: 95, LC CDR2 of SEQ ID NO: 131 and LC CDR3 of SEQ ID NO: 132; (ii) a LC CDR1 of SEQ ID NO: 95, LC CDR2 of SEQ ID NO: 96 and LC CDR3 of SEQ ID NO: 97; (iii) a LC CDR1 of SEQ ID NO: 95, LC CDR2 of SEQ ID NO: 114 and LC CDR3 of SEQ ID NO: 115; or (iv) a LC CDR1 of SEQ ID NO: 95, LC CDR2 of SEQ ID NO: 114 and LC CDR3 of SEQ ID NO: 97; and/or (2) one, two, or three heavy chain (HC) CDRs from one of the following:

(i) a HC CDR1 of SEQ ID NO: 86, HC CDR2 of SEQ ID NO: 130 and HC CDR3 of SEQ ID NO: 88; (ii) a HC CDR1 of SEQ ID NO: 86, HC CDR2 of SEQ ID NO: 87 and HC CDR3 of SEQ ID NO: 88; or (iii) a HC CDR1 of SEQ ID NO: 86, HC CDR2 of SEQ ID NO: 109 and HC CDR3 of SEQ ID NO: 88.

In certain embodiments, the CAR molecule described herein or the anti-BCMA binding domain described herein includes:

(1) one, two, or three light chain (LC) CDRs from one of the following:

(i) a LC CDR1 of SEQ ID NO: 147, LC CDR2 of SEQ ID NO: 182 and LC CDR3 of SEQ ID NO: 183; (ii) a LC CDR1 of SEQ ID NO: 147, LC CDR2 of SEQ ID NO: 148 and LC CDR3 of SEQ ID NO: 149; or (iii) a LC CDR1 of SEQ ID NO: 147, LC CDR2 of SEQ ID NO: 170 and LC CDR3 of SEQ ID NO: 171; and/or (2) one, two, or three heavy chain (HC) CDRs from one of the following:

(i) a HC CDR1 of SEQ ID NO: 179, HC CDR2 of SEQ ID NO: 180 and HC CDR3 of SEQ ID NO: 181; (ii) a HC CDR1 of SEQ ID NO: 137, HC CDR2 of SEQ ID NO: 138 and HC CDR3 of SEQ ID NO: 139; or (iii) a HC CDR1 of SEQ ID NO: 160, HC CDR2 of SEQ ID NO: 161 and HC CDR3 of SEQ ID NO: 162.

In some embodiments, the HC CDR1, HC CDR2, HC CDR3, LC CDR1, LC CDR2, and LC CDR3 comprise the amino acid sequences of SEQ ID NOs: 44, 45, 84, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 46, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 68, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 76, 54, 55, and 56, respectively.

In some embodiments, the HC CDR1, HC CDR2, HC CDR3, LC CDR1, LC CDR2, and LC CDR3 comprise the amino acid sequences of SEQ ID NOs: 47, 48, 84, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 46, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 68, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 76, 57, 58, and 59, respectively.

In some embodiments, the HC CDR1, HC CDR2, HC CDR3, LC CDR1, LC CDR2, and LC CDR3 comprise the amino acid sequences of SEQ ID NOs: 49, 50, 85, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 51, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 69, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 77, 60, 58, and 56, respectively.

In some embodiments, the human anti-BCMA binding domain comprises a scFv comprising a VH (for example, a VH described herein) and VL (for example, a VL described herein). In some embodiments, the VH is attached to the VL via a linker, for example, a linker described herein, for example, a linker described in Table 1. In some embodiments, the human anti-BCMA binding domain comprises a (Gly4-Ser)n linker, wherein n is 1, 2, 3, 4, 5, or 6, preferably 3 or 4 (SEQ ID NO: 26). The light chain variable region and heavy chain variable region of a scFv can be, for example, in any of the following orientations: light chain variable region-linker-heavy chain variable region or heavy chain variable region-linker-light chain variable region.

In some embodiments, the anti-BCMA binding domain is a fragment, for example, a single chain variable fragment (scFv). In some embodiments, the anti-BCMA binding domain is a Fv, a Fab, a (Fab')2, or a bi-functional (for example bi-specific) hybrid antibody (for example, Lanzavecchia et al., Eur. J. Immunol. 17, 105 (1987)). In some embodiments, the antibodies and fragments thereof of the invention binds a BCMA protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (for example, a Ser-Gly linker) with an optimized length and/or amino acid composition. The linker length can greatly affect how the variable regions of a scFv fold and interact. In fact, if a short polypeptide linker is employed (for example, between 5-10 amino acids) intrachain folding is prevented. Interchain folding is also required to bring the two variable regions together to form a functional epitope binding site. For examples of linker orientation and size see, for example, Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In some embodiments, the linker sequence comprises sets of glycine and serine repeats such as $(Gly_4Ser)n$, where n is a positive integer equal to or greater than 1 (SEQ ID NO: 25). In some embodiments, the linker can be $(Gly_4Ser)_4$ (SEQ ID NO: 27) or $(Gly_4Ser)_3$(SEQ ID NO: 28). Variation in the linker length may retain or enhance activity, giving rise to superior efficacy in activity studies.

CD20 CAR

In some embodiments, the CAR-expressing cell described herein is a CD20 CAR-expressing cell (for example, a cell expressing a CAR that binds to human CD20). In some embodiments, the CD20 CAR-expressing cell includes an antigen binding domain according to WO2016164731 and WO2018067992, incorporated herein by reference. Exemplary CD20-binding sequences or CD20 CAR sequences are disclosed in, for example, Tables 1-5 of WO2018067992. In some embodiments, the CD20 CAR comprises a CDR, variable region, scFv, or full-length sequence of a CD20 CAR disclosed in WO2018067992 or WO2016164731.

CD22 CAR

In some embodiments, the CAR-expressing cell described herein is a CD22 CAR-expressing cell (for example, a cell expressing a CAR that binds to human CD22). In some embodiments, the CD22 CAR-expressing cell includes an antigen binding domain according to WO2016164731 and WO2018067992, incorporated herein by reference. Exemplary CD22-binding sequences or CD22 CAR sequences are disclosed in, for example, Tables 6A, 6B, 7A, 7B, 7C, 8A, 8B, 9A, 9B, 10A, and 10B of WO2016164731 and Tables 6-10 of WO2018067992. In some embodiments, the CD22 CAR sequences comprise a CDR, variable region, scFv or full-length sequence of a CD22 CAR disclosed in WO2018067992 or WO2016164731.

In embodiments, the CAR molecule comprises an antigen binding domain that binds to CD22 (CD22 CAR). In some embodiments, the antigen binding domain targets human CD22. In some embodiments, the antigen binding domain includes a single chain Fv sequence as described herein.

The sequences of human CD22 CAR are provided below. In some embodiments, a human CD22 CAR is CAR22-65.

Human CD22 CAR scFv sequence (SEQ ID NO: 285)

EVQLQQSGPGLVKPSQTLSLTCAISGDSMLSNSDTWNWIRQSPSRGLEWL

GRTYHRSTWYDDYASSVRGRVSINVDTSKNQYSLQLNAVTPEDTGVYYCA

RVRLQDGNSWSDAFDVWGQGTMVTVSSGGGGSGGGGSGGGGSQSALTQPA

SASGSPGQSVTISCTGTSSDVGGYNYVSWYQQHPGKAPKLMIYDVSNRPS

GVSNRFSGSKSGNTASLTISGLQAEDEADYYCSSYTSSSTLYVFGTGTQL

TVL

Human CD22 CAR heavy chain variable region (SEQ ID NO 286)

EVQLQQSGPGLVKPSQTLSLTCAISGDSMLSNSDTWNWIRQSPSRGLEWL

GRTYHRSTWYDDYASSVRGRVSINVDTSKNQYSLQLNAVTPEDTGVYYCA

RVRLQDGNSWSDAFDVWGQGTMVTVSS

Human CD22 CAR light chain variable region (SEQ ID NO 287)

QSALTQPASASGSPGQSVTISCTGTSSDVGGYNYVSWYQQHPGKAPKLMI

YDVSNRPSGVSNRFSGSKSGNTASLTISGLQAEDEADYYCSSYTSSSTLY

VFGTGTQLTVL

TABLE 16

Heavy Chain Variable Domain CDRs of CD22 CAR (CAR22-65)

| Candidate | HCDR1 | SEQ ID NO: | HCDR2 | SEQ ID NO: | HCDR3 | SEQ ID NO: |
|---|---|---|---|---|---|---|
| CAR22-65 Combined | GDSML SNSDT WN | 288 | RTYHRSTWYDDYA SSVRG | 290 | VRLQDGNSWSD AFDV | 291 |

TABLE 16-continued

| Heavy Chain Variable Domain CDRs of CD22 CAR (CAR22-65) | | | | | | |
|---|---|---|---|---|---|---|
| Candidate | HCDR1 | SEQ ID NO: | HCDR2 | SEQ ID NO: | HCDR3 | SEQ ID NO: |
| CAR22-65 Kabat | SNSDT WN | 289 | RTYHRSTWYDDYA SSVRG | 290 | VRLQDGNSWSD AFDV | 291 |

TABLE 17

| Light Chain Variable Domain CDRs of CD22 CAR (CAR22-65). The LC CDR sequences in this table have the same sequence under the Kabat or combined definitions. | | | | | | |
|---|---|---|---|---|---|---|
| Candidate | LCDR1 | SEQ ID NO: | LCDR2 | SEQ ID NO: | LCDR3 | SEQ ID NO: |
| CAR22-65 Combined | TGTSSDVGGYNYVS | 95 | DVSNRPS | 96 | SSYTSSSTLYV | 97 |

In some embodiments, the antigen binding domain comprises a HC CDR1, a HC CDR2, and a HC CDR3 of any heavy chain binding domain amino acid sequences listed in Table 16. In embodiments, the antigen binding domain further comprises a LC CDR1, a LC CDR2, and a LC CDR3. In embodiments, the antigen binding domain comprises a LC CDR1, a LC CDR2, and a LC CDR3 amino acid sequences listed in Table 17.

In some embodiments, the antigen binding domain comprises one, two or all of LC CDR1, LC CDR2, and LC CDR3 of any light chain binding domain amino acid sequences listed in Table 17, and one, two or all of HC CDR1, HC CDR2, and HC CDR3 of any heavy chain binding domain amino acid sequences listed in Table 16.

In some embodiments, the CDRs are defined according to the Kabat numbering scheme, the Chothia numbering scheme, or a combination thereof.

The order in which the VL and VH domains appear in the scFv can be varied (i.e., VL-VH, or VH-VL orientation), and where any of one, two, three or four copies of the "G4S" subunit (SEQ ID NO: 25), in which each subunit comprises the sequence GGGGS (SEQ ID NO: 25) (for example, $(G4S)_3$ (SEQ ID NO: 28) or $(G4S)_4$ (SEQ ID NO: 27)), can connect the variable domains to create the entirety of the scFv domain. Alternatively, the CAR construct can include, for example, a linker including the sequence GSTSGSGKPGSGEGSTKG (SEQ ID NO: 43). Alternatively, the CAR construct can include, for example, a linker including the sequence LAEAAAK (SEQ ID NO: 308). In some embodiments, the CAR construct does not include a linker between the VL and VH domains.

These clones all contained a Q/K residue change in the signal domain of the costimulatory domain derived from CD3zeta chain.

EGFR CAR

In some embodiments, the CAR-expressing cell described herein is an EGFR CAR-expressing cell (for example, a cell expressing a CAR that binds to human EGFR). In some embodiments, the CAR-expressing cell described herein is an EGFRvIII CAR-expressing cell (for example, a cell expressing a CAR that binds to human EGFRvIII). Exemplary EGFRvIII CARs can include sequences disclosed in WO2014/130657, for example, Table 2 of WO2014/130657, incorporated herein by reference.

Exemplary EGFRvIII-binding sequences or EGFR CAR sequences may comprise a CDR, a variable region, an scFv, or a full-length CAR sequence of a EGFR CAR disclosed in WO2014/130657.

Mesothelin CAR

In some embodiments, the CAR-expressing cell described herein is a mesothelin CAR-expressing cell (for example, a cell expressing a CAR that binds to human mesothelin). Exemplary mesothelin CARs can include sequences disclosed in WO2015090230 and WO2017112741, for example, Tables 2, 3, 4, and 5 of WO2017112741, incorporated herein by reference.

Other Exemplary CARs

In other embodiments, the CAR-expressing cells can specifically bind to CD123, for example, can include a CAR molecule (for example, any of the CAR1 to CAR8), or an antigen binding domain according to Tables 1-2 of WO 2014/130635, incorporated herein by reference. The amino acid and nucleotide sequences encoding the CD123 CAR molecules and antigen binding domains (for example, including one, two, three VH CDRs; and one, two, three VL CDRs according to Kabat or Chothia), are specified in WO 2014/130635. In other embodiments, the CAR-expressing cells can specifically bind to CD123, for example, can include a CAR molecule (for example, any of the CAR123-1 to CAR123-4 and hzCAR123-1 to hzCAR123-32), or an antigen binding domain according to Tables 2, 6, and 9 of WO2016/028896, incorporated herein by reference. The amino acid and nucleotide sequences encoding the CD123 CAR molecules and antigen binding domains (for example, including one, two, three VH CDRs; and one, two, three VL CDRs according to Kabat or Chothia), are specified in WO2016/028896.

In some embodiments, the CAR molecule comprises a CLL1 CAR described herein, for example, a CLL1 CAR described in US2016/0051651A1, incorporated herein by reference. In embodiments, the CLL1 CAR comprises an amino acid, or has a nucleotide sequence shown in US2016/0051651A1, incorporated herein by reference. In other embodiments, the CAR-expressing cells can specifically bind to CLL-1, for example, can include a CAR molecule, or an antigen binding domain according to Table 2 of WO2016/014535, incorporated herein by reference. The amino acid and nucleotide sequences encoding the CLL-1 CAR molecules and antigen binding domains (for example, including one, two, three VH CDRs; and one, two, three VL CDRs according to Kabat or Chothia), are specified in WO2016/014535.

In some embodiments, the CAR molecule comprises a CD33 CAR described herein, e.g a CD33 CAR described in US2016/0096892A1, incorporated herein by reference. In embodiments, the CD33 CAR comprises an amino acid, or has a nucleotide sequence shown in US2016/0096892A1, incorporated herein by reference. In other embodiments, the CAR-expressing cells can specifically bind to CD33, for example, can include a CAR molecule (for example, any of CAR33-1 to CAR-33-9), or an antigen binding domain according to Table 2 or 9 of WO2016/014576, incorporated herein by reference. The amino acid and nucleotide sequences encoding the CD33 CAR molecules and antigen binding domains (for example, including one, two, three VH CDRs; and one, two, three VL CDRs according to Kabat or Chothia), are specified in WO2016/014576.

In some embodiments, the antigen binding domain comprises one, two three (for example, all three) heavy chain CDRs, HC CDR1, HC CDR2 and HC CDR3, from an antibody described herein (for example, an antibody described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference), and/or one, two, three (for example, all three) light chain CDRs, LC CDR1, LC CDR2 and LC CDR3, from an antibody described herein (for example, an antibody described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference). In some embodiments, the antigen binding domain comprises a heavy chain variable region and/or a variable light chain region of an antibody listed above.

In embodiments, the antigen binding domain is an antigen binding domain described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference.

In embodiments, the antigen binding domain targets BCMA and is described in US-2016-0046724-A1. In embodiments, the antigen binding domain targets CD19 and is described in US-2015-0283178-A1. In embodiments, the antigen binding domain targets CD123 and is described in US2014/0322212A1, US2016/0068601A1. In embodiments, the antigen binding domain targets CLL1 and is described in US2016/0051651A1. In embodiments, the antigen binding domain targets CD33 and is described in US2016/0096892A1.

Exemplary target antigens that can be targeted using the CAR-expressing cells, include, but are not limited to, CD19, CD123, EGFRvIII, CD33, mesothelin, BCMA, and GFR ALPHA-4, among others, as described in, for example, WO2014/153270, WO 2014/130635, WO2016/028896, WO 2014/130657, WO2016/014576, WO 2015/090230, WO2016/014565, WO2016/014535, and WO2016/025880, each of which is herein incorporated by reference in its entirety.

In other embodiments, the CAR-expressing cells can specifically bind to GFR ALPHA-4, for example, can include a CAR molecule, or an antigen binding domain according to Table 2 of WO2016/025880, incorporated herein by reference. The amino acid and nucleotide sequences encoding the GFR ALPHA-4 CAR molecules and antigen binding domains (for example, including one, two, three VH CDRs; and one, two, three VL CDRs according to Kabat or Chothia), are specified in WO2016/025880.

In some embodiments, the antigen binding domain of any of the CAR molecules described herein (for example, any of CD19, CD123, EGFRvIII, CD33, mesothelin, BCMA, and GFR ALPHA-4) comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antigen binding domain listed above. In some embodiments, the antigen binding domain comprises a heavy chain variable region and/or a variable light chain region of an antibody listed or described above.

In some embodiments, the antigen binding domain comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antibody listed above. In some embodiments, the antigen binding domain comprises a heavy chain variable region and/or a variable light chain region of an antibody listed or described above.

In some embodiments, the tumor antigen is a tumor antigen described in International Application WO2015/142675, filed Mar. 13, 2015, which is herein incorporated by reference in its entirety. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the antigen binding domain comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antibody listed above. In some embodiments, the antigen binding domain comprises a heavy chain variable region and/or a variable light chain region of an antibody listed or described above.

In some embodiments, the anti-tumor antigen binding domain is a fragment, for example, a single chain variable fragment (scFv). In some embodiments, the anti-a cancer associate antigen as described herein binding domain is a Fv, a Fab, a (Fab')2, or a bi-functional (for example bi-specific) hybrid antibody (for example, Lanzavecchia et al., Eur. J. Immunol. 17, 105 (1987)). In some embodiments, the antibodies and fragments thereof of the invention binds a cancer associate antigen as described herein protein with wild-type or enhanced affinity.

In some instances, scFvs can be prepared according to a method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (for example, a Ser-Gly linker) with an optimized length and/or amino acid composition. The linker length can greatly affect how the variable regions of a scFv fold and interact. In fact, if a short polypeptide linker is employed (for example, between 5-10 amino acids) intrachain folding is prevented. Interchain folding is also required to bring the two variable regions together to form a functional epitope binding site. For examples of linker orientation and size see, for example, Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, which are incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In some embodiments, the linker sequence comprises sets of glycine and serine repeats such as (Gly4Ser)n, where n is a positive integer equal to or greater than 1 (SEQ ID NO: 25). In some embodiments, the linker can be $(Gly_4Ser)_4$ (SEQ ID NO: 27) or $(Gly_4Ser)_3$(SEQ ID NO: 28). Variation in the linker length may retain or enhance activity, giving rise to superior efficacy in activity studies.

In some embodiments, the antigen binding domain is a T cell receptor ("TCR"), or a fragment thereof, for example, a single chain TCR (scTCR). Methods to make such TCRs are known in the art. See, for example, Willemsen R A et al, Gene Therapy 7: 1369-1377 (2000); Zhang T et al, Cancer Gene Ther 11: 487-496 (2004); Aggen et al, Gene Ther. 19(4):365-74 (2012) (references are incorporated herein by its entirety). For example, scTCR can be engineered that contains the Vα and Vβ genes from a T cell clone linked by a linker (for example, a flexible peptide). This approach is very useful to cancer associated target that itself is intracellular, however, a fragment of such antigen (peptide) is presented on the surface of the cancer cells by MHC.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, for example, one or more amino acid associated with the extracellular region of the protein from which the transmembrane was derived (for example, 1, 2, 3, 4, 5, 6, 7, 8, 9, 10 up to 15 amino acids of the extracellular region) and/or one or more additional amino acids associated with the intracellular region of the protein from which the transmembrane protein is derived (for example, 1, 2, 3, 4, 5, 6, 7, 8, 9, 10 up to 15 amino acids of the intracellular region). In some embodiments, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, for example, to minimize interactions with other members of the receptor complex. In some embodiments, the transmembrane domain is capable of homodimerization with another CAR on the CAR-expressing cell, for example, CART cell, surface. In some embodiments the amino acid sequence of the transmembrane domain may be modified or substituted so as to minimize interactions with the binding domains of the native binding partner present in the same CAR-expressing cell, for example, CART.

The transmembrane domain may be derived either from a natural or from a recombinant source. Where the source is natural, the domain may be derived from any membrane-bound or transmembrane protein. In some embodiments the transmembrane domain is capable of signaling to the intracellular domain(s) whenever the CAR has bound to a target. A transmembrane domain of particular use in this invention may include at least the transmembrane region(s) of, for example, the alpha, beta or zeta chain of T-cell receptor, CD28, CD3 epsilon, CD45, CD4, CD5, CD8 (for example, CD8 alpha, CD8 beta), CD9, CD16, CD22, CD33, CD37, CD64, CD80, CD86, CD134, CD137, CD154. In some embodiments, a transmembrane domain may include at least the transmembrane region(s) of a costimulatory molecule, for example, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some instances, the transmembrane domain can be attached to the extracellular region of the CAR, for example, the antigen binding domain of the CAR, via a hinge, for example, a hinge from a human protein. For example, in some embodiments, the hinge can be a human Ig (immunoglobulin) hinge, for example, an IgG4 hinge, or a CD8a hinge. In some embodiments, the hinge or spacer comprises (for example, consists of) the amino acid sequence of SEQ ID NO: 2. In some embodiments, the transmembrane domain comprises (for example, consists of) a transmembrane domain of SEQ ID NO: 6.

In some embodiments, the hinge or spacer comprises an IgG4 hinge. For example, in some embodiments, the hinge or spacer comprises a hinge of SEQ ID NO: 3. In some embodiments, the hinge or spacer comprises a hinge encoded by the nucleotide sequence of SEQ ID NO: 14.

In some embodiments, the hinge or spacer comprises an IgD hinge. For example, in some embodiments, the hinge or spacer comprises a hinge of the amino acid sequence of SEQ ID NO: 4. In some embodiments, the hinge or spacer comprises a hinge encoded by the nucleotide sequence of SEQ ID NO:15.

In some embodiments, the transmembrane domain may be recombinant, in which case it will comprise predominantly hydrophobic residues such as leucine and valine. In some embodiments, a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in some embodiments, the linker comprises the amino acid sequence of SEQ ID NO: 5. In some embodiments, the linker is encoded by a nucleotide sequence of SEQ ID NO: 16.

In some embodiments, the hinge or spacer comprises a KIR2DS2 hinge.

Cytoplasmic Domain

The cytoplasmic domain or region of a CAR of the present invention includes an intracellular signaling domain. An intracellular signaling domain is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, for example, a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In some embodiments, a CAR of the invention comprises an intracellular signaling domain, for example, a primary signaling domain of CD3-zeta.

In some embodiments, a primary signaling domain comprises a modified ITAM domain, for example, a mutated ITAM domain which has altered (for example, increased or decreased) activity as compared to the native ITAM domain. In some embodiments, a primary signaling domain comprises a modified ITAM-containing primary intracellular signaling domain, for example, an optimized and/or truncated ITAM-containing primary intracellular signaling domain. In some embodiments, a primary signaling domain comprises one, two, three, four or more ITAM motifs.

Further examples of molecules containing a primary intracellular signaling domain that are of particular use in the invention include those of DAP10, DAP12, and CD32.

The intracellular signaling domain of the CAR can comprise the primary signaling domain, for example, CD3-zeta signaling domain, by itself or it can be combined with any other desired intracellular signaling domain(s) useful in the context of a CAR of the invention. For example, the intracellular signaling domain of the CAR can comprise a primary signaling domain, for example, CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (for example, 2, 3, 4, 5, 6, 7, 8, 9, or 10 amino acids) in length may form the linkage between intracellular signaling sequence. In some embodiments, a glycine-serine doublet can be used as a suitable linker. In some embodiments, a single amino acid, for example, an alanine, a glycine, can be used as a suitable linker.

In some embodiments, the intracellular signaling domain is designed to comprise two or more, for example, 2, 3, 4, 5, or more, costimulatory signaling domains. In some embodiments, the two or more, for example, 2, 3, 4, 5, or more, costimulatory signaling domains, are separated by a linker molecule, for example, a linker molecule described herein. In some embodiments, the intracellular signaling domain comprises two costimulatory signaling domains. In some embodiments, the linker molecule is a glycine residue. In some embodiments, the linker is an alanine residue.

In some embodiments, the intracellular signaling domain is designed to comprise the signaling domain of CD3-zeta and the signaling domain of CD28. In some embodiments, the intracellular signaling domain is designed to comprise the signaling domain of CD3-zeta and the signaling domain of 4-1BB. In some embodiments, the signaling domain of 4-1BB is a signaling domain of SEQ ID NO: 7. In some embodiments, the signaling domain of CD3-zeta is a signaling domain of SEQ ID NO: 9 (mutant CD3zeta) or SEQ ID NO: 10 (wild type human CD3zeta).

In some embodiments, the intracellular signaling domain is designed to comprise the signaling domain of CD3-zeta and the signaling domain of CD27. In some embodiments, the signaling domain of CD27 comprises the amino acid sequence of SEQ ID NO: 8. In some embodiments, the signaling domain of CD27 is encoded by the nucleic acid sequence of SEQ ID NO: 19.

In some embodiments, the intracellular is designed to comprise the signaling domain of CD3-zeta and the signaling domain of CD28. In some embodiments, the signaling domain of CD28 comprises the amino acid sequence of SEQ ID NO: 36. In some embodiments, the signaling domain of CD28 is encoded by the nucleic acid sequence of SEQ ID NO: 37. In some embodiments, the intracellular is designed to comprise the signaling domain of CD3-zeta and the signaling domain of ICOS. In some embodiments, the signaling domain of ICOS comprises the amino acid sequence of SEQ ID NO: 38. In some embodiments, the signaling domain of ICOS is encoded by the nucleic acid sequence of SEQ ID NO: 39.

Co-Expression of CAR with Other Molecules or Agents

Co-Expression of a Second CAR

In some embodiments, the CAR-expressing cell described herein can further comprise a second CAR, for example, a second CAR that includes a different antigen binding domain, for example, to the same target (for example, CD19) or a different target (for example, a target other than CD19, for example, a target described herein). In some embodiments, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, for example, 4-1BB, CD28, CD27, OX-40 or ICOS, onto the first CAR, and the primary signaling domain, for example, CD3 zeta, on the second CAR can limit the CAR activity to cells where both targets are expressed. In some embodiments, the CAR expressing cell comprises a first CAR that includes an antigen binding domain, a transmembrane domain and a costimulatory domain and a second CAR that targets another antigen and includes an antigen binding domain, a transmembrane domain and a primary signaling domain. In some embodiments, the CAR expressing cell comprises a first CAR that includes an antigen binding domain, a transmembrane domain and a primary signaling domain and a second CAR that targets another antigen and includes an antigen binding domain to the antigen, a transmembrane domain and a costimulatory signaling domain.

In some embodiments, the CAR-expressing cell comprises an XCAR described herein and an inhibitory CAR. In some embodiments, the inhibitory CAR comprises an antigen binding domain that binds an antigen found on normal cells but not cancer cells, for example, normal cells that also express X. In some embodiments, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (CEACAM-1, CEACAM-3, and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGF (for example, TGF beta).

In some embodiments, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, for example, as a fragment, for example, an scFv, that does not form an association with the antigen binding domain of the second CAR, for example, the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In some embodiments, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (for example, selected by phage display).

It has also been discovered, that cells having a plurality of chimeric membrane embedded receptors comprising an antigen binding domain that interactions between the antigen binding domain of the receptors can be undesirable, for example, because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In some embodiments the antigen binding domain of one of the first and the second non-naturally occurring chimeric membrane embedded receptor, comprises an scFv, and the other comprises a single VH domain, for example, a camelid, shark, or lamprey single VH domain, or a single VH domain derived from a human or mouse sequence.

In some embodiments, a composition herein comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, for example, a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, for example, a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is at least 85%, 90%, 95%, 96%, 97%, 98% or 99%, for example, 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another at least 85%, 90%, 95%, 96%, 97%, 98% or 99% less than, for example, 85%, 90%, 95%, 96%, 97%, 98% or 99% less than if both were scFv antigen binding domains.

Co-expression of an Agent that Enhances CAR Activity In some embodiments, the CAR-expressing cell described herein can further express another agent, for example, an agent that enhances the activity or fitness of a CAR-expressing cell.

For example, in some embodiments, the agent can be an agent which inhibits a molecule that modulates or regulates, for example, inhibits, T cell function. In some embodiments, the molecule that modulates or regulates T cell function is an inhibitory molecule. Inhibitory molecules, for example, PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, or TGF beta.

In embodiments, an agent, for example, an inhibitory nucleic acid, for example, a dsRNA, for example, an siRNA or shRNA; or for example, an inhibitory protein or system, for example, a clustered regularly interspaced short palindromic repeats (CRISPR), a transcription-activator like effector nuclease (TALEN), or a zinc finger endonuclease (ZFN), for example, as described herein, can be used to inhibit expression of a molecule that modulates or regulates, for example, inhibits, T-cell function in the CAR-expressing cell. In some embodiments the agent is an shRNA, for example, an shRNA described herein. In some embodiments, the agent that modulates or regulates, for example, inhibits, T-cell function is inhibited within a CAR-expressing cell. For example, a dsRNA molecule that inhibits expression of a molecule that modulates or regulates, for example, inhibits, T-cell function is linked to the nucleic acid that encodes a component, for example, all of the components, of the CAR.

In some embodiments, the agent which inhibits an inhibitory molecule comprises a first polypeptide, for example, an inhibitory molecule, associated with a second polypeptide that provides a positive signal to the cell, for example, an intracellular signaling domain described herein. In some embodiments, the agent comprises a first polypeptide, for example, of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, or TGF beta, or a fragment of any of these (for example, at least a portion of an extracellular domain of any of these), and a second polypeptide which is an intracellular signaling domain described herein (for example, comprising a costimulatory domain (for example, 41BB, CD27 or CD28, for example, as described herein) and/or a primary signaling domain (for example, a CD3 zeta signaling domain described herein). In some embodiments, the agent comprises a first polypeptide of PD1 or a fragment thereof (for example, at least a portion of an extracellular domain of PD1), and a second polypeptide of an intracellular signaling domain described herein (for example, a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In some embodiments, the agent comprises the extracellular domain (ECD) of an inhibitory molecule, for example, Programmed Death 1 (PD1), can be fused to a transmembrane domain and intracellular signaling domains such as 41BB and CD3 zeta (also referred to herein as a PD1 CAR). In some embodiments, the PD1 CAR, when used in combinations with an XCAR described herein, improves the persistence of the T cell. In some embodiments, the CAR is a PD1 CAR comprising the extracellular domain of PD1 indicated as underlined in SEQ ID NO: 24. In some embodiments, the PD1 CAR comprises the amino acid sequence of SEQ ID NO: 24.

In some embodiments, the PD1 CAR comprises the amino acid sequence of SEQ ID NO: 22.

In some embodiments, the agent comprises a nucleic acid sequence encoding the PD1 CAR, for example, the PD1 CAR described herein. In some embodiments, the nucleic acid sequence for the PD1 CAR is provided as SEQ ID NO: 23, with the PD1 ECD underlined.

In another example, in some embodiments, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83., for example, as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In some embodiments, the costimulatory molecule ligand is 4-1BBL. In some embodiments, the costimulatory ligand is CD80 or CD86. In some embodiments, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein, for example, CD19 CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., *J Immunother.* 2010 October; 33(8):780-8 and Kershaw et al., *Hum Gene Ther.* 2002 Nov. 1; 13(16):1971-80). Thus, without wishing to be bound by theory, it is believed that chemokine receptors expressed in CAR-expressing cells that recognize chemokines secreted by tumors, for example, solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (for example, CAR-Tx) described herein include a CXC chemokine receptor (for example, CXCR1, CXCR2, CXCR3, CXCR4, CXCR5, CXCR6, or CXCR7), a CC chemokine receptor (for example, CCR1, CCR2, CCR3, CCR4, CCR5, CCR6, CCR7, CCR8, CCR9, CCR10, or CCR11), a CX3C chemokine receptor (for example, CX3CR1), a XC chemokine receptor (for example, XCR1), or a chemokine-binding fragment thereof. In some embodiments, the chemokine receptor molecule to be expressed with a CAR described herein is selected based on the chemokine(s) secreted by the tumor. In some embodiments, the CAR-expressing cell described herein further comprises, for example, expresses, a CCR2b receptor or a CXCR2 receptor. In some embodiments, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs Encoding a CAR

The present invention also provides an immune effector cell, for example, made by a method described herein, that includes a nucleic acid molecule encoding one or more CAR constructs described herein. In some embodiments, the nucleic acid molecule is provided as a messenger RNA transcript. In some embodiments, the nucleic acid molecule is provided as a DNA construct.

The nucleic acid molecules described herein can be a DNA molecule, an RNA molecule, or a combination thereof. In some embodiments, the nucleic acid molecule is an mRNA encoding a CAR polypeptide as described herein. In other embodiments, the nucleic acid molecule is a vector that includes any of the aforesaid nucleic acid molecules.

In some embodiments, the antigen binding domain of a CAR of the invention (for example, a scFv) is encoded by a nucleic acid molecule whose sequence has been codon optimized for expression in a mammalian cell. In some embodiments, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, for example, methods disclosed in at least U.S. Pat. Nos. 5,786,464 and 6,114,148.

Accordingly, in some embodiments, an immune effector cell, for example, made by a method described herein, includes a nucleic acid molecule encoding a chimeric antigen receptor (CAR), wherein the CAR comprises an antigen binding domain that binds to a tumor antigen described herein, a transmembrane domain (for example, a transmembrane domain described herein), and an intracellular signaling domain (for example, an intracellular signaling domain described herein) comprising a stimulatory domain, for example, a costimulatory signaling domain (for example, a costimulatory signaling domain described herein) and/or a primary signaling domain (for example, a primary signaling domain described herein, for example, a zeta chain described herein).

The present invention also provides vectors in which a nucleic acid molecule encoding a CAR, for example, a nucleic acid molecule described herein, is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, for example, a gammaretroviral vector. A gammaretroviral vector may include, for example, a promoter, a packaging signal (w), a primer binding site (PBS), one or more (for example, two) long terminal repeats (LTR), and a transgene of interest, for example, a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, for example, in Tobias Maetzig et al., "Gammaretroviral Vectors: Biology, Technology and Application" Viruses. 2011 June; 3(6): 677-713.

In some embodiments, the vector comprising the nucleic acid encoding the desired CAR is an adenoviral vector (A5/35). In some embodiments, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (for example, WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used.

Additional promoter elements, for example, enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR encoding nucleic acid molecule in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from nucleic acid molecules cloned into a lentiviral vector. See, for example, Milone et al., Mol. Ther. 17(8): 1453-1464 (2009). In some embodiments, the EF1a promoter comprises the sequence provided in the Examples.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-la promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (for example, a PGK promoter with one or more, for example, 1, 2, 5, 10, 100, 200, 300, or 400, nucleotide deletions when compared to the wild-type PGK promoter sequence) may be desired.

The nucleotide sequences of exemplary PGK promoters are provided below.

```
WT PGK Promoter:
                                              (SEQ ID NO: 190)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT
```

Exemplary Truncated PGK Promoters:

```
PGK100:
                                              (SEQ ID NO: 198)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
                                              (SEQ ID NO: 191)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:
                                              (SEQ ID NO: 192)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:
                                              (SEQ ID NO: 193)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG
```

-continued

```
TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG
```

A vector may also include, for example, a signal sequence to facilitate secretion, a polyadenylation signal and transcription terminator (for example, from Bovine Growth Hormone (BGH) gene), an element allowing episomal replication and replication in prokaryotes (for example SV40 origin and ColE1 or others known in the art) and/or elements to allow selection (for example, ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, for example, enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (for example, Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In embodiments, the vector may comprise two or more nucleic acid sequences encoding a CAR, for example, a CAR described herein, for example, a CD19 CAR, and a second CAR, for example, an inhibitory CAR or a CAR that specifically binds to an antigen other than CD19. In such embodiments, the two or more nucleic acid sequences encoding the CAR are encoded by a single nucleic molecule in the same frame and as a single polypeptide chain. In some embodiments, the two or more CARs, can, for example, be separated by one or more peptide cleavage sites. (for example, an auto-cleavage site or a substrate for an intracellular protease). Examples of peptide cleavage sites include T2A, P2A, E2A, or F2A sites.

Methods of introducing and expressing genes into a cell are known in the art. In the context of an expression vector, the vector can be readily introduced into a host cell, for example, mammalian, bacterial, yeast, or insect cell by any method, for example, one known in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A suitable method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, for example, human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (for example, an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In some embodiments, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant nucleic acid sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, for example, by immunological means (ELISAs and Western blots) or by assays described herein to identify agents falling within the scope of the invention.

Natural Killer Cell Receptor (NKR) CARs

In some embodiments, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), for example, KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), for example, NKp30, NKp44, NKp46; signaling lymphocyte activation molecule (SLAM) family of immune cell receptors, for example, CD48, CD229, 2B4, CD84, NTB-A, CRACC, BLAME, and CD2F-10; Fc receptor (FcR), for example, CD16, and CD64; and Ly49 receptors, for example, LY49A, LY49C. The NKR-CAR molecules described herein may interact with an adaptor molecule or intracellular signaling domain, for example, DAP12. Exemplary configurations and sequences of CAR molecules comprising NKR components are described in International Publication No. WO2014/145252, the contents of which are hereby incorporated by reference.

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (for example, 41BB), and the cell also expresses a second CAR having a second antigen binding domain and an intracellular signaling domain (for example, CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

Strategies for Regulating Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, for example, a caspase fused to a dimerization domain (see, for example, Di Stasa et al., N Engl. J. Med. 2011 Nov. 3; 365(18):1673-1683), can be used as a safety switch in the CAR therapy of the instant invention. In some embodiments, the cells (for example, T cells or NK cells) expressing a CAR of the present invention further comprise an inducible apoptosis switch, wherein a human caspase (for example, caspase 9) or a modified version is fused to a modification of the human FKB protein that allows conditional dimerization. In the presence of a small molecule, such as a rapalog (for example, AP 1903, AP20187), the inducible caspase (for example, caspase 9) is activated and leads to the rapid apoptosis and death of the cells (for example, T cells or NK cells) expressing a CAR of the present invention. Examples of a caspase-based inducible apoptosis switch (or one or more aspects of such a switch) have been described in, for example, US2004040047; US20110286980; US20140255360; WO1997031899; WO2014151960; WO2014164348; WO2014197638; WO2014197638; all of which are incorporated by reference herein.

In another example, CAR-expressing cells can also express an inducible Caspase-9 (iCaspase-9) molecule that, upon administration of a dimerizer drug (for example, rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, for example, Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, for example, by deleting CAR-expressing cells, for example, by inducing antibody dependent cell-mediated cytotoxicity (ADCC). For example, CAR-expressing cells described herein may also express an antigen that is recognized by molecules capable of inducing cell death, for example, ADCC or complement-induced cell death. For example, CAR expressing cells described herein may also express a receptor capable of being targeted by an antibody or antibody fragment. Examples of such receptors include EpCAM, VEGFR, integrins (for example, integrins αvβ3, α4, αI¾β3, α4β7, α5β1, αvβ3, αv), members of the TNF receptor superfamily (for example, TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/1gE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (for example, versions preserving one or more extracellular epitopes but lacking one or more regions within the cytoplasmic domain).

For example, a CAR-expressing cell described herein may also express a truncated epidermal growth factor receptor (EGFR) which lacks signaling capacity but retains the epitope that is recognized by molecules capable of inducing ADCC, for example, cetuximab (ERBITUX®), such that administration of cetuximab induces ADCC and subsequent depletion of the CAR-expressing cells (see, for example, WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, for example, by ADCC (see, for example, Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, for example, CAR-expressing cells, for destruction, for example, by inducing ADCC. In other embodiments, the CAR-expressing cell can be selectively targeted using a CAR ligand, for example, an anti-idiotypic antibody. In some embodiments, the anti-idiotypic antibody can cause effector cell activity, for example, ADCC or ADC activities, thereby reducing the number of CAR-expressing cells. In other embodiments, the CAR ligand, for example, the anti-idiotypic antibody, can be coupled to an agent that induces cell killing, for example, a toxin, thereby reducing the number of CAR-expressing cells. Alternatively, the CAR molecules themselves can be configured such that the activity can be regulated, for example, turned on and off, as described below.

In other embodiments, a CAR-expressing cell described herein may also express a target protein recognized by the T cell depleting agent. In some embodiments, the target protein is CD20 and the T cell depleting agent is an anti-CD20 antibody, for example, rituximab. In some embodiments, the T cell depleting agent is administered once it is desirable to reduce or eliminate the CAR-expressing cell, for example, to mitigate the CAR induced toxicity. In other embodiments, the T cell depleting agent is an anti-CD52 antibody, for example, alemtuzumab, as described in the Examples herein.

In other embodiments, an RCAR comprises a set of polypeptides, typically two in the simplest embodiments, in which the components of a standard CAR described herein, for example, an antigen binding domain and an intracellular signaling domain, are partitioned on separate polypeptides or members. In some embodiments, the set of polypeptides include a dimerization switch that, upon the presence of a dimerization molecule, can couple the polypeptides to one another, for example, can couple an antigen binding domain to an intracellular signaling domain. In some embodiments, a CAR of the present invention utilizes a dimerization switch as those described in, for example, WO2014127261, which is incorporated by reference herein. Additional description and exemplary configurations of such regulatable CARs are provided herein and in, for example, paragraphs 527-551 of International Publication No. WO 2015/090229 filed Mar. 13, 2015, which is incorporated by reference in its entirety. In some embodiments, an RCAR involves a switch domain, for example, a FKBP switch domain, as set out SEQ ID NO: 275, or comprise a fragment of FKBP having the ability to bind with FRB, for example, as set out in SEQ ID NO: 276. In some embodiments, the RCAR involves a switch domain comprising a FRB sequence, for example, as set out in SEQ ID NO: 277, or a mutant FRB sequence, for example, as set out in any of SEQ ID NOs. 278-283.

(SEQ ID NO: 275)
DVPDYASLGGPSSPKKKRKVSRGVQVETISPGDGRTFPKRGQTCVVHYTG

MLEDGKKFDSSRDRNKPFKFMLGKQEVIRGWEEGVAQMSVGQRAKLTISP

DYAYGATGHPGIIPPHATLVFDVELLKLETSY (SEQ ID NO: 276)
VQVETISPGDGRTFPKRGQTCVVHYTGMLEDGKKFDSSRDRNKPFKFMLG

KQEVIRGWEEGVAQMSVGQRAKLTISPDYAYGATGHPGIIPPHATLVFDV

ELLKLETS (SEQ ID NO: 277)
ILWHEMWHEGLEEASRLYFGERNVKGMFEVLEPLHAMMERGPQTLKETSF

NQAYGRDLMEAQEWCRKYMKSGNVKDLTQAWDLYYHVFRRISK

TABLE 18

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAYG RDLMEAQEWCRKYMKSGNVKDLTQAWDLYYHVFRRISKTS | 278 |
| E2032L mutant | ILWHEMWHEGLLEASRLYFGERNVKGMFEVLEPLHAMMERGPQTLKETSFNQAYG RDLMEAQEWCRKYMKSGNVKDLTQAWDLYYHVFRRISKTS | 279 |
| 12098L mutant | ILWHEMWHEGLEEASRLYFGERNVKGMFEVLEPLHAMMERGPQTLKETSFNQAYG RDLMEAQEWCRKYMKSGNVKDLLQAWDLYYHVFRRISKTS | 280 |
| E2032, T2098 mutant | ILWHEMWHEGL**X**EASRLYFGERNVKGMFEVLEPLHAMMERGPQTLKETSFNQAYG RDLMEAQEWCRKYMKSGNVKDL**X**QAWDLYYHVFRRISKTS | 281 |
| E20321, T2098L mutant | ILWHEMWHEGLIEASRLYFGERNVKGMFEVLEPLHAMMERGPQTLKETSFNQAYG RDLMEAQEWCRKYMKSGNVKDLLQAWDLYYHVFRRISKTS | 282 |

TABLE 18-continued

Exemplary mutant FRB having increased affinity for a dimerization molecule.

| FRB mutant | Amino Acid Sequence | SEQ ID NO: |
| --- | --- | --- |
| E2032L, T2098L mutant | ILWHEMWHEGLLEASRLYFGERNVKGMFEVLEPLHAMMERGPQTLKETSFNQAYG RDLMEAQEWCRKYMKSGNVKDLLQAWDLYYHVFRRISKTS | 283 |

RNA Transfection

Disclosed herein are methods for producing an in vitro transcribed RNA CAR. RNA CAR and methods of using the same are described, for example, in paragraphs 553-570 of in International Application WO2015/142675, filed Mar. 13, 2015, which is herein incorporated by reference in its entirety.

An immune effector cell can include a CAR encoded by a messenger RNA (mRNA). In some embodiments, the mRNA encoding a CAR described herein is introduced into an immune effector cell, for example, made by a method described herein, for production of a CAR-expressing cell.

In some embodiments, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR described herein. For example, the template for the RNA CAR comprises an extracellular region comprising a single chain variable domain of an antibody to a tumor associated antigen described herein; a hinge region (for example, a hinge region described herein), a transmembrane domain (for example, a transmembrane domain described herein such as a transmembrane domain of CD8a); and a cytoplasmic region that includes an intracellular signaling domain, for example, an intracellular signaling domain described herein, for example, comprising the signaling domain of CD3-zeta and the signaling domain of 4-1BB.

In some embodiments, the DNA to be used for PCR contains an open reading frame. The DNA can be from a naturally occurring DNA sequence from the genome of an organism. In some embodiments, the nucleic acid can include some or all of the 5' and/or 3' untranslated regions (UTRs). The nucleic acid can include exons and introns. In some embodiments, the DNA to be used for PCR is a human nucleic acid sequence. In some embodiments, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In some embodiments, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA in embodiments has 5' and 3' UTRs. In some embodiments, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In some embodiments, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In some embodiments, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In some embodiments, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of poly(A)/T stretches into a DNA template is molecular cloning. However, poly(A)/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with poly(A)/T 3' stretch without cloning highly desirable.

The poly(A)/T segment of the transcriptional DNA template can be produced during PCR by using a reverse primer containing a polyT tail, such as 100T tail (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In some embodiments, the poly(A) tail is between 100 and 5000 adenosines (for example, SEQ ID NO: 33).

Poly(A) tails of RNAs can be further extended following in vitro transcription with the use of a poly(A) polymerase, such as *E. coli* poly(A) polymerase (E-PAP). In some embodiments, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In some embodiments, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as “gene guns” (see, for example, Nishikawa, et al. Hum Gene Ther., 12(8):861-70 (2001).

Non-Viral Delivery Methods

In some embodiments, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac™ (PB) transposon system. See, for example, Aronovich et al. Hum. Mol. Genet. 20.R1(2011): R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013):166; Williams. Molecular Therapy 16.9 (2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, for example, Aronovich et al. supra.

Exemplary transposons include a pT2-based transposon. See, for example, Grabundzija et al. Nucleic Acids Res. 41.3(2013):1829-47; and Singh et al. Cancer Res. 68.8 (2008): 2961-2971, all of which are incorporated herein by reference. Exemplary transposases include a Tc1/mariner-type transposase, for example, the SB10 transposase or the SB11 transposase (a hyperactive transposase which can be expressed, for example, from a cytomegalovirus promoter). See, for example, Aronovich et al.; Kebriaei et al.; and Grabundzija et al., all of which are incorporated herein by reference.

Use of the SBTS permits efficient integration and expression of a transgene, for example, a nucleic acid encoding a CAR described herein. Provided herein are methods of generating a cell, for example, T cell or NK cell, that stably expresses a CAR described herein, for example, using a transposon system such as SBTS.

In accordance with methods described herein, in some embodiments, one or more nucleic acids, for example, plasmids, containing the SBTS components are delivered to a cell (for example, T or NK cell). For example, the nucleic acid(s) are delivered by standard methods of nucleic acid (for example, plasmid DNA) delivery, for example, methods described herein, for example, electroporation, transfection, or lipofection. In some embodiments, the nucleic acid contains a transposon comprising a transgene, for example, a nucleic acid encoding a CAR described herein. In some embodiments, the nucleic acid contains a transposon comprising a transgene (for example, a nucleic acid encoding a CAR described herein) as well as a nucleic acid sequence encoding a transposase enzyme. In other embodiments, a system with two nucleic acids is provided, for example, a dual-plasmid system, for example, where a first plasmid contains a transposon comprising a transgene, and a second plasmid contains a nucleic acid sequence encoding a transposase enzyme. For example, the first and the second nucleic acids are co-delivered into a host cell.

In some embodiments, cells, for example, T or NK cells, are generated that express a CAR described herein by using a combination of gene insertion using the SBTS and genetic editing using a nuclease (for example, Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, for example, T or NK cells, and direct infusion of the cells into a subject. Advantages of non-viral vectors include but are not limited to the ease and relatively low cost of producing sufficient amounts required to meet a patient population, stability during storage, and lack of immunogenicity.

Methods of Manufacture/Production

In some embodiments, the methods disclosed herein further include administering a T cell depleting agent after treatment with the cell (for example, an immune effector cell as described herein), thereby reducing (for example, depleting) the CAR-expressing cells (for example, the CD19CAR-expressing cells). Such T cell depleting agents can be used to effectively deplete CAR-expressing cells (for example, CD19CAR-expressing cells) to mitigate toxicity. In some embodiments, the CAR-expressing cells were manufactured according to a method herein, for example, assayed (for example, before or after transfection or transduction) according to a method herein.

In some embodiments, the T cell depleting agent is administered one, two, three, four, or five weeks after administration of the cell, for example, the population of immune effector cells, described herein.

In some embodiments, the T cell depleting agent is an agent that depletes CAR-expressing cells, for example, by inducing antibody dependent cell-mediated cytotoxicity (ADCC) and/or complement-induced cell death. For example, CAR-expressing cells described herein may also express an antigen (for example, a target antigen) that is recognized by molecules capable of inducing cell death, for example, ADCC or complement-induced cell death. For example, CAR expressing cells described herein may also express a target protein (for example, a receptor) capable of being targeted by an antibody or antibody fragment. Examples of such target proteins include, but are not limited to, EpCAM, VEGFR, integrins (for example, integrins αvβ3, α4, αI¾β3, α4β7, α5β1, αvβ3, αv), members of the TNF receptor superfamily (for example, TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/1gE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (for example, versions preserving one or more extracellular epitopes but lacking one or more regions within the cytoplasmic domain).

In some embodiments, the CAR expressing cell co-expresses the CAR and the target protein, for example, naturally expresses the target protein or is engineered to express the target protein. For example, the cell, for example, the population of immune effector cells, can include a nucleic acid (for example, vector) comprising the CAR nucleic acid (for example, a CAR nucleic acid as described herein) and a nucleic acid encoding the target protein.

In some embodiments, the T cell depleting agent is a CD52 inhibitor, for example, an anti-CD52 antibody molecule, for example, alemtuzumab.

In other embodiments, the cell, for example, the population of immune effector cells, expresses a CAR molecule as described herein (for example, CD19CAR) and the target protein recognized by the T cell depleting agent. In some embodiments, the target protein is CD20. In embodiments where the target protein is CD20, the T cell depleting agent is an anti-CD20 antibody, for example, rituximab.

In further embodiments of any of the aforesaid methods, the methods further include transplanting a cell, for example, a hematopoietic stem cell, or a bone marrow, into the mammal.

In some embodiments, the invention features a method of conditioning a mammal prior to cell transplantation. The method includes administering to the mammal an effective amount of the cell comprising a CAR nucleic acid or polypeptide, for example, a CD19 CAR nucleic acid or polypeptide. In some embodiments, the cell transplantation is a stem cell transplantation, for example, a hematopoietic stem cell transplantation, or a bone marrow transplantation. In other embodiments, conditioning a subject prior to cell transplantation includes reducing the number of target-expressing cells in a subject, for example, CD19-expressing normal cells or CD19-expressing cancer cells.

Elutriation

In some embodiments, the methods described herein feature an elutriation method that removes unwanted cells, for example, monocytes and blasts, thereby resulting in an improved enrichment of desired immune effector cells suitable for CAR expression. In some embodiments, the elutriation method described herein is optimized for the enrichment of desired immune effector cells suitable for CAR expression from a previously frozen sample, for example, a thawed sample. In some embodiments, the elutriation method described herein provides a preparation of cells with improved purity as compared to a preparation of cells collected from the elutriation protocols known in the art. In some embodiments, the elutriation method described herein includes using an optimized viscosity of the starting sample, for example, cell sample, for example, thawed cell sample, by dilution with certain isotonic solutions (for example, PBS), and using an optimized combination of flow rates and collection volume for each fraction collected by an elutriation device. Exemplary elutriation methods that could be applied in the present invention are described on pages 48-51 of WO 2017/117112, herein incorporated by reference in its entirety.

Density Gradient Centrifugation

Manufacturing of adoptive cell therapeutic product requires processing the desired cells, for example, immune effector cells, away from a complex mixture of blood cells and blood elements present in peripheral blood apheresis starting materials. Peripheral blood-derived lymphocyte samples have been successfully isolated using density gradient centrifugation through Ficoll solution. However, Ficoll is not a preferred reagent for isolating cells for therapeutic use, as Ficoll is not qualified for clinical use. In addition, Ficoll contains glycol, which has toxic potential to the cells. Furthermore, Ficoll density gradient centrifugation of thawed apheresis products after cryopreservation yields a suboptimal T cell product, for example, as described in the Examples herein. For example, a loss of T cells in the final product, with a relative gain of non-T cells, especially undesirable B cells, blast cells and monocytes was observed in cell preparations isolated by density gradient centrifugation through Ficoll solution.

Without wishing to be bound by theory, it is believed that immune effector cells, for example, T cells, dehydrate during cryopreservation to become denser than fresh cells. Without wishing to be bound by theory, it is also believed that immune effector cells, for example, T cells, remain denser longer than the other blood cells, and thus are more readily lost during Ficoll density gradient separation as compared to other cells. Accordingly, without wishing to be bound by theory, a medium with a density greater than Ficoll is believed to provide improved isolation of desired immune effector cells in comparison to Ficoll or other mediums with the same density as Ficoll, for example, 1.077 g/mL.

In some embodiments, the density gradient centrifugation method described herein includes the use of a density gradient medium comprising iodixanol. In some embodiments, the density gradient medium comprises about 60% iodixanol in water.

In some embodiments, the density gradient centrifugation method described herein includes the use of a density gradient medium having a density greater than Ficoll. In some embodiments, the density gradient centrifugation method described herein includes the use of a density gradient medium having a density greater than 1.077 g/mL, for example, greater than 1.077 g/mL, greater than 1.1 g/mL, greater than 1.15 g/mL, greater than 1.2 g/mL, greater than 1.25 g/mL, greater than 1.3 g/mL, greater than 1.31 g/mL. In some embodiments, the density gradient medium has a density of about 1.32 g/mL.

Additional embodiments of density gradient centrifugation are described on pages 51-53 of WO 2017/117112, herein incorporated by reference in its entirety.

Enrichment by Selection

Provided herein are methods for selection of specific cells to improve the enrichment of the desired immune effector cells suitable for CAR expression. In some embodiments, the selection comprises a positive selection, for example, selection for the desired immune effector cells. In some embodiments, the selection comprises a negative selection, for example, selection for unwanted cells, for example, removal of unwanted cells. In embodiments, the positive or negative selection methods described herein are performed under flow conditions, for example, by using a flow-through device, for example, a flow-through device described herein. Exemplary positive and negative selections are described on pages 53-57 of WO 2017/117112, herein incorporated by reference in its entirety. Selection methods can be performed under flow conditions, for example, by using a flow-through device, also referred to as a cell processing system, to further enrich a preparation of cells for desired immune effector cells, for example, T cells, suitable for CAR expression. Exemplary flow-through devices are described on pages 57-70 of WO 2017/117112, herein incorporated by reference in its entirety. Exemplary cell separation and debeading methods are described on pages 70-78 of WO 2017/117112, herein incorporated by reference in its entirety.

Selection procedures are not limited to ones described on pages 57-70 of WO 2017/117112. Negative T cell selection via removal of unwanted cells with CD19, CD14 and CD26 Miltenyi beads in combination with column technology (CliniMACS® Plus or CliniMACS® Prodigy®) or positive T cell selection with a combination of CD4 and CD8 Miltenyi beads and column technology (CliniMACS® Plus or CliniMACS® Prodigy®) can be used. Alternatively, column-free technology with releasable CD3 beads (GE Healthcare) can be used.

In addition, bead-free technologies such as ThermoGenesis X-series devices can be utilized as well.

Clinical Applications

All of the processes herein may be conducted according to clinical good manufacturing practice (cGMP) standards.

The processes may be used for cell purification, enrichment, harvesting, washing, concentration or for cell media exchange, particularly during the collection of raw, starting materials (particularly cells) at the start of the manufacturing process, as well as during the manufacturing process for the selection or expansion of cells for cell therapy.

The cells may include any plurality of cells. The cells may be of the same cell type, or mixed cell types. In addition, the cells may be from one donor, such as an autologous donor or a single allogenic donor for cell therapy. The cells may be obtained from patients by, for example, leukapheresis or apheresis. The cells may include T cells, for example may include a population that has greater than 50% T cells, greater than 60% T cells, greater than 70% T cells, greater than 80% T cells, or 90% T cells.

Selection processes may be particularly useful in selecting cells prior to culture and expansion. For instance, paramagnetic particles coated with anti-CD3 and/or anti CD28 may be used to select T cells for expansion or for introduction of a nucleic acid encoding a chimeric antigen receptor (CAR)

or other protein. Such a process is used to produce CTL019 T cells for treatment of acute lymphoblastic leukemia (ALL).

The debeading processes and modules disclosed herein may be particularly useful in the manufacture of cells for cell therapy, for example in purifying cells prior to, or after, culture and expansion. For instance, paramagnetic particles coated with anti-CD3 and/or anti CD28 antibodies may be used to selectively expand T cells, for example T cells that are, or will be, modified by introduction of a nucleic acid encoding a chimeric antigen receptor (CAR) or other protein, such that the CAR is expressed by the T cells. During the manufacture of such T cells, the debeading processes or modules may be used to separate T cells from the paramagnetic particles. Such a debeading process or module is used to produce, for example, CTL019 T cells for treatment of acute lymphoblastic leukemia (ALL).

In one such process, illustrated here by way of example, cells, for example, T cells, are collected from a donor (for example, a patient to be treated with an autologous chimeric antigen receptor T cell product) via apheresis (for example, leukapheresis). Collected cells may then be optionally purified, for example, by an elutriation step, or via positive or negative selection of target cells (for example, T cells). Paramagnetic particles, for example, anti-CD3/anti-CD28-coated paramagnetic particles, may then be added to the cell population, to expand the T cells. The process may also include a transduction step, wherein nucleic acid encoding one or more desired proteins, for example, a CAR, for example a CAR targeting CD19, is introduced into the cell. The nucleic acid may be introduced in a lentiviral vector. The cells, for example, the lentivirally transduced cells, may then be expanded for a period of days, for example, 1, 2, 3, 4, 5, 6, 7, 8, 9, 10, or more days, for example in the presence of a suitable medium. After expansion, the debeading processes/modules disclosed herein may be used to separate the desired T cells from the paramagnetic particles. The process may include one or more debeading steps according to the processes of the present disclosure. The debeaded cells may then be formulated for administration to the patient. Examples of CAR T cells and their manufacture are further described, for example, in WO2012/079000, which is incorporated herein by reference in its entirety. The systems and methods of the present disclosure may be used for any cell separation/purification/debeading processes described in or associated with WO2012/079000. Additional CAR T manufacturing processes are described in, for example, WO2016109410 and WO2017117112, herein incorporated by reference in their entireties.

The systems and methods herein may similarly benefit other cell therapy products by wasting fewer desirable cells, causing less cell trauma, and more reliably removing magnetic and any non-paramagnetic particles from cells with less or no exposure to chemical agents, as compared to conventional systems and methods.

Although only exemplary embodiments of the disclosure are specifically described above, it will be appreciated that modifications and variations of these examples are possible without departing from the spirit and intended scope of the disclosure. For example, the magnetic modules and systems containing them may be arranged and used in a variety of configurations in addition to those described. Besides, non-magnetic modules can be utilized as well. In addition, the systems and methods may include additional components and steps not specifically described herein. For instance, methods may include priming, where a fluid is first introduced into a component to remove bubbles and reduce resistance to cell suspension or buffer movement. Furthermore, embodiments may include only a portion of the systems described herein for use with the methods described herein. For example, embodiments may relate to disposable modules, hoses, etc. usable within non-disposable equipment to form a complete system able to separate or debead cells to produce a cell product.

Additional manufacturing methods and processes that can be combined with the present invention have been described in the art. For examples, pages 86-91 of WO 2017/117112 describe improved wash steps and improved manufacturing process.

Sources of Immune Effector Cells

This section provides additional methods or steps for obtaining an input sample comprising desired immune effector cells, isolating and processing desired immune effector cells, for example, T cells, and removing unwanted materials, for example, unwanted cells. The additional methods or steps described in this section can be used in combination with any of the elutriation, density gradient centrifugation, selection under flow conditions, or improved wash step described in the preceding sections.

A source of cells, for example, T cells or natural killer (NK) cells, can be obtained from a subject. Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In some embodiments of the present disclosure, immune effector cells, for example, T cells, can be obtained from a unit of blood collected from a subject using any number of techniques known to the skilled artisan, and any of the methods disclosed herein, in any combination of steps thereof. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and, optionally, to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. In some embodiments, the cells are washed using the improved wash step described herein.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate™, or the Haemonetics Cell Saver 5), Haemonetics Cell Saver Elite (GE Healthcare Sepax or Sefia), or a device utilizing the spinning membrane filtration technology (Fresenius Kabi LOVO), according to the manufacturer's instructions. After washing, the cells may be resuspended in a variety of biocompatible buffers, such as, for example, Ca-free, Mg-free PBS, PlasmaLyte A, PBS-EDTA supplemented with human serum albumin (HSA), or other saline solution with or without buffer. Alternatively, the undesirable components of the apheresis sample may be removed and the cells directly resuspended in culture media.

In some embodiments, desired immune effector cells, for example, T cells, are isolated from peripheral blood lymphocytes by lysing the red blood cells and depleting the monocytes, for example, by centrifugation through a PERCOLL™ gradient or by counterflow centrifugal elutriation.

The methods described herein can include, for example, selection of a specific subpopulation of immune effector cells, for example, T cells, that are a T regulatory cell-depleted population, for example, CD25+ depleted cells or $CD25^{high}$ depleted cells, using, for example, a negative selection technique, for example, described herein. In some embodiments, the population of T regulatory-depleted cells contains less than 30%, 25%, 20%, 15%, 10%, 5%, 4%, 3%, 2%, 1% of CD25+ cells or $CD25^{high}$ cells.

In some embodiments, T regulatory cells, for example, CD25+ T cells or $CD25^{high}$ T cells, are removed from the population using an anti-CD25 antibody, or fragment thereof, or a CD25-binding ligand, for example IL-2. In some embodiments, the anti-CD25 antibody, or fragment thereof, or CD25-binding ligand is conjugated to a substrate, for example, a bead, or is otherwise coated on a substrate, for example, a bead. In some embodiments, the anti-CD25 antibody, or fragment thereof, is conjugated to a substrate as described herein.

In some embodiments, the T regulatory cells, for example, CD25+ T cells or $CD25^{high}$ T cells, are removed from the population using CD25 depleting reagent from Miltenyi™. In some embodiments, the ratio of cells to CD25 depletion reagent is 1e7 cells to 20 μL, or 1e7 cells to 15 μL, or 1e7 cells to 10 μL, or 1e7 cells to 5 μL, or 1e7 cells to 2.5 μL, or 1e7 cells to 1.25 μL. In some embodiments, for example, for T regulatory cells, greater than 500 million cells/ml is used. In some embodiments, a concentration of cells of 600, 700, 800, or 900 million cells/ml is used.

In some embodiments, the population of immune effector cells to be depleted includes about $6\times10^9$ CD25+ T cells. In some embodiments, the population of immune effector cells to be depleted include about $1\times10^9$ to $1\times10^{10}$ CD25+ T cell, and any integer value in between. In some embodiments, the resulting population T regulatory-depleted cells has $2\times10^9$ T regulatory cells, for example, CD25+ cells or $CD25^{high}$ cells, or less (for example, $1\times10^9$, $5\times10^8$, $1\times10^8$, $5\times10^7$, $1\times10^7$, or less T regulatory cells).

In some embodiments, the T regulatory cells, for example, CD25+ cells or $CD25^{high}$ cells, are removed from the population using the CliniMAC system with a depletion tubing set, such as, for example, tubing 162-01. In some embodiments, the CliniMAC system is run on a depletion setting such as, for example, DEPLETION2.1.

Without wishing to be bound by a particular theory, decreasing the level of negative regulators of immune cells (for example, decreasing the number of unwanted immune cells, for example, Treg cells), in a subject prior to apheresis or during manufacturing of a CAR-expressing cell product significantly reduces the risk of subject relapse. For example, methods of depleting Treg cells are known in the art. Methods of decreasing Treg cells include, but are not limited to, cyclophosphamide, anti-GITR antibody (an anti-GITR antibody described herein), CD25-depletion, and combinations thereof.

In some embodiments, the manufacturing methods comprise reducing the number of (for example, depleting) Treg cells prior to manufacturing of the CAR-expressing cell. For example, manufacturing methods comprise contacting the sample, for example, the apheresis sample, with an anti-GITR antibody and/or an anti-CD25 antibody (or fragment thereof, or a CD25-binding ligand), for example, to deplete Treg cells prior to manufacturing of the CAR-expressing cell (for example, T cell, NK cell) product.

Without wishing to be bound by a particular theory, decreasing the level of negative regulators of immune cells (for example, decreasing the number of unwanted immune cells, for example, Treg cells), in a subject prior to apheresis or during manufacturing of a CAR-expressing cell product can reduce the risk of a subject's relapse. In some embodiments, a subject is pre-treated with one or more therapies that reduce Treg cells prior to collection of cells for CAR-expressing cell product manufacturing, thereby reducing the risk of subject relapse to CAR-expressing cell treatment. In some embodiments, methods of decreasing Treg cells include, but are not limited to, administration to the subject of one or more of cyclophosphamide, anti-GITR antibody, CD25-depletion, or a combination thereof. In some embodiments, methods of decreasing Treg cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product. Administration of one or more of cyclophosphamide, anti-GITR antibody, CD25-depletion, or a combination thereof, can occur before, during or after an infusion of the CAR-expressing cell product.

In some embodiments, the manufacturing methods comprise reducing the number of (for example, depleting) Treg cells prior to manufacturing of the CAR-expressing cell. For example, manufacturing methods comprise contacting the sample, for example, the apheresis sample, with an anti-GITR antibody and/or an anti-CD25 antibody (or fragment thereof, or a CD25-binding ligand), for example, to deplete Treg cells prior to manufacturing of the CAR-expressing cell (for example, T cell, NK cell) product.

In some embodiments, a subject is pre-treated with cyclophosphamide prior to collection of cells for CAR-expressing cell product manufacturing, thereby reducing the risk of subject relapse to CAR-expressing cell treatment (for example, CTL019 treatment). In some embodiments, a subject is pre-treated with an anti-GITR antibody prior to collection of cells for CAR-expressing cell (for example, T cell or NK cell) product manufacturing, thereby reducing the risk of subject relapse to CAR-expressing cell treatment.

In some embodiments, the CAR-expressing cell (for example, T cell, NK cell) manufacturing process is modified to deplete Treg cells prior to manufacturing of the CAR-expressing cell (for example, T cell, NK cell) product (for example, a CTL019 product). In some embodiments, CD25-depletion is used to deplete Treg cells prior to manufacturing of the CAR-expressing cell (for example, T cell, NK cell) product (for example, a CTL019 product).

In some embodiments, the population of cells to be removed are neither the regulatory T cells or tumor cells, but cells that otherwise negatively affect the expansion and/or function of CART cells, for example cells expressing CD14, CD11b, CD33, CD15, or other markers expressed by potentially immune suppressive cells. In some embodiments, such cells are envisioned to be removed concurrently with regulatory T cells and/or tumor cells, or following said depletion, or in another order.

The methods described herein can include more than one selection step, for example, more than one depletion step. Enrichment of a T cell population by negative selection can be accomplished, for example, with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, for example, a tumor antigen that does not comprise CD25, for example, CD19, CD30, CD38, CD123, CD20, CD14 or CD11b, to thereby provide a population of T regulatory-depleted, for example, CD25+ depleted or $CD25^{high}$ depleted, and tumor antigen depleted cells that are suitable for expression of a CAR, for example, a CAR described herein. In some embodiments, tumor antigen expressing cells are removed simultaneously with the T regulatory, for example, CD25+ cells or $CD25^{high}$ cells. For example, an anti-CD25 antibody, or fragment thereof, and an anti-tumor antigen antibody, or fragment thereof, can be attached to the same substrate, for example, bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, for example, CD25+ cells or $CD25^{high}$ cells, and the removal of the tumor antigen expressing cells is sequential, and can occur, for example, in either order.

Also provided are methods that include removing cells from the population which express a check point inhibitor, for example, a check point inhibitor described herein, for example, one or more of PD1+ cells, LAG3+ cells, and TIM3+ cells, to thereby provide a population of T regulatory-depleted, for example, CD25+ depleted cells, and check point inhibitor depleted cells, for example, PD1+, LAG3+ and/or TIM3+ depleted cells. Exemplary check point inhibitors include PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGF (for example, TGF beta), for example, as described herein. In some embodiments, check point inhibitor expressing cells are removed simultaneously with the T regulatory, for example, CD25+ cells or $CD25^{high}$ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, for example, CD25+ cells or $CD25^{high}$ cells, and the removal of the check point inhibitor expressing cells is sequential, and can occur, for example, in either order.

Methods described herein can include a positive selection step. For example, T cells can isolated by incubation with anti-CD3/anti-CD28 (for example, 3×28)-conjugated beads, such as Dynabeads® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least 1, 2, 3, 4, 5, or 6 hours. In some embodiments, the time period is 10 to 24 hours, for example, 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In some embodiments, a T cell population can be selected that expresses one or more of IFN-γ, TNFα, IL-17A, IL-2, IL-3, IL-4, GM-CSF, IL-10, IL-13, granzyme B, and perforin, or other appropriate molecules, for example, other cytokines. Methods for screening for cell expression can be determined, for example, by the methods described in PCT Publication No.: WO 2013/126712.

For isolation of a desired population of cells by positive or negative selection, the concentration of cells and surface (for example, particles such as beads) can be varied. In some embodiments, it may be desirable to significantly decrease the volume in which beads and cells are mixed together (for example, increase the concentration of cells), to ensure maximum contact of cells and beads. For example, in some embodiments, a concentration of 10 billion cells/ml, 9 billion/ml, 8 billion/ml, 7 billion/ml, 6 billion/ml, or 5 billion/ml is used. In some embodiments, a concentration of 1 billion cells/ml is used. In some embodiments, a concentration of cells from 75, 80, 85, 90, 95, or 100 million cells/ml is used. In some embodiments, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (for example, leukemic blood, tumor tissue, etc.). Such populations of cells may have therapeutic value and would be desirable to obtain. For example, using high concentration of cells allows more efficient selection of CD8+ T cells that normally have weaker CD28 expression.

In some embodiments, it may be desirable to use lower concentrations of cells. By significantly diluting the mixture of T cells and surface (for example, particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C. or at room temperature.

In some embodiments, a plurality of the immune effector cells of the population do not express diaglycerol kinase (DGK), for example, is DGK-deficient. In some embodiments, a plurality of the immune effector cells of the population do not express Ikaros, for example, is Ikaros-deficient. In some embodiments, a plurality of the immune effector cells of the population do not express DGK and Ikaros, for example, is both DGK and Ikaros-deficient.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In some embodiments a blood sample or an apheresis is taken from a generally healthy subject. In some embodiments, a blood sample or an apheresis is taken from a generally healthy subject who is at risk of developing a disease, but who has not yet developed a disease, and the cells of interest are isolated and frozen for later use. In some embodiments, the T cells may be expanded, frozen, and used at a later time. In some embodiments, samples are collected from a patient shortly after diagnosis of a particular disease as described herein but prior to any treatments. In some embodiments, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In some embodiments of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In some embodiments, the immune effector cells expressing a CAR molecule, for example, a CAR molecule described herein, are obtained from a subject that has received a low, immune enhancing dose of an mTOR inhibitor. In some embodiments, the population of immune effector cells, for example, T cells, to be engineered to express a CAR, are harvested after a sufficient time, or after sufficient dosing of the low, immune enhancing, dose of an mTOR inhibitor, such that the level of PD1 negative immune effector cells, for example, T cells, or the ratio of PD1 negative immune effector cells, for example, T cells/PD1 positive immune effector cells, for example, T cells, in the subject or harvested from the subject has been, at least transiently, increased.

In other embodiments, population of immune effector cells, for example, T cells, which have, or will be engineered to express a CAR, can be treated ex vivo by contact with an amount of an mTOR inhibitor that increases the number of PD1 negative immune effector cells, for example, T cells or increases the ratio of PD1 negative immune effector cells, for example, T cells/PD1 positive immune effector cells, for example, T cells.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS™ Immune Cell Serum Replacement" Clinical & Translational Immunology (2015) 4, e31; doi:10.1038/cti.2014.31.

In some embodiments, the methods of the application can utilize media conditions comprising at least about 0.1%, 0.5%, 1.0%, 1.5%, 2%, 2.5%, 3%, 3.5%, 4%, 4.5%, 5%, 6%, 7%, 8%, 9% or 10% serum. In some embodiments, the media comprises about 0.5%-5%, about 0.5%-4.5%, about 0.5%-4%, about 0.5%-3.5%, about 0.5%-3%, about 0.5%-2.5%, about 0.5%-2%, about 0.5%-1.5%, about 0.5%-1.0%, about 1.0%-5%, about 1.5%-5%, about 2%-5%, about 2.5%-5%, about 3%-5%, about 3.5%-5%, about 4%-5%, or about 4.5%-5% serum. In some embodiments, the media comprises about 0.5% serum. In some embodiments, the media comprises about 0.5% serum. In some embodiments, the media comprises about 1% serum. In some embodiments, the media comprises about 1.5% serum. In some embodiments, the media comprises about 2% serum. In some embodiments, the media comprises about 2.5% serum. In some embodiments, the media comprises about 3% serum. In some embodiments, the media comprises about 3.5% serum. In some embodiments, the media comprises about 4% serum. In some embodiments, the media comprises about 4.5% serum. In some embodiments, the media comprises about 5% serum. In some embodiments, the serum comprises human serum, e.g., human AB serum. In some embodiments, the serum is human serum that has been allowed to naturally coagulate after collection, e.g., off-the-clot (OTC) serum. In some embodiments, the serum is plasma-derived serum human serum. Plasma-derived serum can be produced by defibrinating pooled human plasma collected in the presence of an anticoagulant, e.g., sodium citrate.

In some embodiments, the methods of the application can utilize culture media conditions comprising serum-free medium. In some embodiments, the serum free medium is OpTmizer™ CTS™ (LifeTech), Immunocult™ XF (Stemcell technologies), CellGro™ (CellGenix), TexMacs™ (Miltenyi), Stemline™ (Sigma), Xvivo15™ (Lonza), PrimeXV® (Irvine Scientific), or StemXVivo® (RandD systems). The serum-free medium can be supplemented with a serum substitute such as ICSR (immune cell serum replacement) from LifeTech. The level of serum substitute (for example, ICSR) can be, for example, up to 5%, for example, about 1%, 2%, 3%, 4%, or 5%. In some embodiments, the serum-free medium can be supplemented with serum, e.g., human serum, e.g., human AB serum. In some embodiments, the serum is human serum that has been allowed to naturally coagulate after collection, e.g., off-the-clot (OTC) serum. In some embodiments, the serum is plasma-derived human serum. Plasma-derived serum can be produced by defibrinating pooled human plasma collected in the presence of an anticoagulant, e.g., sodium citrate.

In some embodiments, a T cell population is diaglycerol kinase (DGK)-deficient. DGK-deficient cells include cells that do not express DGK RNA or protein, or have reduced or inhibited DGK activity. DGK-deficient cells can be generated by genetic approaches, for example, administering RNA-interfering agents, for example, siRNA, shRNA, miRNA, to reduce or prevent DGK expression. Alternatively, DGK-deficient cells can be generated by treatment with DGK inhibitors described herein.

In some embodiments, a T cell population is Ikaros-deficient. Ikaros-deficient cells include cells that do not express Ikaros RNA or protein, or have reduced or inhibited Ikaros activity, Ikaros-deficient cells can be generated by genetic approaches, for example, administering RNA-interfering agents, for example, siRNA, shRNA, miRNA, to reduce or prevent Ikaros expression. Alternatively, Ikaros-deficient cells can be generated by treatment with Ikaros inhibitors, for example, lenalidomide.

In embodiments, a T cell population is DGK-deficient and Ikaros-deficient, for example, does not express DGK and Ikaros, or has reduced or inhibited DGK and Ikaros activity. Such DGK and Ikaros-deficient cells can be generated by any of the methods described herein.

In some embodiments, the NK cells are obtained from the subject. In some embodiments, the NK cells are an NK cell line, for example, NK-92 cell line (Conkwest).

Allogeneic CAR-Expressing Cells

In embodiments described herein, the immune effector cell can be an allogeneic immune effector cell, for example, T cell or NK cell. For example, the cell can be an allogeneic T cell, for example, an allogeneic T cell lacking expression of a functional T cell receptor (TCR) and/or human leukocyte antigen (HLA), for example, HLA class I and/or HLA class II.

A T cell lacking a functional TCR can be, for example, engineered such that it does not express any functional TCR on its surface, engineered such that it does not express one or more subunits that comprise a functional TCR (for example, engineered such that it does not express (or exhibits its reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, for example, by expression of mutated or truncated forms of one or more of the subunits of the TCR. The term "substantially impaired TCR" means that this TCR will not elicit an adverse immune reaction in a host.

A T cell described herein can be, for example, engineered such that it does not express a functional HLA on its surface. For example, a T cell described herein, can be engineered such that cell surface expression HLA, for example, HLA class 1 and/or HLA class II, is downregulated. In some embodiments, downregulation of HLA may be accomplished by reducing or eliminating expression of beta-2 microglobulin (B2M).

In some embodiments, the T cell can lack a functional TCR and a functional HLA, for example, HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, for example by any method described herein. For example, the cell can be a cell that does not express or expresses at low levels an inhibitory molecule, for example, that can decrease the ability of a CAR-expressing cell to mount an immune effector response. Examples of inhibitory molecules include PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF (for example, TGF beta). Inhibition of an inhibitory molecule, for example, by inhibition at the DNA, RNA or protein level, can optimize a CAR-expressing cell performance. In embodiments, an inhibitory nucleic acid, for example, an inhibitory nucleic acid, for example, a dsRNA, for example, an siRNA or shRNA, a clustered regularly interspaced short palindromic repeats (CRISPR), a transcription-activator like effector nuclease (TALEN), or a zinc finger endonuclease (ZFN), for example, as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

Expression systems for siRNA and shRNAs, and exemplary shRNAs, are described, for example, in paragraphs 649 and 650 of International Application WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

The CRISPR/Cas system, and uses thereof, are described, for example, in paragraphs 651-658 of International Application WO2015/142675, filed Mar. 13, 2015, which is incorporated by reference in its entirety.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

TALENs, and uses thereof, are described, for example, in paragraphs 659-665 of International Application WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

ZFNs, and uses thereof, are described, for example, in paragraphs 666-671 of International Application WO2015/142675, filed Mar. 13, 2015, which is incorporated by reference in its entirety.

Telomerase Expression

Telomeres play a crucial role in somatic cell persistence, and their length is maintained by telomerase (TERT). Telomere length in CLL cells may be very short (Roth et al., "Significantly shorter telomeres in T-cells of patients with ZAP-70+/CD38 chronic lymphocytic leukaemia" British Journal of Haematology, 143, 383-386., Aug. 28 2008), and may be even shorter in manufactured CAR-expressing cells, for example, CART19 cells, limiting their potential to expand after adoptive transfer to a patient. Telomerase expression can rescue CAR-expressing cells from replicative exhaustion.

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in some embodiments, an immune effector cell, for example, a T cell, ectopically expresses a telomerase subunit, for example, the catalytic subunit of telomerase, for example, TERT, for example, hTERT. In some embodiments, this disclosure provides a method of producing a CAR-expressing cell, comprising contacting a cell with a nucleic acid encoding a telomerase subunit, for example, the catalytic subunit of telomerase, for example, TERT, for example, hTERT. The cell may be contacted with the nucleic acid before, simultaneous with, or after being contacted with a construct encoding a CAR.

Telomerase expression may be stable (for example, the nucleic acid may integrate into the cell's genome) or transient (for example, the nucleic acid does not integrate, and expression declines after a period of time, for example, several days). Stable expression may be accomplished by transfecting or transducing the cell with DNA encoding the telomerase subunit and a selectable marker, and selecting for stable integrants. Alternatively or in combination, stable expression may be accomplished by site-specific recombination, for example, using the Cre/Lox or FLP/FRT system.

Transient expression may involve transfection or transduction with a nucleic acid, for example, DNA or RNA such as mRNA. In some embodiments, transient mRNA transfection avoids the genetic instability sometimes associated with stable transfection with TERT. Transient expression of exogenous telomerase activity is described, for example, in International Application WO2014/130909, which is incorporated by reference herein in its entirety. In embodiments, mRNA-based transfection of a telomerase subunit is performed according to the messenger RNA Therapeutics™ platform commercialized by Moderna Therapeutics. For instance, the method may be a method described in U.S. Pat. Nos. 8,710,200, 8,822,663, 8,680,069, 8,754,062, 8,664,194, or 8680069.

In some embodiments, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 284)

```
MPRAPRCRAVRSLLRSHYREVLPLATFVRRLGPQGWRLVQRGDPAAFRAL
VAQCLVCVPWDARPPPAAPSFRQVSCLKELVARVLQRLCERGAKNVLAFG
FALLDGARGGPPEAFTTSVRSYLPNTVTDALRGSGAWGLLLRRVGDDVLV
HLLARCALFVLVAPSCAYQVCGPPLYQLGAATQARPPPHASGPRRRLGCE
RAWNHSVREAGVPLGLPAPGARRRGGSASRSLPLPKRPRRGAAPEPERTP
VGQGSWAHPGRTRGPSDRGFCVVSPARPAEEATSLEGALSGTRHSHPSVG
RQHHAGPPSTSRPPRPWDTPCPPVYAETKHFLYSSGDKEQLRPSFLLSSL
RPSLTGARRLVETIFLGSRPWMPGTPRRLPRLPQRYWQMRPLFLELLGNH
AQCPYGVLLKTHCPLRAAVTPAAGVCAREKPQGSVAAPEEEDTDPRRLVQ
LLRQHSSPWQVYGFVRACLRRLVPPGLWGSRHNERRFLRNTKKFISLGKH
AKLSLQELTWKMSVRGCAWLRRSPGVGCVPAAEHRLREEILAKFLHWLMS
```

-continued

VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD

In some embodiments, the hTERT has a sequence at least 80%, 85%, 90%, 95%, 96%, 97%, 98%, or 99% identical to the sequence of SEQ ID NO: 284. In some embodiments, the hTERT has a sequence of SEQ ID NO: 284. In some embodiments, the hTERT comprises a deletion (for example, of no more than 5, 10, 15, 20, or 30 amino acids) at the N-terminus, the C-terminus, or both. In some embodiments, the hTERT comprises a transgenic amino acid sequence (for example, of no more than 5, 10, 15, 20, or 30 amino acids) at the N-terminus, the C-terminus, or both.

In some embodiments, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795).

Activation and Expansion of Immune Effector Cells (for Example, T Cells)

Immune effector cells such as T cells generated or enriched by the methods described herein may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (for example, bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the costimulatory signal is bound to a cell surface and the agent providing the primary activation signal is in solution or coupled to a surface. In some embodiments, both agents can be in solution. In some embodiments, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In some embodiments, a 1:1 ratio of each antibody bound to the beads for CD4+ T cell expansion and T cell growth is used. In some embodiments of the present invention, a ratio of anti CD3:CD28 antibodies bound to the beads is used such that an increase in T cell expansion is observed as compared to the expansion observed using a ratio of 1:1. In some embodiments an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In some embodiments, more anti-CD28 antibody is bound to the particles than anti-CD3 antibody, i.e., the ratio of CD3:CD28 is less than one. In some embodiments, the ratio of anti CD28 antibody to anti CD3 antibody bound to the beads is greater than 2:1. In some embodiments, a 1:100 CD3:CD28 ratio of antibody bound to beads is used. In some embodiments, a 1:75 CD3:CD28 ratio of antibody bound to beads is used. In some embodiments, a 1:50 CD3:CD28 ratio of antibody bound to beads is used. In some embodiments, a 1:30 CD3:CD28 ratio of antibody bound to beads is used. In some embodiments, a 1:10 CD3:CD28 ratio of antibody bound to beads is used. In some embodiments, a 1:3 CD3:CD28 ratio of antibody bound to the beads is used. In some embodiments, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In some embodiments the ratio of cells to particles ranges from 1:100 to 100:1 and any integer values in-between and in some embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain suitable values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one suitable ratio being at least 1:1 particles per T cell. In some embodiments, a ratio of particles to cells of 1:1 or less is used. In some embodiments, a suitable particle: cell ratio is 1:5. In some embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In some embodiments, the ratio of particles to cells is 1:1 on the first day of stimulation and adjusted to 1:5 on the third and fifth days of stimulation. In some embodiments, particles are added on a daily or every other day basis to a final ratio of 1:1 on the first day, and 1:5 on the third and fifth days of stimulation. In some embodiments, the ratio of particles to cells is 2:1 on the first day of stimulation and adjusted to 1:10 on the third and fifth days of stimulation. In some embodiments, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In some embodiments, the most typical ratios for use are in the neighborhood of 1:1, 2:1 and 3:1 on the first day.

In some embodiments, the cells, such as T cells, are combined with agent-coated beads, the beads and the cells are subsequently separated, and then the cells are cultured. In some embodiments, prior to culture, the agent-coated beads and cells are not separated but are cultured together. In some embodiments, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, $10^4$ to $10^9$ T cells) and beads (for example, Dynabeads® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In some embodiments, it may be desirable to significantly decrease the volume in which particles and cells are mixed together (i.e., increase the concentration of cells), to ensure maximum contact of cells and particles. For example, in some embodiments, a concentration of about 10 billion cells/ml, 9 billion/ml, 8 billion/ml, 7 billion/ml, 6 billion/ml, 5 billion/ml, or 2 billion cells/ml is used. In some embodiments, greater than 100 million cells/ml is used. In some embodiments, a concentration of cells of 10, 15, 20, 25, 30, 35, 40, 45, or 50 million cells/ml is used. In some embodiments, a concentration of cells from 75, 80, 85, 90, 95, or 100 million cells/ml is used. In some embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in some embodiments. For example, using high concentration of cells allows more efficient selection of CD8+ T cells that normally have weaker CD28 expression.

In some embodiments, cells transduced with a nucleic acid encoding a CAR, for example, a CAR described herein, for example, a CD19 CAR described herein, are expanded, for example, by a method described herein. In some embodiments, the cells are expanded in culture for a period of several hours (for example, about 2, 3, 4, 5, 6, 7, 8, 9, 10, 15, 18, 21 hours) to about 14 days (for example, 1, 2, 3, 4, 5, 6, 7, 8, 9, 10, 11, 12, 13 or 14 days). In some embodiments, the cells are expanded for a period of 4 to 9 days. In some embodiments, the cells are expanded for a period of 8 days or less, for example, 7, 6 or 5 days. In some embodiments, the cells are expanded in culture for 5 days, and the resulting cells are more potent than the same cells expanded in culture for 9 days under the same culture conditions. Potency can be defined, for example, by various T cell functions, for example proliferation, target cell killing, cytokine production, activation, migration, surface CAR expression, CAR quantitative PCR, or combinations thereof. In some embodiments, the cells, for example, a CD19 CAR cell described herein, expanded for 5 days show at least a one, two, three or four-fold increase in cells doublings upon antigen stimulation as compared to the same cells expanded in culture for 9 days under the same culture conditions. In some embodiments, the cells, for example, the cells expressing a CD19 CAR described herein, are expanded in culture for 5 days, and the resulting cells exhibit higher proinflammatory cytokine production, for example, IFN-γ and/or GM-CSF levels, as compared to the same cells expanded in culture for 9 days under the same culture conditions. In some embodiments, the cells, for example, a CD19 CAR cell described herein, expanded for 5 days show at least a one, two, three, four, five, ten-fold or more increase in pg/ml of proinflammatory cytokine production, for example, IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (for example, Minimal Essential Media, α-MEM, RPMI Media 1640, AIM-V, DMEM, F-12, or X-vivo 15 (Lonza), X-Vivo 20, OpTmizer, and IMDM) that may contain factors necessary for proliferation and viability, including serum (for example, fetal bovine or human serum), interleukin-2 (IL-2), insulin, IFNγ, IL-4, IL-7, GM-CSF, IL-10, IL-12, IL-15, TGFβ, and TNFα or any other additives for the growth of cells known to the skilled artisan. Other additives for the growth of cells include, but are not limited to, surfactant, plasmanate, and reducing agents such as N-acetyl-cysteine and 2-mercaptoethanol. Media can include, but is not limited to RPMI 1640, AIM-V, DMEM, MEM, α-MEM, F-12, X-Vivo 15, X-Vivo 20, OpTmizer, and IMDM with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, for example, penicillin and streptomycin, are included only in experimental cultures, not in cultures of cells that are to be infused into a subject. The target cells are maintained under conditions necessary to support growth, for example, an appropriate temperature (for example, 37° C.) and atmosphere (for example, air plus 5% $CO_2$).

In some embodiments, the cells are expanded in an appropriate media (for example, media described herein) that includes one or more interleukin that result in at least a 200-fold (for example, 200-fold, 250-fold, 300-fold, 350-fold) increase in cells over a 14-day expansion period, for example, as measured by a method described herein such as flow cytometry. In some embodiments, the cells are expanded in the presence IL-15 and/or IL-7 (for example, IL-15 and IL-7).

In embodiments, methods described herein, for example, CAR-expressing cell manufacturing methods, comprise removing T regulatory cells, for example, CD25+ T cells or $CD25^{high}$ T cells, from a cell population, for example, using an anti-CD25 antibody, or fragment thereof, or a CD25-binding ligand, IL-2. Methods of removing T regulatory cells, for example, CD25+ T cells or $CD25^{high}$ T cells, from a cell population are described herein. In embodiments, the methods, for example, manufacturing methods, further comprise contacting a cell population (for example, a cell population in which T regulatory cells, such as CD25+ T cells or $CD25^{high}$ T cells, have been depleted; or a cell population that has previously contacted an anti-CD25 antibody, fragment thereof, or CD25-binding ligand) with IL-15 and/or IL-7. For example, the cell population (for example, that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide for example, hetIL-15, during the manufacturing of the CAR-expressing cell, for example, ex vivo. In embodiments, a CAR-expressing cell described herein is contacted with a composition comprising a IL-15 polypeptide during the manufacturing of the CAR-expressing cell, for example, ex vivo. In embodiments, a CAR-expressing cell described herein is contacted with a composition comprising a combination of both a IL-15 polypeptide and a IL-15 Ra polypeptide during the manufacturing of the CAR-expressing cell, for example, ex vivo. In embodiments, a CAR-expressing cell described herein is contacted with a composition comprising hetIL-15 during the manufacturing of the CAR-expressing cell, for example, ex vivo.

In some embodiments the CAR-expressing cell described herein is contacted with a composition comprising hetIL-15 during ex vivo expansion. In some embodiments, the CAR-expressing cell described herein is contacted with a composition comprising an IL-15 polypeptide during ex vivo expansion. In some embodiments, the CAR-expressing cell described herein is contacted with a composition comprising both an IL-15 polypeptide and an IL-15Ra polypeptide during ex vivo expansion. In some embodiments the contacting results in the survival and proliferation of a lymphocyte subpopulation, for example, CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR of the present invention are described in further detail below Western blot analysis of CAR expression in primary T cells can be used to detect the presence of monomers and dimers, for example, as described in paragraph 695 of International Application WO2015/142675, filed Mar. 13, 2015, which is herein incorporated by reference in its entirety.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, for example, Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein$^+$ K562 cells (K562-expressing a cancer associated antigen as described herein), wild-type K562 cells (K562 wild type) or K562 cells expressing hCD32 and 4-1BBL in the presence of antiCD3 and anti-CD28 antibody (K562-BBL-3/28). Exogenous IL-2 is added to the cultures every other day at 100 IU/ml. GFP T cells are enumerated by flow cytometry using bead-based counting. See, for example, Milone et al., Molecular Therapy 17(8): 1453-1464 (2009).

Sustained $CAR^+$ T cell expansion in the absence of re-stimulation can also be measured. See, for example, Milone et al., Molecular Therapy 17(8): 1453-1464 (2009). Briefly, mean T cell volume (fl) is measured on day 8 of culture using a Coulter Multisizer III particle counter or a higher version, a Nexcelom Cellometer Vision, Millipore Scepter or other cell counters, following stimulation with αCD3/αCD28 coated magnetic beads on day 0, and transduction with the indicated CAR on day 1.

Animal models can also be used to measure a CAR-expressing cell activity, for example, as described in paragraph 698 of International Application WO2015/142675, filed Mar. 13, 2015, which is herein incorporated by reference in its entirety.

Dose dependent CAR treatment response can be evaluated, for example, as described in paragraph 699 of International Application WO2015/142675, filed Mar. 13, 2015, which is herein incorporated by reference in its entirety.

Assessment of cell proliferation and cytokine production has been previously described, as described in paragraph 700 of International Application WO2015/142675, filed Mar. 13, 2015, which is herein incorporated by reference in its entirety.

Cytotoxicity can be assessed by a standard 51Cr-release assay, for example, as described in paragraph 701 of International Application WO2015/142675, filed Mar. 13, 2015, which is herein incorporated by reference in its entirety. Alternative non-radioactive methods can be utilized as well.

Cytotoxicity can also be assessed by measuring changes in adherent cell's electrical impedance, for example, using an xCELLigence real time cell analyzer (RTCA). In some embodiments, cytotoxicity is measured at multiple time points.

Imaging technologies can be used to evaluate specific trafficking and proliferation of CARs in tumor-bearing animal models, for example, as described in paragraph 702 of International Application WO2015/142675, filed Mar. 13, 2015, which is herein incorporated by reference in its entirety.

Other assays, including those described in the Example section herein as well as those that are known in the art can also be used to evaluate the CARs described herein.

Alternatively, or in combination to the methods disclosed herein, methods and compositions for one or more of: detection and/or quantification of CAR-expressing cells (for example, in vitro or in vivo (for example, clinical monitoring)); immune cell expansion and/or activation; and/or CAR-specific selection, that involve the use of a CAR ligand, are disclosed. In some embodiments, the CAR ligand is an antibody that binds to the CAR molecule, for example, binds to the extracellular antigen binding domain of CAR (for example, an antibody that binds to the antigen binding domain, for example, an anti-idiotypic antibody; or an antibody that binds to a constant region of the extracellular binding domain). In other embodiments, the CAR ligand is a CAR antigen molecule (for example, a CAR antigen molecule as described herein).

In some embodiments, a method for detecting and/or quantifying CAR-expressing cells is disclosed. For example, the CAR ligand can be used to detect and/or quantify CAR-expressing cells in vitro or in vivo (for example, clinical monitoring of CAR-expressing cells in a patient, or dosing a patient). The method includes:

providing the CAR ligand (optionally, a labelled CAR ligand, for example, a CAR ligand that includes a tag, a bead, a radioactive or fluorescent label);

acquiring the CAR-expressing cell (for example, acquiring a sample containing CAR-expressing cells, such as a manufacturing sample or a clinical sample);

contacting the CAR-expressing cell with the CAR ligand under conditions where binding occurs, thereby detecting the level (for example, amount) of the CAR-expressing cells present. Binding of the CAR-expressing cell with the CAR ligand can be detected using standard techniques such as FACS, ELISA and the like.

In some embodiments, a method of expanding and/or activating cells (for example, immune effector cells) is disclosed. The method includes:

providing a CAR-expressing cell (for example, a first CAR-expressing cell or a transiently expressing CAR cell);

contacting said CAR-expressing cell with a CAR ligand, for example, a CAR ligand as described herein), under conditions where immune cell expansion and/or proliferation occurs, thereby producing the activated and/or expanded cell population.

In certain embodiments, the CAR ligand is present on a substrate (for example, is immobilized or attached to a substrate, for example, a non-naturally occurring substrate). In some embodiments, the substrate is a non-cellular substrate. The non-cellular substrate can be a solid support chosen from, for example, a plate (for example, a microtiter plate), a membrane (for example, a nitrocellulose membrane), a matrix, a chip or a bead. In embodiments, the CAR ligand is present in the substrate (for example, on the substrate surface). The CAR ligand can be immobilized, attached, or associated covalently or non-covalently (for example, cross-linked) to the substrate. In some embodiments, the CAR ligand is attached (for example, covalently attached) to a bead. In the aforesaid embodiments, the immune cell population can be expanded in vitro or ex vivo. The method can further include culturing the population of immune cells in the presence of the ligand of the CAR molecule, for example, using any of the methods described herein.

In other embodiments, the method of expanding and/or activating the cells further comprises addition of a second stimulatory molecule, for example, CD28. For example, the CAR ligand and the second stimulatory molecule can be immobilized to a substrate, for example, one or more beads, thereby providing increased cell expansion and/or activation.

In some embodiments, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In some embodiments, the CAR ligand is coupled to a toxic agent (for example, a toxin or a cell ablative drug). In some embodiments, the anti-idiotypic antibody can cause effector cell activity, for example, ADCC or ADC activities.

Exemplary anti-CAR antibodies that can be used in the methods disclosed herein are described, for example, in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference.

In some embodiments, the compositions and methods herein are optimized for a specific subset of T cells, for example, as described in US Serial No. PCT/US2015/043219 filed Jul. 31, 2015, the contents of which are incorporated herein by reference in their entirety. In some embodiments, the optimized subsets of T cells display an enhanced persistence compared to a control T cell, for example, a T cell of a different type (for example, CD8+ or CD4+) expressing the same construct.

In some embodiments, a CD4+ T cell comprises a CAR described herein, which CAR comprises an intracellular signaling domain suitable for (for example, optimized for, for example, leading to enhanced persistence in) a CD4+ T cell, for example, an ICOS domain. In some embodiments, a CD8+ T cell comprises a CAR described herein, which CAR comprises an intracellular signaling domain suitable for (for example, optimized for, for example, leading to enhanced persistence of) a CD8+ T cell, for example, a 4-1BB domain, a CD28 domain, or another costimulatory domain other than an ICOS domain. In some embodiments, the CAR described herein comprises an antigen binding domain described herein, for example, a CAR comprising an antigen binding domain.

In some embodiments, described herein is a method of treating a subject, for example, a subject having cancer. The method includes administering to said subject, an effective amount of:

1) a CD4+ T cell comprising a CAR (the CARCD4+) comprising:
- an antigen binding domain, for example, an antigen binding domain described herein;
- a transmembrane domain; and
- an intracellular signaling domain, for example, a first costimulatory domain, for example, an ICOS domain; and 2) a CD8+ T cell comprising a CAR (the CARCD8+) comprising:
- an antigen binding domain, for example, an antigen binding domain described herein;
- a transmembrane domain; and
- an intracellular signaling domain, for example, a second costimulatory domain, for example, a 4-1BB domain, a CD28 domain, or another costimulatory domain other than an ICOS domain;
- wherein the CARCD4+ and the CARCD8+ differ from one another.

Optionally, the method further includes administering:

3) a second CD8+ T cell comprising a CAR (the second CARCD8+) comprising:
- an antigen binding domain, for example, an antigen binding domain described herein;
- a transmembrane domain; and
- an intracellular signaling domain, wherein the second CARCD8+ comprises an intracellular signaling domain, for example, a costimulatory signaling domain, not present on the CARCD8+, and, optionally, does not comprise an ICOS signaling domain.

Biopolymer Delivery Methods

In some embodiments, one or more CAR-expressing cells as disclosed herein can be administered or delivered to the subject via a biopolymer scaffold, for example, a biopolymer implant. Biopolymer scaffolds can support or enhance the delivery, expansion, and/or dispersion of the CAR-expressing cells described herein. A biopolymer scaffold comprises a biocompatible (for example, does not substantially induce an inflammatory or immune response) and/or a biodegradable polymer that can be naturally occurring or synthetic. Exemplary biopolymers are described, for example, in paragraphs 1004-1006 of International Application WO2015/142675, filed Mar. 13, 2015, which is herein incorporated by reference in its entirety.

Pharmaceutical Compositions and Treatments

In some embodiments, the disclosure provides a method of treating a patient, comprising administering CAR-expressing cells produced as described herein, optionally in combination with one or more other therapies. In some embodiments, the disclosure provides a method of treating a patient, comprising administering a reaction mixture comprising CAR-expressing cells as described herein, optionally in combination with one or more other therapies. In some embodiments, the disclosure provides a method of shipping or receiving a reaction mixture comprising CAR-expressing cells as described herein. In some embodiments, the disclosure provides a method of treating a patient, comprising receiving a CAR-expressing cell that was produced as described herein, and further comprising administering the CAR-expressing cell to the patient, optionally in combination with one or more other therapies. In some embodiments, the disclosure provides a method of treating a patient, comprising producing a CAR-expressing cell as described herein, and further comprising administering the CAR-expressing cell to the patient, optionally in combination with one or more other therapies. The other therapy may be, for example, a cancer therapy such as chemotherapy.

In some embodiments, cells expressing a CAR described herein are administered to a subject in combination with a molecule that decreases the Treg cell population. Methods that decrease the number of (for example, deplete) Treg cells are known in the art and include, for example, CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (for example, Tregs) in the tumor microenvironment and reduces the subject's risk of relapse.

In some embodiments, a therapy described herein, for example, a CAR-expressing cell, is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In some embodiments, the GITR binding molecules and/or molecules modulating GITR functions (for example, GITR agonist and/or Treg depleting GITR antibodies) are administered prior to the CAR-expressing cell. For example, in some embodiments, a GITR agonist can be administered prior to apheresis of the cells. In embodiments, cyclophosphamide is administered to the subject prior to administration (for example, infusion or re-infusion) of the CAR-expressing cell or prior to apheresis of the cells. In embodiments, cyclophosphamide and an anti-GITR antibody are administered to the subject prior to administration (for example, infusion or re-infusion) of the CAR-expressing cell or prior to apheresis of the cells. In some embodiments, the subject has cancer (for example, a solid cancer or a hematological cancer such as ALL or CLL). In some embodiments, the subject has CLL. In embodiments, the subject has ALL. In embodiments, the subject has a solid cancer, for example, a solid cancer described herein. Exemplary GITR agonists include, for example, GITR fusion proteins and anti-GITR antibodies (for example, bivalent anti-GITR antibodies) such as, for example, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, for example, in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In some embodiments, a CAR expressing cell described herein is administered to a subject in combination with a GITR agonist, for example, a GITR agonist described herein. In some embodiments, the GITR agonist is administered prior to the CAR-expressing cell. For example, in some embodiments, the GITR agonist can be administered prior to apheresis of the cells. In some embodiments, the subject has CLL.

The methods described herein can further include formulating a CAR-expressing cell in a pharmaceutical composition. Pharmaceutical compositions may comprise a CAR-expressing cell, for example, a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (for example, aluminum hydroxide); and preservatives. Compositions can be formulated, for example, for intravenous administration.

In some embodiments, the pharmaceutical composition is substantially free of, for example, there are no detectable levels of a contaminant, for example, selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In some embodiments, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-cancer effective amount," "a cancer-inhibiting effective amount," or "therapeutic amount" is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells (for example, T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, for example, Rosenberg et al., New Eng. J. of Med. 319:1676, 1988).

In some embodiments, a dose of CAR cells (for example, CD19 CAR cells) comprises about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises about $1.1\times10^6$-$1.8\times10^7$ cells/kg. In some embodiments, a dose of CAR cells (for example, CD19 CAR cells) comprises about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (for example, CD19 CAR cells) comprises at least about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (for example, CD19 CAR cells) comprises up to about $1\times10^7$, $2\times10^7$, $5\times10^7$, $1\times10^8$, $2\times10^8$, $5\times10^8$, $1\times10^9$, $2\times10^9$, or $5\times10^9$ cells.

In some embodiments, it may be desired to administer activated immune effector cells (for example, T cells, NK cells) to a subject and then subsequently redraw blood (or have an apheresis performed), activate immune effector cells (for example, T cells, NK cells) therefrom, and reinfuse the patient with these activated and expanded immune effector cells (for example, T cells, NK cells). This process can be carried out multiple times every few weeks. In some embodiments, immune effector cells (for example, T cells, NK cells) can be activated from blood draws of from 10cc to 400cc. In some embodiments, immune effector cells (for example, T cells, NK cells) are activated from blood draws of 20cc, 30cc, 40cc, 50cc, 60cc, 70cc, 80cc, 90cc, or 100cc.

The administration of the subject compositions may be carried out in any convenient manner. The compositions described herein may be administered to a patient trans arterially, subcutaneously, intradermally, intratumorally, intranodally, intramedullary, intramuscularly, by intravenous (i.v.) injection, or intraperitoneally, for example, by intradermal or subcutaneous injection. The compositions of immune effector cells (for example, T cells, NK cells) may be injected directly into a tumor, lymph node, or site of infection.

Dosage Regimen

In some embodiments, a dose of viable CAR-expressing cells (for example, viable CD19, BCMA, CD20, or CD22 CAR-expressing cells) comprises about $0.5\times10^6$ viable CAR-expressing cells to about $1.25\times10^9$ viable CAR-expressing cells (for example, $0.5\times10^6$ viable CAR-expressing cells to $1.25\times10^9$ viable CAR-expressing cells). In some embodiments, a dose of viable CAR-expressing cells (for example, viable CD19, BCMA, CD20, or CD22 CAR-expressing cells) comprises about $1\times10^6$, about $2.5\times10^6$, about $5\times10^6$, about $1.25\times10^7$, about $2.5\times10^7$, about $5\times10^7$, about $5.75\times10^7$, or about $8\times10^7$ viable CAR-expressing cells.

Patient Selection

In some embodiments of any of the methods of treating a subject, or composition for use disclosed herein, the subject has a cancer, for example, a hematological cancer. In some embodiments, the cancer is chosen from lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, chronic myeloid leukemia, myeloproliferative neoplasms, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia, myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, acute myeloid leukemia (AML), or unclassifiable lymphoma. In some embodiments, the cancer is a relapsed and/or refractory cancer.

In some embodiments of any of the methods of treating a subject, or composition for use disclosed herein, the subject has CLL or SLL. In some embodiments, the subject having CLL or SLL has previously been administered a BTK inhibitor therapy, for example, ibrutinib, for least 1-12 months, for example, 6 months. In some embodiments, the BTK inhibitor therapy, for example, ibrutinib therapy, is a second line therapy. In some embodiments, the subject had a partial response, or had stable disease in response to the BTK inhibitor therapy. In some embodiments, the subject did not response to the BTK inhibitor therapy. In some embodiments, the subject developed resistance, for example, developed ibrutinib resistance mutations. In some embodiments, the ibrutinib resistance mutations comprise a mutation in the gene encoding BTK and/or the gene encoding PLCg2. In some embodiments, the subject is an adult, for example, at least 18 years of age.

In some embodiments of any of the methods of treating a subject, or composition for use disclosed herein, the subject has DLBCL, for example, relapsed and/or refractory DLBCL. In some embodiments, the subject having DLBCL, for example, relapsed and/or refractory DLBCL, has previously been administered at least 2 lines of chemotherapy, for example, an anti-CD20 therapy and/or an anthracycline-based chemotherapy. In some embodiments, the subject has previously received stem cell therapy, for example, autologous stem cell therapy, and has not responded to said stem cell therapy. In some embodiments, the subject is not eligible for stem cell therapy, for example, autologous stem cell therapy. In some embodiments, the subject is an adult, for example, at least 18 years of age.

Biomarkers for Evaluating CAR-Effectiveness

In some embodiments, disclosed herein is a method of evaluating or monitoring the effectiveness of a CAR-expressing cell therapy (for example, a CD19 or BCMA CAR therapy), in a subject (for example, a subject having a cancer, for example, a hematological cancer). The method includes acquiring a value of effectiveness to the CAR therapy, wherein said value is indicative of the effectiveness or suitability of the CAR-expressing cell therapy.

In embodiments, the value of effectiveness to the CAR therapy in a subject having CLL or SLL, comprises a measure of one, two, three, or all of the following parameters:

(i) a mutation in a gene encoding BTK in a sample (for example, an apheresis sample or a manufactured CAR-expressing cell product sample);

(ii) a mutation in a gene encoding PLCg2 in a sample (for example, an apheresis sample or a manufactured CAR-expressing cell product sample);

(iii) minimal residual disease, for example, as evaluated by the level and/or activity of CD8, CD4, CD3, CD5, CD19, CD20, CD22, CD43, CD79b, CD27, CD45RO, CD45RA, CCR7, CD95, Lag3, PD-1, Tim-3, and/or CD81; or as evaluated by immunoglobulin deep sequencing; in a sample (for example, an apheresis sample or tumor sample from the subject); or (iv) the level or activity of one, two, three, four, five, six, seven, eight, nine, ten or all of the cytokines chosen from IFN-g, IL-2, IL-4, IL-6, IL-8, IL-10, IL-15, TNF-a, IP-10, MCP1, MIP1a, in a sample, for example, an apheresis sample from the subject.

In embodiments, the value of effectiveness to the CAR therapy in a subject having DLBCL, for example, relapsed and/or refractory DLBCL, comprises a measure of one or both the following parameters:

(i) minimal residual disease, for example, as evaluated by the level and/or activity of CD8, CD4, CAR19, CD3, CD27, CD45RO, CD45RA, CCR7, CD95, Lag3, PD-1, and/or Tim-3; or as evaluated by immunoglobulin deep sequencing; in a sample (for example, an apheresis sample or tumor sample from the subject); or (ii) the level or activity of one, two, three, four, five, six, seven, eight, nine, ten or all of the cytokines chosen from IFN-g, IL-2, IL-4, IL-6, IL-8, IL-10, IL-15, TNF-a, IP-10, MCP1, MIP1a, in a sample (for example, an apheresis sample from the subject).

In other embodiments, the value of effectiveness to the CAR therapy, further comprises a measure of one, two, three, four, five, six or more (all) of the following parameters:

(i) the level or activity of one, two, three, or more (for example, all) of resting $T_{EFF}$ cells, resting $T_{REG}$ cells, younger T cells (for example, naïve T cells (for example, naïve CD4 or CD8 T cells, naïve gamma/delta T cells), or stem memory T cells (for example, stem memory CD4 or CD8 T cells, or stem memory gamma/delta T cells), or early memory T cells, or a combination thereof, in a sample (for example, an apheresis sample or a manufactured CAR-expressing cell product sample);

(ii) the level or activity of one, two, three, or more (for example, all) of activated $T_{EFF}$ cells, activated $T_{REG}$ cells, older T cells (for example, older CD4 or CD8 cells), or late memory T cells, or a combination thereof, in a sample (for example, an apheresis sample or a manufactured CAR-expressing cell product sample);

(iii) the level or activity of an immune cell exhaustion marker, for example, one, two or more immune checkpoint inhibitors (for example, PD-1, PD-L1, TIM-3, TIGIT and/or LAG-3) in a sample (for example, an apheresis sample or a manufactured CAR-expressing cell product sample). In some embodiments, an immune cell has an exhausted phenotype, for example, co-expresses at least two exhaustion markers, for example, co-expresses PD-1 and TIM-3. In other embodiments, an immune cell has an exhausted phenotype, for example, co-expresses at least two exhaustion markers, for example, co-expresses PD-1 and LAG-3;

(iv) the level or activity of CD27 and/or CD45RO− (for example, CD27+CD45RO−) immune effector cells, for example, in a CD4+ or a CD8+ T cell population, in a sample (for example, an apheresis sample or a manufactured CAR-expressing cell product sample);

(v) the level or activity of one, two, three, four, five, six, seven, eight, nine, ten, eleven or all of the biomarkers chosen from CCL20, IL-17a, IL-6, PD-1, PD-L1, LAG-3, TIM-3, CD57, CD27, CD122, CD62L, KLRG1;

(vi) a cytokine level or activity (for example, quality of cytokine reportoire) in a CAR-expressing cell product sample, for example, CLL-1-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (for example, a population) of CAR-expressing immune effector cells, for example, a plurality (for example, a population) of T cells or NK cells, or a combination thereof. In some embodiments, the CAR-expressing cell therapy is a CD19 CAR therapy.

In some embodiments of any of the methods disclosed herein, the measure of one or more of the parameters disclosed herein is obtained from an apheresis sample acquired from the subject. The apheresis sample can be evaluated prior to infusion or re-infusion.

In some embodiments of any of the methods disclosed herein, the measure of one or more of the parameters disclosed herein is obtained from a tumor sample acquired from the subject.

In some embodiments of any of the methods disclosed herein, the measure of one or more of the parameters disclosed herein is obtained from a manufactured CAR-expressing cell product sample, for example, CD19 CAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of the parameters disclosed herein evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of the parameters disclosed herein.

In some embodiments of any of the methods disclosed herein, a responder, for example, complete responder has, or is identified as having, a greater, for example, a statistically significant greater, percentage of CD8+ T cells compared to a reference value, for example, a non-responder percentage of CD8+ T cells.

In some embodiments of any of the methods disclosed herein, a responder, for example, complete responder has, or is identified as having, a greater percentage of CD27+ CD45RO− immune effector cells, for example, in the CD8+ population, compared to a reference value, for example, a non-responder number of CD27+ CD45RO− immune effector cells.

In some embodiments of any of the methods disclosed herein, a responder, for example, complete responder or a partial responder has, or is identified as having, a greater, for example, a statistically significant greater, percentage of CD4+ T cells compared to a reference value, for example, a non-responder percentage of CD4+ T cells.

In some embodiments of any of the methods disclosed herein, a responder, for example, complete responder has, or is identified as having, a greater percentage of one, two, three, or more (for example, all) of resting $T_{EFF}$ cells, resting $T_{REG}$ cells, younger T cells, or early memory T cells, or a combination thereof, compared to a reference value, for example, a non-responder number of resting $T_{EFF}$ cells, resting $T_{REG}$ cells, younger T cells, or early memory T cells.

In some embodiments of any of the methods disclosed herein, a non-responder has, or is identified as having, a greater percentage of one, two, three, or more (for example, all) of activated $T_{EFF}$ cells, activated $T_{REG}$ cells, older T cells (for example, older CD4 or CD8 cells), or late memory T cells, or a combination thereof, compared to a reference value, for example, a responder number of activated $T_{EFF}$ cells, activated $T_{REG}$ cells, older T cells (for example, older CD4 or CD8 cells), or late memory T cells.

In some embodiments of any of the methods disclosed herein, a non-responder has, or is identified as having, a greater percentage of an immune cell exhaustion marker, for example, one, two or more immune checkpoint inhibitors (for example, PD-1, PD-L1, TIM-3, TIGIT, and/or LAG-3). In some embodiments, a non-responder has, or is identified as having, a greater percentage of PD-1, PD-L1, or LAG-3 expressing immune effector cells (for example, CD4+ T cells and/or CD8+ T cells) (for example, CAR-expressing CD4+ cells and/or CD8+ T cells) compared to the percentage of PD-1 or LAG-3 expressing immune effector cells from a responder.

In some embodiments, a non-responder has, or is identified as having, a greater percentage of immune cells having an exhausted phenotype, for example, immune cells that co-express at least two exhaustion markers, for example, co-expresses PD-1, PD-L1 and/or TIM-3. In other embodiments, a non-responder has, or is identified as having, a greater percentage of immune cells having an exhausted phenotype, for example, immune cells that co-express at least two exhaustion markers, for example, co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (for example, a CLL-1 CAR+ cell population) compared to a responder (for example, a complete responder) to the CAR-expressing cell therapy.

In some embodiments of any of the methods disclosed herein, the responder (for example, the complete or partial responder) has one, two, three or more (or all) of the following profile:

(i) has a greater number of CD27+ immune effector cells compared to a reference value, for example, a non-responder number of CD27+ immune effector cells;

(ii) has a greater number of CD8+ T cells compared to a reference value, for example, a non-responder number of CD8+ T cells;

(iii) has a lower number of immune cells expressing one or more checkpoint inhibitors, for example, a checkpoint inhibitor chosen from PD-1, PD-L1, LAG-3, TIM-3, or KLRG-1, or a combination, compared to a reference value, for example, a non-responder number of cells expressing one or more checkpoint inhibitors; or (iv) has a greater number of one, two, three, four or more (all) of resting $T_{EFF}$ cells, resting $T_{REG}$ cells, naïve CD4 cells, unstimulated memory cells or early memory T cells, or a combination thereof, compared to a reference value, for example, a non-responder number of resting $T_{EFF}$ cells, resting $T_{REG}$ cells, naïve CD4 cells, unstimulated memory cells or early memory T cells.

In embodiments, a subject who is a responder, a non-responder, a relapser or a non-relapser identified by the methods herein can be further evaluated according to clinical criteria. For example, a complete responder has, or is identified as, a subject having a disease, for example, a cancer, who exhibits a complete response, for example, a complete remission, to a treatment. A complete response may be identified, for example, using the NCCN Guidelines®, or the International Workshop on Chronic Lymphocytic Leukemia (iwCLL) 2018 guidelines as disclosed in Hallek M et al., Blood (2018) 131:2745-2760 "iwCLL guidelines for diagnosis, indications for treatment, response assessment, and supportive management of CLL," the entire contents of which are hereby incorporated by reference in its entirety. A partial responder has, or is identified as, a subject having a disease, for example, a cancer, who exhibits a partial response, for example, a partial remission, to a treatment. A partial response may be identified, for example, using the NCCN Guidelines®, or iwCLL 2018 criteria as described herein. A non-responder has, or is identified as, a subject having a disease, for example, a cancer, who does not exhibit a response to a treatment, for example, the patient has stable disease or progressive disease. A non-responder may be identified, for example, using the NCCN Guidelines®, or iwCLL 2018 criteria as described herein.

Alternatively, or in combination with the methods disclosed herein, responsive to said value, performing one, two, three four or more of:

- administering for example, to a responder or a non-relapser, a CAR-expressing cell therapy;
- administered an altered dosing of a CAR-expressing cell therapy;
- altering the schedule or time course of a CAR-expressing cell therapy;
- administering, for example, to a non-responder or a partial responder, an additional agent in combination with a CAR-expressing cell therapy, for example, a checkpoint inhibitor, for example, a checkpoint inhibitor described herein;
- administering to a non-responder or partial responder a therapy that increases the number of younger T cells in the subject prior to treatment with a CAR-expressing cell therapy;
- modifying a manufacturing process of a CAR-expressing cell therapy, for example, enriching for younger T cells prior to introducing a nucleic acid encoding a CAR, or increasing the transduction efficiency, for example, for a subject identified as a non-responder or a partial responder;
- administering an alternative therapy, for example, for a non-responder or partial responder or relapser; or
- if the subject is, or is identified as, a non-responder or a relapser, decreasing the $T_{REG}$ cell population and/or $T_{REG}$ gene signature, for example, by one or more of CD25 depletion, administration of cyclophosphamide, anti-GITR antibody, or a combination thereof.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Generation of CARTs with Cytokine Stimulation

Summary

This example describes a CART manufacturing process called "cytokine process." In some embodiments, cells (for example, T cells) are seeded in media (for example, serum-containing media, for example, media containing 2% serum). One or more cytokines (for example, one or more cytokines chosen from IL-2, IL-7, IL-15 (for example, hetIL-15 (IL15/sIL-15Ra)), IL-21, or IL-6 (for example, IL-6/sIL-6Ra) as well as vectors (for example, lentiviral vectors) encoding a CAR are added to the cells. After incubation for 20-24 hours, cells are washed, formulated, and cryopreserved. Exemplary cytokine process is shown in FIG. 1A.

Compared to the traditional CART manufacturing process, this revised process eliminates CD3/CD28 stimulation as well as ex vivo T cell expansion. Without wishing to be bound by theory, anti-CD3/anti-CD28 beads drive differentiation into central memory cells; and in contrast, cytokines such as IL-15, IL-21, and IL-7 may help preserve the undifferentiated phenotype of transduced CD3+ T cells. As a consequence, the cytokine process which does not involve CD3/CD28 activation may generate CART cells with a higher percentage of naïve/stem T cells, compared to CART cells generated using the traditional approach.

Methods

After obtaining an apheresis within 24 hours of collection, T cells were purified and the purity of the T-cells obtained was assessed by flow cytometry. The T cells were frozen and placed in the liquid nitrogen until required for use.

Alternatively, a cryopreserved apheresis sample is prepared and enriched for CD4+ T cells and/or CD8+ T cells using a Prodigy® machine.

IL-7 and IL-15 were prepared at 1,000 folds of the final concentration required. IL-2 was prepared by a 10-fold dilution in media.

TABLE 19

Cytokine conditions

| | Conditions |
|---|---|
| 1. | IL2 |
| 2. | IL-7 |
| 3. | IL-15 |
| 4. | IL2 + IL7 |
| 5. | IL-7 + IL-15 |
| 6. | IL2 + IL-15 |
| 7. | Beads + IL2 |
| 8. | Beads + IL15 |

In the expander bead stimulated conditions, calculations were performed to plate cells with a final concentration of bead to cell ratio of 3:1. The Dynabeads® magnetic beads were washed twice using a Dynamag® and resuspended in the required volume of media for the experiment. The washed beads were added to the tubes that contained the specific cytokines and cells.

At the time of plating, the cells were transduced with a lentiviral vector with a multiplicity of infection (MOI) of 1. The specific volume of vector to be transduced was calculated based on the multiplicity of infection (MOI) and concentration (titer) of the vector lot in use. The titer and the MOI were measured based on primary T cell lines.

In the conditions where cytokines alone were utilized for stimulation, the cells were resuspended post wash at a concentration of 1E7/ml and added to a conical tube that already contained the cytokines depending on the condition (Table 19). After the cells and cytokines were added the lentiviral vector was added followed by the media.

In all of the conditions the cells were mixed and 1 ml was plated in 14 wells of a 24 well plate. The cells were placed in an incubator that was at 37° C. and 5% $CO_2$.

On the following day the cells were harvested, the concentration and viability of the cells was noted. Their function was measured using a cytotoxicity and proliferation (EDU) incorporation assay. These cells were referred to as "day 1 CARTs."

The cells were immunophenotyped for T cell differentiation status and transduction of the CAR was assessed using flow cytometry. The cells were washed, viability dye was added followed by the antibody cocktail (Table 20), and the plates were incubated for 20 minutes at room temperature. After the incubation, the cells were washed twice and fixed prior to being analyzed on the BD fortessa.

TABLE 20

| Antigens of the panel of antibodies used to determine the differentiation status of the T-cells<br>Antigen |
|---|
| Viability |
| CD3 |
| CD4 |
| CD8 |
| HLADR |
| CD28 |
| CD45RO |
| CD95 |
| CCR7 |
| Anti-Idiotype |

To determine if the day 1 CARTs still maintained the ability to expand post-harvest, 5e6 cells/condition were expanded using CD3/CD28 beads in a T25 flask at a ratio of 3:1 (beads to cells). The Dynabeads® magnetic beads were washed as previously described. The media contained no cytokines. The cells were placed in an incubator that was at 37° C. and 5% $CO_2$.

In the case of the T cells expanded with the CD3/CD28 beads every 2 days, the cells were counted and spilt up to 10 days in culture. On day 10 the cells were harvested, counted, immunophenotyped using the differentiation panel (Table 20) and frozen in Cryostor 10™. The cells were thawed for functional assays that included cytotoxicity assay, proliferation assay and cytokine secretion assay.

The cells expanded in the presence of CD3/CD28 beads in vitro for 10 days were referred to as "day 10 CARTs."

Results

Figure 1B:
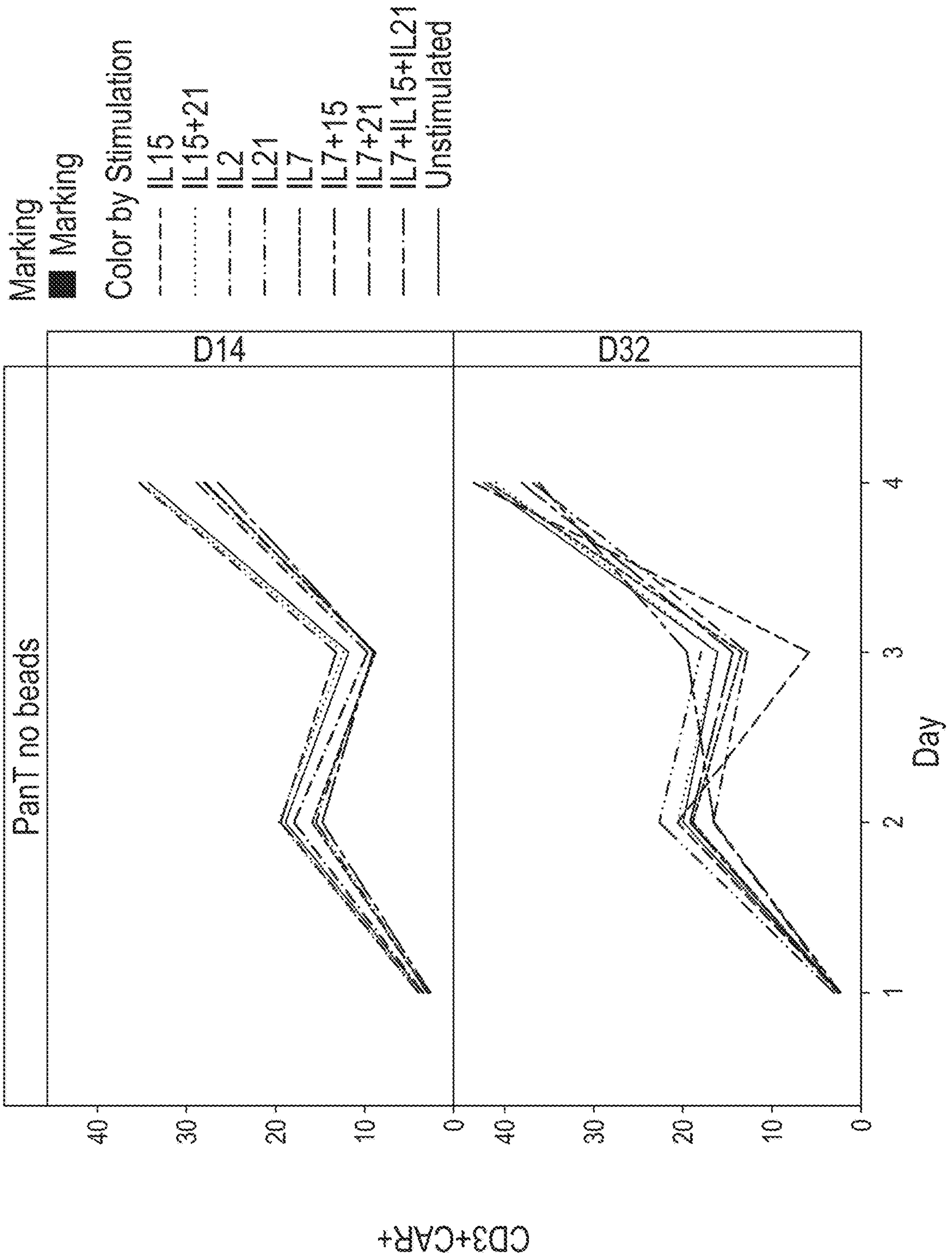
Figure 1C:
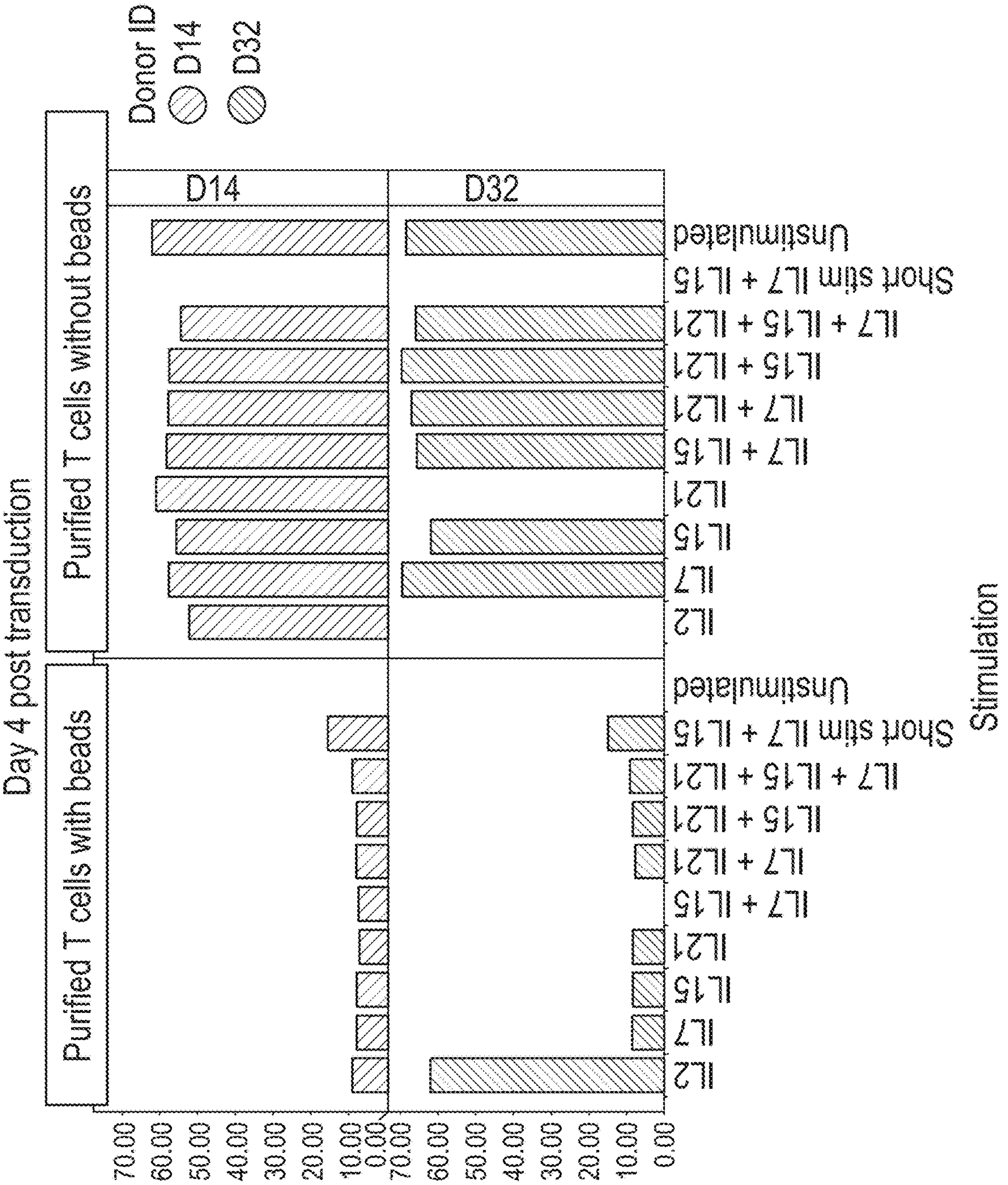
Figure 1D:
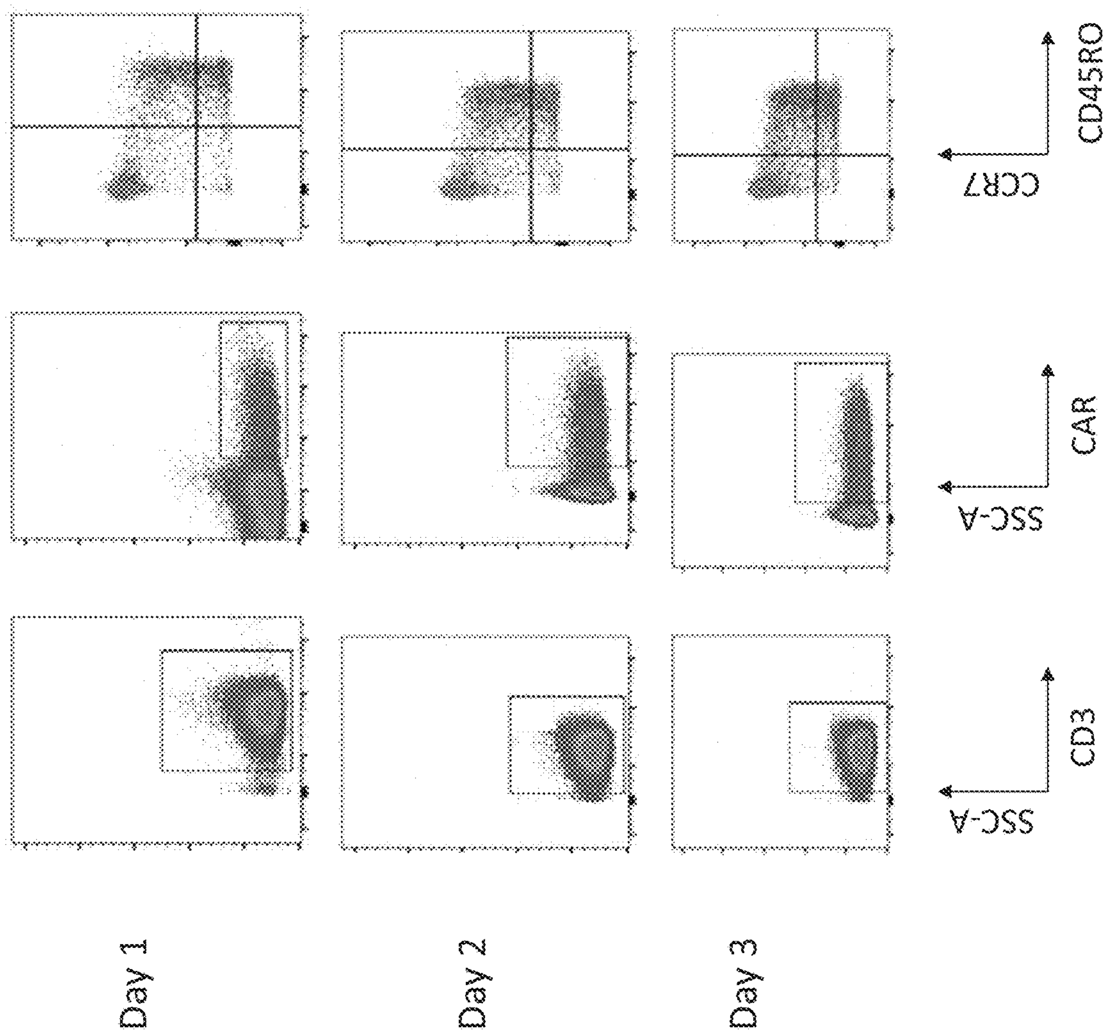
Figure 1E:
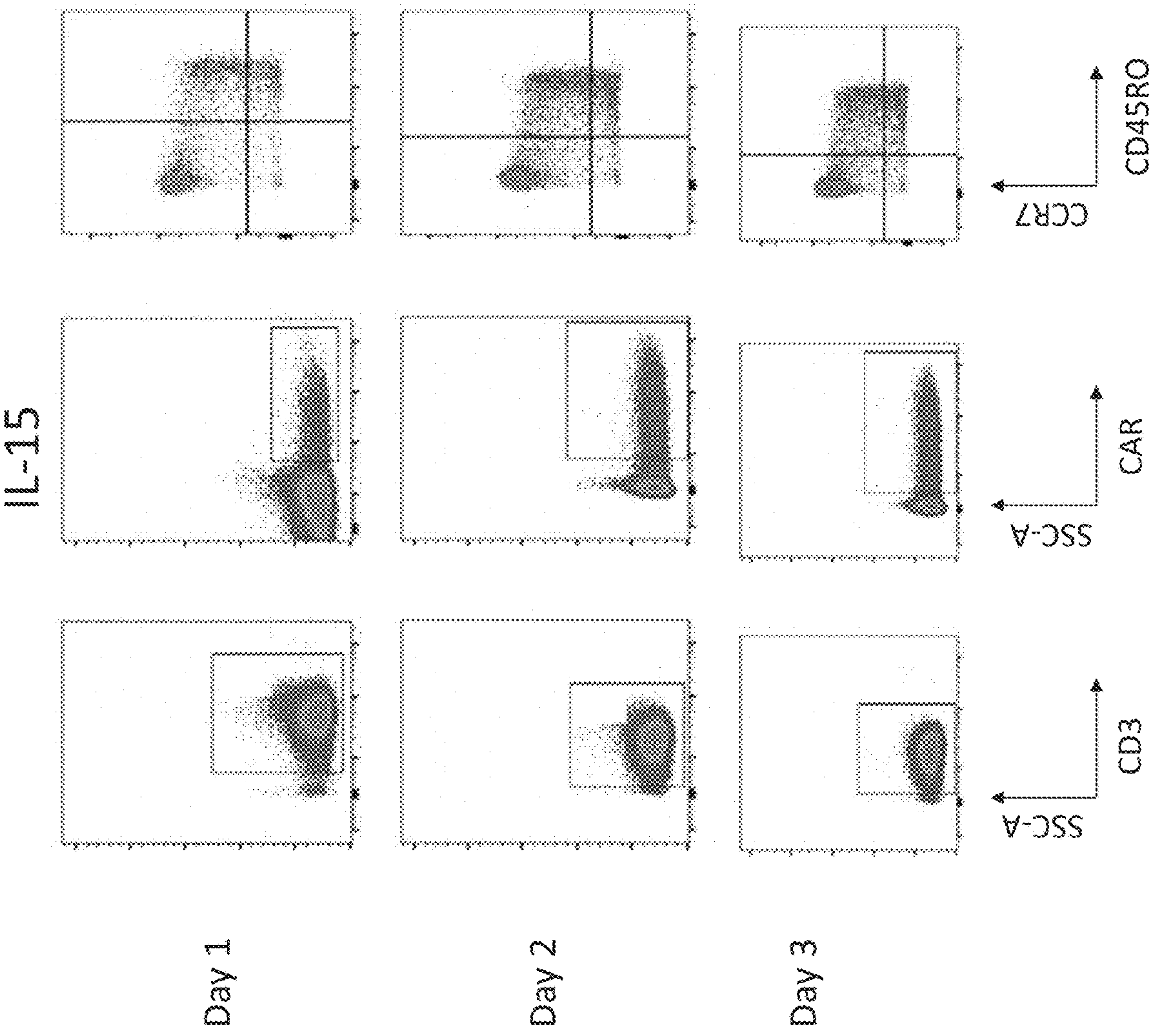
Figure 1F:
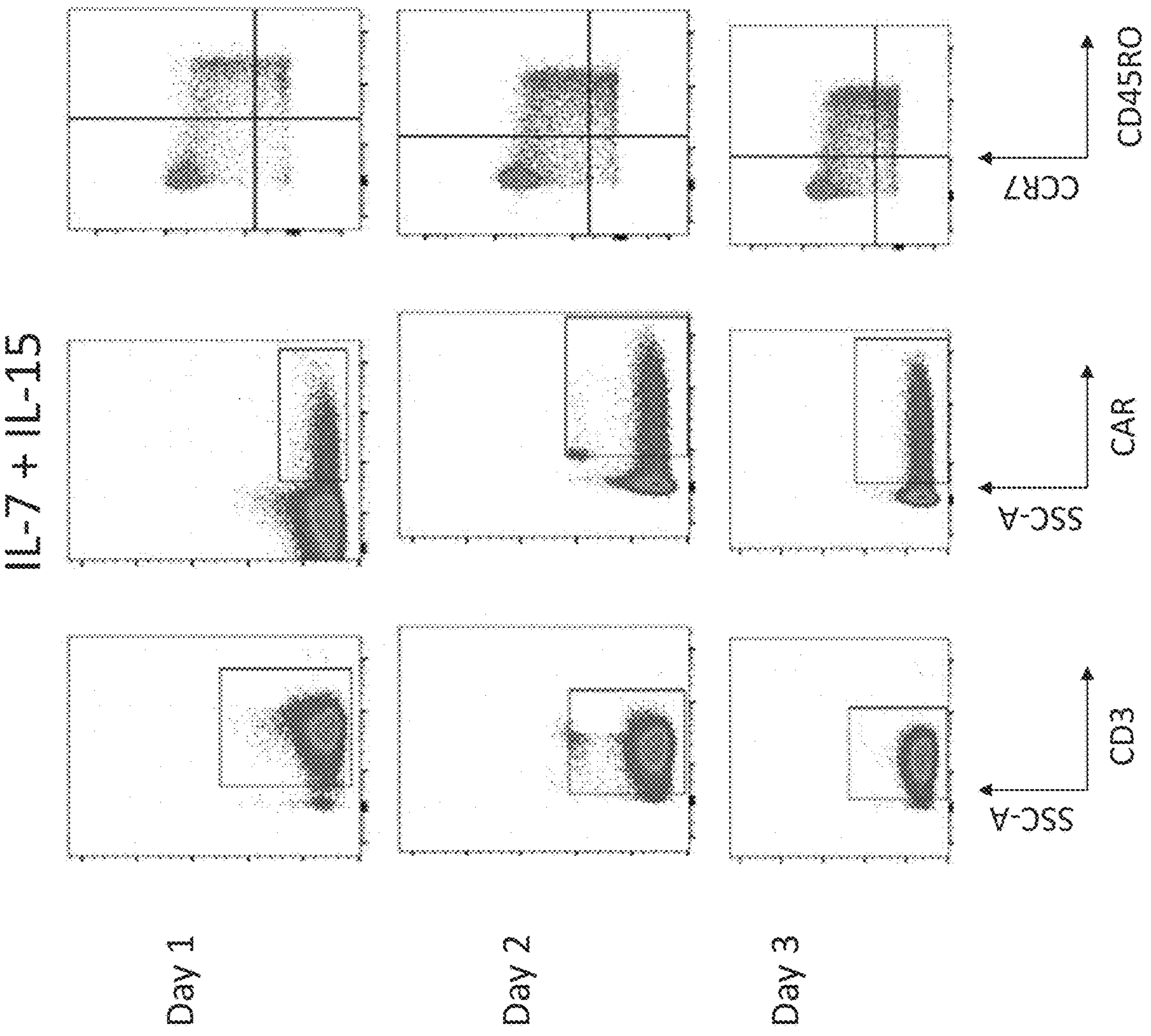
Figure 1G:
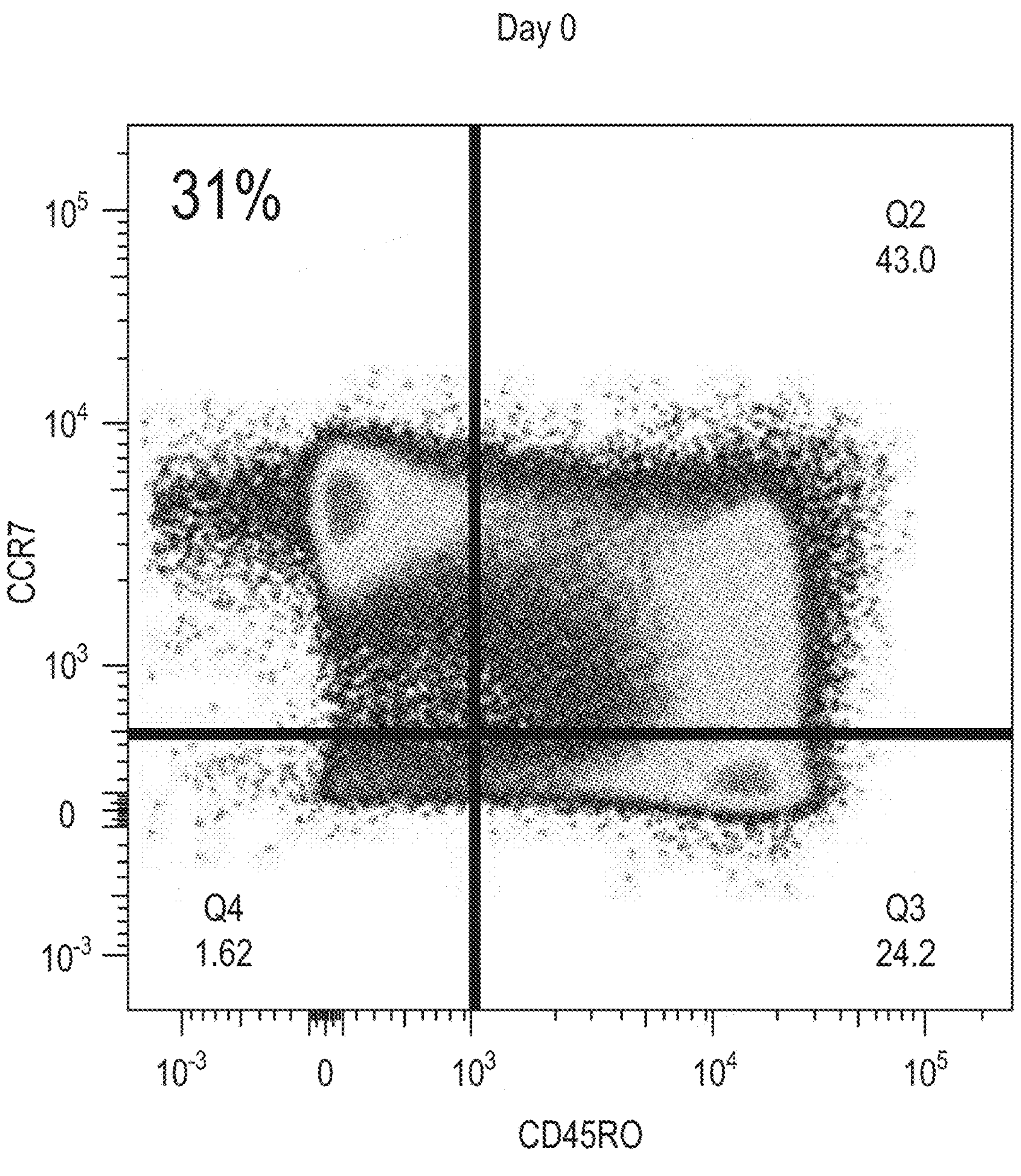
Figure 1G:
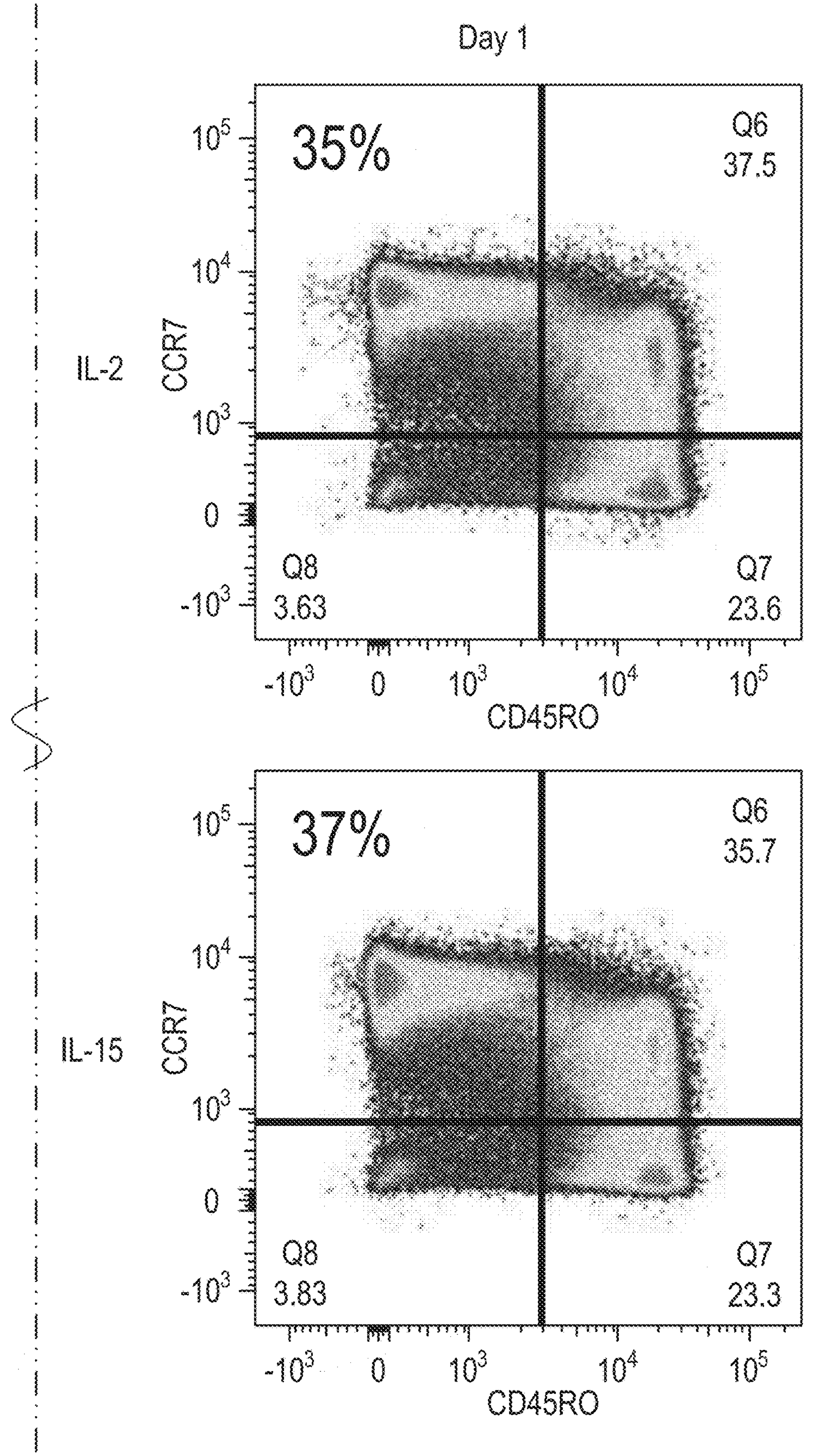
Figure 1H:
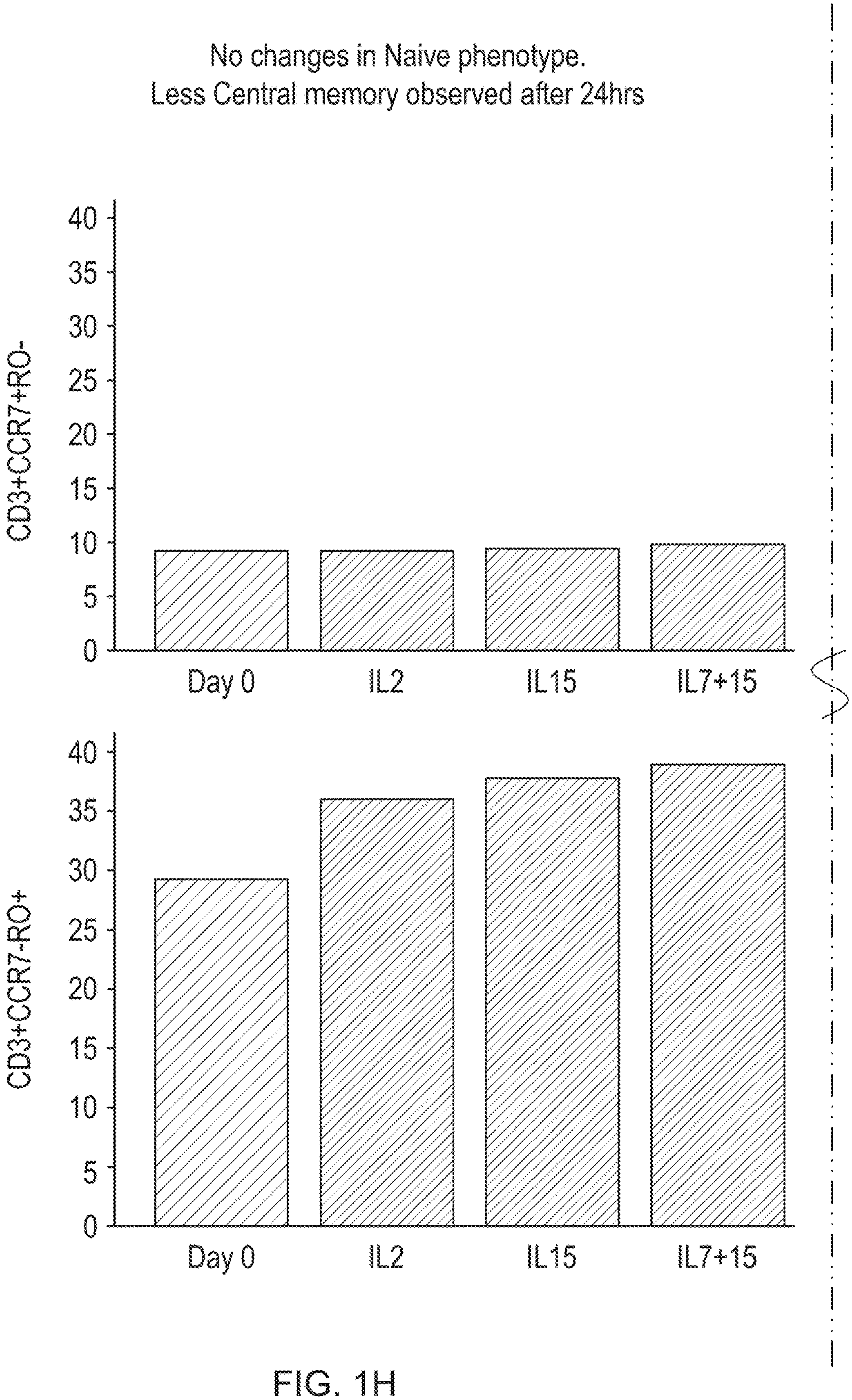
Figure 1I:
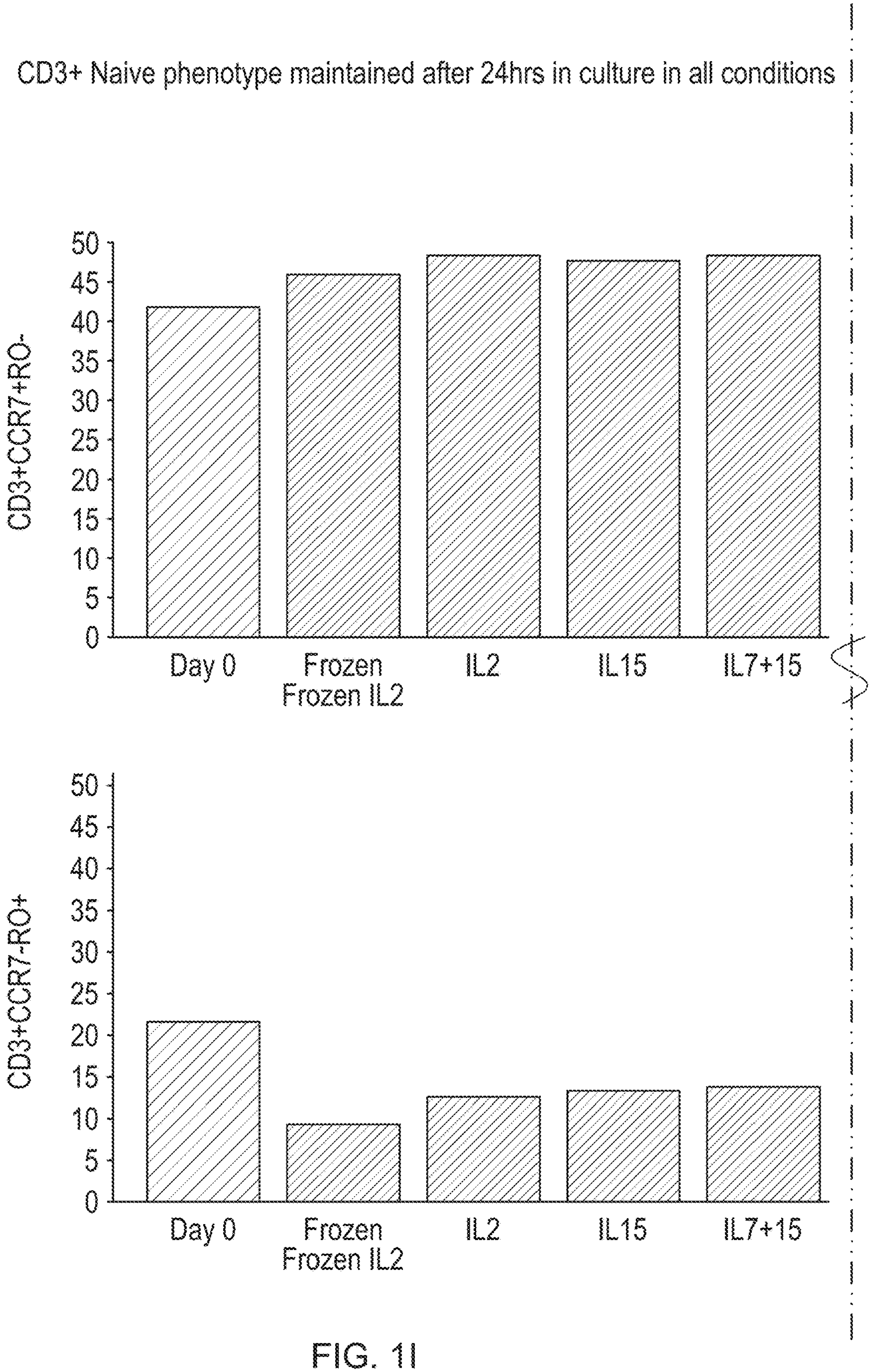

When purified T cells were incubated with cytokines in the absence of any other activation stimulus, there was an increase in transduction from day 1 to day 4 (FIG. 1B). Independent of the time point and cytokine condition, the predominant population within the CAR positive population was naïve (FIGS. 1D, 1E, and 1F). The elimination of the activation agent led to an enhancement of transduction with the primitive population. Notably, exposure to IL-2 or IL-15 maintained self-renewing T cells in vitro (FIG. 1G). Similar phenomenon was observed under the other cytokine treatments tested (IL-7; IL2+IL7; IL-7+IL-15; and IL2+IL-15) (data not shown). The cytokine process (using IL2 or IL-15 in this specific example) maintained or slightly increased the percentage of CD45RO−CCR7+ cells (FIG. 1G). Similar data are shown in FIGS. 1H and 1I for IL-2, IL-15, and a combination of IL-7 and IL-15. Culturing T cells with the indicated cytokines for 24 hours maintained the naïve phenotype of CD3+ T cells, and reduced the percentage of central memory T cells (FIGS. 1H and 1I).

Figure 2A:
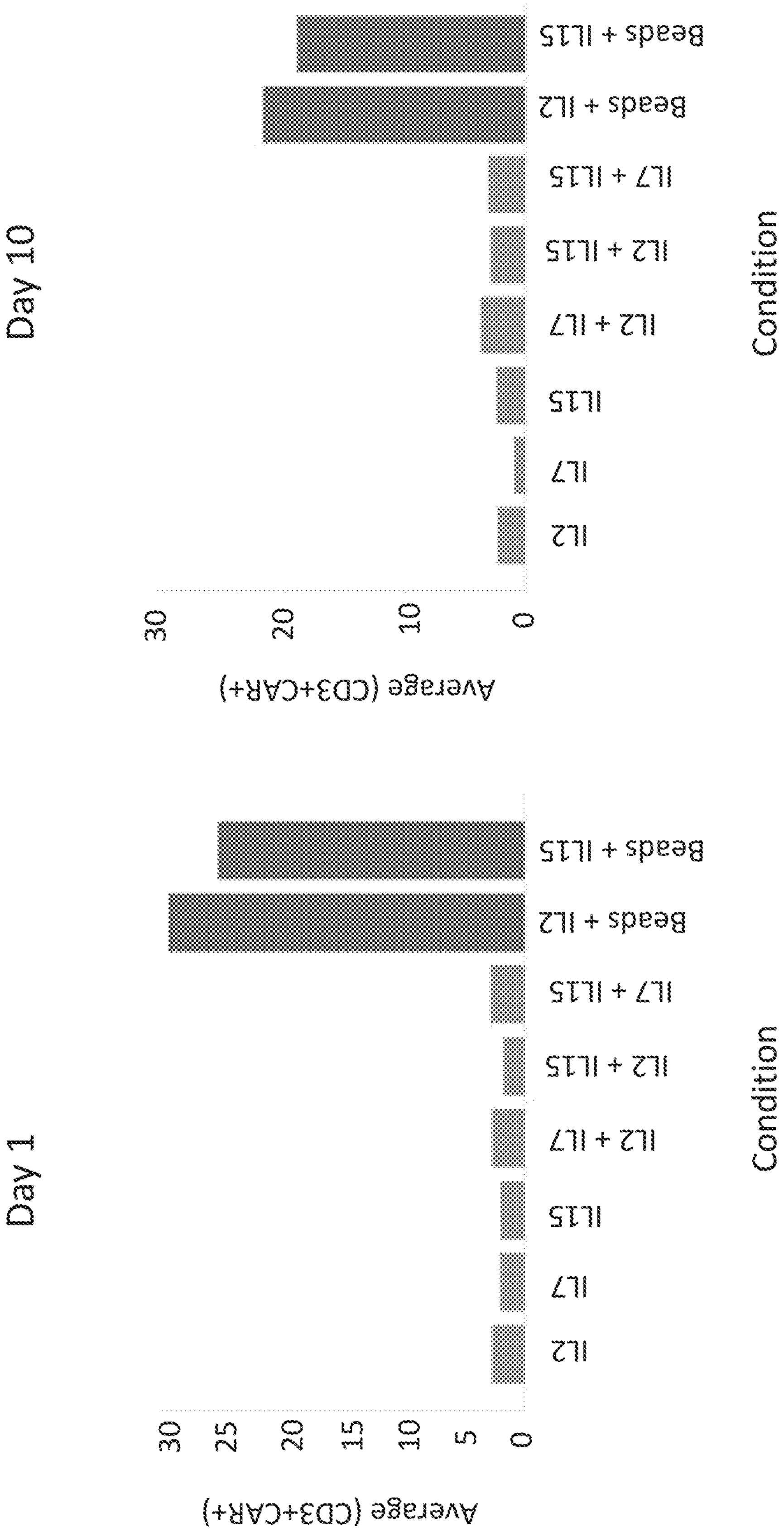
FIGS. 2A-2D: CARTs generated with one day of cytokine stimulation were functional.

To ensure that the transduction observed within 24 hours was stable, the CARTs generated within 24 hours were washed to remove any residual virus and expanded over 10 days using CD3/D28 expansion beads. The expanded cells demonstrated almost equivalent transduction to the day 1 CARTs indicating that the transduction was stable (FIG. 2A).

Figure 2B:
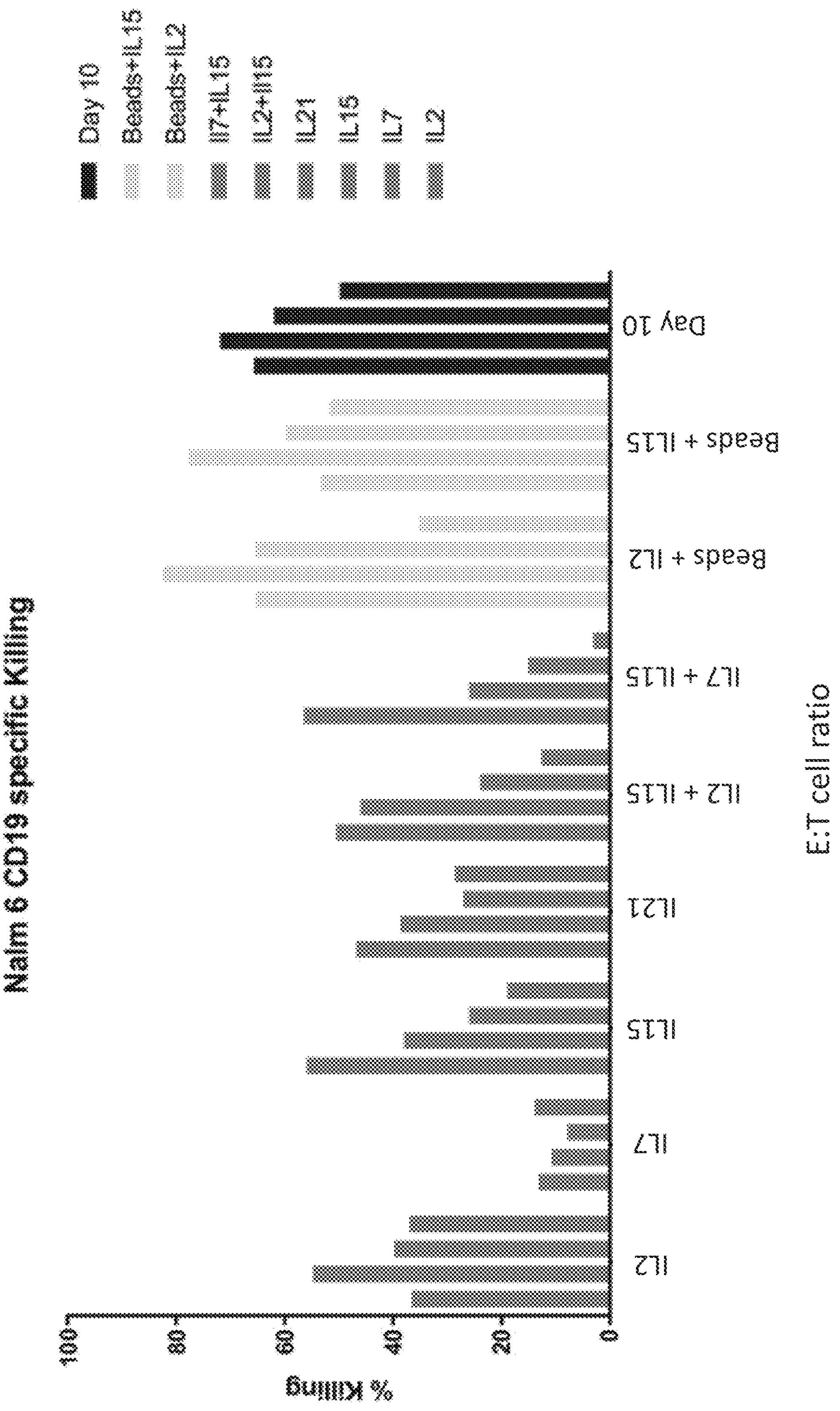
Figure 2C:
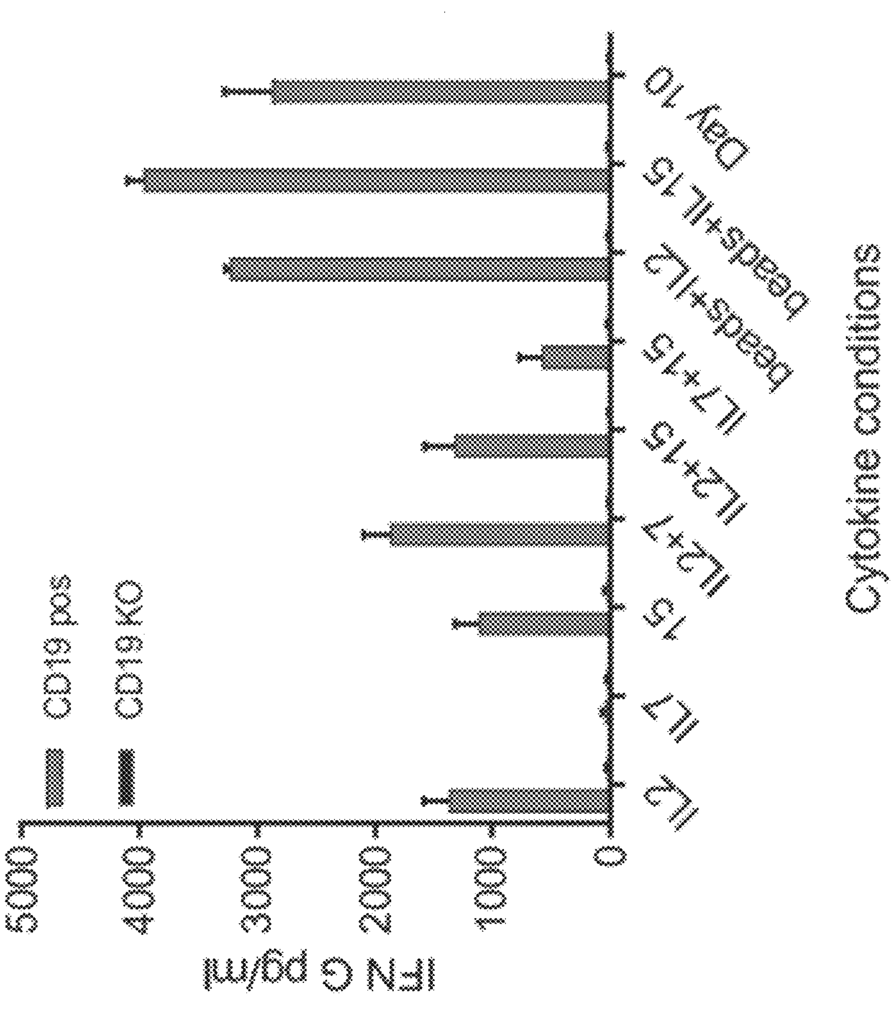
Figure 2D:
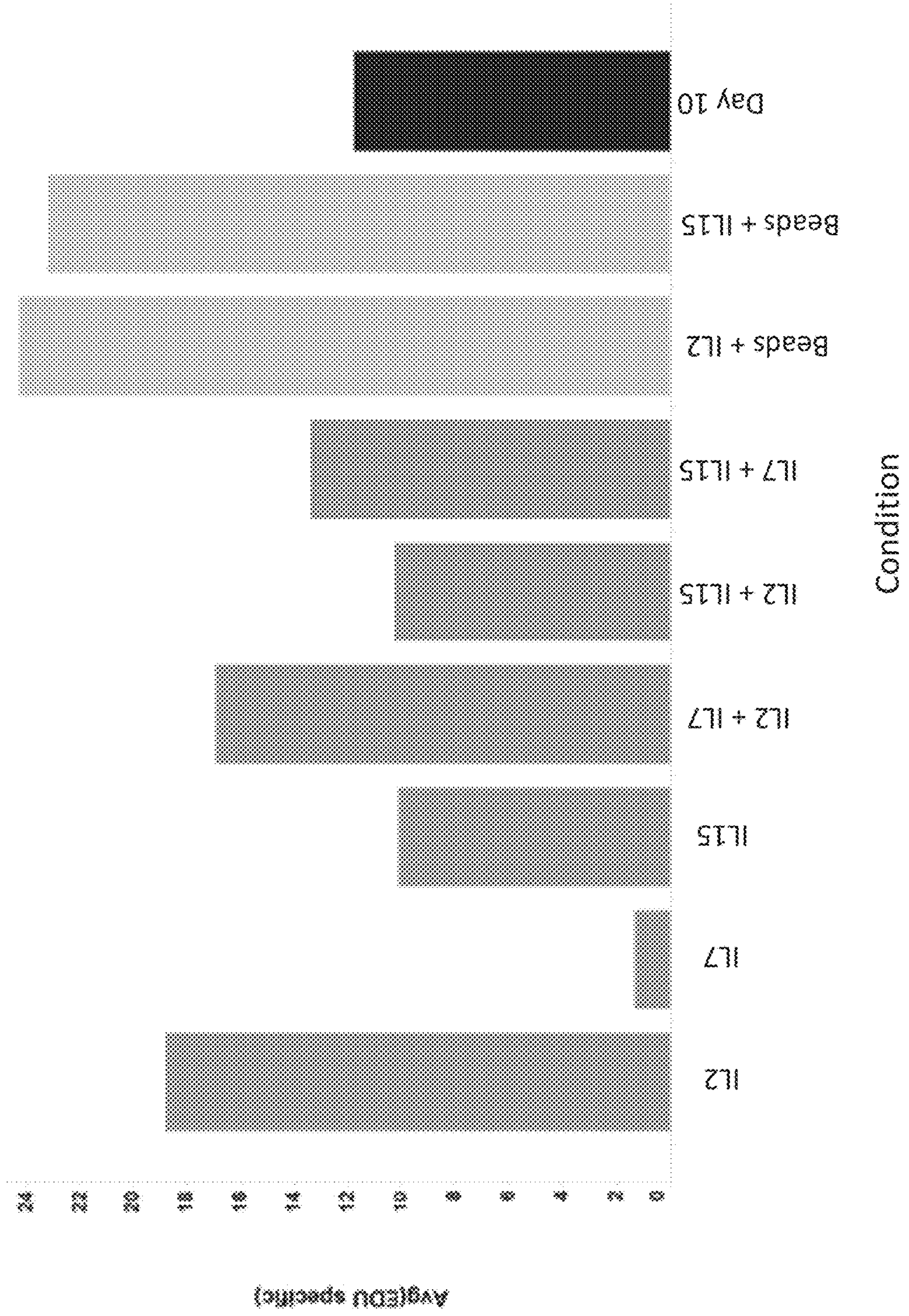

The functionality of the day 1 CARTs and day 10 CARTs was tested using a cytotoxicity, a cytokine release, and a proliferation assay. The target cells were Nalm6 cells, a B cell ALL cell line that expresses CD19. The cytotoxicity assay demonstrated that the day 1 CARTs post expansion were equivalent at killing as compared to the day 10 CARTs (FIG. 2B) even though the day 1 CARTs had much fewer transduced cells. The same day 1 CARTs that had been expanded were compared for the secretion for IFN-gamma and found to have a lower secretion of IFN-gamma as compared to the day 10 CARTs (FIG. 2C), which was likely due to the difference in the number of transduced cells. In separate studies where the day 1 CARTs had a higher level of transduction, they secreted a higher level of IFN-gamma (data not shown). Furthermore, the day 1 CARTs from all the treatment conditions except the IL7-only condition showed similar or higher proliferation than the day 10 CARTs (FIG. 2D). The data shown in FIG. 2D were not normalized for transduction levels.

Figure 3A:
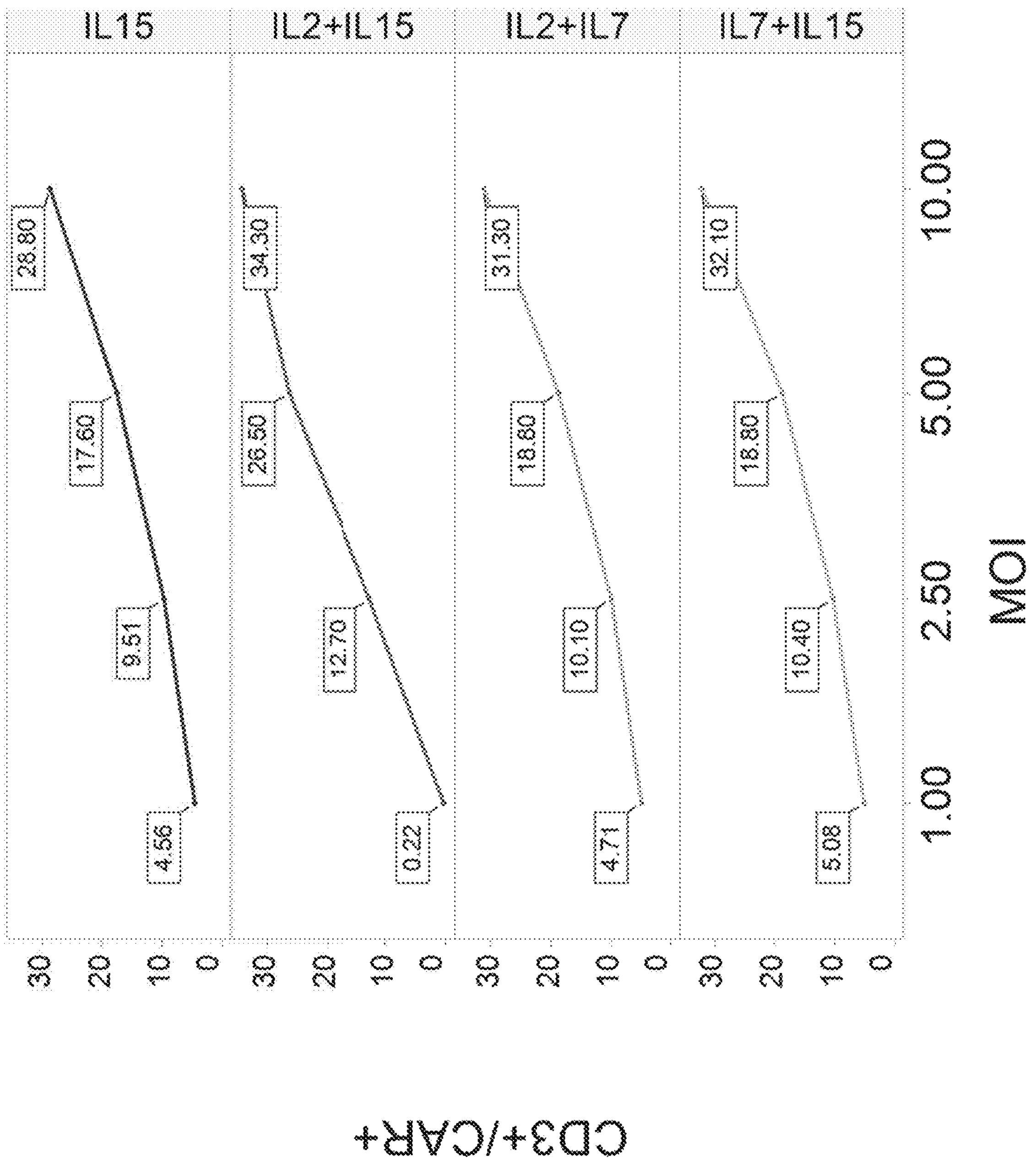
FIGS. 3A-3B: The impact of MOI and media composition on transduction on day 0.

Although stable transduction was observed in the day 10 CARTs, the efficiency was consistently low. A titration of increasing multiplicity of infection (MOI) of the lentiviral vector was tested in four cytokine conditions and in all conditions tested a linear relationship with transduction was observed (FIG. 3A).

Figure 3B:
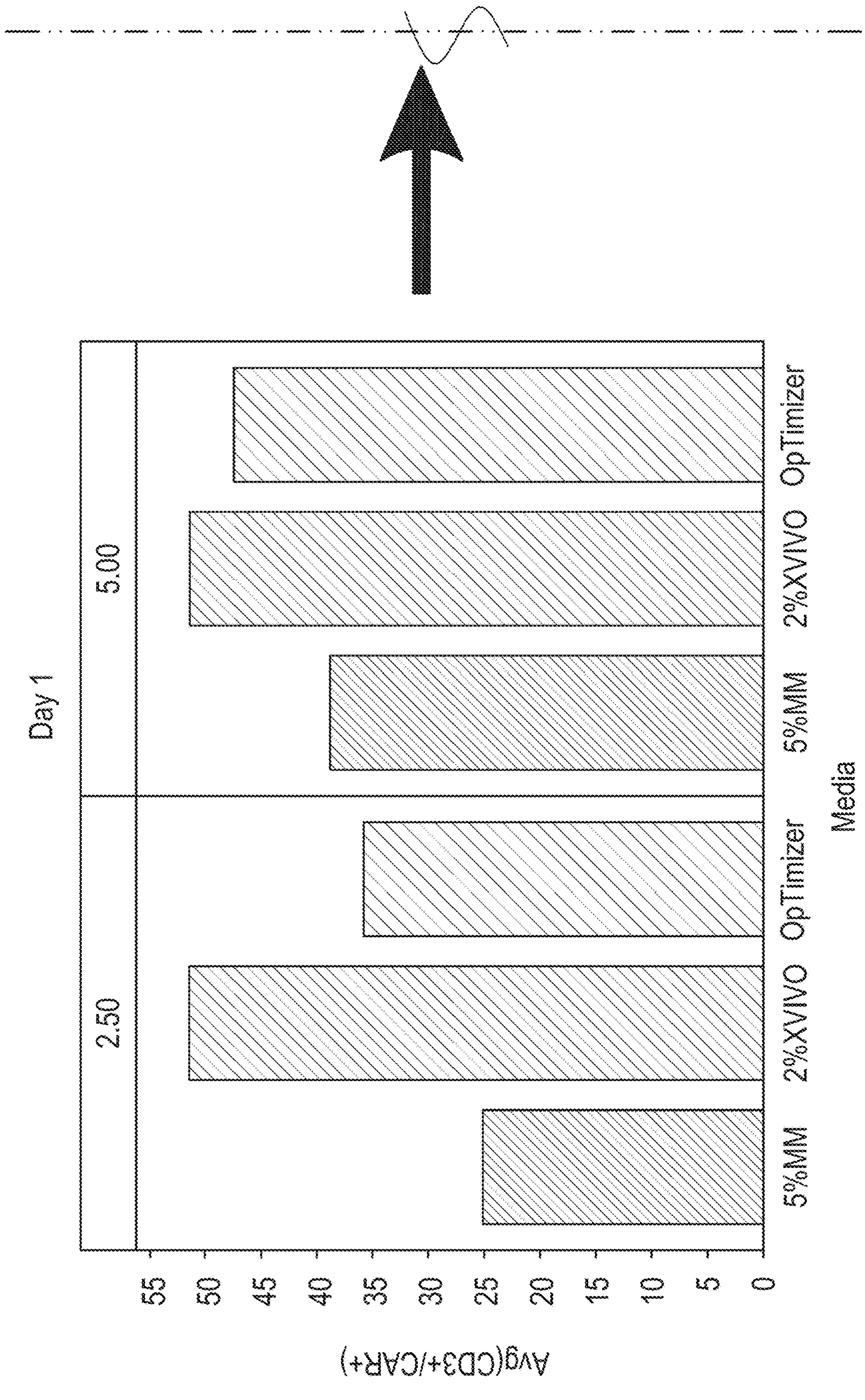
Figure 3B:
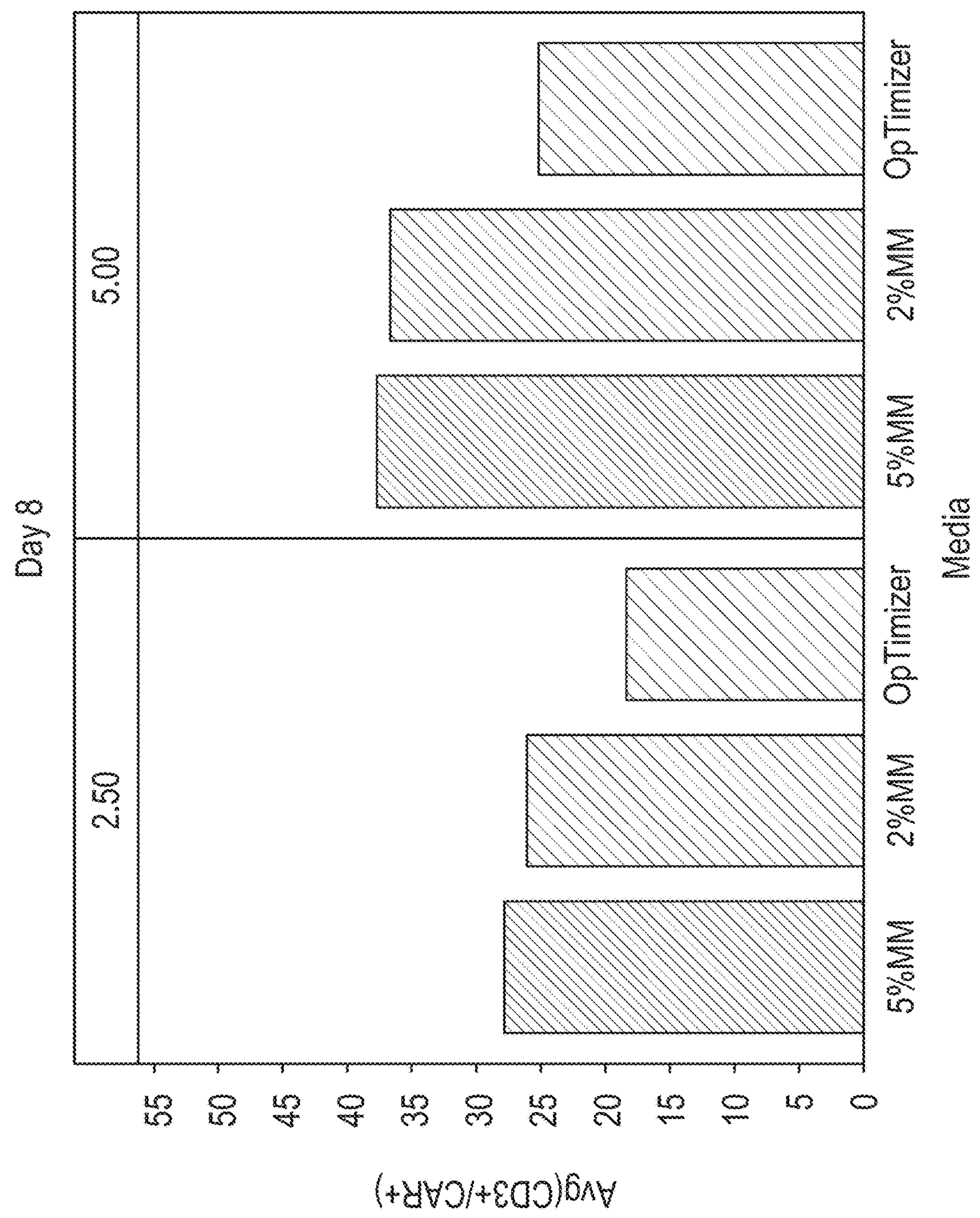

Furthermore, different media compositions (mainly a reduction in serum concentration from 5% to 2% to serum free) were compared to determine whether they impact the transduction efficiency. The reduction in serum to 2% human serum led to the highest transduction efficiency (FIG. 3B). The addition of Glutamax alone was also considered to have a significant impact on transduction efficiency.

Figure 4D:
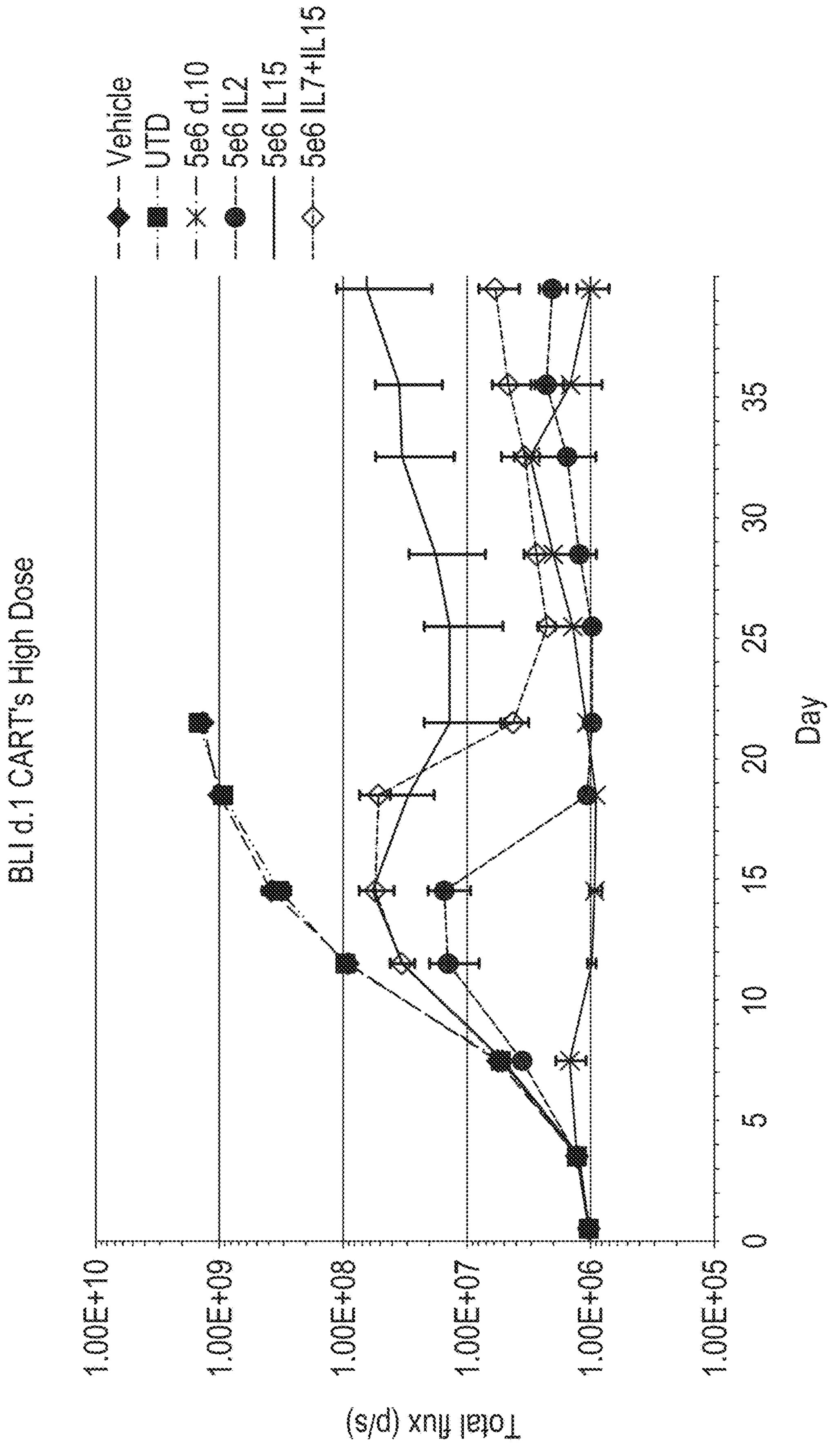

Next, the day 1 CARTs and day 10 CARTs were examined for their anti-tumor activity in vivo using a mouse ALL model. Briefly, day 1 CARTs and day 10 CARTs were manufactured as described above with a viability above 80% (FIGS. 4A and 4B). CARTs were administered in tumor-bearing mice and monitored for expansion in vivo. As shown in FIG. 4C, day 1 CARTs showed a higher level of in vivo expansion than their day 10 counterparts. In particular, CARTs manufactured in the presence of IL-2 showed the highest level of in vivo expansion (FIG. 4C). All the CARTs tested inhibited tumor growth in vivo, although day 1 CARTs showed a delayed kinetics as compared to the day 10 CARTs (FIG. 4D). In this specific donor, the IL2 condition demonstrated the greatest ability to eliminate the tumor in vivo (FIG. 4D).

Figure 5A:
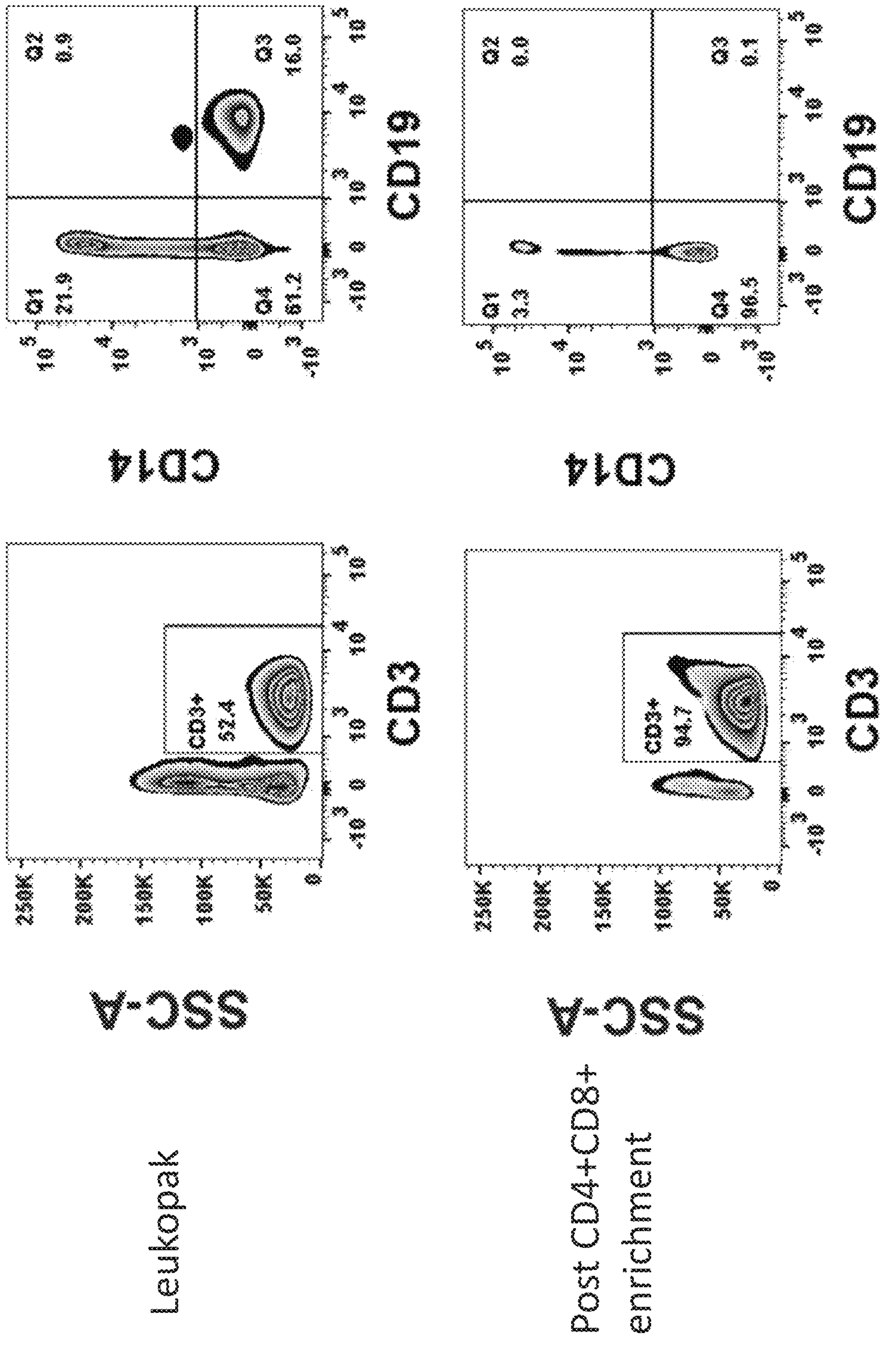
FIGS. 5A-5B: The cytokine process was scalable.
Figure 5B:
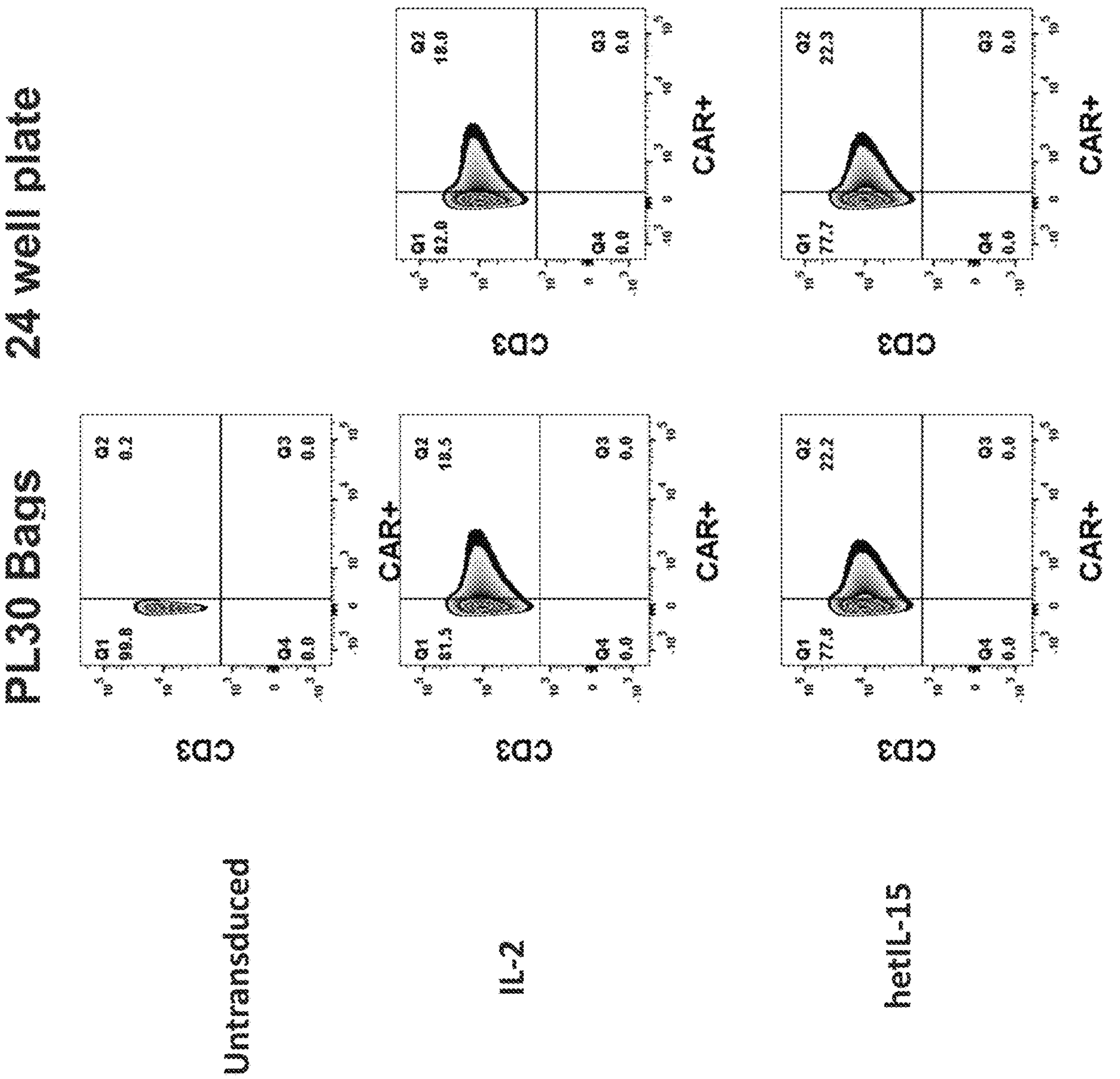

Furthermore, it was tested whether this manufacturing process was scalable. Purified T cells from a frozen apheresis sample were transduced with CAR19 in either a 24 well plate or a PL30 bag post enrichment, in the presence of either IL2 or hetIL-15 (IL15/sIL-15Ra). hetIL-15 has been described in WO 2014/066527, herein incorporated by reference in its entirety, and comprises human IL-15 complexed with a soluble form of human IL-15Ra. Cells were harvested 24 hours later and tested for expression of CAR. As shown in FIG. 5B, there was no impact on transduction observed when the process was scaled from a 24 well plate to a PL30 bag in the presence of either IL2 or hetIL-15.

Example 2: Generation of CARTs with TCR Stimulation

Summary

This example describes a CART manufacturing process called "activation process." In some embodiments, cells (for example, T cells) are seeded in media (for example, serum-free media, for example, OpTmizer™ media) containing IL-2 (for example, OpTmizer™ media containing OpTmizer™ supplement, GlutaMAX and 100 IU/ml of IL-2), placed in a cell culture device, and contacted with anti-CD3/anti-CD28 (for example, TransAct). After 12 hours, a vector (for example, a lentiviral vector) encoding a CAR is added to the cells and the cells are returned to an incubator. At 24 hours from initiation of the cell culture, the cells are harvested, sampled, and formulated. Without wishing to be bound by theory, brief CD3 and CD28 activation, for example, using anti-CD3/anti-CD28 (for example, TransAct), promotes efficient transduction of self-renewing T cells.

In this and other examples, a CART manufacturing process called "traditional manufacturing (TM)" process was used as a control. In some embodiments, T cells are selected from a fresh or cryopreserved leukapheresis sample (for example, using positive or negative selection), activated (for example, using anti-CD3/anti-CD28 antibody coated Dynabeads®), contacted with a nucleic acid molecule encoding a CAR molecule (for example, transduced with a lentiviral vector comprising a nucleic acid molecule encoding the CAR molecule), and expanded in vitro for, for example, 7, 8, 9, 10, or 11 days. An exemplary (TM) process is provided in this example as the methods used to manufacture CAR cells from the d9 control arms.

Methods

In some embodiments, the activation process provided herein starts with a frozen or fresh leukapheresis product. After a sample for counting and QC is obtained, the product is attached to a cell sorting machine (for example, an installed CliniMACS® Prodigy® device kit) and the program begins. The cells are washed and incubated with microbeads that bind to desired surface marker or markers (such as CD3, CD4, CD8, CD27, CD28, CD45RO, CCR7, CD62L, CD14, CD34, CD95, CD19, CD20, CD22, and/or CD56). The bead-labeled cells are selected by passing the cells through a magnetic column. If desired, cells can be further separated by incubating the negative fraction with beads that bind to a second set of surface markers (such as CD3, CD4, CD8, CD27, CD28, CD45RO, CCR7, CD62L, CD14, CD34, CD95, CD19, CD20, CD22, and/or CD56) and again passing the cells through a magnetic separation column. Isolated cells are washed again and the separation buffer is exchanged for cell media. Purified cells then either proceed to culture or are cryopreserved for later use. Cryopreserved cells can be thawed, washed in pre-warmed cell media, and resuspended in cell media. Fresh cells can be added to culture directly. The cells are seeded into membrane bioreactors at 0.4-1.2e6 cells/$cm^2$ of membrane, an activating reagent such as anti-CD3/anti-CD28 beads/polymers, nanoparticles, or nanocolloids (and/or any of the following co-activators alone or in combination: a reagent that stimulates ICOS, CD27, HVEM, LIGHT, CD40, 4-1BB, OX40, DR3, GITR, CD30, TIM1, CD2, or CD226) is added, and cell media is added to a final volume of 0.25-2m1/$cm^2$ of membrane. A vector (for example, a lentiviral vector) encoding the CAR is added immediately or up to 18 hours after culture initiation. The cells are incubated with the vector and the activating reagent described above for a total of 24 hours post culture initiation. Once culture has proceeded for 24 hours, the cells are resuspended mechanically by swirling or pipetting or otherwise agitating, and simulating reagent scaffolds are dissolved with appropriate buffers. The cells are washed to remove unnecessary reagents and reformulated in cryopreservation media. The cells are cryopreserved until needed for administration.

Figure 6A:
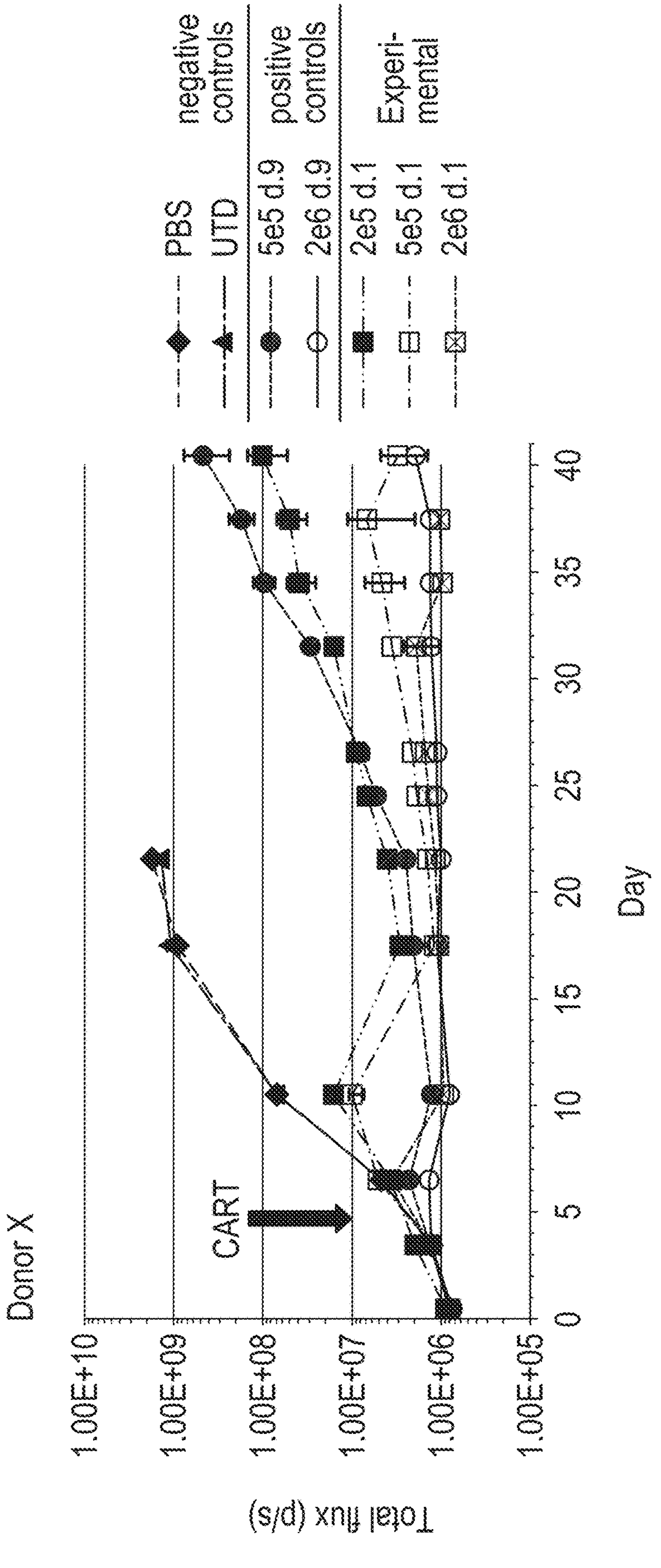
FIGS. 6A-6C: The CARTs manufactured by the activation process showed superior anti-tumor efficacy in vivo.
Figure 6B:
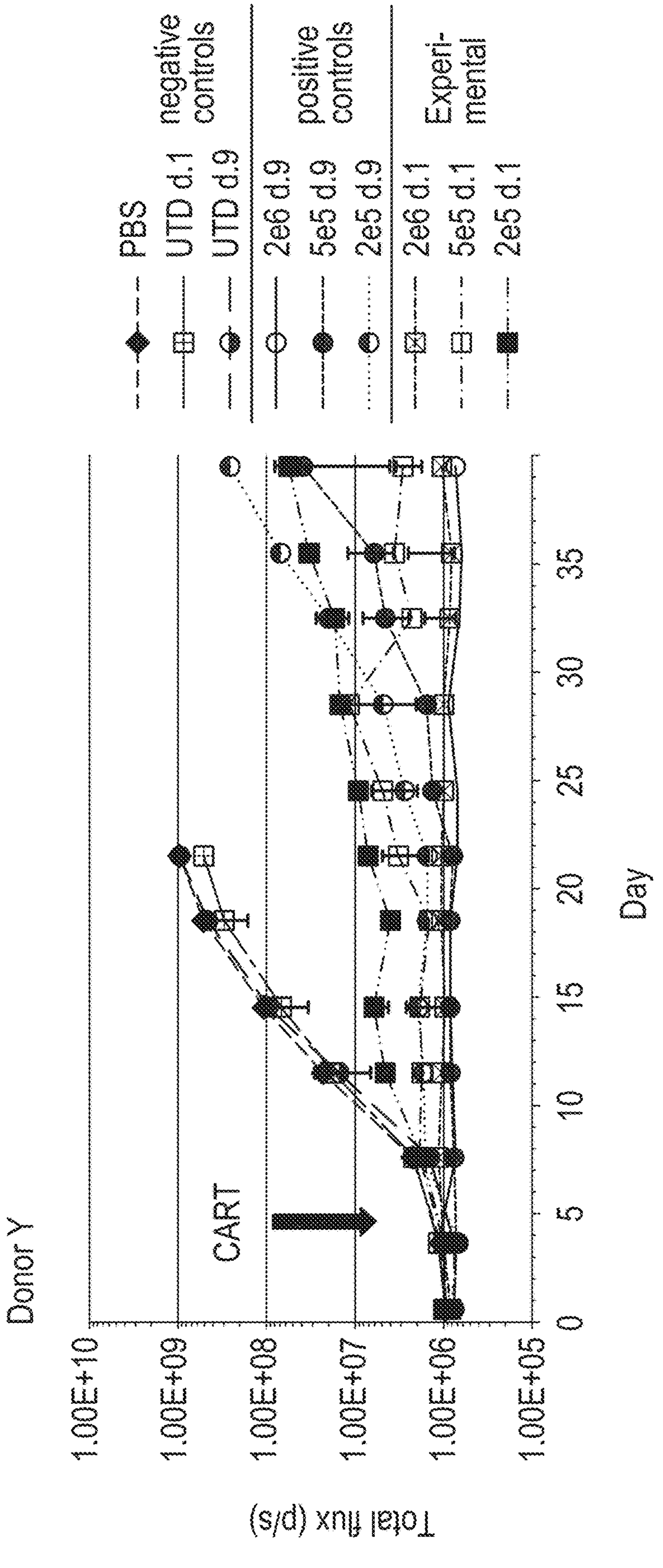
Figure 6C:
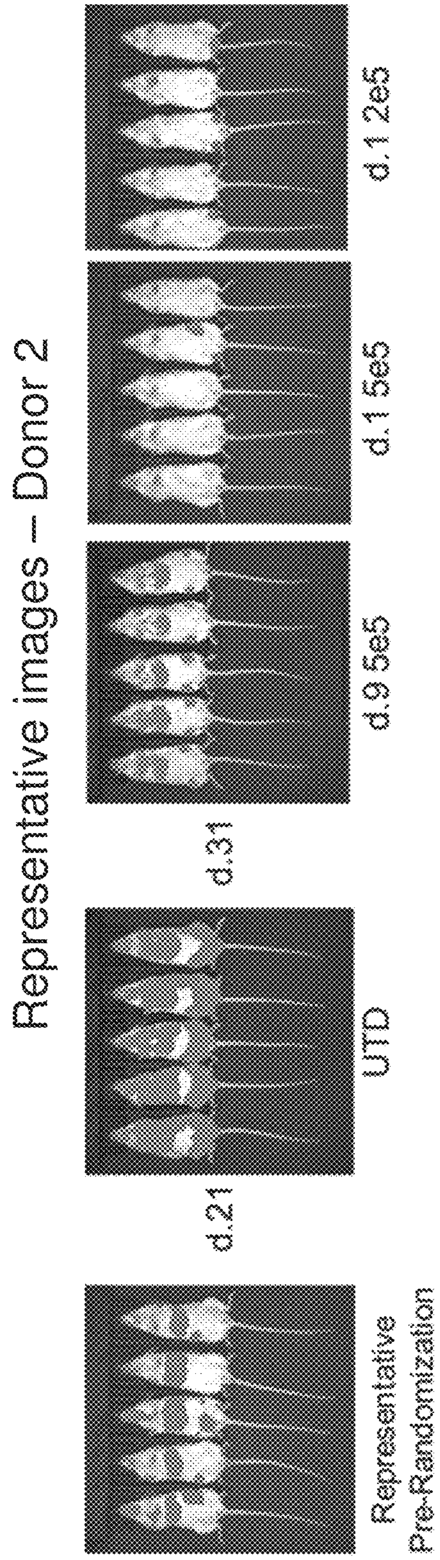

For studies related to FIGS. 6A-6C, the following protocol was used.

Cells were purified from a fresh ¼ leukopack using automated ficoll (Sepax 2, BioSafe) to generate peripheral blood mononuclear cells (PBMC). These PBMCs were further purified using immunomagnetic negative selection (PanT Negative Selection Kit, Miltenyi) to generate CD3 T-cells of high purity (98-100%). These cells were placed in culture with OpTmizer™ (Thermo) complete media (formulated per package insert and supplemented with IL-2 at 100 IU/ml (Proleukin, Prometheus)) and an anti-CD3/CD28 activation reagent at the recommended dose (TransAct, Milenyi) in a membrane bioreactor. Cells were then incubated at 37° C., 5% $CO_2$ for 12 hours for activation. Cells were removed from the incubator and freshly thawed lentiviral vector was added to the cultures at a multiplicity of infection (MOI) of 2.5 tu/cell. Cells were returned to the incubator for another 12 hours for transduction. Cells were harvested, washed twice with media, and formulated directly into sterile PBS (Invitrogen) and injected into NSG mice via the tail vein. Cells from the d9 control arms were grown in flasks (T25-T225, Corning) using RPMI media (Thermo) supplemented with 10% fetal bovine serum (Seradigm) (complete media a.k.a "R10") and anti CD3/28 Expander Dynabeads® (Thermo) at 3 beads per T-cell. Cells were then incubated at 37° C., 5% $CO_2$ for 24 hours for activation. Cells were removed from the incubator and freshly thawed lentiviral vector was added to the cultures at a MOI of 2.5 tu/cell. Cells were returned to the incubator for an additional 7 days, splitting every 2 days to maintain a concentration of 5e5 cells/ml. Expanded cells were transferred to 50m1 centrifuge tubes (Corning) and subjected to two rounds of bead removal using a standing magnet (Dynamag-50, Thermo). Debeaded cells were then washed twice with media, and formulated into CryoStor10 cryomedia (STEMCELL Technologies), cryopreserved using a CoolCell device (BioCision), and kept in vapor phase liquid nitrogen for a minimum of 48 hours. Cells were thawed into pre-warmed R10 media, washed twice with media, then formulated into sterile PBS (Invitrogen) and injected into NSG mice via the tail vein.

6-8 week old NSG mice (NOD.Cg-PrkdcscidIl2rgtm1Wjl/SzJl, Jackson Labs) were injected with luciferized NALM6 tumor cells (ATCC CRL-3273, ATCC) at 1e6 cells/mouse 4 day prior to CART injection without preconditioning. PBS formulated CART cells were injected at 2e6, 5e5, or 2e5 CAR+ cells per NSG or a matched dose of untransduced expanded T-cells or a PBS vehicle control. Mice were monitored by weekly blood draw, bi-weekly luciferase imaging (Xenogen IVIS, PerkinElmer), and bi-weekly weight measurements. All animals were monitored for signs of toxicity (weight loss, moribund) and euthanized if symptomatic. All surviving mice were euthanized at study termination (week 5) and terminal blood, bone marrow, and spleen samples were obtained. Study was performed according to IACUC and all other applicable guidelines.

Results

CART cells were generated using the activation process described above and characterized for their in vivo anti-tumor activity in a mouse ALL model. As shown in FIGS. 6A-6C, CART cells manufactured using the activation process showed strong anti-tumor activity in vivo.

Example 3: IL6R Expression on T Cells and Cytokine Effect on T Cell Expansion Material and Methods T Cell Culture Previously frozen T cells were thawed and contacted with αCD3/αCD28 dynal beads (cell to bead ratio of 1 to 3) in the presence of indicated cytokines at day 0. From day 3, twice more T cell growth media (RPMI1640, 10% FBS, 2 mM L-glutamin, 100 μM non-essential amino acids, 1 mM sodium pyruvate, 10 mM Hepes, 55 μM β-mercaptoethanol, 10% FBS, and 100 U/ml of penicillin-streptomycin) was added to the plate with indicated cytokines (without cytokine, rhIL2 (501 U/ml, Novartis), IL6 (10 ng/ml, R&D systems), IL7 (10 ng/ml, Peprotech), IL15 (10 ng/ml, Peprotech), and IL21 (10 ng/ml, Peprotech)) at day 3, 5, 6, 9, 12, 15, and 18. Cells treated without cytokine, IL6, or IL21 were cultured until day 18 and cells treated with IL2, IL7, or IL15 were cultured until day 25.

Cell Surface Staining

Cells were harvested at indicated time points and then stained with live/dead dye (eFluro780, eBioscience), CD3 (BioLegend, clone #: OKT3), CD4 (BioLegend, clone #: OKT4), CD8 (BD Bioscience, clone #: RPA-T8), CD45RO (BioLegend, clone #: UCHL1), CCR7 (BioLegend, clone #: G043H7), CD27 (BD Horizon, clone #: L128), CD127 (BioLegend, clone #: A019D5), CD57 (BioLegend, clone #: HCD57), CD126 (BioLegend, clone #: UV4), and CD130 (R&D Systems, clone #: 28126) antibodies. The cells were acquired by FACS Fortessa and then FlowJo program was used for data analysis.

Intracellular Cytokine Staining

To examine percent of cytokine producing cells, at day 25, T cells were harvested and then briefly activated with PMA (50 ng/ml, Sigma-Aldrich) and lonomycin (1 μM, Sigma-Aldrich) for 4 hours in the presence of Brefeldin A (BioLegend) at 37° C. incubator. T cells were then stained with live/dead dye (eFluro780, eBioscience), CD3 (BioLegend, clone #: OKT3), CD4 (BioLegend, clone #: OKT4), CD8 (BD Bioscience, clone #: RPA-T8) antibodies followed by fixation and permeabilization. Then, T cells were further stained with antibodies against IFN-γ (BioLegend, clone #: 4S.B3), IL-2 (BioLegend, MQ1-17H12), and TNF-α (BioLegend, Mab11). The cells were acquired by FACS Fortessa and then FlowJo program was used for data analysis.

Results

Figure 7A:
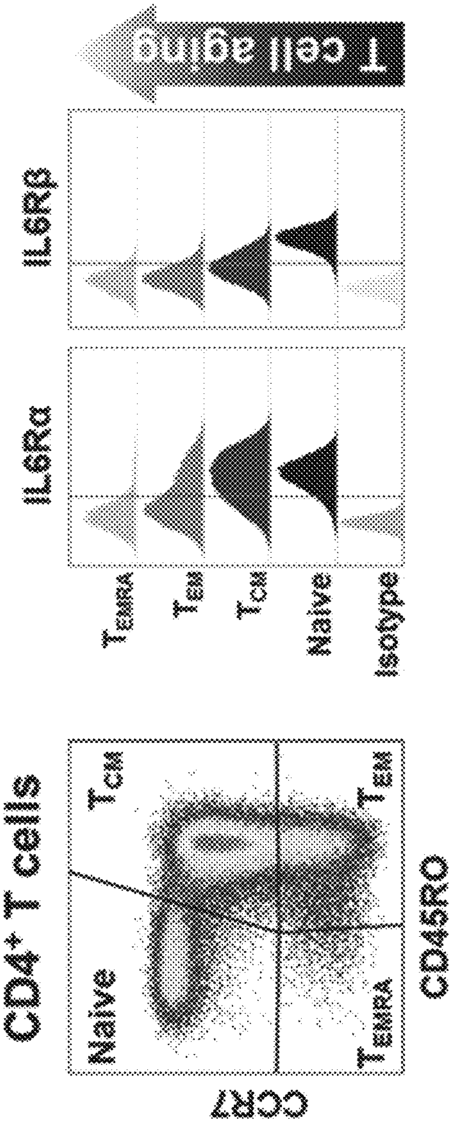
FIGS. 7A-7B: IL6Rα and IL6Rβ expressing cells were enriched in less differentiated T cell population. Fresh T cells were stained for indicated surface antigens and examined for expression levels of IL6Rα and IL6Rβ on CD4 (FIG. 7A) and CD8 (FIG. 7B) T cell subsets.
Figure 7B:
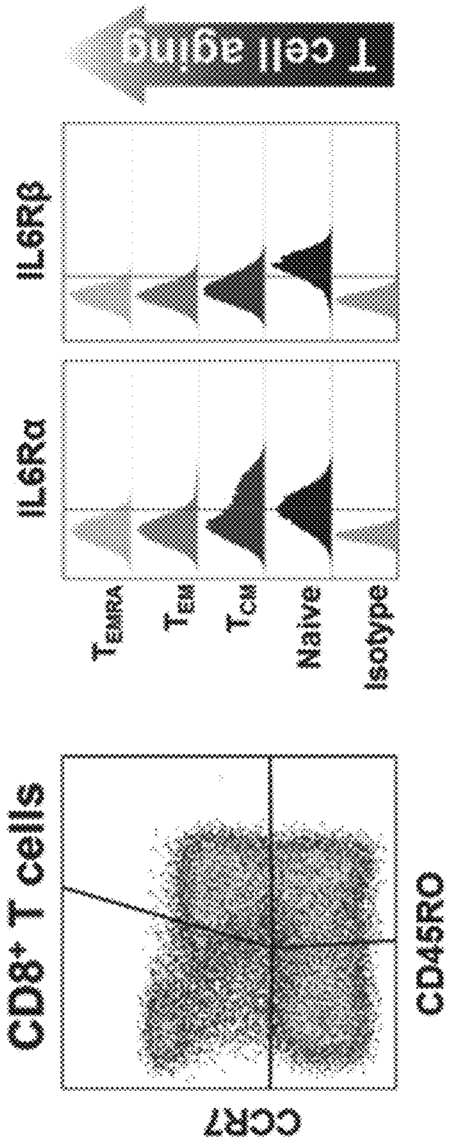
Figures 8A, 8B:
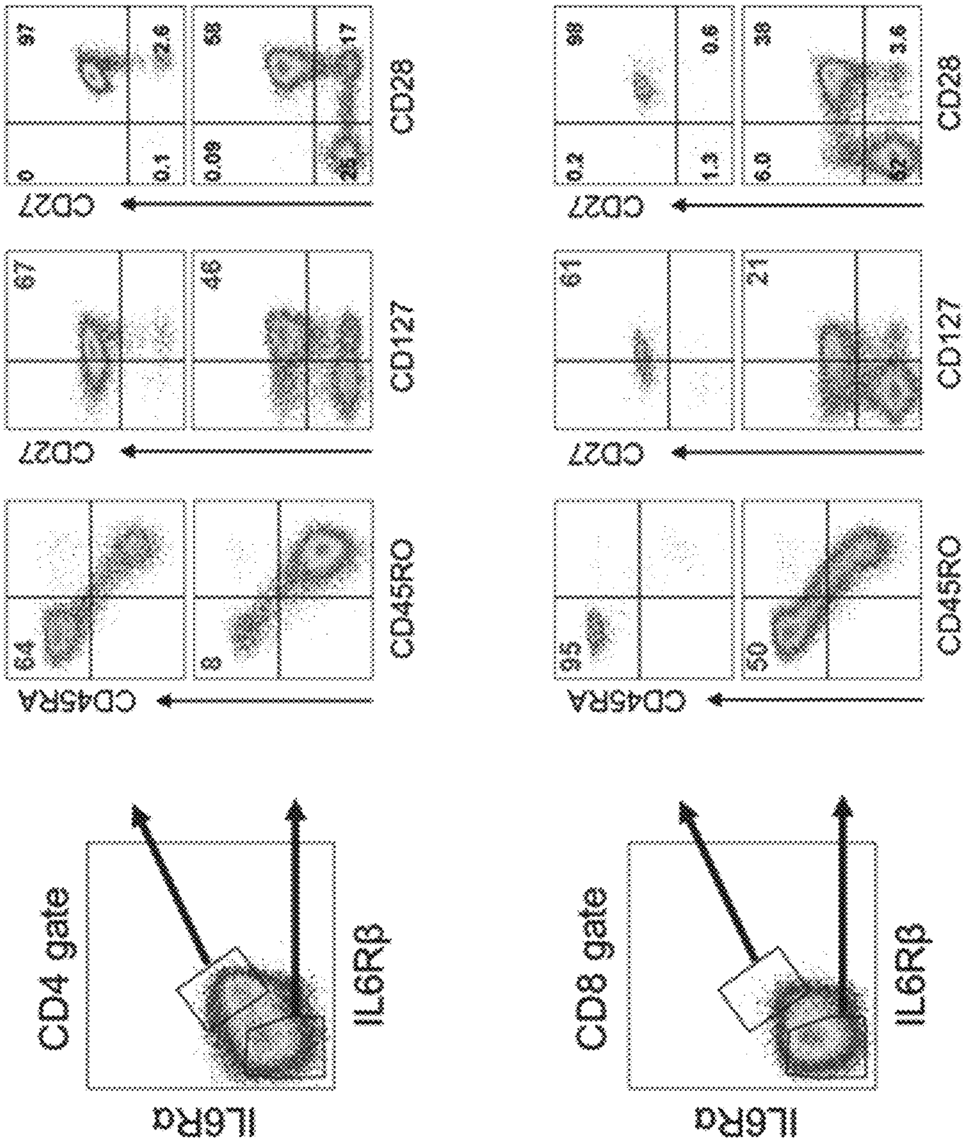
FIGS. 8A and 8B: Both IL6Rα and IL6Rβ expressing cells were enriched in less differentiated T cell population. Fresh T cells were stained for indicated surface antigens and examined for expression levels of indicated surface antigens on CD4 (FIG. 8A) and CD8 (FIG. 8B) T cell subsets.
Figure 9:
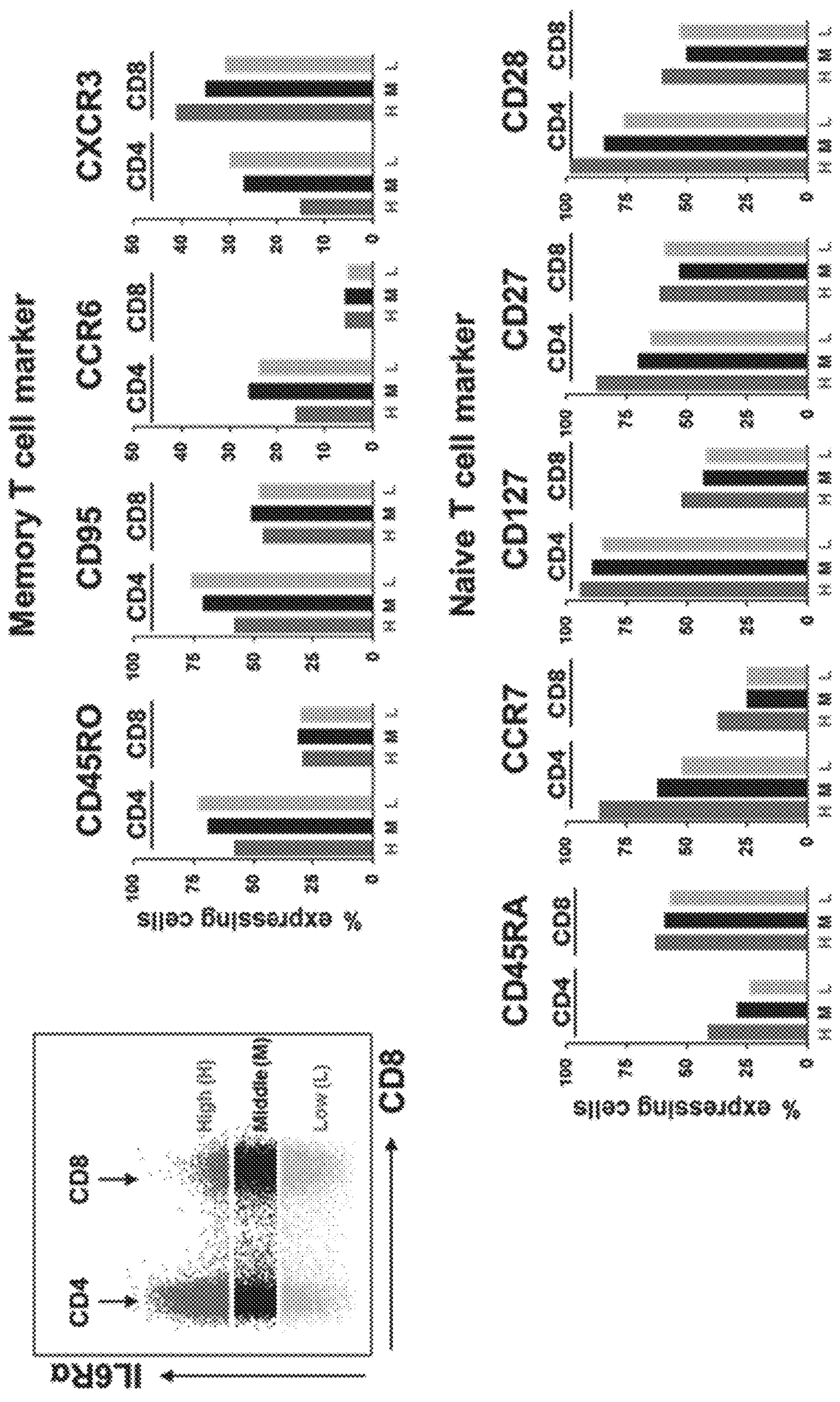
FIG. 9: IL6Rα expressing cells expressed surface markers of less differentiated T cells. Fresh T cells were stained for indicated surface antigens and examined for expression levels of various surface antigens in IL6Rα high, middle, and low expressing cell subsets.
Figure 10:
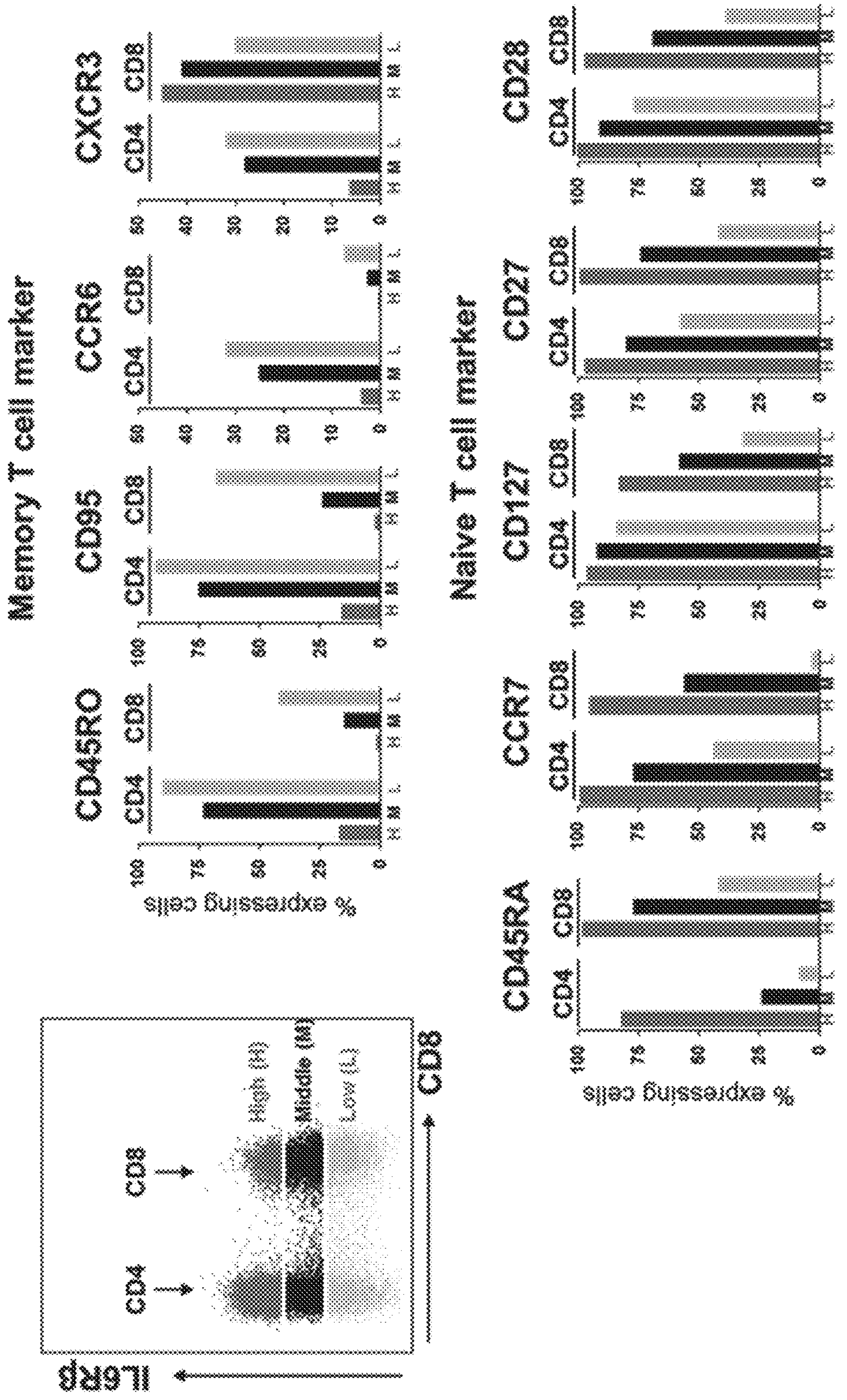
FIG. 10: IL6Rβ expressing cells expressed surface markers of less differentiated T cells. Fresh T cells were stained for indicated surface antigens and examined for expression levels of various surface antigens in IL6Rβ high, middle, and low expressing cell subsets.
Figure 11:
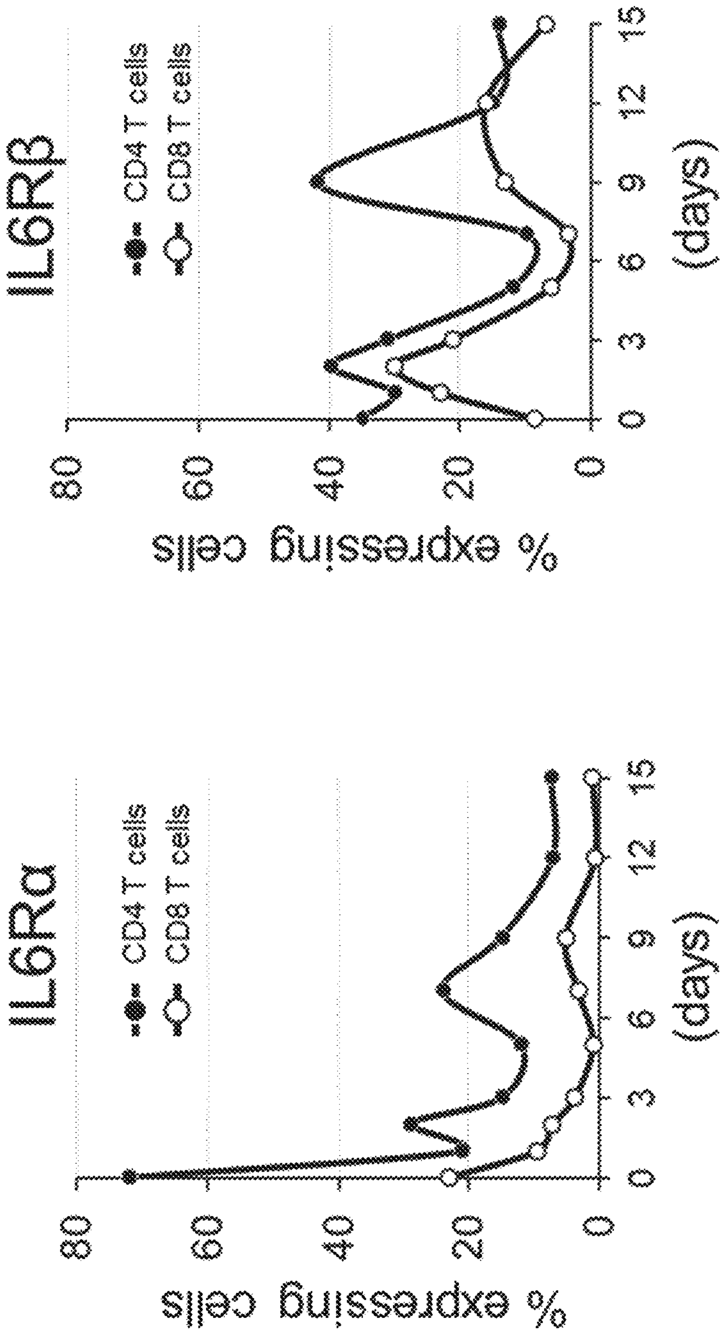
FIG. 11: IL6Rα but not IL6Rβ expression was downregulated following TCR engagement. T cells were activated with αCD3αCD28 beads at day 0 and then examined for expression levels of IL6Rα and IL6Rβ at indicated time points.

IL6Rα and/or IL6Rβ expressing cells were enriched in less differentiated T cell subsets in both CD4 and CD8 T cells. As shown in FIGS. 7A and 7B, naïve CD4 and CD8 T cells expressed higher levels of IL6Rα and IL6Rβ than the corresponding memory T cells. T cells that expressed both IL6Rα and IL6Rβ were predominantly CD45RA+ CD45RO−CD27+CD28+ cells (FIGS. 8A and 8B). Upon TCR stimulation, IL6Rα but not IL6Rβ expression was down-regulated (FIG. 11).

Figure 12:
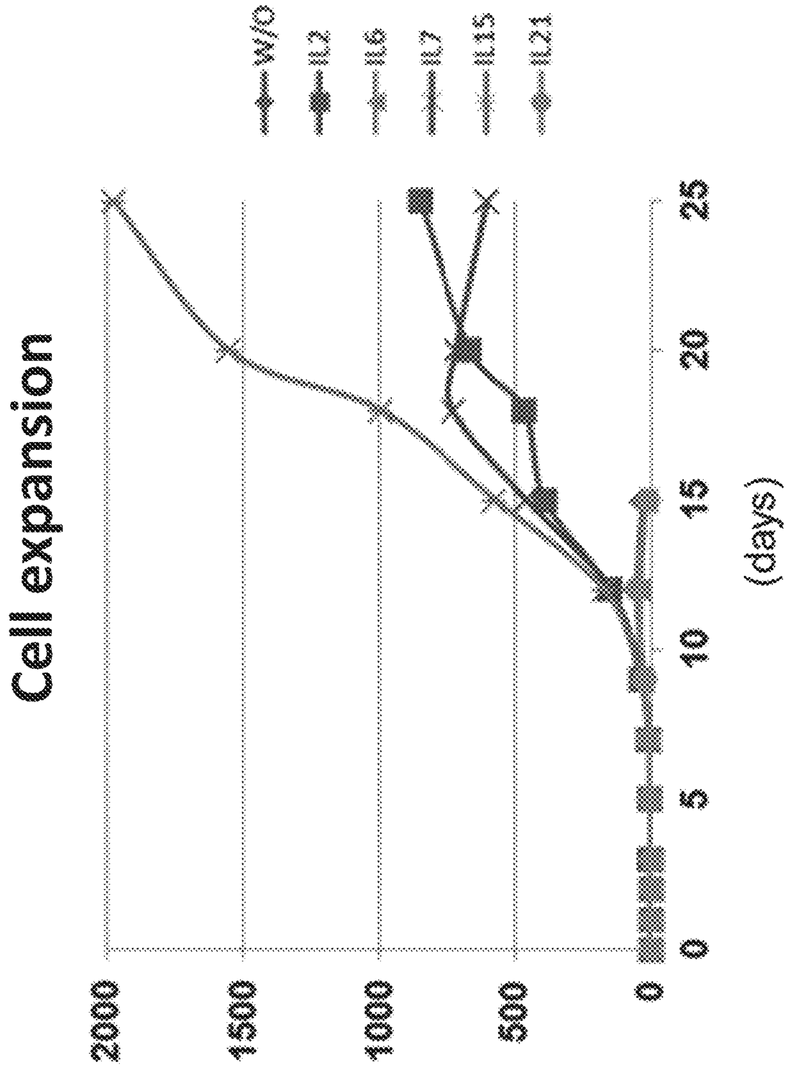
FIG. 12: Fold expansion of cytokine treated T cells after TCR engagement. T cells were activated with αCD3αCD28 beads at day 0 in the presence of indicated cytokines and then monitored for cell numbers at indicated time points.
Figure 13A:
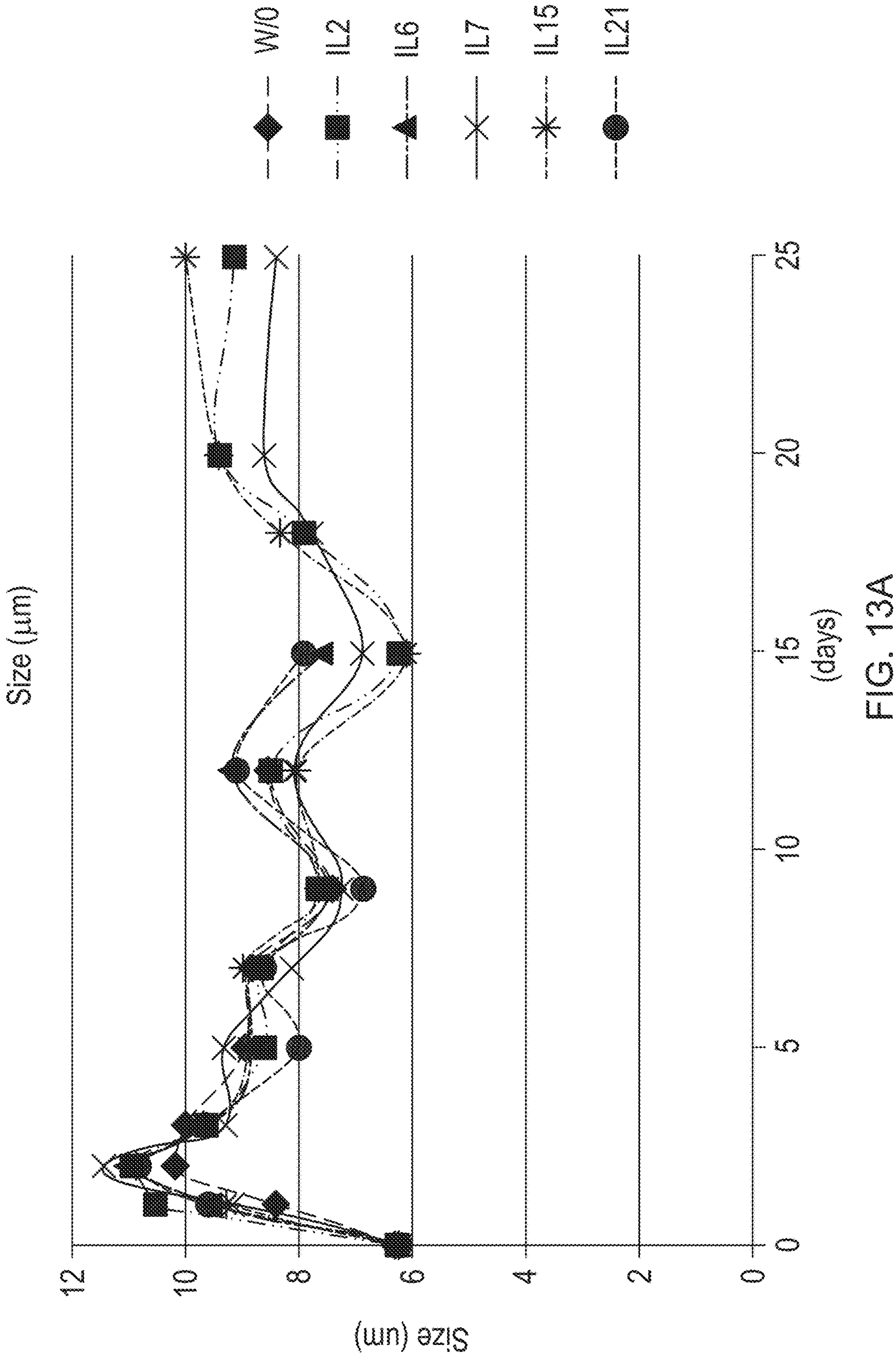
FIGS. 13A and 13B: IL2, IL7, and IL15 treatment did not affect cell size and viability after TCR engagement. T cells were activated with αCD3αCD28 beads at day 0 in the presence of indicated cytokines and then monitored for cell size (FIG. 13A) and viability (FIG. 13B) at indicated time points.
Figure 13B:
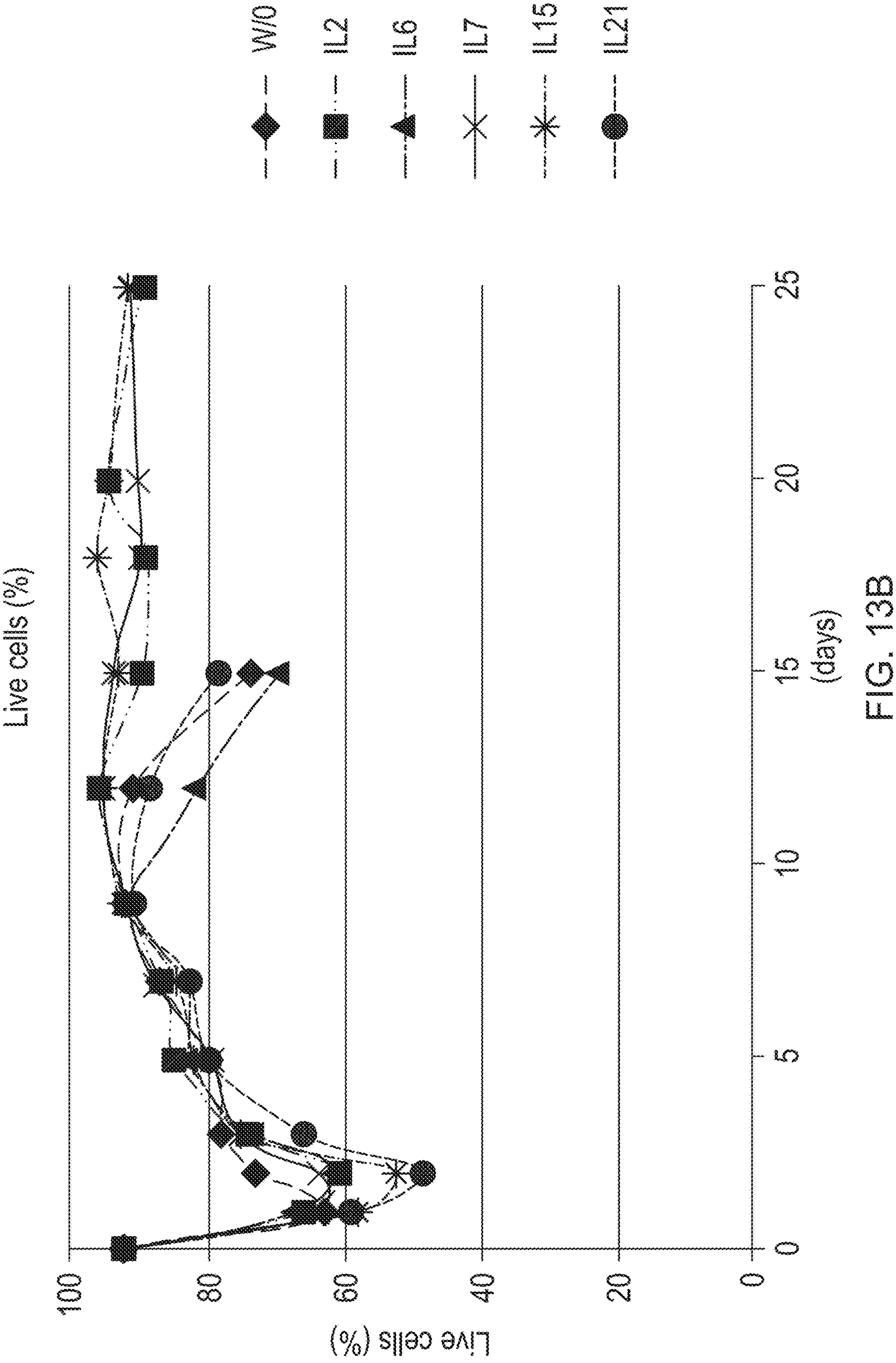
Figure 14:
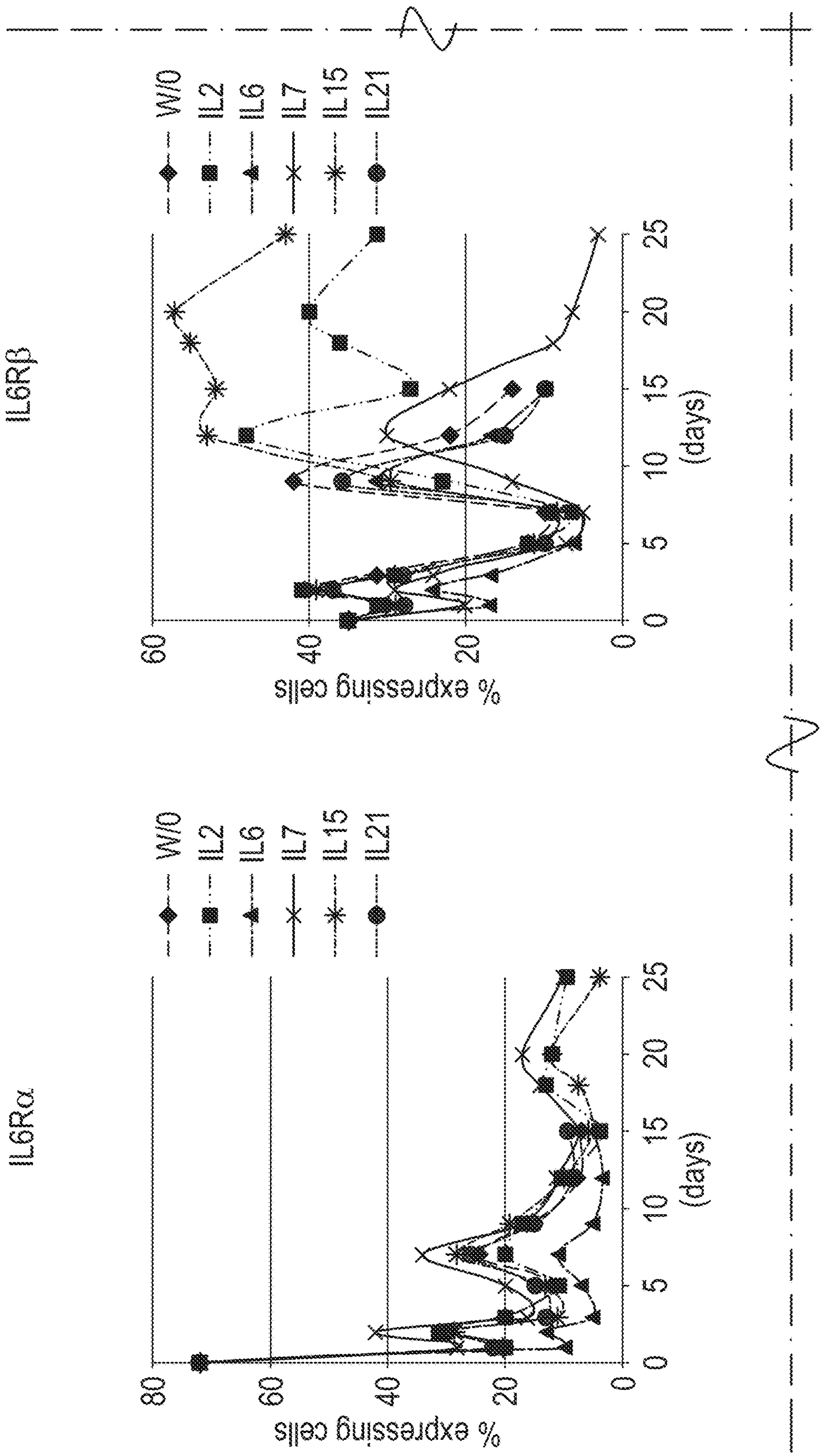
FIG. 14: Expression kinetics of various surface molecules on CD4 T cells after cytokine treatment. T cells were activated with αCD3αCD28 beads at day 0 in the presence of indicated cytokines and then examined for expression of various surface molecules by flow cytometry at indicated time points.
Figure 14:
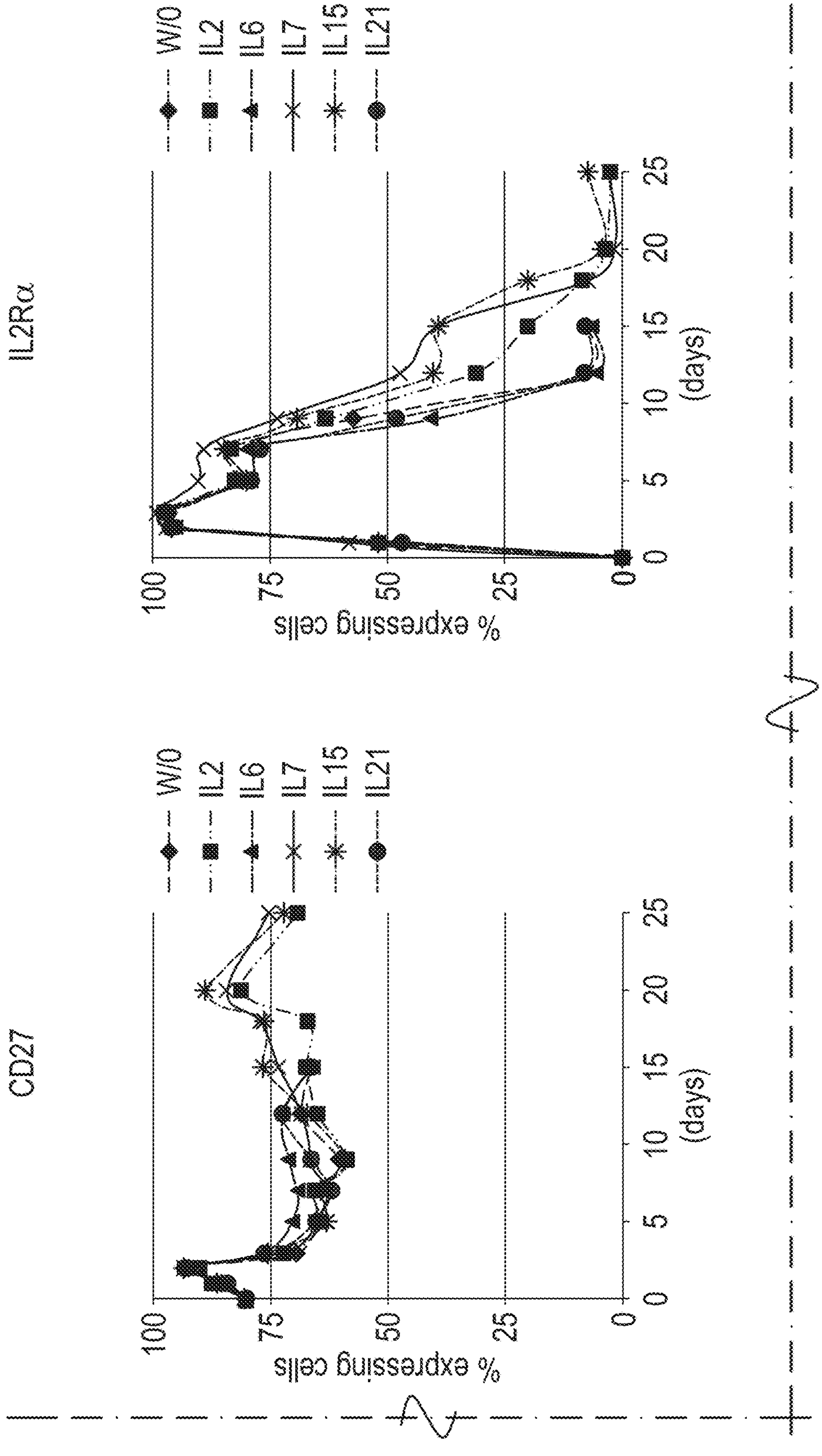
Figure 14:
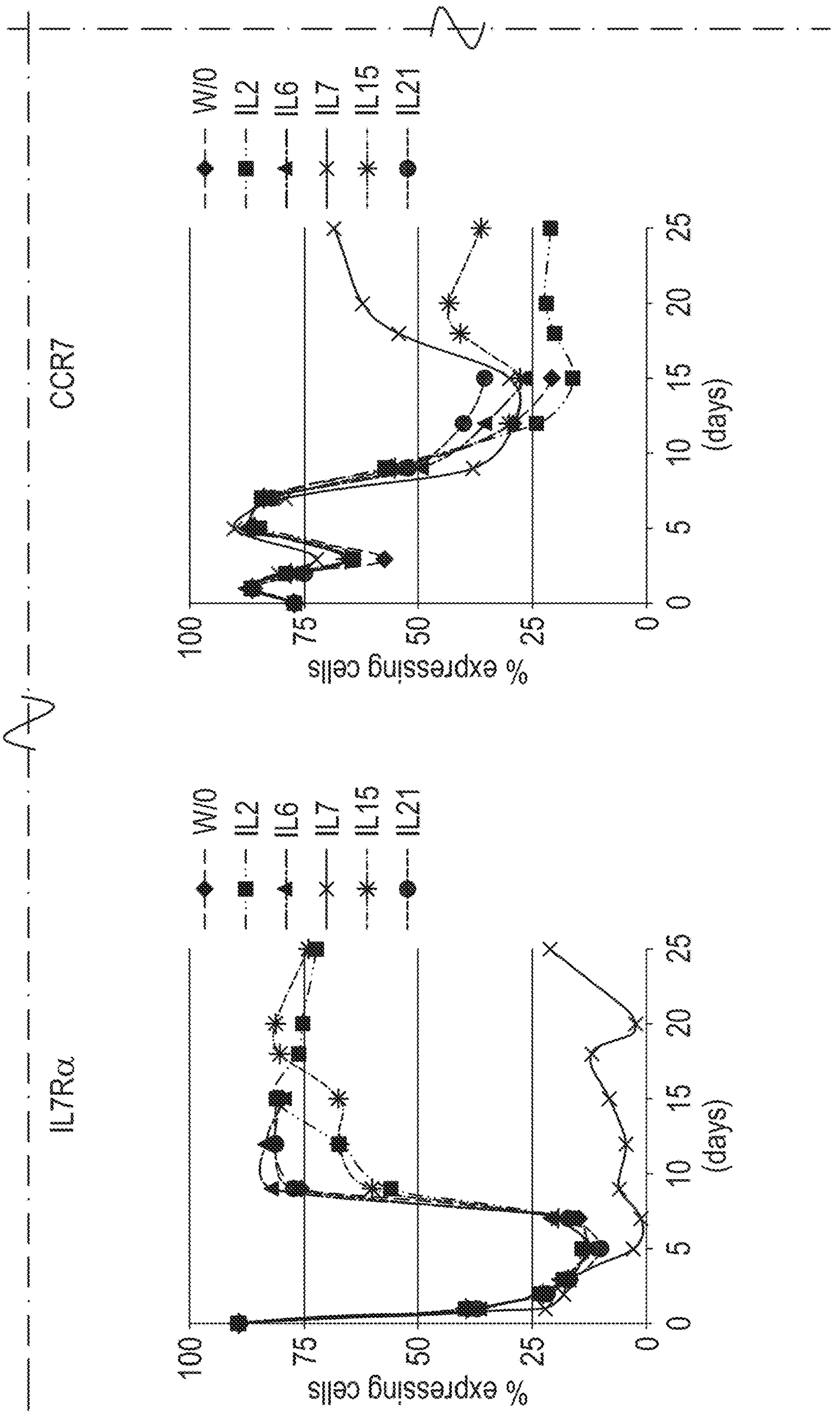
Figure 14:
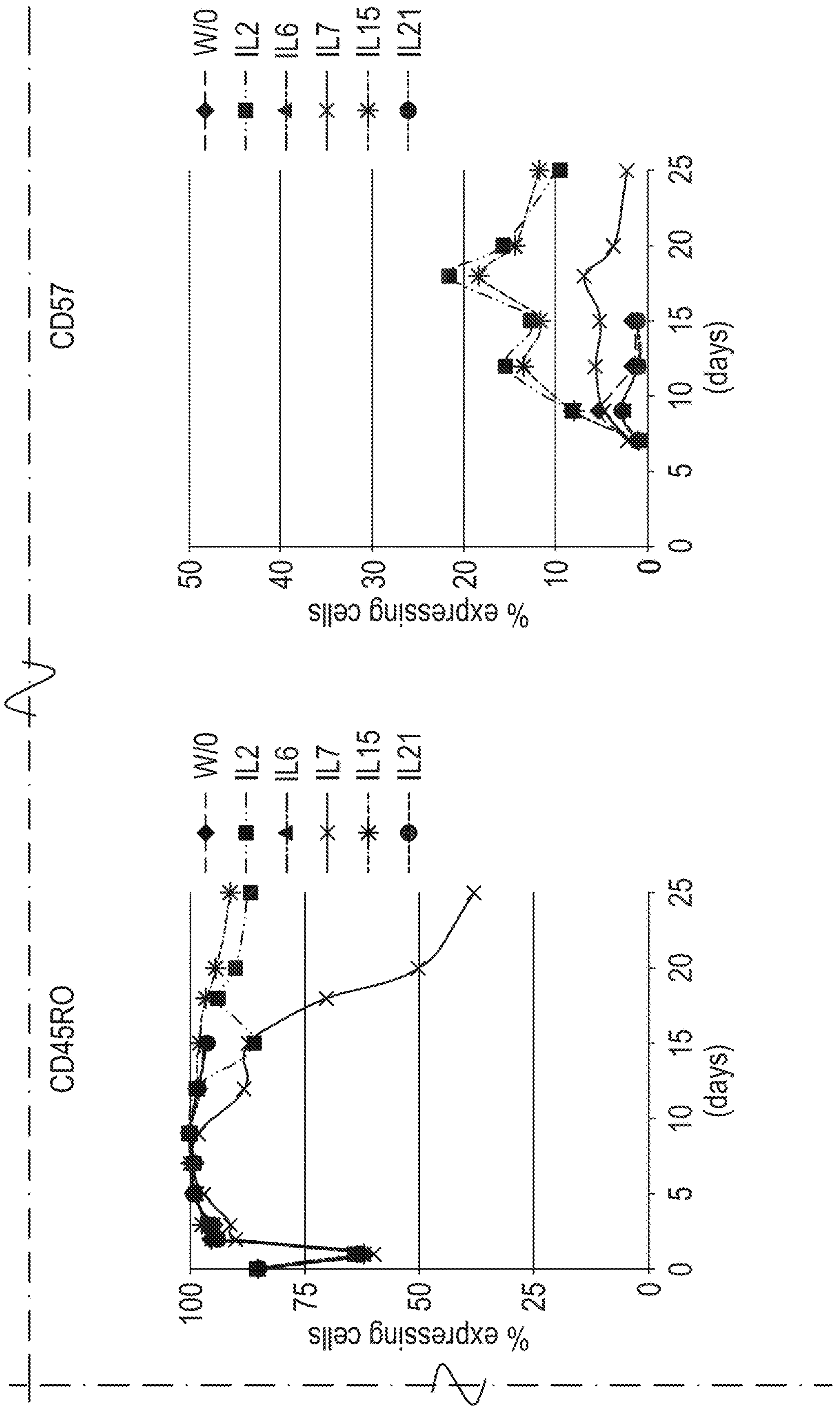
Figure 15:
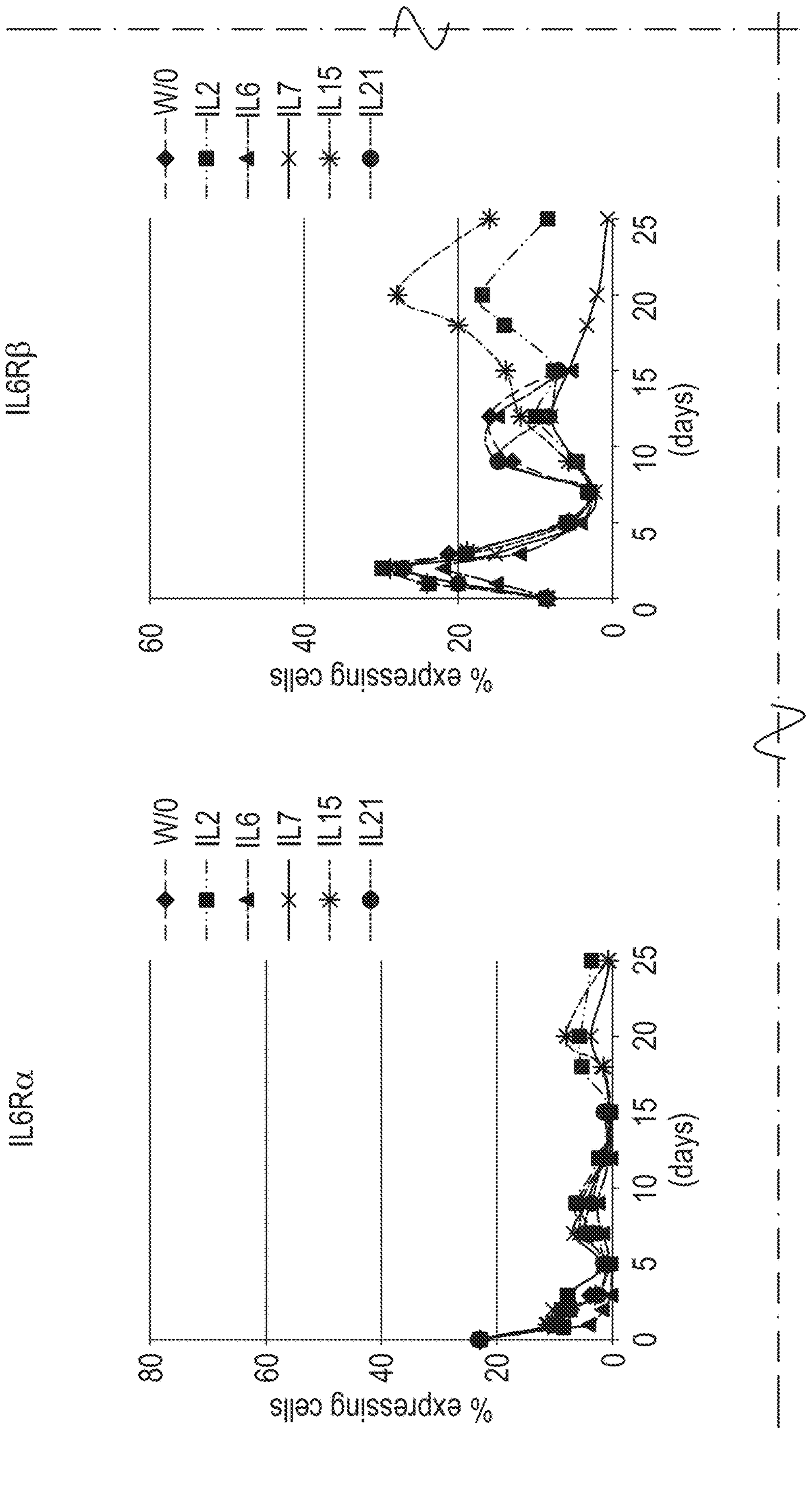
FIG. 15: Expression kinetics of various surface molecules on CD8 T cells after cytokine treatment. T cells were activated with αCD3αCD28 beads at day 0 in the presence of indicated cytokines and then examined for expression of various surface molecules by flow cytometry at indicated time points.
Figure 15:
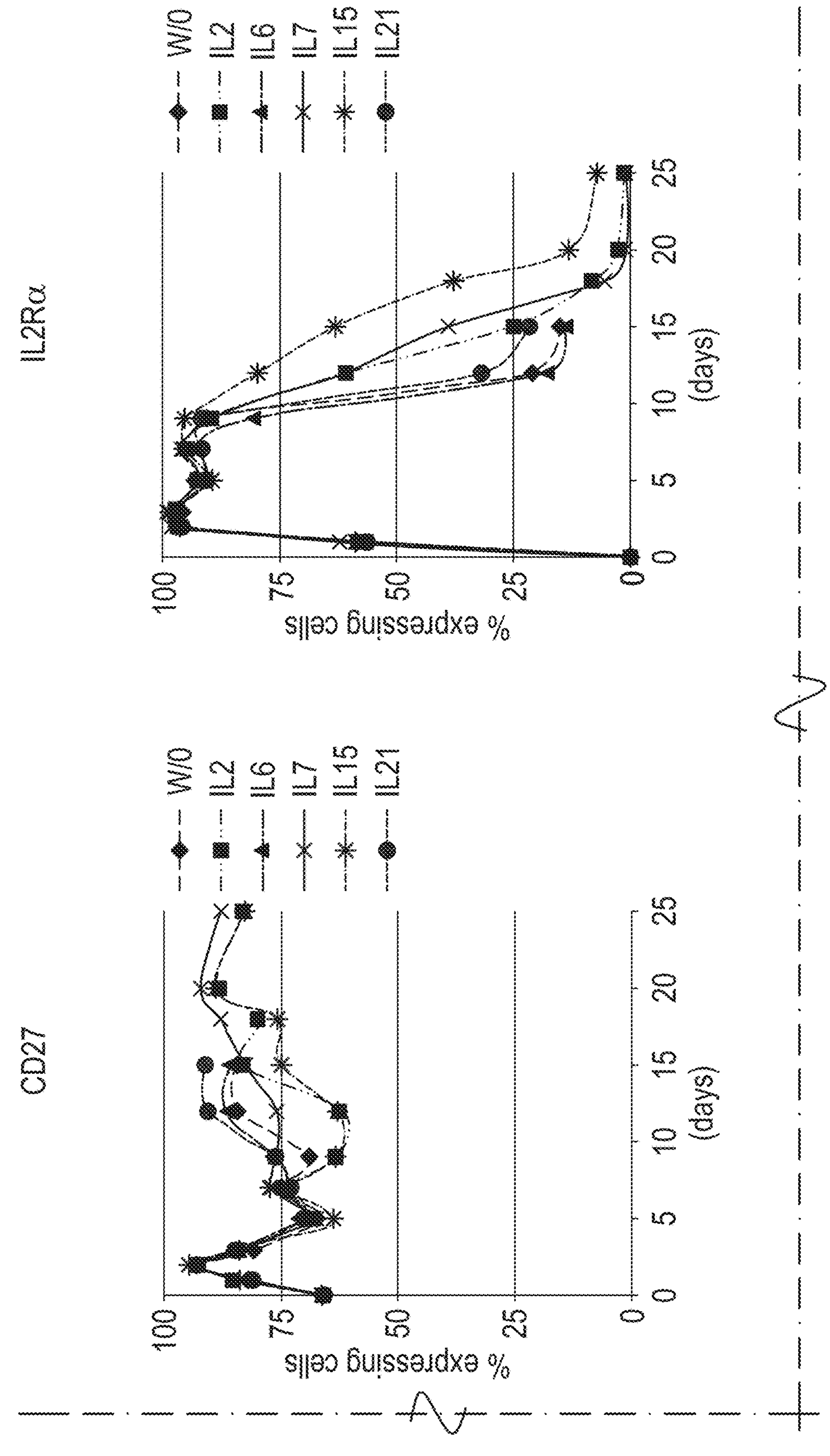
Figure 15:
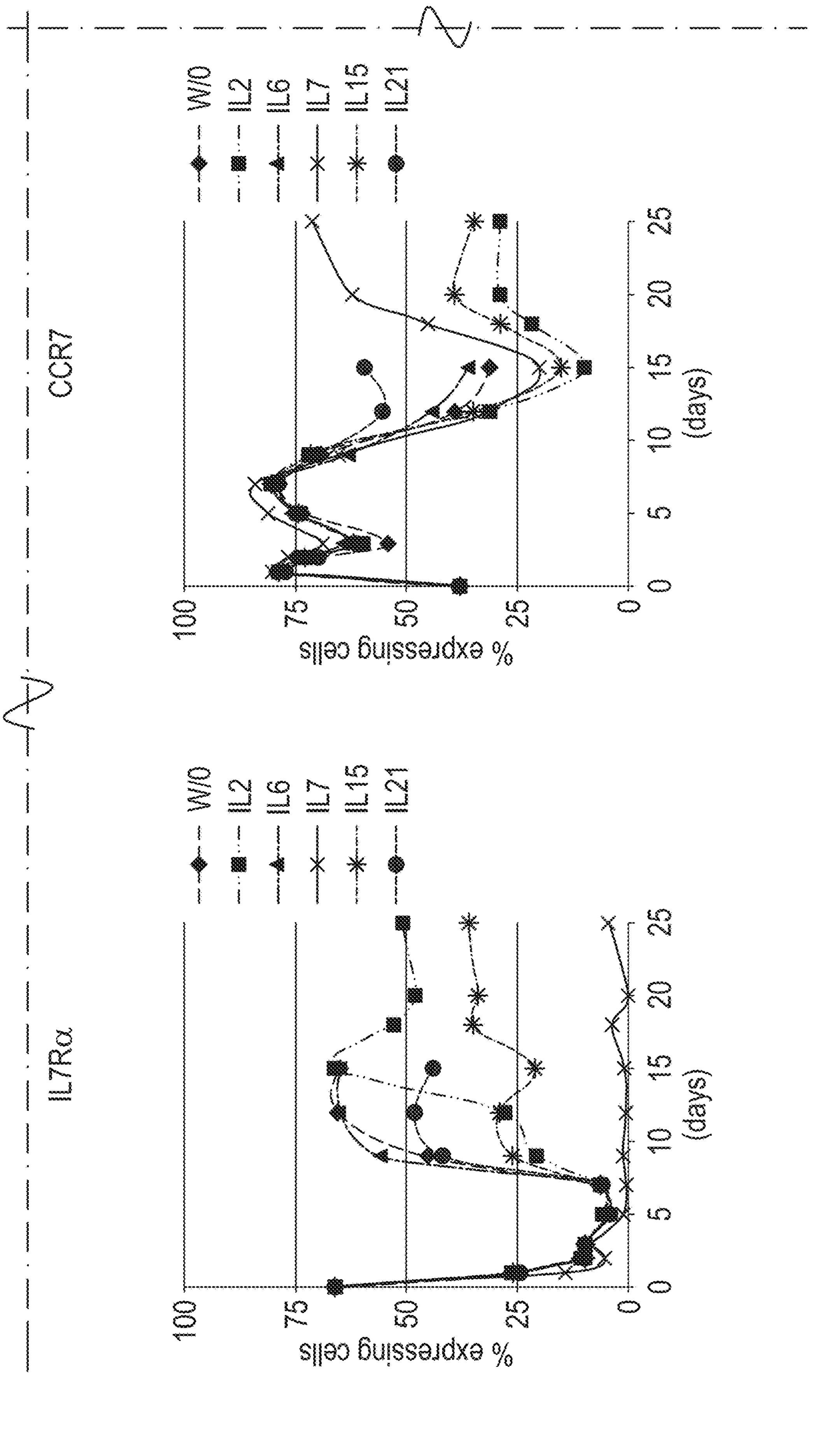
Figure 15:
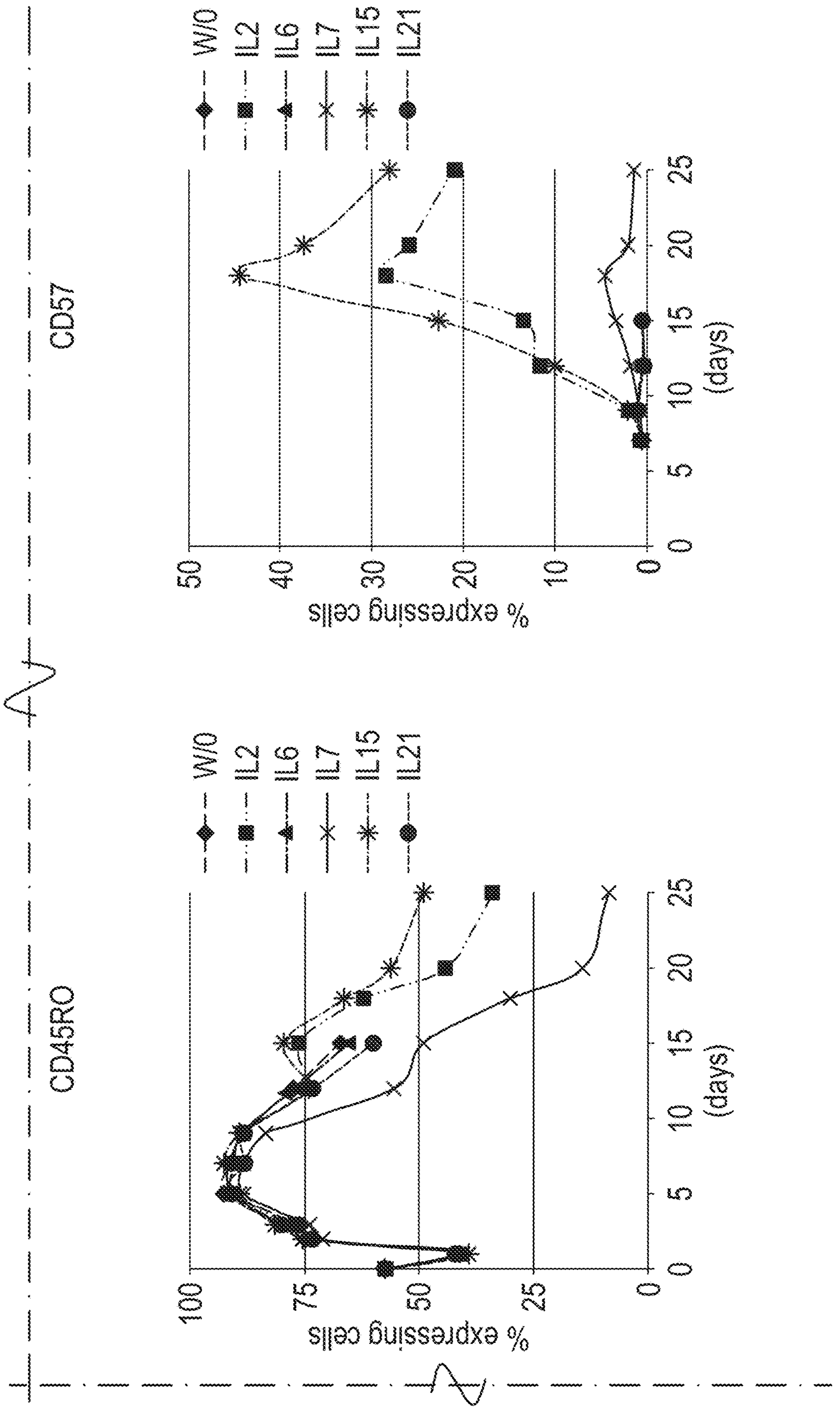
Figure 16:
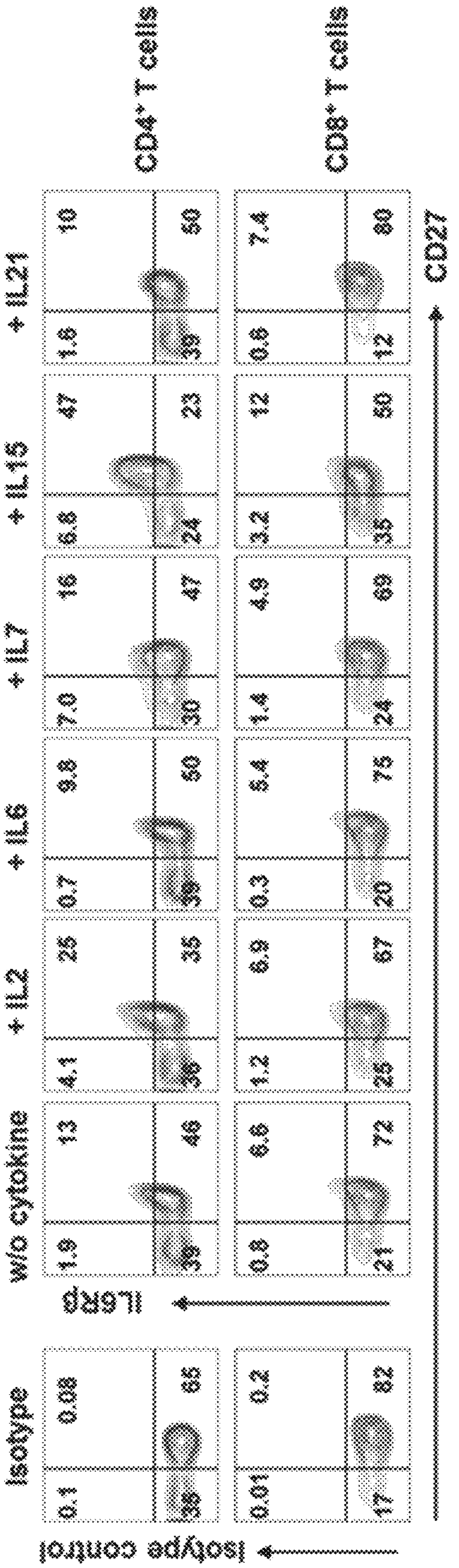
FIG. 16: IL6Rβ expression was mainly restricted on CD27 expressing T cell subsets after TCR engagement. T cells were activated with αCD3αCD28 beads at day 0 in the presence of indicated cytokines and then examined for IL6Rβ expression by flow cytometry at day 15.
Figure 17:
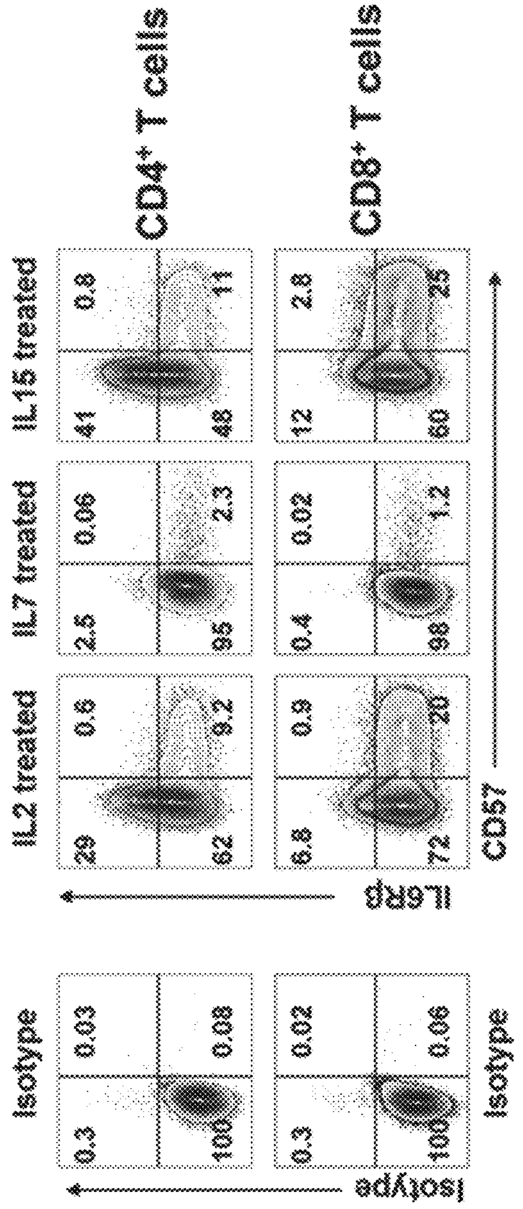
FIG. 17: IL6Rβ expression was mainly restricted on CD57 non-expressing T cell subsets after TCR engagement. T cells were activated with αCD3αCD28 beads at day 0 in the presence of indicated cytokines and then examined for IL6Rβ expression by flow cytometry at day 25.
Figure 18:
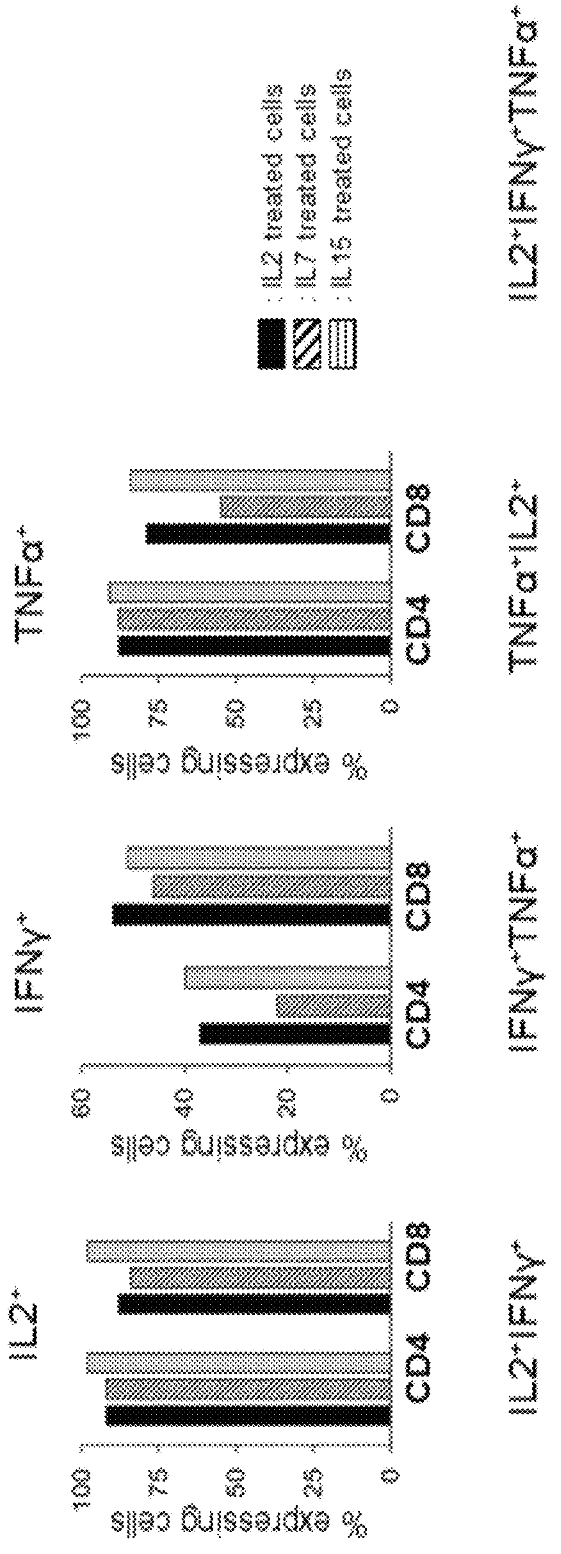
FIG. 18: Common γ-chain cytokine treated T cells produced functional cytokines at day 25. T cells were activated with αCD3αCD28 beads at day 0 in the presence of indicated cytokines and then examined for percentages of IL2, IFNγ, and TNFα producing T cells by flow cytometry at day 25.

Next, different cytokines were compared for their impact on T cell expansion. Among the cytokines tested, IL15, IL2, and IL7 enhanced T cell expansion, with IL15 showing the greatest enhancement (FIG. 12). Cytokine treatment did not affect cell size (FIG. 13A) or viability (FIG. 13B). IL15 treatment also enhanced expansion of IL6Rβ expressing cells (FIG. 14). IL6Rβ expressing cells were mainly in the CD27+ (FIG. 16) or CD57− (FIG. 17) T cell subsets in both CD4 and CD8 at day 15 after TCR engagement and produced IL2, IFNγ, and TNFα cytokines at day 25 after TCR activation (FIG. 18).

Example 4: Generation of CARTs with TCR Stimulation for Preclinical Studies

Day 0 unit operations of the engineering runs for preclinical studies began with the manufacturing of the media used on Day 0: Rapid Buffer and Rapid Media (Table 21). The Rapid Buffer (RB) contains the CliniMACS® buffer (Miltenyi) with 0.5% HSA. The Rapid Media (Table 21) was formulated on Day 0 of manufacturing and the base media contains the off-the-shelf media called OpTmizer™ which has Glutamax, IL-2, CTS™ supplement, and ICSR. The Prodigy® machine was primed for use on Day 0.

TABLE 21

Media type and point of use during CART manufacturing

| Media/Buffer Type | Composition | Point of Use |
|---|---|---|
| Rapid Buffer (RB) | CliniMACS ® Buffer (+0.5% human serum albumin (HSA)) | Day 0 Processing on Cell Wash/Separator |
| Rapid Media (RM) | OpTmizer ™ Media, CTS ™ IL-2, Glutamax and ICSR | Day 0 for Processing on Cell Wash/Separator and Cell Seeding |
| Harvest Buffer (HB) (also called Harvest Buffer Solution) | PBS no EDTA and 2% HSA | Harvest Wash Buffer (Day 1) |
| Cryomedia | Cryostor10 (CS10) | Harvest Formulation |

As the Prodigy® machine was priming on Day 0, the healthy donor leukapheresis material was thawed and the apheresis material was combined into a 600-mL transfer bag that can later be welded onto the Prodigy®. An IPC sample was extracted from the 600 mL transfer bag and measured by NC200 to obtain both the viable cell count and the viability percentage for the starting apheresis material. After priming of the Prodigy® was finished, the apheresis material was transferred to the application bag. After the apheresis entered the Prodigy® machine after initiation of the TCT program, the program ran from 3 h 45 min to 4 h 15 min depending on how many positive selection separations it performed. The TCT program on Day 0 washed out the DMSO in the Centricult with the Rapid Buffer, performed a platelet wash, volume reduction, incubation of the apheresis with the CD4 and CD8 Microbeads in the Centricult, and then selection of the T cells with the Microbeads via positive selection using the magnet on the Prodigy®. The T cells selected with the CD4 and CD8 reagents were eluted into the reapplication bag with the Rapid Media. An in-process control (IPC) sample was taken from the reapplication bag to determine the total viable cell number available for seeding in the culture vessel (G-Rex500MCS).

The G-Rex culture device was first primed with the Rapid Media and then the target cell volume from the reapplication bag was added to the culture vessel. The activation reagent (TransACT) was then added to the culture vessel. The lentiviral vector was then added to the culture vessel after the introduction of TransACT and the vector addition was performed using a MOI of 1.0. The G-Rex500MCS culture vessel was then flushed with the Rapid Media to a final media volume of 250 mL plus the volume of the vector addition. The G-Rex culture vessel was then placed into the incubator to allow the culture to incubate for a target 24 h with a range of 20-28 hours.

After the target 24 h incubation, the CART culture was taken out of the incubator and a sample was extracted to obtain the viable cell count and viability of the cell culture before the Harvest Wash. The sample take at Pre-Harvest was an IPC and was used as an input into the LOVO wash device to determine the flow rate of cells into the spinning filtration membrane. The LOVO used the viable WBC concentration as the IPC. The program used for the CART manufacturing process was described as 4 Washes with one solution and utilized the Harvest Buffer (PBS+2.0% HSA). During the LOVO wash, the IPC bag was used to both reduce the volume and wash the cells with Harvest Buffer before it was finally eluted into the output bag. The output bag from the LOVO wash was then sampled to obtain the viable cell count and viability in order to perform the manual centrifugation with the sanisure bottle and to perform the final steps of the final formulation with the cryomedia.

Example 5: Generation of BCMA CARTs Using the Activated Rapid Manufacturing (ARM) Process Summary This example describes a CART manufacturing process called "activated rapid manufacturing (ARM)." In some embodiments, cells (for example, T cells) are cultured in a cell culture device containing media (for example, serum-free media, for example, OpTmizer™ media), recombinant human IL-2 (for example, OpTmizer™ media containing OpTmizer™ supplement, GlutaMAX and 100 IU/ml of IL-2), anti-CD3/anti-CD28 (for example, TransAct) and a vector (for example, a lentiviral vector) encoding a BCMA CAR. After 24 hours, the cells, referred as "day 1 CART product" are harvested, sampled, and formulated. Without wishing to be bound by theory, brief CD3 and CD28 activation, for example, using anti-CD3/anti-CD28 (for example, TransAct), promotes efficient transduction of self-renewing T cells. In some cases, some cells are harvested at 48 h, 72 h, and 96 h or 7 days after culture for measuring BCMA CAR expression kinetics in vitro. The day 1 CART responses include, but are not limited to, in vivo cytolytic activity and expansion.

Generation of Day 1 BCMA CARTs Using the ARM Process

In some embodiments, the activation process provided herein starts with a frozen or fresh leukapheresis product. After a sample for counting and QC is obtained, the product is attached to a cell sorting machine (for example, an installed CliniMACS® Prodigy® device kit) and the program begins. The cells are washed and incubated with microbeads that bind to desired surface markers, such as CD4 and CD8. The bead-labeled cells are selected by passing the cells through a magnetic column. Isolated cells are washed again and the separation buffer is exchanged for cell media. Purified T cells then either proceed to culture or are cryopreserved for later use. Purity of the isolated T cells will pass a QC step by flow cytometry assessment. Cryopreserved cells can be thawed, washed in pre-warmed cell media, and resuspended in cell media. Fresh cells can be added to culture directly. The cells are seeded into membrane bioreactors at 0.4-1.2e$^6$ cells/cm$^2$ of membrane, an activating reagent, such as anti-CD3/anti-CD28 beads/polymers, nanoparticles, or nanocolloids, is added, and cell media is added to a final volume of 0.25-2ml/cm$^2$ of membrane. At the time of plating, the cells are transduced with a lentiviral vector encoding BCMA CAR at various multiplicity of infections (MOIs). The titer and the MOI are measured based on cell lines such as SupT1. At 24 hours, the cells are washed to remove unnecessary reagents before staining to measure the CAR expression by flow cytometry and reformulated in cryopreservation media as "day 1 CART product" for in vivo study.

Described in this example are the generation and characterization of T cells expressing BCMA CAR R1B6, R1F2, R1G5, PI61, B61-02, B61-10, or Hy03, manufactured using the ARM process. The sequences of R1B6, R1F2, and R1G5 are disclosed in Tables 3-6. The sequences of PI61, B61-02, and B61-10 are disclosed in Tables 7-11. The sequences of Hy03 are disclosed in Tables 12-15.

Figures 19A, 19B:
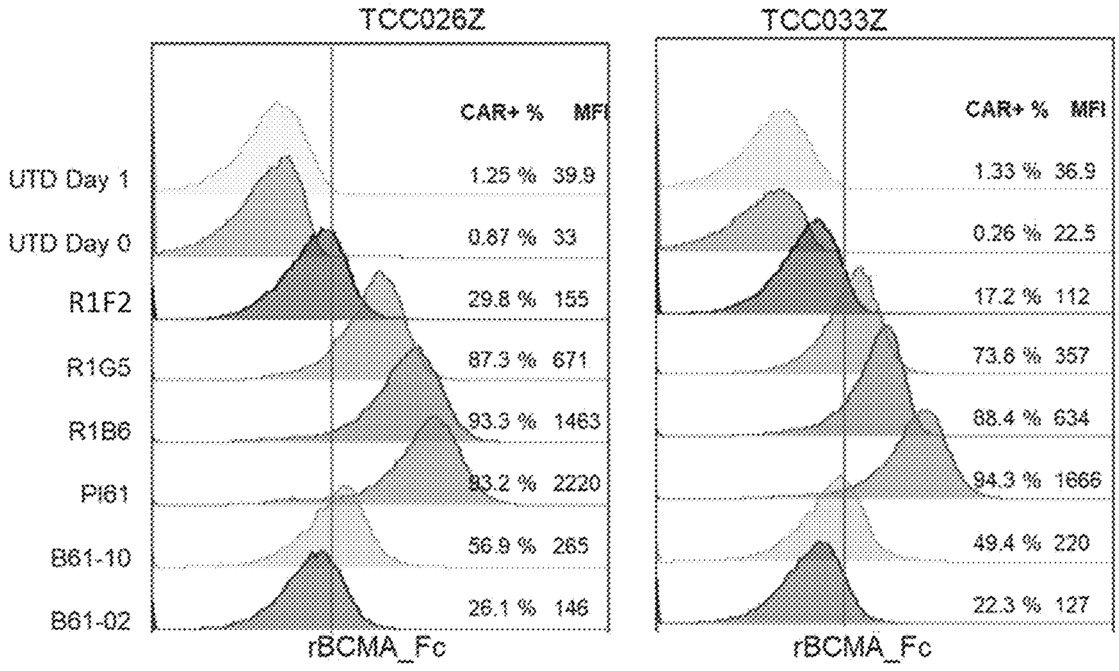
FIGS. 19A and 19B: BCMA CAR expression on Day 1 using ARM at MOI=2.5 in T cells from two healthy donors.

Twenty-four hours after T cells were transduced using lentiviral vectors encoding BCMA CARs at a MOI of 2.5, the expression of CAR was measured by flow cytometry using rBCMA_Fc. As shown in FIG. 19A, it was observed that the whole population of the live CD3+ T cells shifted to the right at different degrees. Cells transduced to express R1G5, R1B6 or PI61 showed the highest CAR expression (FIG. 19A). This pattern of expression as measured by flow cytometry was different from a typical flow cytometry histogram of cells transduced to express a CAR, where a CAR positive population is clearly separated from a negative population. FIG. 19A indicates that there may be "pseudotransduction or transient expression" detected by rBCMA_Fc, which does not always indicate real gene expression. It has been previously reported that lentiviral pseudotransduction was observed beginning at the time of vector addition and lasting up to 24 hours in CD34+ cells and up to 72 hours in 293 cells (Haas D L, et al. Mol Ther. 2000. 291: 71-80). Integrase-defective lentiviral vector caused transient eGFP expression for up to 10 days in CD34+ cells and for up to 14 days in 293 cells. Though lentiviral pseudotransduction has not been extensively studied in T cells, this possibility of transient expression in such a short time cannot be ruled out. Therefore, in vitro kinetic study was performed to measure CAR expression of cells manufactured using ARM as indicated below.

In Vitro CAR Expression Kinetics Study of Cells Manufactured Using the ARM Process The study described here examines how cells manufactured using the ARM process express CAR molecules over time. Briefly, T cells from a healthy donor were manufactured to express a BCMA CAR using the ARM process at a MOI of 1 and were kept in culture for different time periods and harvested at 24 h, 48 h, 72 h, 96 h, and day 7 for assessing CAR expression kinetics by flow cytometry using AF647 labeled rBCMA_Fc. Understanding the CAR expression kinetics helps to find a surrogate time point for real and stable expression for in vivo triage or clinical dosing strategy.

Figure 20A:
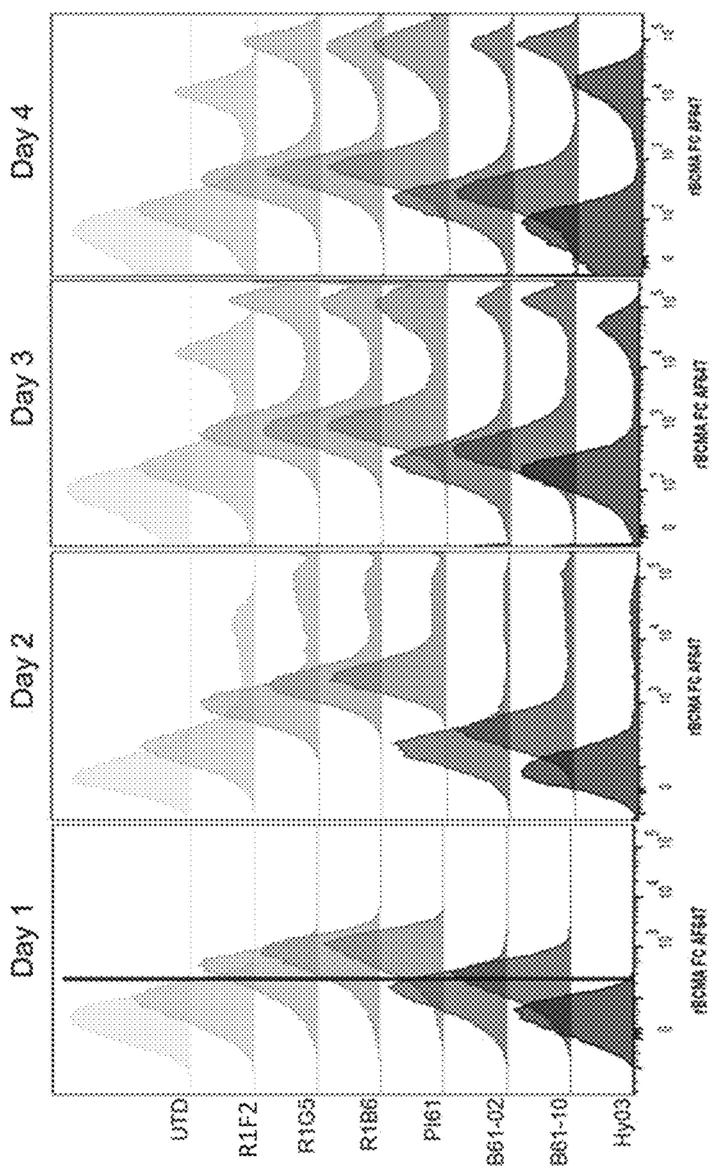
FIGS. 20A, 20B, and 20C: In vitro CAR expression kinetics from day 1 to day 4 of cells manufactured using the ARM process. CARs were stably expressed on day 3.
Figure 20B:
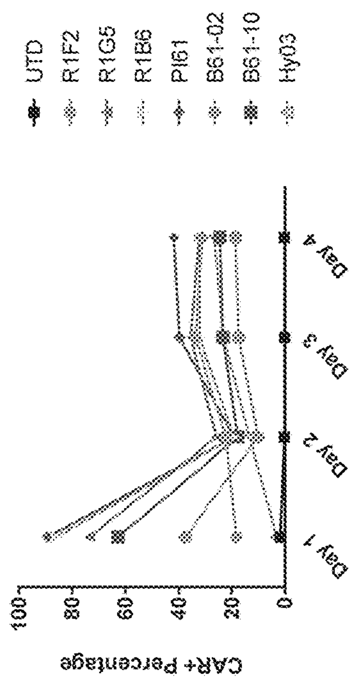
Figure 20C:
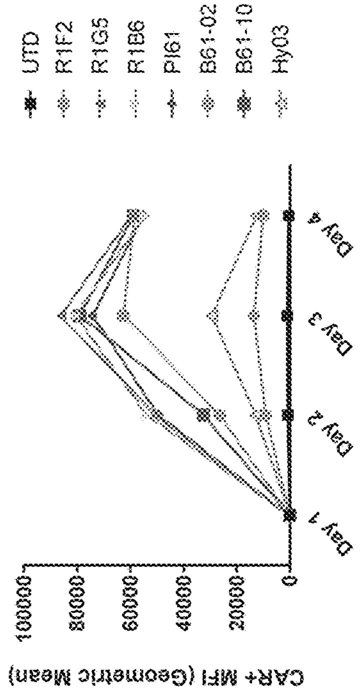

At day 1, the CAR expression pattern of cells transduced at a MOI of 1 (FIG. 20A) is similar to that of cells transduced at a MOI of 2.5 (FIG. 19A). Both MOI conditions showed a pseudo or transient expression pattern at day 1 (FIGS. 19A and 20A). However, at day 2, a rBCMA_Fc positive population started to be separated from the UTD negative control group (FIG. 20A). At day 3 and day 4, a rBCMA_Fc positive population, which represents the BCMA CAR-expressing cells and is absent in the UTD group, clearly showed up in all the groups where cells were transduced to express a BCMA CAR. From day 3 to day 4, the CAR+% was relatively stable for each CAR construct (FIG. 20B), with the highest MFI observed at day 3 (FIG. 20C) (the cells were the largest at this time point). Consistent with the data shown in FIG. 19A, cells transduced to express PI61, R1G5 and R1B6 were the highest CAR expressers (FIG. 20A). Notably, cells transduced with vectors encoding R1F2 or Hy03 did not show transient CAR expression at day 1 but clearly expressed BCMA CAR molecules later at day 3 and day 4 (FIG. 20A). In conclusion, vectors encoding different CARs may have different CAR expression kinetics over time, and day 3 was chosen as a surrogate time point for CAR expression.

Evaluating Functionality of the Day 1 ARM Processed BCMA CART In Vivo

Figure 21A:
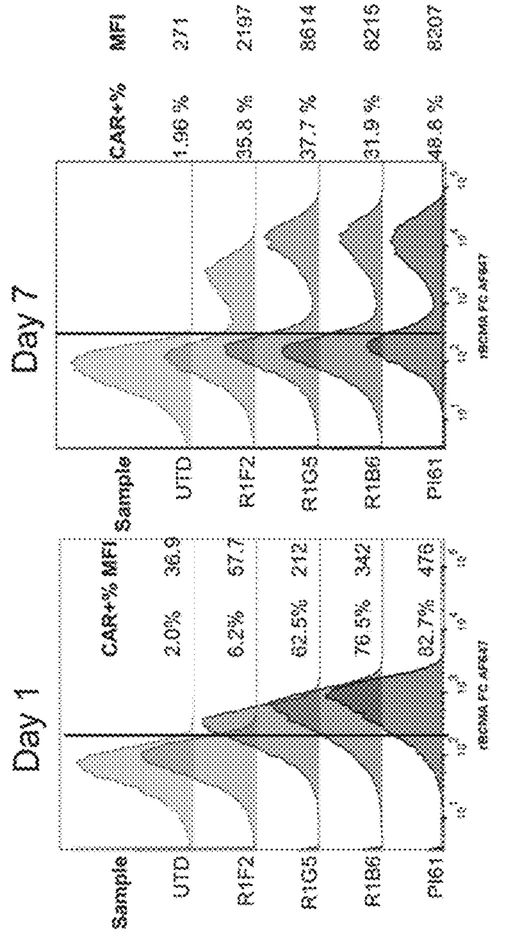
FIGS. 21A and 21B: In vivo triage in a KMS-11-luc multiple myeloma xenograft mouse model. Each mouse received 1.5E6 of day 1 CART product.
Figure 21B:
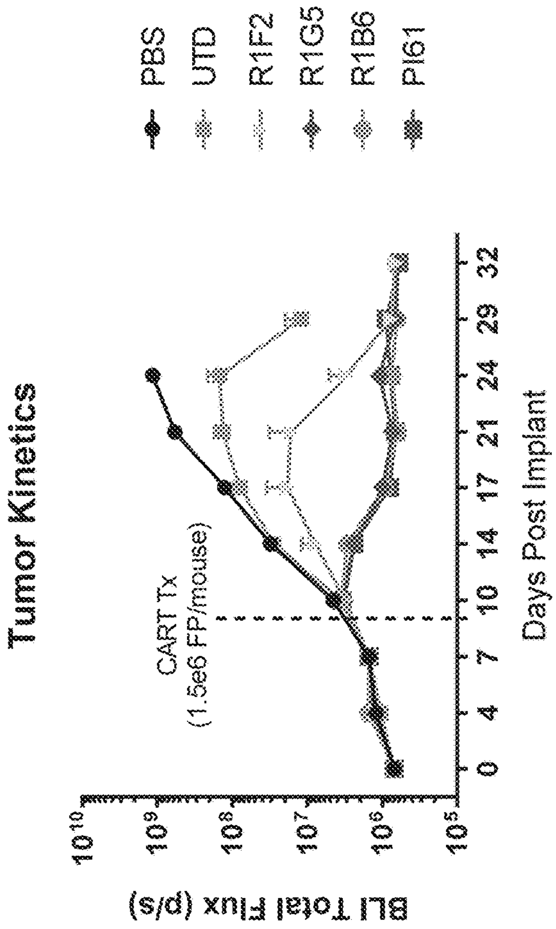
Figure 22A:
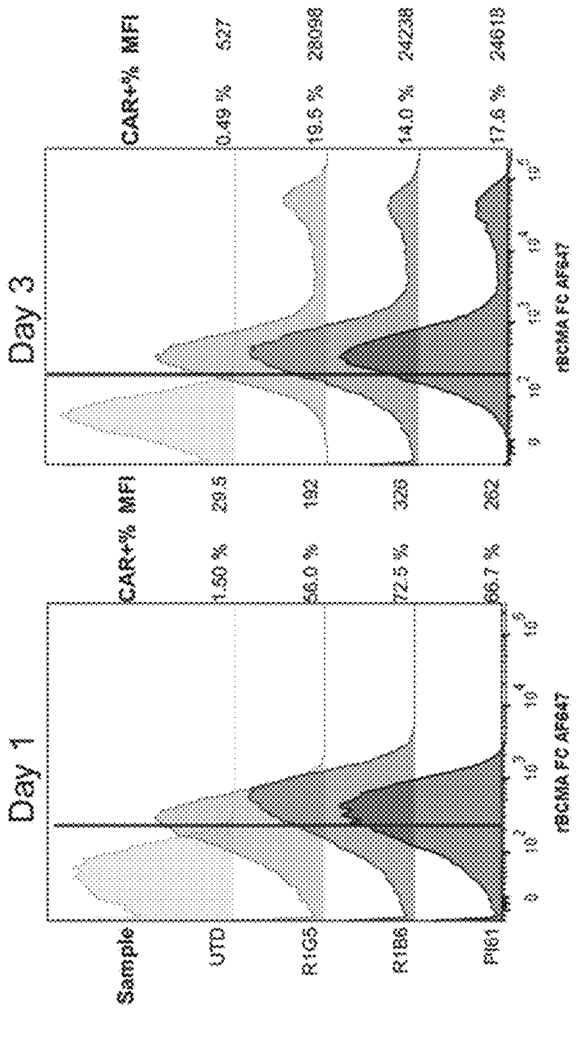
FIGS. 22A, 22B, and 22C: In vivo triage of BCMA CAR using dose titration in a KMS-11-luc multiple myeloma xenograft mouse model.
Figure 22B:
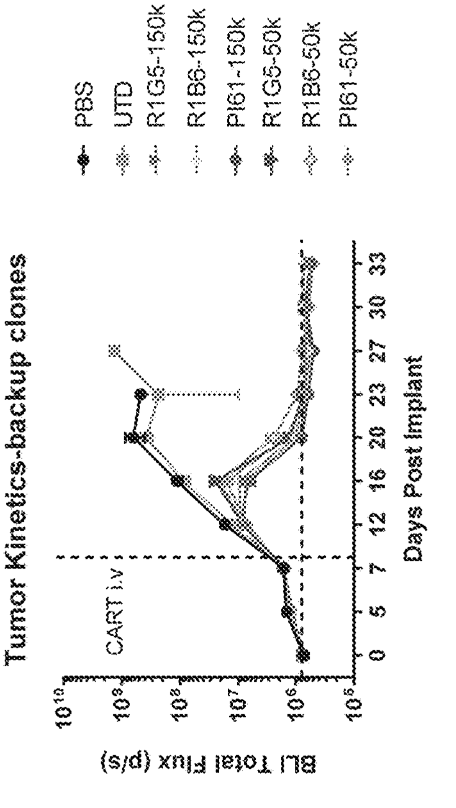
Figure 22C:
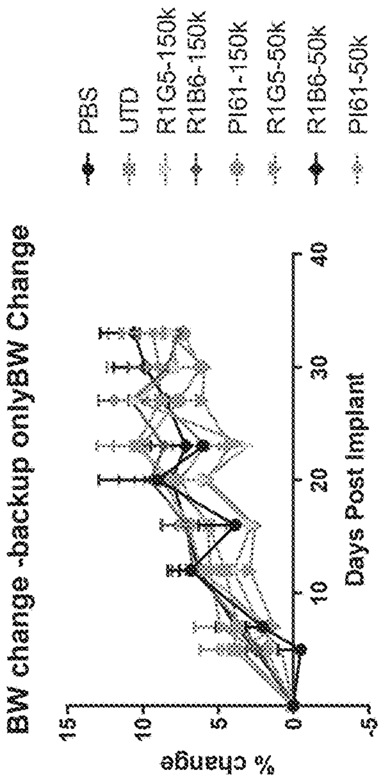

The day 1 CARTs were examined for their anti-tumor activity in vivo using a disseminated KMS-11-luc multiple myeloma xenograft mouse model. The luciferase reporter allows for monitoring of disease burden by quantitative bioluminescence imaging (BLI). Briefly, day 1 CARTs manufactured as described above were administered in tumor-bearing mice. In the first in vivo study (FIGS. 21A and 21B), each mouse received a final CART product at a dose of 1.5E6 cells. CAR expression was analyzed at day 1 and day 7 (FIG. 21A). In the in vivo efficacy study, cells expressing PI61, R1G5 or R1B6 demonstrated potent anti-tumor activities (FIG. 21B). Cells expressing R1F2 showed a delayed efficacy (FIG. 21B). The UTD group also showed partial anti-tumor activity 14 days after CART injection, which could be due to alloreaction (FIG. 21B). A second in vivo study tested dose titration of the CAR+T cells. The doses of CAR+T cells were based on CAR+ % at day 3 (FIG. 22A). Tumor intake kinetics was monitored twice a week by BLI measurement. FIG. 22A shows CAR expression detected at day 1 and day 3. The in vivo results indicate that all three clones PI61, R1B6 and R1G5 at both doses of 1.5e5 CAR+ T cells and 5e4 CAR+ T cells were able to reject and clear tumor as shown in FIG. 22B. FIG. 22C shows body weight changes over the course of this study, displaying no indication of GVHD.

Example 6: Kinetics of Rapid CARTs Harvested Between 12-24 Hours

Introduction

To determine whether a rapid CART product could be generated in less than 24 hours, the kinetics for harvesting rapid CARTs generated after 12-24 hours in culture was characterized. This evaluation was performed at small scale using T cells enriched from cryopreserved healthy donor apheresis and simultaneous addition of TransAct activation reagent and technical grade CTL019 vector at seeding. Primary readouts were viability, viable cell recovery post-expansion, leukocyte and T cell subset composition, and transduction efficiency (as determined via surface immunophenotyping) on freshly harvested CART products.

Methods

Lentivirus production and titer determination: The lentiviral vector encoding CTL019 was prepared with a HEK293T-based qPCR titer of 4.7×107 TU/mL and an approximated T cell-based titer of 1.88×107 TU/mL.

T cell isolation: A cryopreserved leukopak (LKPK) of healthy donor apheresis was obtained from Hemacare and stored in liquid nitrogen until needed. On Day 0, the apheresis was thawed until a small ice crystal remained, and then diluted with Prodigy® process buffer. Automated CD4/CD8 positive selection was then performed on the CliniMACS® Prodigy® with the TS 520 tubing set and T Cell Transduction (TCT) program software version 1.0. The final Prodigy® product was eluted in OpTmizer™ complete T cell medium, and cell concentration and viability were determined by AO/PI staining as enumerated by the Cellometer Vision (Nexcelom).

Culture initiation and transduction: Cells from the Prodigy® product were immediately seeded into a total of seven vessels: five vessels for transduced cultures and two vessels for untransduced (UTD) cultures. At timepoint zero, each vessel was seeded at a density of $0.6\times10^6$ viable cells per $cm^2$ of membrane, plus GMP-grade TransAct, and brought to a final concentration of $1.2\times10^6$ viable cells/mL with OpTmizer™ complete T cell media containing IL-2. Vector was thawed at room temperature and added to each transduced culture at a MOI of 0.45 based on the approximated T cell titer. No virus was added to the UTD controls. Once seeded, cultures were incubated at 37° C. and 5% $CO_2$ until ready for harvest.

Harvest: At each timepoint 12 to 24 hours after culture initiation, one transduced culture was selected for harvest. Cells were harvested by swirling the vessel to gently resuspend the cells off the membrane, then the full culture volume resuspended and transferred by serological pipette to a conical tube. A small aliquot was taken for a pre-wash count, viability determination, and flow staining. The remainder of each culture was washed twice in 50 mL (twice in 100 mL for UTD vessels), resuspended, and a post-wash aliquot taken to examine counts and viability.

Flow cytometry of leukocyte composition and CD19-CAR expression during CART manufacturing: In-process samples before and after culturing were stained for leukocyte composition, T cell phenotype, and CAR expression where applicable. CTL019-CAR expression on transduced T cells was evaluated using a custom-ordered fluorophore-labeled anti-idiotype antibody (eBioscience). At each harvest timepoint, aliquots of the culture were immediately stained with viability dye (Biolegend), washed, then stained with two flow panels both containing a CD3 stain and the anti-idiotype antibody and fixed in paraformaldehyde for acquisition. Samples were measured on a flow cytometer (BD LSRFortessa; single color controls were used for compensation), and data was analyzed with FlowJo software. For analysis, all samples stained for leukocyte composition were pre-gated on viable CD45+ singlet events and all samples stained for T cell subsets were pre-gated on viable CD3+ singlet events. Gates for CD45RO and CCR7 were established using fluorescence minus one (FMO) controls.

Results

The leukocyte composition of the LKPK, Prodigy® product before culture, and the CART products after culture were characterized using flow cytometry on Day 0 and each harvest time point. The cell types identified were T cells (CD3+), monocytes (CD14+), B cells (CD19+), natural killer (NK) cells (CD3-56+), and other cells (Table 22). Prodigy® enrichment produced a Day 0 starting material that was highly viable (92.9%) and enriched for T cells (from 48% to 92%) while reducing contaminating B cells (6% to 0.10%) and monocytes and NK cells to under 4% each. After 12-24 hours in culture, the purity of the viable cells increased an additional 3-4.4%, corresponding with an immediate reduction of monocytes and B cells by hour 12 and gradual reduction of NK cells between hours 12 and 24. Of the leukocytes that express extracellular CAR by flow cytometry, less than 3% were contaminant cells (i.e. not T cells), with the greatest jump in CAR purity (96.6% to 99.2%) occurring between 15 and 18 hours after seeding.

TABLE 22

| Gross leukocyte composition of CART products % of population | | | | | | |
|---|---|---|---|---|---|---|
| Timepoint | Product or Subpopulation | CD3+ | CD14+ | CD19+ | CD3-CD56+ | Other |
| Day 0 | LKPK | 48% | 29% | 6.0% | 11.6% | 5.0% |
| | Prodigy ® Product | 92% | 3% | 0.10% | 3.7% | 0.4% |
| CARTs pre-freeze | 12 hr | 95.3% | 0.2% | 0.02% | 3.3% | 1.1% |
| | 15 hr | 95.6% | 0.2% | 0.01% | 3.3% | 0.9% |
| | 18 hr | 96.4% | 0.1% | 0.0% | 2.7% | 0.9% |
| | 21 hr | 96.3% | 0.2% | 0.0% | 2.3% | 1.2% |
| | 24 hr | 96.2% | 0.2% | 0.0% | 2.2% | 1.5% |
| | 24 hr UTD (n = 2) | 96.4% | 0.1% | 0.06% | 2.4% | 1.1% |
| | 12 hr (of CAR+ only) | 97.1% | 0.6% | 0.0% | 2.4% | 0.0% |
| | 15 hr (of CAR+ only) | 96.6% | 0.9% | 0.0% | 2.5% | 0.0% |
| | 18 hr (of CAR+ only) | 99.2% | 0.1% | 0.0% | 0.7% | 0.0% |
| | 21 hr (of CAR+ only) | 99.1% | 0.3% | 0.0% | 0.7% | 0.0% |
| | 24 hr (of CAR+ only) | 98.9% | 0.3% | 0.0% | 0.8% | 0.0% |

Figure 23A:
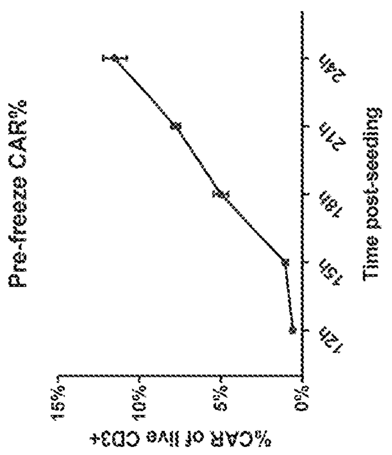
FIGS. 23A, 23B, and 23C.
Figure 23B:
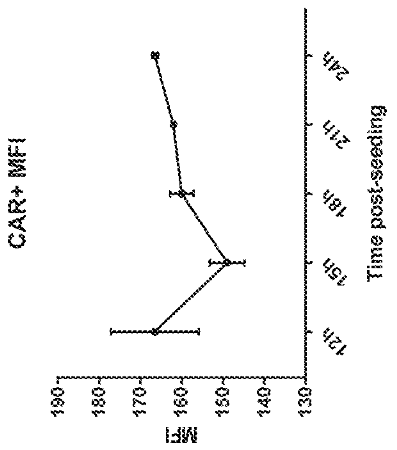
Figure 23C:
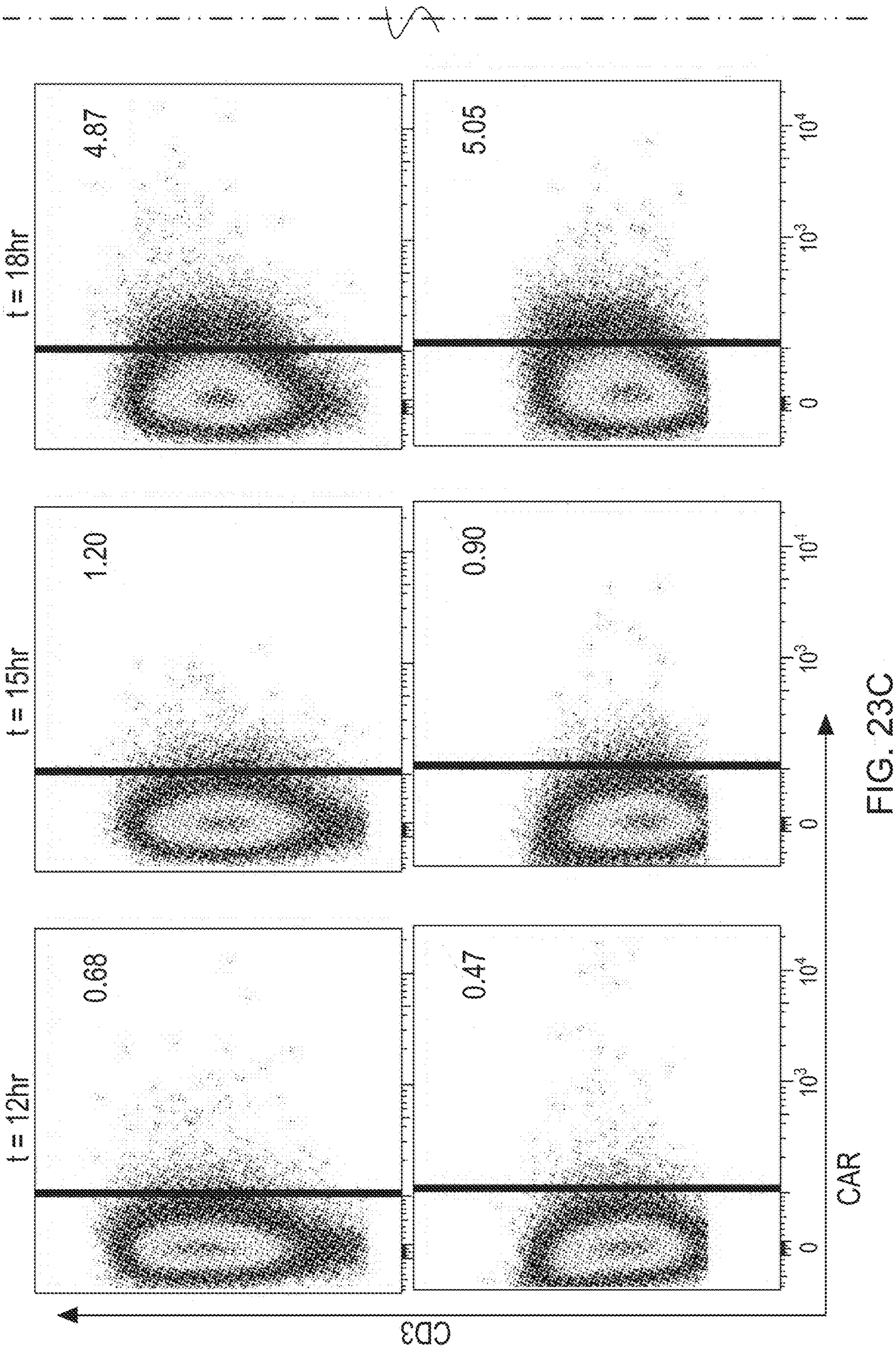
Figure 23C:
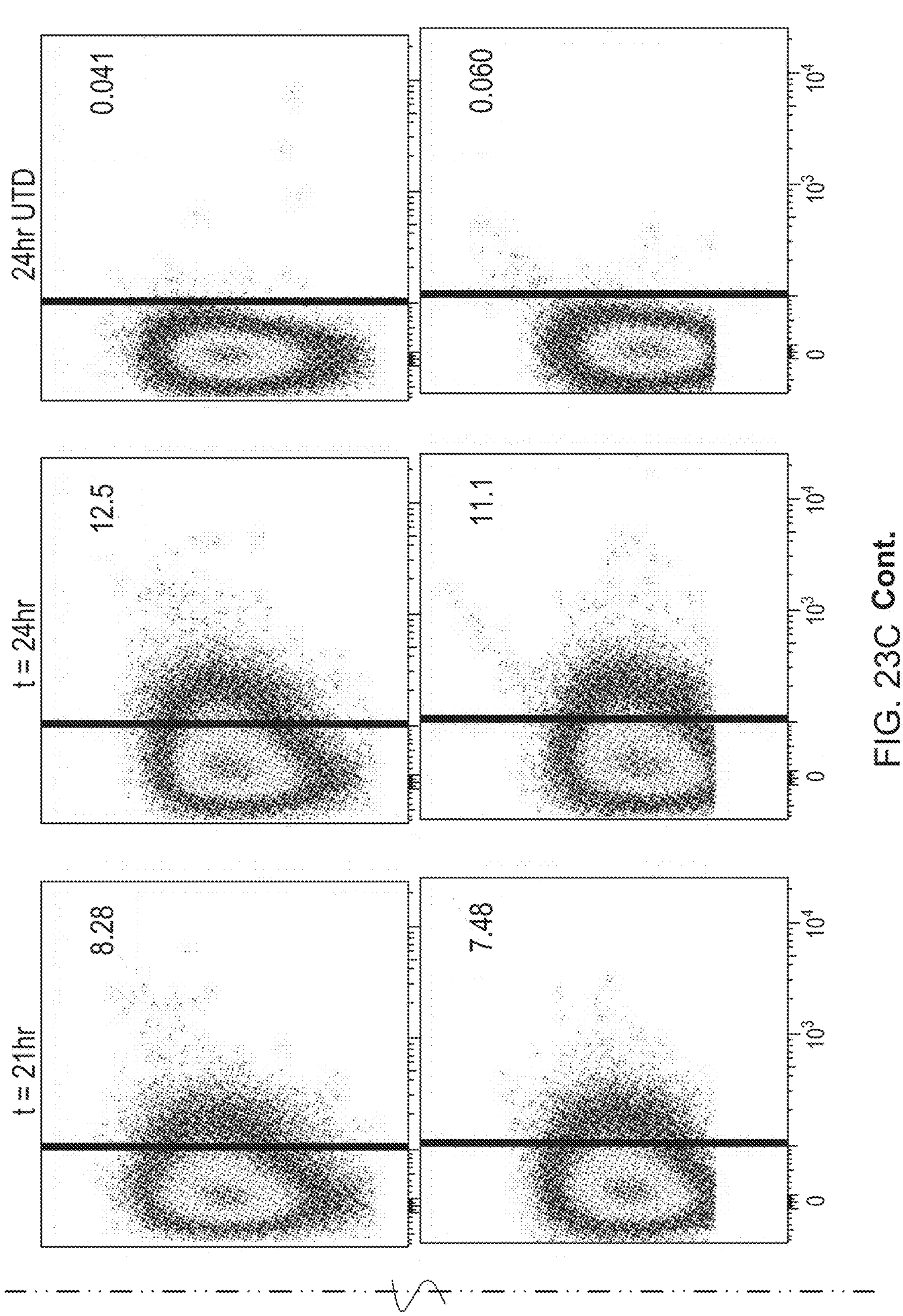

The increase in purity of CAR-expressing cells 18 hours into culture (Table 22) coincides with an increase in the percentage of T cells with CAR surface expression (FIGS. 23A and 23C). As observed previously with rapid CART products evaluated by flow cytometry after 24 hours in culture (see Example 5), CAR surface expression did not lead to distinct positive and negative populations. Gating for CAR positivity was therefore established using the UTD samples as the lower bound. The proportion of CD3+ cells expressing extracellular CAR remained below 1% until 15 hours post-seeding; and CAR expression then increased 3-4% every three hours to a maximum of 11.8% without saturating (FIG. 23A). The intensity of CAR expression as determined by MFI also increased slightly >18 hours in culture but remained dim through hour 24 (FIG. 23B).

Figure 24A:
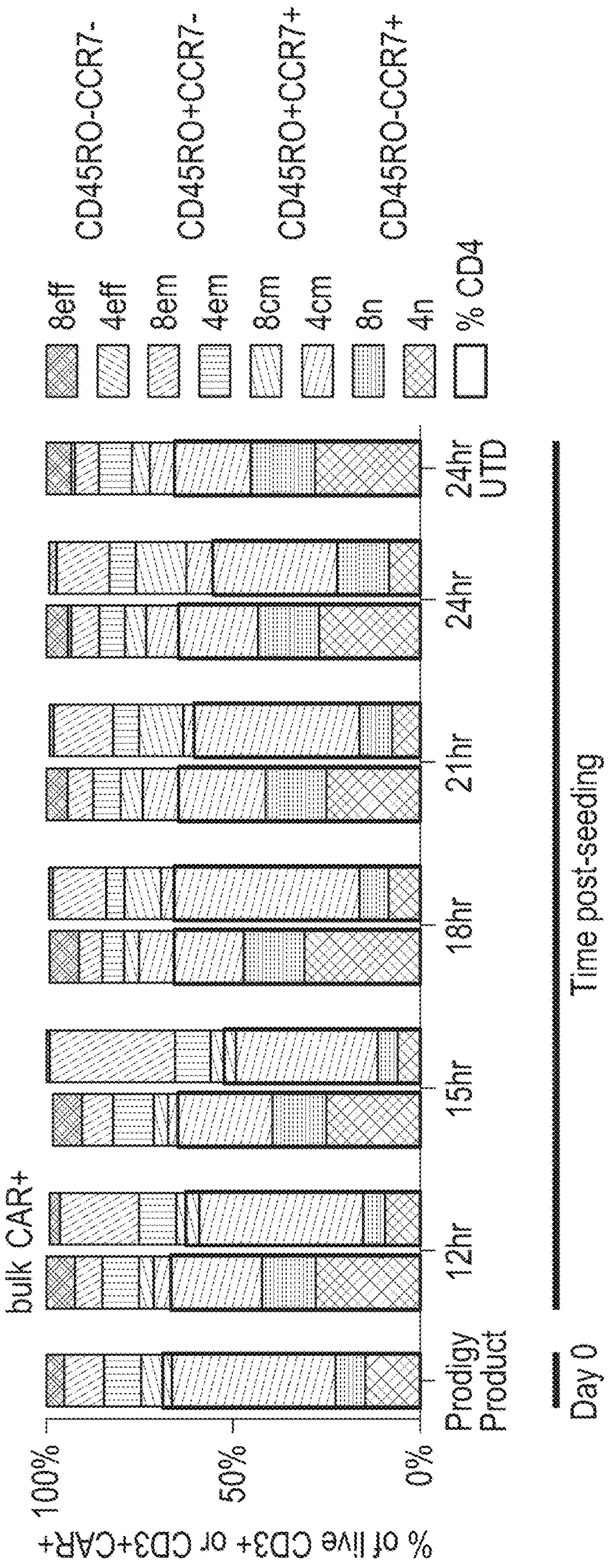
FIGS. 24A and 24B.
Figure 24B:
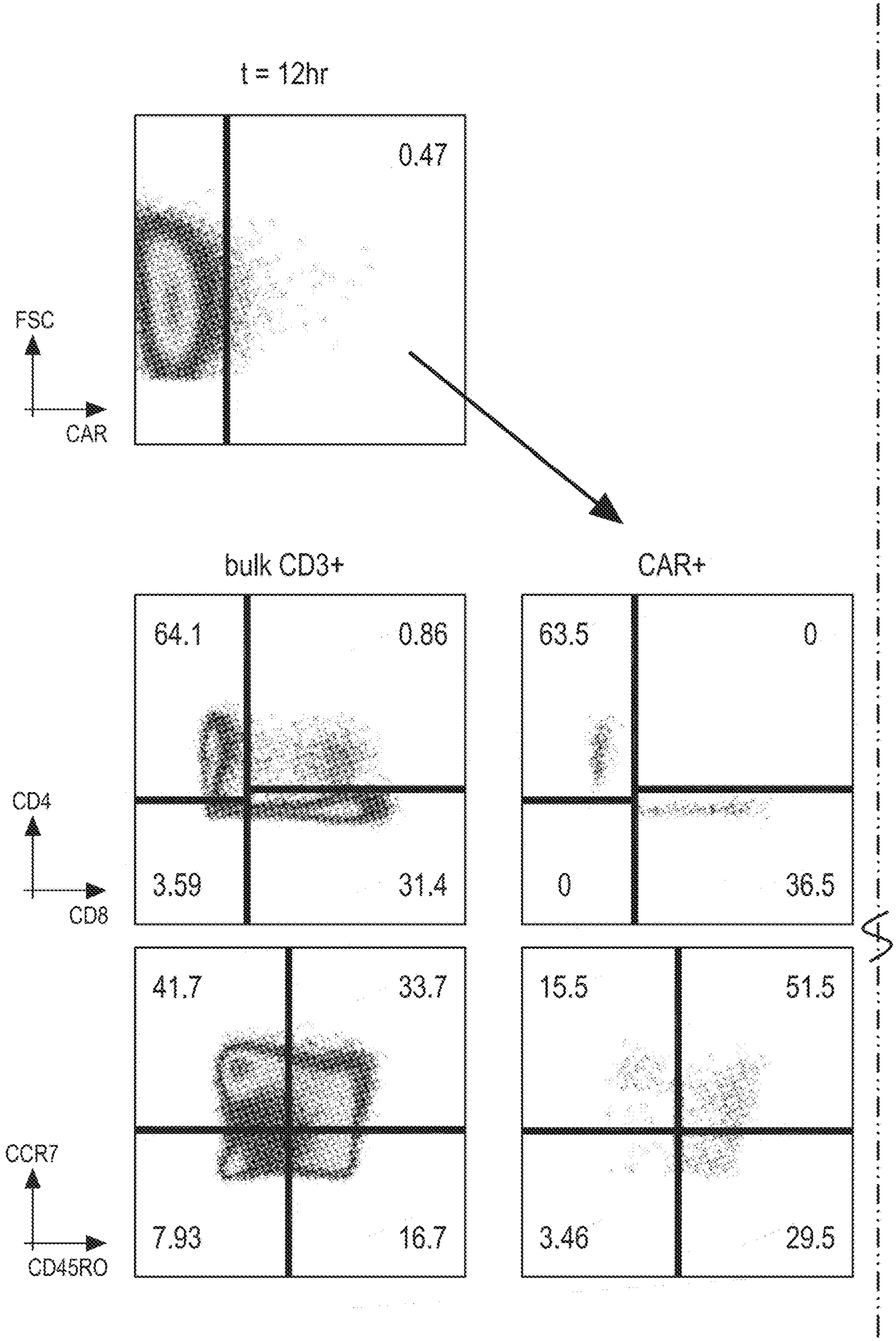
Figure 24B:
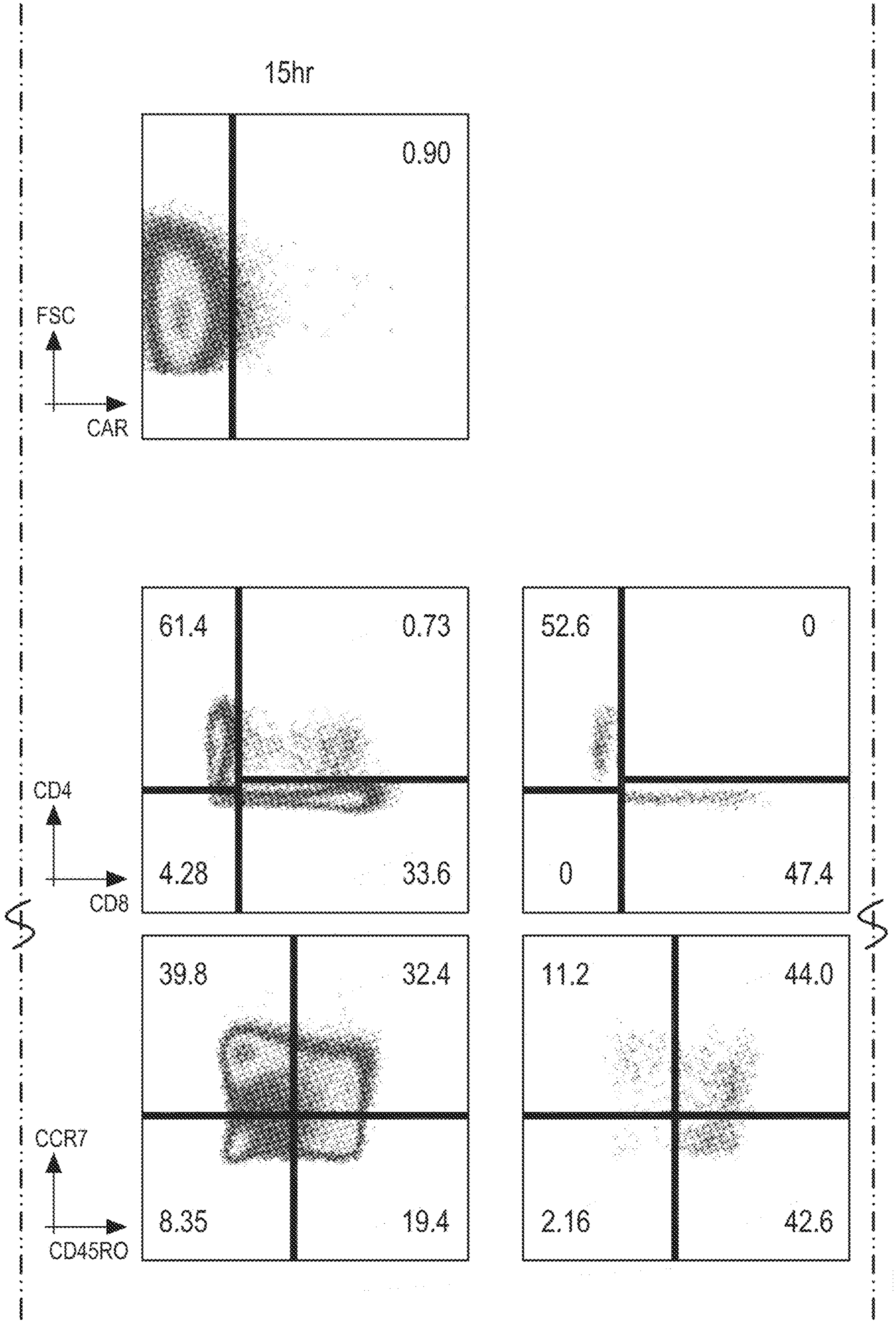
Figure 24B:
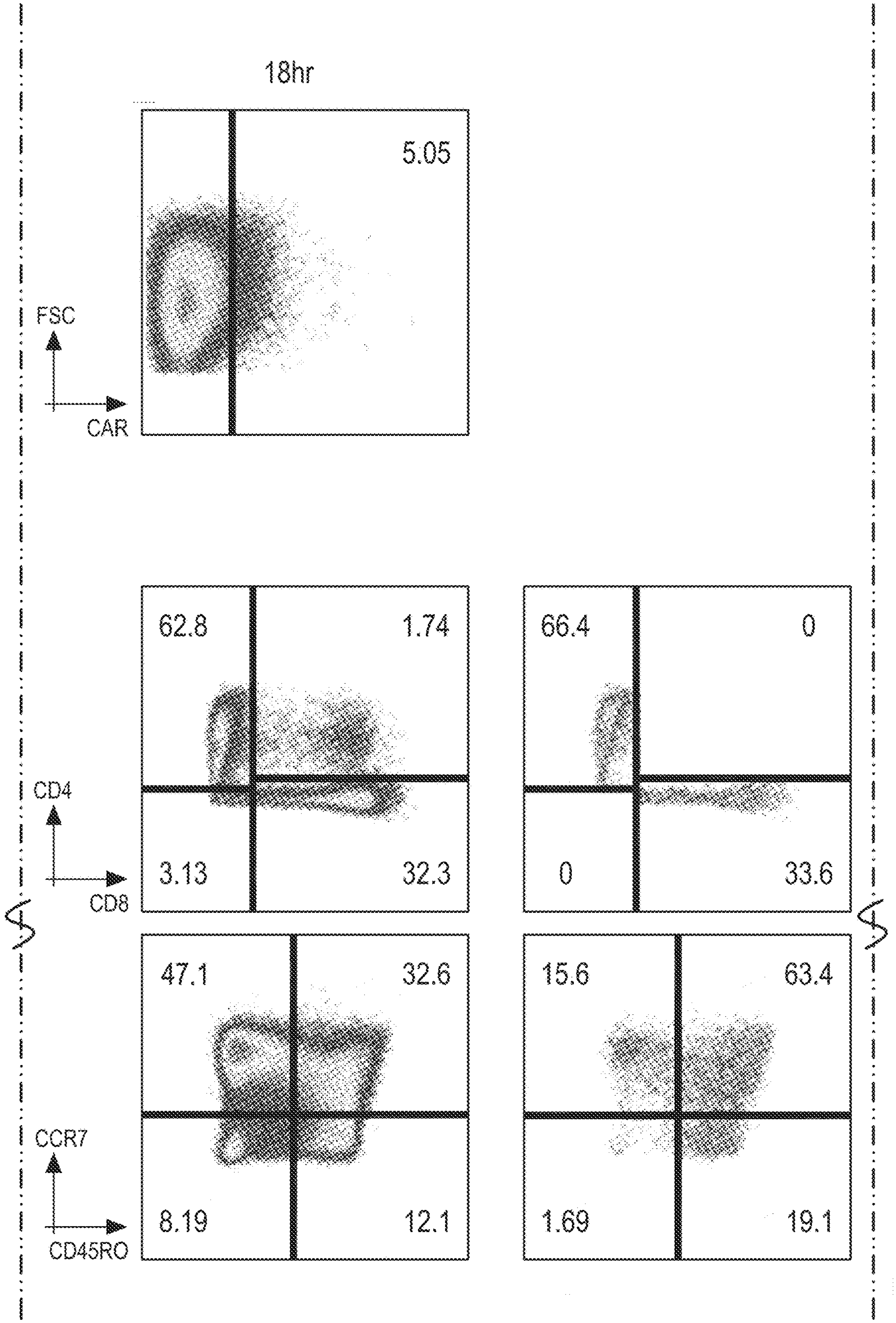
Figure 24B:
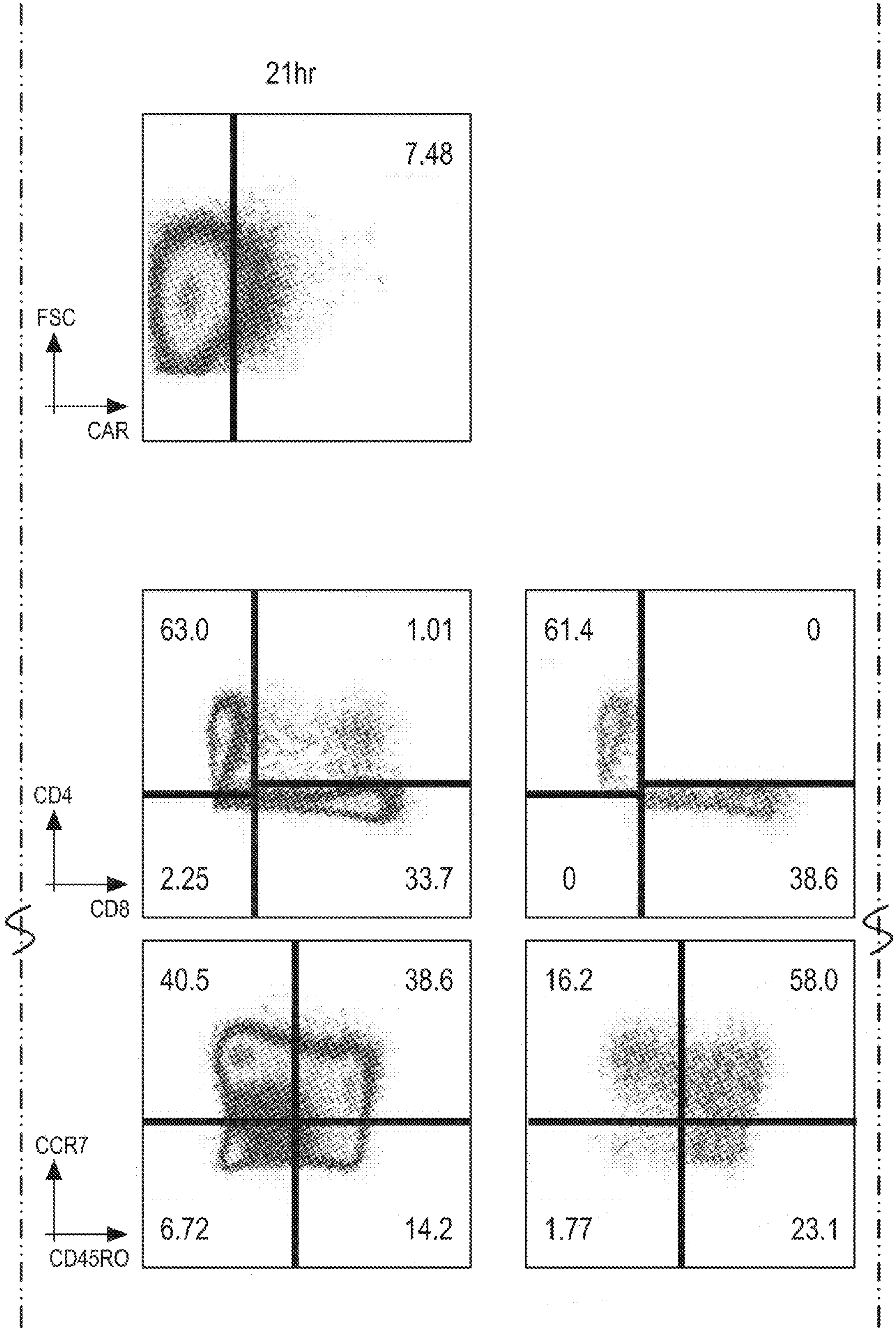
Figure 24B:
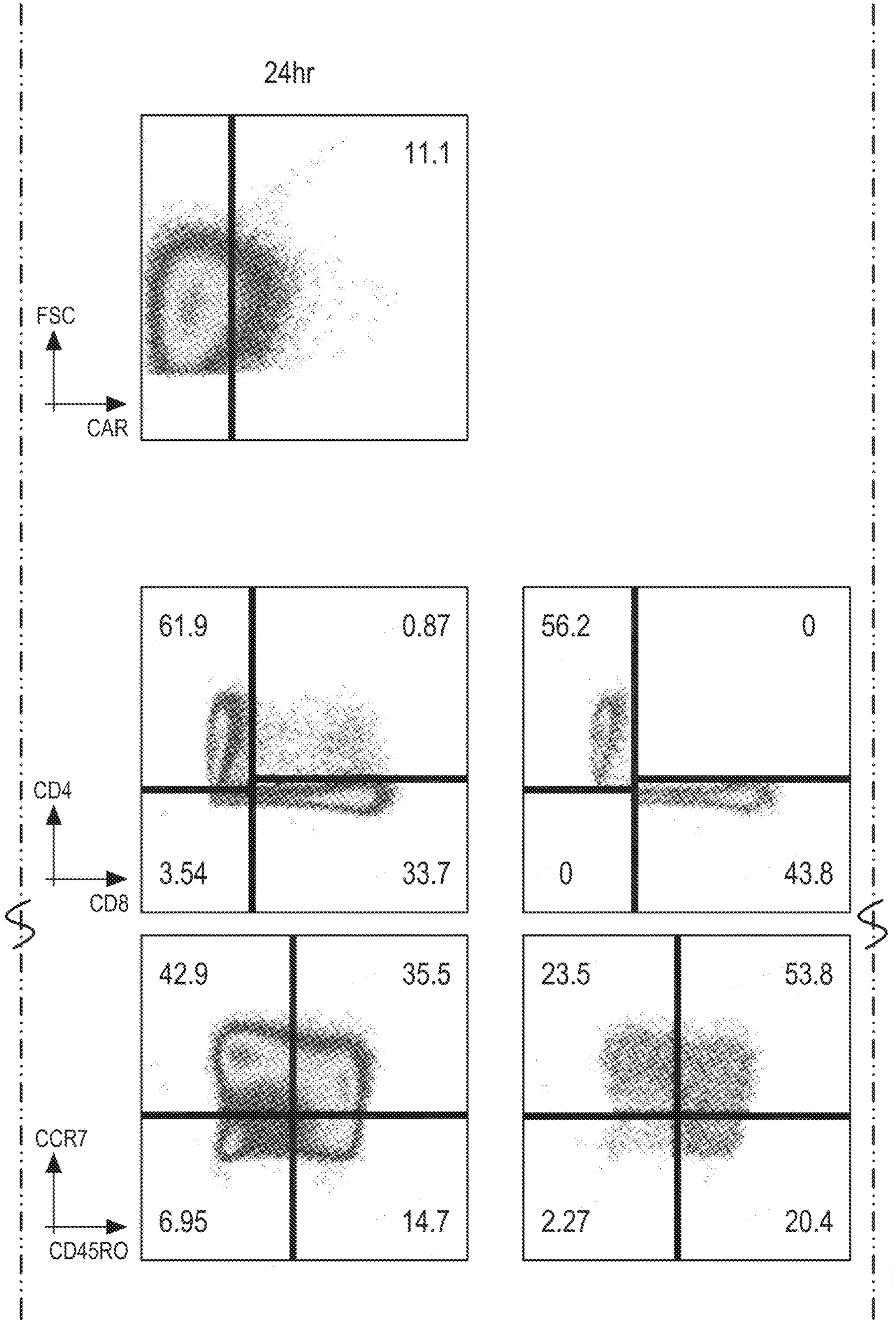
Figure 24B:
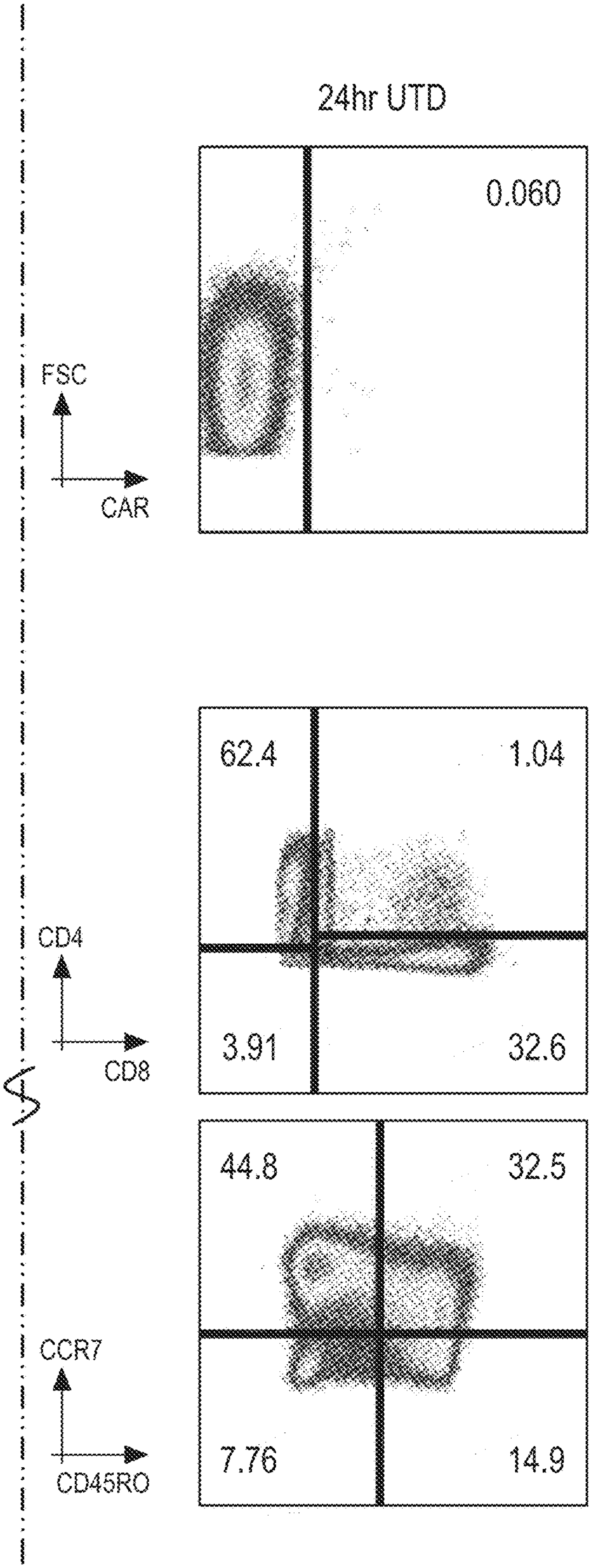
Figure 25:
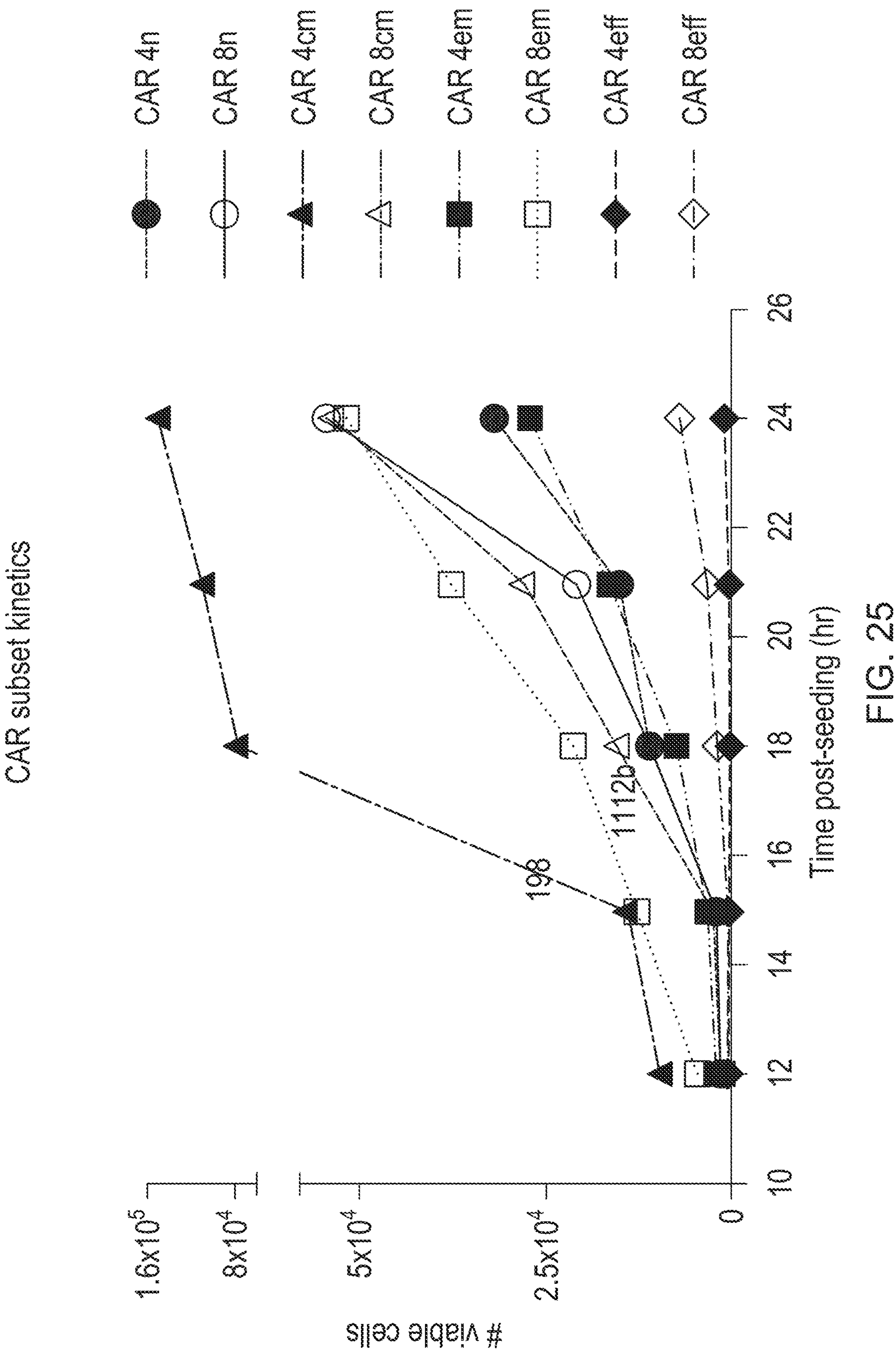
FIG. 25. Kinetics of T cell subsets expressing surface CAR over time, expressed as number of viable cells in the respective subsets.

T cell subsets (CD4:CD8 ratio and memory subset composition) were also evaluated at each timepoint (FIGS. 24A and 24B) using a combination of CD4, CD8, CD45RO, and CCR7; where undifferentiated naive-like T cells were defined as CCR7+CD45RO−, central memory cells as CCR7+CD45RO+, effector memory cells as CCR7−CD45RO+, and highly differentiated effector T cells as CCR7−CD45RO−. Across all timepoints evaluated, including the UTD, cultures contained a greater proportion of naive cells (40-47%) and lower proportion of central memory cells (33-39%) than the initial starting material (23% and 52%, respectively). Interestingly, although the frequency of naïve or central memory T cells in the bulk composition did not change between 12 to 24 hours, later harvests were correlated with a greater frequency of extracellular CAR-expressing cells that were naïve and a lower frequency of extracellular CAR-expressing cells that were central memory (16% naïve/63% central memory among CAR-expressing cells at 18 hours vs. 24% naïve/54% central memory among CAR-expressing cells at 24 hours). Similarly, while bulk CD4:CD8 ratio did not change significantly, the CD4 fraction of the CAR+ cells decreased by 10% (66% to 56%) between 18-24 hours. Converting these frequencies to total cell numbers (FIG. 25) reveals that the subsets of T cells that appeared to express the CAR the earliest are mostly naive CD4 cells between 15-18 hours in culture; naive CD8 CARs and central memory CD8 CARs then rapidly increase in frequency.

Figure 26:
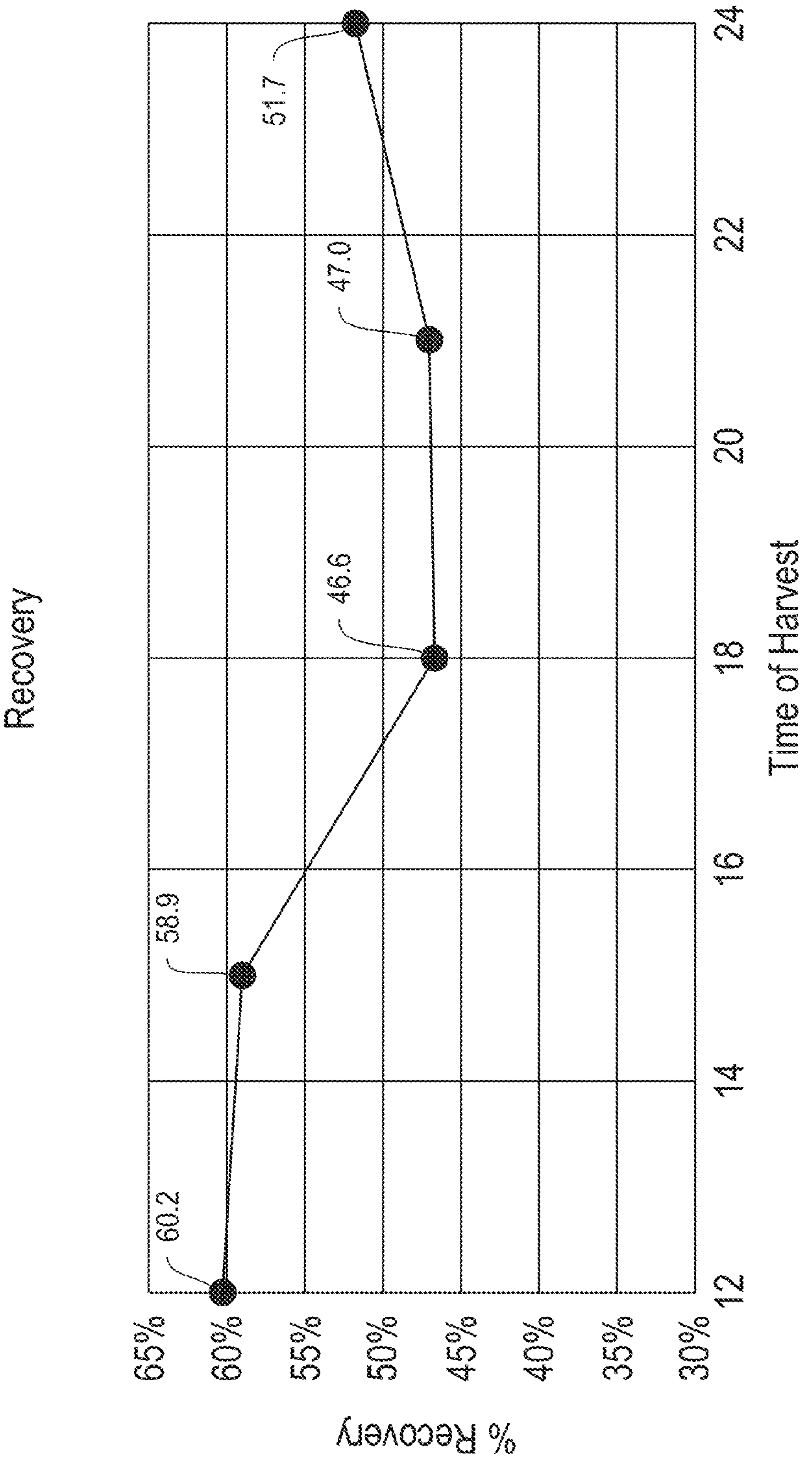
FIG. 26. Viable cell recovery (number of viable cells recovered at harvest versus number of viable cells seeded) 12 to 24 hours after culture initiation as determined from pre-wash counts.
Figure 27:
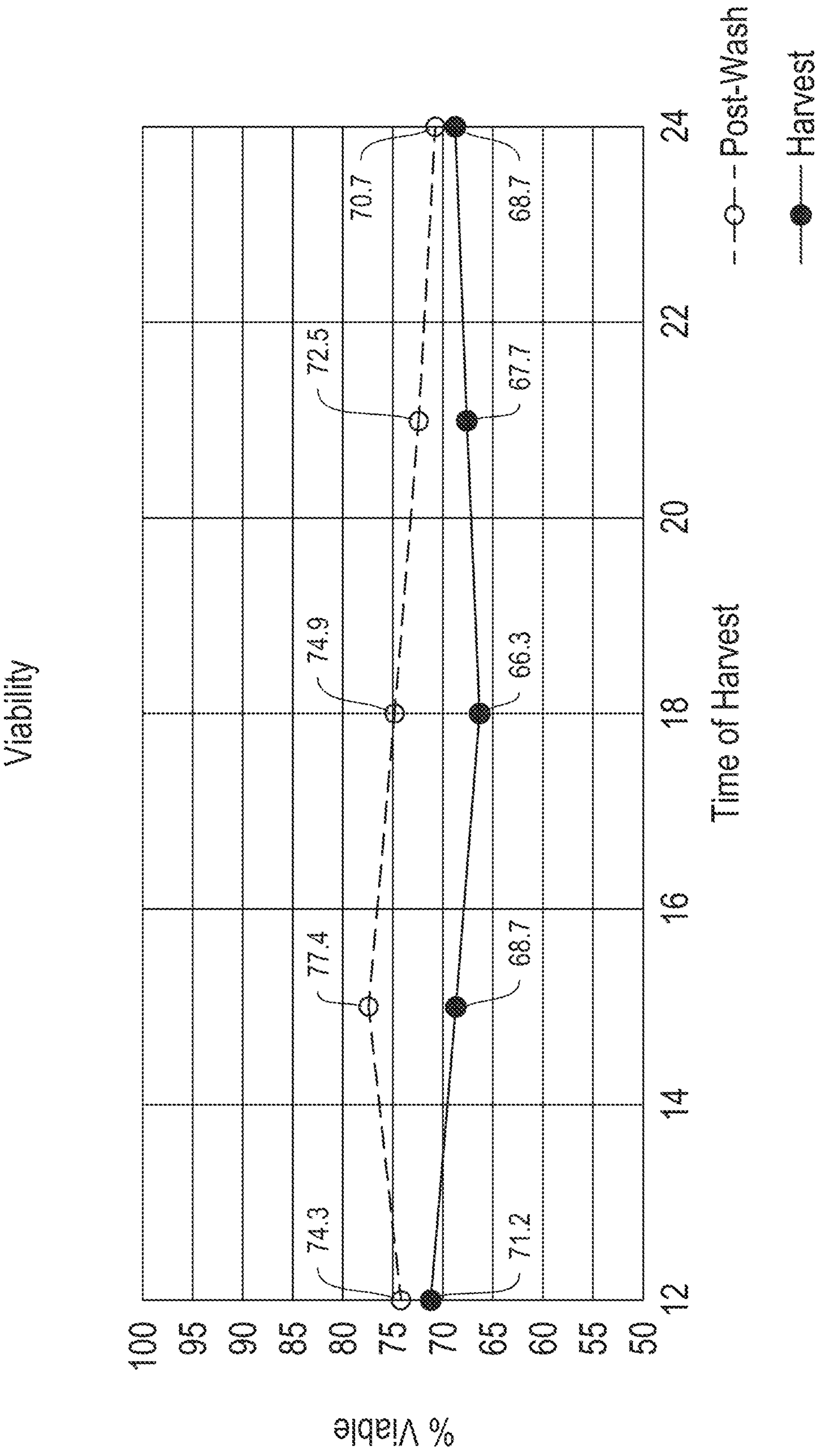
FIG. 27. Viability of rapid CARTs harvested 12 to 24 hours after culture initiation, as determined pre-wash and post-wash at the time of harvest.

Viable cell recovery (or fold expansion) as well as pre- and post-wash viability were determined at each harvest time point (FIGS. 26 and 27). Recovery of viable cells decreased by 13% until 18 hours post-seeding (lowest 46%, coinciding with the increased rate of extracellular CAR expression), then increased slightly to 52% for cultures harvested at later time points (FIG. 26). Product viability increased after washing to 71-77% with viability decreasing for harvests between 15-24 hours (FIG. 27).

Conclusion

Of time points tested between 12-24 hours, rapid CARTs seeded simultaneously with TransAct and technical grade CTL019 vector show the highest CAR surface expression at 24 hours. Very few cells are CAR+ (as measured at the time of harvest) until 15 hours post-seeding, after which % CAR increases more rapidly. The intensity of CAR expression is dim but increases slowly after 18 hours post-seeding.

Rapid CART products become purer (greater % T cells) than the starting material at all points between 12 to 24 hours post-seeding due to monocyte loss in the first 12 hours, followed by a minor loss of NK cells and any residual B cells not removed by Prodigy® enrichment.

Although overall cell recovery is lowest when harvested 18 hours post-seeding (improving slightly by 24 hours), the overall T cell composition does not change between 12 and 24 hours post-seeding. T cells that first express extracellular CAR are mostly central memory CD4s between 15 and 18 hours post-seeding, then naive and central memory CD8s show CAR expression.

Example 7: Description of the Activated Rapid Manufacturing (ARM) Process

In some embodiments, CART cells are manufactured using a continuous Activated Rapid Manufacturing (ARM) process, over approximately 2 days, which will potentially allow for a greater number of less differentiated T cells (T naïve and $T_{SCM}$ (stem central memory T) cells) to be returned to a patient for in vivo cellular expansion. The short manufacturing time period allows the early differentiated T cells profile to proliferate in the body for their desired terminal differentiated state rather that in an ex vivo culture vessel.

In some embodiments, CART cells are manufactured using cryopreserved leukapheresis source material, for example, non-mobilized autologous peripheral blood leukapheresis (LKPK) material. Cryopreserved source material undergoes processing steps for T cell enrichment on the first day of production (Day 0) by means of anti-CD4/anti-CD8 immunomagnetic system. Positive fraction is then seeded in G-rex culture vessel, activated with an anti-CD3/CD28 system (TransACT) and on the same day transduced with a lentiviral vector (LV) encoding a CAR. On the following day, after 20-28 hours of transduction, the T cells are harvested, washed four times, formulated in freezing medium and then frozen by a Controlled Rate Freezer (CRF). From the start of the process on Day 0 to the initiation of harvest on the following day, cells are cultured for 20-28 hours with a target of 24 hours after Day 0 seeding.

Media for Day 0 were prepared according to Table 21. The cryopreserved leukapheresis material is thawed. The thawed cells are diluted with the Rapid Buffer (Table 21) and washed on the CliniMACS® Prodigy® device. The T cells are selected by CliniMACS® CD4 and CD8 microbeads. Once the program is finished for T cell selection (approximately 3 h 40 min to 4 h 40 min), the reapplication bag containing the cells suspended in Rapid Media (Table 21) are transferred in a transfer pack. A sample is taken for viability and cell count. The cell count and viability data from the positive fraction bag is used to determine the cell concentration when seeding the culture vessel for activation and vector transduction.

Following positive selection of T cells via the CliniMACS® microbeads (CD4 and CD8), the cells are seeded in the culture vessel, G-Rex. Once the cells are seeded, the activation reagent (TransACT) is then added to the culture vessel. The cells are then transduced with a lentiviral vector encoding a CAR at a target MOI of 1.0 (0.8-1.2). Following the vector addition, the culture vessel is transported to an incubator where it is incubated for a target of 24 hours (operating range 20-28 hours) at a nominal temperature of 37° C. (operating range 36-38° C.) with nominal 5% $CO_2$ (operating range 4.5-5.5%). Following the incubation, the cells are washed with Harvest Wash Solution (Table 21) four times to remove any non-integrated vector and residual viral particles, as well as any other process related impurities. Then, the cells are eluted and a sample for cell count and viability is taken for testing and the results are used to determine the volume required to re-suspend the cells for final formulation with CryoStor® CS10. The cells are then centrifugated to remove the Harvest Wash Solution and proceed with cryopreservation.

In some embodiments, the CAR expressed in CART cells binds to CD19. In some embodiments, IL-2 used in the Rapid Media (RM) (Table 21) can be replaced with IL-15, hetIL-15 (IL-15/sIL-15Ra), IL-6, or IL-6/sIL-6Ra.

In some embodiments, the CAR expressed in CART cells binds to BCMA. In some embodiments, IL-2 used in the Rapid Media (RM) (Table 21) can be replaced with IL-15, hetIL-15 (IL-15/sIL-15Ra), IL-6, or IL-6/sIL-6Ra.

Example 8: Characterization of CD19 CART Cells Manufactured Using the Activated Rapid Manufacturing (ARM) Process Disclosed herein is an anti-CD19 CAR-T cell product manufactured using the activated rapid manufacturing (ARM) process. The ARM process reduces the turnaround time compared to traditional manufacturing (TM) processes, prospectively allowing a timely infusion of the anti-CD19 CAR-T cell product to patients. Moreover, the ARM process also preserves putative stem memory T ($T_{stem}$) cells, a cellular subset associated with improved antitumor efficacy. The main difference in manufacturing is that while the TM process includes an expansion phase in which anti-CD19 CAR T cells are cultured in vitro for 9 days with interleukin (IL-) 2 before being formulated, the ARM process allows formulation after only 24 hours of culture. This is made possible by the use of a fully biocompatible nanomatrix coupled to monoclonal antibodies (mAb) with agonistic activity against CD3 and CD28, which differently from the CD3/CD28 paramagnetic beads used in the TM process, can be washed away with the residual lentiviral vector right after transduction. Results from a xenograft mouse model, as well as final product enrichment for $T_{stem}$ cells, a subpopulation associated with increased persistence and long-term antitumor effects, suggest an overall improved therapeutic potential of anti-CD19 CAR T cells manufactured using the ARM process as compared to anti-CD19 CAR T cells manufactured using the TM process. Another important difference revealed by the xenograft mouse model is a potential delayed cellular kinetics expansion of anti-CD19 CAR T cells manufactured using the ARM process for approximately one week compared to the counterparts manufactured using the TM process. This delay is estimated to be approximately 1 week, which imposes corresponding prolongation of the window for careful monitoring of potential toxicities from 3 weeks, as with anti-CD19 CAR T cells manufactured using the TM process, to 4 weeks. Conversely, non-clinical safety data from an in vitro cytokine release model indicate that anti-CD19 CAR T cells manufactured using the ARM process and those manufactured using the TM process might have a similar potential to induce IL-6 production in vivo and therefore carry a similar cytokine release syndrome (CRS) risk. Based on this evidence, anti-CD19 CAR T cells manufactured using the ARM process will be investigated in a Phase I, open label clinical study in patients with advanced small lymphocytic lymphoma (SLL)/chronic lymphocytic leukemia (CLL) in combination with the Bruton tyrosine kinase inhibitor (BTKi) ibrutinib (Imbruvica), an already approved drug in this indication, and as single agent in DLBCL.

Generation and In Vitro Analysis

Figure 28A:
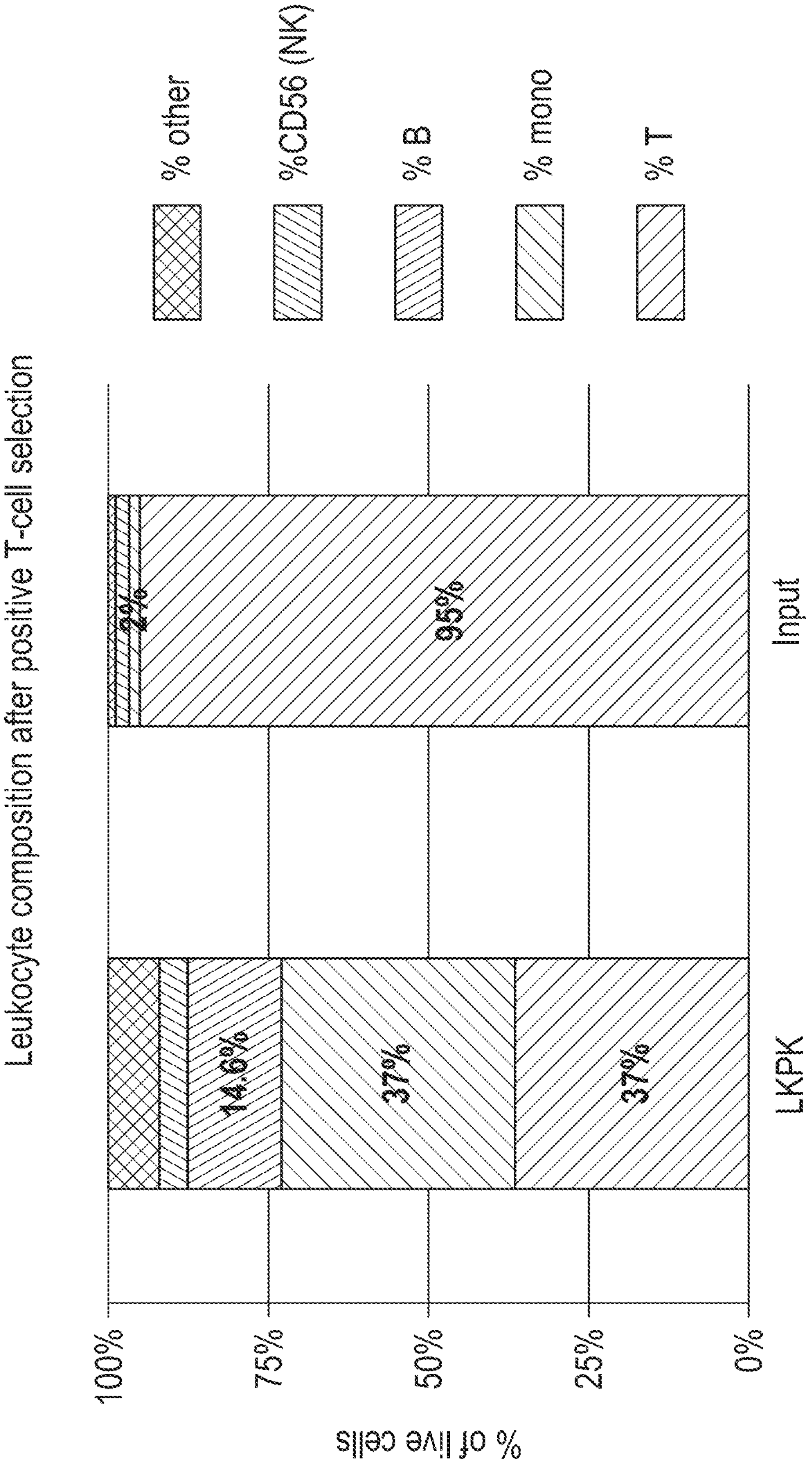

To test the ARM process for anti-CD19 CAR T cell manufacturing at clinical scale, a frozen healthy donor leukapheresis product (Leukopak, LKPK) was used as starting material, described in FIG. 28A as a representative example. The LKPK contained 37% T cells, 4% NK cells, 37% monocytes and 15% B cells (FIG. 28A). After thawing, T cells were positively selected using anti-CD4 and anti-CD8 microbeads. The composition of the product after positive T cell selection was 95.4% T cells, 1.9% NK cells, 1.7% monocytes, and 0.1% B cells (FIG. 28A).

Figure 28B:
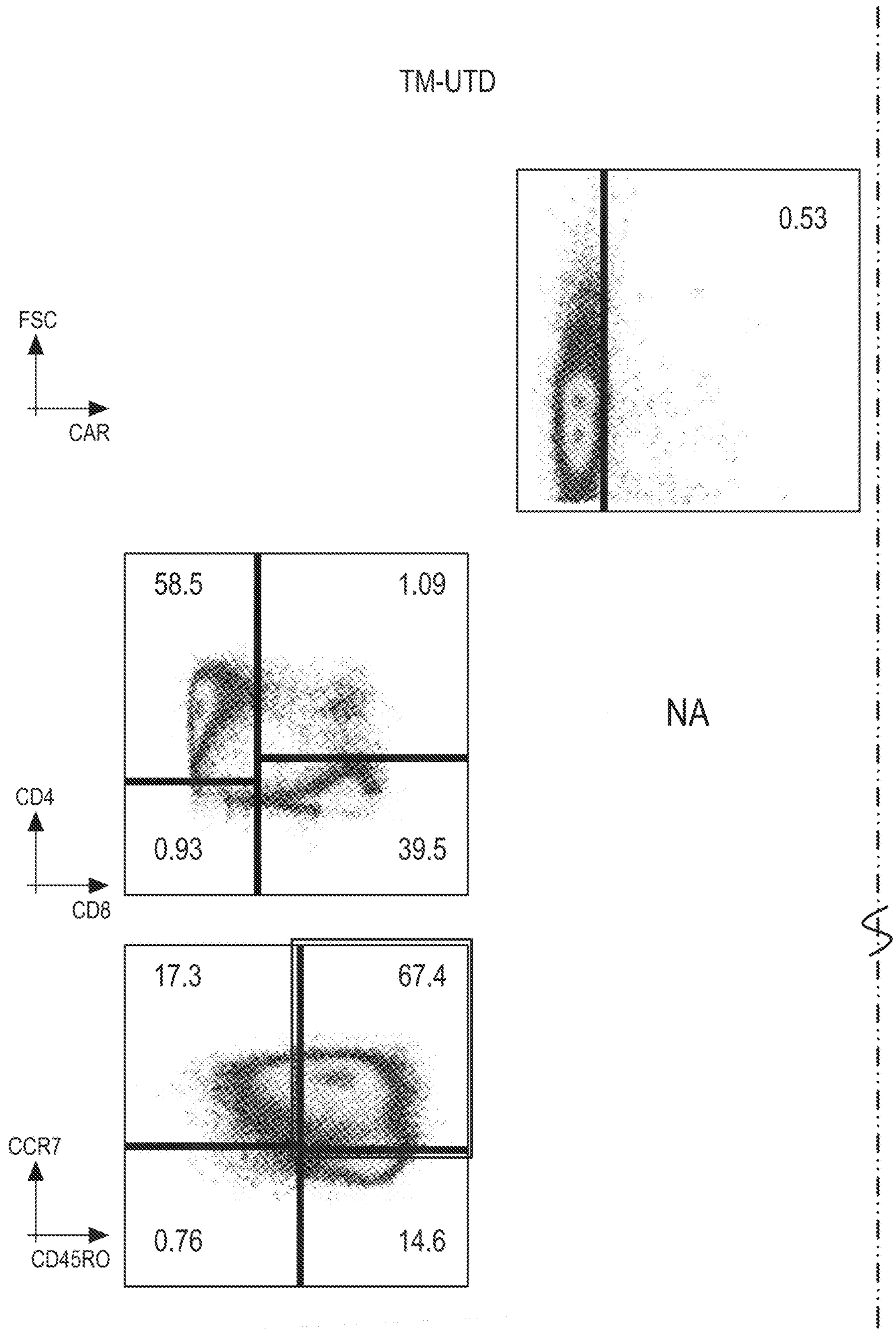
Figure 28B:
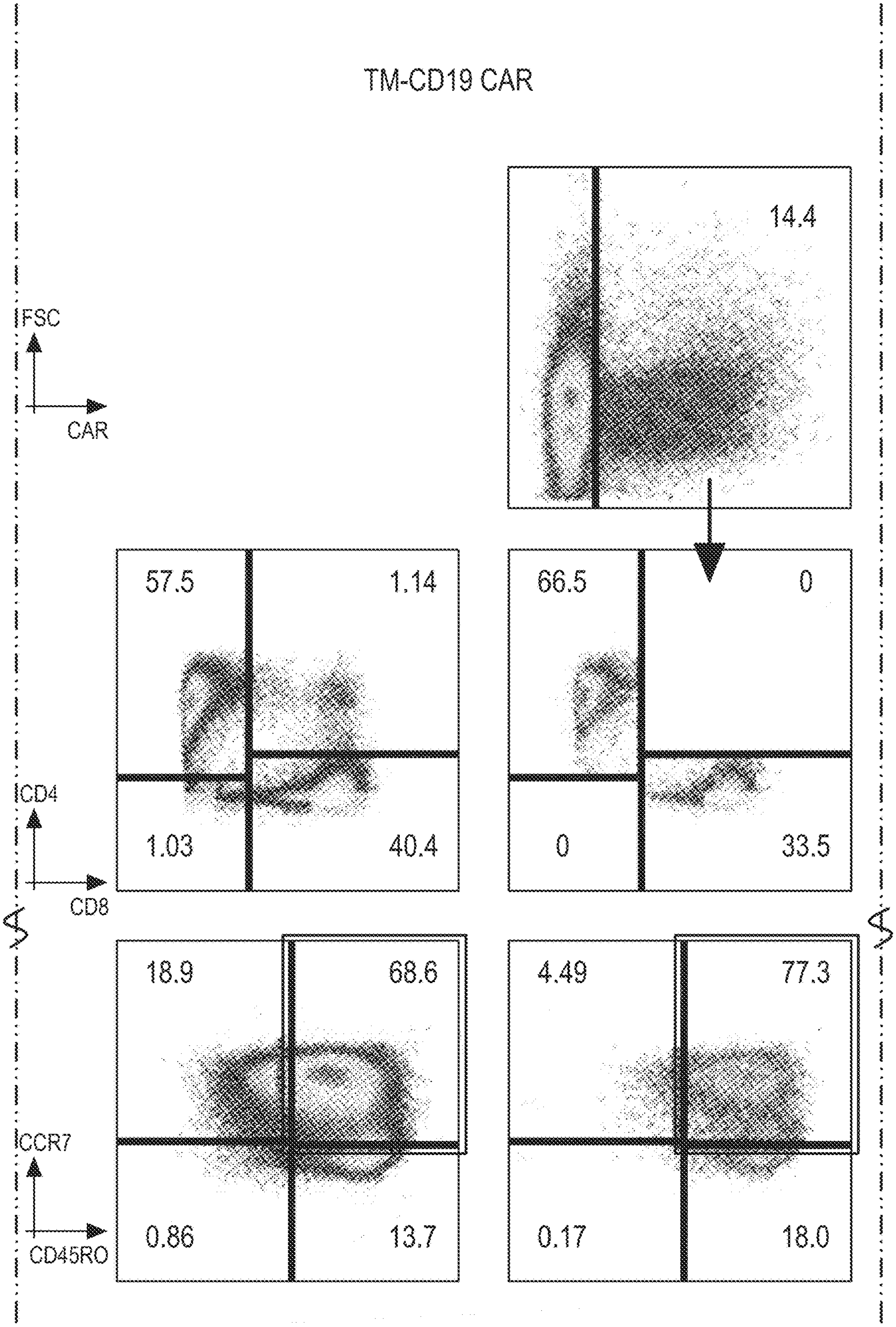
Figure 28B:
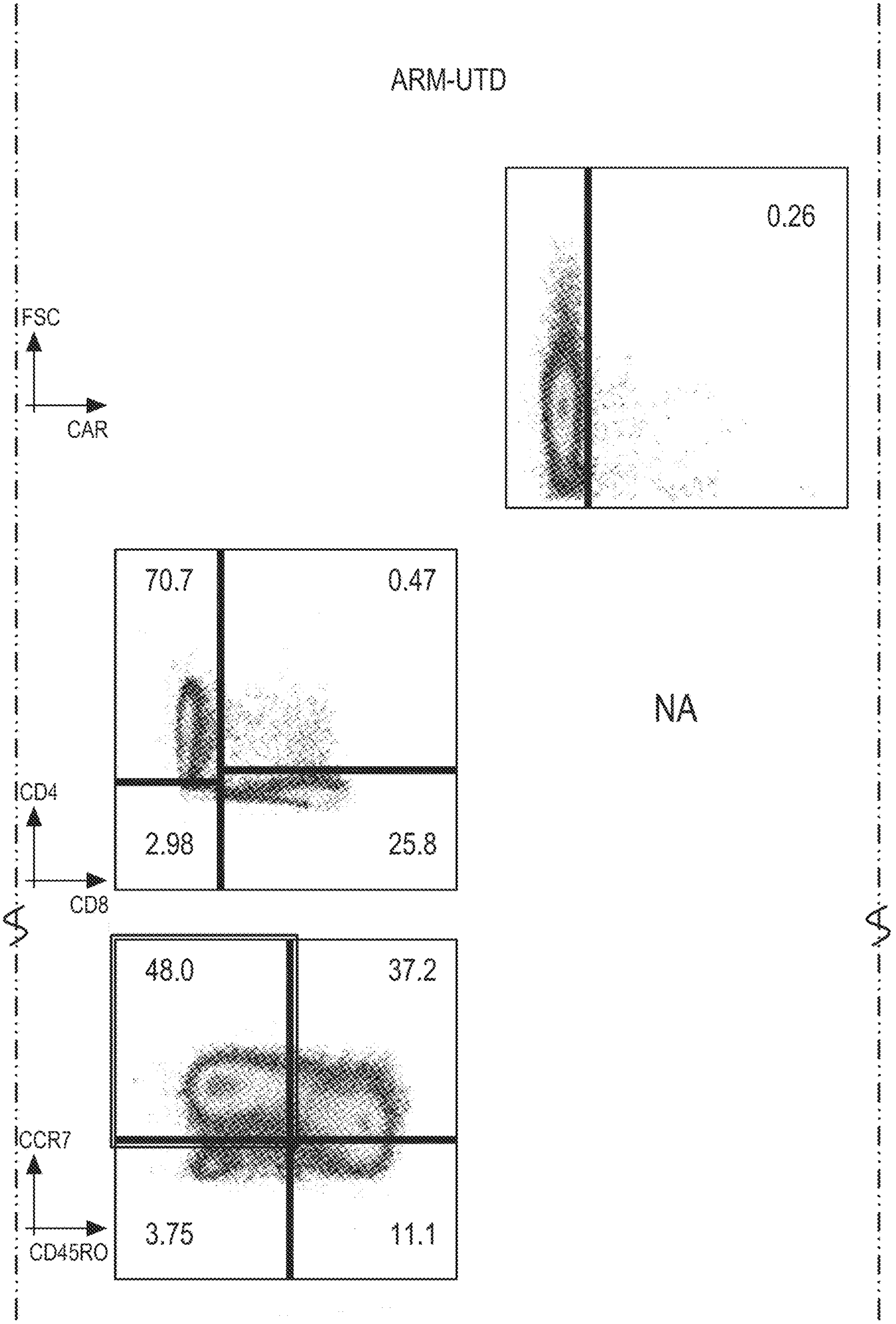
Figure 28B:
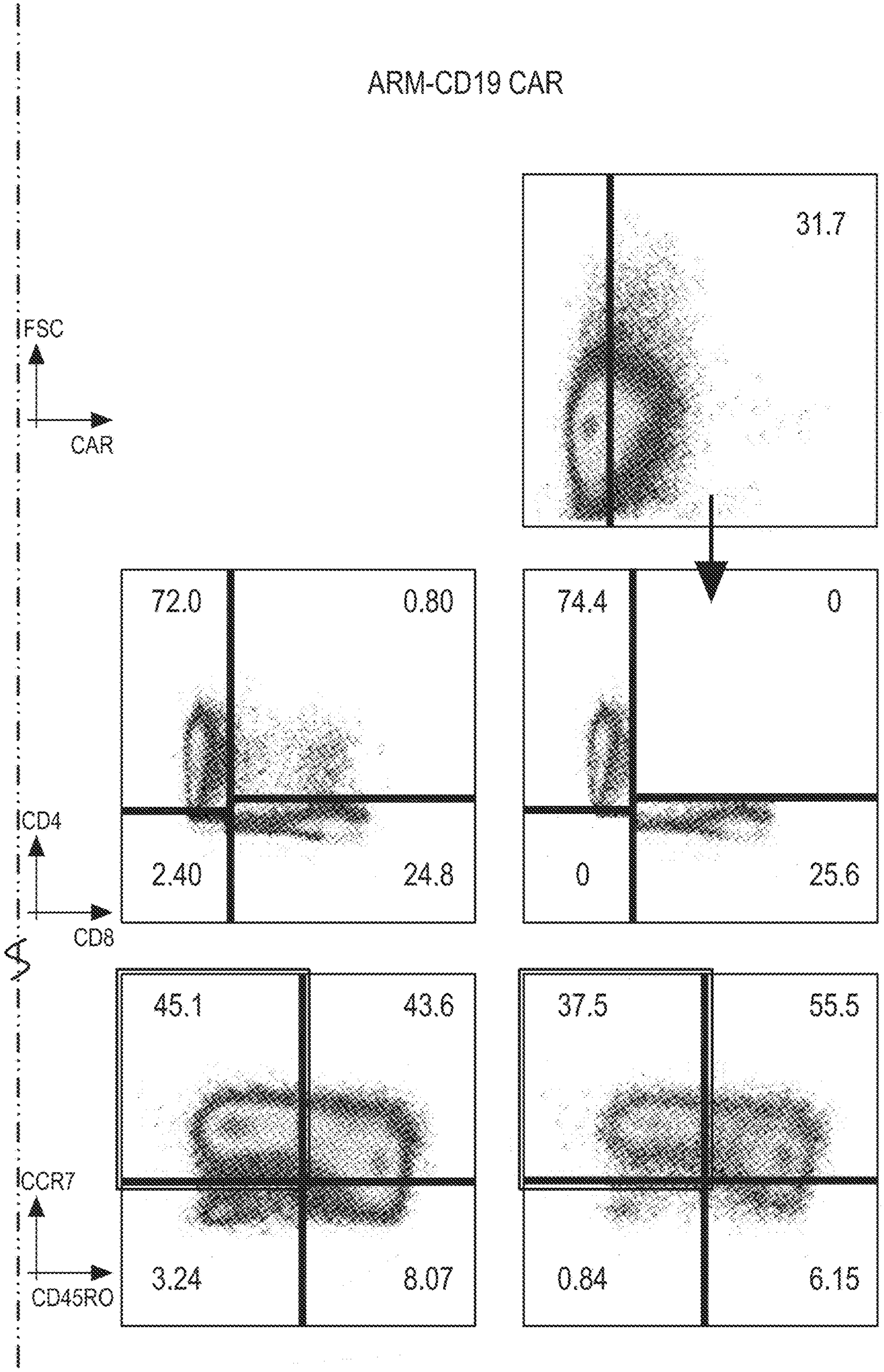
Figure 28C:
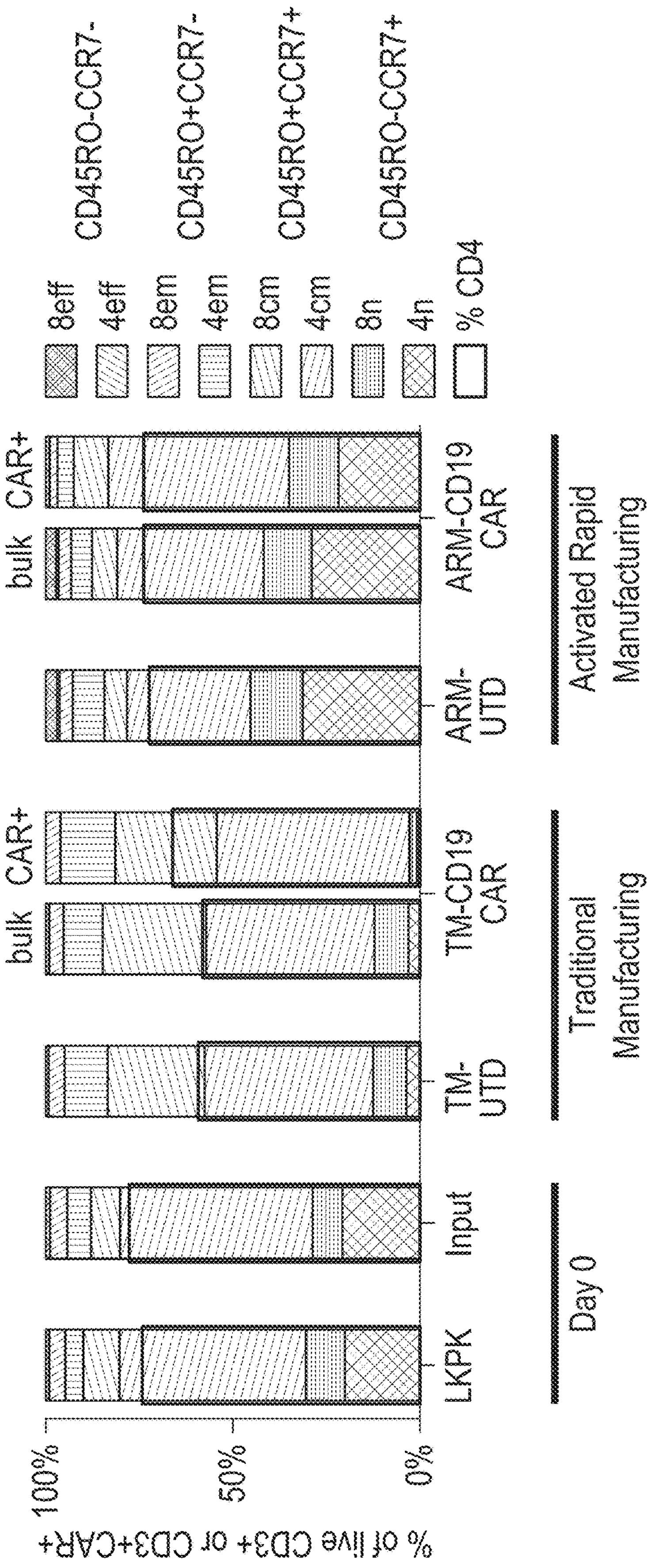

Positively selected T cells were activated using a polymeric nanomatrix conjugated to anti-CD3 and anti-CD28 agonist monoclonal antibodies and transduced with a lentiviral vector encoding anti-CD19 CAR. After 24 hours in culture, cells were harvested and cryopreserved (such cells are referred to as “ARM-CD19 CAR” in this example). In parallel, CAR-T cells were generated using a traditional manufacturing (TM) process (such cells are referred to as “TM-CD19 CAR” in this example), using the same donor T cells and lentiviral vector. The TM process utilized paramagnetic beads coupled to anti-CD3 and anti-CD28 antibodies and a 9-day culture period in tissue-culture flasks, followed by the same harvest and freezing procedure. CAR-T cells generated by each process were analyzed by flow cytometry to evaluate CAR expression post thaw, as well as the Tcell phenotype (FIGS. 28B-28D). Analysis of the T-cell phenotype revealed that the ARM process retained naïve-like T cells (45.1% CD45RO−/CCR7+) in both the CD8 and CD4 compartments, while the TM process mainly resulted in central-memory T ($T_{CM}$) cells (68.6% CD45RO+/CCR7+ compared to 43.6% for ARM-CD19 CAR) (FIGS. 28C and 28D). Importantly, the ARM process better maintained the initial naïve-like CD45RO−/CCR7+ T-cell population as compared to the TM process, also in the CAR+ population (28.6% in starting material, 37.5% for ARM-CD19 CAR and 4.5% for TM-CD19 CAR) (FIGS. 28C and 28D). This T-cell population largely overlaps with CD45RO−/CD27+ Tstem cells described by Fraietta, et al (2018) Nat Med, 24(5); 563-571 and associated with sustained remission in a CLL phase I clinical trial.

Figure 29A:
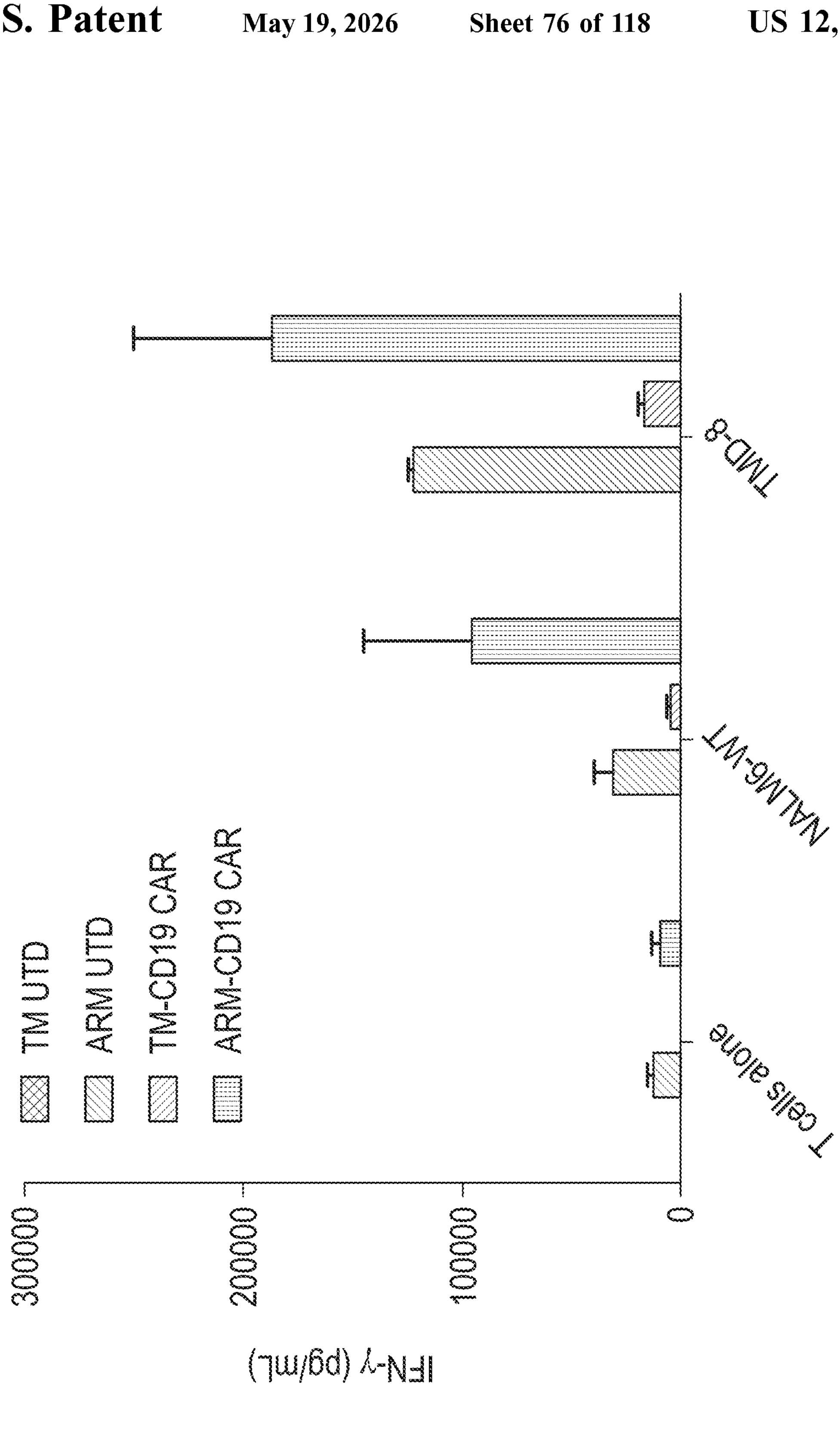
FIGS. 29A, 29B, 29C, and 29D. Cytokine concentration in cell culture supernatants. IFN-γ (FIGS. 29A and 29B) and IL-2 (FIGS. 29C and 29D).
Figure 29B:
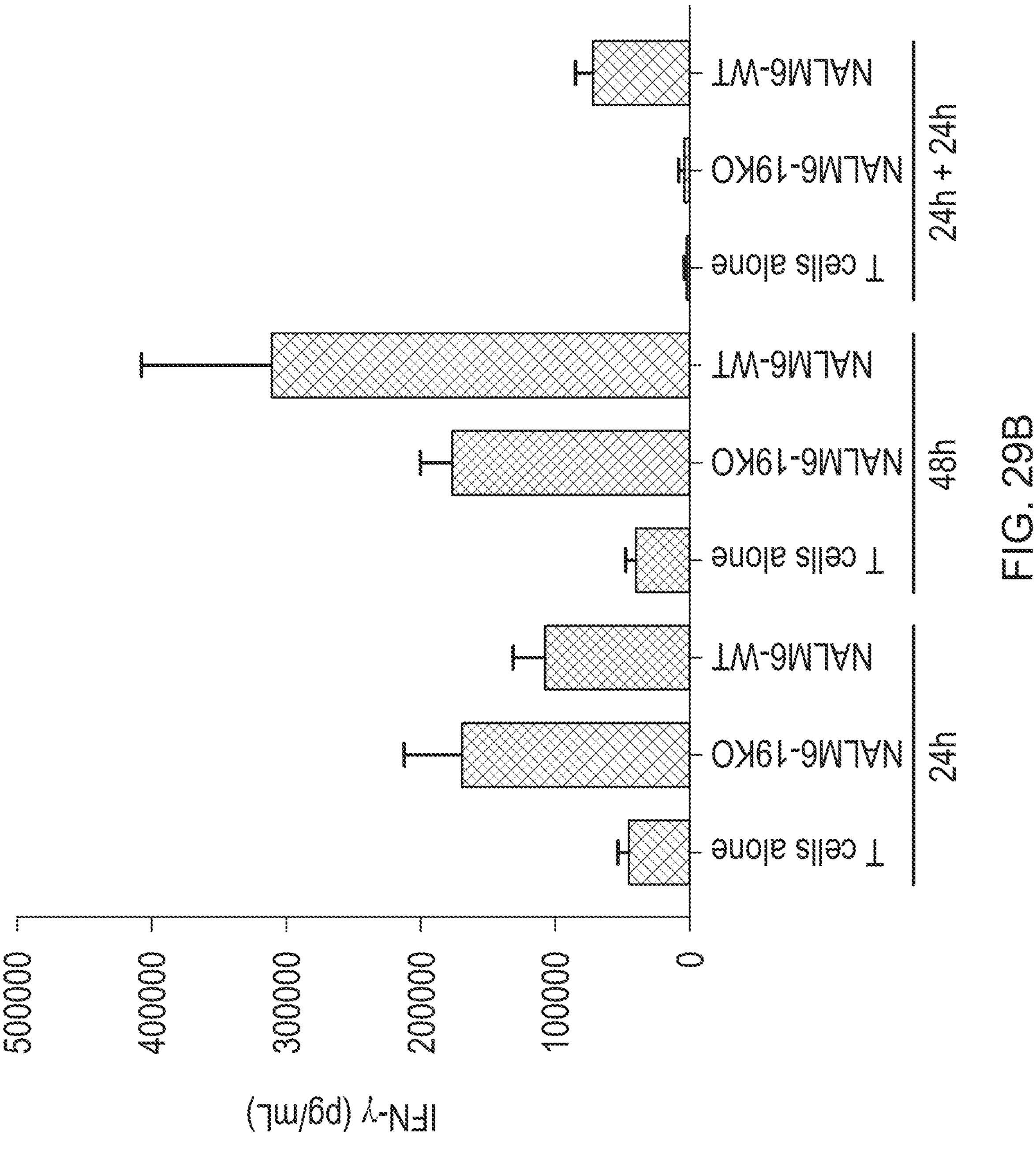
Figure 29C:
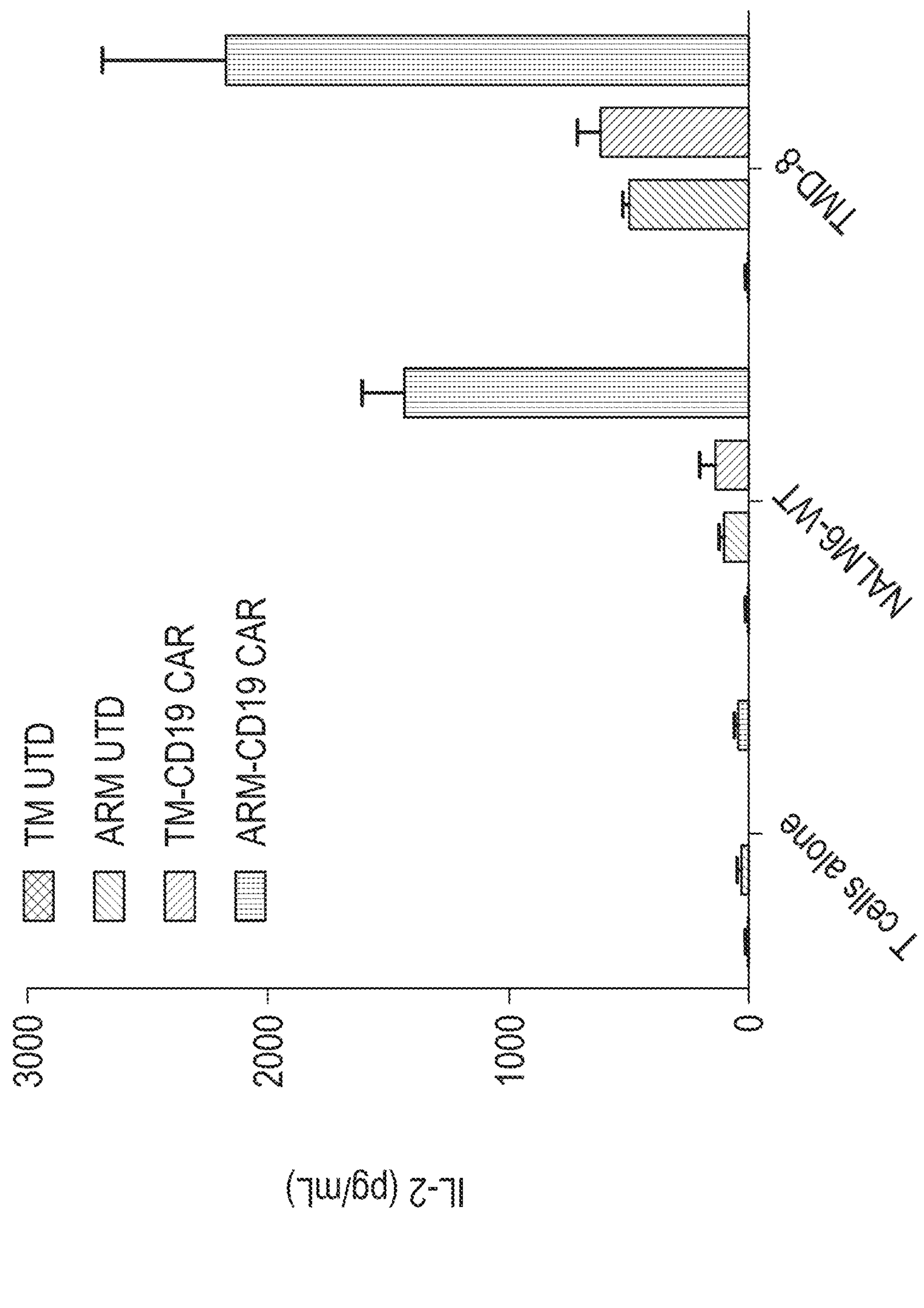
Figure 29D:
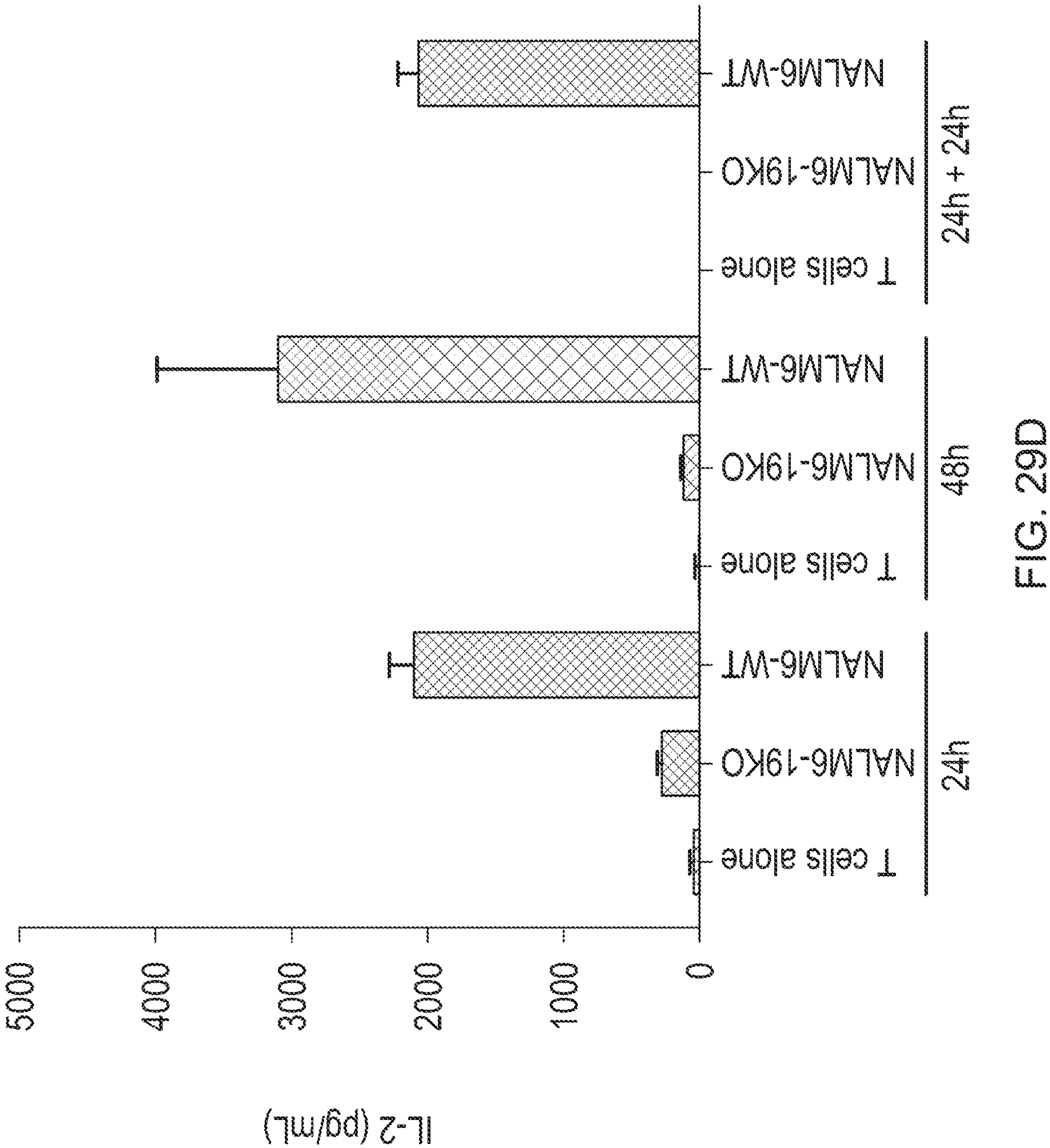

In addition to its phenotype, the final ARM-CD19 CAR cell product was also assessed for its function in vitro. ARM-CD19 CAR and TM-CD19 CAR were thawed and co-cultured with the CD19-expressing cell lines NALM6 (ALL) or TMD-8 (DLBCL). Comparison of cytokine levels in the supernatants 48 hours after co-culture revealed a 11- to 17-fold increase of IFN-γ and a 3.5- to 10-fold increase in levels of IL-2 secreted by ARM-CD19 CAR as compared to TM-CD19 CAR, depending on the stimulating cancer cells (NALM6 or TMD-8, FIGS. 29A and 29C). Experiments with untransduced (UTD) cells that underwent the ARM or TM process (FIG. 29C), or with CD19-negative NALM6 (NALM6-19KO) target cells (FIG. 29D) confirmed CD19-specific recognition by ARM-CD19 CAR and TM-CD19 CAR. Higher background of IFN-γ secretion by ARM-UTD and ARM-CD19 CAR in the absence of CD19-specific stimulation (FIGS. 29A and 29B, respectively) is likely due to the activated nature of these products. This background secretion decreased by 48 hours of coculture (FIGS. 29B and 29D). An intermediate wash of the cells after the first 24 hours of coculture with target cells, followed by co-culture for additional 24 hours (24 h+24 h) further enhanced the difference between background and CD19-specific cytokine secretion. This 24 h+24 h condition highlights that background IFN-γ secretion by ARM-CD19 CAR abates after the first 24 hours.

In summary, the ARM process used to generate ARM-CD19 CAR results in T cells with CAR-expression similar or higher than that of TM-CD19 CAR. Importantly, the ARM process maintains a T-cell phenotype similar to the input material. ARM-CD19 CAR demonstrates CD19-specific activation in vitro, and secretes higher levels of IL-2 as compared to TM-CD19 CAR, which correlates with its $T_{stem}$ phenotype.

In Vivo Efficacy

Figure 30A:
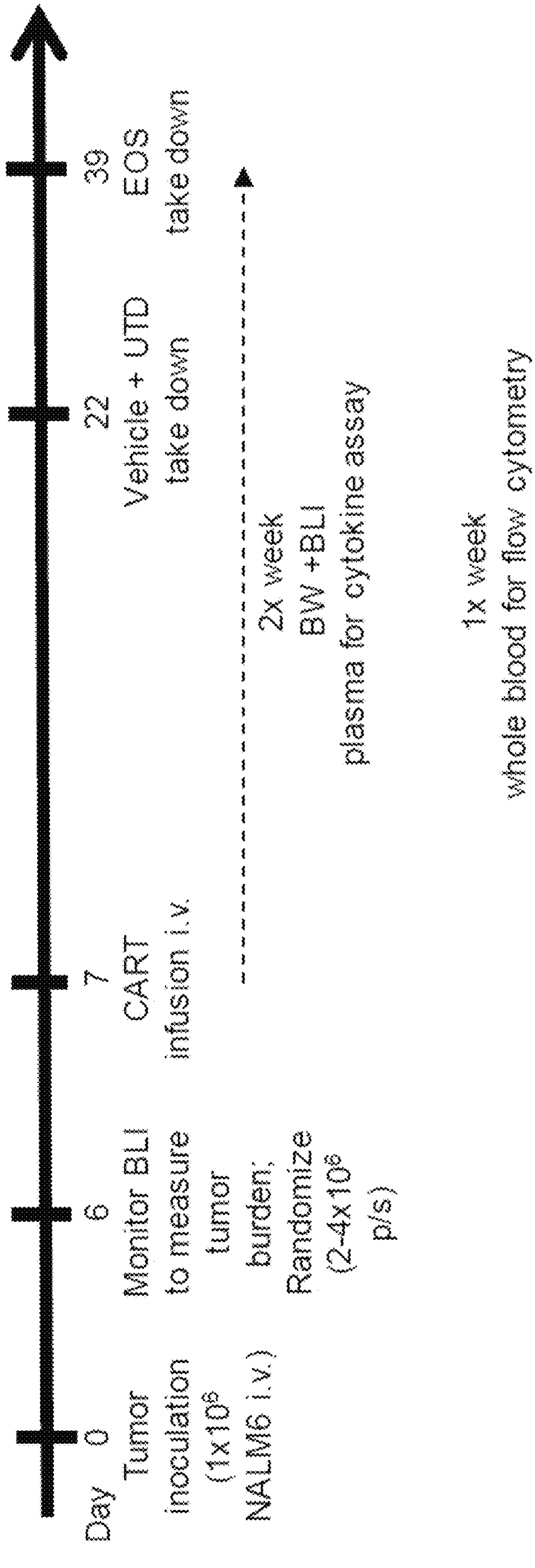
FIGS. 30A, 30B, and 30C.

Efficacy studies in vivo were used to guide the development of the ARM process, ultimately leading to the process that will be used for clinical anti-CD19 CAR T cell manufacturing. For the experiment described here, ARM-CD19 CAR was generated at clinical scale. In parallel, TM-CD19 CAR was generated using the same lentiviral vector and T cells from the same donor. The efficacy of CAR-T cells generated using the different processes was evaluated in immunodeficient NSG mice (NOD-scid IL2Rg-null), which were inoculated with the pre-B ALL cell line NALM6. This tumor cell line engrafts in the bone marrow, but in case of high tumor burdens can also be detected in the circulation. Seven days after leukemia inoculation, cohorts of mice received a single infusion of CAR+ T cells (FIG. 30A). Planned doses of $0.2\times10^6$, $0.5\times10^6$ and $2\times10^6$ viable CAR+ T cells were determined based on post thaw flow analysis of TM-CD19 CAR and ARM-CD19 CAR on day 0.

Figure 30B:
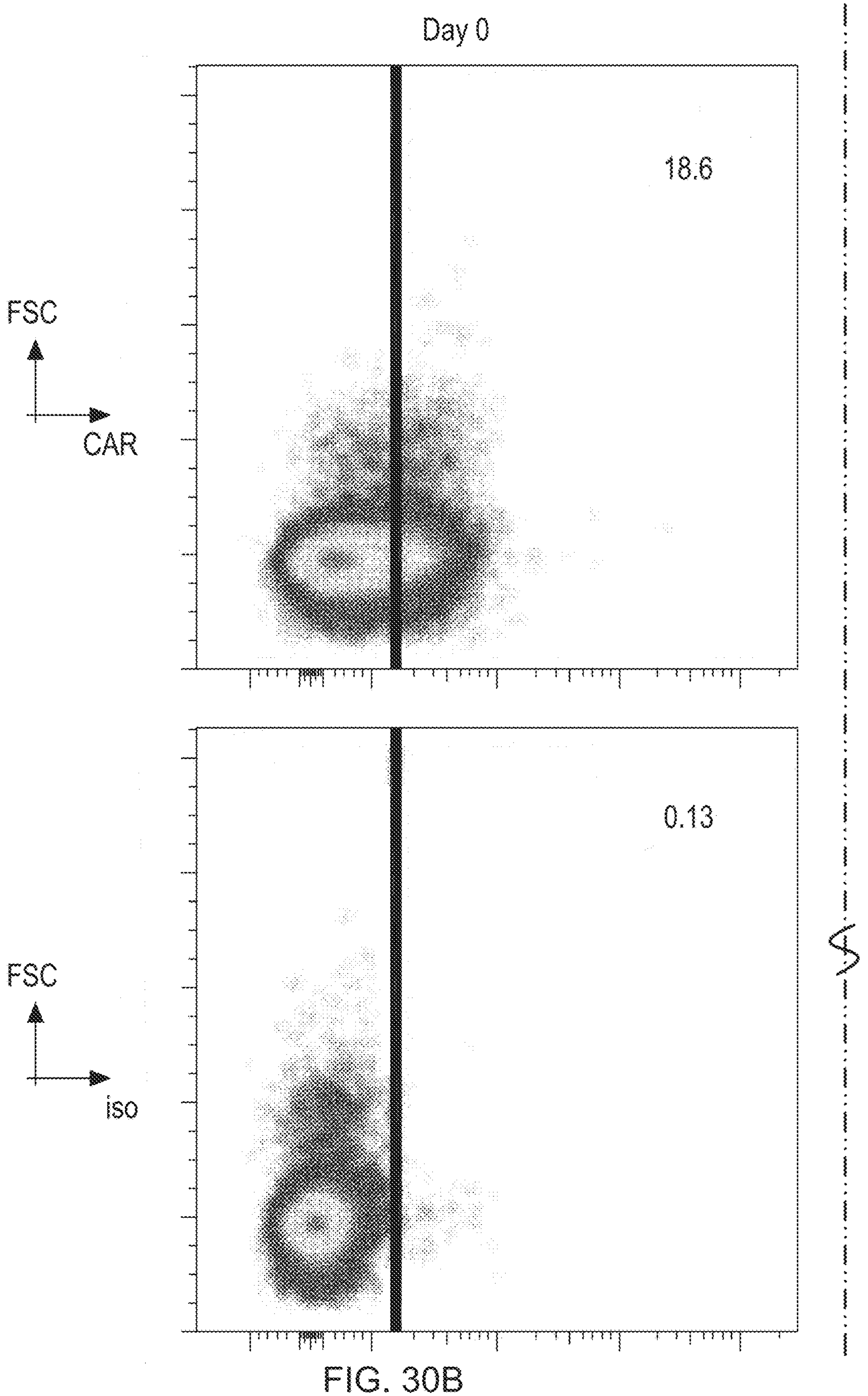
Figure 30B:
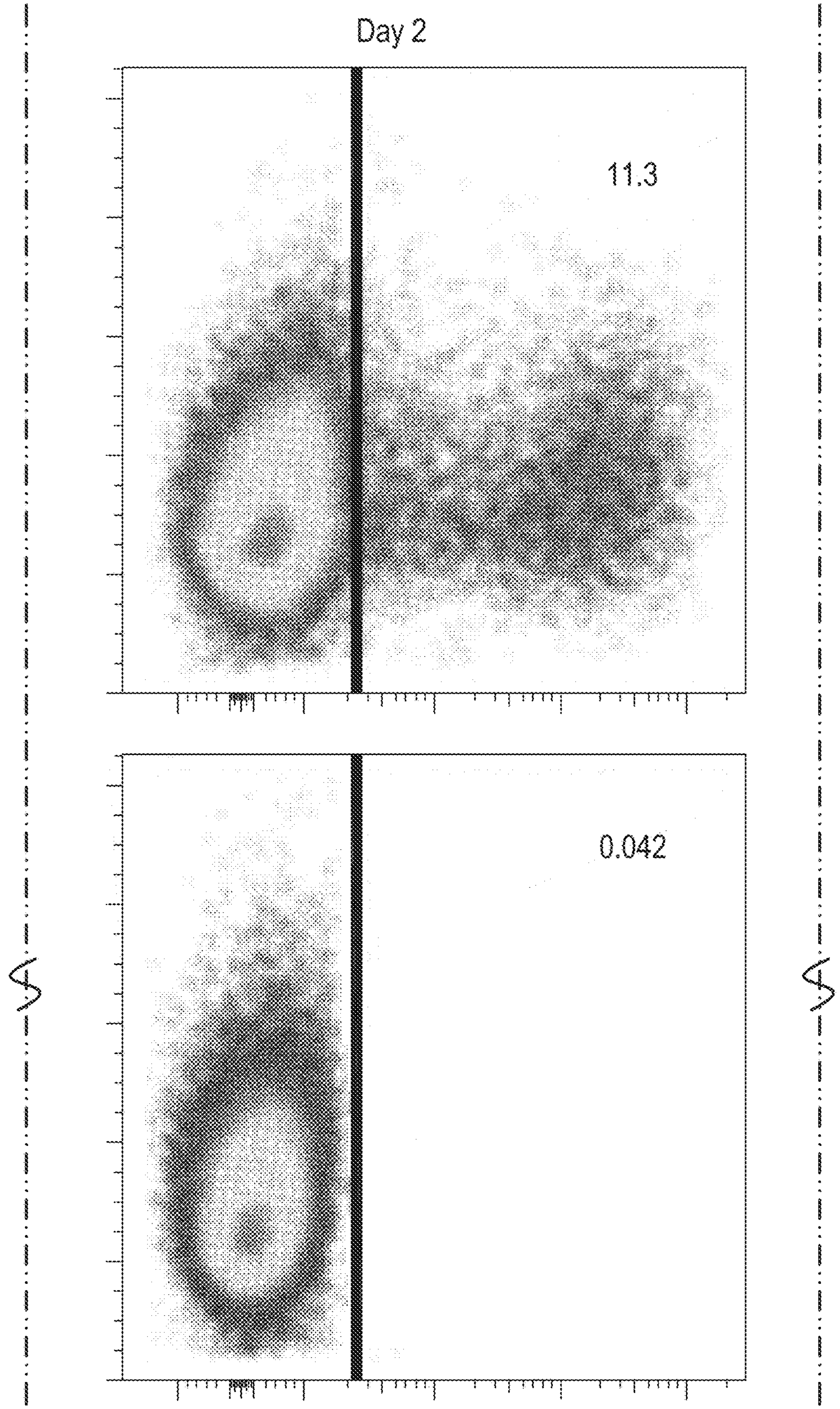
Figure 30B:
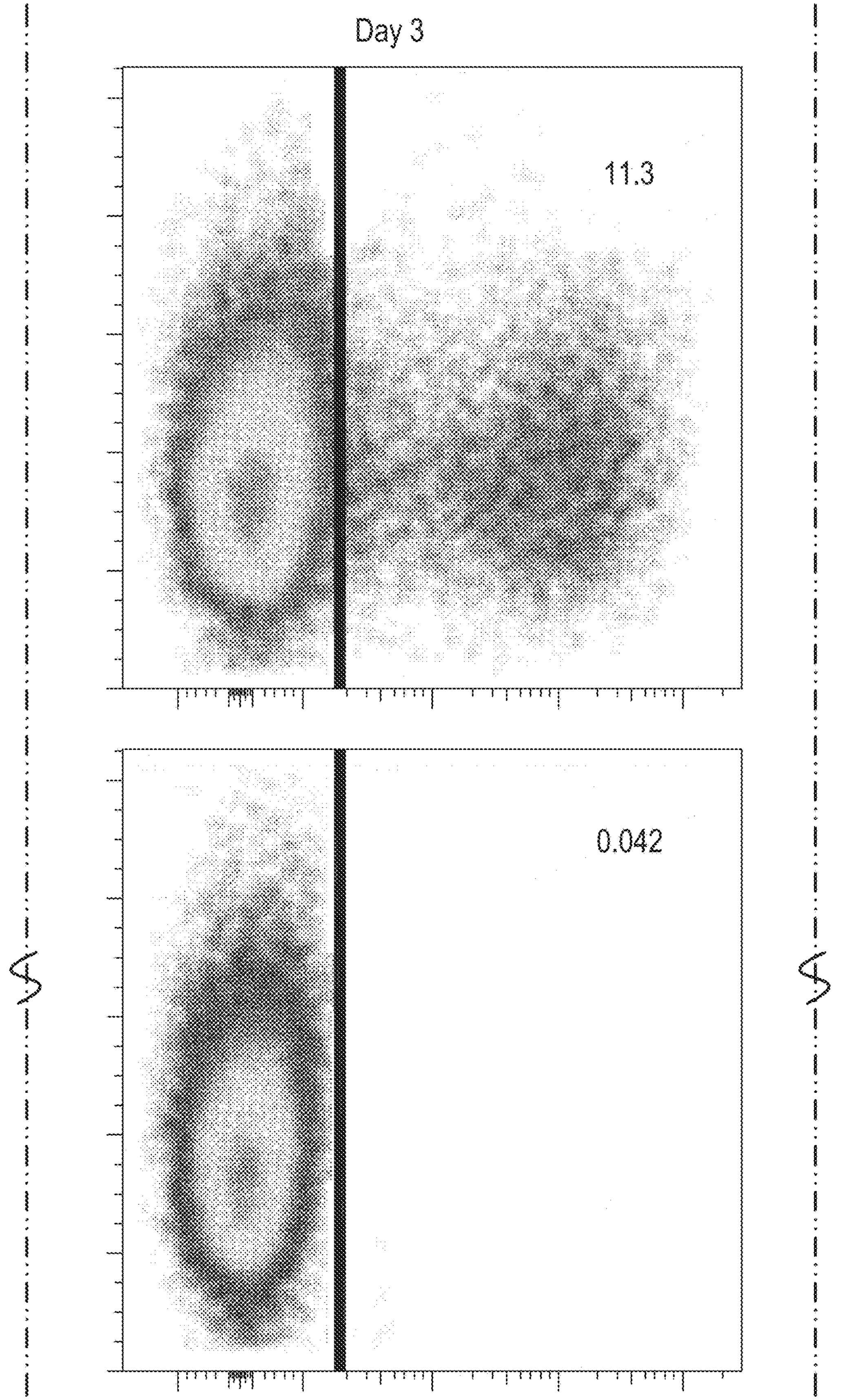
Figure 30B:
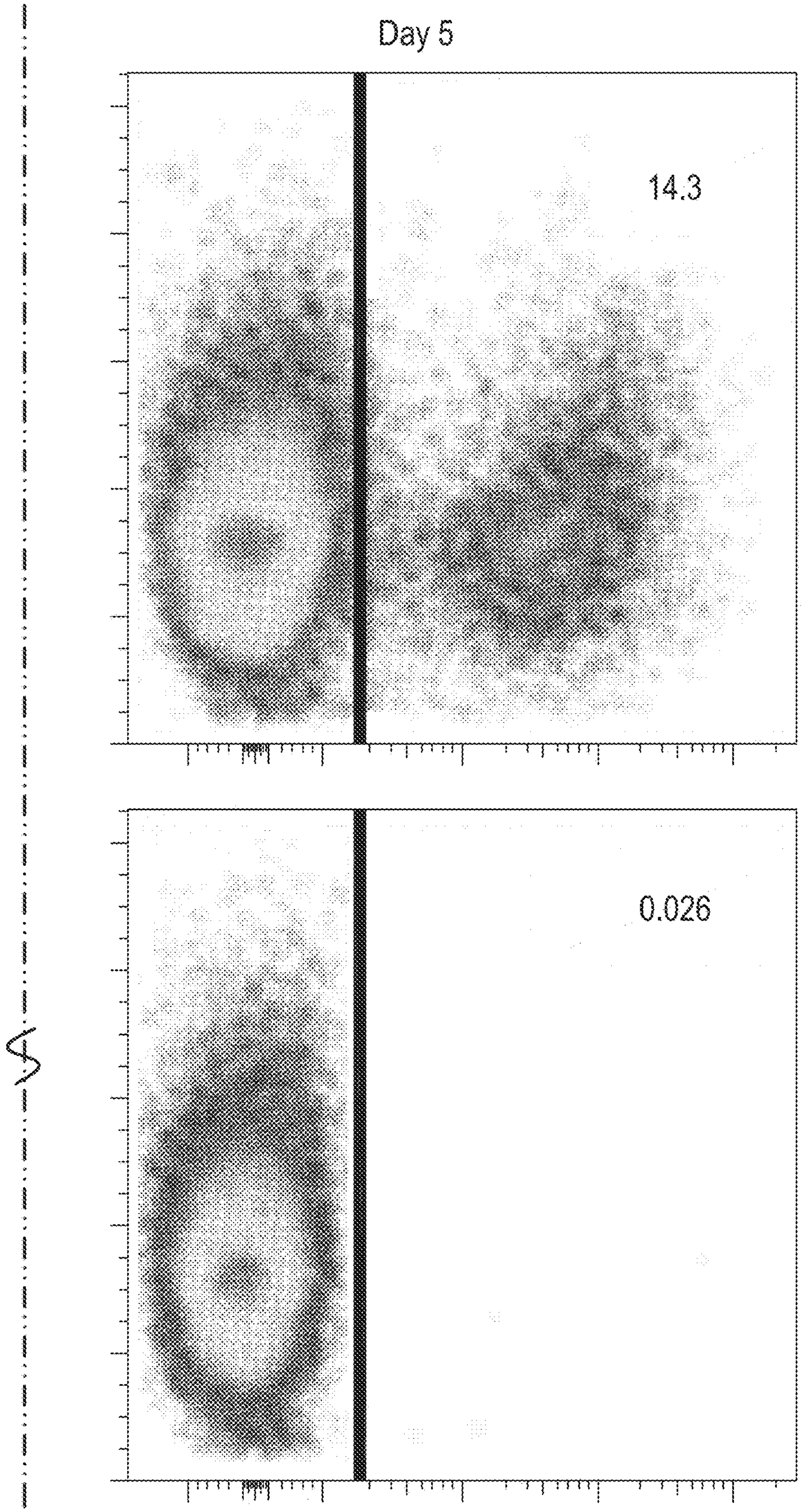

Because of the concern of pseudo-transduction for ARM-CD19 CAR on day 0 post thaw, a sentinel vial was thawed and cultured for up to 5 days, and CAR expression (percentage and mean fluorescence intensity) was analyzed by flow cytometry at different time points (FIG. 30B). The percentage of positive cells on later time points was lower as compared to the day 0 post-thaw sample. At the same time, CAR mean fluorescence intensity was higher per cell, reflective of stably transduced CAR-T cells. The measurement on day 3 was used to determine the actual dose of ARM-CD19 CAR, which was determined to be $0.1\times10^6$, $0.25\times10^6$ and $1\times10^6$ viable CAR+ T cells. The TM-CD19 CAR dose remained unchanged ($0.2\times10^6$, $0.5\times10^6$ and $2\times10^6$ viable CAR+ T cells), as the flow analysis of post-thaw samples was performed on rested, fully integrated CART cells.

Figure 30C:
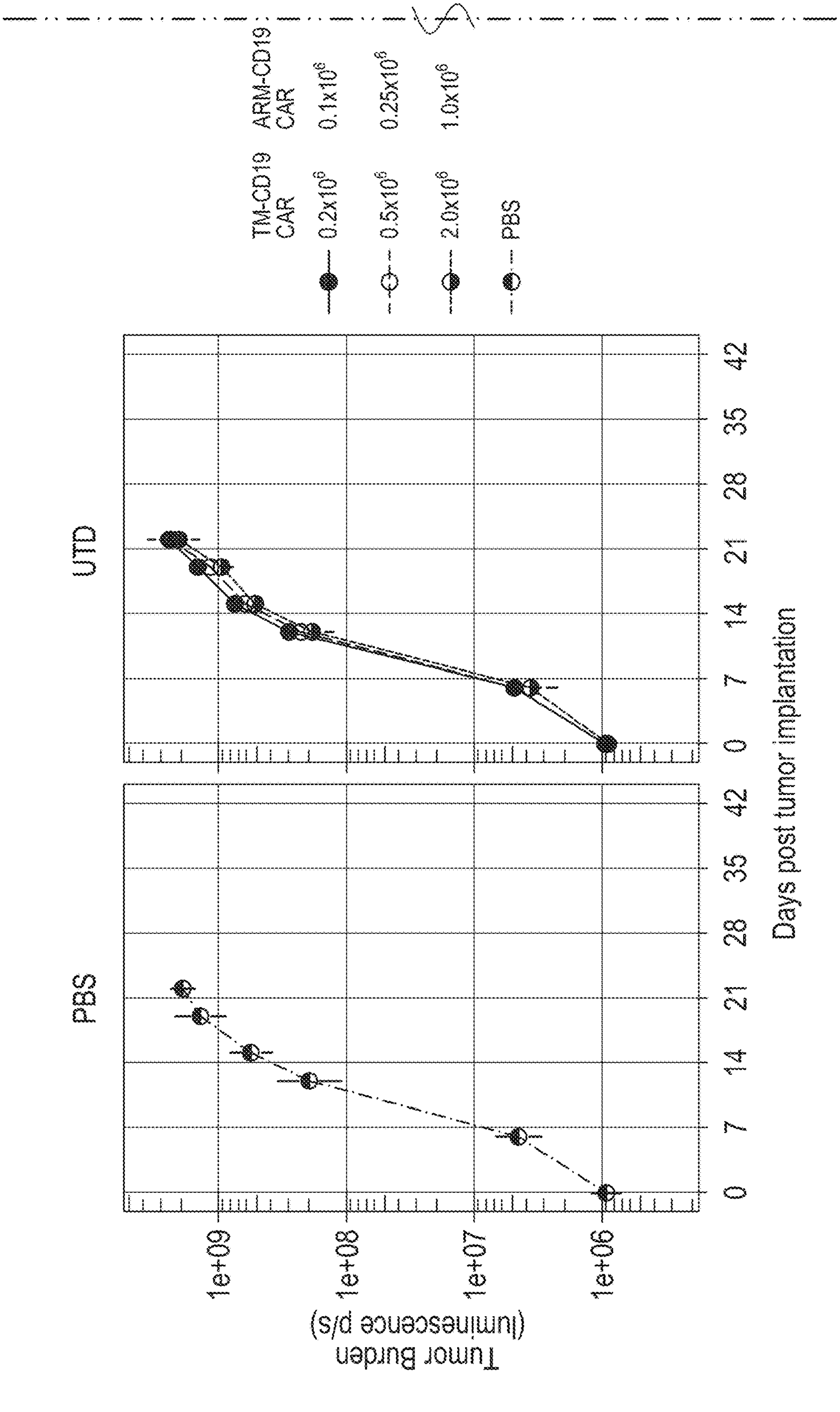
Figure 30C:
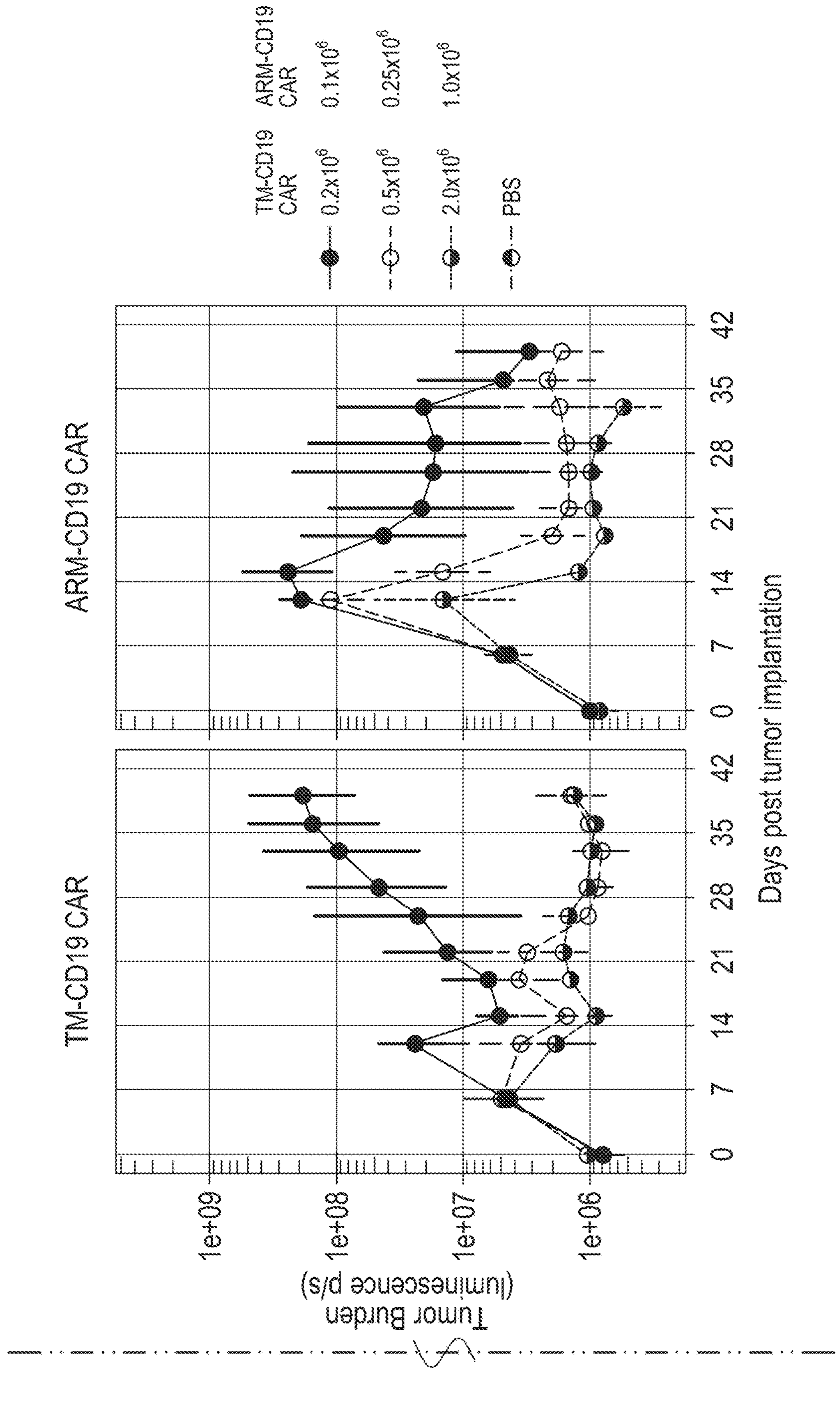

Both ARM-CD19 CAR and TM-CD19 CAR induced tumor-regression in a dose-dependent manner (FIG. 30C). Mice treated with $0.5\times10^6$ or $2\times10^6$ TM-CD19 CAR cells, or $0.25\times10^6$ or $1\times10^6$ ARM-CD19 CAR cells, experienced durable tumor regression. Interestingly, at the respective lowest dose tested ($0.2\times10^6$ TM-CD19 CAR cells or $0.1\times10^6$ ARM-CD19 CAR cells), response to TM-CD19 CAR was not sustained and all mice eventually relapsed after initial partial leukemia control. In contrast, at the lowest dose ($0.1\times10^6$) ARM-CD19 CAR-treated mice showed a steady decline of tumor burden that lasted until the end of study. The kinetics of tumor regression suggest a delayed activation of ARM-CD19 CAR by about 1 week, suggesting that $T_{stem}$ cells need to proliferate and differentiate into effector cells in order to exert their antitumor activity.

Figures 31A, 31B, 31C, 31D:
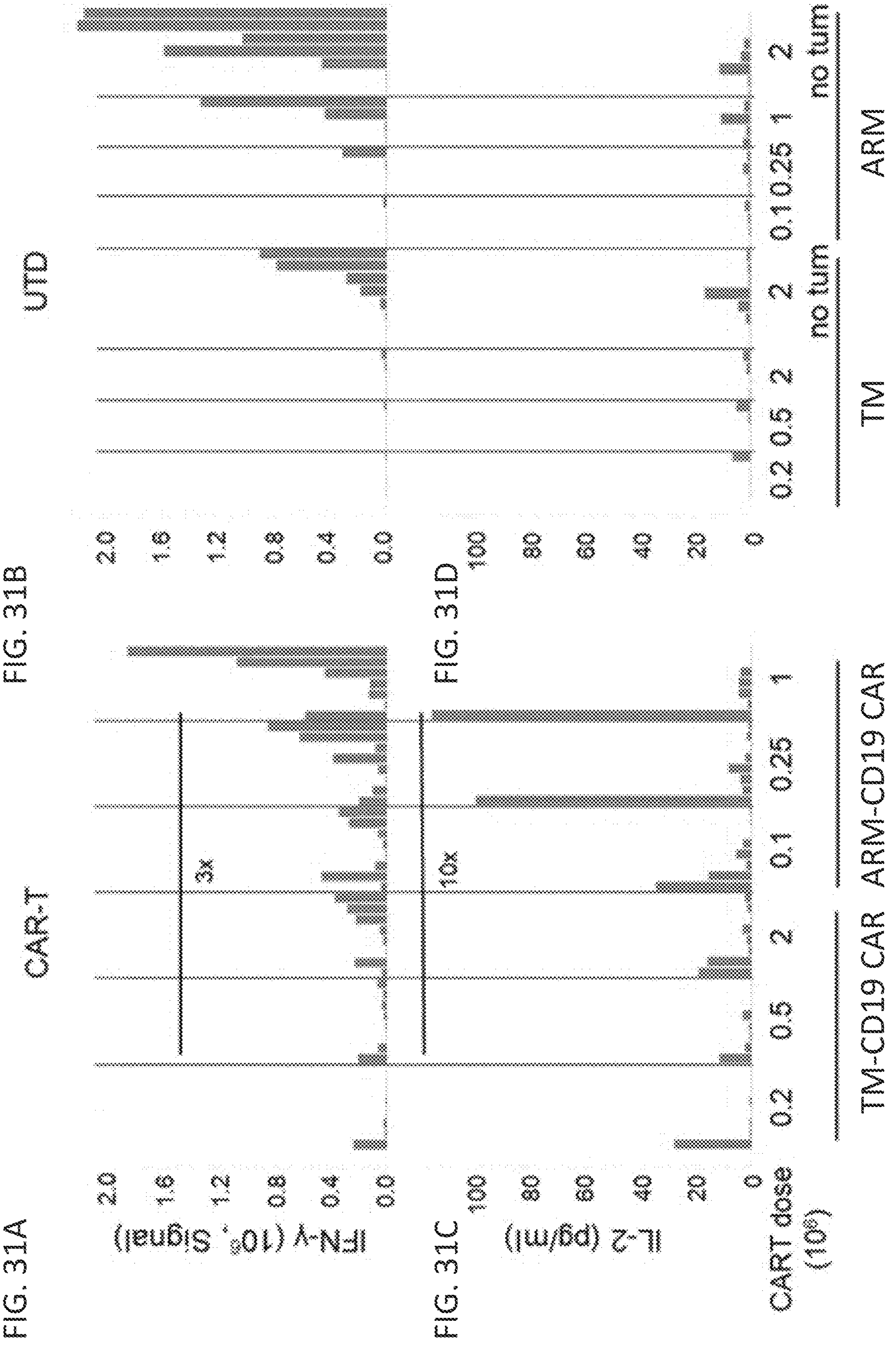
FIGS. 31A, 31B, 31C, and 31D. Plasma cytokine levels of NALM6 tumor-bearing mice treated with ARM-CD19 CAR or TM-CD19 CAR at respective CAR-T cell doses. Mice were bled and plasma cytokine measured by MSD assay. IFN-γ (FIGS. 31A and 31B) and IL-2 (FIGS. 31C and 31D) are shown for mice treated with CAR-T (FIGS. 31A and 31C) or ARM- and TM-UTD cells (FIGS. 31B and 31D). Bars within each dose represent the mean cytokine level within the group at different time points (from left: day 4, 7, 10, 12, 16, 19, 23, 26). Horizontal bars and numbers indicate the fold-change comparisons between ARM-CD19 CAR ($1\times10^6$ dose group) and TM-CD19 CAR ($0.5\times10^6$ dose group) described in the text: 3-fold for IFN-γ; and 10-fold for IL-2. Groups taken down due to tumor burden or body weight loss do not show the last time points. Plasma cytokine levels were measured for 2 studies. no tum: no tumor.

Mice treated with CAR-T cells and UTD cells generated by the two manufacturing processes were bled twice weekly to measure cytokine levels (FIGS. 31A-31D). Circulating IFN-γ levels in mice infused with CAR-T cells, either ARM-CD19 CAR or TM-CD19 CAR, showed a bi-phasic pattern (FIG. 31A). An early IFN-γ peak was observed at days 4-7 after CAR-T cell infusion and likely related to CD19-specific activation following tumor recognition, since it was not evident in mice infused with TM-UTD or ARM-UTD (FIG. 31B). Early CD19-mediated activation was confirmed by a concomitant rise of in vivo IL-2 levels (FIG. 31C), which however abated at later time points.

In Vivo Cellular Kinetics

Figure 32:
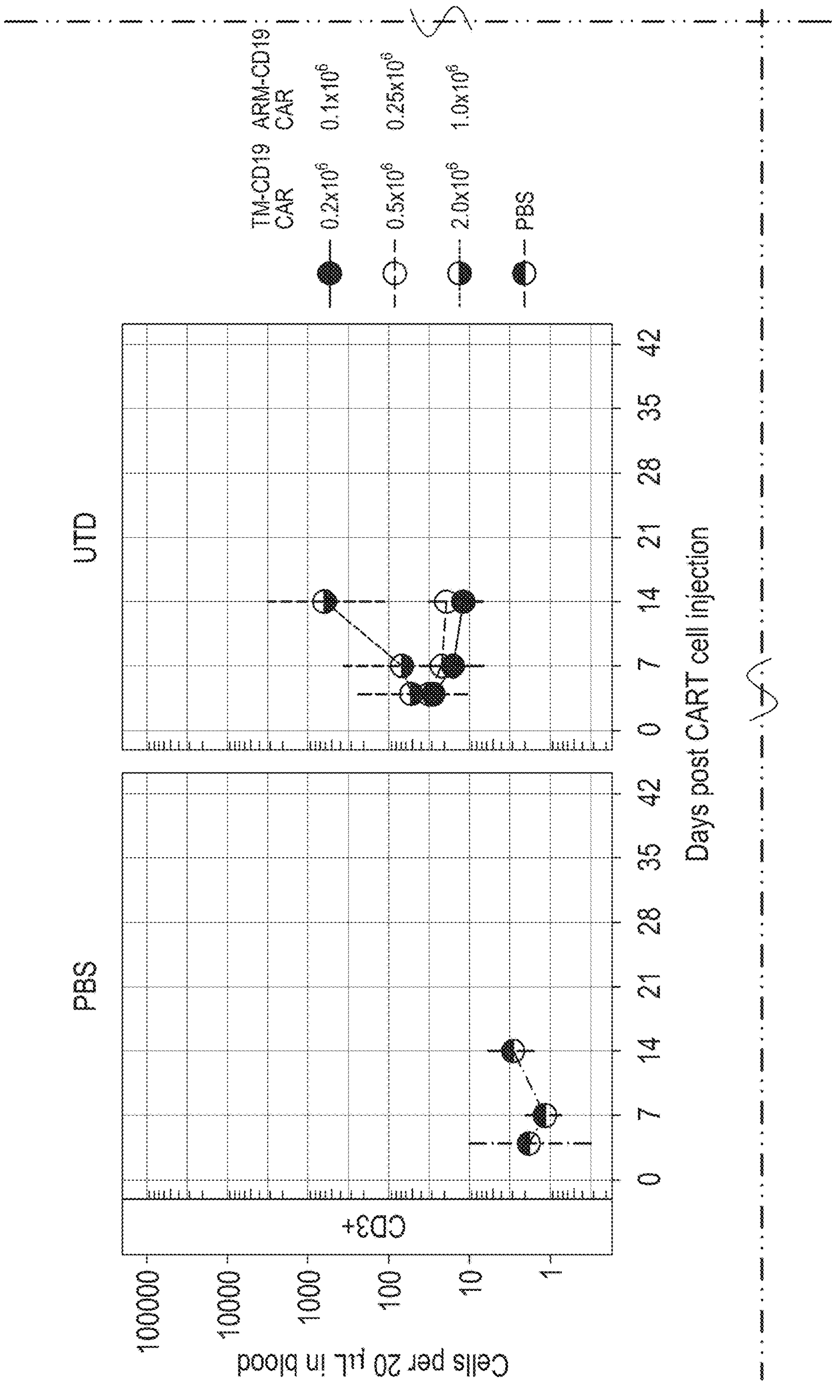
FIG. 32. Time course of total and CAR+ T cell concentrations in NALM6 tumor-bearing mice treated with PBS vehicle, UTD, TM-CD19 CAR, or ARM-CD19 CAR. Blood samples were taken at 4, 7, 14, 21 and 28 days post CAR-T cell injection. Total T cells (CD3+, upper) and CAR+ T cell (CD3+CAR+, lower) concentrations were analyzed by flow cytometry at designed time points, depicted as mean cells with 95% confidence interval.
Figure 32:
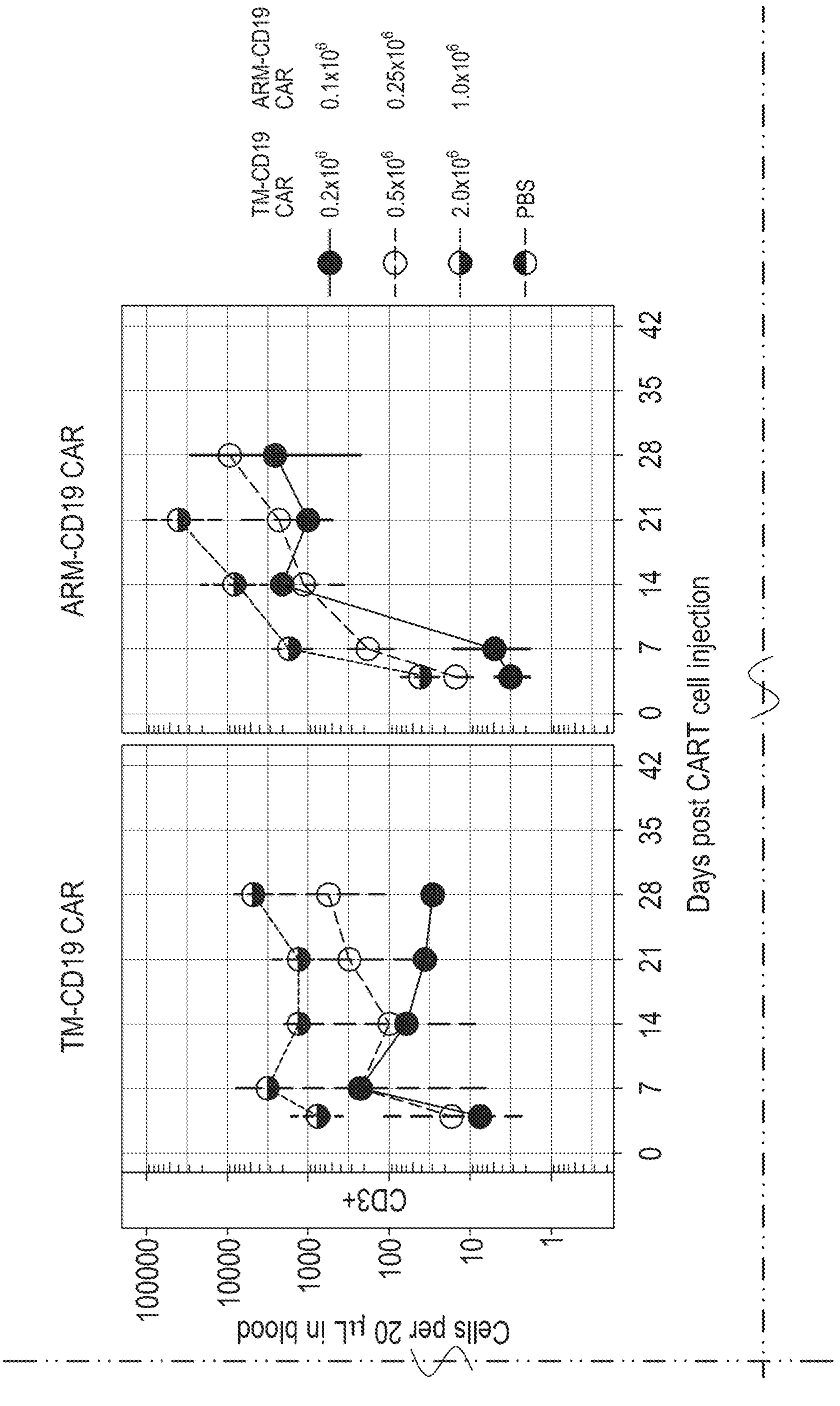
Figure 32:
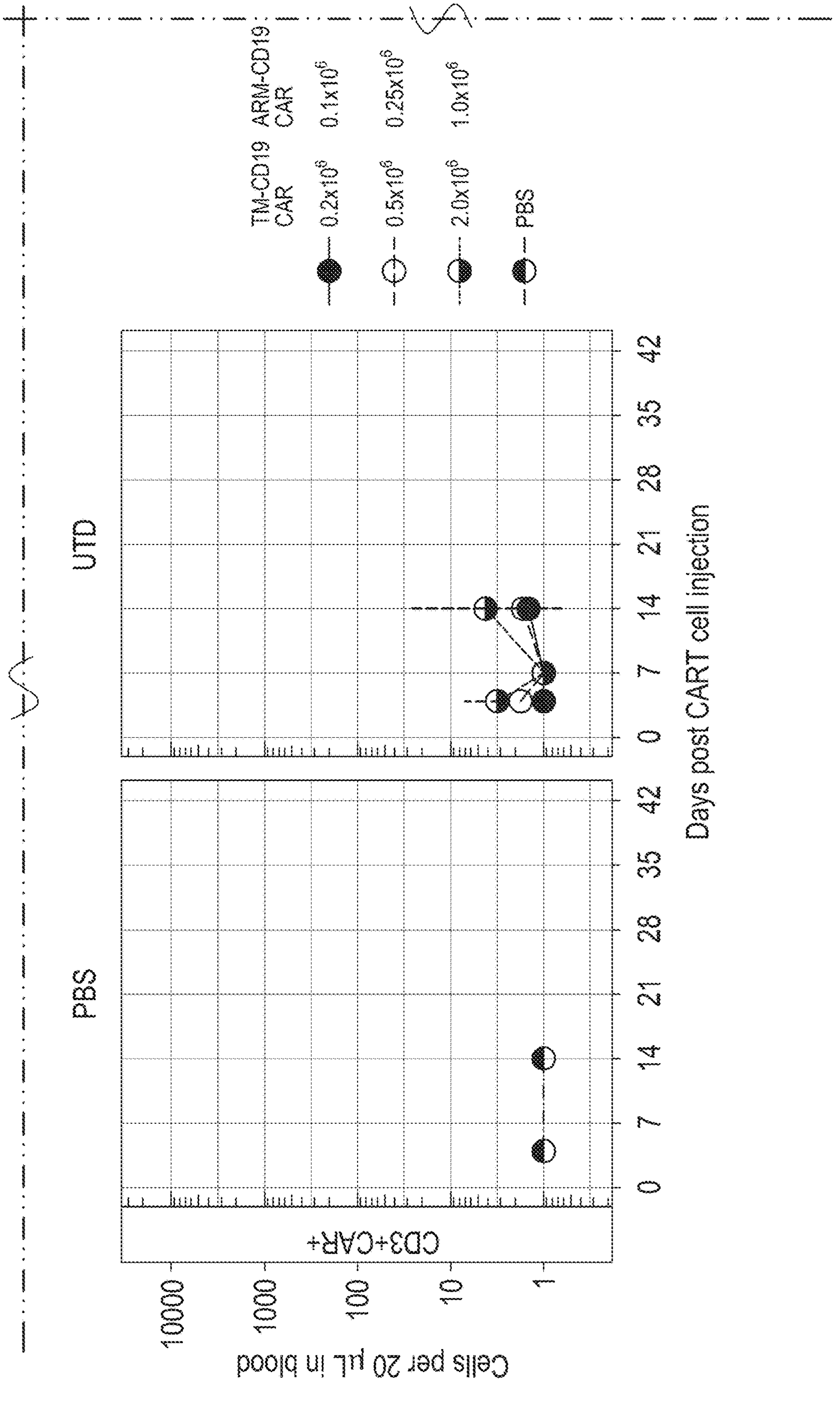
Figure 32:
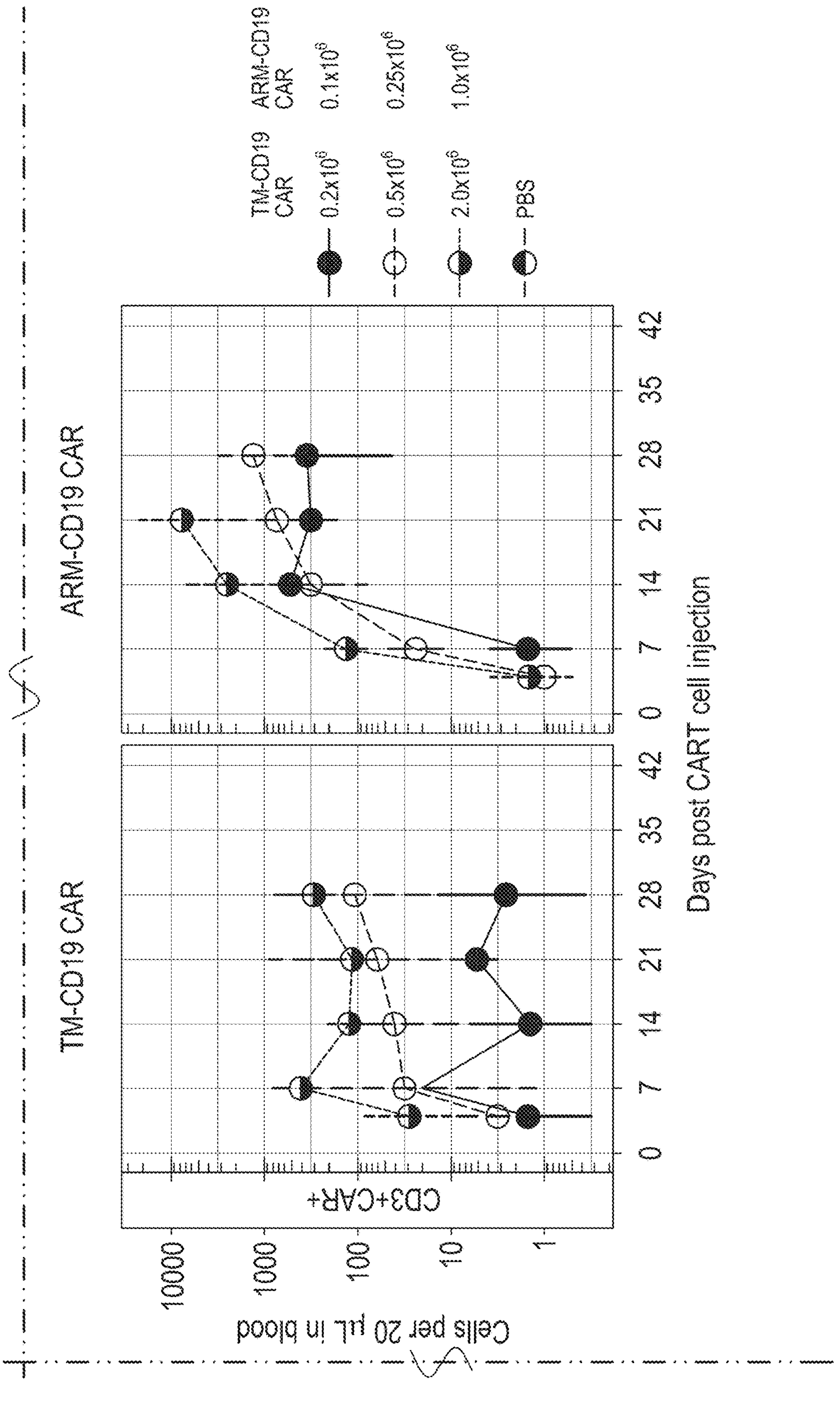

As part of a pharmacology study to evaluate the efficacy of ARM-CD19 CAR in NSG mice, the expansion of CAR+ T cells was assessed in vivo (FIG. 32). CD3+/CAR+ T-cell concentration in blood was analyzed by flow cytometry up to 4 weeks after infusion. CAR-T cell expansion can be inferred. However, long-term persistence cannot be assessed due to limited study time dictated by onset of X-GVHD. Cellular expansion was observed for both ARM-CD19 CAR and TM-CD19 CAR at all doses, except for TM-CD19 CAR at the lowest dose of $0.2\times10^6$ cells. Exposure (Cmax and AUC within 21 days post cell injection) increased with increasing dose for both TM-CD19 CAR and ARM-CD19 CAR. To compare the expansion of ARM-CD19 CAR to TM-CD19 CAR at the same dose level, exposure of TM-CD19 CAR was interpolated to comparable doses of ARM-CD19 CAR ($0.25\times10^6$ and $1\times10^6$ cells). The Cmax was 24- to 46-times higher and the AUC0-21d was 18- to 33-times higher compared to TM-CD19 CAR at doses of $0.25\times10^6$ and $1\times10^6$ cells. The time to ARM-CD19 CAR peak expansion (Tmax) was delayed for at least 1 week compared to TM-CD19 CAR.

In summary, pharmacology studies evaluating ARM-CD19 CAR in vitro show that ARM-CD19 CAR has an early-differentiated phenotype and has the potential to secrete more IFN-γ and IL-2. In vivo, ARM-CD19 CAR demonstrated delayed but higher cellular expansion, induced more IL-2 secretion, and controlled tumor growth at lower doses as compared to TM-CD19 CAR. Other features of ARM-CD19 CAR discussed, such as elevated levels of plasma IFN-γ at later time points and earlier occurrence of X-GVHD were seen both for ARM-CD19 CAR, as well as for ARM-UTD, underlying the limitations of the xenograft mouse model used here. Together, these results support the hypothesis that ARM-CD19 CAR contains T cells with more stemness features, enabling ARM-CD19 CAR to effectively engraft, expand and reject tumors.

In Vitro IL-6 Release Assay

A three-party co-culture model for the in vitro investigation of IL-6 induction potential by CART cells was first published by Norelli, et al (2018) Nat Med., June; 24(6); 739-748 and applied here with some adaptations. This model consists of CAR-T cells, leukemic target cells and bystander THP-1 monocytic cells, as a source of myeloid cells for maximized IL-6 production. In this in vitro cellular model, IL-6 secretion by either ARM-CD19 CAR or TM-CD19

Figure 33A:
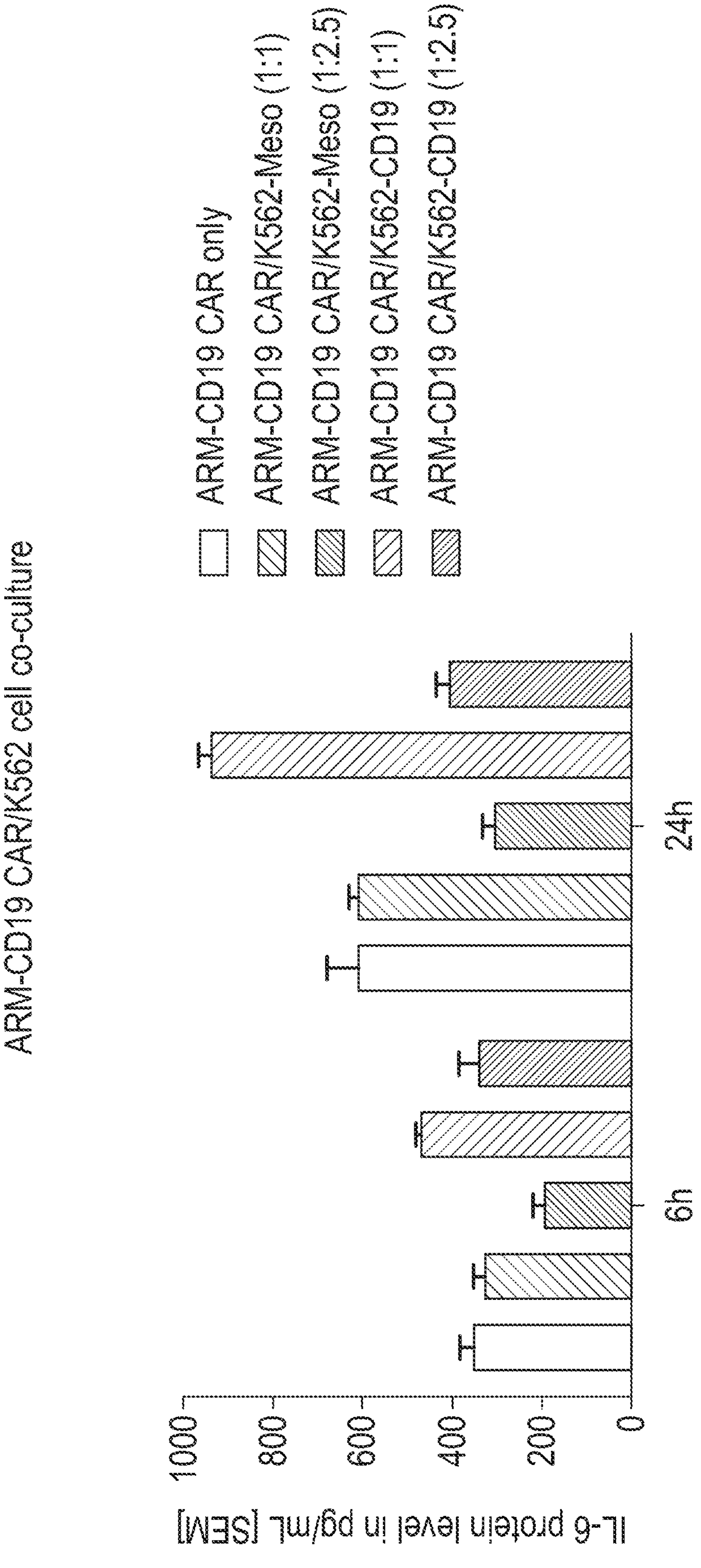
FIGS. 33A and 33B. IL-6 protein levels in three-party co-culture supernatants in pg/mL. ARM-CD19 CAR/K562 co-cultured cells (FIG. 33A) or TM-CD19 CAR/K562 cell co-cultured cells (FIG. 33B), for 6 or 24 hours incubated at different ratios (1:1 and 1:2.5), were then added to PMA-differentiated THP-1 cells for another 24 hours. Results from CAR-T cells co-cultured with K562-CD19 cells, CAR-T cells co-cultured with K562-Mesothelin cells, and CAR-T cells alone are shown. 1:5 ratios are not shown for clarity. ARM-CD19 CAR only and TM-CD19 CAR only designated bars represent CAR-T cell cultures (6 h, 24 h) without target cells. Mean+SEM, duplicates of n=1 (TM-CD19 CAR) and n=3 (ARM-CD19 CAR).
Figure 33B:
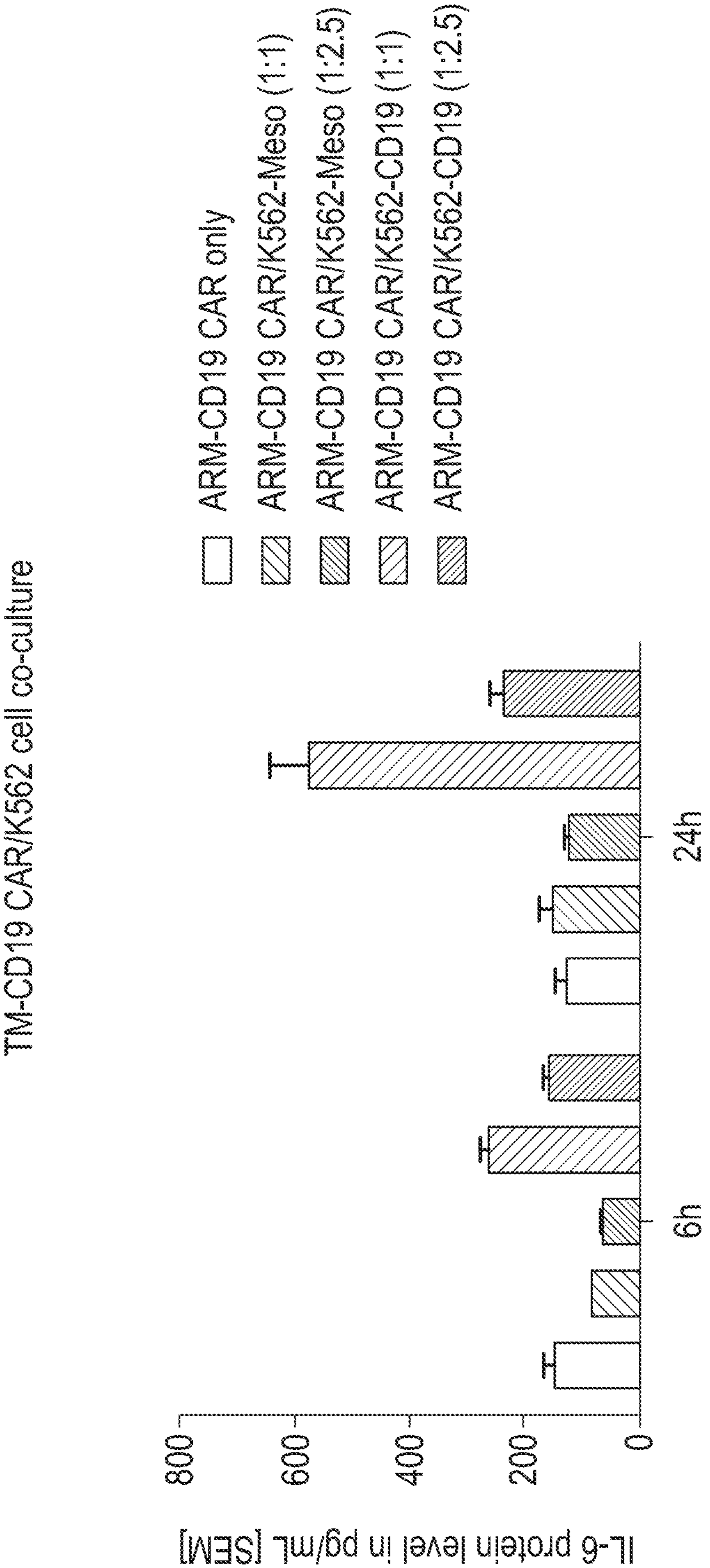

CAR alone was increased by co-culturing with CD19-expressing targets and THP-1 cells (FIGS. 33A and 33B). Importantly, time-dependent CD19-specific IL-6 secretion induced by ARM-CD19 CAR was superimposable to that induced by TM-CD19 CAR. In the same in vitro model, CD19-specific IFN-γ secretion in the ARM-CD19 CAR condition was 10-fold higher than in the TM-CD19 CAR condition (data not shown).

Summary

These results suggest that ARM-CD19 CAR might have greater antitumor potential and a similar safety profile as compared to TM-CD19 CAR. Greater antitumor potential is inferred by better tumor control at the lowest dose tested and by higher in vivo cellular expansion. Such a calculation may however be an underestimation of the overall therapeutic potential of ARM-CD19 CAR, since this was assayed in an ALL model (NALM6) which is more aggressive than the two disease indications (CLL and DLBCL) in which ARM-CD19 CAR will be initially investigated. In CLL, in particular, where in vivo CAR-T cell expansion robustly correlates with tumor regression (Mueller, et al (2017) Blood. 130(21); 2317-2325; Fraietta, et al (2018) Nat Med, 24(5); 563-571), significantly higher proliferative potential of ARM-CD19 CAR (up to 20-fold) might result in meaningful superior efficacy compared to TM-CD19 CAR.

In mice, the early systemic release of IFN-γ and IL-2 by ARM-CD19 CAR associated with CAR-mediated tumor regression was 3-fold and 10-fold higher than that induced by traditionally manufactured CAR-T cells, respectively. IL-6 levels were not studied in vivo, since in this strain lack of functional myeloid cells results in the inability to produce inflammatory cytokines (Norelli, et al (2018) Nat Med., June; 24(6); 739-748; Giavridis, et al (2018) Nat Med., June; 24(6); 731-738). To obviate this and evaluate the potential for in vivo IL-6 release induced by ARM-CD19 CAR, an in vitro three-party co-culture system was employed, in which bystander monocytic cells are added as a source of inflammatory cytokines (Norelli, et al (2018) Nat Med., June; 24(6); 739-748). In this system, IL-6 production was similar between ARM-CD19 CAR and traditionally manufactured CAR-T cells, suggesting a similar risk for CRS. Conversely, the delayed kinetics of ARM-CD19 CAR cellular expansion will require an extension of the CRS monitoring period from the 3 weeks typical of TM-CD19 CAR, to 4 weeks. In vitro experiments with ARM-CD19 CAR also revealed the potential for transient, non-CAR-mediated IFN-γ and IL-2 secretion by ARM-CD19 CAR during the first 3 days of culture after thawing. A comprehensive risk assessment based on data from patients receiving recombinant human IL-2 (Proleukin) and recombinant human IFN-γ (ACTIMMUNE), and taking in consideration the projected exposures following ARM-CD19 CAR infusion indicates that the risk for constitutional symptoms (fever, chills, erythema) as described in these patients, would be very low. To further mitigate this risk, patients receiving ARM-CD19 CAR will be hospitalized for at least 72 hours after infusion of the cellular product.

Finally, in the non-GLP compliant toxicology study, NSG mice engrafted with ARM-CD19 CAR did not show unexpected behavior in comparison to traditionally manufactured CAR-T cells and untransduced cells undergoing the ARM process, when assessed by blood or lymphatic organ immunophenotyping, as well as histological evaluation of a relevant set of organs.

Example 9: BCMA CART Cells Manufactured Using the ARM Process

Methods

T Cell Isolation

Fresh leukopak of healthy donor aphereses were obtained from Hemacare and stored in vapor phase liquid nitrogen (LN2) until needed. On Day 0, two quarter leukopaks were removed from LN2, warmed in the Plasmatherm (Barkey, Leopoldshohe, Germany) until a small ice crystal remained, and diluted with Prodigy® process buffer. Automated CD4/CD8 positive selection was then performed on the CliniMACS® Prodigy® with the TS 520 tubing set and T Cell Transduction (TCT) program software version 1.0. Cell count and viability for each Prodigy® output (product, waste, and nontarget cells) were determined by AO/PI staining as enumerated by the Cellometer Vision (Nexcelom, Lawrence, MA) to assess total cell recovery and T cell recovery. The CD4/CD8-enriched product was eluted in OpTmizer™ complete T cell medium and divided for further culturing using either the 24 h or traditional 9-day process (TM). Remaining T cells were frozen down in LN tank. T cell purity was evaluated by flow cytometry analyses.

CAR-T Cells Production Using the ARM Process

T cells purified by Prodigy® were seeded into different scales of vessels, such as plate, flask, G-REX vessel or full clinical scale in centricult. Upon seeding, TransAct (Miltenyi Biotec)), a polymeric nanomatrix conjugated to anti-CD3 and anti-CD28 agonist, was added, in addition to clinical-grade lentiviral vector. Cells were incubated in OpTmizer™ complete T cell media containing 100 IU/mL human recombinant IL-2 (Prometheus, San Diego, CA), 2% ICRS (Life Technologies) for 24 h prior to harvest and cryopreservation.

Aliquots of cryopreserved CAR-T cells were thawed into pre-warmed OpTmizer™ complete media, washed twice with 20× volume of pre-warmed medium before culturing and flow cytometry analyses for assessing BCMA-CAR expression and stemness features at different time points post-thaw. Aliquots of the cell products were co-cultured with target cell lines to assess cytokine release in response to specific antigen stimulation.

CAR-T Cells Production Using TM Process

Prodigy® processed T cells were resuspended in warm RPMI complete T cell medium and plated in 24-well plates. T cells were incubated overnight at 37° C. with Human T-Expander CD3/CD28 beads at a 3:1 ratio of beads-to-cells.

On Day 1, lentiviruses were added at a MOI of 2, based on the SUP-T1titer. No virus was added to the untransduced control (UTD). The T cells were incubated overnight at 37° C. followed by the addition of 1 mL complete T cell medium per well, after which they were incubated overnight at 37° C. For the remaining seven days of culture expansion, the T cells were transferred into tissue culture flasks and diluted with complete T cell medium every two days.

Between Days 8 to 9, the T cells were de-beaded, harvested and cryopreserved in CryoStor CS10 freezing medium, frozen at −80° C. in CoolCell Cell Freezing Containers (Biocision), and transferred to LN2 the following day. Small aliquots of T cells were stained for CAR expression. Single color controls were included for compensation. Samples were measured on a flow cytometer (BD LSR-Fortessa), and data were analyzed with FlowJo software.

Target Cell Line and Culture

Nalm6 cells were transfected with a lentiviral firefly luciferase reporter construct to create the Nalm6-luc cell line. The cells were grown in incubators at 37° C. with 5% $CO_2$. An aliquot of cells was used for detection of tumor antigen BCMA expression prior to use.

In Vitro Cytokine Secretion Assay

Cytokine secretion of anti-BCMA CAR-T (referred to as effector cells) in response to a BCMA-expressing target cell was evaluated by incubating CAR-T cells with target cells at 2.5-fold E:T ratio for 20 h in 96-well flat-bottom plates. Effector cells were PI61, R1G5 and BCMA10 CART cells generated using either the ARM or TM process. CART cells manufactured using the ARM process were plated for a 24 h washout condition to allow the cells to rest and minimize non-specific activity. Target cells include BCMA positive KMS11-luc or BCMA negative NALM6-luc. These target cells were added to the freshly plated T cells or T cells from the 24 h washout condition (ARM cells only). For this assay, the % transduction of CAR-T cells was normalized by addition of UTD to the BCMA CAR-Ts. This allowed for the comparison of the same number of CAR-Ts and same total T cell number in each sample. Supernatants from the 20-hour co-culture time point of effector to target were harvested from each well and frozen at −20° C. to be used for MSD cytokine analysis. The custom MSD V-PLEX Human IFN-γ, IL-2 Kit (#K151A0H-4A) was used to quantify the secreted cytokines in each of the supernatant samples.

Results

ARM Process Preserves T Cell Stemness

Figures 34A, 34B, 34C:
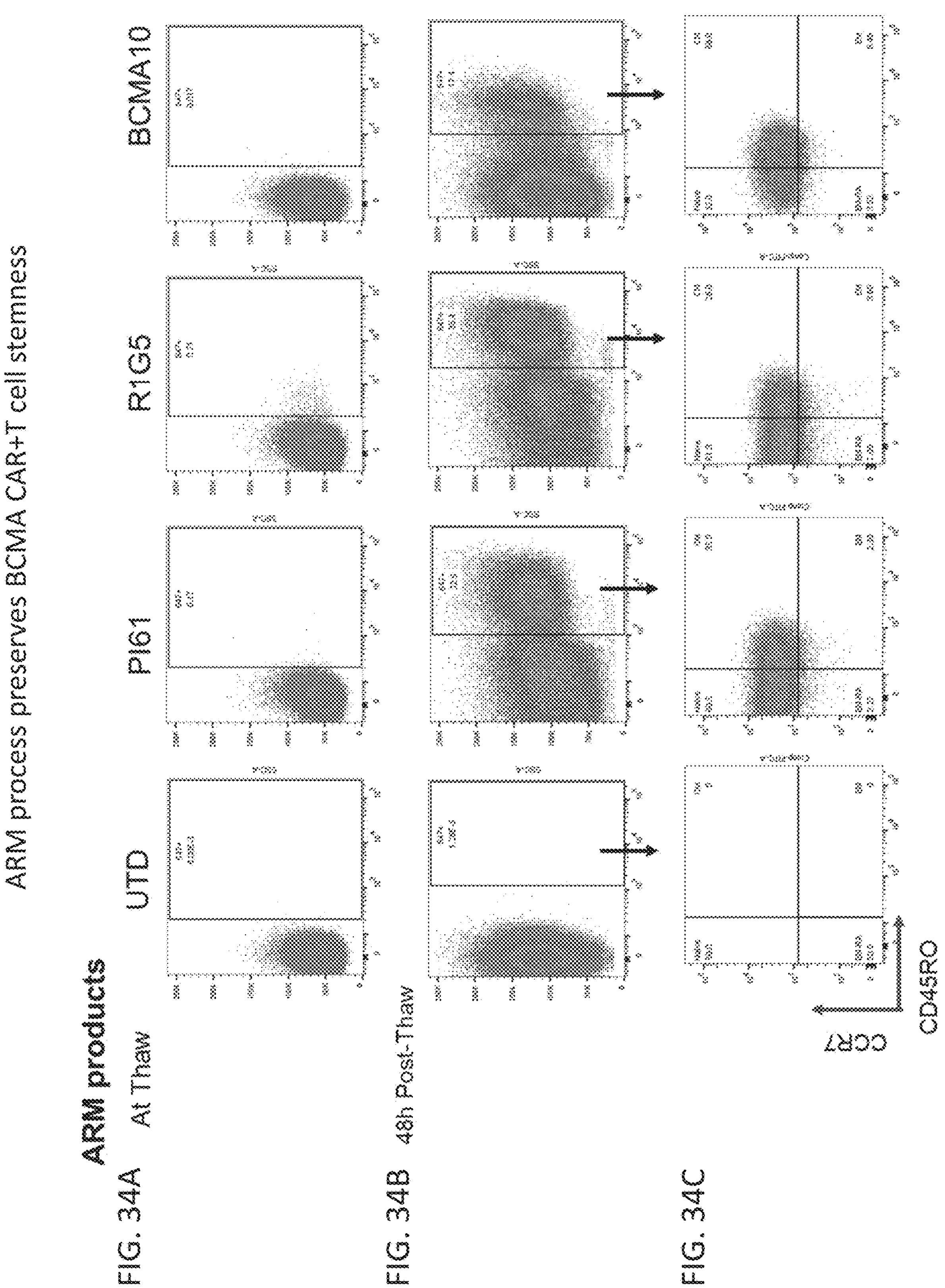
FIGS. 34A, 34B, and 34C. ARM process preserves BCMA CAR+ T cell stemness. PI61, R1G5 and BCMA10 CART cells manufactured using the ARM process were assessed for CAR expression at thaw (FIG. 34A) and 48 h post-thaw (FIG. 34B). CCR7/CD45RO markers were also assessed for the 48 h post-thaw product (FIG. 34C). Data shown is one representative from two experiments performed using two donor T cells.
Figure 35A:
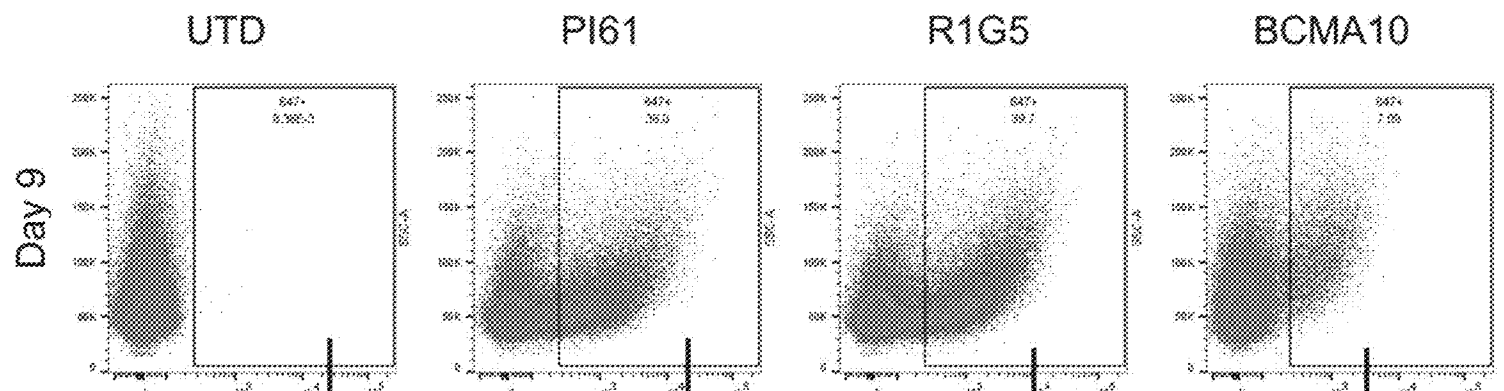
FIGS. 35A and 35B. The TM process mainly resulted in central-memory T cells (TCM) (CD45RO+/CCR7+), while the naive-like T cell population is almost gone in the CAR+T cells with TM process. PI61, R1G5 and BCMA10 CART cells manufactured using the TM process were assessed for CAR expression at day 9 (FIG. 35A). CCR7/CD45RO markers were also assessed at day 9 post-thaw product (FIG. 35B). Data shown is one representative from two experiments performed using two donor T cells.
Figure 35B:
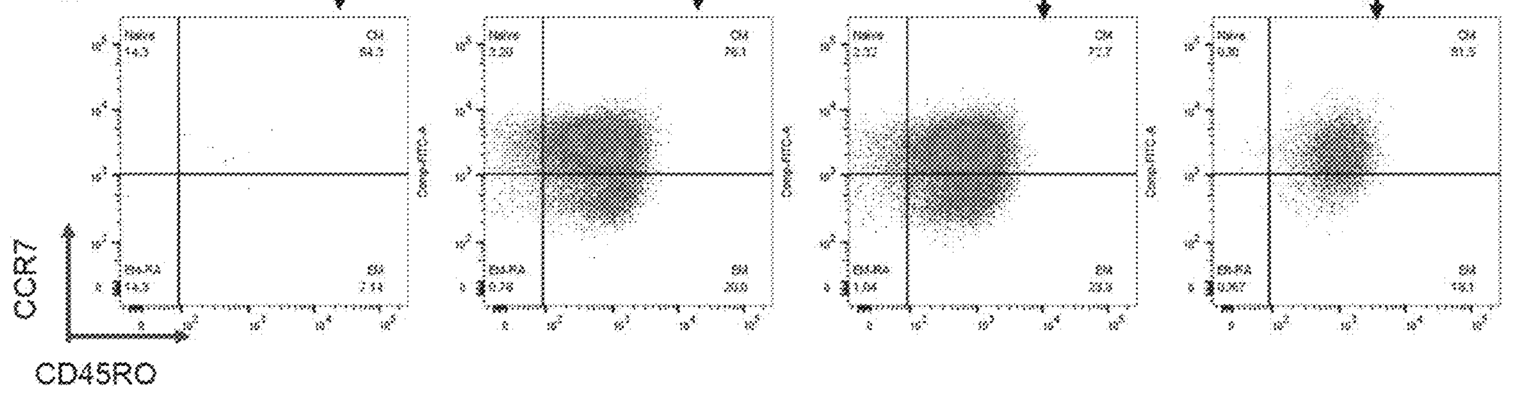
Figure 36A:
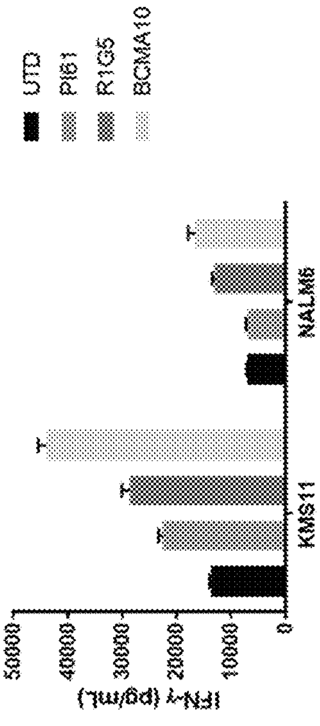
FIGS. 36A, 36B, 36C, and 36D. ARM processed BCMA CAR-T cells demonstrates BCMA-specific activation and secretes higher levels of IL2 and IFN-γ. IL-2 and IFN-γ concentrations in cell culture supernatants. PI61, R1G5 and BCMA10 CART cells manufactured using the ARM or TM process, and respective UTD were co-cultured with KMS-11 at 2.5:1 ratio. Supernatants were collected 20 h later. For the ARM products, IFN-γ concentrations are shown in FIG. 36A and IL-2 concentrations are shown in FIG. 36B. For the TM products, IFN-γ concentrations are shown in FIG. 36C and IL-2 concentrations are shown in FIG. 36D. Data shown is one representative from two experiments performed using two donor T cells.
Figure 36B:
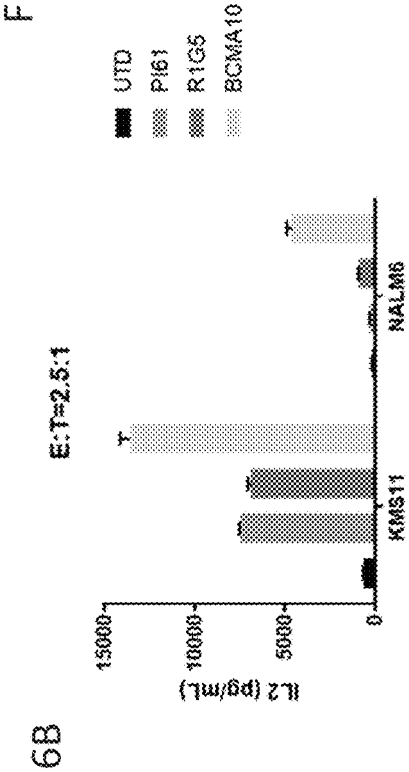
Figure 36C:
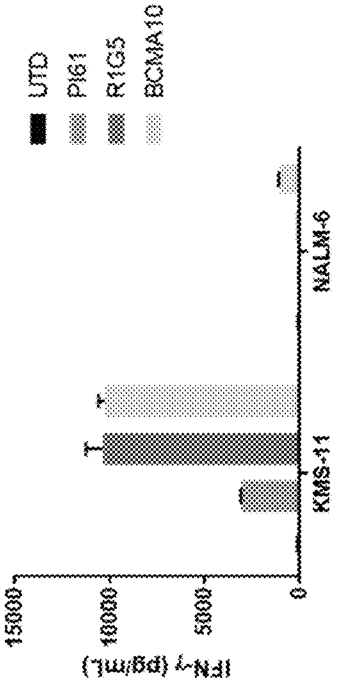
Figure 36D:
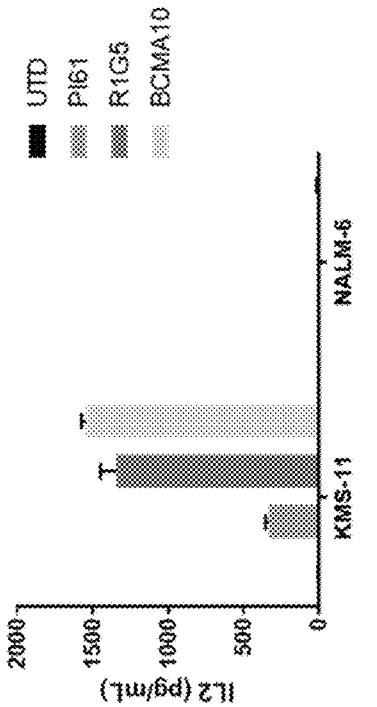

CAR-T cells generated using the ARM process were analyzed by flow cytometry to evaluate their CAR expression at thaw and 48 h post thaw, as well as the T-cell phenotype (FIGS. 34A, 34B, and 34C). For CAR-T cells manufactured using the TM process, CAR expression was assessed at day 9 before harvest (FIG. 35A). BCMA-CAR was almost undetectable at thaw shown in FIG. 34A. However, at 48 h post-thaw, BCMA-CAR was clearly being expressed as 32.9% for PI61, 35.9% for R1G5 and 17.4% for BCMA10. The day 9 cells generated using the TM process show BCMA-CAR expression to be 36% for PI61, 40% for R1G5 and 7% for BCMA10 (FIG. 35A). Analysis of the CAR+T-cell phenotype revealed that the ARM process retained naïve-like T cells (~60% of CD45RO−/CCR7+ for PI61 and R1G5, 32% of CD45RO−/CCR7+ for BCMA10) (FIG. 34C). The TM process mainly resulted in central-memory T cells (TCM) (72 ~81% CD45RO+/CCR7+ for all three BCMA CAR-Ts), while the naive-like T cell population was almost gone in the CAR+T cells manufactured using the TM process (FIG. 35B). Overall, the naïve T-cell population largely overlaps with CD45RO−/CD27+ Tstem cells described by previous reports (Cohen A D, et al (2019). J Clin Invest. 130. pii: 126397. doi: 10.1172/JCI126397; Fraietta, J A, et al (2018). Nat Med, 24(5); 563-571) and is associated with responses and CAR-T expansion.

In addition to its phenotype, the final PI61, R1G5 and BCMA10 CART cell products were also assessed for their function in vitro. PI61, R1G5 and BCMA10 cell products were thawed and co-cultured with the BCMA-expressing cell line KMS-11 at 1:1 ratio. Post-thaw ARM processed cells were rested for 24 h prior to co-culture being established. Comparing cytokine levels in the supernatants 24 hours after co-culture revealed a ~5 to 25-fold increase of IL-2 and a ~3 to 7-fold increase in levels of IFN-γ secreted by ARM products as compared to TM products as shown in FIGS. 36A-36D. Experiments with untransduced (UTD) cells that underwent the ARM or TM process confirmed BCMA-specific recognition by PI61, R1G5 and BCMA10.

In summary, PI61, R1G5 and BCMA10 CART cells produced using the ARM process demonstrate BCMA-specific activation in vitro and secretes higher levels of IL-2 and IFN-γ as compared to TM processed products, which correlates with the Tstem phenotype of CART cells produced using the ARM process.

Example 10: Gene Signature Analysis of CART Cells Manufactured Using the ARM Process Methods Single Cell RNAseq Single cell RNAseq libraries were generated using the 10× Genomics Chromium Controller instrument and supporting library construction kits.

Cryopreserved cells were thawed, counted and flow sorted (if required for study question), prior to being loaded on a 10× Genomics Instrument. Individual cells were loaded into droplets and RNA within individual droplets was barcoded via a GemCode bead. Barcoded RNA was released from droplets and converted into a whole transcriptome Illumina compatible sequencing library.

Generated libraries were sequenced on an Illumina HiSeq Instrument and analyzed using 10× Genomics analysis pipeline and Loupe Cell Browser software.

Single Cell Immune Cell Profiling

Whole transcriptome 10× Genomics single cell libraries were used as a template material to generate immune cell profiling and repertoire analysis. T cell receptor sequences were PCR amplified from Chromium Single Cell 5' Libraries and analyzed on an Illumina sequencing instrument.

Analysis Pipeline

Single cell RNAseq data was processed through the Cell Ranger analysis pipeline starting with FASTQ files. A detailed description of the Cell Ranger analysis pipeline can be found at: https://support.10xgenomics.com/single-cell-gene-expression/software/pipelines/latest/what-is-cell-ranger. The general pipeline included alignment, filtering, barcode counting, and UMI counting. Cellular barcodes were used to generate gene-barcode matrices, determine clusters, and perform gene expression analysis. Gene expression count data was normalized using the Seurat Bioconductor package. Cells were discarded from the analysis that had less than 200 expressed genes. Genes were discarded from the analysis that were only expressed in 2 cells or less. The remaining data was normalized with the Seurat log normalization method using a scale factor of 10,000. Data was scaled by regressing on the number of detected molecules per cell. The gene set score (GeneSetScore) was calculated by taking the mean log normalized gene expression value of all the genes in the gene set. Each gene is z-score normalized so that the mean expression of the gene across samples is 0 and standard deviation is 1. The gene set score is then calculated as the mean of the normalized values of the genes in the gene set. An exemplary gene set score calculation is described below.

For this example of gene set score calculation, the normalized gene expression of two (2) samples for six (6) genes is provided in Table 23. For the purposes of this exemplary calculation, the gene set consists of genes 1-4. Therefore, Sample 1 and 2 both have gene set scores of 0.

TABLE 23

| Exemplary dataset for gene set score calculation | | |
|---|---|---|
| | Sample 1 | Sample 2 |
| Gene 1 | −3 | 0 |
| Gene 2 | 3 | 0 |
| Gene 3 | 1 | 0 |
| Gene 4 | −1 | 0 |
| Gene 5 | 10 | 4 |
| Gene 6 | −5 | 3 |

The gene set "Up TEM vs. Down TSCM" includes the following genes: MXRA7, CLIC1, NAT13, TBC1D2B, GLCCI1, DUSP10, APOBEC3D, CACNB3, ANXA2P2, TPRG1, EOMES, MATK, ARHGAP10, ADAM8, MAN1A1, SLFN12L, SH2D2A, EIF2C4, CD58, MYO1F, RAB27B, ERN1, NPC1, NBEAL2, APOBEC3G, SYTL2, SLC4A4, PIK3AP1, PTGDR, MAF, PLEKHA5, ADRB2, PLXND1, GNAO1, THBS1, PPP2R2B, CYTH3, KLRF1, FLJ16686, AUTS2, PTPRM, GNLY, and GFPT2.

The gene set "Up Treg vs. Down Teff" includes the following genes: C12orf75, SELPLG, SWAP70, RGS1, PRR11, SPATS2L, SPATS2L, TSHR, C14orf145, CASP8, SYT11, ACTN4, ANXA5, GLRX, HLA-DMB, PMCH, RAB11FIP1, IL32, FAM160B1, SHMT2, FRMD4B, CCR3, TNFRSF13B, NTNG2, CLDND1, BARD1, FCER1G, TYMS, ATP1B1, GJB6, FGL2, TK1, SLC2A8, CDKN2A, SKAP2, GPR55, CDCA7, S100A4, GDPD5, PMA1P1, ACOT9, CEP55, SGMS1, ADPRH, AKAP2, HDAC9, IKZF4, CARD17, VAV3, OBFC2A, ITGB1, CIITA, SETD7, HLA-DMA, CCR10, KIAA0101, SLC14A1, PTTG3P, DUSP10, FAM164A, PYHIN1, MYO1F, SLC1A4, MYBL2, PTTG1, RRM2, TP53INP1, CCR5, ST8SIA6, TOX, BFSP2, ITPRIPL1, NCAPH, HLA-DPB2, SYT4, NINJ2, FAM46C, CCR4, GBP5, C15orf53, LMCD1, MKI67, NUSAP1, PDE4A, E2F2, CD58, ARHGEF12, LOC100188949, FAS, HLA-DPB1, SELP, WEE1, HLA-DPA1, FCRL1, ICA1, CNTNAP1, OAS1, METTL7A, CCR6, HLA-DRB4, ANXA2P3, STAM, HLA-DQB2, LGALS1, ANXA2, PI16, DUSP4, LAYN, ANXA2P2, PTPLA, ANXA2P1, ZNF365, LAIR2, LOC541471, RASGRP4, BCAS1, UTS2, MIAT, PRDM1, SEMA3G, FAM129A, HPGD, NCF4, LGALS3, CEACAM4, JAKMIP1, TIGIT, HLA-DRA, IKZF2, HLA-DRB1, FANK1, RTKN2, TRIB1, FCRL3, and FOXP3.

The gene set "Down sternness" includes the following genes: ACE, BATF, CDK6, CHD2, ERCC2, HOXB4, MEOX1, SFRP1, SP7, SRF, TAL1, and XRCC5.

The gene set "Up hypoxia" includes the following genes: ABCB1, ACAT1, ADM, ADORA2B, AK2, AK3, ALDH1A1, ALDH1A3, ALDOA, ALDOC, ANGPT2, ANGPTL4, ANXA1, ANXA2, ANXA5, ARHGAP5, ARSE, ART1, BACE2, BATF3, BCL2L1, BCL2L2, BHLHE40, BHLHE41, BIK, BIRC2, BNIP3, BNIP3L, BPI, BTG1, C11orf2, C7orf68, CA12, CA9, CALD1, CCNG2, CCT6A, CD99, CDK1, CDKN1A, CDKN1B, CITED2, CLK1, CNOT7, COL4A5, COL5A1, COL5A2, COL5A3, CP, CTSD, CXCR4, D4S234E, DDIT3, DDIT4, 1-Dec, DKC1, DR1, EDN1, EDN2, EFNA1, EGF, EGR1, EIF4A3, ELF3, ELL2, ENG, ENO1, ENO3, ENPEP, EPO, ERRFI1, ETS1, F3, FABP5, FGF3, FKBP4, FLT1, FN1, FOS, FTL, GAPDH, GBE1, GLRX, GPI, GPRC5A, HAP1, HBP1, HDAC1, HDAC9, HERC3, HERPUD1, HGF, HIF1A, HK1, HK2, HLA-DQB1, HMOX1, HMOX2, HSPA5, HSPD1, HSPH1, HYOU1, ICAM1, ID2, IFI27, IGF2, IGFBP1, IGFBP2, IGFBP3, IGFBP5, IL6, IL8, INSIG1, IRF6, ITGA5, JUN, KDR, KRT14, KRT18, KRT19, LDHA, LDHB, LEP, LGALS1, LONP1, LOX, LRP1, MAP4, MET, MIF, MMP13, MMP2, MMP7, MPI, MT1L, MTL3P, MUC1, MXI1, NDRG1, NFIL3, NFKB1, NFKB2, NOS1, NOS2, NOS2P1, NOS2P2, NOS3, NR3C1, NR4A1, NT5E, ODC1, P4HA1, P4HA2, PAICS, PDGFB, PDK3, PFKFB1, PFKFB3, PFKFB4, PFKL, PGAM1, PGF, PGK1, PGK2, PGM1, PIM1, PIM2, PKM2, PLAU, PLAUR, PLIN2, PLOD2, PNN, PNP, POLM, PPARA, PPAT, PROK1, PSMA3, PSMD9, PTGS1, PTGS2, QSOX1, RBPJ, RELA, RIOK3, RNASEL, RPL36A, RRP9, SAT1, SERPINB2, SERPINE1, SGSM2, SIAH2, SIN3A, SIRPA, SLC16A1, SLC16A2, SLC20A1, SLC2A1, SLC2A3, SLC3A2, SLC6A10P, SLC6A16, SLC6A6, SLC6A8, SORL1, SPP1, SRSF6, SSSCA1, STC2, STRA13, SYT7, TBPL1, TCEAL1, TEK, TF, TFF3, TFRC, TGFA, TGFB1, TGFB3, TGFBI, TGM2, TH, THBS1, THBS2, TIMM17A, TNFAIP3, TP53, TPBG, TPD52, TPI1, TXN, TXNIP, UMPS, VEGFA, VEGFB, VEGFC, VIM, VPS11, and XRCC6.

The gene set "Up autophagy" includes the following genes: ABL1, ACBD5, ACIN1, ACTRT1, ADAMTS7, AKR1E2, ALKBH5, ALPK1, AMBRA1, ANXA5, ANXA7, ARSB, ASB2, ATG10, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATP13A2, ATP1B1, ATPAF1-AS1, ATPIF1, BECN1, BECN1P1, BLOC1S1, BMP2KL, BNIP1, BNIP3, BOC, C11orf2, C11orf41, C12orf44, C12orf5, C14orf133, C1orf210, C5, C6orf106, C7orf59, C7orf68, C8orf59, C9orf72, CA7, CALCB, CALCOCO2, CAPS, CCDC36, CD163L1, CD93, CDC37, CDKN2A, CHAF1B, CHMP2A, CHMP2B, CHMP3, CHMP4A, CHMP4B, CHMP4C, CHMP6, CHST3, CISD2, CLDN7, CLEC16A, CLN3, CLVS1, COX8A, CPA3, CRNKL1, CSPG5, CTSA, CTSB, CTSD, CXCR7, DAP, DKKL1, DNAAF2, DPF3, DRAM1, DRAM2, DYNLL1, DYNLL2, DZANK1, EI24, EIF2S1, EPG5, EPM2A, FABP1, FAM125A, FAM131B, FAM134B, FAM13B, FAM176A, FAM176B, FAM48A, FANCC, FANCF, FANCL, FBXO7, FCGR3B, FGF14, FGF7, FGFBP1, FIS1, FNBP1L, FOXO1, FUNDC1, FUNDC2, FXR2, GABARAP, GABARAPL1, GABARAPL2, GABARAPL3, GABRA5, GDF5, GMIP, HAP1, HAPLN1, HBXIP, HCAR1, HDAC6, HGS, HIST1H3A, HIST1H3B, HIST1H3C, HIST1H3D, HIST1H3E, HIST1H3F, HIST1H3G, HIST1H3H, HIST1H3I, HIST1H3J, HK2, HMGB1, HPR, HSF2BP, HSP90AA1, HSPA8, IFI16, IPPK, IRGM, IST1, ITGB4, ITPKC, KCNK3, KCNQ1, KIAA0226, KIAA1324, KRCC1, KRT15, KRT73, LAMP1, LAMP2, LAMTOR1, LAMTOR2, LAMTOR3, LARP1B, LENG9, LGALS8, LIX1, LIX1L, LMCD1, LRRK2, LRSAM1, LSM4, MAP1A, MAP1LC3A, MAP1LC3B, MAP1LC3B2, MAP1LC3C, MAP1S, MAP2K1, MAP3K12, MARK2, MBD5, MDH1, MEX3C, MFN1, MFN2, MLST8, MRPS10, MRPS2, MSTN, MTERFD1, MTMR14, MTMR3, MTOR, MTSS1, MYH11, MYLK, MYOM1, NBR1, NDUFB9, NEFM, NHLRC1, NME2, NPC1, NR2C2, NRBF2, NTHL1, NUP93, OBSCN, OPTN, P2RX5, PACS2, PARK2, PARK7, PDK1, PDK4, PEX13, PEX3, PFKP, PGK2, PHF23, PHYHIP, PI4K2A, PIK3C3, PIK3CA, PIK3CB, PIK3R4, PINK1, PLEKHM1, PLOD2, PNPO, PPARGC1A, PPY, PRKAA1, PRKAA2, PRKAB1, PRKAB2, PRKAG1, PRKAG2, PRKAG3, PRKD2, PRKG1, PSEN1, PTPN22, RAB12, RAB1A, RAB1B, RAB23, RAB24, RAB33B, RAB39, RAB7A, RB1CC1, RBM18, REEP2, REP15, RFWD3, RGS19, RHEB, RIMS3, RNF185, RNF41, RPS27A, RPTOR, RRAGA, RRAGB, RRAGC, RRAGD, S100A8, S100A9, SCN1A, SERPINB10, SESN2, SFRP4, SH3GLB1, SIRT2, SLC1A3, SLC1A4, SLC22A3, SLC25A19, SLC35B3, SLC35C1, SLC37A4, SLC6A1, SLCO1A2, SMURF1, SNAP29, SNAPIN, SNF8, SNRPB, SNRPB2, SNRPD1, SNRPF, SNTG1, SNX14, SPATA18, SQSTM1, SRPX, STAM, STAM2, STAT2, STBD1, STK11, STK32A, STOM, STX12, STX17, SUPT3H, TBC1D17, TBC1D25, TBC1D5, TCIRG1, TEAD4, TECPR1, TECPR2, TFEB, TM9SF1, TMBIM6, TMEM203, TMEM208, TMEM39A, TMEM39B, TMEM59, TMEM74, TMEM93, TNIK, TOLLIP, TOMM20, TOMM22, TOMM40, TOMM5, TOMM6, TOMM7, TOMM70A, TP53INP1, TP53INP2, TRAPPC8, TREM1, TRIM17, TRIMS, TSG101, TXLNA, UBA52, UBB, UBC, UBQLN1, UBQLN2, UBQLN4, ULK1, ULK2, ULK3, USP10, USP13, USP30, UVRAG, VAMP7, VAMP8, VDAC1, VMP1, VPS11, VPS16, VPS18, VPS25, VPS28, VPS33A, VPS33B, VPS36, VPS37A, VPS37B, VPS37C, VPS37D, VPS39, VPS41, VPS4A, VPS4B, VTA1, VTI1A, VTI1B, WDFY3, WDR45, WDR45L, WIPI1, WIPI2, XBP1, YIPF1, ZCCHC17, ZFYVE1, ZKSCAN3, ZNF189, ZNF593, and ZNF681.

The gene set “Up resting vs. Down activated” includes the following genes: ABCA7, ABCF3, ACAP2, AMT, ANKH, ATF7IP2, ATG14, ATP1A1, ATXN7, ATXN7L3B, BCL7A, BEX4, BSDC1, BTG1, BTG2, BTN3A1, C11orf21, C19orf22, C21orf2, CAMK2G, CARS2, CCNL2, CD248, CD5, CD55, CEP164, CHKB, CLK1, CLK4, CTSL1, DBP, DCUN1D2, DENND1C, DGKD, DLG1, DUSP1, EAPP, ECE1, ECHDC2, ERBB2IP, FAM117A, FAM134B, FAM134C, FAM169A, FAM190B, FAU, FJL10038, FOXJ2, FOXJ3, FOXL1, FOXO1, FXYD5, FYB, HLA-E, HSPA1L, HYAL2, ICAM2, IFIT5, IFITM1, IKBKB, IQSEC1, IRS4, KIAA0664L3, KIAA0748, KLF3, KLF9, KRT18, LEF1, LINC00342, LIPA, LIPT1, LLGL2, LMBR1L, LPAR2, LTBP3, LYPD3, LZTFL1, MANBA, MAP2K6, MAP3K1, MARCH8, MAU2, MGEA5, MMP8, MPO, MSL1, MSL3, MYH3, MYLIP, NAGPA, NDST2, NISCH, NKTR, NLRP1, NOSIP, NPIP, NUMA1, PAIP2B, PAPD7, PBXIP1, PCIF1, PI4KA, PLCL2, PLEKHA1, PLEKHF2, PNISR, PPFIBP2, PRKCA, PRKCZ, PRKD3, PRMT2, PTP4A3, PXN, RASA2, RASA3, RASGRP2, RBM38, REPIN1, RNF38, RNF44, ROR1, RPL30, RPL32, RPLP1, RPS20, RPS24, RPS27, RPS6, RPS9, RXRA, RYK, SCAND2, SEMA4C, SETD1B, SETD6, SETX, SF3B1, SH2B1, SLC2A4RG, SLC35E2B, SLC46A3, SMAGP, SMARCE1, SMPD1, SNPH, SP140L, SPATA6, SPG7, SREK11P1, SRSF5, STAT5B, SVIL, SYF2, SYNJ2BP, TAF1C, TBC1D4, TCF20, TECTA, TES, TMEM127, TMEM159, TMEM30B, TMEM66, TMEM8B, TP53TG1, TPCN1, TRIM22, TRIM44, TSC1, TSC22D1, TSC22D3, TSPYL2, TTC9, TTN, UBE2G2, USP33, USP34, VAMP1, VILL, VIPR1, VPS13C, ZBED5, ZBTB25, ZBTB40, ZC3H3, ZFP161, ZFP36L1, ZFP36L2, ZHX2, ZMYM5, ZNF136, ZNF148, ZNF318, ZNF350, ZNF512B, ZNF609, ZNF652, ZNF83, ZNF862, and ZNF91.

The gene set “Progressively up in memory differentiation” includes the following genes: MTCH2, RAB6C, KIAA0195, SETD2, C2orf24, NRD1, GNA13, COPA, SELT, TNIP1, CBFA2T2, LRP10, PRKCI, BRE, ANKS1A, PNPLA6, ARL6IP1, WDFY1, MAPK1, GPR153, SHKBP1, MAP1LC3B2, PIP4K2A, HCN3, GTPBP1, TLN1, C4orf34, KIF3B, TCIRG1, PPP3CA, ATG4D, TYMP, TRAF6, C17orf76, WIPF1, FAM108A1, MYL6, NRM, SPCS2, GGT3P, GALK1, CLIP4, ARL4C, YWHAQ, LPCAT4, ATG2A, IDS, TBC1D5, DMPK, ST6GALNAC6, REEP5, ABHD6, KIAA0247, EMB, TSEN54, SPIRE2, PIWIL4, ZSCAN22, ICAM1, CHD9, LPIN2, SETD8, ZC3H12A, ULBP3, IL15RA, HLA-DQB2, LCP1, CHP, RUNX3, TMEM43, REEP4, MEF2D, ABL1, TMEM39A, PCBP4, PLCD1, CHST12, RASGRP1, C1orf58, C11orf63, C6orf129, FHOD1, DKFZp434F142, PIK3CG, ITPR3, BTG3, C4orf50, CNNM3, IFI16, AK1, CDK2AP1, REL, BCL2L1, MVD, TTC39C, PLEKHA2, FKBP11, EML4, FANCA, CDCA4, FUCA2, MFSD10, TBCD, CAPN2, IQGAP1, CHST11, PIK3R1, MYO5A, KIR2DL3, DLG3, MXD4, RALGDS, S1PR5, WSB2, CCR3, TIPARP, SP140, CD151, SOX13, KRTAP5-2, NF1, PEA15, PARP8, RNF166, UEVLD, LIMK1, CACNB1, TMX4, SLC6A6, LBA1, SV2A, LLGL2, IRF1, PPP2R5C, CD99, RAPGEF1, PPP4R1, OSBPL7, FOXP4, SLA2, TBC1D2B, ST7, JAZF1, GGA2, PI4K2A, CD68, LPGAT1, STX11, ZAK, FAM160B1, RORA, C8orf80, APOBEC3F, TGFBI, DNAJC1, GPR114, LRP8, CD69, CMIP, NAT13, TGFB1, FLJ00049, ANTXR2, NR4A3, IL12RB1, NTNG2, RDX, MLLT4, GPRIN3, ADCY9, CD300A, SCD5, ABI3, PTPN22, LGALS1, SYTL3, BMPR1A, TBK1, PMAIP1, RASGEF1A, GCNT1, GABARAPL1, STOM, CALHM2, ABCA2, PPP1R16B, SYNE2, PAM, C12orf75, CLCF1, MXRA7, APOBEC3C, CLSTN3, ACOT9, HIP1, LAG3, TNFAIP3, DCBLD1, KLF6, CACNB3, RNF19A, RAB27A, FADS3, DLG5, APOBEC3D, TNFRSF1B, ACTN4, TBKBP1, ATXN1, ARAP2, ARHGEF12, FAM53B, MAN1A1, FAM38A, PLXNC1, GRLF1, SRGN, HLA-DRB5, B4GALT5, WIPI1, PTPRJ, SLFN11, DUSP2, ANXA5, AHNAK, NEO1, CLIC1, EIF2C4, MAP3K5, IL2RB, PLEKHG1, MYO6, GTDC1, EDARADD, GALM, TARP, ADAM8, MSC, HNRPLL, SYT11, ATP2B4, NHSL2, MATK, ARHGAP18, SLFN12L, SPATS2L, RAB27B, PIK3R3, TP53INP1, MBOAT1, GYG1, KATNAL1, FAM46C, ZC3HAV1L, ANXA2P2, CTNNA1, NPC1, C3AR1, CRIM1, SH2D2A, ERN1, YPEL1, TBX21, SLC1A4, FASLG, PHACTR2, GALNT3, ADRB2, PIK3AP1, TLR3, PLEKHA5, DUSP10, GNAO1, PTGDR, FRMD4B, ANXA2, EOMES, CADM1, MAF, TPRG1, NBEAL2, PPP2R2B, PELO, SLC4A4, KLRF1, FOSL2, RGS2, TGFBR3, PRF1, MYO1F, GAB3, C17orf66, MICAL2, CYTH3, TOX, HLA-DRA, SYNE1, WEE1, PYHIN1, F2R, PLD1, THBS1, CD58, FAS, NETO2, CXCR6, ST6GALNAC2, DUSP4, AUTS2, C1orf21, KLRG1, TNIP3, GZMA, PRR5L, PRDM1, ST8SIA6, PLXND1, PTPRM, GFPT2, MYBL1, SLAMF7, FLJ16686, GNLY, ZEB2, CST7, IL18RAP, CCL5, KLRD1, and KLRB1.

The gene set “Up TEM vs. Down TN” includes the following genes: MYO5A, MXD4, STK3, S1PR5, GLCCI1, CCR3, SOX13, KRTAP5-2, PEA15, PARP8, RNF166, UEVLD, LIMK1, SLC6A6, SV2A, KPNA2, OSBPL7, ST7, GGA2, PI4K2A, CD68, ZAK, RORA, TGFBI, DNAJC1, JOSD1, ZFYVE28, LRP8, OSBPL3, CMIP, NAT13, TGFB1, ANTXR2, NR4A3, RDX, ADCY9, CHN1, CD300A, SCD5, PTPN22, LGALS1, RASGEF1A, GCNT1, GLUL, ABCA2, CLDND1, PAM, CLCF1, MXRA7, CLSTN3, ACOT9, METRNL, BMPR1A, LRIG1, APOBEC3G, CACNB3, RNF19A, RAB27A, FADS3, ACTN4, TBKBP1, FAM53B, MAN1A1, FAM38A, GRLF1, B4GALT5, WIPI1, DUSP2, ANXA5, AHNAK, CLIC1, MAP3K5, ST8SIA1, TARP, ADAM8, MATK, SLFN12L, PIK3R3, FAM46C, ANXA2P2, CTNNA1, NPC1, SH2D2A, ERN1, YPEL1, TBX21, STOM, PHACTR2, GBP5, ADRB2, PIK3AP1, DUSP10, PTGDR, EOMES, MAF, TPRG1, NBEAL2, NCAPH, SLC4A4, FOSL2, RGS2, TGFBR3, MYO1F, C17orf66, CYTH3, WEE1, PYHIN1, F2R, THBS1, CD58, AUTS2, FAM129A, TNIP3, GZMA, PRR5L, PRDM1, PLXND1, PTPRM, GFPT2, MYBL1, SLAMF7, ZEB2, CST7, CCL5, GZMK, and KLRB1.

Other gene sets describing similar processes and/or characteristics can also be used to characterize cell phenotypes described above.

Cell Ranger VDJ was used to generate single cell VDJ sequences and annotations for each single cell 5' library. Loupe Cell Browser software and Bioconductor packages were used for data analysis and visualization.

Results

This example aims to compare T cell states between purified T cells which served as input cells, CART cells manufactured using the ARM process (labeled as "Day 1" cells), and CART cells manufactured using the TM process (labeled as "Day 9" cells) using single-cell RNA-seq (scRNA-seq). In addition, single-cell TCR-seq (scTCR-seq) was performed to study clonality and track cell differentiation from input to post-manufacturing materials.

Figure 37A:
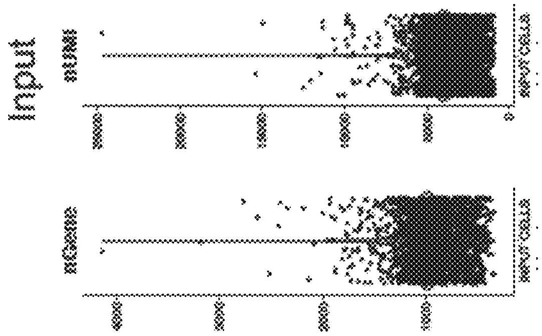
FIGS. 37A, 37B, and 37C. Single cell RNA-seq data for input cells (FIG. 37A), Day 1 cells (FIG. 37B), and Day 9 cells (FIG. 37C). The "nGene" graphs show the number of expressed genes per cell. The "nUMI" graphs show the number of unique molecular identifiers (UMIs) per cell.
Figure 37B:
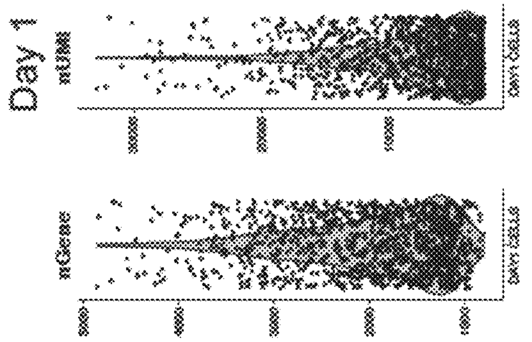
Figure 37C:
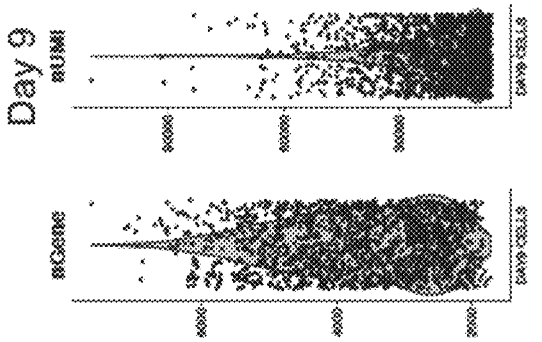
Figure 38A:
FIGS. 38A, 38B, 38C, and 38D. T-Distributed Stochastic Neighbor Embedding (TSNE) plots comparing input cells (FIG. 38A), Day 1 cells (FIG. 38B), and Day 9 cells (FIG. 38C) for a proliferation signature, which was determined based on expression of genes CCNB1, CCND1, CCNE1, PLK1, and MKI67. Each dot represents a cell in that sample. Cells shown as light grey do not express the proliferation genes whereas dark shaded cells express one or more of the proliferation genes.
Figure 38B:
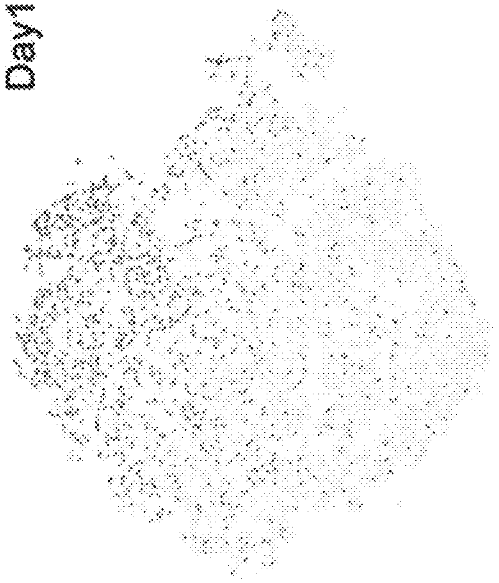
Figure 38C:
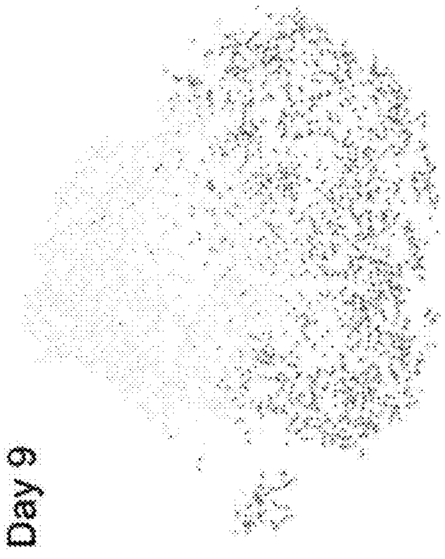
Figure 38D:
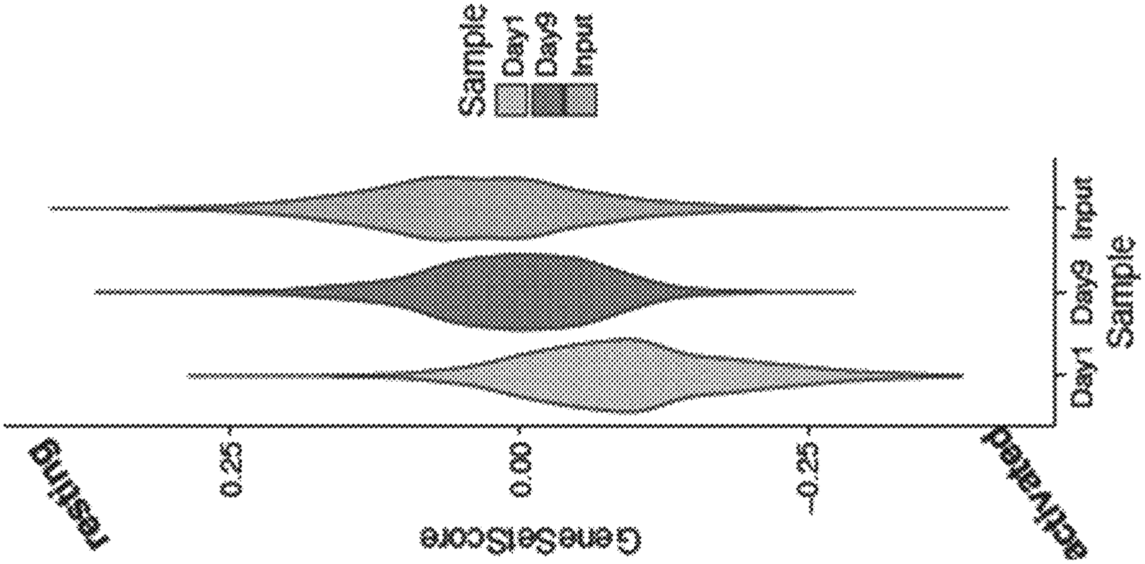

As shown in FIGS. 37A-37C, input cells had the fewest expressed genes and UMIs, suggesting these cells were not transcriptionally active and were in a resting state. Day 1 and Day 9 cells were expressing more genes, with Day 9 cells being the most transcriptionally active. Similar results are shown in FIGS. 38A-38D. Input cells were not expressing proliferation genes (FIGS. 38A and 38D).

Figure 39B:
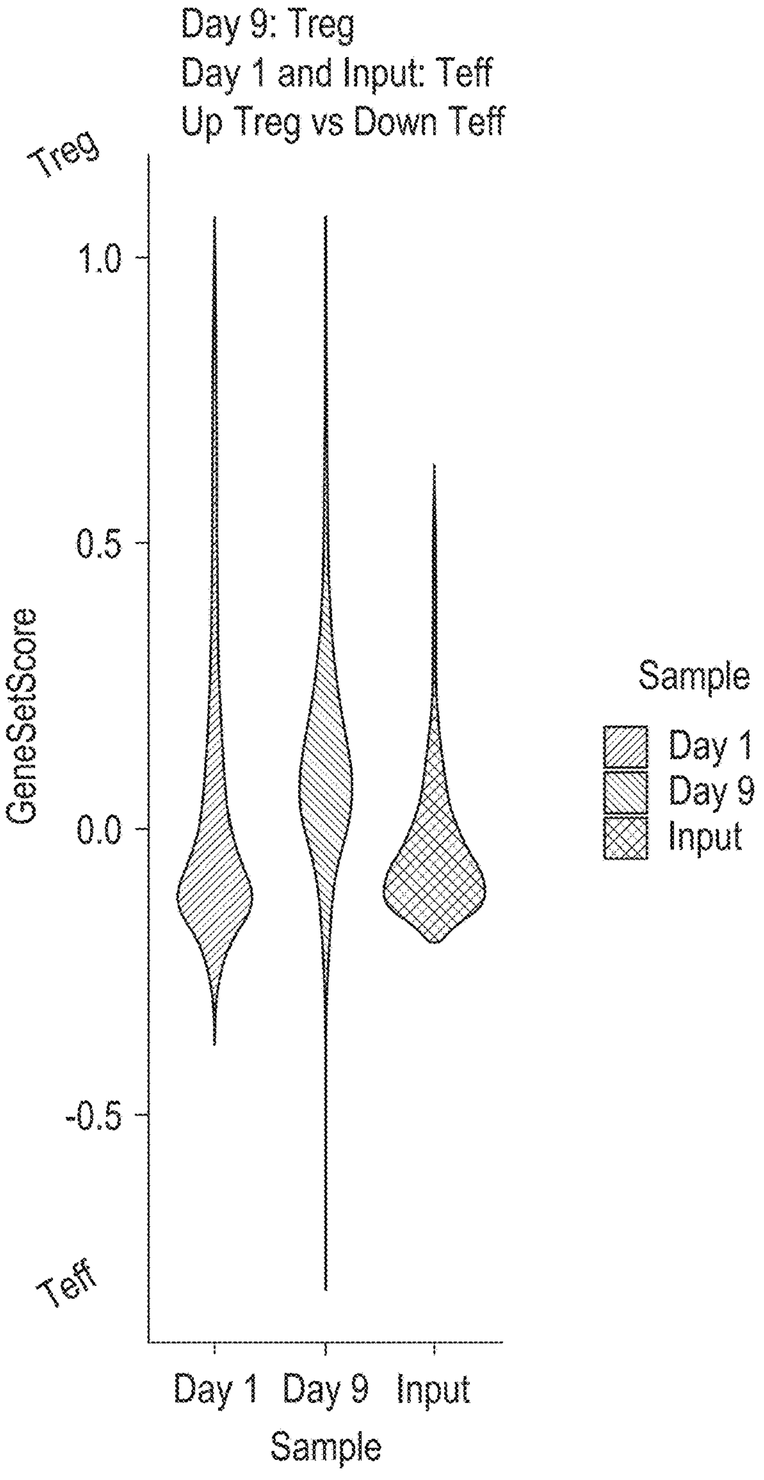
Figure 39C:
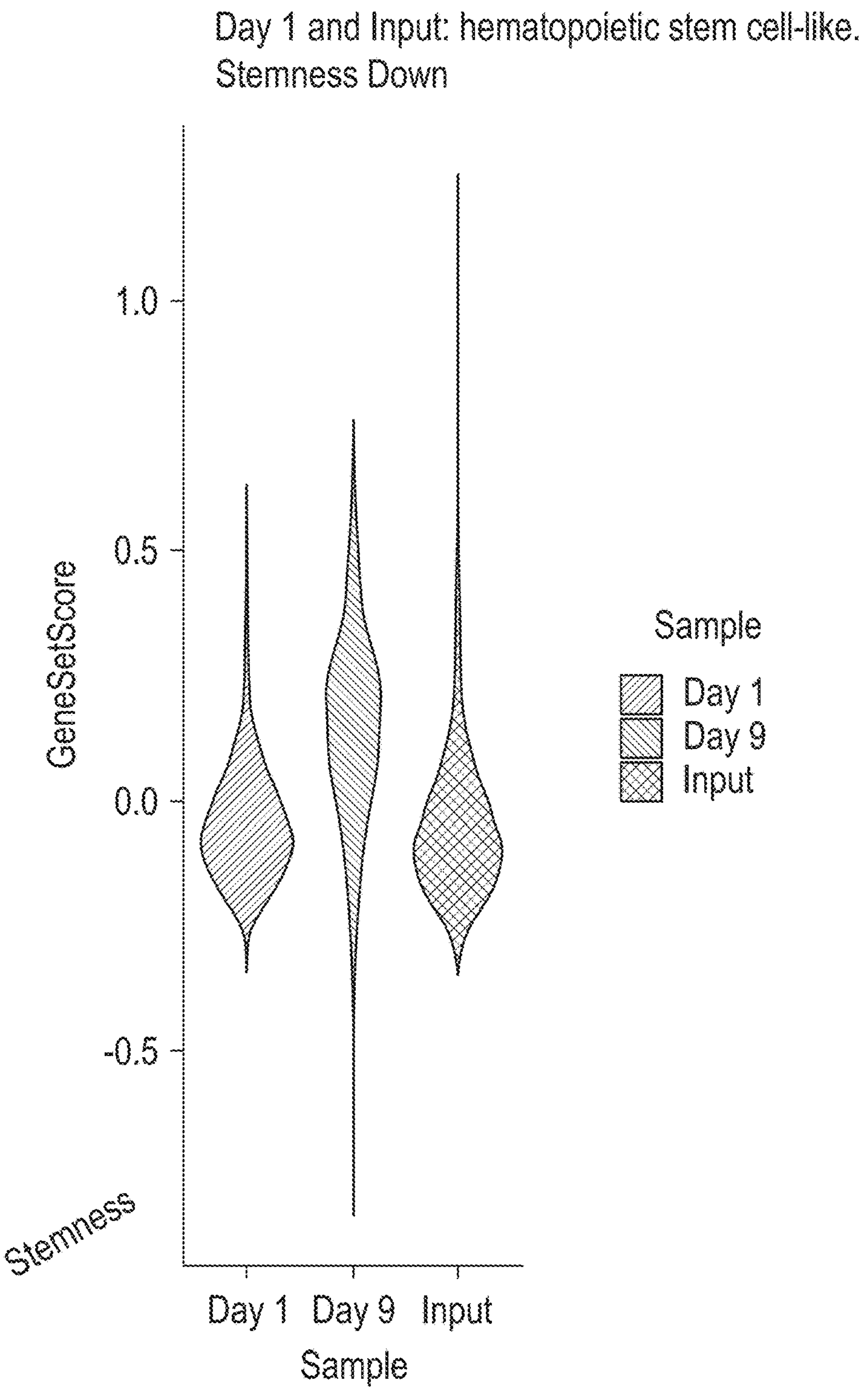

Additional gene set analysis data are shown in FIGS. 39A-39E. Different populations of cells were compared using the median gene set scores. Day 1 cells and input cells were in a younger, more stem-like memory state (FIGS. 39A-39C). In FIG. 39A, the median GeneSetScore (Up TEM vs. Down TSCM) values for Day 1 cells, Day 9 cells, and input cells are −0.084, 0.035, and −0.1, respectively. In FIG. 39B, the median GeneSetScore (Up Treg vs. Down Teff) values for Day 1 cells, Day 9 cells, and input cells are −0.082, 0.087, and −0.071, respectively. In FIG. 39C, the median GeneSetScore (Down stemness) values for Day 1 cells, Day 9 cells, and input cells are −0.062, 0.14, and −0.081, respectively.

Figure 39D:
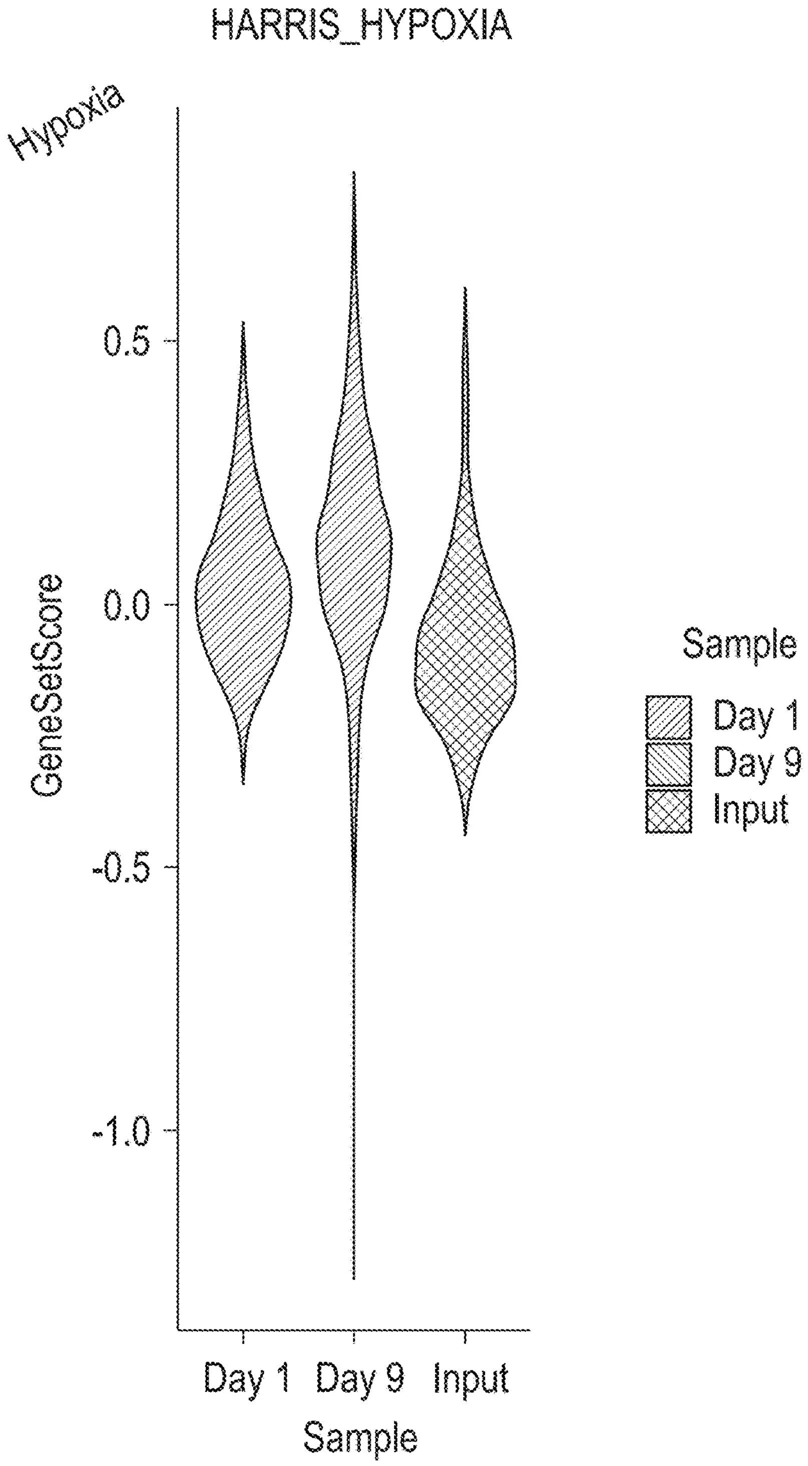
Figure 39E:
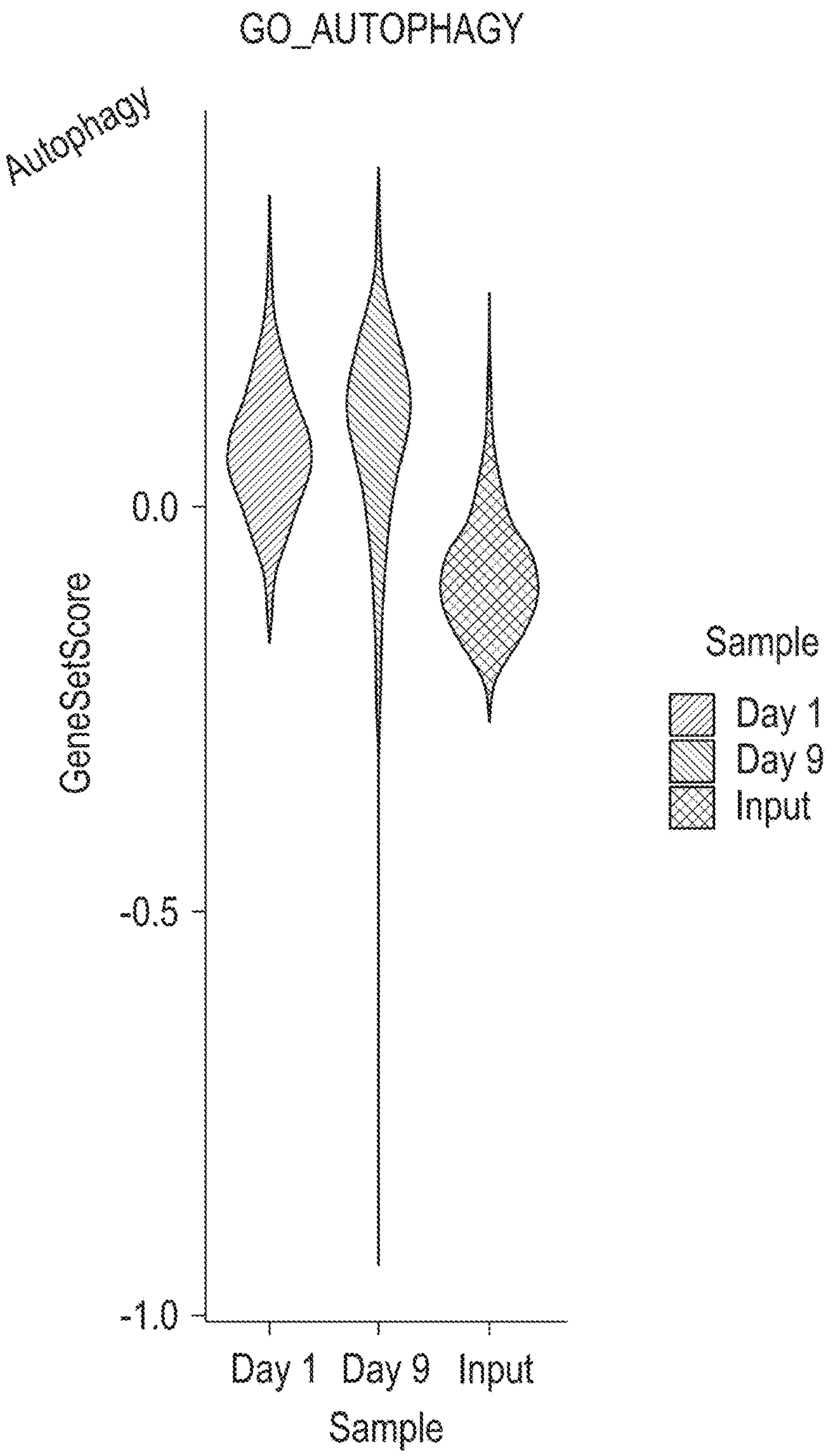

In addition, Day 1 cells were in a more ideal metabolic state compared to Day 9 cells (FIGS. 39D and 39E). In FIG. 39D, the median GeneSetScore (Up hypoxia) values for Day 1 cells, Day 9 cells, and input cells are 0.019, 0.11, and −0.096, respectively. In FIG. 39E, the median GeneSetScore (Up autophagy) values for Day 1 cells, Day 9 cells, and input cells are 0.066, 0.11, and −0.09, respectively.

Based on gene expression, the input cells contain four clusters. Cluster 0 is characterized by high expression of LMNA, S100A4, etc. Cluster 1 is characterized by high expression of RP913, PRKCQ-AS1, etc. Cluster 2 is characterized by high expression of PR11-291B21.2, CD8B, etc. Cluster 3 is characterized by high expression of NKG7, GZMH, CCL5, CST7, GNLY, FGFBP2, GZMA, CCL4, CTSW, CD8A, etc. In a T-Distributed Stochastic Neighbor Embedding (TSNE) plot for the input cells, Cluster 3 stood out from the other cells, and Cluster 1 and Cluster 2 were hard to differentiate.

Figure 40C:
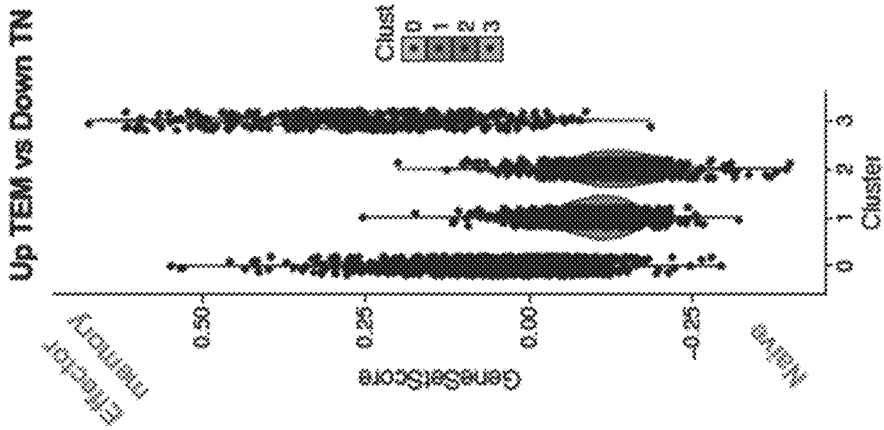
FIGS. 40A, 40B, and 40C. Gene cluster analysis for input cells.
Figure 40B:
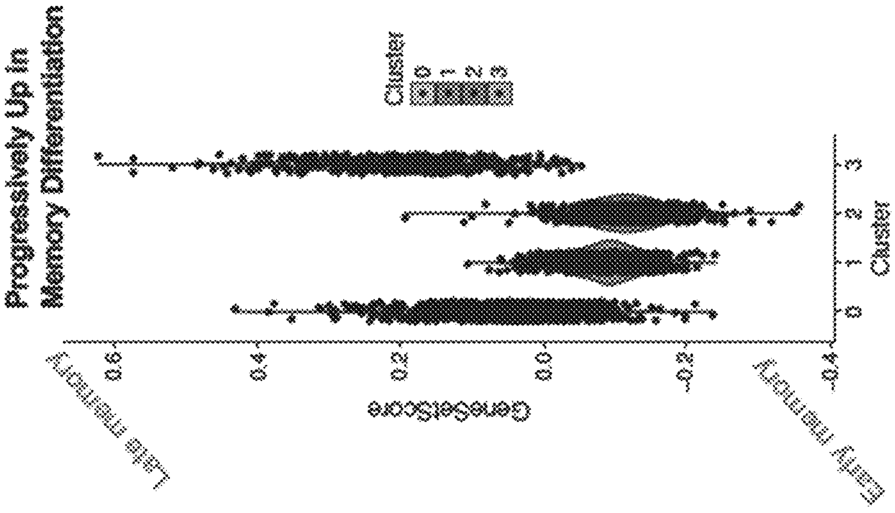
Figure 40A:
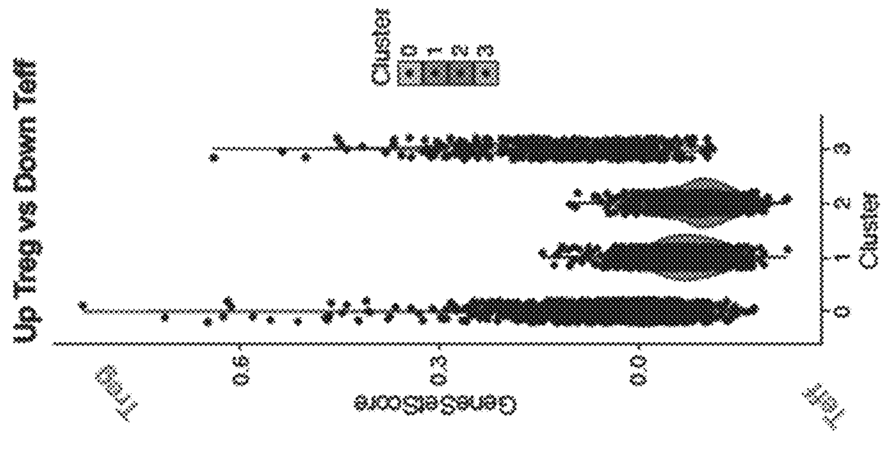

According to the gene set analysis shown in FIGS. 40A-40C, Cluster 0 and Cluster 3 were enriched for a T regulatory phenotype compared to Cluster 1 and Cluster 2 which were enriched for a T effector phenotype. Cluster 3 was dominated by late memory/effector memory (TEM) cells, Cluster 1 and Cluster 2 were early memory and naïve cells, and Cluster 0 is in the middle. The majority of the input cells were in an early memory, naïve state. Without wishing to be bound by theory, these cells may do the best during the manufacturing procedure.

Less transcriptional heterogeneity was seen in Day 1 cells and Day 9 cells (data not shown).

Like the input population, Day 1 cells showed a large cluster of early memory cells and a smaller cluster of late memory cells in a TSNE plot. similar to what was seen with Cluster 3 of the input cells. In contrast, Day 9 cells did not show distinct clusters of early memory cells in a TSNE plot. This implies that by day 9, the cells had become more homogeneous.

Figure 41A:
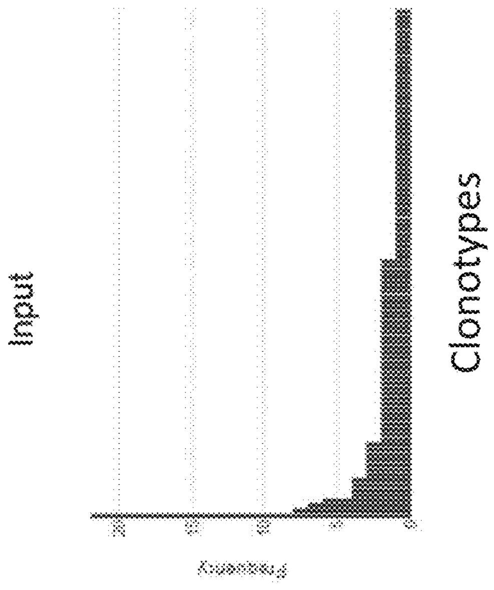
FIGS. 41A, 41B, and 41C. TCR sequencing and measuring clonotype diversity. Day 9 cells have flatter distribution of clonotype frequencies (higher diversity).
Figure 41B:
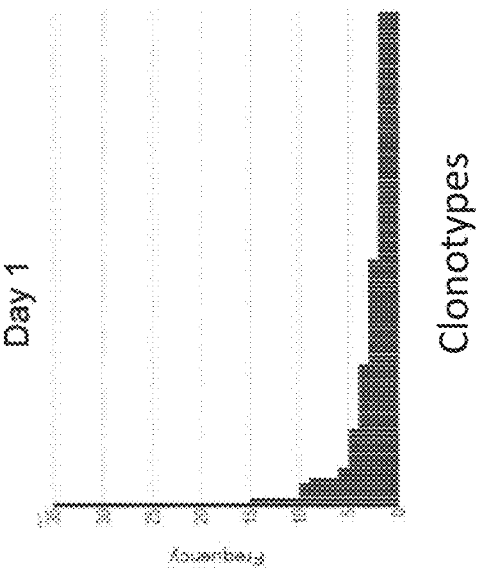
Figure 41C:
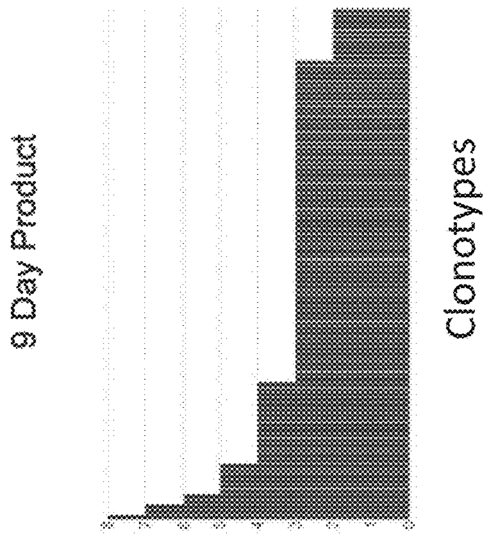

TCRs were sequenced and clonotype diversity was measured. Overall, the three clonotype profiles were very flat—most clones were only picked up once (FIGS. 41A-41C and Table 24). Shannon entropy in Table 24 measures the flatness of the distribution. The dominant clones in the input cells were late memory cells. Day 1 cells looked similar to the input cells but started to even out. By day 9, the dominate clones had substantially evened out and the distribution was much more flat. The diversity measurement was the highest at day 9 because there was a much more even and flat distribution in Day 9 cells than in the input cells or Day 1 cells.

TABLE 24

Measurements of TCR diversity

| | Input | Day 1 product | Day 9 product |
|---|---|---|---|
| Average clones per clonotype | 1.10 | 1.05 | 1.07 |
| Estimated number of cells | 7344 | 7687 | 7233 |
| Total number of clonotypes | 5325 | 7403 | 6736 |
| Diversity | 342.27 | 802.94 | 3382.62 |
| Normalized Shannon entropy | 9.98E−01 | 9.95E−01 | 9.96E−01 |

Summary

There were significant T cell state differences between Day 1 and Day 9 products. Day 1 cells were much more similar to input cells and had enrichment for stemness signatures, indicating a more efficacious product.

Example 11: Phase I, Open Label, Study of B-Cell Maturation Antigen (BCMA)-Directed CAR-T Cells in Adult Patients with Relapsed and/or Refractory Multiple Myeloma (MM)

This study evaluates the safety and tolerability of anti-BCMA CART-T cell therapy in adult MM subjects who are relapsed and/or refractory to at least two prior treatment regimens, including an IMiD (e.g. lenalidomide or pomalidomide), a proteasome inhibitor (e.g. bortezomib, carfilzomib), and an approved anti-CD38 antibody (e.g. daratumumab), if available, and have documented evidence of disease progression (IMWG criteria).

The anti-BCMA CAR comprises a PI61 anti-BCMA scFv, a CD8 hinge and transmembrane region, a 4-1BB costimulatory domain, and a CD3 zeta signaling domain. In this study, the anti-BCMA CAR-T cell products are manufactured using the Activated Rapid Manufacturing (ARM) process. Such cells are referred to as "ARM-BCMA CAR." Specifically, T cells are enriched from a subject's leukapheresis unit using commercially available magnetic beads capturing CD4 and CD8 co-receptors on the T cell surface. Enriched T cells are then stimulated with a colloidal polymeric nanomatrix covalently attached to humanized recombinant agonist antibodies against human CD3 and CD28. Twenty-four hours after seeding, activation and transduction, CAR-T cells are harvested and washed to remove residual non-integrated vector and non-bound activating matrix. After the wash, BCMA CART cell therapy is concentrated and cryopreserved. Results from a release testing procedure are required prior to release of the product for administration.

Compared to the TM process for CAR-T cells, which relies on an ex vivo T-cell expansion period lasting 7-8 days after transduction with lentiviral vector, the ARM process does not include ex vivo T-cell expansion. In contrast, ARM produced T cells are harvested 24 hours after gene transfer, allowing them to expand in vivo in patients. The greater in vivo T cell expansion achieved with the ARM process is predicted to result in a less differentiated T cell phenotype, preserving a greater fraction of memory stem T cells in the final cell product. The presence of less differentiated, memory CAR-T cells has been associated with improved antitumor efficacy in clinical studies (Fraietta J A, et al., (2018) Nat Med, 24(5); 563-71). Without wishing to be bound by theory, BCMA CART cells comprised of a greater fraction of memory T stem cells result in enhanced CAR-T cell expansion in patients, thus overcoming effector T cell exhaustion and resulting in more durable efficacy in MM patients compared with BCMA CARTs produced under traditional manufacturing processes.

The ARM process produces CAR-T cells composed of a significantly greater proportion of naïve-like memory T cells (CCR7+/CD45RO−) in both the overall product and the CAR-positive fraction as compared to CART cells manufactured using the traditional manufacturing TM process. ARM-BCMA CAR has shown tumor eradication in preclinical MM models in a dose responsive fashion. ARM-BCMA CAR is at least five-fold more potent as compared to BCMA CAR-T cells generated with the TM process and led to extended CAR-T expansion in vivo, with higher levels of systemic cytokines. Together, these results support the hypothesis that anti-BCMA CAR-T cell products manufactured with the ARM process contain T cells with a pronounced memory stem cell phenotype, resulting in a BCMA CAR-T cell product with enhanced engraftment, expansion, and anti-MM properties.

In this phase I study, each subject is first evaluated for clinical eligibility during screening. Subjects eligible for inclusion in this study must meet all of the following criteria: (1) ≥18 years of age at the time of ICF signature; (2) ECOG performance status that is either 0 or 1 at screening; (3) subjects with MM who are relapsed and/or refractory to at least 2 prior treatment regimens, including an IMiD (e.g. lenalidomide or pomalidomide), a proteasome inhibitor (e.g. bortezomib, carfilzomib), and an approved anti-CD38 antibody (e.g. daratumumab) (if available) and have documented evidence of disease progression (IMWG criteria); (4) subjects must have measurable disease defined by at least 1 of the following 3 measurements: serum M-protein ≥1.0 g/dL, urine M-protein ≥200 mg/24 hours, or serum free light chain (sFLC) >100 mg/L of involved FLC; (5) All patients must be suitable for serial bone marrow biopsy and/or aspirate collection according to institution's guidelines and be willing to undergo this repeated procedure as described for this study; (6) subjects must meet the following hematological values at screening: absolute neutrophil count (ANC) ≥1,000/$mm^3$ (≥$1\times10^9$/L) without growth factor support within 7 days prior to testing, absolute number of CD3+ T cells >150/$mm^3$ (>$0.15\times10^9$/L) without transfusion support within 7 days prior to testing, platelets ≥50 000/$mm^3$ (≥$50\times10^9$/L), and hemoglobin ≥8.0 g/dl (≥4.9 mmol/L); (7) patient must be deemed suitable by investigator to undergo fludarabine/cyclophosphamide LD regimen; and (8) must have a leukapheresis material of non-mobilized cells accepted for manufacturing. If eligible, a subject has a leukapheresis product collected and submitted for CAR-T manufacture. The subject is enrolled with the acceptance of their leukapheresis product for the start of manufacture.

Figure 42:
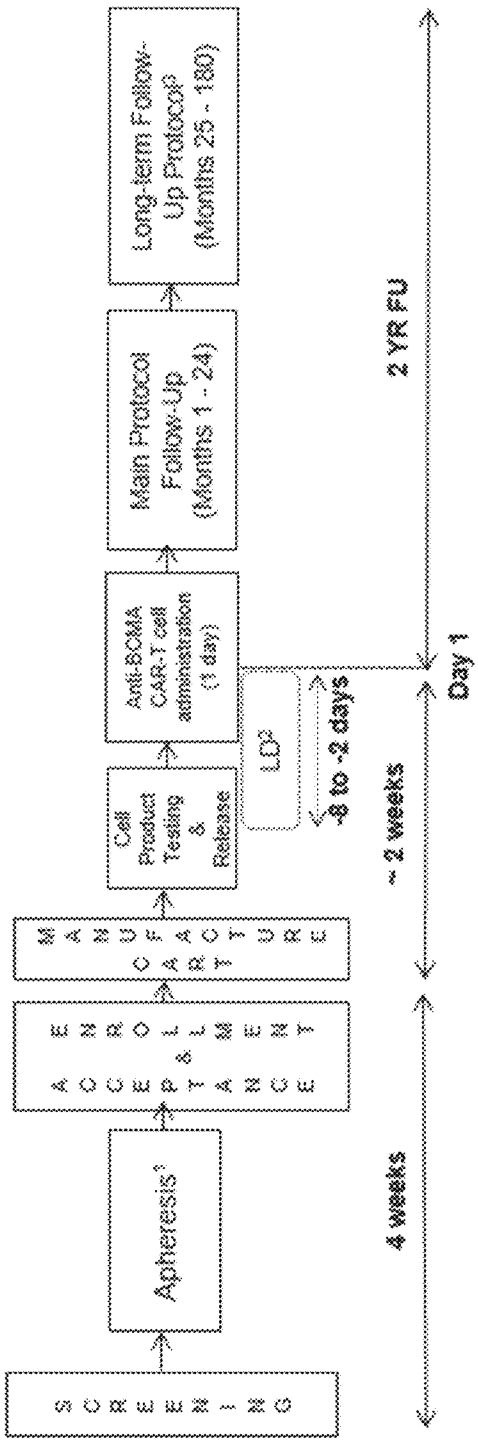
FIG. 42 is a flow chart showing the design of a Phase I clinical trial testing BCMA CART cells manufactured using the ARM process in adult patients with relapsed and/or refractory multiple myeloma.

Subjects receive lymphodepletion (LD) chemotherapy only after the final product has been confirmed to be available. Following LD chemotherapy, a single dose of anti-BCMA CAR-T cell product is administered via an intravenous (i.v.) injection to a subject within 90 minutes from thawing (FIG. 42). The starting dose of ARM-BCMA CAR is $1\times10^7$ viable CAR-positive T cells. The dose of $5\times10^7$ viable CAR-positive T cells is also tested. Each subject is hospitalized for the first 72 hours following anti-BCMA CAR-T cell administration.

For pharmacokinetic analysis, serial blood samples are collected at different time points to measure ARM-BCMA CAR cellular kinetics in peripheral blood by flow cytometry and qPCR, in bone marrow by flow cytometry and qPCR, to measure cellular and humoral immunogenicity, and to measure potential pharmacodynamic markers including sBCMA, BAFF, and APRIL, in peripheral blood by ELISA. In particular, subjects are analyzed for the amount of CAR transgene in peripheral blood, bone marrow, or other relevant tissues; the surface expression of CAR-positive T cells in the peripheral blood or bone marrow; the anti-mCAR antibodies in the serum; the percentage of IFN-γ positive CD4/CD8 T cells in PBMC; markers of immune cell activation; soluble immune factors and cytokines (e.g., sBCMA, IFN-γ, IL-2, IL-4, IL-6, IL-8, IL-10, IL-15, TNF-α), CAR-T clonality; and the levels of soluble BCMA, APRIL, and BAFF in the serum.

Example 12: Manufacturing BCMA CART Cells Using the Activated Rapid Manufacturing (ARM) Process The ARM process of BCMA CART cells initiates with the preparation of the media as outlined in Table 25.

Cryopreserved leukapheresis product is used as the starting material and is processed for T cell enrichment. When available, the apheresis paper work is utilized to define the T cell percentage. In the absence of the T cell percentage data on the apheresis paperwork, the sentinel vial testing is performed on incoming cryopreserved leukapheresis products to obtain T cell percentage target for the apheresis. The results for the T cell percentage determine how many bags are thawed on Day 0 of the ARM process.

TABLE 25

Media and Buffer type and point of use during BCMA CART manufacturing

| Media Type | Source | Point of Use |
|---|---|---|
| CliniMACS ® Buffer/ human serum albumin (HSA) (0.5% in working concentration) | Prepared by operator on day 0 | Day 0 Processing on Cell Wash/Separator |
| Rapid Media | Prepared by operator on day 0 | Day 0 for Cell Seeding |

TABLE 25-continued

| Media and Buffer type and point of use during BCMA CART manufacturing | | |
|---|---|---|
| Media Type | Source | Point of Use |
| PBS/ HSA (1% or 2% in working concentration) | Prepared by operator on day 0 | Harvest and culture Wash Media (Day 1) |
| Cryostor10 (CS10) | Commercially available | Harvest Formulation |

Cryopreserved leukapheresis is thawed, washed, and then undergoes T cell selection and enrichment using CliniMACS® microbead technology. Viable nucleated cells (VNCs) are activated with TransACT (Miltenyi) and transduced with a lentiviral vector encoding the CAR. The viable cells selected with the Miltenyi microbeads are seeded into the centricult on the Prodigy®, which is a non-humidified incubation chamber. While in culture, the cells are suspended in Rapid media, which is an OpTmizer™ CTS™ based medium that contains the CTS™ Supplement (ThermoFisher), Glutamax, IL-2 and 2% Immune cell serum replacement amongst its components to promote T cell activation and transduction. Lentiviral transduction is performed once on the day of seeding after the TransACT has been added to the diluted cells in the culture media. Lentiviral vector will be thawed immediately prior to use on day of seeding for up to 30 minutes at room temperature.

From the start of the process on Day 0 to the initiation of the culture wash and harvest, BCMA CART cells are cultured for 20-28 hours from seeding. Following culture, the cell suspension undergoes two culture washes and one harvest wash within the centricult chamber (Miltenyi Biotech).

After the harvest wash on the CliniMACS® Prodigy® on day 1, the cell suspension is sampled to determine viable cell count and viability. Cell suspension is then transferred to a centrifuge to be pelleted manually. The supernatant is removed, and the cell pellet is resuspended in CS10 (BioLife Solution), resulting in a product formulation with a final DMSO concentration of ~10.0%. The viable cell count is formulated at the end of harvest for dosing. The doses are then distributed into individual cryobags and analytical sampling into cryovials.

Cryopreserved products are stored in monitored LN2 storage tanks, in a secure, limited access area until final release and shipping.

Example 13: Characterization of BCMA CART Cells Manufactured Using the Activated Rapid Manufacturing (ARM) Process Summary This example describes characterization of BCMA CART cells manufactured using the ARM process. The ARM process produces CAR-T cells composed of a significantly greater proportion of naïve-like memory T cells (CCR7+/CD45RO−) as compared to the traditional manufacturing (TM) product. In a preclinical model of multiple myeloma (MM), BCMA CART cells manufactured using the ARM process induced tumor regression in a dose-dependent manner and was up to 5-fold more efficacious in killing tumors compared to BCMA CART cells manufactured using the TM process. In addition, ARM-manufactured cells showed extended CART expansion in vivo (up to 3 folds higher Cmax and AUC0-21d) and induced higher systemic cytokines (IFN-γ by 3.5 folds) compared to TM-manufactured cells. Together, these results support the hypothesis that BCMA CART cells manufactured with the ARM process contain T cells with a pronounced memory stem cell phenotype and an enhanced in vivo expansion potential.

Using the ARM process, CAR could be stably expressed at 96 h after viral addition (also referred to as 72 h at post-thaw of the product). Therefore, 96 h post-viral addition or 72 h post-thaw is considered to be a surrogate time point for CAR expression for in vitro and in vivo activity. BCMA CART cells manufactured using the ARM process preserve a less differentiated cell population, and show higher target specific cytokine production in vitro, when compared to BCMA CART cells manufactured under the TM process.

BCMA CART cells manufactured using the ARM process demonstrated high specificity to BCMA using a commercial human plasma membrane protein array. The assay detected binding to BCMA (TNFRSF17) but no other strong, medium, or weak binders. The screen did not identify with any high confidence the presence of cross-reacting proteins of the anti-human BCMA single chain antibody variable fragment (scFv) (PI61) expressed in the BCMA CART product. Target distribution studies were performed to determine potential off-tumor on-target toxicity. Immunohistochemistry (IHC), in situ hybridization (ISH), and polymerase chain reaction (PCR) assays were utilized to examine the distribution of BCMA in normal human tissues. These analyses demonstrated that BCMA expression was limited to sites containing normal plasma cells (PCs), such as secondary lymphoid organs, bone marrow and mucosal associated lymphoid tissues. Because central nervous system (CNS) neurotoxicity has been a concern with other cell-based therapies, expression in brain was examined. No staining in the CNS was observed by immunohistochemistry using a commercially available antibody shown to be specific for BCMA nor by binding assays using a human-rabbit chimeric tool antibody containing a BCMA targeting scFv. These findings were confirmed by the absence of BCMA mRNA in these tissues as measured by in situ hybridization and PCR based splice variant analysis. BCMA CART targeting of normal PCs and BCMA-expressing plasmacytoid dendritic cells is likely to result in their depletion; however, targeting of other cell types is not anticipated.

Results

The studies described below compared BCMA CART cells manufactured using the ARM process (referred to as "ARM-BCMA CAR") with BCMA CART cells manufactured using the TM process (referred to as "TM-BCMA CAR" or "TM-BCMA CAR*"). The CAR expressed in ARM-BCMA CAR and the CAR expressed in TM-BCMA CAR*have the same sequence, comprising a PI61 scFv, a CD8 hinge and transmembrane region, a 4-1BB costimulatory domain, and a CD3 zeta signaling domain. The CAR expressed in TM-BCMA CAR comprises a BCMA10 scFv, a CD8 hinge and transmembrane region, a 4-1BB costimulatory domain, and a CD3 zeta signaling domain.

ARM-BCMA CAR Expression Kinetics In Vitro

In contrast to TM which measures lentiviral integration of the CAR transgene after 8-9 days, in the ARM process, the lentiviral transgene may not be fully integrated and truly expressed within 24 h post lentiviral addition, as lentiviral pseudotransduction could occur (Haas D L, et al., (2000) Mol Ther; 2(1):71-80; Galla M, et al., (2004) Mol Cell; 16(2):309-15). Therefore, the BCMA-CAR expression pattern was evaluated over time by extended culturing of ARM-BCMA CAR in vitro in the presence or absence of 3'-azido-3'-deoxythymidine (AZT) to evaluate the potential pseudotransduction versus stable integration and expression of the CAR transgene. Flow cytometry (FACS) analyses were performed to detect CAR surface expression at 24 h, 48 h, 72 h, 96 h and 168 h post T cell activation and transduction with the lentiviral vector. In some cases, ARM-BCMA CAR and an aliquot of this product were frozen down immediately upon harvest for additional characterization in other assays.

Figure 43:
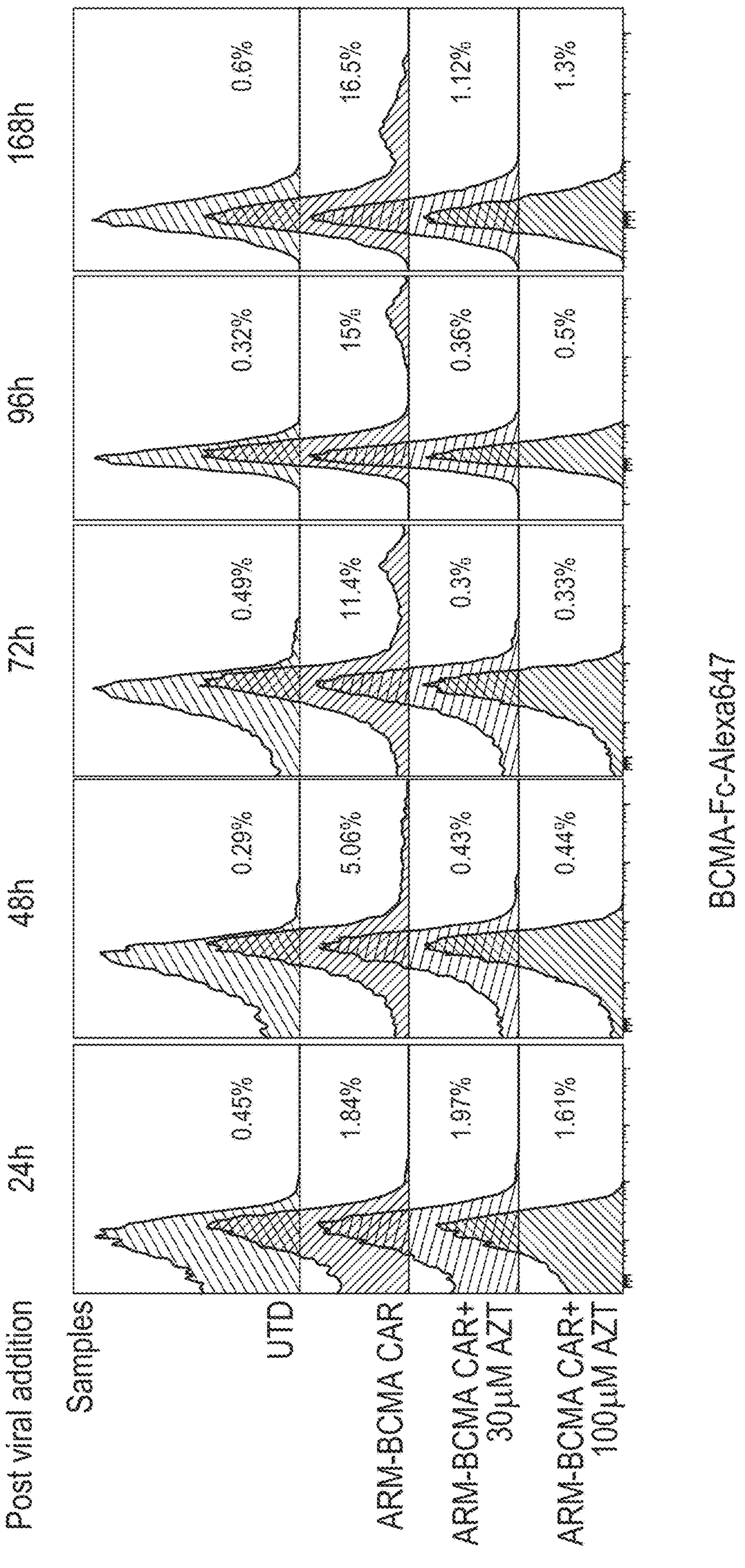
FIG. 43 is a graph showing FACS analyses for ARM-BCMA CAR expression at different collection time points post viral addition in the presence or absence of AZT at two different concentrations (30 μM and 100 μM). Lentiviral vector was added 1 h later prior to AZT treatment at the time of activation and cell seeding.

As shown in FIG. 43, FACS analyses indicate that the BCMA-CAR revealed practically no expression at 24 h after the addition of the lentiviral vector. However, the CAR+ population initially emerged at 48 h. The CAR+ population slightly increased at each time point from 48 h to 168 h after viral addition. CAR seemed to be stably expressed starting from 96 h. This contrasts with the untransduced (UTD) and AZT treated samples, which showed no CAR+ population at any time point from 48 h (FIG. 43). AZT was able to effectively inhibit CAR expression at both the 30 μM and 100 μM doses, suggesting that BCMA-CAR expression is due to viral gene integration into the host cell genome and unlikely a consequence of lentiviral pseudo-transduction.

ARM-BCMA CAR Preserves T Cell Sternness

Figure 44A:
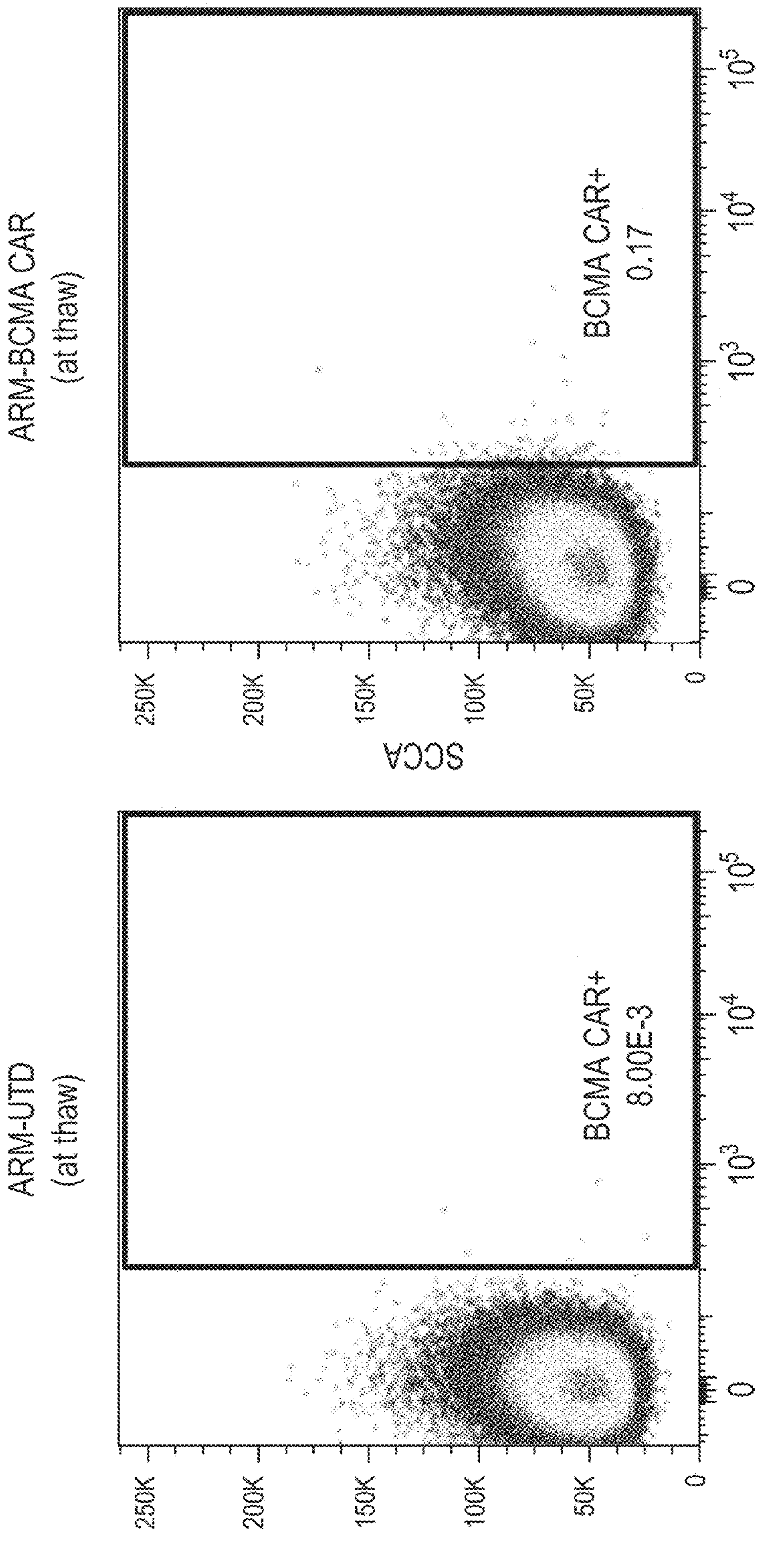
FIGS. 44A and 44B are graphs showing assessment of ARM-BCMA CAR for CAR expression at thaw (FIG. 44A) and 48 h post-thaw and CCR7/CD45RO markers at 48 h post-thaw product as well as day 9 for TM-BCMA CAR (FIG. 44B). Data shown is one representative from two experiments performed using T cells from two donors.
Figure 44B:
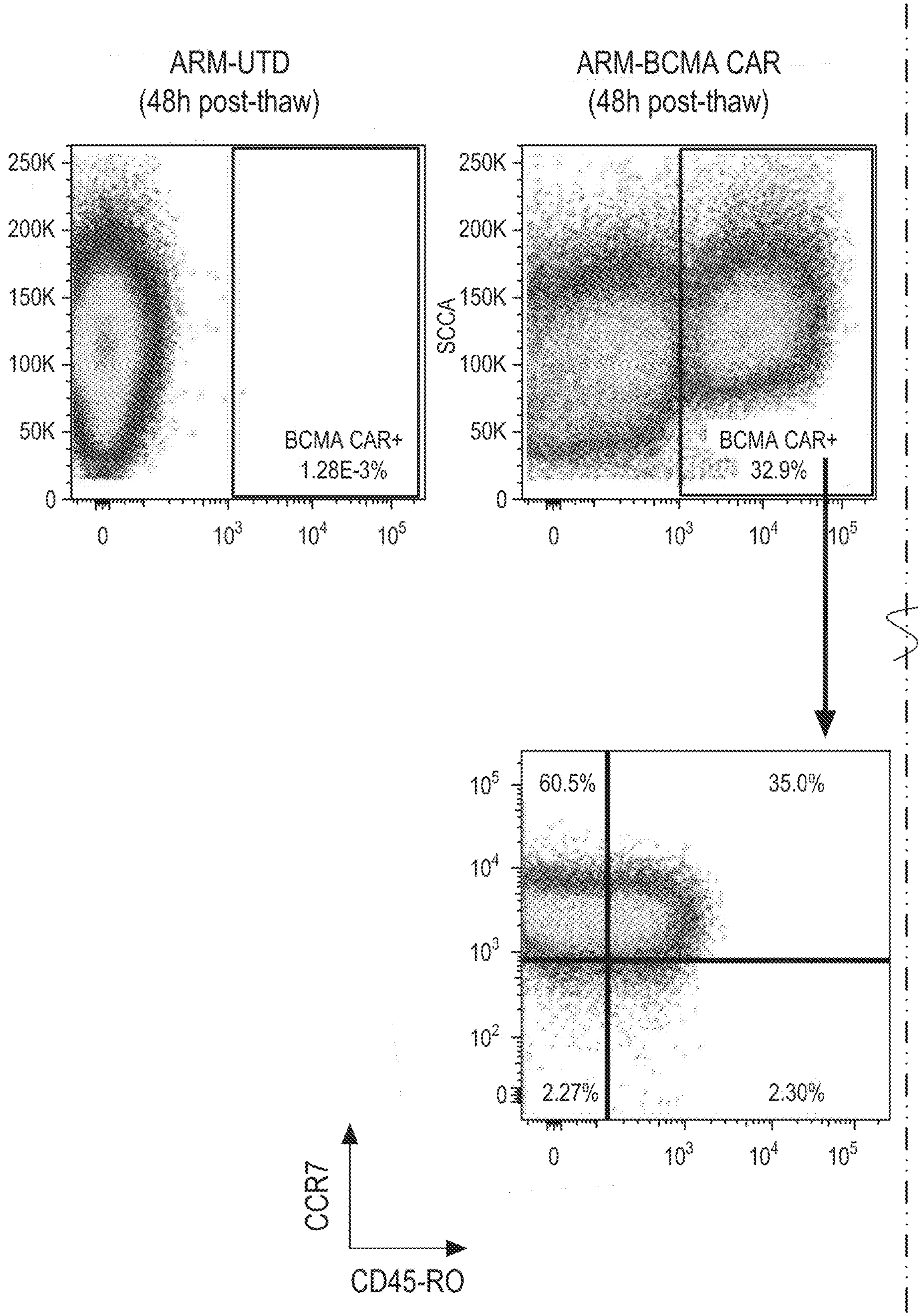
Figure 44B:
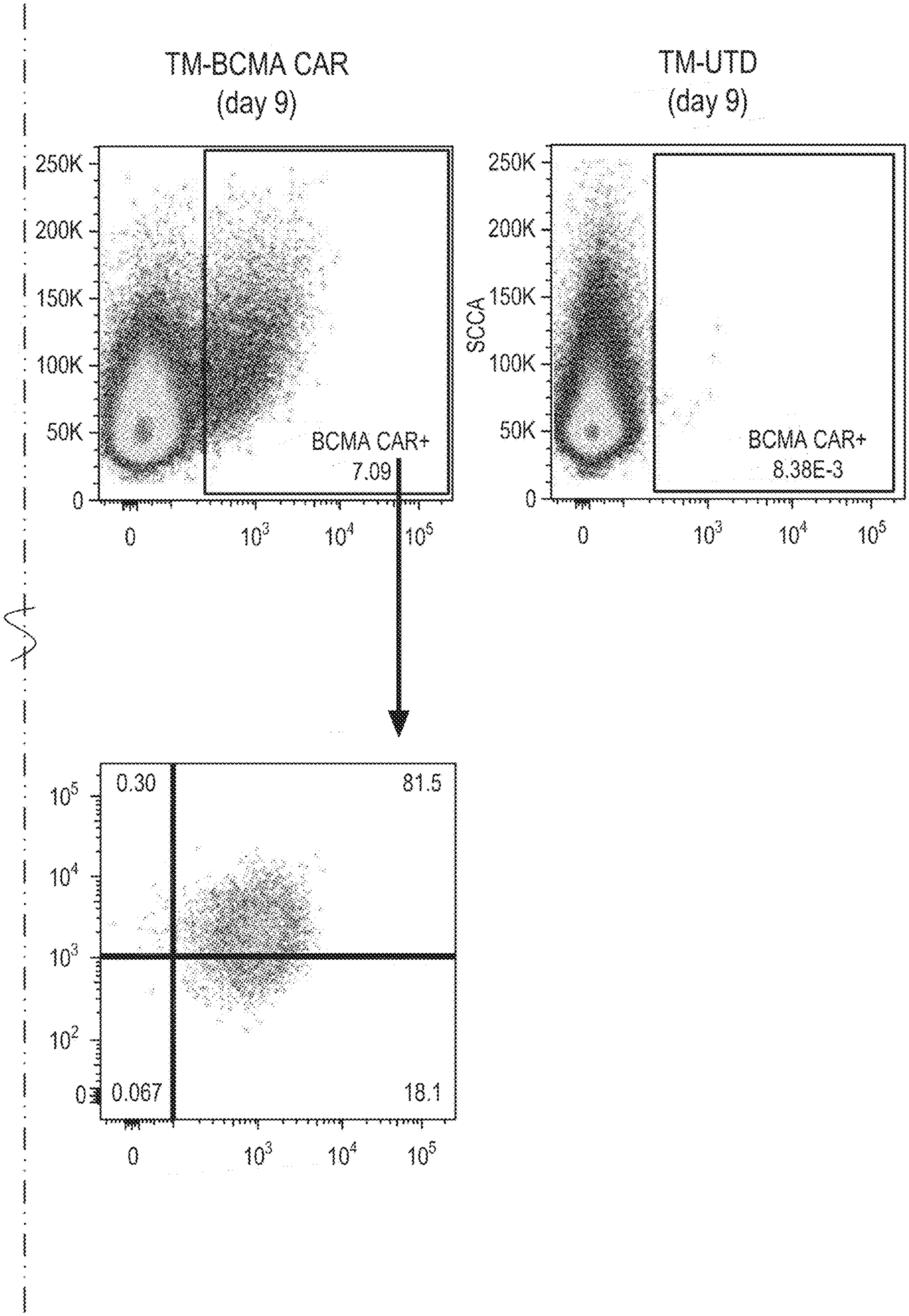

ARM-BCMA CAR and TM-BCMA CAR were analyzed by FACS to evaluate CAR expression at thaw, as well as the T-cell phenotype at 48 h post thaw (FIGS. 44A and 44B). BCMA-CAR was almost undetectable at thaw seen in two donors (FIG. 44A), which is consistent with the observation in the CAR expression kinetics study shown in FIG. 43. However, at 48 h post-thaw, BCMA-CAR expression was 32.9% for ARM-BCMA CAR. In contrast, TM-BCMA CAR revealed BCMA-CAR expression of 7% (FIG. 44B). Analysis of the CAR+ T-cell phenotype revealed that the ARM process retained naïve-like T cells (60% CD45RO−/CCR7+), which proved to be 26 folds more than the effector memory T cell population (CD45RO+/CCR7−). The TM process mainly resulted in central-memory T cells (81% CD45RO+/CCR7+) within CAR+ T cells. The naive-like T cell population was nearly absent with the TM process. This naive T-cell population largely overlaps with CD45RO−/CD27+ Tstem cells (described by Cohen A D, et al., (2019) J Clin Invest; 129(6):2210-21; and Fraietta, et al (2018) Nat Med, 24(5); 563-571) and is associated with enhanced CAR-T expansion and clinical responses.

Figure 45A:
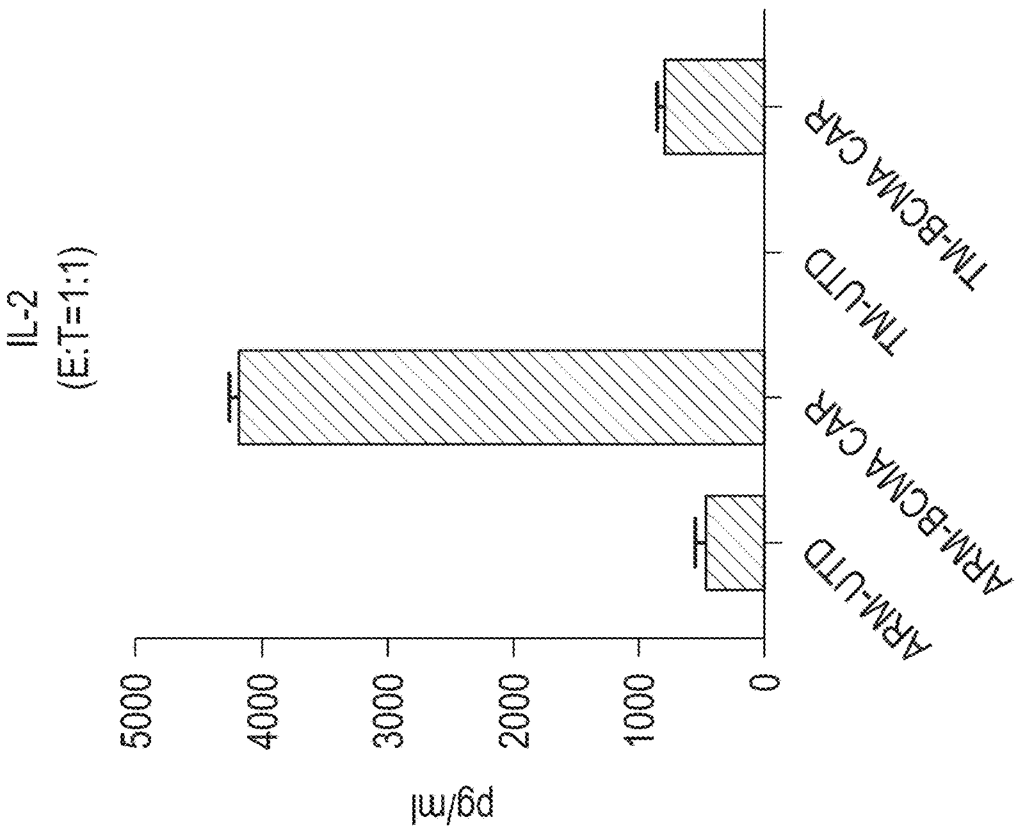
FIGS. 45A and 45B are graphs showing cytokine concentrations in cell culture supernatants. ARM-BCMA CAR and TM-BCMA CAR, and respective UTD were co-cultured with KMS-11. Supernatant was collected 24 h later. Data shown is one representative from two experiments performed using T cells from two donors.
Figure 45B:
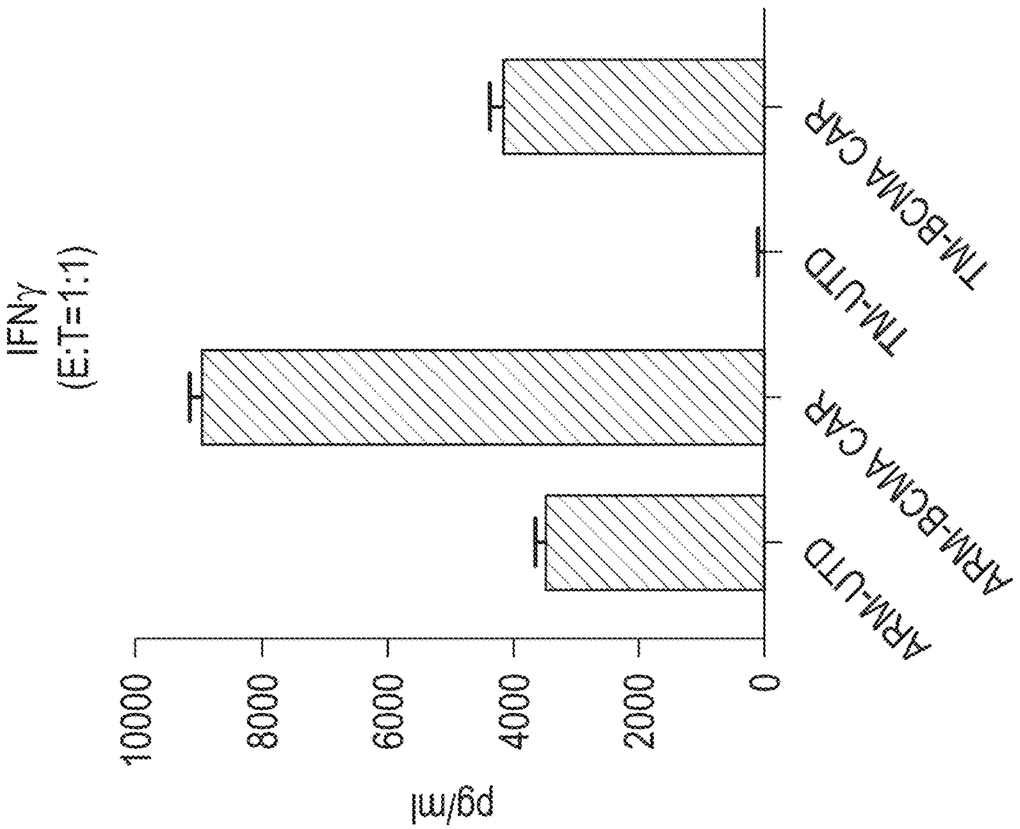

In addition to its phenotype, the final ARM-BCMA CAR cell product was also assessed for its activation in vitro. ARM-BCMA CAR and TM-BCMA CAR were thawed and co-cultured with the BCMA-expressing cell line KMS-11. Post-thaw ARM-BCMA CAR cells were rested for 24 h prior to co-culture being established. Comparing cytokine levels in the supernatants 24 hours after co-culture revealed a 5-fold increase of IL-2 and a 2-fold increase in levels of IFN-γ secreted by ARM-BCMA CAR as compared to TM-BCMA CAR as shown in FIGS. 45A and 45B. Experiments with UTD cells that underwent the ARM or TM process confirmed BCMA-specific recognition by ARM-BCMA CAR and TM-BCMA CAR. However, the higher background of IFN-γ secretion by ARM-UTD in the absence of BCMA-specific stimulation (FIG. 45B) is likely due to the activated nature of the ARM products.

In summary, the ARM process used to generate BCMA CART cells results in T cells with CAR-expression higher than that of the TM process. ARM-BCMA CAR demonstrates BCMA-specific activation in vitro and secretes higher levels of IL-2 as compared to TM-BCMA CAR, which correlates with its Tstem phenotype.

Efficacy of ARM-BCMA CAR and TM-BCMA CAR in a Xenograft Model

Figure 46:
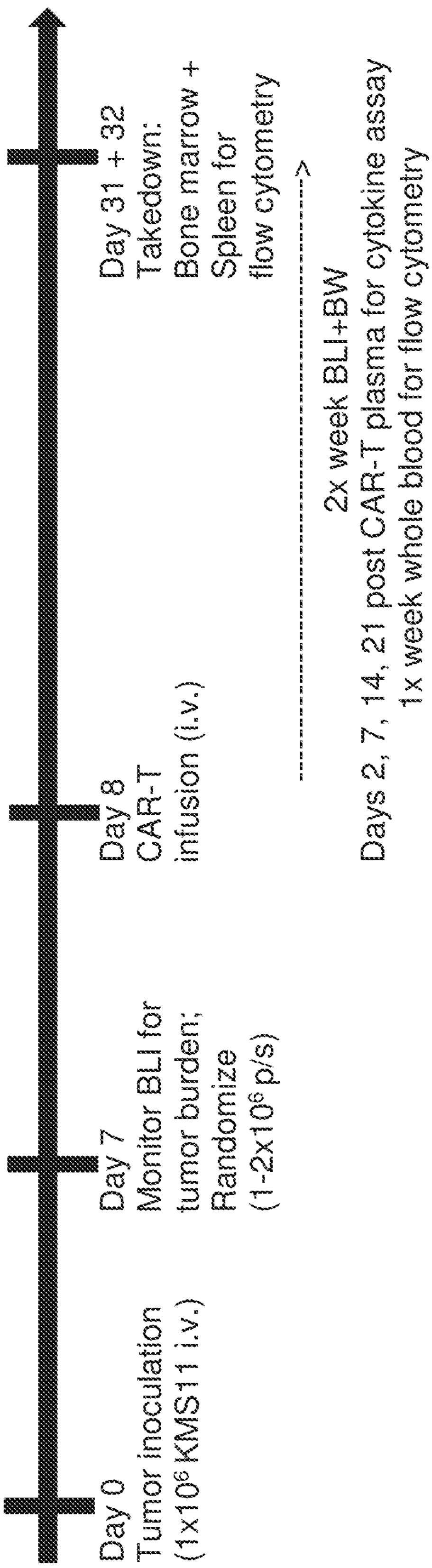
FIG. 46 is a graph showing outline of xenograft efficacy study to test ARM-BCMA.

Pharmacology studies in vivo were used to guide the development of ARM-BCMA CAR. For the experiment described in FIG. 46, ARM-BCMA CAR was generated with GMP material. In parallel, TM-BCMA CAR was made using the same batch of T cells but with TM. For dose calculation using ARM-BCMA CAR, the measurement of % CAR+ at 72 h post-thaw of product was used to calculate the dose; while for TM-BCMA CAR, % CAR+ on day 9 TM products was used to calculate the dose. The efficacy of CAR-T cells generated using the different processes was evaluated in immunodeficient NSG mice (NOD-scid IL2Rg-null), which were inoculated with the MM cell line KMS-11-Luc. This tumor cell line engrafts in the bone marrow. Eight days after MM inoculation, cohorts of mice received a single infusion of CAR+ T cells. Doses were normalized to total CAR-T cells for the matched dose group. UTD T cells were prepared similarly and given as an independent group to control for allogeneic response to the tumor. The UTD dose reflected the highest total T cell dose of the respective process we could achieve for both TM and ARM.

TABLE 26

Summary of the study design for different dose groups, and time points for blood pharmacokinetic (PK) and plasma cytokine measurement.

| Cell process | Group/arm | CAR+ product/mouse | Blood cellular kinetics and plasma cytokine post CAR-T injection |
|---|---|---|---|
| | PBS | | Cytokines: Day 2, 7, 14, and 21 |
| ARM | UTD | | |
| | ARM-BCMA CAR | $1.5e^5$ | PK: Day 7, 14, and 21 |
| | ARM-BCMA CAR | $5e^4$ | |
| | ARM-BCMA CAR | $1e^4$ | |
| TM | UTD | | |
| | TM-BCMA CAR | $5e^5$ | |
| | TM-BCMA CAR | $1.5e^5$ | |
| | TM-BCMA CAR | $5e^4$ | |

Figure 47:
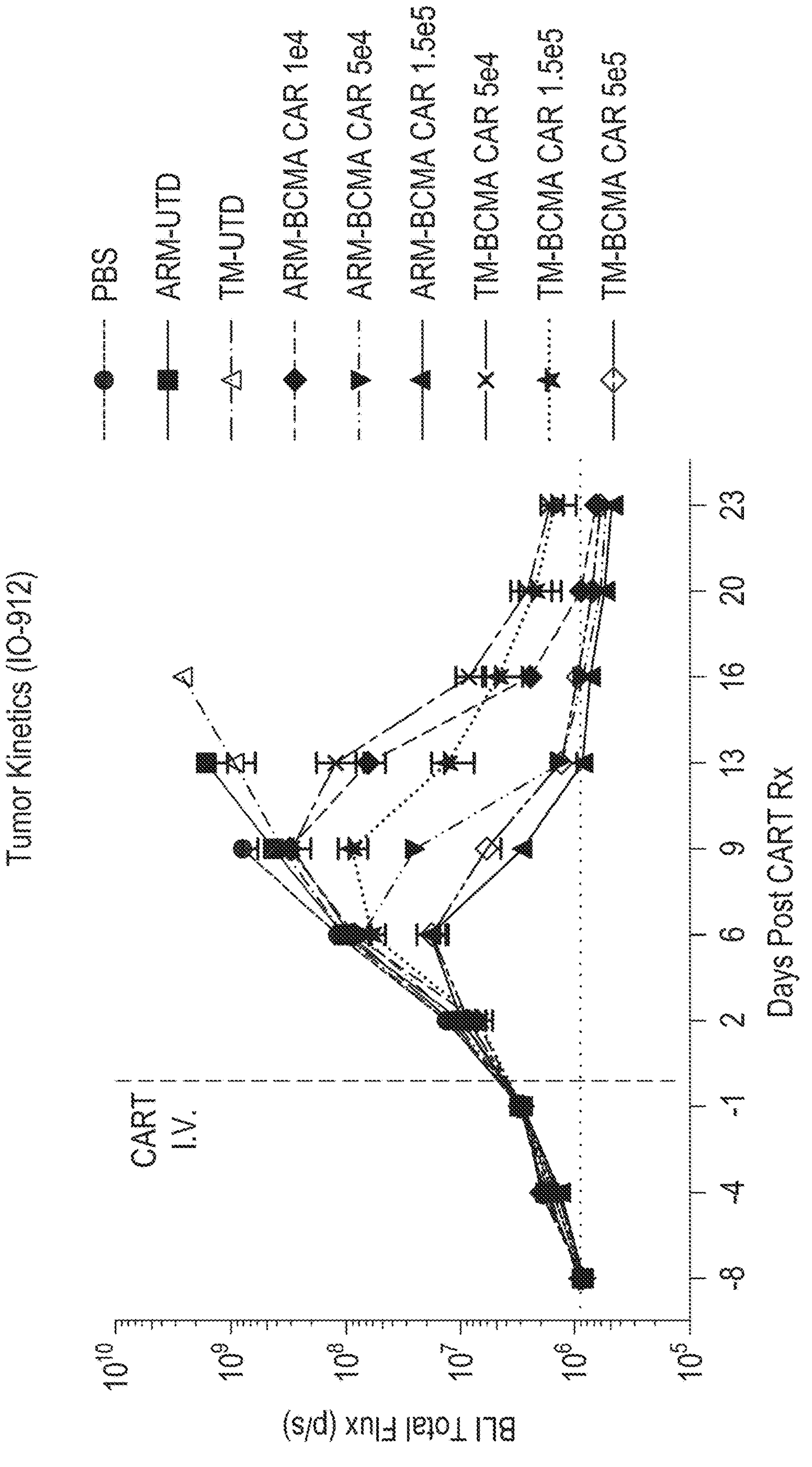
FIG. 47 is a graph comparing the efficacy of ARM-BCMA CAR with that of TM-BCMA CAR in a xenograft model. NSG mice were injected with MM cell line KMS11, expressing the luciferase reporter gene. The tumor burden is expressed as total body luminescence (p/s), depicted as mean tumor burden +SEM. On day 8 post tumor inoculation, mice were treated with ARM-BCMA CAR or TM-BCMA CAR at the respective doses (number of viable CAR+ T cells). Vehicle (PBS) and UTD T cells served as negative controls. N=5 mice for all groups, except N=4 for ARM-BCMA CAR (1e4 cells), PBS, and UTD groups.

FIG. 47 is the tumor regression curve for all the groups. Both BCMA CAR-T products (ARM-BCMA CAR and TM-BCMA CAR) were able to eliminate tumor at the tested dose levels, even at the lowest dose group. Tumor-regression was induced in a dose-dependent manner. The on-set of effect in tumor-killing was delayed for about a week at the low dose group compared to the high dose group. ARM-BCMA CAR induced similar tumor regression at doses 3-5 folds lower than TM-BCMA CAR, indicating that ARM-BCMA CAR is 3-5 folds more potent compared to TM-BCMA CAR in tumor-killing.

Moreover, in this study, the efficacy of TM-BCMA CAR*was also evaluated. TM-BCMA CAR*and ARM-BCMA CAR expressed the same anti-BCMA CAR, but were manufactured using different processes: the TM process and the ARM process, respectively. The results demonstrated that ARM-BCMA CAR induced similar tumor regression at doses 1-5 folds lower than TM-BCMA CAR*.

Figure 48A:
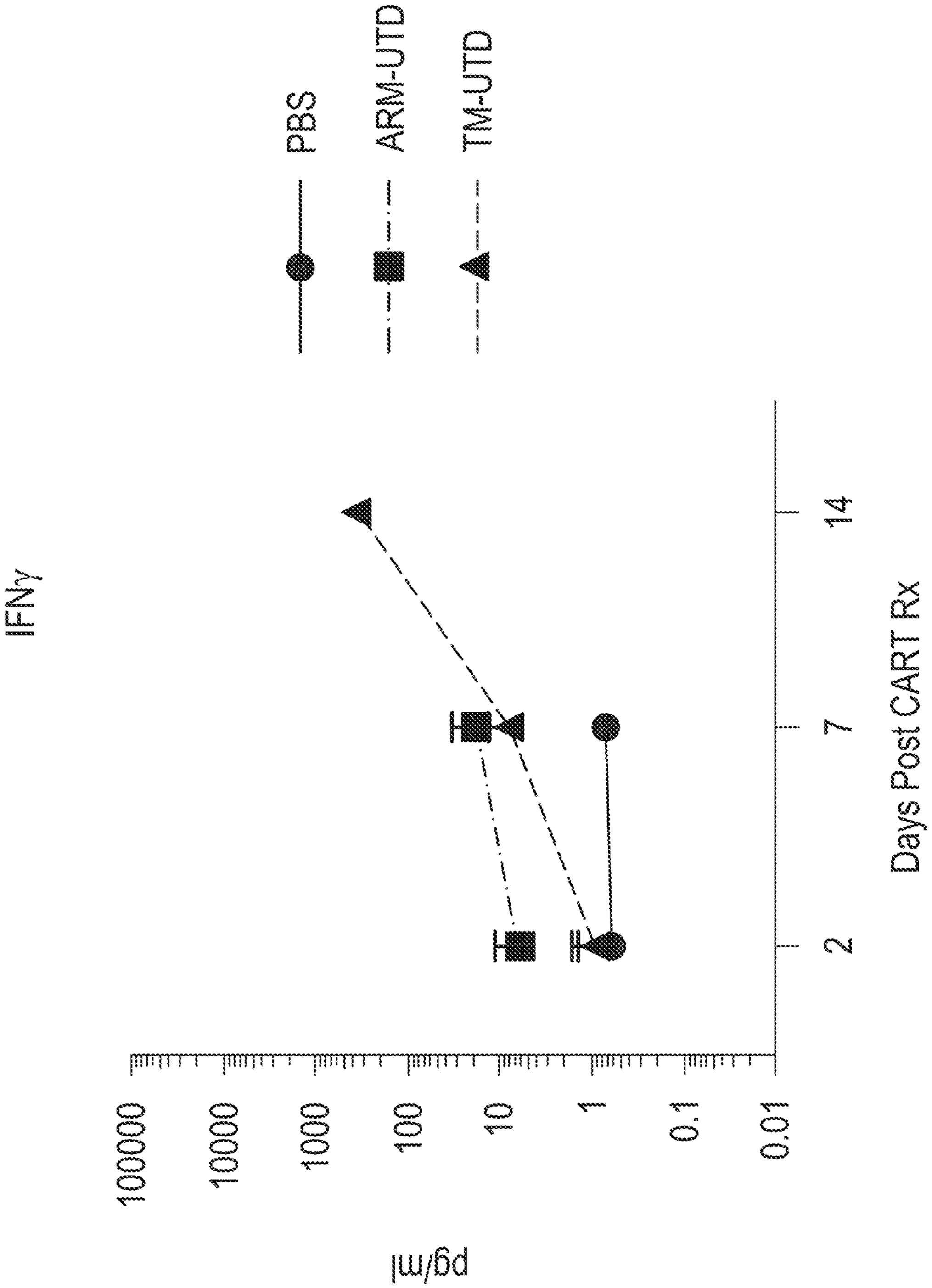
FIGS. 48A, 48B, and 48C are graphs showing plasma IFN-γ kinetics of mice treated with ARM-BCMA CAR or TM-BCMA CAR. Plasma IFN-γ levels of KMS11-luc tumor-bearing mice treated with UTD, ARM-BCMA CAR, or TM-BCMA CAR at respective CAR-T doses. All IFN-γ levels were depicted as mean±SEM. Mice were bled and plasma cytokine measured by Meso Scale Discovery (MSD) assay.
Figure 48B:
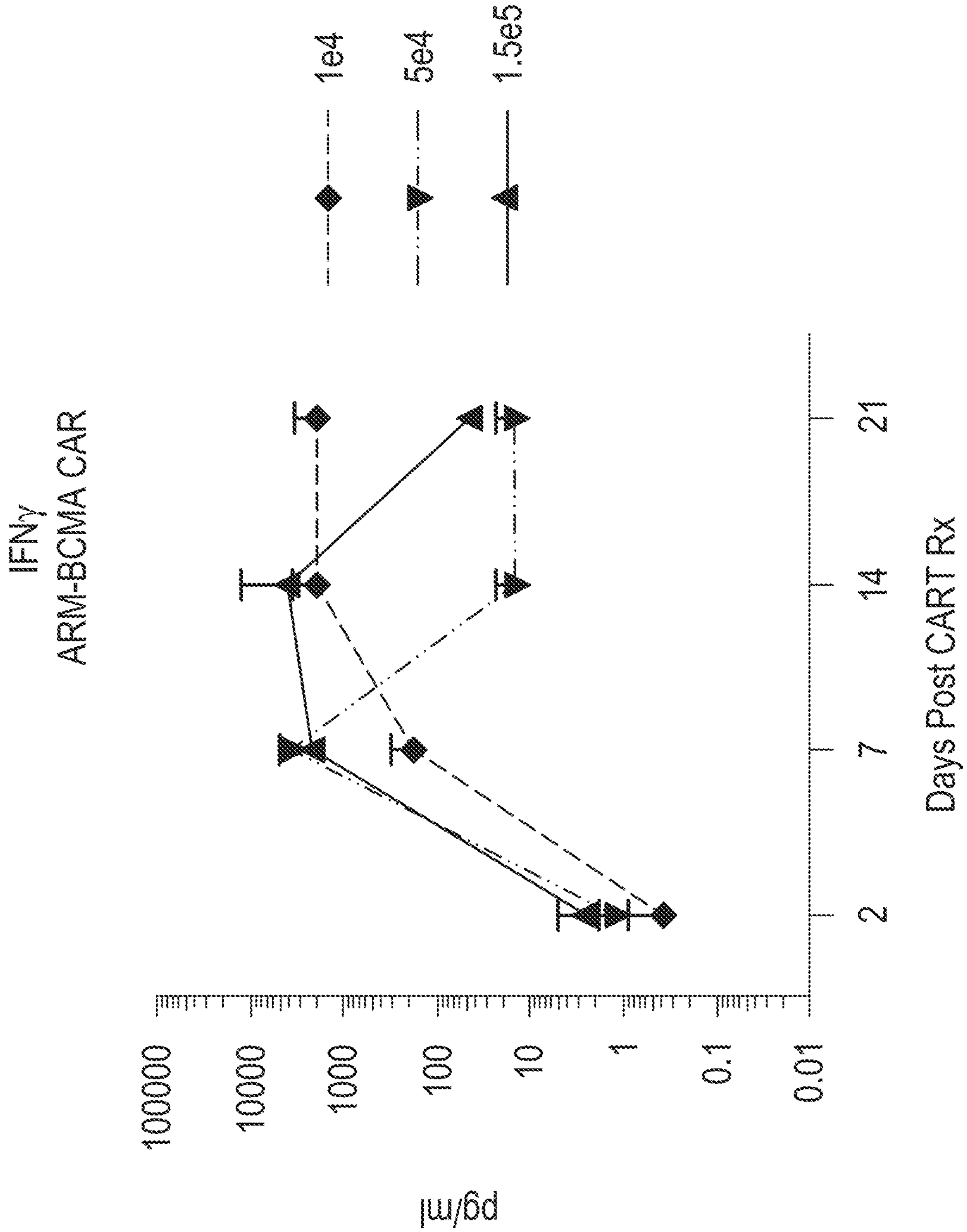
Figure 48C:
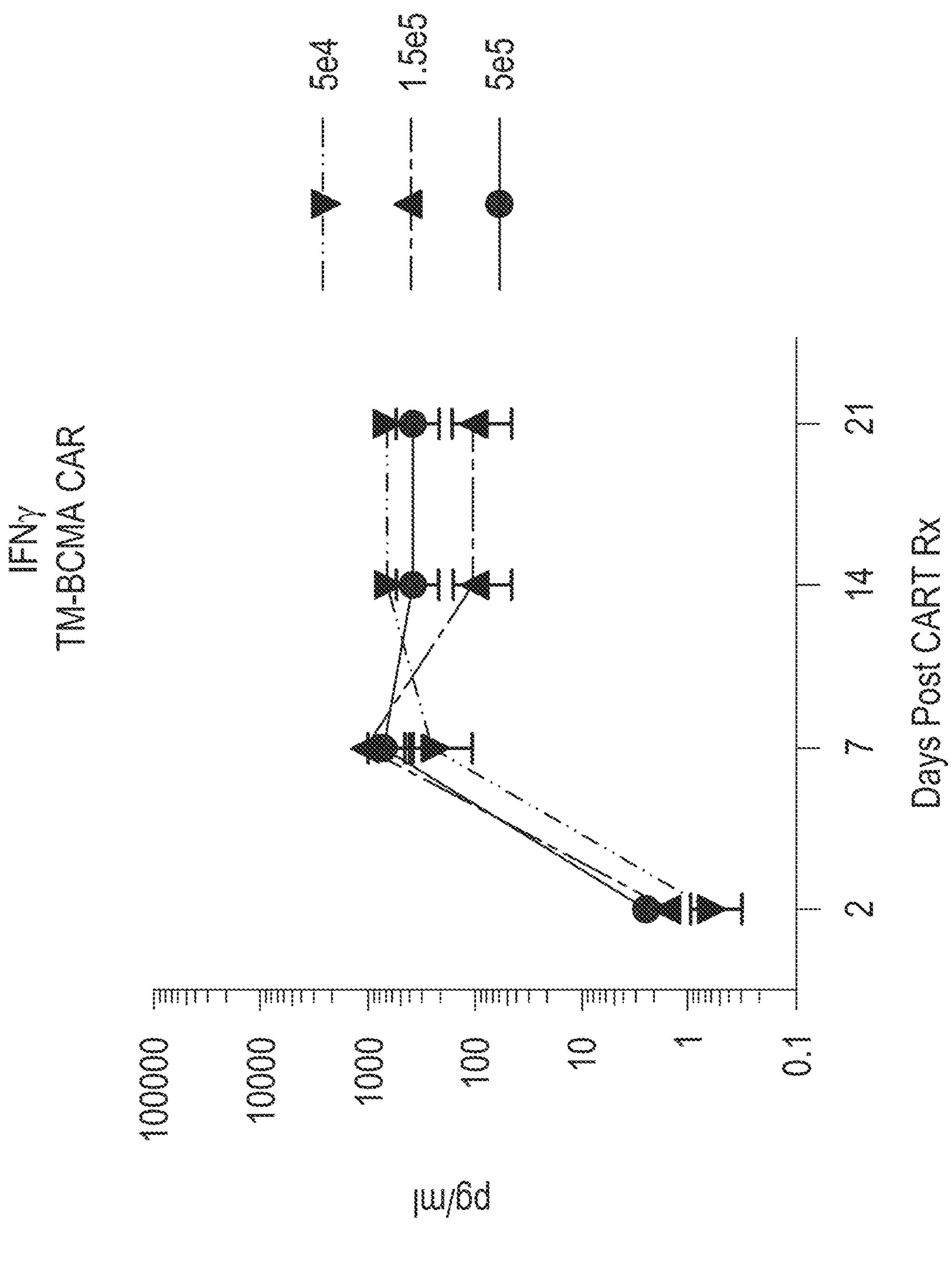

All mice were bled at day 2, 7, 14, and 21 post CAR-T therapy to measure plasma IFN-γ (FIGS. 48A-48C). No early peak was observed and all groups showed very low level of circulating IFN-γ (<10 pg/ml) at day 2. Peaks for all the groups were observed within 14 days post CAR-T dose. However, IFN-γ levels were 3.5-fold higher for ARM-BCMA CAR compared to TM-BCMA CAR. ARM-UTD groups produce little or no IFN-γ at day 2 and day 7 prior to study termination. IFN-γ declined in the higher dose groups at day 21, when compared to the ARM-BCMA CAR 1e4 and TM-BCMA CAR 5e4 groups as the CAR+ T cells were still expanding with delayed tumor inhibition in these two groups.

In Vivo ARM-BCMA CAR Cellular Kinetics

Figure 49:
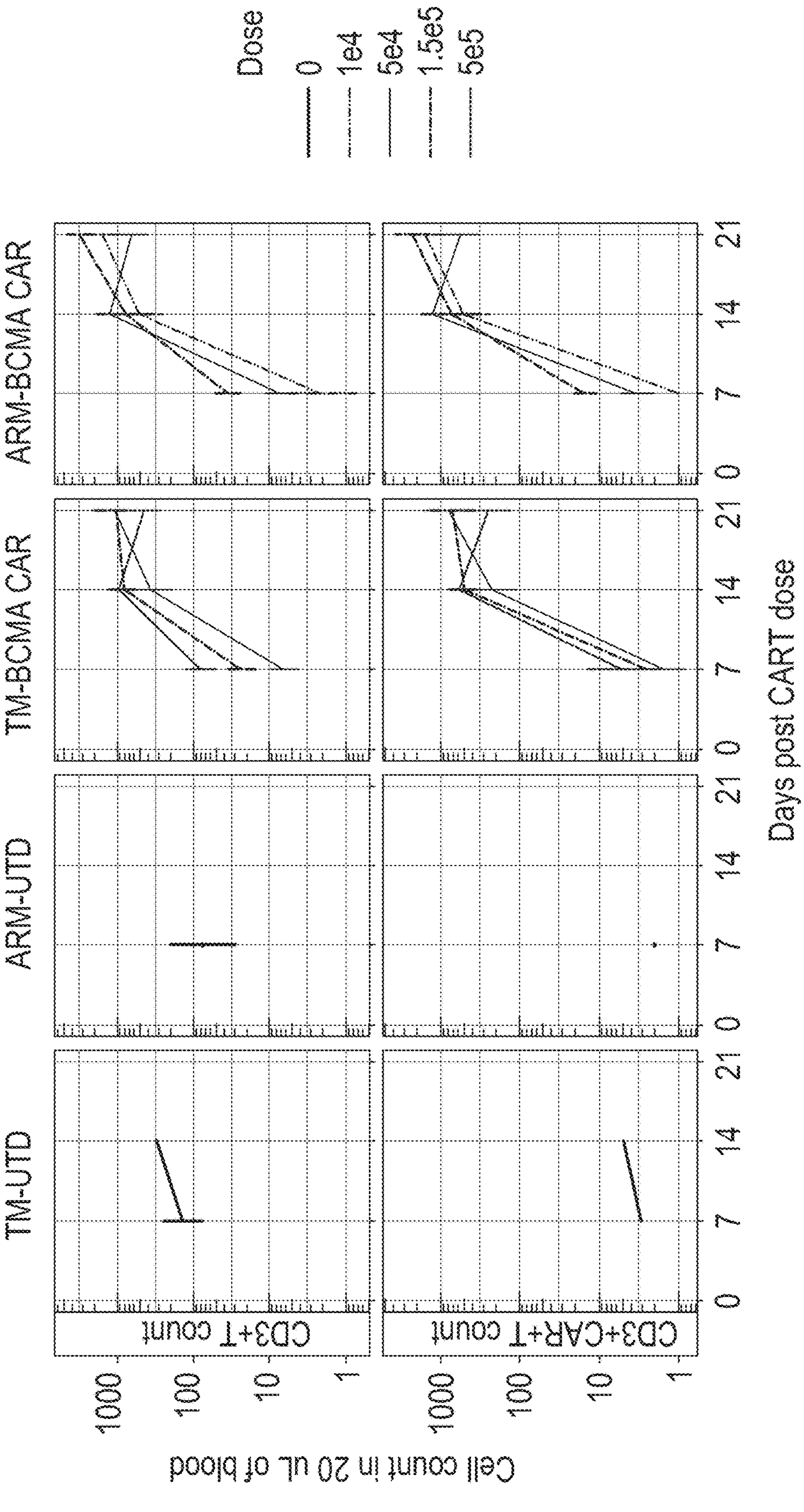
FIG. 49 is a graph showing cellular kinetics of ARM-BCMA CAR and TM-BCMA CAR in vivo. Cellular kinetics in peripheral blood of KMS11 tumor-bearing mice treated with TM UTD, ARM UTD, ARM-BCMA CAR, and TM-BCMA CAR at different doses. Cell count is expressed as mean cell count +SD. On day 8 post tumor inoculation, mice were treated with ARM-BCMA CAR or TM-BCMA CAR at the respective doses (number of viable CAR+ T cells). Vehicle (PBS) and UTD T cells served as negative controls. Blood samples were taken at 7, 14, and 21 days post CAR-T injection and were analyzed by flow cytometry at designed time points. N=5 mice for all groups, except N=4 for ARM-BCMA CAR (1e4 cells), PBS, and UTD groups

As part of this pharmacology study to assess efficacy in NSG mice, the expansion of peripheral blood CAR-T cells was analyzed by FACS up to 3 weeks after infusion. Both CD3+ T cell and CAR+ T cell expansion were observed in all CAR-T treated groups. There was no clear dose-dependent expansion for ARM-BCMA CAR or TM-BCMA CAR with respect to Cmax or AUC0-21d. The peak of cellular expansion for ARM-BCMA CAR or MTV273 was not achieved within 21 days. However, TM-BCMA CAR at dose group of 5e5 and ARM-BCMA CAR at dose group of 0.5e5 achieved apparent peak expansion at day 14 (FIG. 49). Comparing the expansion of ARM-BCMA CAR with that of TM-BCMA CAR in 21 days, both Cmax and AUC0-21d of ARM-BCMA CAR were 2 to 3 times higher.

Example 14: Manufacturing BCMA CART Cells Using the Activated Rapid Manufacturing (ARM) Process Using IL-15 or hetIL-15 (IL-15/sIL-15Ra)

The ARM process of BCMA CART cells initiates with the preparation of the media as outlined in Table 25.

Cryopreserved leukapheresis product is used as the starting material and is processed for T cell enrichment. When available, the apheresis paper work is utilized to define the T cell percentage. In the absence of the T cell percentage data on the apheresis paperwork, the sentinel vial testing is performed on incoming cryopreserved leukapheresis products to obtain T cell percentage target for the apheresis. The results for the T cell percentage determine how many bags are thawed on Day 0 of the ARM process.

Cryopreserved leukapheresis is thawed, washed, and then undergoes T cell selection and enrichment using CliniMACS® microbead technology. Viable nucleated cells (VNCs) are activated with TransACT (Miltenyi) and transduced with a lentiviral vector encoding the CAR. The viable cells selected with the Miltenyi microbeads are seeded into the centricult on the Prodigy®, which is a non-humidified incubation chamber. While in culture, the cells are suspended in Rapid media, which is an OpTmizer™ CTS™ based medium that contains the CTS™ Supplement (ThermoFisher), Glutamax, IL-15 or hetIL-15 (IL-15/sIL-15Ra), and 2% Immune cell serum replacement amongst its components to promote T cell activation and transduction. Lentiviral transduction is performed once on the day of seeding after the TransACT has been added to the diluted cells in the culture media. Lentiviral vector will be thawed immediately prior to use on day of seeding for up to 30 minutes at room temperature.

From the start of the process on Day 0 to the initiation of the culture wash and harvest, BCMA CART cells are cultured for 20-28 hours from seeding. Following culture, the cell suspension undergoes two culture washes and one harvest wash within the centricult chamber (Miltenyi Biotech).

After the harvest wash on the CliniMACS® Prodigy® on day 1, the cell suspension is sampled to determine viable cell count and viability. Cell suspension is then transferred to a centrifuge to be pelleted manually. The supernatant is removed, and the cell pellet is resuspended in CS10 (BioLife Solution), resulting in a product formulation with a final DMSO concentration of ~10.0%. The viable cell count is formulated at the end of harvest for dosing. The doses are then distributed into individual cryobags and analytical sampling into cryovials.

Cryopreserved products are stored in monitored LN2 storage tanks, in a secure, limited access area until final release and shipping.

In some embodiments, IL-15 or hetIL-15 used in the OpTmizer™ CTS™ based medium can be replaced with IL-6 or IL-6/sIL-6Ra.

Example 15: Manufacturing CD19 CART Cells Using the Activated Rapid Manufacturing (ARM) Process The ARM process of CD19 CART cells initiates with the preparation of the media as outlined in Table 25.

Cryopreserved leukapheresis product is used as the starting material and is processed for T cell enrichment. When available, the apheresis paper work is utilized to define the T cell percentage. In the absence of the T cell percentage data on the apheresis paperwork, the sentinel vial testing is performed on incoming cryopreserved leukapheresis products to obtain T cell percentage target for the apheresis. The results for the T cell percentage determine how many bags are thawed on Day 0 of the ARM process.

Cryopreserved leukapheresis is thawed, washed, and then undergoes T cell selection and enrichment using CliniMACS® microbead technology. Viable nucleated cells (VNCs) are activated with TransACT (Miltenyi) and transduced with a lentiviral vector encoding the CAR. The viable cells selected with the Miltenyi microbeads are seeded into the centricult on the Prodigy®, which is a non-humidified incubation chamber. While in culture, the cells are suspended in Rapid media, which is an OpTmizer™ CTS™ based medium that contains the CTS™ Supplement (ThermoFisher), Glutamax, IL-2 and 2% Immune cell serum replacement amongst its components to promote T cell activation and transduction. Lentiviral transduction is performed once on the day of seeding after the TransACT has been added to the diluted cells in the culture media. Lentiviral vector will be thawed immediately prior to use on day of seeding for up to 30 minutes at room temperature.

From the start of the process on Day 0 to the initiation of the culture wash and harvest, CD19 CART cells are cultured for 20-28 hours from seeding. Following culture, the cell suspension undergoes two culture washes and one harvest wash within the centricult chamber (Miltenyi Biotech).

After the harvest wash on the CliniMACS® Prodigy® on day 1, the cell suspension is sampled to determine viable cell count and viability. Cell suspension is then transferred to a centrifuge to be pelleted manually. The supernatant is removed, and the cell pellet is resuspended in CS10 (BioLife Solution), resulting in a product formulation with a final DMSO concentration of ~10.0%. The viable cell count is formulated at the end of harvest for dosing. The doses are then distributed into individual cryobags and analytical sampling into cryovials.

Cryopreserved products are stored in monitored LN2 storage tanks, in a secure, limited access area until final release and shipping.

In some embodiments, IL-2 used in the OpTmizer™ CTS™ based medium can be replaced with IL-15, hetIL-15 (IL-15/sIL-15Ra), IL-6, or IL-6/sIL-6Ra.

EQUIVALENTS

The disclosures of each and every patent, patent application, and publication cited herein are hereby incorporated herein by reference in their entirety. While this invention has been disclosed with reference to certain embodiments, it is apparent that further embodiments and variations of this invention may be devised by others skilled in the art without departing from the true spirit and scope of the invention. The appended claims are intended to be construed to include all such embodiments and equivalent variations.

What is claimed is:

1. A method of making a population of cells that express a chimeric antigen receptor (CAR), the method comprising:
   (i) contacting a population of cells with an agent that stimulates a CD3/TCR complex and/or an agent that stimulates a costimulatory molecule on the surface of the cells;
   (ii) contacting the population of cells with a nucleic acid molecule encoding the CAR, thereby providing a population of cells comprising the nucleic acid molecule; and
   (iii) harvesting the population of cells for storage or administration;
   wherein step (ii) is performed together with step (i) or less than 18 hours after the beginning of step (i), and step (iii) is performed no later than 48 hours after the beginning of step (i).

2. The method of claim 1, wherein:
   (a) the nucleic acid molecule in step (ii) is on a viral vector;
   (b) the population of cells comprises a population of T cells;
   (c) the storage of step (iii) comprises reformulating the population of cells in cryopreservation media;
   (d) the population of T-cells is isolated from a frozen or fresh leukapheresis product; and/or
   (e) the population of cells contacted in step (i) comprises CD4+ and/or CD8+ T cells selected from an apheresis sample.

3. The method of claim 1, wherein:
   (a) the agent that stimulates a CD3/TCR complex is an agent that stimulates CD3;
   (b) the agent that stimulates a CD3/TCR complex or the agent that stimulates a costimulatory molecule is chosen from an antibody, a small molecule, or a ligand;
   (c) the agent that stimulates a CD3/TCR complex or the agent that stimulates a costimulatory molecule does not comprise a bead;
   (d) the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof;
   (e) the agent that stimulates a CD3/TCR complex is an anti-CD3 antibody;
   (f) the agent that stimulates a CD3/TCR complex comprises an anti-CD3 antibody and the agent that stimulates a costimulatory molecule comprises an anti-CD28 antibody covalently attached to a colloidal polymeric nanomatrix and the agent that stimulates a costimulatory molecule comprises an anti-CD28 antibody covalently attached to a colloidal polymeric nanomatrix; and/or
   (g) the agent that stimulates a CD3/TCR complex and the agent that stimulates a costimulatory molecule comprise T Cell TransAct™.

4. The method of claim 3, wherein:
(a) the antibody is a single-domain antibody, a heavy chain variable domain antibody, a peptibody, a Fab fragment, or a scFv; and/or
(b) the ligand is a naturally-existing, recombinant, or chimeric ligand.

5. The method of claim 1, wherein the agent that stimulates a CD3/TCR complex comprises an anti-CD3 antibody and the agent that stimulates a costimulatory molecule comprises an anti-CD28 antibody.

6. The method of claim 1, wherein:
(a) the percentage of naïve cells in the population of cells from step (iii) is the same as or differs by no more than 5 or 10% from the percentage of naïve cells in the population of cells at the beginning of step (i);
(b) the percentage of naïve cells in the population of cells from step (iii) does not decrease, or decreases by no more than 5 or 10%, as compared to the percentage of naïve cells in the population of cells at the beginning of step (i);
(c) the percentage of central memory cells in the population of cells from step (iii) is the same as or differs by no more than 5 or 10% from the percentage of central memory cells in the population of cells at the beginning of step (i); and/or
(d) the percentage of central memory cells in the population of cells from step (iii) does not increase, or increases by no more than 5 or 10%, as compared to the percentage of central memory cells in the population of cells at the beginning of step (i).

7. The method of claim 6, wherein:
(a) the naïve cells are naïve T cells or CD45RA+ CD45RO− CCR7+ T cells; and/or
(b) the central memory cells are central memory T cells, CD95+ central memory T cells, or CCR7+CD45RO+ cells.

8. The method of claim 1, wherein:
(a) the percentage of naïve cells in the population of cells from step (iii) is higher than the percentage of naïve cells in cells made by an otherwise similar method in which step (iii) is performed more than 5 days after the beginning of step (i);
(b) the percentage of CAR-expressing naïve T cells in the population of cells from step (iii) is higher than the percentage of CAR-expressing naïve T cells in cells made by an otherwise similar method in which step (iii) is performed more than 5 days after the beginning of step (i);
(c) the percentage of naïve cells in the population of cells from step (iii) is higher than the percentage of naïve cells in cells made by an otherwise similar method which further comprises, after step (ii) and prior to step (iii), expanding the population of cells in vitro for more than 3 days;
(d) the percentage of CAR-expressing naïve T cells in the population of cells from step (iii) is higher than the percentage of CAR-expressing naïve T cells in cells made by an otherwise similar method which further comprises, after step (ii) and prior to step (iii), expanding the population of cells in vitro for more than 3 days;
(e) the percentage of naïve cells in the population of cells from step (iii) is increased, as compared to the percentage of naïve cells, in the population of cells at the beginning of step (i); or
(f) the percentage of CAR-expressing naïve T cells in the population of cells increases during the duration of step (ii) or between 18-24 hours after the beginning of step (ii).

9. The method of claim 1, wherein:
(a) the percentage of central memory cells in the population of cells from step (iii) is lower than the percentage of central memory cells in cells made by an otherwise similar method in which step (iii) is performed more than 5 days after the beginning of step (i);
(b) the percentage of CAR-expressing central memory T cells in the population of cells from step (iii) is lower than the percentage of CAR-expressing central memory T cells, in cells made by an otherwise similar method in which step (iii) is performed more than 5 days after the beginning of step (i);
(c) the percentage of central memory cells in the population of cells from step (iii) is lower than the percentage of central memory cells in cells made by an otherwise similar method which further comprises, after step (ii) and prior to step (iii), expanding the population of cells in vitro for more than 3 days;
(d) the percentage of CAR-expressing central memory T cells in the population of cells from step (iii) is lower than the percentage of CAR-expressing central memory T cells in cells made by an otherwise similar method which further comprises, after step (ii) and prior to step (iii), expanding the population of cells in vitro for more than 3 days;
(e) the percentage of central memory cells in the population of cells from step (iii) is reduced by at least 20%, as compared to the percentage of central memory cells in the population of cells at the beginning of step (i); or
(f) the percentage of CAR-expressing central memory T cells decreases during the duration of step (ii) or between 18-24 hours after the beginning of step (ii).

10. The method of claim 1, wherein:
(a) the percentage of stem memory T cells in the population of cells from step (iii) is increased, as compared to the percentage of stem memory T cells in the population of cells at the beginning of step (i);
(b) the percentage of CAR-expressing stem memory T cells in the population of cells from step (iii) is increased, as compared to the percentage of CAR-expressing stem memory T cells in the population of cells at the beginning of step (i);
(c) the percentage of stem memory T cells, in the population of cells from step (iii) is higher than the percentage of stem memory T cells in cells made by an otherwise similar method in which step (iii) is performed more than 5 days after the beginning of step (i);
(d) the percentage of CAR-expressing stem memory T cells in the population of cells from step (iii) is higher than the percentage of CAR-expressing stem memory T cells in cells made by an otherwise similar method in which step (iii) is performed more than 5 days after the beginning of step (i);
(e) the percentage of stem memory T cells in the population of cells from step (iii) is higher than the percentage of stem memory T cells in cells made by an otherwise similar method which further comprises, after step (ii) and prior to step (iii), expanding the population of cells in vitro for more than 3 days; or
(f) the percentage of CAR-expressing stem memory T cells in the population of cells from step (iii) is higher than the percentage of CAR-expressing stem memory T cells in cells made by an otherwise similar method which further comprises, after step (ii) and prior to step (iii), expanding the population of cells in vitro for more than 3 days.

11. The method of claim 1, wherein:

(a) step (i) increases the percentage of CAR-expressing cells in the population of cells from step (iii), compared with cells made by an otherwise similar method without step (i);

(b) the population of cells from step (iii), after being incubated with a cell expressing an antigen recognized by the CAR, secretes IL-2 at a higher level than cells made by an otherwise similar method in which step (iii) is performed more than 5 days after the beginning of step (i), or cells made by an otherwise similar method which further comprises, after step (ii) and prior to step (iii), expanding the population of cells in vitro for more than 3 days;

(b) the population of cells from step (iii), after being administered in vivo, persists longer or expands at a higher level, compared with cells made by an otherwise similar method in which step (iii) is performed more than 5 days after the beginning of step (i), or compared with cells made by an otherwise similar method which further comprises, after step (ii) and prior to step (iii), expanding the population of cells in vitro for more than 3 days; and/or (c) the population of cells from step (iii), after being administered in vivo, shows a stronger anti-tumor activity than cells made by an otherwise similar method in which step (iii) is performed more than 5 days after the beginning of step (i), or cells made by an otherwise similar method which further comprises, after step (ii) and prior to step (iii), expanding the population of cells in vitro for more than 3 days.

12. The method of claim 1, wherein:

(a) the population of cells from step (iii) are expanded by no more than 5, 10, 15, 20, 25, 30, 35, or 40%, compared to the population of cells at the beginning of step (i);

(b) the population of cells from step (iii) are expanded by no more than 10%, compared to the population of cells at the beginning of step (i);

(c) the population of cells from step (iii) are not expanded, or expanded by no more than 5, 10, 15, 20, 25, 30, 35, or 40%, as assessed by the number of living cells, compared to the population of cells at the beginning of step (i);

(d) the number of living cells in the population of cells from step (iii) decreases from the number of living cells in the population of cells at the beginning of step (i);

(e) step (ii) is performed no later than 12, 13, 14, 15, 16, or 17 hours after the beginning of step (i), and/or step (iii) is performed no later than 22, 23, 24, 25, 26, 27, 28, 29, or 30 hours after the beginning of step (i);

(f) step (ii) is performed less than 18 hours after the beginning of step (i), and step (iii) is performed no later than 24 hours after the beginning of step (i);

(g) the population of cells from step (iii) are not expanded;

(h) the population of cells from step (iii) are not expanded, as assessed by the number of living cells, compared to the population of cells at the beginning of step (i); and/or (i) step (ii) is performed after the beginning of step (i).

13. The method of claim 1, wherein:

(a) steps (i) and/or (ii) are performed in cell media comprising IL-2, IL-15, IL-7, IL-21, IL-6, hetIL-15 (IL15/sIL15Ra), IL-6/IL-6Ra, a LSD1 inhibitor, a MALT1 inhibitor, or a combination thereof;

(b) steps (i) and/or (ii) are performed in serum-free media comprising IL-2, IL-15, IL-7, IL-21, IL-6, hetIL-15 (IL15/sIL15Ra), IL-6/IL-6Ra, a LSD1 inhibitor, a MALT1 inhibitor, or a combination thereof;

(c) steps (i) and/or (ii) are performed in serum-free cell media comprising a serum replacement; and/or (d) steps (i) and/or (ii) are performed in serum-free cell media comprising CTS™ Immune Cell Serum Replacement (ICSR).

14. The method of claim 1, further comprising prior to step (i):

(I) (iv) receiving a fresh leukapheresis product or an alternative source of hematopoietic tissue, from an entity; and (v) isolating the population of cells contacted in step (i) from a fresh leukapheresis product or an alternative source of hematopoietic tissue;

(II) receiving cryopreserved T cells isolated from a leukapheresis product or an alternative source of hematopoietic tissue, from an entity;

(III) (iv) receiving a cryopreserved leukapheresis product or an alternative source of hematopoietic tissue, from an entity; and (v) isolating the population of cells contacted in step (i) from a cryopreserved leukapheresis product or an alternative source of hematopoietic tissue;

(IV) providing an apheresis sample from a subject;

shipping the apheresis sample to a cell manufacturing facility either as a frozen sample and then thawing it or as a not frozen sample;

selecting T cells from the apheresis sample; and seeding the selected population of cells for CAR T cell manufacture; or (V) providing an apheresis sample from a subject;

selecting T cells, from the apheresis sample;

shipping the selected population of cells to a cell manufacturing facility as a frozen sample; and thawing the frozen sample and seeding the selected population of cells for CAR T cell manufacture.

15. The method of claim 14, wherein:

(i) step (iii) is performed no later than 35 hours after the beginning of step (v);

(ii) the population of cells from step (iii) are not expanded, or expanded by no more than 40%, compared to the population of cells at the end of step (v);

(iii) the selected cells undergo one or more rounds of freeze-thaw before the seeding step;

(iv) the alternative source of hematopoietic tissue is T cells isolated from:

cryopreserved whole blood, bone marrow, or tumor or organ biopsy or removal, or thymectomy; or fresh whole blood, bone marrow, or tumor or organ biopsy or removal, or thymectomy;

(v) the T cells are CD4+ T cells and/or CD8+ T cells;

(vi) the entity is a laboratory, hospital, or healthcare provider;

(vii) the apheresis sample is a leukapheresis sample; and/or (viii) the apheresis sample is a fresh product.

16. The method of claim 1, further comprising step (vi): culturing a portion of the population of cells from step (iii) for at least 2 days, and measuring CAR expression level or the percentage of viable, CAR-expressing cells in the portion.

17. The method of claim 16, wherein step (iii) comprises harvesting and freezing the population of cells and step (vi) comprises thawing a portion of the population of cells from step (iii), culturing the portion for at least 2 days, and measuring CAR expression level or the percentage of viable, CAR-expressing cells in the portion.

18. The method of claim 1, wherein:

(a) the population of cells at the beginning of step (i) has been enriched for IL6R-expressing cells and/or cells that are positive for IL6Rα and/or IL6Rβ;

(b) the population of cells at the beginning of step (i) comprises no less than 50% of IL6R-expressing cells and/or cells that are positive for IL6Rα and/or IL6Rβ;

(c) steps (i) and (ii) are performed in cell media comprising IL-15 or hetIL-15 (IL15/sIL-15Ra); and/or (d) IL-15 increases the ability of the population of cells to expand or the percentage of IL6Rβ-expressing cells in the population of cells.

19. The method of claim 1, wherein the CAR comprises an antigen binding domain, a transmembrane domain, and an intracellular signaling domain.

20. The method of claim 19, wherein:

(a) the antigen binding domain:

(i) binds to an antigen chosen from: CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, Lewis Y, CD24, PDGFR-beta, SSEA-4, folate receptor alpha, ERBBs, ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC; and/or (ii) comprises a VH and a VL, wherein the VH and VL are connected by a linker, wherein the linker comprises the amino acid sequence of SEQ ID NO: 63 or 104;

(b) the transmembrane domain comprises a transmembrane domain of a protein chosen from the alpha, beta or zeta chain of T-cell receptor, CD28, CD3 epsilon, CD45, CD4, CD5, CD8, CD9, CD16, CD22, CD33, CD37, CD64, CD80, CD86, CD134, CD137 and CD154;

(c) the transmembrane domain comprises a transmembrane domain of CD8;

(d) the transmembrane domain comprises the amino acid sequence of SEQ ID NO: 6, or an amino acid sequence having at least about 85% sequence identity thereto; and/or (e) the nucleic acid molecule comprises a nucleic acid sequence encoding the transmembrane domain, wherein the nucleic acid sequence comprises the nucleic acid sequence of SEQ ID NO: 17, or a nucleic acid sequence having at least about 85% sequence identity thereto.

21. The method of claim 19, wherein:

the antigen binding domain is connected to the transmembrane domain by a hinge region, wherein:

(a) the hinge region comprises the amino acid sequence of SEQ ID NO: 2, 3, or 4, or an amino acid sequence having at least about 85% sequence identity thereto, or (b) the nucleic acid molecule comprises a nucleic acid sequence encoding the hinge region, wherein the nucleic acid sequence comprises the nucleic acid sequence of SEQ ID NO: 13, 14, or 15, or a nucleic acid sequence having at least about 85% sequence identity thereto.

22. The method of claim 19, wherein the intracellular signaling domain comprises a primary signaling domain and/or a costimulatory signaling domain.

23. The method of claim 22, wherein:

(a) the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d;

(b) the primary signaling domain comprises a functional signaling domain derived from CD3 zeta;

(c) the primary signaling domain comprises the amino acid sequence of SEQ ID NO: 9 or 10, or an amino acid sequence having at least about 85% sequence identity thereto;

(d) the nucleic acid molecule comprises a nucleic acid sequence encoding the primary signaling domain, wherein the nucleic acid sequence comprises the nucleic acid sequence of SEQ ID NO: 20 or 21, or a nucleic acid sequence having at least about 85% sequence identity thereto;

(e) the costimulatory signaling domain comprises a functional signaling domain derived from a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83;

(f) the costimulatory signaling domain comprises a functional signaling domain derived from 4-1BB;

(g) the costimulatory signaling domain comprises the amino acid sequence of SEQ ID NO: 7, or an amino acid sequence having at least about 85% sequence identity thereto; and/or (h) the nucleic acid molecule comprises a nucleic acid sequence encoding the costimulatory signaling domain, wherein the nucleic acid sequence comprises the nucleic acid sequence of SEQ ID NO: 18, or a nucleic acid sequence having at least about 85% sequence identity thereto.

24. The method of claim 19, wherein:

(a) the intracellular signaling domain comprises a functional signaling domain derived from 4-1BB and a functional signaling domain derived from CD3 zeta;

(b) the intracellular signaling domain comprises the amino acid sequence of SEQ ID NO: 7, or an amino acid sequence having at least about 85% sequence identity thereto, and the amino acid sequence of SEQ ID NO: 9 or 10, or an amino acid sequence having at least about 85% sequence identity thereto;

(c) the intracellular signaling domain comprises the amino acid sequence of SEQ ID NO: 7 and the amino acid sequence of SEQ ID NO: 9 or 10; and/or (d) the CAR further comprises a leader sequence comprising the amino acid sequence of SEQ ID NO: 1.

25. The method of claim 1, wherein the CAR comprises an antigen binding domain, a transmembrane domain, and an intracellular signaling domain, wherein the antigen binding domain binds to CD19 and comprises a heavy chain complementarity determining region 1 (HC CDR1) comprising the amino acid sequence of SEQ ID NO: 295, an HC CDR2 comprising the amino acid sequence of SEQ ID NO: 296, an HC CDR3 comprising the amino acid sequence of SEQ ID NO: 297, a light chain complementarity determining region 1 (LC CDR1) comprising the amino acid sequence of SEQ ID NO: 298, an LC CDR2 comprising the amino acid sequence of SEQ ID NO: 299, and an LC CDR3 comprising the amino acid sequence of SEQ ID NO: 300.

26. The method of claim 1, wherein the CAR comprises an antigen binding domain, a transmembrane domain, and an intracellular signaling domain, wherein the antigen binding domain binds to BCMA and comprises:

(i) a heavy chain complementarity determining region 1 (HC CDR1) comprising the amino acid sequence of SEQ ID NO: 44, an HC CDR2 comprising the amino acid sequence of SEQ ID NO: 45, an HC CDR3 comprising the amino acid sequence of SEQ ID NO: 46, 68, or 76, a light chain complementarity determining region 1 (LC CDR1) comprising the amino acid sequence of SEQ ID NO: 54, an LC CDR2 comprising the amino acid sequence of SEQ ID NO: 55, and an LC CDR3 comprising the amino acid sequence of SEQ ID NO: 56;

(ii) an HC CDR1 comprising the amino acid sequence of SEQ ID NO: 47, an HC CDR2 comprising the amino acid sequence of SEQ ID NO: 48, an HC CDR3 comprising the amino acid sequence of SEQ ID NO: 46, 68, or 76, an LC CDR1 comprising the amino acid sequence of SEQ ID NO: 57, an LC CDR2 comprising the amino acid sequence of SEQ ID NO: 58, and an LC CDR3 comprising the amino acid sequence of SEQ ID NO: 59;

(iii) an HC CDR1 comprising the amino acid sequence of SEQ ID NO: 49, an HC CDR2 comprising the amino acid sequence of SEQ ID NO: 50, an HC CDR3 comprising the amino acid sequence of SEQ ID NO: 51, 69, or 77, an LC CDR1 comprising the amino acid sequence of SEQ ID NO: 60, an LC CDR2 comprising the amino acid sequence of SEQ ID NO: 58, and an LC CDR3 comprising the amino acid sequence of SEQ ID NO: 56;

(iv) an HC CDR1 comprising the amino acid sequence of SEQ ID NO: 86, an HC CDR2 comprising the amino acid sequence of SEQ ID NO: 87, an HC CDR3 comprising the amino acid sequence of SEQ ID NO: 88, an LC CDR1 comprising the amino acid sequence of SEQ ID NO: 95, an LC CDR2 comprising the amino acid sequence of SEQ ID NO: 96, and an LC CDR3 comprising the amino acid sequence of SEQ ID NO: 97;

(v) an HC CDR1 comprising the amino acid sequence of SEQ ID NO: 47, an HC CDR2 comprising the amino acid sequence of SEQ ID NO: 89, an HC CDR3 comprising the amino acid sequence of SEQ ID NO: 88, an LC CDR1 comprising the amino acid sequence of SEQ ID NO: 98, an LC CDR2 comprising the amino acid sequence of SEQ ID NO: 99, and an LC CDR3 comprising the amino acid sequence of SEQ ID NO: 100;

(vi) an HC CDR1 comprising the amino acid sequence of SEQ ID NO: 90, an HC CDR2 comprising the amino acid sequence of SEQ ID NO: 91, an HC CDR3 comprising the amino acid sequence of SEQ ID NO: 92, an LC CDR1 comprising the amino acid sequence of SEQ ID NO: 101, an LC CDR2 comprising the amino acid sequence of SEQ ID NO: 99, and an LC CDR3 comprising the amino acid sequence of SEQ ID NO: 97;

(vii) an HC CDR1 comprising the amino acid sequence of SEQ ID NO: 86, an HC CDR2 comprising the amino acid sequence of SEQ ID NO: 109, an HC CDR3 comprising the amino acid sequence of SEQ ID NO: 88, an LC CDR1 comprising the amino acid sequence of SEQ ID NO: 95, an LC CDR2 comprising the amino acid sequence of SEQ ID NO: 114, and an LC CDR3 comprising the amino acid sequence of SEQ ID NO: 97 or 115;

(viii) an HC CDR1 comprising the amino acid sequence of SEQ ID NO: 47, an HC CDR2 comprising the amino acid sequence of SEQ ID NO: 110, an HC CDR3 comprising the amino acid sequence of SEQ ID NO: 88, an LC CDR1 comprising the amino acid sequence of SEQ ID NO: 98, an LC CDR2 comprising the amino acid sequence of SEQ ID NO: 116, and an LC CDR3 comprising the amino acid sequence of SEQ ID NO: 100 or 117;

(ix) an HC CDR1 comprising the amino acid sequence of SEQ ID NO: 90, an HC CDR2 comprising the amino acid sequence of SEQ ID NO: 111, an HC CDR3 comprising the amino acid sequence of SEQ ID NO: 92, an LC CDR1 comprising the amino acid sequence of SEQ ID NO: 101, an LC CDR2 comprising the amino acid sequence of SEQ ID NO: 116, and an LC CDR3 comprising the amino acid sequence of SEQ ID NO: 97 or 115;

(x) an HC CDR1 comprising the amino acid sequence of SEQ ID NO: 137, an HC CDR2 comprising the amino acid sequence of SEQ ID NO: 138, an HC CDR3 comprising the amino acid sequence of SEQ ID NO: 139, an LC CDR1 comprising the amino acid sequence of SEQ ID NO: 147, an LC CDR2 comprising the amino acid sequence of SEQ ID NO: 148, and an LC CDR3 comprising the amino acid sequence of SEQ ID NO: 149;

(xi) an HC CDR1 comprising the amino acid sequence of SEQ ID NO: 140, an HC CDR2 comprising the amino acid sequence of SEQ ID NO: 141, an HC CDR3 comprising the amino acid sequence of SEQ ID NO: 139, an LC CDR1 comprising the amino acid sequence of SEQ ID NO: 150, an LC CDR2 comprising the amino acid sequence of SEQ ID NO: 151, and an LC CDR3 comprising the amino acid sequence of SEQ ID NO: 152;

(xii) an HC CDR1 comprising the amino acid sequence of SEQ ID NO: 142, an HC CDR2 comprising the amino acid sequence of SEQ ID NO: 143, an HC CDR3 comprising the amino acid sequence of SEQ ID NO: 144, an LC CDR1 comprising the amino acid sequence of SEQ ID NO: 153, an LC CDR2 comprising the amino acid sequence of SEQ ID NO: 151, and an LC CDR3 comprising the amino acid sequence of SEQ ID NO: 149;

(xiii) an HC CDR1 comprising the amino acid sequence of SEQ ID NO: 160, an HC CDR2 comprising the amino acid sequence of SEQ ID NO: 161, an HC CDR3 comprising the amino acid sequence of SEQ ID NO: 162, an LC CDR1 comprising the amino acid sequence of SEQ ID NO: 147, an LC CDR2 comprising the amino acid sequence of SEQ ID NO: 170, and an LC CDR3 comprising the amino acid sequence of SEQ ID NO: 171;

(xiv) an HC CDR1 comprising the amino acid sequence of SEQ ID NO: 163, an HC CDR2 comprising the amino acid sequence of SEQ ID NO: 164, an HC CDR3 comprising the amino acid sequence of SEQ ID NO: 162, an LC CDR1 comprising the amino acid sequence of SEQ ID NO: 150, an LC CDR2 comprising the amino acid sequence of SEQ ID NO: 151, and an LC CDR3 comprising the amino acid sequence of SEQ ID NO: 172; or (xv) an HC CDR1 comprising the amino acid sequence of SEQ ID NO: 165, an HC CDR2 comprising the amino acid sequence of SEQ ID NO: 166, an HC CDR3 comprising the amino acid sequence of SEQ ID NO: 167, an LC CDR1 comprising the amino acid sequence of SEQ ID NO: 153, an LC CDR2 comprising the amino acid sequence of SEQ ID NO: 151, and an LC CDR3 comprising the amino acid sequence of SEQ ID NO: 171.

27. The method of claim 1, wherein the CAR comprises an antigen binding domain that binds to CD19, and wherein:

(a) the CAR comprises an scFv comprising the amino acid sequence of SEQ ID NO: 303, or a sequence having at least 90% identity thereto;

(b) the CAR comprises the amino acid sequence of SEQ ID NO: 292 or SEQ ID NO: 301, or a sequence having at least 90% identity thereto; and/or (c) the nucleotide sequence encoding the CAR comprises the nucleotide sequence of SEQ ID NO: 302, or a sequence having at least 90% identity thereto.

28. The method of claim 1, wherein the method further comprises formulating the harvested cells in a pharmaceutical composition.

29. The method of claim 28, wherein the harvested cells are formulated in combination with one or more pharmaceutically or physiologically acceptable carriers, diluents or excipients.

30. A population of CAR-expressing cells made by the method of claim 1.

31. A pharmaceutical composition comprising the population of CAR-expressing cells of claim 30.

32. A method of increasing an immune response in a subject, comprising administering the population of CAR-expressing cells of claim 30 to the subject, thereby increasing an immune response in the subject.

33. A method of treating a cancer in a subject, comprising administering the population of CAR-expressing cells of claim 30 to the subject, thereby treating the cancer in the subject.

34. The method of claim 1, wherein the CAR comprises an antigen binding domain that binds to BCMA, and wherein:

(a) the CAR comprises a heavy chain variable region (VH) comprising the amino acid sequence of SEQ ID NO: 93, or an amino acid sequence having at least 90% sequence identity thereto; and a light chain variable region (VL) comprising the amino acid sequence of SEQ ID NO: 102, or amino acid sequence having at least 90% sequence identity thereto;

(b) the CAR comprises a VH comprising the amino acid sequence of SEQ ID NO: 52, or an amino acid sequence having at least 90% sequence identity thereto; and a VL comprising the amino acid sequence of SEQ ID NO: 61, or amino acid sequence having at least 90% sequence identity thereto;

(c) the CAR comprises a VH comprising the amino acid sequence of SEQ ID NO: 70, or an amino acid sequence having at least 90% sequence identity thereto; and a VL comprising the amino acid sequence of SEQ ID NO: 61, or amino acid sequence having at least 90% sequence identity thereto;

(d) the CAR comprises a VH comprising the amino acid sequence of SEQ ID NO: 78, or an amino acid sequence having at least 90% sequence identity thereto; and a VL comprising the amino acid sequence of SEQ ID NO: 61, or amino acid sequence having at least 90% sequence identity thereto;

(e) the CAR comprises a VH comprising the amino acid sequence of SEQ ID NO: 112, or an amino acid sequence having at least 90% sequence identity thereto; and a VL comprising the amino acid sequence of SEQ ID NO: 118, or amino acid sequence having at least 90% sequence identity thereto;

(f) the CAR comprises a VH comprising the amino acid sequence of SEQ ID NO: 112, or an amino acid sequence having at least 90% sequence identity thereto; and a VL comprising the amino acid sequence of SEQ ID NO: 124, or amino acid sequence having at least 90% sequence identity thereto;

(g) the CAR comprises a VH comprising the amino acid sequence of SEQ ID NO: 145, or an amino acid sequence having at least 90% sequence identity thereto; and a VL comprising the amino acid sequence of SEQ ID NO: 154, or amino acid sequence having at least 90% sequence identity thereto;

(h) the CAR comprises a VH comprising the amino acid sequence of SEQ ID NO: 168, or an amino acid sequence having at least 90% sequence identity thereto; and a VL comprising the amino acid sequence of SEQ ID NO: 173, or amino acid sequence having at least 90% sequence identity thereto;

(i) the CAR comprises an scFv comprising the amino acid sequence of any one of SEQ ID NOs: 64, 72, 80, 105, 120, 126, 156, or 175, or an amino acid sequence having at least 90% identity thereto;

(j) the CAR comprises the amino acid sequence of any one of SEQ ID NOs: 66, 74, 82, 107, 122, 128, 158, 177, or 257, or an amino acid sequence having at least 90% identity thereto; and/or (k) the nucleotide sequence encoding the CAR comprises the nucleotide sequence of any one of SEQ ID NOs: 67, 75, 83, 106, 108, 123, 129, 159, 178, or 258, or a nucleotide sequence having at least 90% identity thereto.

35. The method of claim 1, wherein the CAR comprises an antigen binding domain, a transmembrane domain, and an intracellular signaling domain, wherein the antigen binding domain binds to CD22 and comprises:

(i) a heavy chain complementarity determining region 1 (HC CDR1) comprising the amino acid sequence of SEQ ID NO: 288 or SEQ ID NO: 289; an HC CDR2 comprising the amino acid sequence of SEQ ID NO: 290; an HC CDR3 comprising the amino acid sequence of SEQ ID NO: 291; a light chain complementarity determining region 1 (LC CDR1) comprising the amino acid sequence of SEQ ID NO: 95; an LC CDR2 comprising the amino acid sequence of SEQ ID NO: 96; and an LC CDR3 comprising the amino acid sequence of SEQ ID NO: 97;

(ii) a heavy chain variable region (VH) comprising the amino acid sequence of SEQ ID NO: 286, or a amino acid sequence having at least 90% identity thereto; and a light chain variable region (VL) comprising the amino acid sequence of SEQ ID NO: 287, or an amino acid sequence having at least 90% identity thereto; and/or (iii) an scFv comprising the amino acid sequence of SEQ ID NO: 285, or an amino acid sequence having at least 90% identity thereto.

36. The method of claim 1, wherein step (iii) is performed no later than 30 hours after the beginning of step (i).

37. The method of claim 1, wherein the CAR comprises an antigen binding domain that binds to CD19 and wherein:

(i) the CAR comprises a heavy chain complementarity determining region 1 (HC CDR1) comprising the amino acid sequence of SEQ ID NO: 295, an HC CDR2 comprising the amino acid sequence of SEQ ID NO: 304, an HC CDR3 comprising the amino acid sequence of SEQ ID NO: 297, a light chain complementarity determining region 1 (LC CDR1) comprising the amino acid sequence of SEQ ID NO: 298, an LC CDR2 comprising the amino acid sequence of SEQ ID NO: 299, and an LC CDR3 comprising the amino acid sequence of SEQ ID NO: 300;

(ii) the CAR comprises an scFv comprising the amino acid sequence of SEQ ID NO: 293, or an amino acid sequence having at least 90% identity thereto;

(iii) the CAR comprises the amino acid sequence of SEQ ID NO: 294 or SEQ ID NO: 306, or an amino acid sequence having at least 90% identity thereto; and/or (iv) the nucleotide sequence encoding the CAR comprises the nucleotide sequence of SEQ ID NO: 305 or SEQ ID NO: 307, or a nucleotide sequence having at least 90% identity thereto.

38. A method of treating an autoimmune disease in a subject, comprising administering the population of CAR-expressing cells of claim 30 to the subject, thereby treating the autoimmune disease in the subject.

* * * * *